(12) United States Patent
Stege et al.

(10) Patent No.: US 9,234,216 B2
(45) Date of Patent: Jan. 12, 2016

(54) VARIANT CBH I POLYPEPTIDES

(75) Inventors: Justin T. Stege, San Diego, CA (US); Alexander Varvak, Netanya (IL); John Poland, San Diego, CA (US); Chris S. Lyon, San Diego, CA (US); Shaun Healey, Carlsbad, CA (US); Peter Luginbuhl, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 13/824,315

(22) PCT Filed: Oct. 6, 2011

(86) PCT No.: PCT/US2011/055180
§ 371 (c)(1),
(2), (4) Date: Mar. 15, 2013

(87) PCT Pub. No.: WO2012/051055
PCT Pub. Date: Apr. 19, 2012

(65) Prior Publication Data
US 2013/0203128 A1    Aug. 8, 2013

(51) Int. Cl.
*C12P 7/14* (2006.01)
*C12N 9/42* (2006.01)
*C12P 19/02* (2006.01)
*C12P 19/14* (2006.01)

(52) U.S. Cl.
CPC ............. *C12P 7/14* (2013.01); *C12N 9/2437* (2013.01); *C12P 19/02* (2013.01); *C12P 19/14* (2013.01); *C12Y 302/01091* (2013.01); *Y02E 50/16* (2013.01); *Y02E 50/17* (2013.01)

(58) Field of Classification Search
CPC .................. C12N 9/2437; C11D 3/38645
See application file for complete search history.

(56) References Cited

U.S. PATENT DOCUMENTS

| | | | | |
|---|---|---|---|---|
| 5,763,254 A | * | 6/1998 | Woldike et al. | 435/209 |
| 8,580,536 B2 | * | 11/2013 | McBrayer et al. | 435/41 |
| 2009/0162916 A1 | | 6/2009 | Adney | |
| 2011/0124074 A1 | * | 5/2011 | Den Haan et al. | 435/170 |

FOREIGN PATENT DOCUMENTS

EP        2357227        8/2011
WO    WO 2004/078919    9/2004

OTHER PUBLICATIONS

Johansson et al. 1989. Isolated fungal cellulose termina domains ad a synthetic minimum analogue bind to cellulose. FEBS Letters. 243(2): 389-393.*
Linder et al. 1996; The cellulose-binding domain of the major cellobiohydrolase of Trichoderma reesei exhibits true reversibiltity and high exchange rate on crystalline cellulose. PNAS 93: 12251-12255.*
Federova et al. 2007; The genome sequence of Penicilium marneffei stain ATCC 18224. EMBL: EEA23157.1.*

* cited by examiner

*Primary Examiner* — Karen Cochrane Carlson
(74) *Attorney, Agent, or Firm* — DLA Piper LLP (US)

(57) ABSTRACT

In alternative embodiments, the invention provides polypeptides having a lignocellulolytic (lignocellulosic) activity, e.g., a ligninolytic and cellulolytic activity, including, e.g., a glycosyl hydrolase, a cellulase, an endoglucanase, a cellobiohydrolase (cbhl) (e.g., an exo-cellobiohydrolase, e.g., having an "exo" activity that can processively release cellobiose units β-1,4 glucose-glucose disaccharide), a beta-glucosidase, a xylanase, a mannanse, a xylosidase (e.g., a (β-xylosidase) and/or an arabinofuranosidase activity, polynucleotides encoding these polypeptides, and methods of making and using these polynucleotides and polypeptides. In one embodiment, the invention provides thermostable and thermotolerant forms of polypeptides of the invention. The polypeptides and nucleic acids of the invention are used in a variety of pharmaceutical, agricultural and industrial contexts; for example, as enzymes for the bioconversion of a biomass, e.g., lignocellulosic residues, into fermentable sugars, where in one aspect these sugars are used as a chemical feedstock for the production of ethanol and fuels, e.g., biofuels, e.g., synthetic liquid or gas fuels, including ethanol, methanol and the like.

197 Claims, 21 Drawing Sheets

| | | | | | | | | |
|---|---|---|---|---|---|---|---|---|
| | 10 | 20 | 30 | 40 | 50 | 60 | 70 | 80 |

```
wild type     ................................................................................
SEQ ID NO:2   MSALNSFNMYKSALILGSLLATAGAQQIGTYTAETHPSLSWSTCKSGGSCTTNSGAITLDANWRWVHGVNTSTNCYTGNT
SEQ ID NO:4   MSALNSFNMYKSALILGSLLATAGAQQIGTYTAETHPSLSWSTCKSGGSCTTNSGAITLDANWRWVHGVNTSTNCYTGNT
SEQ ID NO:6   MSALNSFNMYKSALILGSLLATAGAQQIGTYTAETHPSLSWSTCKSGGSCTTNSGAITLDANWRWVHGVNTSTNCYTGNT
SEQ ID NO:8   MSALNSFNMYKSALILGSLLATAGAQQIGTYTAETHPSLSWSTCKSGGSCTTNSGAITLDANWRWVHGVNTSTNCYTGNT
SEQ ID NO:10  MSALNSFNMYKSALILGSLLATAGAQQIGTYTAETHPSLSWSTCKSGGSCTTNSGAITLDANWRWVHGVNTSTNCYTGNT
SEQ ID NO:12  MSALNSFNMYKSALILGSLLATAGAQQIGTYTAETHPSLSWSTCKSGGSCTTNSGAITLDANW RWVHGVNTSTNCYTGNT
SEQ ID NO:14  MSALNSFNMYKSALILGSLLATAGAQQIGTYTAETHPSLSWSTCKSGGSCTTNSGAITLDANWRWVHGVNTSTNCYTGNT
SEQ ID NO:16  MSALNSFNMYKSALILGSLLATAGAQQIGTYTAETHPSLSWSTCKSGGSCTTNSGAITLDANWRWVHGVNTSTNCYTGNT
SEQ ID NO:18  MSALNSFNMYKSALILGSLLATAGAQQIGTYTAETHPSLSWSTCKSGGSCTTNSGAITLDANWRWVHGVNTSTNCYTGNT
SEQ ID NO:20  MSALNSFNMYKSALILGSLLATAGAQQIGTYTAETHPSLSWSTCKSGGSCTTNSGAITLDANWRWVHGVNTSTNCYTGNT
SEQ ID NO:22  MSALNSFNMYKSALILGSLLATAGAQQIGTYTAETHPSLSWSTCKSGGSCTTNSGAITLDANWRWVHGVNTSTNCYTGNT
SEQ ID NO:24  MSALNSFNMYKSALILGSLLATAGAQQIGTYTAETHPSLSWSTCKSGGSCTTNSGAITLDANWRWVHGVNTSTNCYTGNT
SEQ ID NO:26  MSALNSFNMYKSALILGSLLATAGAQQIGTYTAETHPSLSWSTCKSGGSCTTNSGAITLDANWRWVHGVNTSTNCYTGNT
SEQ ID NO:28  MSALNSFNMYKSALILGSLLATAGAQQIGTYTAETHPSLSWSTCKSGGSCTTNSGAITLDANWRWVHGVNTSTNCYTGNT
SEQ ID NO:30  MSALNSFNMYKSALILGSLLATAGAQQIGTYTAETHPSLSWSTCKSGGSCTTNSGAITLDANWRWVHGVNTSTNCYTGNT
SEQ ID NO:32  MSALNSFNMYKSALILGSLLATAGAQQIGTYTAETHPSLSWSTCKSGGSCTTNSGAITLDANWRWVHGVNTSTNCYTGNT
SEQ ID NO:34  MSALNSFNMYKSALILGSLLATAGAQQIGTYTAETHPSLSWSTCKSGGSCTTNSGAITLDANWRWVHGVNTSTNCYTGNT
SEQ ID NO:36  MSALNSFNMYKSALILGSLLATAGAQQIGTYTAETHPSLSWSTCKSGGSCTTNSGAITLDANWRWVHGVNTSTNCYTGNT
SEQ ID NO:38  MSALNSFNMYKSALILGSLLATAGAQQIGTYTAETHPSLSWSTCKSGGSCTTNSGAITLDANWRWVHGVNTSTNCYTGNT
SEQ ID NO:40  MSALNSFNMYKSALILGSLLATAGAQQIGTYTAETHPSLSWSTCKSGGSCTTNSGAITLDANWRWVHGVNTSTNCYTGNT
SEQ ID NO:42  MSALNSFNMYKSALILGSLLATAGAQQIGTYTAETHPSLSWSTCKSGGSCTTNSGAITLDANWRWVHGVNTSTNCYTGNT
SEQ ID NO:44  MSALNSFNMYKSALILGSLLATAGAQQIGTYTAETHPSLSWSTCKSGGSCTTNSGAITLDANWRWVHGVNTSTNCYTGNT
SEQ ID NO:46  MSALNSFNMYKSALILGSLLATAGAQQIGTYTAETHPSLSWSTCKSGGSCTTNSGAITLDANWRWVHGVNTSTNCYTGNT
SEQ ID NO:48  MSALNSFNMYKSALILGSLLATAGAQQIGTYTAETHPSLSWSTCKSGGSCTTNSGAITLDANWRWVHGVNTSTNCYTGNT
SEQ ID NO:50  MSALNSFNMYKSALILGSLLATAGAQQIGTYTAETHPSLSWSTCKSGGSCTTNSGAITLDANWRWVHGVNTSTNCYTGNT
SEQ ID NO:52  MSALNSFNMYKSALILGSLLATAGAQQIGTYTAETHPSLSWSTCKSGGSCTTNSGAITLDANWRWVHGVNTSTNCYTGNT
SEQ ID NO:54  MSALNSFNMYKSALILGSLLATAGAQQIGTYTAETHPSLSWSTCKSGGSCTTNSGAITLDANWRWVHGVNTSTNCYTGNT
SEQ ID NO:56  MSALNSFNMYKSALILGSLLATAGAQQIGTYTAETHPSLSWSTCKSGGSCTTNSGAITLDANWRWVHGVNTSTN CYTGNT
SEQ ID NO:58  MSALNSFNMYKSALILGSLLATAGAQQIGTYTAETHPSLSWSTCKSGGSCTTNSGAITLDANWRWVHGVNTSTNCYTGNT
```

Figure 1A

Figure 1B

```
                         10         20         30         40         50         60         70         80
                 ....|....|....|....|....|....|....|....|....|....|....|....|....|....|....|....|
SEQ ID NO:120    MSALNSFNMYKSALILGSLLATAGAQQIGTYYTAETHPSLSWSTCKSGGSCTTNSGAITLDANWRWVHGVNTSTNCYTGNT
SEQ ID NO:122    MSALNSFNMYKSALILGSLLATAGAQQIGTYYTAETHPSLSWSTCKSGGSCTTNSGAITLDANWRWVHGVNTSTNCYTGNT
SEQ ID NO:124    MSALNSFNMYKSALILGSLLATAGAQQIGTYYTAETHPSLSWSTCKSGGSCTTNSGAITLDANWRWVHGVNTSTNCYTGNT
SEQ ID NO:126    MSALNSFNMYKSALILGSLLATAGAQQIGTYYTAETHPSLSWSTCKSGGSCTTNSGAITLDANWRWVHGVNTSTNCYTGNT
SEQ ID NO:128    MSALNSFNMYKSALILGSLLATAGAQQIGTYYTAETHPSLSWSTCKSGGSCTTNSGAITLDANWRWVHGVNTSTNCYTGNT
SEQ ID NO:130    MSALNSFNMYKSALILGSLLATAGAQQIGTYYTAETHPSLSWSTCKSGGSCTTNSGAITLDANWRWVHGVNTSTNCYTGNT
SEQ ID NO:132    MSALNSFNMYKSALILGSLLATAGAQQIGTYYTAETHPSLSWSTCKSGGSCTTNSGAITLDANWRWVHGVNTSTNCYTGNT
SEQ ID NO:134    MSALNSFNMYKSALILGSLLATAGAQQIGTYYTAETHPSLSWSTCKSGGSCTTNSGAITLDANWRWVHGVNTSTNCYTGNT
SEQ ID NO:136    MSALNSFNMYKSALILGSLLATAGAQQIGTYYTAETHPSLSWSTCKSGGSCTTNSGAITLDANWRWVHGVNTSTNCYTGNT
```

Figure 1C

```
                            90        100       110       120       130       140       150       160
                    ....|....|....|....|....|....|....|....|....|....|....|....|....|....|....|....|
Wild type         .........................................................................................
SEQ ID NO:1       WNTAICDTDASCAQDCALDGADYSGTYGITTSGNSLRLNFVTG----SNVGSRTYLMADNTHYQIFDLLNQEFTFTVDVS
SEQ ID NO:3       WNTAICDTDASCAQDCALDGADYSGTYGITTSGNSLRLNFVTG----SNVGSRTYLMADNTHYQIFDLLNQEFTFTVDVS
SEQ ID NO:5       WNTAICDTDASCAQDCALDGADYSGTYGITTSGNSLRLNFVTG----SNVGSRTYLMADNTHYQIFDLLNQEFTFTVDVS
SEQ ID NO:7       WNTAICDTDASCAQDCALDGADYSGTYGITTSGNSLRLNFVTG----SNVGSRTYLMADNTHYQIFDLLNQEFTFTVDVS
SEQ ID NO:9       WNTAICDTDASCAQDCALDGADYSGTYGITTSGNSLRLNFVTG----SNVGSRTYLMADNTHYQIFDLLNQEFTFTVDVS
SEQ ID NO:11      WNTAICDTDASCAQDCALDGADYSGTYGITTSGNSLRLNFVTG----SNVGSRTYLMADNTHYQIFDLLNQEFTFTVDVS
SEQ ID NO:13      WNTAICDTDASCAQDCALDGADYSGTYGITTSGNSLRLNFVTG----SNVGSRTYLMADNTHYQIFDLLNQEFTFTVDVS
SEQ ID NO:15      WNTAICLTDASCAQDCALDGADYSGTYGITTSGNSLRLNFVTG----SNVGSRTYLMADNTHYQIFDLLNQEFTFTVDVS
SEQ ID NO:17      WNTAICDTDASCAQDCALDGADYSGTYGITTSGNSLRLNFVTG----SNVGSRTYLMADNTHYQIFDLLNQEFTFTVDVS
SEQ ID NO:19      WNTAICDTDASCAQDCALDGADYSGTYGITTSGNSLRLNFVTG----SNVGSRTYLMADNTHYQIFDLLNQEFTFTVDVS
SEQ ID NO:21      WNTAICDTDASCAQDCALDGADYSGTYGITTSGNSLRLNFVTG----SNVGSRTYLMADNTHYQIFDLLNQEFTFTVDVS
SEQ ID NO:23      WNTAICDTDASCAQDCALDGADYSGTYGITTSGNSLRLNFVTG----SNVGSRTYLMADNTHYQIFDLLNQEFTFTVDVS
SEQ ID NO:25      WNTAICDTDASCAQDCALDGADYSGTYGITTSGNSLRLNFVTG----SNVGSRTYLMADNTHYQIFDLLNQEFTFTVDVG
SEQ ID NO:27      WNTAICDTDASCAQDCALDGADYSGTYGITTSGNSLRLNFVTG----SNVGSRTYLMADNTHYQIFDLLNQEFTFTVDVS
SEQ ID NO:29      WNTAICDTDASCAQDCALDGADYSGTYGITTSGNSLRLNFVTG----SNVGSRTYLMADNTHYQIFDLLNQEFTFTVDVS
SEQ ID NO:31      WNTAICDTDASCAQDCALDGADYSGTYGITTSGNSLRLNFVTG----SNVGSRTYLMADNTHYQIFDLLNQEFTFTVDVS
SEQ ID NO:33      WNTAICDTDASCAQDCALDGADYSGTYGITTSGNSLRLNFVTG----SNVGSRTYLMADNTHYQIFDLLNQEFTFTVDVS
SEQ ID NO:35      WNTAICDTDASCAQDCALDGADYSGTYGITTSGNSLRLNFVTG----SNVGSRTYLMADNTHYQIFDLLNQEFTFTVDVS
SEQ ID NO:37      WNTAICDTDASCAQDCALDGADYSGTYGITTSGNSLRLNFVTG----SNVGSRTYLMADNTHYQIFDLLNQEFTFTVDVS
SEQ ID NO:39      WNTAICDTDASCAQDCALDGADYSGTYGITTSGNSLRLNFVTG----SNVGSRTYLMADNTHYQIFDLLNQEFTFTVDVS
SEQ ID NO:41      WNTAICDTDASCAQDCALDGADYSGTYGITTSGNSLRLNFVTG----SNVGSRTYLMADNTHYQIFDLLNQEFTFTVDVS
SEQ ID NO:43      WNTAICDTDASCAQDCALDGADYSGTYGITTSGNSLRLNFVTG----SNVGSRTYLMADNTHYQIFDLLNQEFTFTVDVS
SEQ ID NO:45      WNTAICDTDASCAQDCALDGADYSGTYGITTSGNSLRLNFVTG----SNVGSRTYLMADNTHYQIFDLLNQEFTFTVDVS
SEQ ID NO:47      WNTAICDTDASCAQDCALDGADYSGTYGITTSGNSLRLNFVTG----SNVGSRTYLMADNTHYQIFDLLNQEFTFTVDVS
SEQ ID NO:49      WNTAICDTDASCAQDCALDGADYSGTYGITTSGNSLRLNFVTG----SNVGSRTYLMADNTHYQIFDLLNQEFTFTVDVS
SEQ ID NO:51      WNTAICDTDASCAQDCALDGADYSGTYGITTSGNSLRLNFVTG----SNVGSRTYLMADNTHYQIFDLLNQEFTFTVDVS
SEQ ID NO:53      WNTAICDTDASCAQDCALDGADYSGTYGITTSGNSLRLNFVTG----SNVGSRTYLMADNTHYQIFDLLNQEFTFTVDVS
SEQ ID NO:55      WNTAICDTDASCAQDCALDGADYSGTYGITTSGNSLRLNFVTG----SNVGSRTYLMADNTHYQIFDLLNQEFTFTVDVS
SEQ ID NO:57      WNTAICDTDASCAQDCALDGADYSGTYGITTSGNSLRLNFVTG----SNVGSRTYLMADNTHYQIFDLLNQEFTFTVDVS
```

Figure 1D

Figure 1E

```
                 90        100       110       120       130        140       150       160
                 ....|....|....|....|....|....|....|....|....|....|....|....|....|....|....|....|
SEQ ID NO:59     ..........................................................................---
SEQ ID NO:61     WNTAICDTDASCAQDCALDGADYSGTYGITTSGNSLRLNFVTG-----SNVGSRTYLMADNTHYQIFDLLNQEFTFTVDVS
SEQ ID NO:63     WNTAICDTDASCAQDCALDGADYSGTYGITTSGNSLRLNFVTG-----SNVGSRTYLMADNTHYQIFDLLNQEFTFTVDVS
SEQ ID NO:65     WNTAICDTDASCAQDCALDGADYNGTYSGTYGITTSGNSLRLNFSTG-----SNVGSRTYLMADNTHYQIFDLLNQEFTFTVDVS
SEQ ID NO:67     WNTAICDTDASCAQDCALDGADYSGTYGITTSGNSLRLNFTTG-----SNVGSRTYLMADNTHYQIFDLLNQEFTFTVDVS
SEQ ID NO:69     WNTAICDTDASCAQDCALDGADYSGTYGITTSGNNSLRLNFVTG-----SNVGSRTYLMADNTHYQIFDLLNQEFTFTVDVS
SEQ ID NO:71     WNTAICDTDASCAQDCALDGADYSGTYGITTSGNSLRINFVTG-----SNVGSRTYLMADNTHYQIFDLLNQEFTFTVDVS
SEQ ID NO:73     WNTAICDTDASCAQDCALDGADYSGTYGITTSGNSLRLNFVTG-----SNVGSRTYLMADNTHYQIFDLLNQEFTFTVDVS
SEQ ID NO:75     WNTAICDTDASCAQDCALDGADYSGTYGITTSGNSLRLNFVTG-----SNVGSRTYLMADNTHYQIFDLLNQEFTFTVDVS
SEQ ID NO:77     WNTAICDTDASCAQDCALDGADYSGTYGITTSGNSLRLNFVTG-----SNVGSRTYLMADNTHYQIFDLLNQEFTFTVDVS
SEQ ID NO:79     WNTAICDTDASCAQDCALDGADYSGTYGITTSGNSLRLNFVTG-----SNVGSRTYLMADNTHYQIFDLLNQEFTFTVDVS
SEQ ID NO:81     WNTAICDTDASCAQDCALDGADYSGTYGITTSGNSLRLNFVTG-----SNVGSRTYLMADNTHYQIFDLLNQEFTFTVDVS
SEQ ID NO:83     WNTAICDTDASCAQDCALDGADYSGTYGITTSGNSLRLNFVTG-----SNVGSRTYLMADNTHYQIFDLLNQEFTFTVDVS
SEQ ID NO:85     WNTAICDTDASCAQDCALDGADYSGTYGITTSGNSLRLNFVTG-----SNVGSRTYLMADNTHYQIFDLLNQEFTFTVDVS
SEQ ID NO:87     WNTAICDTDASCAQDCALDGADYSGTYGITTSGNSLRLNFVTG-----SNVGSRTYLMADNTHYQIFDLLNQEFTFTVDVS
SEQ ID NO:89     WNTAICDTDASCAQDCALDGADYSGTYGITTSGNSLRLNFVTG-----SNVGSRTYLMADNTHYQIFDLLNQEFTFTVDVS
SEQ ID NO:91     WNTAICDTDASCAQDCALDGADYSGTYGITTSGNSLRLNFVTG-----SNVGSRTYLMADNTHYQIFDLLNQEFTFTVDVS
SEQ ID NO:93     WNTAICDTDASCAQDCALDGADYSGTYGITTSGNSLRLNFVTG-----SNVGSRTYLMADNTHYQIFDLLNQEFTFTVDVS
SEQ ID NO:95     WNTAICDTDASCAQDCALDGADYSGTYGITTSGNSLRLNFVQQGPYSKNVGSRTYLMADNTHYQIFDLLNQEFTFTVDVS
SEQ ID NO:97     WNTAICDTDASCAQDCALDGADYSGTYGITTSGNSLRLNFVQQGPYSKNVGSRTYLMADNTHYQIFDLLNQEFTFTVDVS
SEQ ID NO:99     WNTAICDTDASCAQDCALDGADYSGTYGITTSGNSLRLNFVQQGPYSKNVGSRTYLMADNTHYQIFDLLNQEFTFTVDVS
SEQ ID NO:101    WNTAICDTDASCAQDCALDGADYSGTYGITTSGNSLRLNFVTKGSFSSNIGSRTYLMADNTHYQIFDLLNQEFTFTVDVS
SEQ ID NO:103    WNTAICDTDASCAQDCALDGADYSGTYGITTSGNSLRLNFVTQSAQ-KNVGARTYLMADNTHYQIFDLLNQEFTFTVDVS
SEQ ID NO:105    WNTAICDTDASCAQDCALDGADYSGTYGITTSGNSLRLNFVTGS-----NVGSRTYLMADNTHYQIFDLLNQEFTFTVDVS
SEQ ID NO:107    WNTAICDTDASCAQDCALDGADYSGTYGITTSGNSLRLNFVTGS-----NVGSRTYLMADNTHYQIFDLLNQEFTFTVDVS
SEQ ID NO:109    WNTAICDTDASCAQDCALDGADYSGTYGITTSGNSLRLNFVTGS-----NVGSRTYLMADNTHYQIFDLLNQEFTFTVDVS
SEQ ID NO:111    WNTAICDTDASCAQDCALDGADYSGTYGITTSGNSLRLNFVTGS-----NVGSRTYLMADNTHYQIFDLLNQEFTFTVDVS
SEQ ID NO:113    WNTAICDTDASCAQDCALDGADYSGTYGITTSGNSLRLNFVQQGPYSKNVGSRTYLMADNTHYQIFDLLNQEFTFTVDVS
SEQ ID NO:115    WNTAICDTDASCAQDCALDGADYSGTYGITTSGNSLRLNFVTGS-----NVGSRTYLMADNTHYQIFDLLNQEFTFTVDVS
SEQ ID NO:117    WNTAICDTDASCAQDCALDGADYSGTYGITTSGNSLRLNFVQQGPYSKNVGSRTYLMADNTHYQIFDLLNQEFTFTVDVS
```

```
                      90        100       110       120       130       140       150       160
                      ....|....|....|....|....|....|....|....|....|....|....|....|....|....|....|....|
SEQ ID NO:119   WNTAICDTDASCAQDCALDGADYSGTYGITTSGNSLRLNFVTG----SNVGSRTYLMADNTHYQIFDLLNQEFTFTVDVS
SEQ ID NO:121   WNTAICDTDASCAQDCALDGADYSGTYGITTSGNSLRLNFVTG----SNVGSRTYLMADNTHYQIFDLLNQEFTFTVDVS
SEQ ID NO:123   WNTAICDTDASCAQDCALDGADYSGTYGITTSGNSLRLNFVTG----SNVGSRTYLMADNTHYQIFDLLNQEFTFTVDVS
SEQ ID NO:125   WNTAICDTDASCAQDCALDGADYSGTYGITTSGNSLRLNFVTG----SNVGSRTYLMADNTHYQIFDLLNQEFTFTVDVS
SEQ ID NO:127   WNTAICDTDASCAQDCALDGADYSGTYGITTSGNSLRLNFVTG----SNVGSRTYLMADNTHYQIFDLLNQEFTFTVDVS
SEQ ID NO:129   WNTAICDTDASCAQDCALDGADYSGTYGITTSGNSLRLNFVTG----SNVGSRTYLMADNTHYQIFDLLNQEFTFTVDVS
SEQ ID NO:131   WNTAICDTDASCAQDCALDGADYSGTYGITTSGNSLRLNFVTG----SNVGSRTYLMADNTHYQIFDLLNQEFTFTVDVS
SEQ ID NO:133   WNTAICDTDASCAQDCALDGADYSGTYGITTSGNSLRLNFVTG----SNVGSRTYLMADNTHYQIFDLLNQEFTFTVDVS
SEQ ID NO:135   WNTAICDTDASCAQDCALDGADYSGTYGITTSGNSLRLNFVTG----SNVGSRTYLMADNTHYQIFDLLNQEFTFTVDVS
```

```
                        170       180       190       200       210       220       230       240
                    ....|....|....|....|....|....|....|....|....|....|....|....|....|....|....|....|
SEQ ID NO:59        HLPCGLNGALYFVTMDADGGVSKYPNNKAGAQYGVGYCDSQCPRDLKFIAGQANVEGWTPSSNNANTGLGNHGACCAELD
SEQ ID NO:61        HLPCGLNGALYFVTMDADGGVSKYPNNKAGAQYGVGYCDSQCPRDLKFIAGQANVEGWTPSSNNANTGLGNHGACCAELD
SEQ ID NO:63        HLPCGLNGALYFVTMDADGGVSKYPNNKAGAQYGVGYCDSQCPRDLKFIAGQANVEGWTPSSNNANTGLGNHGACCAELD
SEQ ID NO:65        HLPCGLNGALYFVTMDADGGVSKYPNNKAGAQYGVGYCDSQCPRDLKFIAGQANVEGWTPSSNNANTGLGNHGACCAELD
SEQ ID NO:67        HLPCGLNGALYFVTMDADGGVSKYPNNKAGAQYGVGYCDSQCPRDLKFIAGQANVEGWTPSSNNANTGLGNHGACCAELD
SEQ ID NO:69        HLPCGLNGALYFVTMDADGGVSKYPNNKAGAQYGVGYCDSQCPRDLKFIAGQANVEGWTPSSNNANTGLGNHGACCAELD
SEQ ID NO:71        HLPCGLNGALYFVTMDADGGVSKYPNNKAGAQYGVGYCDSQCPRDLKFIAGQANVEGWTPSSNNANTGLGNHGACCAELD
SEQ ID NO:73        HLPCGLNGALYFVTMDADGGVSKYPNNKAGAQYGVGYCDSQCPRDLKFIAGQANVEGWTPSSNNANTGLGNHGACCAELD
SEQ ID NO:75        HLPCGLNGALYFVTMDADGGVSKYPNNKAGAQYGVGYCDSQCPRDLKFIAGQANVEGWTPSSNNANTGLGNHGACCAELD
SEQ ID NO:77        HLPCGLNGALYFVTMDADGGVSKYPNNKAGAQYGVGYCDSQCPRDLKFIAGQANVEGWTPSSNNANTGLGNHGACCAELD
SEQ ID NO:79        HLPCGLNGALYFVTMDADGGVSKYPNNKAGAQYGVGYCDSQCPRDLKFIAGQANVEGWTPSSNNANTGLGNHGACCAELD
SEQ ID NO:81        HLPCGLNGALYFVTMDADGGVSKYPNNKAGAQYGVGYCDSQCPRDLKFIAGQANVEGWTPSSNNANTGLGNHGACCAELD
SEQ ID NO:83        HLPCGLNGALYFVTMDADGGVSKYPNNKAGAQYGVGYCDSQCPRDLKFIAGQANVEGWTPSSNNANTGLGNHGACCAELD
SEQ ID NO:85        HLPCGLNGALYFVTMDADGGVSKYPNNKAGAQYGVGYCDSQCPRDLKFIAGQANVEGWTPSSNNANTGLGNHGACCAELD
SEQ ID NO:87        HLPCGLNGALYFVTMDADGGVSKYPNNKAGAQYGVGYCDSQCPRDLKFIAGQANVEGWTPSSNNANTGLGNHGACCAELD
SEQ ID NO:89        HLPCGLNGALYFVTMDADGGVSKYPNNKAGAQYGVGYCDSQCPRDLKFIAGQANVEGWTPSSNVNTGLGNHGACCAELD
SEQ ID NO:91        HLPCGLNGALYFVTMDADGGVSKYPNNKAGAQYGVGYCDSQCPRDLKFIAGQANVEGWTPSSNNANTGLGNHGACCAELD
SEQ ID NO:93        HLPCGLNGALYFVTMDADGGVSKYPNNKAGAQYGVGYCDSQCPRDLKFIAGQANVEGWTPSSNNANTGLGNHGACCAELD
SEQ ID NO:95        HLPCGLNGALYFVTMDADGGVSKYPNNKAGAQYGVGYCDSQCPRDLKFIAGQANVEGWTPSSNNANTGLGNHGACCAELD
SEQ ID NO:97        HLPCGLNGALYFVTMDADGGVSKYPNNKAGAQYGVGYCDSQCPRDLKFIAGQANVEGWTPSSNNANTGLGNHGACCAELD
SEQ ID NO:99        HLPCGLNGALYFVTMDADGGVSKYPNNKAGAQYGVGYCDSQCPRDLKFIAGQANVEGWTPSSNNANTGLGNHGACCAELD
SEQ ID NO:101       HLPCGLNGALYFVTMDADGGVSKYPNNKAGAQYGVGYCDSQCPRDLKFIAGQANVEGWTPSSNNANTGLGNHGACCAELD
SEQ ID NO:103       HLPCGLNGALYFVTMDADGGVSKYPNNKAGAQYGVGYCDSQCPRDLKFIAGQANVEGWTPSSNNANTGLGNHGACCAELD
SEQ ID NO:105       HLPCGLNGALYFVTMDADGGVSKYPNNKAGAQYGVGYCDSQCPRDLKFIAGQANVEGWTPSSNNANTGLGNHGACCAELD
SEQ ID NO:107       HLPCGLNGALYFVTMDADGGVSKYPNNKAGAQYGVGYCDSQCPRDLKFIAGQANVEGWTPSSNNANTGLGNHGACCAELD
SEQ ID NO:109       HLPCGLNGALYFVTMDADGGVSKYPNNKAGAQYGVGYCDSQCPRDLKFIAGQANVEGWTPSSNNANTGLGNHGACCAELD
SEQ ID NO:111       HLPCGLNGALYFVTMDADGGVSKYPNNKAGAQYGVGYCDSQCPRDLKFIAGQANVEGWTPSSNNANTGLGNHGACCAELD
SEQ ID NO:113       HLPCGLNGALYFVTMDADGGVSKYPNNKAGAQYGVGYCDSQCPRDLKFIAGQANVEGWTPSSNNANTGLGNHGACCAELD
SEQ ID NO:115       HLPCGLNGALYFVTMDADGGVSKYPNNKAGAQYGVGYCDSQCPRDLKFIAGQANVEGWTPSSNNANTGLGNHGACCAELD
SEQ ID NO:117       HLPCGLNGALYFVTMDADGGVSKYPNNKAGAQYGVGYCDSQCPRDLKFIAGQANVEGWTPSSNNANTGLGNHGACCAELD
```

```
SEQ ID NO:119    HLPCGLNGALYFVTMDADGGVSKYPNNKAGAQYGVGYCDSQCPRDLKFIAGQANVEGWTPSSNNANTGLGNHGACCAELD
SEQ ID NO:121    HLGCGLNGALYFVTMDADGGVSKYPNNKAGAQYGVGYCDSQCPRDLKFIAGQANVEGWTPKSNNAHTGYGNHGACCAELD
SEQ ID NO:123    HLPCGLNGALYFVTMDADGGVSKYPNNKAGAQYGVGYCDSQCPRDLKFIAGQANVEGWTPSSNNAHTGYGNHGACCAELD
SEQ ID NO:125    HLPCGLNGALYFVTMDADGGVSKYPNNKAGAQYGVGYCDSQCPRDLKFIAGQANVEGWTPSSNNANTGYGNHGACCAELD
SEQ ID NO:127    HLPCGLNGALYFVTMDADGGVSKYPNNKAGAQYGVGYCDSQCPRDLKFIAGQANVEGWTPSSNNANTGLGNHGACCAELD
SEQ ID NO:129    HLGCGLNGALYFVTMDADGGVSKYPNNKAGAQYGVGYCDSQCPRDLKFIAGQANVEGWTPKSNNAHTGYGNHGACCAELD
SEQ ID NO:131    HLPCGLNGALYFVTMDADGGVSKYPNNKAGAQYGVGYCDSQCPRDLKFIAGQANVEGWTPSSNNANTGLGNHGACCAELD
SEQ ID NO:133    HLPCGLNGALYFVTMDADGGVSKYPNNKAGAQYGVGYCDSQCPRDLKFIAGQANVEGWTPSSNNANTGLGNHGACCAELD
SEQ ID NO:135    HLPCGLNGALYFVTMDADGGVSKYPNNKAGAQYGVGYCDSQCPRDLKFIAGQANVEGWTPSSNNANTGLGNHGACCAELD
```

Figure 1I

```
                    250         260         270         280         290         300         310         320
                      |           |           |           |           |           |           |           |
Wild type   IWEANSISEALTPHPCDTPGLSVCTTDACGGTYSSDRYAGTCDPDGCDFNPYRLGVTDFYGSGKTVDTTKPITVVTQFVT
SEQ ID NO:1  IWEANSISEALTPHPCDTPGLSVCTTDACGGTYSSDRYAGTCDPDGCDFNPYRLGVTDFYGSGKTVDTTKPITVVTQFVT
SEQ ID NO:3  IWEANSISEALTPHPCDTPGLSVCTTDACGGTYSSDRYAGTCDPDGCDFNPYRLGVTDFYGSGKTVDTTKPITVVTQFVT
SEQ ID NO:5  IWEANSISEALTPHPCDTPGLSVCTTDACGGTYSSDRYAGTCDPDGCDFNPYRLGVTDFYGSGKTVDTTKPITVVTQFVT
SEQ ID NO:7  IWEANSISEALTPHPCDTPGLSVCTTDACGGTYSSDRYAGTCDPDGCDFNPYRLGVTDFYGSGKTVDTTKPITVVTQFVT
SEQ ID NO:9  IWEANSISEALTPHPCDTPGLSVCTTDACGGTYSSDRYAGTCDPDGCDFNPYRLGVTDFYGSGKTVDTTKPITVVTQFVT
SEQ ID NO:11 IWEANSISEALTPHPCDTPGLSVCTTDACGGTYSSDRYAGTCDPDGCDFNPYRLGVTDFYGSGKTVDTTKPITVVTQFVT
SEQ ID NO:13 IWEANSISEALTPHPCDTPGLSVCTTDACGGTYSSDRYAGTCDPDGCDFNPYRLGVTDFYGSGKTVDTTKPITVVTQFVT
SEQ ID NO:15 IWEANSISEALTPHPCDTPGLSVCTTDACGGTYSSDRYAGTCDPDGCDFNPYRLGVTDFYGSGKTVDTTKPITVVTQFVT
SEQ ID NO:17 IWEANSISEALTPHPCDTP͟ILSVCTTDACGGTYSSDRYAGTCDPDGCDFNPYRLGVTDFYGSGKTVDTTKPITVVTQFVT
SEQ ID NO:19 IWEANSISEALTPHPCDTPGLSVCTTDACGGTYSSDRYAGTCDPDGCDFNPYRLGVTDFYGSGKTVDTTKPITVVTQFVT
SEQ ID NO:21 IWEANSISEALTPHPCDTPGLSVCTTDACGGTYSSDRYAGTCDPDGCDFNPYRLGVTDFYGSGKTVDTTKPITVVTQFVT
SEQ ID NO:23 IWEANSISEALTPHPCDTPGLSVCTTDACGGTYSSDRYAGTCDPDGCDFNPYRLGVTDFYGSGKTVDTTKPITVVTQFVT
SEQ ID NO:25 IWEANSISEALTPHPCDTPGLSVCTTDACGGTYSSDRYAGTCDPDGCDFNPYRLGVTDFYGSGKTVDTTKPITVVTQFVT
SEQ ID NO:27 IWEANSISEALTPHPCDTPGLSVCTTDACGGTYSSDRYAGTCDPDGCDFNPYRLGVTDFYGSGKTVDTTKPITVVTQFVS͟
SEQ ID NO:29 IWEANSISEALTPHPCDTPGLSVCTTDACGGTYSSDRYAGTCDPDGCDFNPYRLGVTDFYGSGKTVDTTKPITVVTQFVT
SEQ ID NO:31 IWEANSISEALTPHPCDTPGLSVCTTDACGGTYSSDRYAGTCDPDGCDFNPYRLGVTDFYGSGKTVDTTKPITVVTQFVT
SEQ ID NO:33 IWEANSISEALTPHPCDTPGLSVCTTDACGGTYSSDRYAGTCDPDGCDFNPYRLGVTDFYGSGKTVDTTKPITVVTQFVT
SEQ ID NO:35 IWEANSISEALTPHPCDTPGLSVCTTDACGGTYSSDRYAGTCDPDGCDFNPYRLGVTDFYGSGKTVDTTKPITVVTQFVT
SEQ ID NO:37 IWEANSISEALTPHPCDTPGLSVCTTDACGGTYSSDRYAGTCDPDGCDFNPYRLGVTDFYGSGKTVDTTKPITVVTQFVT
SEQ ID NO:39 IWEANSISEALTPHPCDTPGLSVCTTDACGGTYSSDRYAGTCDPDGCDFNPYRLGVA͟DFYGSGKTVDTTKPITVVTQFVT
SEQ ID NO:41 IWEANSISEALTPHPCDTPGLSVCTTDACGGTYSSDRYAGTCDPDGCDFNPYRLGVTDFYGSGKTVDTTKPITVVTQFVT
SEQ ID NO:43 IWEANSISEALTPHPCDTPGLSVCTTDACGGTYSSDRYAGTCDPDGCDFNPYRLGVTDFYGSGKTVDTTKPITVVTQFVT
SEQ ID NO:45 IWEANSISEALTPHPCDTPGLSVCTTDACGGTYSSDRYAGTCDPDGCDFNPYRLGVTDFYGSGKTVDTTKPITVVTQFVT
SEQ ID NO:47 IWEANSISEALTPHPCDTPGLSVCTTDACGGTYSSDRYAGTCDPDGCDFNPYRLGVTDFYGSGKTVDTTKPITVVTQFVT
SEQ ID NO:49 IWEANSISEALTPHPCDTPGLSVCTTDACGGTYSSDRYAGTCDPDGCDFNPYRLGVTDFYGSGKTVDTTKPITVVTQFVT
SEQ ID NO:51 IWEANSISEALTPHPCDTPGLSVCTTDACGGTYSSDRYAGTCDPDGCDFNPYRLGVTDFYGSGKTVDTTKPITVVTQFVT
SEQ ID NO:53 IWEANSISEALTPHPCDTPGLSVCTTDACGGTYSSDRYAGTCDPDGCDFNPYRLGVTDFYGSGKTVDTTKPITVVTQFVT
SEQ ID NO:55 IWEANSISEALTPHPCDTPGLSVCTTDACGGTYSSDRYAGTCDPDGCDFNPYRLGVTDFYGSGKTVDTTKPITVVTQFVT
SEQ ID NO:57 IWEANSISEALTPHPCDTPGLSVCTTDACGGTYSSDRYAGTCDPDGCDFNPYRLGVTDFYGSGKTVDTTKPITVVTQFVT
```

Figure 1J

```
                         250        260        270        280        290        300        310        320
                    ....|....|....|....|....|....|....|....|....|....|....|....|....|....|....|....|
SEQ ID NO:59        IWEANSISEALTPHPCDTPGLSVCTTDACGGTYSSDRYAGTCDPDGCDFNPYRLGVTDFYGSGKTVDTTKPITVVTQFVT
SEQ ID NO:61        IWEANSISEALTPHPCDTPGLSVCTTDACGGTYSSDRYAGTCDPDGCDFNPYRLGVTDFYGSGKTVDTTKPITVVTQFVT
SEQ ID NO:63        IWEANSISEALTPHPCDTPGLSVCTTDACGGTYSSDRYAGTCDPDGCDFNPYRLGVTDFYGSGKTVDTTKPITVVTQFVT
SEQ ID NO:65        IWEANSISEALTPHPCDTPGLSVCTTDACGGTYSSDRYAGTCDPDGCDFNPYRLGVTDFYGSGKTVDTTKPITVVTQFVT
SEQ ID NO:67        IWEANSISEALTPHPCDTPGLSVCTTDACGGTYSSDRYAGTCDPDGCDFNPYRLGVTDFYGSGKTVDTTKPITVVTQFVT
SEQ ID NO:69        IWEANSISEALTPHPCDTPGLSVCTTDACGGTYSSDRYAGTCDPDGCDFNPYRLGVTDFYGSGKTVDTTKPITVVTQFVT
SEQ ID NO:71        IWEANSISEALTPHPCDTPGLSVCTTDACGGTYSSDRYAGTCDPDGCDFNPYRLGVTDFYGSGKTVDTTKPITVVTQFVT
SEQ ID NO:73        IWEANSISEALTPHPCDTPGLSVCTTDACGGVYSSDRYAGTCDPDGCDFNPYRLGVTDFYGSGKTVDTTKPITVVTQFVT
SEQ ID NO:75        IWEANSISEALTPHPCDTPGLSVCTTDACGGTYSSDRYAGTCDPDGCDFNPYRLGVTDFYGSGKTVDTTKPITVVTQFVT
SEQ ID NO:77        IWEANSISEALTPHPCDTPGLSVCTTDACGGTYSSDRYAGTCDPDGCDFNPYRLGVTDFYGSGKTVDTTKPITVVTQFVT
SEQ ID NO:79        IWEANSISEALTPHPCDTPGLSVCTTDACGGTYSSDRYAGTCDPDGCDFNPYRLGVTDFYGSGKTVDTTKPITVVTQFVT
SEQ ID NO:81        IWEANSISEALTPHPCDTPGLSVCTTDACGGTYSSDRYAGTCDPDGCDFNPYRLGVTDFYGSGKTVDTTKPITVVTQFVT
SEQ ID NO:83        IWEANSISEALTPHPCDTPGLSVCTTDACGGTYSSDRYAGTCDPDGCDFNPYRLGVTDFYGSGKTVDTTKPITVVTQFVT
SEQ ID NO:85        IWEANSISEALTPHPCDTPGLSVCTTDACGGTYSSDRYAGTCDPDGCDFNPYRLGVTDFYGSGKTVDTTKPITVVTQFVT
SEQ ID NO:87        IWEANSISEALTPHPCDTPGLSVCTTDACGGTYSSDRYAGTCDPDGCDFNPYRLGVTDFYGSGKTVDTTKPITVVTQFVT
SEQ ID NO:89        IWEANSISEALTPHPCDTPGLSVCTTDACGGTYSSDRYAGTCDPDGCDFNPYRLGVTDFYGSGKTVDTTKPITVVTQFVT
SEQ ID NO:91        IWEANSISEALTPHPCDTPGLSVCTTDACGGTYSSDRYAGTCDPDGCDFNPYRLGVTDFYGSGKTVDTTKPITVVTQFVT
SEQ ID NO:93        IWEANSISEALTPHPCDTPGLSVCTTDACGGTYSSDRYAGTCDPDGCDFNPYRLGVTDFYGSGKTVDTTKPITVVTQFVT
SEQ ID NO:95        IWEANSISEALTPHPCDTPGLSVCTTDACGGTYSSDRYAGTCDPDGCDFNPYRLGVTDFYGSGKTVDTTKPITVVTQFVT
SEQ ID NO:97        IWEANSISEALTPHPCDTPGLSVCTTDACGGTYSSDRYAGTCDPDGCDFNPYRLGVTDFYGSGKTVDTTKPITVVTQFVT
SEQ ID NO:99        IWEANSISEALTPHPCDTPGLSVCTTDACGGTYSSDRYAGTCDPDGCDFNPYRLGVTDFYGSGKTVDTTKPITVVTQFVT
SEQ ID NO:101       IWEANSISEALTPHPCDTPGLSVCTTDACGGTYSSDRYAGTCDPDGCDFNPYRLGVTDFYGSGKTVDTTKPITVVTQFVT
SEQ ID NO:103       IWEANSISEALTPHPCDTPGLSVCTTDACGGTYSSDRYAGTCDPDGCDFNPYRLGVTDFYGSGKTVDTTKPITVVTQFVT
SEQ ID NO:105       IWEANSISEALTPHPCDTPGLSVCTTDACGGTYSSDRYAGTCDPDGCDFNPYRLGVTDFYGSGKTVDTTKPITVVTQFVT
SEQ ID NO:107       IWEANSISEALTPHPCDTPGLSVCTTDACGGTYSSDRYAGTCDPDGCDFNPYRLGVTDFYGSGKTVDTTKPITVVTQFVT
SEQ ID NO:109       IWEANSISEALTPHPCDTPGLSVCTTDACGGTYSSDRYAGTCDPDGCDFNPYRLGVTDFYGSGKTVDTTKPITVVTQFVT
SEQ ID NO:111       IWEANSISEALTPHPCDTPGLSVCTTDACGGTYSSDRYAGTCDPDGCDFNPYRLGVTDFYGSGKTVDTTKPITVVTQFVT
SEQ ID NO:113       IWEANSISEALTPHPCDTPGLSVCTTDACGGTYSSDRYAGTCDPDGCDFNPYRLGVTDFYGSGKTVDTTKPITVVTQFVT
SEQ ID NO:115       IWEANSISEALTPHPCDTPGLSVCTTDACGGTYSSDRYAGTCDPDGCDFNPYRLGVTDFYGSGKTVDTTKPITVVTQFVT
SEQ ID NO:117       IWEANSISEALTPHPCDTPGLSVCTTDACGGTYSSDRYAGTCDPDGCDFNPYRLGVTDFYGSGKTVDTTKPITVVTQFVT
```

Figure 1K

Figure 1L

```
              250        260        270        280        290        300        310        320
              ....|....|....|....|....|....|....|....|....|....|....|....|....|....|....|....|
SEQ ID NO:119 IWEANSISEALTPHPCDTPGLSVCTTDACGGTYSSDRYAGTCDPDGCDFNPYRLGVTDFYGSGKTVDTTKPITVVTQFVT
SEQ ID NO:121 IWEANSISEALTPHPCDTPGLSVCTTDACGGTYSSDRYAGTCDPDGCDFNPYRLGVTDFYGSGKTVDTTKPITVVTQFVT
SEQ ID NO:123 IWEANSISEALTPHPCDTPGLSVCTTDACGGTYSSDRYAGTCDPDGCDFNPYRLGVTDFYGSGKTVDTTKPITVVTQFVT
SEQ ID NO:125 IWEANSISEALTPHPCDTPGLSVCTTDACGGTYSSDRYAGTCDPDGCDFNPYRLGVTDFYGSGKTVDTTKPITVVTQFVT
SEQ ID NO:127 IWEANSISEALTPHPCDTPGLSVCTTDACGGTYSSDRYAGTCDPDGCDFNPYRLGVTDFYGSGKTVDTTKPITVVTQFVT
SEQ ID NO:129 IWEANSISEALTPHPCDTPGLSVCTTDACGGTYSSDRYAGTCDPDGCDFNPYRLGVTDFYGSGKTVDTTKPITVVTQFVT
SEQ ID NO:131 IWEANSISEALTPHPCDTPGLSVCTTDACGGTYSSDRYAGTCDPDGCDFNPYRLGVTDFYGSGKTVDTTKPITVVTQFVT
SEQ ID NO:133 IWEANSISEALTPHPCDTPGLSVCTTDACGGTYSSDRYAGTCDPDGCDFNPYRLGVTDFYGSGKTVDTTKPITVVTQFVT
SEQ ID NO:135 IWEANSISEALTPHPCDTPGLSVCTTDACGGTYSSDKYAGTCDPDGCDFNPYRLGVTDFYGSGKTVDTTKPITVVTQFVT
```

```
                   330        340        350        360        370        380        390        400
                   ....|....|....|....|....|....|....|....|....|....|....|....|....|....|....|....|
Wild type          DDGTSTGTLSEIRRYYVQNGVVIPQPSSKISGVSGNVINSDFCDAEISTFGETASFSKHGGLAKMGAGMEAGMVLVMSLW
SEQ ID NO:1        DDGTSTGTLSEIRRYYVQNGVVIPQPSSKISGVSGNVINSDFCDAEISTFGETASFSKHGGLAKMGAGMEAGMVLVMSLW
SEQ ID NO:3        DDGTSTGTLSEIRRYYVQNGVVIPQPSSKISGVSGNVINSDFCDAEISTFGETASFSKHGGLAKMGAGMEAGMVLVMSLW
SEQ ID NO:5        DDGTSTGTLSEIRRYYVQNGVVIPQPSSKISGVSGNVINSDFCDAEISTFGETASFSKHGGLAKMGAGMEAGMVLVMSLW
SEQ ID NO:7        DDGTSTGTLSEIRRYYVQNGVVIPQPSSKISGVSGNVINSDFCDAEISTFGETASFSKHGGLAKMGAGMEAGMVLVMSLW
SEQ ID NO:9        DDGTSTGTLSEIRRYYVQNGVVIPQPSSKISGVSGNVINSDFCDAEISTFGETASFSKHGGLAKMGAGMEAGMVLVMSLW
SEQ ID NO:11       DDGTSTGTLSEIRRYYVQNGVVIPQPSSKISGVSGNVINSDFCDAEISTFGETASFSKHGGLAKMGAGMEAGMVLVMSLW
SEQ ID NO:13       DDGTSTGTLSEIRRYYVQNGVVIPQPSSKISGVSGNVINSDFCDAEISTFGETASFSKHGGLAKMGAGMEAGMVLVMSLW
SEQ ID NO:15       DDGTSTGTLSEIRRYYVQNGVVIPQPSSKISGVSGNVINSDFCDAEISTFGETASFSKHGGLAKMGAGMEAGMVLVMSLW
SEQ ID NO:17       DDGTSTGTLSEIRRYYVQNGVVIPQPSSKISGVSGNVINSDFCDAEISTFGETASFSKHGGLAKMGAGMEAGMVLVMSLW
SEQ ID NO:19       DDGTSTGTLSEIRRYYVQNGVVIPQPSSKISGVSGNVINSDFCDAEISTFGETASFSKHGGLAKMGAGMEAGMVLVMSLW
SEQ ID NO:21       DDGTSTGTLSEIRRYYVQNGVVIPQPSSKISGVSGNVINSDFCDAEISTFGETASFSKHGGLAKMGAGMEAGMVLVMSLW
SEQ ID NO:23       DDGTSTGTLSEIRRYYVQNGVVIPQPSSKISGVSGNVINSDFCDAEISTFGETASFSKHGGLAKMGAGMEAGMVLVMSLW
SEQ ID NO:25       DDGTSTGTLSEIRRYYVQNGVVIPQPSSKISGVSGNVINSDFCDAEISTFGETASFSKHGGLAKMGAGMEAGMVLVMSLW
SEQ ID NO:27       DDGTSTGTLSEIRRYYVQNGVVIPQPSSKISGVSGNVINSDFCDAEISTFGETASFSKHGGLAKMGAGMEAGMVLVMSLW
SEQ ID NO:29       DDGTSSGTLSEIRRYYVQNGVVIPQPSSKISGVSGNVINSDFCDAEISTFGETASFSKHGGLAKMGAGMEAGMVLVMSLW
SEQ ID NO:31       DQGTSTGTLSEIRRYYVQNGVVIPQPSSKISGVSGNVINSDFCDAEVSTFGETASFSKHGGLAKMGAGMEAGMVLVMSLW
SEQ ID NO:33       DDGTSTGTGRLSEIRRYYVQNGVVIPQPSSKISGVSGNVINSDFCDAEISTFGETASFSKHGGLAKMGAGMEAGMVLVMSLW
SEQ ID NO:35       DDGTSTGTLLEIRRYYVQNGVVIPQPSSKISGVSGNVINSDLCDAEISTFGETASFSKHGGLAKMGAGMEAGMVLVMSLW
SEQ ID NO:37       DDGTSTGTLSEIRRYYVQNGVVIPQPSSKISGVSGNVINSDFCDAEISTFGETISFSKHGGLAKMGAGMEAGMVLVMSLW
SEQ ID NO:39       DDGTSTGTLSEIRRYYVQNGVVIPQPSSDISGVSGNVINSDFCDAEISTFGETASFSKHGGLAKMGAGMEAGMVLVMSLW
SEQ ID NO:41       DDGTSTGTLSEIRRYYVQNGVVIPQPSSKISGVCGNVINSDFCDAEISTFGETASFSKHRGLAKMGAGMEAGMVLVMSLW
SEQ ID NO:43       DDGTSTGTLSEIRRYYVQNGVVIPQPSSKISGVSGDNVINSDFCDAEISTFGETASFSKHGGLAKMGAGMEAGMVLVMSLW
SEQ ID NO:45       DDGTSTGTLSEIRRYYVQNGVVIPQPSSKISGVSGNVINSDFCDAEISTFGETASFSKHGGLAKMGAGMSAGMEAGMVLVMSLW
SEQ ID NO:47       DDGTSTGTLSEIRRYYVQNGVVIPQPSSKISGVSGNVINSDFCDAEISTFGETASFSKHGGLAKMGAGMEAGMVLVMSLW
SEQ ID NO:49       DDGTSTGTLSEIRRYYVQNGVVIPQPSSKISGVSGNVINSDFCDAEISTFGETASFSKHGGLAKMGAGMEAGMVLVMSLW
SEQ ID NO:51       DDGTSTGTLSEIRRYYVQNGVVIPQPSSKISGVSGNVINSDFCDAEISTFGETASFSKHGGLAKMGAGMEAGMVLVMSLW
SEQ ID NO:53       DDGTSTGTLSEIRRYYVQNGVVIPQPSSKISGVSGNVINSDFCDAEISTFGETASFSKHGGLAKMGAGMEAGMVLVMSLW
SEQ ID NO:55       DDGTSTGTLSEIRRYYVQNGVVIPQPSSKISGVSGNVINSDFCDAEISTFGETASFSKHGGLAKMGAGMEAGMVLVMSLW
SEQ ID NO:57       DDGTSTGTLSEIRRYYVQNGVVIPQPSSKISGVSGNVINSDFCDAEISTFGETASFSKHGGLAKMGAGMEAGMVLVMSLW
```

Figure 1M

| SEQ ID NO:59  | DDGTSTGTLSEIRRYYVQNGVVIPQPSSKISGVSGNVINSDFCDAEISTFGETASFSKHGGLAKMGAGMEAGMVLVMSLW |
| SEQ ID NO:61  | DDGTSTGTLSEIRRYYVQNGVVIPQPSSKISGVSGNVINSDFCDAEISTFGETASFSKHGGLAKMGAGMEAGMVLVMSLW |
| SEQ ID NO:63  | DDGTSTGTLSEIRRYYVQNGVVIPQPSSKISGVSGNVINSDFCDAEISTFGETASFSKHGGLAKMGAGMEAGMVLVMSLW |
| SEQ ID NO:65  | DDGTSTGTLSEIRRYYVQNGVVIPQPSSKISGVSGNVINSDFCDAEISTFGETASFSKHGGLAKMGAGMEAGMVLVMSLW |
| SEQ ID NO:67  | DDGTSTGTLSEIRRYYVQNGVVIPQPSSKISGVSGNVINSDFCDAEISTFGETASFSKHGGLAKMGAGMEAGMVLVMSLW |
| SEQ ID NO:69  | DDGTSTGTLSEIRRYYVQNGVVIPQPSSKISGVSGNVINSDFCDAEISTFGETASFSKHGGLAKMGAGMEAGMVLVMSLW |
| SEQ ID NO:71  | DDGTSTGTLSEIRRYYVQNGVVIPQPSSKISGVSGNVINSDFCDAEISTFGETASFSKHGGLAKMGAGMEAGMVLVMSLW |
| SEQ ID NO:73  | DDGTSTGTLSEIRRYYVQNGVVIPQPSSKISGVSGNVINSDFCDAEISTFGETASFSKHGGLAKMGAGMEAGMVLVMSLW |
| SEQ ID NO:75  | DDGTSTGTLSEIRRYYVQNGVVIPQPSSKISGVSGNVINSDFCDAEISTFGETASFSKHGGLAKMGAGMEAGMVLTMSLW |
| SEQ ID NO:77  | DDGTSTGTLSEIRRYYVQNGVVIPQPSSKISGVSGNVINSDFCDAEISTFGETASFSKHGGLAKMGAGMEAGMVLVMSLW |
| SEQ ID NO:79  | DDGTSTGTLSEIRRYYVQNGVVIPQPSSKISGVSGNVINSDFCDAEISTFGETASFSKHGGLAKMGAGMEAGMVLVMSLW |
| SEQ ID NO:81  | DDGTSTGTLSEIRRYYVQNGVVIPQPSSKISGVSGNVINSDFCDAEISTFGETASFSKHGGLAKMGAGMEAGMVLAMSLW |
| SEQ ID NO:83  | DDGTSTGTLSEIRRYYVQNGVVIPQPSSKISGVSGNVINSDFCDAEISTFGETASFSKHGGLAKMGAGMEAGMVLVMSLW |
| SEQ ID NO:85  | DDGTSTGTLSEIRRYYVQNGVVIPQPSSKISGVSGNVINSDFCDAEISTFGETASFSKHGGLAKMGAGMEAGMVLVMSLW |
| SEQ ID NO:87  | DDGTSTGTLSEIRRYYVQNGVVIPQPSSKISGVSGNVINSDFCDAEISTFGETASFSKHGGLAKMGAGMEAGMVLVMSLW |
| SEQ ID NO:89  | DDGTSTGTLSEIRRYYVQNGVVIPQPSSKISGVSGNVINSDFCDAEISTFGETASFSKHGGLAKMGAGMEAGMVLVMSLW |
| SEQ ID NO:91  | DDGTSTGTLSEIRRYYVQNGVVIPQPSSKISGVSGNVINSDFCDAEISTFGETASFSKHGGLAKMGAGMEAGMVLVMSLW |
| SEQ ID NO:93  | DDGTSTGTLSEIRRYYVQNGVVIPQPSSKISGVSGNVINSDFCDAEISTFGETASFSKHGGLAKMGAGMEAGMVLVMSLW |
| SEQ ID NO:95  | DDGTSTGTLSEIRRYYVQNGVVIPQPSSKISGVSGNVINSDFCDAEISTFGETASFSKHGGLAKMGAGMEAGMVLVMSLW |
| SEQ ID NO:97  | DDGTSTGTLSEIRRYYVQNGVVIPQPSSKISGVSGNVINSDFCDAEISTFGETASFSKHGGLAKMGAGMEAGMVLVMSLW |
| SEQ ID NO:99  | DDGTSTGTLSEIRRYYVQNGVVIPQPSSKISGVSGNVINSDFCDAEISTFGETASFSKHGGLAKMGAGMEAGMVLVMSLW |
| SEQ ID NO:101 | DDGTSTGTLSEIRRYYVQNGVVIPQPSSKISGVSGNVINSDFCDAEISTFGETASFSKHGGLAKMGAGMEAGMVLVMSLW |
| SEQ ID NO:103 | DDGTSTGTLSEIRRYYVQNGVVIPQPSSKISGVSGNVINSDFCDAEISTFGETASFSKHGGLAKMGAGMEAGMVLVMSLW |
| SEQ ID NO:105 | DDGTSTGTLSEIRRYYVQNGVVIPQPSSKISGVSGNVINSDFCDAEISTFGETASFSKHGGLAKMGAGMEAGMVLVMSLW |
| SEQ ID NO:107 | DDGTSTGTLSEIRRYYVQNGVVIPQPSSKISGVSGNVINSDFCDAEISTFGETASFSKHGGLAKMGAGMEAGMVLVMSLW |
| SEQ ID NO:109 | DDGTSTGTLSEIRRYYVQNGVVIPQPSSKISGVSGNVINSDFCDAEISTFGETASFSKHGGLAKMGAGMEAGMVLVMSLW |
| SEQ ID NO:111 | DDGTSTGTLSEIRRYYVQNGVVIPQPSSKISGVSGNVINSDFCDAEISTFGETASFSKHGGLAKMGAGMEAGMVLVMSLW |
| SEQ ID NO:113 | DDGTSTGTLSEIRRYYVQNGVVIPQPSSKISGVSGNVINSDFCDAEISTFGETASFSKHGGLAKMGAGMEAGMVLVMSLW |
| SEQ ID NO:115 | DDGTSTGTLSEIRRYYVQNGVVIPQPSSKISGVSGNVINSDFCDAEISTFGETASFSKHGGLAKMGAGMEAGMVLVMSLW |
| SEQ ID NO:117 | DDGTSTGTLSEIRRYYVQNGVVIPQPSSKISGVSGNVINSDFCDAEISTFGETASFSKHGGLAKMGAGMEAGMVLVMSLW |

Figure 1N

```
                       330        340        350        360        370        380        390        400
                       ....|....|....|....|....|....|....|....|....|....|....|....|....|....|....|....|
SEQ ID NO:119   DDGTSTGTLSEIRRYYVQNGVVIPQPSSKISGVSGNVINSDFCDAEISTFGETASFSKHGGLAKMGAGMEAGMVLVMSLW
SEQ ID NO:121   DDGTSTGTLSEIRRYYVQNGVVIPQPSSDISGVSGVVINSDFCDAEISTFGETASFSKHGGLAKMGAGMEAGMVLVMSLW
SEQ ID NO:123   DDGTSTGTLSEIRRYYVQNGVVIPQPSSDISGVSGVVINSDFCDAEISTFGETASFSKHGGLAKMGAGMSAGMVLVMSLW
SEQ ID NO:125   DDGTSTGTLLEIRRYYVQNGVVIPQPSSDISGVSGVINSDFCDAEISTFGETASFSKHGGLAKMGAGMEAGMVLVMSLW
SEQ ID NO:127   DQGTSTGTLGRLLEIRRYYVQNGVVIPQPSSDISGVSGVINSDFCDAEISTFGETASFSKHGGLAKMGAGMSAGMVLVMSLW
SEQ ID NO:129   DDGTSTGTLSEIRRYYVSNGVVIPQPSSDISGVSGNVINSDFCDAEISTFGETASFSKHGGLAKMGAGMSAGMVLVMSLW
SEQ ID NO:131   DDGTSTGTLSEIRRYYVQNGVVIPQPSSKISGVSGNVINSDFCDAEISTFGETASFSKHGGLAKMGAGMSAGMVLVMSLW
SEQ ID NO:133   DDGTSTGTLSEIRRYYVQNGVVIPQPSSKISGVSGNVINSDFCDAEISTFGETASFSKHGGLAKMGAGMEAGMVLVMSLW
SEQ ID NO:135   DDGTSTGTLSEIRRYYVQNGVVIPQPSSKISGVSGNVINSDFCDAEISTFGETASFSKHGGLAKMGAGMEAGMVLVMSLW
```

Figure 10

| | 410 | 420 | 430 | 440 | 450 | 460 | 470 | 480 |
|---|---|---|---|---|---|---|---|---|
Wild type | ........... | .......... | .......... | .......... | .......... | .......... | .......... | .......... |
SEQ ID NO:1 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:3 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:5 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:7 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:9 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:11 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:13 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:15 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:17 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:19 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:21 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:23 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:25 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:27 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:29 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:31 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:33 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:35 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:37 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:39 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:41 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:43 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:45 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:47 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:49 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:51 | DDYSVNMLWLDSTYPTNATGTPGAARGSCPTTSGDPKTVESQSGSSSYVTFSDIRWGPFNSTFSGGSSTGGSSTTTASGTT |
SEQ ID NO:53 | DDYSVNMLWLDSTYPTNATGTPGAARGSCPTTSGDPKTVESQSGSSSYVTFSDIRVGPFGSTFSGGSSTGGSSTTTASGTT |
SEQ ID NO:55 | DDYSVNMLWLDSTYPTNATGTPGAARGSCPTTSGDPKTVESQSGSSSYVTFSDIRVGPFNSTFSGGSSTGGSSTTTASGTT |
SEQ ID NO:57 | DDYSVNMLWLDSTYPTNATGTPGAARGSCPTTSGDPKTVESQSGSSSYVTFSDIRVGPFNSTFSGGSKTGGSSTTTASGTT |

Figure 1P

| | | 410 | 420 | 430 | 440 | 450 | 460 | 470 | 480 |
|---|---|---|---|---|---|---|---|---|---|
| SEQ ID NO:59 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:61 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:63 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:65 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:67 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:69 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:71 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:73 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:75 | | DDYSANMLWLDSTYPTNATGTPGAARGSCPTTSGDPKTVESQSGSSYVTFSDIRVGPFNSTFSGGSSTGGSSTTTASGTT | | | | | | | |
| SEQ ID NO:77 | | DDDSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:79 | | DDYSDNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:81 | | DDYSANMLWLDSTYPTNATGAPGAARGSCPTTSGDPKTVESQSGSSYVTFSDIRVGPFNSTFSGGSSTGGSSTTTASGTT | | | | | | | |
| SEQ ID NO:83 | | DDYSVNMTWLDSTYPTNATGTPGAARGSCPTTSGDPKTVESQSGSSYVTFSDIRVGPFNSTFSGGSSTGGSSTTTASGTT | | | | | | | |
| SEQ ID NO:85 | | DDYSVNMLWLDSTYPTNATGTPGAARGSCPTTSGDPKTVESQSGSSYVTFSDIRVGPFNSTFSGGSYTGGSSTTTASGTT | | | | | | | |
| SEQ ID NO:87 | | DDYSANMLWLDSTYPTNATGTPGAARGSCPTTSGDPKTVESQSGSSYVTFSDIRVGPFNSTFSGGSSTGGSSTTTASWTT | | | | | | | |
| SEQ ID NO:89 | | DDYSVNMLWLDSTYPTNATGTPGAARGSCPTTSGDPKTVESQSGSSYVTFSDIRVGPFNSTFSGGSSTGGSSTTTMSGTT | | | | | | | |
| SEQ ID NO:91 | | DDYSANMLWLDSTYPTNATGTPGAARGSCPTTSGDPKTVESQSGSSYVTFSDIRVGPFNSTFSGGSSTGGSSTTTASGTT | | | | | | | |
| SEQ ID NO:93 | | DDYSANMLWLDSTYPTNATGTPGAARGSCPTTSGDPKTVESQSGSSYVTFSDIRVGPFNSTFSGGSSTGGSSTTTASGTT | | | | | | | |
| SEQ ID NO:95 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:97 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:99 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:101 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:103 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:105 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:107 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:109 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:111 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:113 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:115 | | DDYSVNMLWLDSTYPTNATGTPGAARGSCPTTSGDPKTVESQSGSSYVTFSDIRVGPFNSTFSGGSSTGGSSTTTASGTT | | | | | | | |
| SEQ ID NO:117 | | DDYSVNMLWLDSTYPTNATGTPGAARGSCPTTSGDPKTVESQSGSSYVTFSDIRVGPFNSTFSGGSSTGGSSTTTASGTT | | | | | | | |

Figure 1Q

| | | |
|---|---|---|
| SEQ ID NO:119 | DDYSVNMIWLDSTYPTNATGTPGAARGSCPTTSGDPKTVESQSGSSYVTFSDIRVGPFNSTFSGGSSTGGSSTTTASGTT |
| SEQ ID NO:121 | DDYSVNMIWLDSTYPTNATGTPGAARGSCPTTSGDPKTVESQSGSSYVTFSDIRVGPFNSTFSGGSSTGGSSTTTASGTT |
| SEQ ID NO:123 | DDYSVNMIWLDSTYPTNATGTPGAARGSCPTTSGDPKTVESQSGSSYVTFSDIRVGPFNSTFSGGSSTGGSSTTTASGTT |
| SEQ ID NO:125 | DDYSVNMIWLDSTYPTNATGTPGAARGSCPTTSGDPKTVESQSGSSYVTFSDIRWGPFNSTFSGGSSTGGSSTTTASGTT |
| SEQ ID NO:127 | DDYSVNMIWLDSTYPTNATGTPGAARGSCPTTSGDPKTVESQSGSSYVTFSDIRVGPFNSTFSGGSSTGGSSTTTASGTT |
| SEQ ID NO:129 | DDYSVNMIWLDSTYPTNATGTPGAARGSCPTTSGDPKTVESQSGSSYVTFSDIRWGPFNSTFSGGSSTGGSSTTTASGTT |
| SEQ ID NO:131 | DDYSVNMIWLDSTYPTNATGTPGAARGSCPTTSGDPKTVESQSGSSYVTFSDIRWGPFNSTFSGGSSTGGSSTTTASGTT |
| SEQ ID NO:133 | DDYSVNMIWLDSTYPTNATGTPGAARGSCPTTSGDPKTVESQSGSSYVTFSDIRVGPFNSTFSGGSSTGGSSTTTASGTT |
| SEQ ID NO:135 | DDYSVNMIWLDSTYPTNATGTPGAAKGSCPTTSGDPKTVESQSGSSYVTFSDIRVGPFNSTFSGGSSTGGSSTTTASGTT |

Figure 1R

```
                   490         500         510         520         530
                   ....|....|....|....|....|....|....|....|....|....|
Wild type          TTKASSTSTSSTSTSGTGTGVAAHWGQCGGQGWTGPTTCASGTTCTVVNPYYSQCL
SEQ ID NO:1        TTKASSTSTSSTSTSGTGTGVAAHWGQCGGQGWTGPTTCASGTTCTVVNPYYSQCL
SEQ ID NO:3        TTKASSTSTSSTSTSGTGTGVAAHWGQCGGQGWTGPTTCASGTTCTVVNPYYSQCL
SEQ ID NO:5        TTKASSTSTSSTSTSGTGTGVAAHWGQCGGQGWTGPTTCASGTTCTVVNPYYSQCL
SEQ ID NO:7        TTKASSTSTSSTSTSGTGTGVAAHWGQCGGQGWTGPTTCASGTTCTVVNPYYSQCL
SEQ ID NO:9        TTKASSTSTSSTSTSGTGTGVAAHWGQCGGQGWTGPTTCASGTTCTVVNPYYSQCL
SEQ ID NO:11       TTKASSTSTSSTSTSGTGTGVAASWGQCGGQGWTGPTTCASGTTCTVVNPYYSQCL
SEQ ID NO:13       TTKASSTSTSSTSTSGTGTGVAAHWGQCGGQGWTGPKTCASGTTCTVVNPYYSQCL
SEQ ID NO:15       TTKASSTSTSSTSTSGTGTGVAAHWGQCGGQGWTGPTTCASGTTCTVVNPYYSQCL
SEQ ID NO:17       TTKASSTSTSSTSTSGTGTGVAAHWGQCGGQGWTGPTTCASGTTCTVVNPYYSQCL
SEQ ID NO:19       TTKASSTSTSSTSTSGTGTGVAAHWGQCGGQGWTGPTTCASGTTCTVVNPYYSQCL
SEQ ID NO:21       TTKASSTSTSSTSTSGTGTGVAAHWGQCGGQGWTGPTTCASGTTCTVVNPYYSQCL
SEQ ID NO:23       TTKASSTSTSSTSTSGTGTGVAAHWGQCGGQGWTGPTTCASGTTCTVVNPYYSQCL
SEQ ID NO:25       TTKASSTSTSSTSTSGTGTGVAAHWGQCGGQGWTGPTTCASGTTCTVVNPYYSQCL
SEQ ID NO:27       TTKASSTSTSSTSTSGTGTGVAAHWGQCGGQGWTGPTTCASGTTCTVVNPYYSQCL
SEQ ID NO:29       TTKASSTSTSSTSTSGTGTGVAAHWGQCGGQGWTGPTTCASGTTCTVVNPYYSQCL
SEQ ID NO:31       TTKASSTSTSSTSTSGTGTGVAAHWGQCGGQGWTGPTTCASGTTCTVVNPYYSQCL
SEQ ID NO:33       TTKASSTSTSSTSTSGTGTGVAAHWGQCGGQGWTGPTTCASGTTCTVVNPYYSQCL
SEQ ID NO:35       TTKASSTSTSSTSTSGTGTGVAAHWGQCGGQGWTGPTTCASGTTCTVVNPYYSQCL
SEQ ID NO:37       TTKASSTSTSSTSTSGTGTGVAAHWGQCGGQGWTGPTTCASGTTCTVVNPYYSQCL
SEQ ID NO:39       TTKASSTSTSSTSTSGTGTGVAAHWGQCGGQGWTGPTTCASGTTCTVVNPYYSQCL
SEQ ID NO:41       TTKASSTSTSSTSTSGTGTGVAAHWGQCGGQGWTGPTTCASGTTCTVVNPYYSQCL
SEQ ID NO:43       TTKASSTSTSSTSTSGTGTGVAAHWGQCGGQGWTGPTTCASGTTCTVVNPYYSQCL
SEQ ID NO:45       TTKASSTSTSSTSTSGTGTGVAAHWGQCGGQGWTGPTTCASGTTCTVVNPYYSQCL
SEQ ID NO:47       TTKASSTSTSSTSTSGTGTGVAAHWGQCGGQGWTGPTTCASGTTCTVVNPYYSQCL
SEQ ID NO:49       TTKASSTSTSSTSTSGTGTGVAAHWGQCGGQGWTGPTTCASGTTCTVVNPYYSQCL
SEQ ID NO:51       TTKASSTSTSSTSTSGTGTGVAAHWGQCGGQGWTGPTTCASGTTCTVVNPYYSQCL
SEQ ID NO:53       TTKASSTSTSSTSTSGTGTGVAAHWGQCGGQGWTGPTTCASGTTCTVVNPYYSQCL
SEQ ID NO:55       TTKASSTSTSSTSTSGTGTGVAAHWGQCGGQGWTGPTTCASGTTCTVVNPYYSQCL
SEQ ID NO:57       TTKASSTSTSSTSTSGTGTGVAAHWGQCGGQGWTGPTTCASGTTCTVVNPYYSQCL
```

Figure 1S

|   | 490 | 500 | 510 | 520 | 530 |
|---|---|---|---|---|---|

```
                 ....|....|....|....|....|....|....|....|....|....|....
SEQ ID NO:59     TTTKASSTSTSSTSSTSTGVAAHWGQCGGQGWTGPTTCASGTTCTVVNPYYSQCL
SEQ ID NO:61     TTTKASSTSTSSTSSTSTGVAAHWGQCGGQGWTGPTTCASGTTCTVVNPYYSQCL
SEQ ID NO:63     TTTKASSTSTSSTSSTSTGVAAHWGQCGGQGWTGPTTCASGTTCTVVNPYYSQCL
SEQ ID NO:65     TTTKASSTSTSSTSSTSTGVAAHWGQCGGQGWTGPTTCASGTTCTVVNPYYSQCL
SEQ ID NO:67     TTTKASSTSTSSTSSTSTGVAAHWGQCGGQGWTGPTTCASGTTCTVVNPYYSQCL
SEQ ID NO:69     TTTKASSTSTSSTSSTSTGVAAHWGQCGGQGWTGPTTCASGTTCTVVNPYYSQCL
SEQ ID NO:71     TTTKASSTSTSSTSSTSTGVAAHWGQCGGQGWTGPTTCASGTTCTVVNPYYSQCL
SEQ ID NO:73     TTTKASSTSTSSTSSTSTGVAAHWGQCGGQGWTGPTTCASGTTCTVVNPYYSQCL
SEQ ID NO:75     TTTKASSTSTSSTSSTSTGVAAHWGQCGGQGWTGPTTCASGTTCTVVNPYYSQCL
SEQ ID NO:77     TTTKASSTSTSSTSSTSTGVAAHWGQCGGQGWTGPTTCASGTTCTVVNPYYSQCL
SEQ ID NO:79     TTTKASSTSTSSTSSTSTGVAAHWGQCGGQGWTGPTTCASGTTCTVVNPYYSQCL
SEQ ID NO:81     TTTKASSTSTSSTSSTSTGVAAHWGQCGGQGWTGPTTCASGTTCTVVNPYYSQCL
SEQ ID NO:83     TTTKASSTSTSSTSSTSTGVAAHWGQCGGQGWTGPTTCASGTTCTVVNPYYSQCL
SEQ ID NO:85     TTTKASSTSTSSTSSTSTGVAAHWGQCGGQGWTGPTTCASGTTCTVVNPYYSQCL
SEQ ID NO:87     TTTKASSTSTSSTSSTSTGVAAHWGQCGGQGWTGPTTCASGTTCTVVNPYYSQCL
SEQ ID NO:89     TTTKASSTSTSSTSSTSTGVAAHWGQCGGQGWTGPTTCASGTTCTVVNPYYSQCL
SEQ ID NO:91     TTTKASSTSTSSTSSTSTGVAAHWGQCGGQGWTGPTTCASGTTCTVVNPYYSQCL
SEQ ID NO:93     TTTKASSTSTSSTSSTSTGVAAHWGQCGGQGWTGPTTCASGTTCTVVNPYYSQCL
SEQ ID NO:95     TTTKASSTSTSSTSSTSTGVAAHWGQCGGQGWTGPTTCASGTTCTVVNPYYSQCL
SEQ ID NO:97     TTTKASSTSTSSTSSTSTGVAAHWGQCGGQGWTGPTTCASGTTCTVVNPYYSQCL
SEQ ID NO:99     TTTKASSTSTSSTSSTSTGVAAHWGQCGGQGWTGPTTCASGTTCTVVNPYYSQCL
SEQ ID NO:101    TTTKASSTSTSSTSSTSTGVAAHWGQCGGQGWTGPTTCASGTTCTVVNPYYSQCL
SEQ ID NO:103    TTTKASSTSTSSTSSTSTGVAAHWGQCGGQGWTGPTTCASGTTCTVVNPYYSQCL
SEQ ID NO:105    TTTKASSTSTSSTSSTSTGVAAHWGQCGGQGWTGPTTCASGTTCTVVNPYYSQCL
SEQ ID NO:107    TTTKASSTSTSSTSSTSTGVAAHWGQCGGQGWTGPTTCASGTTCTVVNPYYSQCL
SEQ ID NO:109    TTTKASSTSTSSTSSTSTGVAAHWGQCGGQGWTGPTTCASGTTCTVVNPYYSQCL
SEQ ID NO:111    TTTKASSTSTSSTSSTSTGVAAHWGQCGGQGWTGPTTCASGTTCTVVNPYYSQCL
SEQ ID NO:113    TTTKASSTSTSSTSSTSTGVAAHWGQCGGQGWTGPTTCASGTTCTVVNPYYSQCL
SEQ ID NO:115    TTTKASSTSTSSTSSTSTGVAAHWGQCGGQGWTGPTTCASGTTCTVVNPYYSQCL
SEQ ID NO:117    TTTKASSTSTSSTSSTSTGVAAHWGQCGGQGWTGPTTCASGTTCTVVNPYYSQCL
```

Figure 1T

| | |
|---|---|
| SEQ ID NO:119 | TTKASSTSTSSTSTGTGVAAHWGQCGGQGWTGPTTCASGTTCTVVNPYYSQCL |
| SEQ ID NO:121 | TTKASSTSTSSTSTGTGVAAHWGQCGGQGWTGPTTCASGTTCTVVNPYYSQCL |
| SEQ ID NO:123 | TTKASSTSTSSTSTGTGVAAHWGQCGGQGWTGPTTCASGTTCTVVNPYYSQCL |
| SEQ ID NO:125 | TTKASSTSTSSTSTGTGVAAHWGQCGGQGWTGPTTCASGTTCTVVNPYYSQCL |
| SEQ ID NO:127 | TTKASSTSTSSTSTGTGVAAHWGQCGGQGWTGPTTCASGTTCTVVNPYYSQCL |
| SEQ ID NO:129 | TTKASSTSTSSTSTGTGVAAHWGQCGGQGWTGPTTCASGTTCTVVNPYYSQCL |
| SEQ ID NO:131 | TTKASSTSTSSTSTGTGVAAHWGQCGGQGWTGPTTCASGTTCTVVNPYYSQCL |
| SEQ ID NO:133 | TTKASSTSTSSTSTGTGVAAHWGQCGGQGWTGPTTCASGTTCTVVNPYYSQCL |
| SEQ ID NO:135 | TTKASSTSTSSTSTGTGVAAHWGQCGGQGWTGPTTCASGTTCTVVNPYYSQCL |

Figure 1U

SEQUENCE LISTING

<160> NUMBER OF SEQ ID NOS: 136

<210> SEQ ID NO 1
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gcccatactg gacttggcaa ccacgagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat tcgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctgggtcag    1500 tgtggtggcc agggttggac tggtcctacc acctgcgcta gtgaaccac atgcaccgtc    1560 gtgaaccctt actactctca atgtttgtaa                                     1590
```

<210> SEQ ID NO 2

```
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala His Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365
```

```
Thr Ala Ser Phe Ser Lys His Gly Gly Leu Ala Lys Met Gly Ala Gly
        370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Ser Gly Asp Pro
            420                 425                 430
Lys Thr Val Glu Ser Gln Ser Gly Ser Tyr Val Thr Phe Ser Asp
        435                 440                 445
Ile Arg Val Gly Pro Phe Asn Ser Thr Phe Ser Gly Gly Ser Ser Thr
    450                 455                 460
Gly Gly Ser Ser Thr Thr Thr Ala Ser Gly Thr Thr Thr Lys Ala
465                 470                 475                 480
Ser Ser Thr Ser Thr Ser Ser Thr Ser Thr Gly Thr Gly Val Ala Ala
                485                 490                 495
His Trp Gly Gln Cys Gly Gly Gln Gly Trp Thr Gly Pro Thr Thr Cys
            500                 505                 510
Ala Ser Gly Thr Thr Cys Thr Val Val Asn Pro Tyr Tyr Ser Gln Cys
            515                 520                 525
Leu
```

<210> SEQ ID NO 3
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540
cccaacaaca aggccggcgc tcagtacggt gttggatact gtgactctca atgccctcgt     600
gacttgaaat tcatcgctgg tcaggccaac gttgagggc ggacgccctc ctccaacaac     660
gccgagactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca cctctccga gatcagacgt tactacgttc agaacggtgt tgtcatcccc    1020
cagccttcct ccaagatctc cggagtcagc ggaaatgtca tcaactccga cttctgcgat    1080
```

```
gctgagatct ccacctttgg cgagactgcc tccttcagca aaacacggtgg cctggcaaag   1140 atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccgtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560 gtgaacccctt actactctca atgtttgtaa                                    1590
```

<210> SEQ ID NO 4
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Glu Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255
```

```
Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
            290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
            325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
            370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
            450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu

<210> SEQ ID NO 5
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact      240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
```

```
atcttcgact tgttgaacca ggagttcact ttcaccgtcg atgtctccca cctcccttgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgcccaa gtccaacaac    660
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960 tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acacggtgg cctggcaaag   1140 atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt caactctac gttcagcggt   1380 ggttctagca ccggtggcag ctccactact accgccagcg caccaccac caccaaggcc   1440 tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                     1590
```

<210> SEQ ID NO 6
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140
```

```
Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Lys Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 7
<211> LENGTH: 1590
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 7

```
atgtctgcct tgaactcttt caatatgtac aagagcgccc tcatcttggg ctccttgctg    60
gcaacagctg gtgctcagca aattggtact tataccgctg aaacccatcc ctctttgagc   120
tggtctactt gcaaatcggg tggtagctgc accacaaact ccggtgccat tacgttggat   180
gccaactggc gttgggtcca tggtgtcaat accagcacca actgctacac tggcaacact   240
tggaataccg ccatctgcga cactgatgca tcctgtgccc aggactgtgc tcttgatggt   300
gctgactact ctggcacgta cggtatcact acctccggca actcattgcg cctgaacttc   360
gttaccggtt ccaacgtcgg atctcgtacc tacctgatgg ccgataacac ccactaccaa   420
atcttcgact tgttgaacca ggagttcact ttcaccgtcg atgtctccca cctcccttgc   480
ggtttgaacg gtgccctcta cttcgtgacc atggacgccg acggtggcgt ctccaagtac   540
cccaacaaca aggccggcgc tcagtacggt gttggatact gtgactctca atgccctcgt   600
gacttgaaat tcatcgctgg tcaggccaac gttgagggcg gacgccctc ctccaacaac    660
gccaacactg gatatggcaa ccacggagct tgctgcgcag agcttgatat ctgggaggca   720
aacagcatct cagaggcttt gactcctcac ccttgcgata cacccggtct atctgtttgc   780
actactgatg cctgcggtgg tacctacagc tccgatcgtt acgccggtac ctgcgaccct   840
gatggatgtg acttcaaccc ttaccgtctt ggtgtcactg acttctacgg ctccggcaag   900
accgttgaca ccaccaaacc catcaccgtt gtgactcaat cgtcactga cgacggcaca    960
tccaccggca ccctctccga gatcagacgt tactacgttc agaacggtgt tgtcatcccc  1020
cagccttcct ccaagatctc cggagtcagc ggaaatgtca tcaactccga cttctgcgat  1080
gctgagatct ccacctttgg cgagactgcc tccttcagca acacggtgg cctggcaaag   1140
atgggcgctg gtatggaagc tggtatggtc ttggtcatga gtttgtggga cgactactcc  1200
gtcaacatgc tctggctcga cagcacctac cctacaaacg cgactggtac ccccggtgcc  1260
gctcgtggtt cctgccctac cacttctggg gaccctaaga ccgttgaatc acaatccggc  1320
agctcctatg tcacctttc tgacatccgg gttggtcctt caactctac gttcagcggt    1380
ggttctagca ccggtggcag ctccactact accgccagcg gcaccaccac caccaaggcc  1440
tcttccacct ctacttccag cacctctacc ggcactggag tcgctgctca ctggggtcag  1500
tgtggtggcc agggttggac tggtcctacc acctgcgcta gtggaaccac atgcaccgtc  1560
gtgaacccc actactctca atgtttgtaa                                    1590
```

<210> SEQ ID NO 8
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30
```

-continued

```
Ala Glu Thr His Pro Ser Leu Ser Trp Ser Thr Cys Lys Ser Gly Gly
         35                  40                  45

Ser Cys Thr Thr Asn Ser Gly Ala Ile Thr Leu Asp Ala Asn Trp Arg
 50                  55                  60

Trp Val His Gly Val Asn Thr Ser Thr Asn Cys Tyr Thr Gly Asn Thr
 65                  70                  75                  80

Trp Asn Thr Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
                115                 120                 125

Arg Thr Tyr Leu Met Ala Asp Asn Thr His Tyr Gln Ile Phe Asp Leu
        130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
        210                 215                 220

Tyr Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
        340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
        420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
```

```
            450                 455                 460
Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Val Ala Ala
                485                 490                 495

His Trp Gly Gln Cys Gly Gly Gln Gly Trp Thr Gly Pro Thr Thr Cys
                500                 505                 510

Ala Ser Gly Thr Thr Cys Thr Val Val Asn Pro Tyr Tyr Ser Gln Cys
            515                 520                 525

Leu

<210> SEQ ID NO 9
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atgtctgcct tgaactcttt caatatgtac aagagcgccc tcatcttggg ctccttgctg      60
gcaacagctg gtgctcagca aattggtact tataccgctg aaacccatcc ctctttgagc    120
tggtctactt gcaaatcggg tggtagctgc accacaaact ccggtgccat acgttggat    180 gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg gtgccctcta cttcgtgacc atggacgccg acgtgggcgt ctccaagtac    540
cccaacaaca aggccggcgc tcagtacggt gttggatact gtgactctca atgccctcgt    600
gacttgaaat tcatcgctgg tcaggccaac gttgagggcg gacgccctc ctccaacaac    660 gccaacactg gagtgggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960 tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
```
gtgaaccctt actactctca atgtttgtaa                                                      1590

<210> SEQ ID NO 10
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Val Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Thr Gln Phe Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn

```
              340             345             350
Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu
```

<210> SEQ ID NO 11
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

```
atgtctgcct tgaactcttt caatatgtac aagagcgccc tcatcttggg ctccttgctg     60
gcaacagctg gtgctcagca aattggtact tataccgctg aaacccatcc ctctttgagc    120
tggtctactt gcaaatcggg tggtagctgc accacaaact ccggtgccat acgttggat    180 gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg gtgccctcta cttcgtgacc atggacgccg acgtggcgt ctccaagtac    540 cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg acttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
```

```
accgttgaca ccaccaaacc catcaccgtt gtgactcaat tcgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgcttc gtggggtcag   1500
tgtggtggcc agggttggac tggtcctacc acctgcgcta gtggaaccac atgcaccgtc   1560
gtgaacccct tactactctca atgtttgtaa                                   1590
```

<210> SEQ ID NO 12
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
```

```
                    225                 230                 235                 240
Asn Ser Ile Ser Glu Ala Leu Thr Pro His Pro Cys Asp Thr Pro Gly
                245                 250                 255
Leu Ser Val Cys Thr Thr Asp Ala Cys Gly Gly Thr Tyr Ser Ser Asp
                260                 265                 270
Arg Tyr Ala Gly Thr Cys Asp Pro Asp Gly Cys Asp Phe Asn Pro Tyr
                275                 280                 285
Arg Leu Gly Val Thr Asp Phe Tyr Gly Ser Gly Lys Thr Val Asp Thr
                290                 295                 300
Thr Lys Pro Ile Thr Val Val Thr Gln Phe Val Thr Asp Asp Gly Thr
305                 310                 315                 320
Ser Thr Gly Thr Leu Ser Glu Ile Arg Arg Tyr Tyr Val Gln Asn Gly
                325                 330                 335
Val Val Ile Pro Gln Pro Ser Ser Lys Ile Ser Gly Val Ser Gly Asn
                340                 345                 350
Val Ile Asn Ser Asp Phe Cys Asp Ala Glu Ile Ser Thr Phe Gly Glu
                355                 360                 365
Thr Ala Ser Phe Ser Lys His Gly Gly Leu Ala Lys Met Gly Ala Gly
                370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
                420                 425                 430
Lys Thr Val Glu Ser Gln Ser Gly Ser Ser Tyr Val Thr Phe Ser Asp
                435                 440                 445
Ile Arg Val Gly Pro Phe Asn Ser Thr Phe Ser Gly Gly Ser Ser Thr
                450                 455                 460
Gly Gly Ser Ser Thr Thr Thr Ala Ser Gly Thr Thr Thr Thr Lys Ala
465                 470                 475                 480
Ser Ser Thr Ser Thr Ser Ser Thr Ser Thr Gly Thr Gly Val Ala Ala
                485                 490                 495
Ser Trp Gly Gln Cys Gly Gly Gln Gly Trp Thr Gly Pro Thr Thr Cys
                500                 505                 510
Ala Ser Gly Thr Thr Cys Thr Val Val Asn Pro Tyr Tyr Ser Gln Cys
                515                 520                 525
Leu

<210> SEQ ID NO 13
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcga cactgatgca tcctgtgccc aggactgtgc tcttgatggt     300
```

```
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctaag acctgcgcta gtggaaccac atgcaccgtc   1560
gtgaaccctt actactctca atgtttgtaa                                    1590
```

<210> SEQ ID NO 14
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser

```
                     115                 120                 125
Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
            195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Lys Thr Cys
            500                 505                 510

Ala Ser Gly Thr Thr Cys Thr Val Val Asn Pro Tyr Tyr Ser Gln Cys
            515                 520                 525

Leu
```

<210> SEQ ID NO 15
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcct tactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggc ggacgccctc ctccaacaac     660
gccaacactg gacttggcaa ccacggagct tgctgcgcag agcttgatat ctgggaggca     720
aacagcatct cagaggcttt gactcctcac ccttgcgata caccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca acacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg accctaaga ccgttgaatc acaatccggc    1320
agctcctatg tcaccttttc tgacatccgg gttggtcctt caactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaacccct tactactctca atgtttgtaa                                    1590
```

<210> SEQ ID NO 16
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Met Ser Ala Leu Asn Ser Phe Asn Met Tyr Lys Ser Ala Leu Ile Leu

-continued

```
1               5                   10                  15
Gly Ser Leu Leu Ala Thr Ala Gly Ala Gln Gln Ile Gly Thr Tyr Thr
            20                  25                  30
Ala Glu Thr His Pro Ser Leu Ser Trp Ser Cys Lys Ser Gly Gly
            35                  40                  45
Ser Cys Thr Thr Asn Ser Gly Ala Ile Thr Leu Asp Ala Asn Trp Arg
50                  55                  60
Trp Val His Gly Val Asn Thr Ser Thr Asn Cys Tyr Thr Gly Asn Thr
65                  70                  75                  80
Trp Asn Thr Ala Ile Cys Leu Thr Asp Ala Ser Cys Ala Gln Asp Cys
                85                  90                  95
Ala Leu Asp Gly Ala Asp Tyr Ser Gly Thr Tyr Gly Ile Thr Thr Ser
                100                 105                 110
Gly Asn Ser Leu Arg Leu Asn Phe Val Thr Gly Ser Asn Val Gly Ser
                115                 120                 125
Arg Thr Tyr Leu Met Ala Asp Asn Thr His Tyr Gln Ile Phe Asp Leu
                130                 135                 140
Leu Asn Gln Glu Phe Thr Phe Thr Val Asp Val Ser His Leu Pro Cys
145                 150                 155                 160
Gly Leu Asn Gly Ala Leu Tyr Phe Val Thr Met Asp Ala Asp Gly Gly
                165                 170                 175
Val Ser Lys Tyr Pro Asn Asn Lys Ala Gly Ala Gln Tyr Gly Val Gly
            180                 185                 190
Tyr Cys Asp Ser Gln Cys Pro Arg Asp Leu Lys Phe Ile Ala Gly Gln
            195                 200                 205
Ala Asn Val Glu Gly Trp Thr Pro Ser Ser Asn Asn Ala Asn Thr Gly
            210                 215                 220
Leu Gly Asn His Gly Ala Cys Cys Ala Glu Leu Asp Ile Trp Glu Ala
225                 230                 235                 240
Asn Ser Ile Ser Glu Ala Leu Thr Pro His Pro Cys Asp Thr Pro Gly
                245                 250                 255
Leu Ser Val Cys Thr Thr Asp Ala Cys Gly Gly Thr Tyr Ser Ser Asp
                260                 265                 270
Arg Tyr Ala Gly Thr Cys Asp Pro Asp Gly Cys Asp Phe Asn Pro Tyr
            275                 280                 285
Arg Leu Gly Val Thr Asp Phe Tyr Gly Ser Gly Lys Thr Val Asp Thr
            290                 295                 300
Thr Lys Pro Ile Thr Val Val Thr Gln Phe Val Thr Asp Asp Gly Thr
305                 310                 315                 320
Ser Thr Gly Thr Leu Ser Glu Ile Arg Arg Tyr Tyr Val Gln Asn Gly
                325                 330                 335
Val Val Ile Pro Gln Pro Ser Ser Lys Ile Ser Gly Val Ser Gly Asn
                340                 345                 350
Val Ile Asn Ser Asp Phe Cys Asp Ala Glu Ile Ser Thr Phe Gly Glu
                355                 360                 365
Thr Ala Ser Phe Ser Lys His Gly Gly Leu Ala Lys Met Gly Ala Gly
                370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
                420                 425                 430
```

```
Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Gly Thr Gly Val Ala Ala
            485                 490                 495

His Trp Gly Gln Cys Gly Gly Gln Gly Trp Thr Gly Pro Thr Thr Cys
                500                 505                 510

Ala Ser Gly Thr Thr Cys Thr Val Val Asn Pro Tyr Tyr Ser Gln Cys
            515                 520                 525

Leu

<210> SEQ ID NO 17
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggcg gacgccctc ctccaacaac      660 gccaacactg gacttggcaa ccacggagct tgctgcgcag agcttgatat ctgggaggca     720
aacagcatct cagaggcttt gactcctcac ccttgcgata cacccattct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960 tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccaccttggg cgagactgcc tccttcagca aacacggtgg cctggcaaag    1140
atgggcgctg atatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg accctaagaa ccgttgaatc acaatccggc    1320
agctcctatg tcacctttt ctgacatccgg gttggtcctt tcaactctac gttcagcggt    1380
```

-continued

```
ggttctagca ccggtggcag ctccactact accgccagcg gcaccaccac caccaaggcc    1440
tcttccacct ctactccag cacctctacc ggcactggag tcgctgctca ctggggtcag    1500
tgtggtggcc agggttggac tggtcctacc acctgcgcta gtggaaccac atgcaccgtc    1560
gtgaacccct actactctca atgtttgtaa                                    1590
```

<210> SEQ ID NO 18
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Ile
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320
```

Ser Thr Gly Thr Leu Ser Glu Ile Arg Arg Tyr Tyr Val Gln Asn Gly
            325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu

<210> SEQ ID NO 19
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccgg ctcccttgc      480 ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780

```
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                     1590
```

<210> SEQ ID NO 20
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser Gly Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

```
Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Thr Tyr Ser Ser Asp
                260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
                355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
                435                 440                 445

Ile Arg Val Gly Pro Phe Asn Ser Thr Phe Ser Gly Gly Ser Ser Thr
                450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
                500                 505                 510

Ala Ser Gly Thr Thr Cys Thr Val Val Asn Pro Tyr Tyr Ser Gln Cys
                515                 520                 525

Leu
```

<210> SEQ ID NO 21
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
atgtctgcct tgaactcttt caatatgtac aagagcgccc tcatcttggg ctccttgctg      60
gcaacagctg gtgctcagca aattggtact tataccgctg aaacccatcc ctctttgagc     120
```

| | |
|---|---|
| tggtctactt gcaaatcggg tggtagctgc accacaaact ccggtgccat acgttggat | 180 |
| gccaactggc gttgggtcca tggtgtcaat accagcacca actgctacac tggcaacact | 240 |
| tggaataccg ccatctgcga cactgatgca tcctgtgccc aggactgtgc tcttgatggt | 300 |
| gctgactact ctggcacgta cggtatcact acctccggca actcattgcg cctgaacttc | 360 |
| gttaccggtt ccaacgtcgg atctcgtacc tacctgatgg ccgataacac ccactaccaa | 420 |
| atcttcgact tgttgaacca ggagttcact ttcaccgtcg atgtctccca cctcgggtgc | 480 |
| ggtttgaacg gtgccctcta cttcgtgacc atggacgccg acggtggcgt ctccaagtac | 540 |
| cccaacaaca aggccggcgc tcagtacggt gttggatact gtgactctca atgccctcgt | 600 |
| gacttgaaat tcatcgctgg tcaggccaac gttgagggct ggacgccctc ctccaacaac | 660 |
| gccaacactg gacttggcaa ccacggagct tgctgcgcag agcttgatat ctgggaggca | 720 |
| aacagcatct cagaggcttt gactcctcac ccttgcgata cacccggtct atctgtttgc | 780 |
| actactgatg cctgcggtgg tacctacagc tccgatcgtt acgccggtac ctgcgaccct | 840 |
| gatggatgtg acttcaaccc ttaccgtctt ggtgtcactg acttctacgg ctccggcaag | 900 |
| accgttgaca ccaccaaacc catcaccgtt gtgactcaat cgtcactga cgacggcaca | 960 |
| tccaccggca ccctctccga gatcagacgt tactacgttc agaacggtgt tgtcatcccc | 1020 |
| cagccttcct ccaagatctc cggagtcagc ggaaatgtca tcaactccga cttctgcgat | 1080 |
| gctgagatct ccacctttgg cgagactgcc tccttcagca aacacggtgg cctggcaaag | 1140 |
| atgggcgctg gtatggaagc tggtatggtc ttggtcatga gtttgtggga cgactactcc | 1200 |
| gtcaacatgc tctggctcga cagcacctac cctacaaacg cgactggtac ccccggtgcc | 1260 |
| gctcgtggtt cctgccctac cacttctggg gaccctaaga ccgttgaatc acaatccggc | 1320 |
| agctcctatg tcacctttc tgacatccgg gttggtcctt tcaactctac gttcagcggt | 1380 |
| ggttctagca ccggtggcag ctccactact accgccagcg gcaccaccac caccaaggcc | 1440 |
| tcttccacct ctacttccag cacctctacc ggcactggag tcgctgctca ctggggtcag | 1500 |
| tgtggtggcc agggttggac tggtcctacc acctgcgcta gtggaaccac atgcaccgtc | 1560 |
| gtgaaccctt actactctca atgtttgtaa | 1590 |

<210> SEQ ID NO 22
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 22

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

```
Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
        130                 135                 140

Leu Asn Gln Glu Phe Thr Phe Thr Val Asp Val Ser His Leu Gly Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
            290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Ser Ser Ser Thr
        450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510
```

Ala Ser Gly Thr Thr Cys Thr Val Val Asn Pro Tyr Tyr Ser Gln Cys
        515                 520                 525

Leu

<210> SEQ ID NO 23
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacgcta aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca acacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt caactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 24
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 24

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Ala Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400
```

```
Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Ser Gly Asp Pro
            420                 425                 430

Lys Thr Val Glu Ser Gln Ser Gly Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525
Leu

<210> SEQ ID NO 25
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
atgtctgcct tgaactcttt caatatgtac aagagcgccc tcatcttggg ctccttgctg      60
gcaacagctg gtgctcagca aattggtact tataccgctg aaacccatcc ctctttgagc    120
tggtctactt gcaaatcggg tggtagctgc accacaaact ccggtgccat tacgttggat    180
gccaactggc gttgggtcca tgtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtcggtca cctcccttgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg acttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960 tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
```

```
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 26
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Gly His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285
```

```
Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 27
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
```

```
gacttgaaat tcatcgctgg tcaggccaac gttgagggct ggacgccctc ccccaacaac    660
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtctctga cgacggcaca     960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt    1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                   1590
```

<210> SEQ ID NO 28
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175
```

```
Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
            195                 200                 205

Ala Asn Val Glu Gly Trp Thr Pro Ser Pro Asn Asn Ala Asn Thr Gly
        210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
            245                 250                 255

Leu Ser Val Cys Thr Thr Asp Ala Cys Gly Thr Tyr Ser Ser Asp
        260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Ser Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 29
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
```

```
atgtctgcct tgaactcttt caatatgtac aagagcgccc tcatcttggg ctccttgctg    60
gcaacagctg gtgctcagca aattggtact tataccgctg aaacccatcc ctctttgagc   120
tggtctactt gcaaatcggg tggtagctgc accacaaact ccggtgccat tacgttggat   180
gccaactggc gttgggtcca tggtgtcaat accagcacca actgctacac tgcaacact    240
tggaataccg ccatctgcga cactgatgca tcctgtgccc aggactgtgc tcttgatggt   300
gctgactact ctggcacgta cggtatcact acctccggca actcattgcg cctgaacttc   360
gttaccggtt ccaacgtcgg atctcgtacc tacctgatgg ccgataacac ccactaccaa   420
atcttcgact gttgaacca ggagttcact ttcaccgtcg atgtctccca cctcccttgc    480
ggtttgaacg gtgccctcta cttcgtgacc atggacgccg acggtggcgt ctccaagtac   540
cccaacaaca aggccggcgc tcagtacggt gttggatact gtgactctca atgccctcgt   600
gacttgaaat tcatcgctgg tcaggccaac gttgagggct ggacgccctc ctccaacaac   660
gccaacactg gacttggcaa ccacggagct tgctgcgcag agcttgatat ctgggaggca   720
aacagcatct cagaggcttt gactcctcac ccttgcgata cacccggtct atctgtttgc   780
actactgatg cctgcggtgg tacctacagc tccgatcgtt acgccggtac ctgcgaccct   840
gatggatgtg acttcaaccc ttaccgtctt ggtgtcactg acttctacgg ctccggcaag   900
accgttgaca ccaccaaacc catcaccgtt gtgactcaat cgtcactga ccagggcaca    960
tcctccggca ccctctccga tcagacgt tactacgttc agaacggtgt tgtcatcccc    1020
cagccttcct ccaagatctc cggagtcagc ggaaatgtca tcaactccga cttctgcgat  1080
gctgaggtct ccacctttgg cgagactgcc tccttcagca acacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaacccctt actactctca atgtttgtaa                                  1590
```

<210> SEQ ID NO 30
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 30

Met Ser Ala Leu Asn Ser Phe Asn Met Tyr Lys Ser Ala Leu Ile Leu
 1               5                  10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

```
Trp Val His Gly Val Asn Thr Ser Thr Asn Cys Tyr Thr Gly Asn Thr
 65                  70                  75                  80

Trp Asn Thr Ala Ile Cys Asp Thr Asp Ala Ser Cys Ala Gln Asp Cys
             85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Gln Gly Thr
305                 310                 315                 320

Ser Ser Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Val Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
```

|  | 485 |  |  |  |  | 490 |  |  |  |  | 495 |  |
|---|---|---|---|---|---|---|---|---|---|---|---|---|

His Trp Gly Gln Cys Gly Gly Gln Gly Trp Thr Gly Pro Thr Thr Cys
          500                     505                 510

Ala Ser Gly Thr Thr Cys Thr Val Val Asn Pro Tyr Tyr Ser Gln Cys
        515                 520                 525

Leu

<210> SEQ ID NO 31
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

| atgtctgcct tgaactcttt caatatgtac aagagcgccc tcatcttggg ctccttgctg | 60 |
| gcaacagctg gtgctcagca aattggtact tataccgctg aaacccatcc ctctttgagc | 120 |
| tggtctactt gcaaatcggg tggtagctgc accacaaact ccggtgccat tacgttggat | 180 |
| gccaactggc gttgggtcca tggtgtcaat accagcacca actgctacac tggcaacact | 240 |
| tggaataccg ccatctgcga cactgatgca tcctgtgccc aggactgtgc tcttgatggt | 300 |
| gctgactact ctggcacgta cggtatcact acctccggca actcattgcg cctgaacttc | 360 |
| gttaccggtt ccaacgtcgg atctcgtacc tacctgatgg ccgataacac ccactaccaa | 420 |
| atcttcgact tgttgaacca ggagttcact ttcaccgtcg atgtctccca cctcccttgc | 480 |
| ggtttgaacg gtgccctcta cttcgtgacc atggacgccg acgtggcgt ctccaagtac | 540 |
| cccaacaaca aggccggcgc tcagtacggt gttggatact gtgactctca atgccctcgt | 600 |
| gacttgaaat tcatcgctgg tcaggccaac gttgagggct ggacgccctc ctccaacaac | 660 |
| gccaacactg gacttggcaa ccacggagct tgctgcgcag agcttgatat ctgggaggca | 720 |
| aacagcatct cagaggcttt gactcctcac ccttgcgata caccggtct atctgtttgc | 780 |
| actactgatg cctgcggtgg tacctacagc tccgatcgtt acgccggtac ctgcgaccct | 840 |
| gatggatgtg acttcaaccc ttaccgtctt ggtgtcactg acttctacgg ctccggcaag | 900 |
| accgttgaca ccaccaaacc catcaccgtt gtgactcaat cgtcactga cgacggcaca | 960 |
| tccaccggcc gtctctccga gatcagacgt tactacgttc agaacggtgt tgtcatcccc | 1020 |
| cagccttcct ccaagatctc cggagtcagc ggaaatgtca tcaactccga cttctgcgat | 1080 |
| gctgagatct ccaccttggg cgagactgcc tccttcagca aacacggtgg cctggcaaag | 1140 |
| atgggcgctg gtatggaagc tggtatggtc ttggtcatga gtttgtggga cgactactcc | 1200 |
| gtcaacatgc tctggctcga cagcacctac cctacaaacg cgactggtac ccccggtgcc | 1260 |
| gctcgtggtt cctgccctac cacttctggg gaccctaaga ccgttgaatc acaatccggc | 1320 |
| agctcctatg tcacctttc tgacatccgg gttggtcctt tcaactctac gttcagcggt | 1380 |
| ggttctagca ccggtggcag ctccactact accgccagcg gcaccaccac caccaaggcc | 1440 |
| tcttccacct ctacttccag cacctctacc ggcactggag tcgctgctca ctgggtcag | 1500 |
| tgtggtggcc agggttggac tggtcctacc acctgcgcta gtggaaccac atgcaccgtc | 1560 |
| gtgaaccctt actactctca atgtttgtaa | 1590 |

<210> SEQ ID NO 32
<211> LENGTH: 529

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Arg Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
```

```
            370                 375                 380
Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
                435                 440                 445

Ile Arg Val Gly Pro Phe Asn Ser Thr Phe Ser Gly Gly Ser Ser Thr
            450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu
```

<210> SEQ ID NO 33
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg acttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca cctccttga gatcagacgt tactacgttc agaacggtgt tgtcatcccc    1020
cagccttcct ccaagatctc cggagtcagc ggaaatgtca tcaactccga cttctgcgat    1080
```

```
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt     1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560 gtgaacccctt actactctca atgtttgtaa                                    1590
```

<210> SEQ ID NO 34
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 34

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
```

```
                    260                 265                 270
Arg Tyr Ala Gly Thr Cys Asp Pro Asp Gly Cys Asp Phe Asn Pro Tyr
            275                 280                 285
Arg Leu Gly Val Thr Asp Phe Tyr Gly Ser Gly Lys Thr Val Asp Thr
            290                 295                 300
Thr Lys Pro Ile Thr Val Thr Gln Phe Val Thr Asp Asp Gly Thr
305                 310                 315                 320
Ser Thr Gly Thr Leu Leu Glu Ile Arg Arg Tyr Tyr Val Gln Asn Gly
                325                 330                 335
Val Val Ile Pro Gln Pro Ser Ser Lys Ile Ser Gly Val Ser Gly Asn
            340                 345                 350
Val Ile Asn Ser Asp Phe Cys Asp Ala Glu Ile Ser Thr Phe Gly Glu
            355                 360                 365
Thr Ala Ser Phe Ser Lys His Gly Gly Leu Ala Lys Met Gly Ala Gly
            370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
            420                 425                 430
Lys Thr Val Glu Ser Gln Ser Gly Ser Ser Tyr Val Thr Phe Ser Asp
            435                 440                 445
Ile Arg Val Gly Pro Phe Asn Ser Thr Phe Ser Gly Gly Ser Ser Thr
            450                 455                 460
Gly Gly Ser Ser Thr Thr Thr Ala Ser Gly Thr Thr Thr Lys Ala
465                 470                 475                 480
Ser Ser Thr Ser Thr Ser Ser Ser Thr Gly Thr Gly Val Ala Ala
                485                 490                 495
His Trp Gly Gln Cys Gly Gly Gln Gly Trp Thr Gly Pro Thr Thr Cys
            500                 505                 510
Ala Ser Gly Thr Thr Cys Thr Val Val Asn Pro Tyr Tyr Ser Gln Cys
            515                 520                 525
Leu

<210> SEQ ID NO 35
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180 gccaactggc gttgggtcca tgtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
```

-continued

```
ggtttgaacg gtgccctcta cttcgtgacc atggacgccg acggtggcgt ctccaagtac      540
cccaacaaca aggccggcgc tcagtacggt gttggatact gtgactctca atgccctcgt      600
gacttgaaat tcatcgctgg tcaggccaac gttgagggct ggacgccctc ctccaacaac      660
gccaacactg gacttggcaa ccacggagct tgctgcgcag agcttgatat ctgggaggca      720
aacagcatct cagaggcttt gactcctcac ccttgcgata cacccggtct atctgtttgc      780
actactgatg cctgcggtgg tacctacagc tccgatcgtt acgccggtac ctgcgaccct      840
gatggatgtg acttcaaccc ttaccgtctt ggtgtcactg acttctacgg ctccggcaag      900
accgttgaca ccaccaaacc catcaccgtt gtgactcaat cgtcactga cgacggcaca      960
tccaccggca ccctctccga tcagacgt tactacgtta gtaacggtgt tgtcatcccc     1020
cagccttcct ccaagatctc cggagtcagc ggaaatgtca tcaactccga cttctgcgat     1080
gctgagatct ccacctttgg cgagactgcc tccttcagca aacacggtgg cctggcaaag     1140
atgggcgctg gtatggaagc tggtatggtc ttggtcatga gtttgtggga cgactactcc     1200
gtcaacatgc tctggctcga cagcacctac cctacaaacg cgactggtac ccccggtgcc     1260
gctcgtggtt cctgccctac cacttctggg gaccctaaga ccgttgaatc acaatccggc     1320
agctcctatg tcacctttc tgacatccgg gttggtcctt tcaactctac gttcagcggt     1380
ggttctagca ccggtggcag ctccactact accgccagcg gcaccaccac caccaaggcc     1440
tcttccacct ctacttccag cacctctacc ggcactggag tcgctgctca ctgggtcag     1500
tgtggtggcc agggttggac tggtcctacc acctgcgcta gtggaaccac atgcaccgtc     1560
gtgaacccttt actactctca atgtttgtaa                                      1590
```

<210> SEQ ID NO 36
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
```

145                 150                 155                 160
        Gly Leu Asn Gly Ala Leu Tyr Phe Val Thr Met Asp Ala Asp Gly Gly
                        165                 170                 175

Val Ser Lys Tyr Pro Asn Asn Lys Ala Gly Gln Tyr Gly Val Gly
                        180                 185                 190

Tyr Cys Asp Ser Gln Cys Pro Arg Asp Leu Lys Phe Ile Ala Gly Gln
                        195                 200                 205

Ala Asn Val Glu Gly Trp Thr Pro Ser Asn Asn Ala Asn Thr Gly
            210                 215                 220

Leu Gly Asn His Gly Ala Cys Cys Ala Glu Leu Asp Ile Trp Glu Ala
        225                 230                 235                 240

Asn Ser Ile Ser Glu Ala Leu Thr Pro His Pro Cys Asp Thr Pro Gly
                        245                 250                 255

Leu Ser Val Cys Thr Thr Asp Ala Cys Gly Gly Thr Tyr Ser Ser Asp
                        260                 265                 270

Arg Tyr Ala Gly Thr Cys Asp Pro Asp Gly Cys Asp Phe Asn Pro Tyr
                    275                 280                 285

Arg Leu Gly Val Thr Asp Phe Tyr Gly Ser Gly Lys Thr Val Asp Thr
                    290                 295                 300

Thr Lys Pro Ile Thr Val Val Thr Gln Phe Val Thr Asp Asp Gly Thr
        305                 310                 315                 320

Ser Thr Gly Thr Leu Ser Glu Ile Arg Arg Tyr Tyr Val Ser Asn Gly
                        325                 330                 335

Val Val Ile Pro Gln Pro Ser Ser Lys Ile Ser Gly Val Ser Gly Asn
                        340                 345                 350

Val Ile Asn Ser Asp Phe Cys Asp Ala Glu Ile Ser Thr Phe Gly Glu
                        355                 360                 365

Thr Ala Ser Phe Ser Lys His Gly Gly Leu Ala Lys Met Gly Ala Gly
                        370                 375                 380

Met Glu Ala Gly Met Val Leu Val Met Ser Leu Trp Asp Asp Tyr Ser
        385                 390                 395                 400

Val Asn Met Leu Trp Leu Asp Ser Thr Tyr Pro Thr Asn Ala Thr Gly
                        405                 410                 415

Thr Pro Gly Ala Ala Arg Gly Ser Cys Pro Thr Thr Ser Gly Asp Pro
                        420                 425                 430

Lys Thr Val Glu Ser Gln Ser Gly Ser Ser Tyr Val Thr Phe Ser Asp
                        435                 440                 445

Ile Arg Val Gly Pro Phe Asn Ser Thr Phe Ser Gly Gly Ser Ser Thr
                    450                 455                 460

Gly Gly Ser Ser Thr Thr Thr Ala Ser Gly Thr Thr Thr Lys Ala
        465                 470                 475                 480

Ser Ser Thr Ser Thr Ser Ser Thr Ser Thr Gly Thr Gly Val Ala Ala
                        485                 490                 495

His Trp Gly Gln Cys Gly Gly Gln Gly Trp Thr Gly Pro Thr Thr Cys
                    500                 505                 510

Ala Ser Gly Thr Thr Cys Thr Val Val Asn Pro Tyr Tyr Ser Gln Cys
                    515                 520                 525

Leu

<210> SEQ ID NO 37
<211> LENGTH: 1590
<212> TYPE: DNA
<213> ORGANISM: Artificial Sequence
<220> FEATURE:

<220> FEATURE:
<221> NAME/KEY: source
<223> OTHER INFORMATION: /note="Description of Artificial Sequence: Synthetic polynucleotide"

<400> SEQUENCE: 37

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg acttggcaa ccacggagct tgctgcgcag agcttgatat ctgggaggca      720
aacagcatct cagaggcttt gactcctcac ccttgcgata caccgggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca      960
tccaccggca ccctctccga tcagacgt tactacgttc agaacggtgt tgtcatcccc      1020
cagccttcct ccgatatctc cggagtcagc ggaaatgtca tcaactccga cttctgcgat    1080
gctgagatct ccacctttgg cgagactgcc tccttcagca acacggtgg cctggcaaag    1140
atgggcgctg gtatggaagc tggtatggtc ttggtcatga gttgtggga cgactactcc     1200
gtcaacatgc tctggctcga cagcacctac cctacaaacg cgactggtac ccccggtgcc     1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccgtggcag ctccactact accgccagcg gcaccaccac caccaaggcc     1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 38
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly

```
                35                  40                  45
Ser Cys Thr Thr Asn Ser Gly Ala Ile Thr Leu Asp Ala Asn Trp Arg
 50                  55                  60

Trp Val His Gly Val Asn Thr Ser Thr Asn Cys Tyr Thr Gly Asn Thr
 65                  70                  75                  80

Trp Asn Thr Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Asp Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
450                 455                 460
```

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 39
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcagatcggg tggtagctgc accacaaact ccggtgccat acgttggat      180 gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata caccggtct atctgtttgc     780 actactgatg cctgcggtgg tacctacagc tccgatcgtt acgccggtac ctgcgacccc     840
gatggatgtg acttcaaccc ttaccgtctt ggtgtcgctg acttctacgg ctccggcaag     900
accgttgaca ccaccaaacc catcaccgtt gtgactcaat cgtcactga cgacggcaca     960 tccaccggca ccctctccga gatcagacgt tactacgttc agaacggtgt tgtcatcccc    1020
cagccttcct ccaagatctc cggagtctgt ggaaatgtca tcaactccga cttctgcgat    1080
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctgggtcag    1500 tgtggtggcc agggttggac tggtcctacc acctgcgcta gtggaaccac atgcaccgtc    1560 gtgaacccctt actactctca atgtttgtaa                                        1590

<210> SEQ ID NO 40
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Arg Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Ala Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Cys Gly Asn
            340                 345                 350
```

```
Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu
```

```
<210> SEQ ID NO 41
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180 gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtgggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg acttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
```

-continued

```
tccaccggca ccctctccga gatcagacgt tactacgttc agaacggtgt tgtcatcccc    1020
cagccttcct ccaagatctc cggagtcagc gataatgtca tcaactccga cttctgcgat    1080
gctgagatct ccacctttgg cgagactgcc tccttcagca acacggtgg cctggcaaag     1140 atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560 gtgaacccctt actactctca atgtttgtaa                                    1590
```

<210> SEQ ID NO 42
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240
```

Asn Ser Ile Ser Glu Ala Leu Thr Pro His Pro Cys Asp Thr Pro Gly
            245                 250                 255
Leu Ser Val Cys Thr Thr Asp Ala Cys Gly Gly Thr Tyr Ser Ser Asp
        260                 265                 270
Arg Tyr Ala Gly Thr Cys Asp Pro Asp Gly Cys Asp Phe Asn Pro Tyr
    275                 280                 285
Arg Leu Gly Val Thr Asp Phe Tyr Gly Ser Gly Lys Thr Val Asp Thr
290                 295                 300
Thr Lys Pro Ile Thr Val Val Thr Gln Phe Val Thr Asp Asp Gly Thr
305                 310                 315                 320
Ser Thr Gly Thr Leu Ser Glu Ile Arg Arg Tyr Tyr Val Gln Asn Gly
            325                 330                 335
Val Val Ile Pro Gln Pro Ser Ser Lys Ile Ser Gly Val Ser Asp Asn
        340                 345                 350
Val Ile Asn Ser Asp Phe Cys Asp Ala Glu Ile Ser Thr Phe Gly Glu
    355                 360                 365
Thr Ala Ser Phe Ser Lys His Gly Gly Leu Ala Lys Met Gly Ala Gly
    370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
            405                 410                 415
Thr Pro Gly Ala Ala Arg Gly Ser Cys Pro Thr Thr Ser Gly Asp Pro
        420                 425                 430
Lys Thr Val Glu Ser Gln Ser Gly Ser Ser Tyr Val Thr Phe Ser Asp
    435                 440                 445
Ile Arg Val Gly Pro Phe Asn Ser Thr Phe Ser Gly Gly Ser Ser Thr
    450                 455                 460
Gly Gly Ser Ser Thr Thr Thr Ala Ser Gly Thr Thr Thr Lys Ala
465                 470                 475                 480
Ser Ser Thr Ser Thr Ser Ser Thr Ser Thr Gly Thr Gly Val Ala Ala
            485                 490                 495
His Trp Gly Gln Cys Gly Gly Gln Gly Trp Thr Gly Pro Thr Thr Cys
        500                 505                 510
Ala Ser Gly Thr Thr Cys Thr Val Val Asn Pro Tyr Tyr Ser Gln Cys
    515                 520                 525
Leu

<210> SEQ ID NO 43
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcga cactgatgca tcctgtgccc aggactgtgc tcttgatggt     300

```
gctgactact ctggcacgta cggtatcact acctccggca actcattgcg cctgaacttc      360
gttaccggtt ccaacgtcgg atctcgtacc tacctgatgg ccgataacac ccactaccaa      420
atcttcgact tgttgaacca ggagttcact ttcaccgtcg atgtctccca cctcccttgc      480
ggtttgaacg gtgccctcta cttcgtgacc atggacgccg acggtggcgt ctccaagtac      540
cccaacaaca aggccggcgc tcagtacggt gttggatact gtgactctca atgccctcgt      600
gacttgaaat tcatcgctgg tcaggccaac gttgagggct ggacgccctc ctccaacaac      660
gccaacactg gacttggcaa ccacggagct tgctgcgcag agcttgatat ctgggaggca      720
aacagcatct cagaggcttt gactcctcac ccttgcgata cacccggtct atctgtttgc      780
actactgatg cctgcggtgg tacctacagc tccgatcgtt acgccggtac ctgcgaccct      840
gatggatgtg acttcaaccc ttaccgtctt ggtgtcactg acttctacgg ctccggcaag      900
accgttgaca ccaccaaacc catcaccgtt gtgactcaat cgtcactga cgacggcaca      960
tccaccggca ccctctccga gatcagacgt tactacgttc agaacggtgt tgtcatcccc     1020
cagccttcct ccaagatctc cggagtcagc ggagttgtca tcaactccga cttctgcgat     1080
gctgagatct ccacctttgg cgagactgcc tccttcagca acacggtgg cctggcaaag     1140
atgggcgctg gtatggaagc tggtatggtc ttggtcatga gtttgtggga cgactactcc     1200
gtcaacatgc tctggctcga cagcacctac cctacaaacg cgactggtac ccccggtgcc     1260
gctcgtggtt cctgccctac cacttctggg acccctaaga ccgttgaatc acaatccggc     1320
agctcctatg tcacctttc tgacatccgg gttggtcctt tcaactctac gttcagcggt     1380
ggttctagca ccggtggcag ctccactact accgccagcg gcaccaccac caccaaggcc     1440
tcttccacct ctacttccag cacctctacc ggcactggag tcgctgctca ctggggtcag     1500
tgtggtggcc agggttggac tggtcctacc acctgcgcta gtggaaccac atgcaccgtc     1560
gtgaaccctt actactctca atgtttgtaa                                      1590
```

<210> SEQ ID NO 44
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125
```

```
Arg Thr Tyr Leu Met Ala Asp Asn Thr His Tyr Gln Ile Phe Asp Leu
        130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Val
                340                 345                 350

Val Ile Asn Ser Asp Phe Cys Asp Ala Glu Ile Ser Thr Phe Gly Glu
                355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
                420                 425                 430

Lys Thr Val Glu Ser Gln Ser Gly Ser Ser Tyr Val Thr Phe Ser Asp
                435                 440                 445

Ile Arg Val Gly Pro Phe Asn Ser Thr Phe Ser Gly Gly Ser Ser Thr
450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
                500                 505                 510

Ala Ser Gly Thr Thr Cys Thr Val Asn Pro Tyr Tyr Ser Gln Cys
                515                 520                 525

Leu
```

<210> SEQ ID NO 45
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggtg gacgccctc tccaacaac      660
gccaacactg gacttggcaa ccacggagct tgctgcgcag agcttgatat ctgggaggca     720
aacagcatct cagaggcttt gactcctcac ccttgcgata cccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttgtgcgat    1080
gctgagatct ccacctttgg cgagactgcc tccttcagca acacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                      1590
```

<210> SEQ ID NO 46
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Met Ser Ala Leu Asn Ser Phe Asn Met Tyr Lys Ser Ala Leu Ile Leu
1               5                   10                  15
```

```
Gly Ser Leu Leu Ala Thr Ala Gly Ala Gln Gln Ile Gly Thr Tyr Thr
             20                  25                  30

Ala Glu Thr His Pro Ser Leu Ser Trp Ser Thr Cys Lys Ser Gly Gly
         35                  40                  45

Ser Cys Thr Thr Asn Ser Gly Ala Ile Thr Leu Asp Ala Asn Trp Arg
 50                  55                  60

Trp Val His Gly Val Asn Thr Ser Thr Asn Cys Tyr Thr Gly Asn Thr
 65                  70                  75                  80

Trp Asn Thr Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
             115                 120                 125

Arg Thr Tyr Leu Met Ala Asp Asn Thr His Tyr Gln Ile Phe Asp Leu
         130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Leu Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430
```

```
Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu
```

<210> SEQ ID NO 47
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact      240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac      540 cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg acttggcaa ccacggagct tgctgcgcag agcttgatat ctgggaggca      720
aacagcatct cagaggcttt gactcctcac ccttgcgata cccccggtct atctgtttgc     780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca     960 tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccaccttggg cgagactatt tccttcagca acacggtgg cctggcaaag    1140 atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
```

```
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaacccct actactctca atgtttgtaa                                      1590
```

<210> SEQ ID NO 48
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320
```

Ser Thr Gly Thr Leu Ser Glu Ile Arg Arg Tyr Tyr Val Gln Asn Gly
            325                 330                 335

Val Val Ile Pro Gln Pro Ser Ser Lys Ile Ser Gly Val Ser Gly Asn
        340                 345                 350

Val Ile Asn Ser Asp Phe Cys Asp Ala Glu Ile Ser Thr Phe Gly Glu
            355                 360                 365

Thr Ile Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
        420                 425                 430

Lys Thr Val Glu Ser Gln Ser Gly Ser Ser Tyr Val Thr Phe Ser Asp
    435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
        500                 505                 510

Ala Ser Gly Thr Thr Cys Thr Val Val Asn Pro Tyr Tyr Ser Gln Cys
    515                 520                 525

Leu

<210> SEQ ID NO 49
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
atgtctgcct tgaactcttt caatatgtac aagagcgccc tcatcttggg ctccttgctg      60
gcaacagctg gtgctcagca aattggtact tataccgctg aaacccatcc ctctttgagc    120
tggtctactt gcaaatcggg tggtagctgc accacaaact ccggtgccat tacgttggat    180
gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg gacttggcaa ccacggagct tgctgcgcag agcttgatat ctgggaggca    720
aacagcatct cagaggcttt gactcctcac ccttgcgata caccccggtct atctgtttgc    780

-continued

```
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat tcgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acaccgtggg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccggtggcag ctccactact accgccagcg gcaccaccac caccaaggcc   1440
tcttccacct ctactccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 50
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205
```

```
Ala Asn Val Glu Gly Trp Thr Pro Ser Ser Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Arg Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 51
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
atgtctgcct tgaactcttt caatatgtac aagagcgccc tcatcttggg ctccttgctg      60
gcaacagctg gtgctcagca aattggtact tataccgctg aaacccatcc ctctttgagc    120
tggtctactt gcaaatcggg tggtagctgc accacaaact ccggtgccat tacgttggat    180
```

```
gccaactggc gttgggtcca tggtgtcaat accagcacca actgctacac tggcaacact   240
tggaataccg ccatctgcga cactgatgca tcctgtgccc aggactgtgc tcttgatggt   300
gctgactact ctggcacgta cggtatcact acctccggca actcattgcg cctgaacttc   360
gttaccggtt ccaacgtcgg atctcgtacc tacctgatgg ccgataacac ccactaccaa   420
atcttcgact tgttgaacca ggagttcact ttcaccgtcg atgtctccca cctcccttgc   480
ggtttgaacg tgccctcta cttcgtgacc atggacgccg acggtggcgt ctccaagtac   540
cccaacaaca aggccggcgc tcagtacggt gttggatact gtgactctca atgccctcgt   600
gacttgaaat tcatcgctgg tcaggccaac gttgagggc ggacgccctc ctccaacaac   660
gccaacactg acttggcaa ccacggagct tgctgcgcag agcttgatat ctgggaggca   720
aacagcatct cagaggcttt gactcctcac ccttgcgata cacccggtct atctgtttgc   780
actactgatg cctgcggtgg tacctacagc tccgatcgtt acgccggtac ctgcgaccct   840
gatggatgtg acttcaaccc ttaccgtctt ggtgtcactg acttctacgg ctccggcaag   900
accgttgaca ccaccaaacc catcaccgtt gtgactcaat cgtcactga cgacggcaca   960
tccaccggca ccctctccga gatcagacgt tactacgttc agaacggtgt tgtcatcccc  1020
cagccttcct ccaagatctc cggagtcagc ggaaatgtca tcaactccga cttctgcgat  1080
gctgagatct ccacctttgg cgagactgcc tccttcagca acacggtgg cctggcaaag  1140
atgggcgctg gtatgagtgc tggtatggtc ttggtcatga gtttgtggga cgactactcc  1200
gtcaacatgc tctggctcga cagcacctac cctacaaacg cgactggtac ccccggtgcc  1260
gctcgtggtt cctgccctac cacttctggg accctaaga ccgttgaatc acaatccggc  1320
agctcctatg tcaccttttc tgacatccgg gttggtcctt tcaactctac gttcagcggt  1380
ggttctagca ccggtggcag ctccactact accgccagcg gcaccaccac caccaaggcc  1440
tcttccacct ctacttccag cacctctacc ggcactggag tcgctgctca ctggggtcag  1500
tgtggtggcc agggttggac tggtcctacc acctgcgcta gtggaaccac atgcaccgtc  1560
gtgaaccctt actactctca atgtttgtaa                                   1590
```

<210> SEQ ID NO 52
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95
```

```
Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Ser Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
```

Leu

<210> SEQ ID NO 53
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggcg gacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca acacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg tgggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 54
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
```

|  |  | 405 |  |  | 410 |  |  | 415 |  |

| Thr | Pro | Gly | Ala | Ala | Arg | Gly | Ser | Cys | Pro | Thr | Thr | Ser | Gly | Asp | Pro |
|  |  |  | 420 |  |  |  |  | 425 |  |  |  |  | 430 |  |  |

| Lys | Thr | Val | Glu | Ser | Gln | Ser | Gly | Ser | Ser | Tyr | Val | Thr | Phe | Ser | Asp |
|  |  |  |  | 435 |  |  |  |  | 440 |  |  |  |  | 445 |  |

| Ile | Arg | Trp | Gly | Pro | Phe | Asn | Ser | Thr | Phe | Ser | Gly | Gly | Ser | Ser | Thr |
|  | 450 |  |  |  |  | 455 |  |  |  |  | 460 |  |  |  |  |

| Gly | Gly | Ser | Ser | Thr | Thr | Thr | Ala | Ser | Gly | Thr | Thr | Thr | Thr | Lys | Ala |
| 465 |  |  |  |  | 470 |  |  |  |  | 475 |  |  |  |  | 480 |

| Ser | Ser | Thr | Ser | Thr | Ser | Ser | Thr | Ser | Thr | Gly | Thr | Gly | Val | Ala | Ala |
|  |  |  |  | 485 |  |  |  |  | 490 |  |  |  |  | 495 |  |

| His | Trp | Gly | Gln | Cys | Gly | Gly | Gln | Gly | Trp | Thr | Gly | Pro | Thr | Thr | Cys |
|  |  |  | 500 |  |  |  |  | 505 |  |  |  |  | 510 |  |  |

| Ala | Ser | Gly | Thr | Thr | Cys | Thr | Val | Val | Asn | Pro | Tyr | Tyr | Ser | Gln | Cys |
|  |  |  | 515 |  |  |  |  | 520 |  |  |  |  | 525 |  |  |

Leu

<210> SEQ ID NO 55
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtgggcgt ctccaagtac     540
cccaacaaca aggccggcgc tcagtacggt gttggatact gtgactctca atgccctcgt     600
gacttgaaat tcatcgctgg tcaggccaac gttgagggcg gacgccctc ctccaacaac     660
gccaacactg acttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccaccttggg cgagactgcc tccttcagca aacacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
```

-continued

```
gctcgtggtt cctgccctac cacttctggg gaccctaaga ccgttgaatc acaatccggc   1320
agctcctatg tcaccttttc tgacatccgg gttggtcctt cggttctac gttcagcggt    1380 ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 56
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
```

```
                290                 295                 300
Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
                355                 360                 365

Thr Ala Ser Phe Ser Lys His Gly Gly Leu Ala Lys Met Gly Ala Gly
                370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
                420                 425                 430

Lys Thr Val Glu Ser Gln Ser Gly Ser Ser Tyr Val Thr Phe Ser Asp
                435                 440                 445

Ile Arg Val Gly Pro Phe Gly Ser Thr Phe Ser Gly Gly Ser Ser Thr
                450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
                500                 505                 510

Ala Ser Gly Thr Thr Cys Thr Val Val Asn Pro Tyr Tyr Ser Gln Cys
                515                 520                 525

Leu

<210> SEQ ID NO 57
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
```

```
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960 tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acacggtgg cctggcaaag    1140 atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt    1380
ggttctaaga ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 58
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
```

```
                180                 185                 190
Tyr Cys Asp Ser Gln Cys Pro Arg Asp Leu Lys Phe Ile Ala Gly Gln
                195                 200                 205

Ala Asn Val Glu Gly Trp Thr Pro Ser Ser Asn Asn Ala Asn Thr Gly
        210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
                420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Lys Thr
        450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 59
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
```

-continued

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg acttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca      960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca acacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 60
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr

```
                65                  70                  75                  80
          Trp Asn Thr Ala Ile Cys Asp Thr Asp Ala Ser Cys Ala Gln Asp Cys
                              85                  90                  95

Ala Leu Asp Gly Ala Asp Tyr Ser Gly Thr Tyr Gly Ile Thr Thr Ser
                             100                 105                 110

Gly Asn Ser Leu Arg Leu Asn Phe Val Thr Gly Ser Asn Val Gly Ser
                             115                 120                 125

Arg Thr Tyr Leu Met Ala Asp Asn Thr His Tyr Gln Ile Phe Asp Leu
                 130                 135                 140

Leu Asn Gln Glu Phe Thr Phe Thr Val Asp Val Ser His Leu Pro Cys
          145                 150                 155                 160

Gly Leu Asn Gly Ala Leu Tyr Phe Val Thr Met Asp Ala Asp Gly Gly
                             165                 170                 175

Val Ser Lys Tyr Pro Asn Asn Lys Ala Gly Ala Gln Tyr Gly Val Gly
                             180                 185                 190

Tyr Cys Asp Ser Gln Cys Pro Arg Asp Leu Lys Phe Ile Ala Gly Gln
                             195                 200                 205

Ala Asn Val Glu Gly Trp Thr Pro Ser Ser Asn Asn Ala Asn Thr Gly
                 210                 215                 220

Leu Gly Asn His Gly Ala Cys Cys Ala Glu Leu Asp Ile Trp Glu Ala
          225                 230                 235                 240

Asn Ser Ile Ser Glu Ala Leu Thr Pro His Pro Cys Asp Thr Pro Gly
                             245                 250                 255

Leu Ser Val Cys Thr Thr Asp Ala Cys Gly Gly Thr Tyr Ser Ser Asp
                             260                 265                 270

Arg Tyr Ala Gly Thr Cys Asp Pro Asp Gly Cys Asp Phe Asn Pro Tyr
                             275                 280                 285

Arg Leu Gly Val Thr Asp Phe Tyr Gly Ser Gly Lys Thr Val Asp Thr
                 290                 295                 300

Thr Lys Pro Ile Thr Val Val Thr Gln Phe Val Thr Asp Asp Gly Thr
          305                 310                 315                 320

Ser Thr Gly Thr Leu Ser Glu Ile Arg Arg Tyr Tyr Val Gln Asn Gly
                             325                 330                 335

Val Val Ile Pro Gln Pro Ser Ser Lys Ile Ser Gly Val Ser Gly Asn
                             340                 345                 350

Val Ile Asn Ser Asp Phe Cys Asp Ala Glu Ile Ser Thr Phe Gly Glu
                             355                 360                 365

Thr Ala Ser Phe Ser Lys His Gly Gly Leu Ala Lys Met Gly Ala Gly
                 370                 375                 380

Met Glu Ala Gly Met Val Leu Val Met Ser Leu Trp Asp Asp Tyr Ser
          385                 390                 395                 400

Val Asn Met Leu Trp Leu Asp Ser Thr Tyr Pro Thr Asn Ala Thr Gly
                             405                 410                 415

Thr Pro Gly Ala Ala Arg Gly Ser Cys Pro Thr Thr Ser Gly Asp Pro
                             420                 425                 430

Lys Thr Val Glu Ser Gln Ser Gly Ser Ser Tyr Val Thr Phe Ser Asp
                             435                 440                 445

Ile Arg Val Gly Pro Phe Asn Ser Thr Phe Ser Gly Gly Ser Ser Thr
                 450                 455                 460

Gly Gly Ser Ser Thr Thr Thr Ala Ser Gly Thr Thr Thr Thr Lys Ala
          465                 470                 475                 480

Ser Ser Thr Ser Thr Ser Ser Thr Ser Thr Gly Thr Gly Val Ala Ala
                             485                 490                 495
```

His Trp Gly Gln Cys Gly Gly Gln Gly Trp Thr Gly Pro Thr Thr Cys
             500                 505                 510

Ala Ser Gly Thr Thr Cys Thr Val Val Asn Pro Tyr Tyr Ser Gln Cys
         515                 520                 525

Leu

<210> SEQ ID NO 61
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

| | |
|---|---|
| atgtctgcct tgaactcttt caatatgtac aagagcgccc tcatcttggg ctccttgctg | 60 |
| gcaacagctg gtgctcagca aattggtact tataccgctg aaacccatcc ctctttgagc | 120 |
| tggtctactt gcaaatcggg tggtagctgc accacaaact ccggtgccat tacgttggat | 180 |
| gccaactggc gttgggtcca tggtgtcaat accagcacca actgctacac tggcaacact | 240 |
| tggaataccg ccatctgcga cactgatgca tcctgtgccc aggactgtgc tcttgatggt | 300 |
| gctgactaca atggcacgta cggtatcact acctccggca actcattgcg cctgaacttc | 360 |
| gttaccggtt ccaacgtcgg atctcgtacc tacctgatgg ccgataacac ccactaccaa | 420 |
| atcttcgact tgttgaacca ggagttcact ttcaccgtcg atgtctccca cctcccttgc | 480 |
| ggtttgaacg gtgccctcta cttcgtgacc atggacgccg acggtggcgt ctccaagtac | 540 |
| cccaacaaca aggccggcgc tcagtacggt gttggatact gtgactctca atgccctcgt | 600 |
| gacttgaaat tcatcgctgg tcaggccaac gttgagggct ggacgccctc ctccaacaac | 660 |
| gccaacactg gacttggcaa ccacggagct tgctgcgcag agcttgatat ctgggaggca | 720 |
| aacagcatct cagaggcttt gactcctcac ccttgcgata caccccggtct atctgtttgc | 780 |
| actactgatg cctgcggtgg tacctacagc tccgatcgtt acgccggtac ctgcgaccct | 840 |
| gatggatgtg acttcaaccc ttaccgtctt ggtgtcactg acttctacgg ctccggcaag | 900 |
| accgttgaca ccaccaaacc catcaccgtt gtgactcaat cgtcactga cgacggcaca | 960 |
| tccaccggca ccctctccga gatcagacgt tactacgttc agaacggtgt tgtcatcccc | 1020 |
| cagccttcct ccaagatctc cggagtcagc ggaaatgtca tcaactccga cttctgcgat | 1080 |
| gctgagatct ccacctttgg cgagactgcc tccttcagca aacacggtgg cctggcaaag | 1140 |
| atgggcgctg gtatggaagc tggtatggtc ttggtcatga gtttgtggga cgactactcc | 1200 |
| gtcaacatgc tctggctcga cagcacctac cctacaaacg cgactggtac ccccggtgcc | 1260 |
| gctcgtggtt cctgccctac cacttctggg acccctaaga ccgttgaatc acaatccggc | 1320 |
| agctcctatg tcacctttc tgacatccgg gttggtcctt caactctac gttcagcggt | 1380 |
| ggttctagca ccggtggcag ctccactact accgccagcg gcaccaccac caccaaggcc | 1440 |
| tcttccacct ctacttccag cacctctacc ggcactggag tcgctgctca ctggggtcag | 1500 |
| tgtggtggcc agggttggac tggtcctacc acctgcgcta gtggaaccac atgcaccgtc | 1560 |
| gtgaacccct actactctca atgtttgtaa | 1590 |

<210> SEQ ID NO 62
<211> LENGTH: 529
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Asn Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380
```

```
Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Tyr Val Thr Phe Ser Asp
            435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu
```

<210> SEQ ID NO 63
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcga cactgatgca tcctgtgccc aggactgtgc tcttgatggt     300
gctgactact ctgcacgta cggtatcact acctccggca actcattgcg cctgaacttc     360
agtaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctcccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
```

-continued

```
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560 gtgaacccctt actactctca atgtttgtaa    1590
```

<210> SEQ ID NO 64
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Ser Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270
```

```
Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
            325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu

<210> SEQ ID NO 65
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
actaccggtt ccaacgtcgg atctcgtacc tacctgatgg ccgataacac ccactaccaa     420
atcttcgact tgttgaacca ggagttcact ttcaccgtcg atgtctccca cctcccttgc     480
```

-continued

```
ggtttgaacg gtgccctcta cttcgtgacc atggacgccg acggtggcgt ctccaagtac      540
cccaacaaca aggccggcgc tcagtacggt gttggatact gtgactctca atgccctcgt      600
gacttgaaat tcatcgctgg tcaggccaac gttgagggct ggacgccctc ctccaacaac      660
gccaacactg gacttggcaa ccacggagct tgctgcgcag agcttgatat ctgggaggca      720
aacagcatct cagaggcttt gactcctcac ccttgcgata cacccggtct atctgtttgc      780
actactgatg cctgcggtgg tacctacagc tccgatcgtt acgccggtac ctgcgaccct      840
gatggatgtg acttcaaccc ttaccgtctt ggtgtcactg acttctacgg ctccggcaag      900
accgttgaca ccaccaaacc catcaccgtt gtgactcaat cgtcactga cgacggcaca      960 tccaccggca ccctctccga gatcagacgt tactacgttc agaacggtgt tgtcatcccc     1020
cagccttcct ccaagatctc cggagtcagc ggaaatgtca tcaactccga cttctgcgat     1080
gctgagatct ccacctttgg cgagactgcc tccttcagca aacacggtgg cctggcaaag     1140
atgggcgctg gtatggaagc tggtatggtc ttggtcatga gtttgtggga cgactactcc     1200
gtcaacatgc tctggctcga cagcacctac cctacaaacg cgactggtac ccccggtgcc     1260
gctcgtggtt cctgccctac cacttctggg gaccctaaga ccgttgaatc acaatccggc     1320
agctcctatg tcacctttc tgacatccgg gttggtcctt tcaactctac gttcagcggt     1380
ggttctagca ccggtggcag ctccactact accgccagcg gcaccaccac caccaaggcc     1440
tcttccacct ctacttccag cacctctacc ggcactggag tcgctgctca ctggggtcag     1500
tgtggtggcc agggttggac tggtcctacc acctgcgcta gtggaaccac atgcaccgtc     1560
gtgaaccctt actactctca atgtttgtaa                                      1590
```

<210> SEQ ID NO 66
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Thr Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160
```

Gly Leu Asn Gly Ala Leu Tyr Phe Val Thr Met Asp Ala Asp Gly Gly
                165                 170                 175
Val Ser Lys Tyr Pro Asn Asn Lys Ala Gly Ala Gln Tyr Gly Val Gly
            180                 185                 190
Tyr Cys Asp Ser Gln Cys Pro Arg Asp Leu Lys Phe Ile Ala Gly Gln
        195                 200                 205
Ala Asn Val Glu Gly Trp Thr Pro Ser Ser Asn Asn Ala Asn Thr Gly
    210                 215                 220
Leu Gly Asn His Gly Ala Cys Cys Ala Glu Leu Asp Ile Trp Glu Ala
225                 230                 235                 240
Asn Ser Ile Ser Glu Ala Leu Thr Pro His Pro Cys Asp Thr Pro Gly
                245                 250                 255
Leu Ser Val Cys Thr Thr Asp Ala Cys Gly Gly Thr Tyr Ser Ser Asp
            260                 265                 270
Arg Tyr Ala Gly Thr Cys Asp Pro Asp Gly Cys Asp Phe Asn Pro Tyr
        275                 280                 285
Arg Leu Gly Val Thr Asp Phe Tyr Gly Ser Gly Lys Thr Val Asp Thr
    290                 295                 300
Thr Lys Pro Ile Thr Val Val Thr Gln Phe Val Thr Asp Gly Thr
305                 310                 315                 320
Ser Thr Gly Thr Leu Ser Glu Ile Arg Arg Tyr Tyr Val Gln Asn Gly
                325                 330                 335
Val Val Ile Pro Gln Pro Ser Ser Lys Ile Ser Gly Val Ser Gly Asn
            340                 345                 350
Val Ile Asn Ser Asp Phe Cys Asp Ala Glu Ile Ser Thr Phe Gly Glu
        355                 360                 365
Thr Ala Ser Phe Ser Lys His Gly Gly Leu Ala Lys Met Gly Ala Gly
    370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
            420                 425                 430
Lys Thr Val Glu Ser Gln Ser Gly Ser Ser Tyr Val Thr Phe Ser Asp
        435                 440                 445
Ile Arg Val Gly Pro Phe Asn Ser Thr Phe Ser Gly Gly Ser Ser Thr
    450                 455                 460
Gly Gly Ser Ser Thr Thr Thr Ala Ser Gly Thr Thr Thr Thr Lys Ala
465                 470                 475                 480
Ser Ser Thr Ser Thr Ser Ser Thr Ser Thr Gly Thr Gly Val Ala Ala
                485                 490                 495
His Trp Gly Gln Cys Gly Gly Gln Gly Trp Thr Gly Pro Thr Thr Cys
            500                 505                 510
Ala Ser Gly Thr Thr Cys Thr Val Val Asn Pro Tyr Tyr Ser Gln Cys
        515                 520                 525
Leu

<210> SEQ ID NO 67
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 67

```
atgtctgcct tgaactcttt caatatgtac aagagcgccc tcatcttggg ctccttgctg    60
gcaacagctg gtgctcagca aattggtact tataccgctg aaacccatcc ctctttgagc   120
tggtctactt gcaaatcggg tggtagctgc accacaaact ccggtgccat tacgttggat   180
gccaactggc gttgggtcca tggtgtcaat accagcacca actgctacac tgcaacact    240
tggaataccg ccatctgcga cactgatgca tcctgtgccc aggactgtgc tcttgatggt   300
gctgactact ctggcacgta cggtatcact acctccaata actcattgcg cctgaacttc   360
gttaccggtt ccaacgtcgg atctcgtacc tacctgatgg ccgataacac ccactaccaa   420
atcttcgact tgttgaacca ggagttcact ttcaccgtcg atgtctccca cctcccttgc   480
ggtttgaacg gtgccctcta cttcgtgacc atggacgccg acggtggcgt ctccaagtac   540
cccaacaaca aggccggcgc tcagtacggt gttggatact gtgactctca atgccctcgt   600
gacttgaaat tcatcgctgg tcaggccaac gttgagggct ggacgccctc ctccaacaac   660
gccaacactg gacttggcaa ccacggagct tgctgcgcag agcttgatat ctgggaggca   720
aacagcatct cagaggcttt gactcctcac ccttgcgata cacccggtct atctgtttgc   780
actactgatg cctgcggtgg tacctacagc tccgatcgtt acgccggtac ctgcgaccct   840
gatggatgtg acttcaaccc ttaccgtctt ggtgtcactg acttctacgg ctccggcaag   900
accgttgaca ccaccaaacc catcaccgtt gtgactcaat cgtcactga cgacggcaca    960
tccaccggca ccctctccga gatcagacgt tactacgttc agaacggtgt tgtcatcccc  1020
cagccttcct ccaagatctc cggagtcagc ggaaatgtca tcaactccga cttctgcgat  1080
gctgagatct ccacctttgg cgagactgcc tccttcagca acacggtgg cctggcaaag   1140
atgggcgctg gtatggaagc tggtatggtc ttggtcatga gtttgtggga cgactactcc  1200
gtcaacatgc tctggctcga cagcacctac cctacaaacg cgactggtac ccccggtgcc  1260
gctcgtggtt cctgccctac cacttctggg gaccctaaga ccgttgaatc acaatccggc  1320
agctcctatg tcaccttttc tgacatccgg gttggtcctt tcaactctac gttcagcggt  1380
ggttctagca ccggtggcag ctccactact accgccagcg gcaccaccac caccaaggcc  1440
tcttccacct ctacttccag cacctctacc ggcactggag tcgctgctca ctggggtcag  1500
tgtggtggcc agggttggac tggtcctacc acctgcgcta gtggaaccac atgcaccgtc  1560
gtgaacccctt actactctca atgtttgtaa                                  1590
```

<210> SEQ ID NO 68
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 68

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

-continued

```
Ser Cys Thr Thr Asn Ser Gly Ala Ile Thr Leu Asp Ala Asn Trp Arg
 50              55                  60

Trp Val His Gly Val Asn Thr Ser Thr Asn Cys Tyr Thr Gly Asn Thr
 65              70                  75                  80

Trp Asn Thr Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
                100                 105                 110

Asn Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
        130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
450                 455                 460
```

Gly Gly Ser Ser Thr Thr Ala Ser Gly Thr Thr Thr Lys Ala
465                 470                 475                 480

Ser Ser Thr Ser Thr Ser Ser Ser Thr Gly Thr Gly Val Ala Ala
            485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu

<210> SEQ ID NO 69
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcaacgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg acttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac cccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 70
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Thr Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350
```

Val Ile Asn Ser Asp Phe Cys Asp Ala Glu Ile Ser Thr Phe Gly Glu
           355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 71
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 71
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tgcaacactt     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tgtttacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960

```
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560 gtgaacccctt actactctca atgtttgtaa                                   1590
```

<210> SEQ ID NO 72
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240
```

```
Asn Ser Ile Ser Glu Ala Leu Thr Pro His Pro Cys Asp Thr Pro Gly
            245                 250                 255
Leu Ser Val Cys Thr Thr Asp Ala Cys Gly Gly Val Tyr Ser Ser Asp
        260                 265                 270
Arg Tyr Ala Gly Thr Cys Asp Pro Asp Gly Cys Asp Phe Asn Pro Tyr
    275                 280                 285
Arg Leu Gly Val Thr Asp Phe Tyr Gly Ser Gly Lys Thr Val Asp Thr
290                 295                 300
Thr Lys Pro Ile Thr Val Thr Gln Phe Val Thr Asp Asp Gly Thr
305                 310                 315                 320
Ser Thr Gly Thr Leu Ser Glu Ile Arg Arg Tyr Tyr Val Gln Asn Gly
            325                 330                 335
Val Val Ile Pro Gln Pro Ser Ser Lys Ile Ser Gly Val Ser Gly Asn
        340                 345                 350
Val Ile Asn Ser Asp Phe Cys Asp Ala Glu Ile Ser Thr Phe Gly Glu
    355                 360                 365
Thr Ala Ser Phe Ser Lys His Gly Gly Leu Ala Lys Met Gly Ala Gly
370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
            405                 410                 415
Thr Pro Gly Ala Ala Arg Gly Ser Cys Pro Thr Thr Ser Gly Asp Pro
        420                 425                 430
Lys Thr Val Glu Ser Gln Ser Gly Ser Ser Tyr Val Thr Phe Ser Asp
    435                 440                 445
Ile Arg Val Gly Pro Phe Asn Ser Thr Phe Ser Gly Gly Ser Ser Thr
450                 455                 460
Gly Gly Ser Ser Thr Thr Thr Ala Ser Gly Thr Thr Thr Lys Ala
465                 470                 475                 480
Ser Ser Thr Ser Thr Ser Ser Ser Thr Gly Thr Gly Val Ala Ala
            485                 490                 495
His Trp Gly Gln Cys Gly Gly Gln Gly Trp Thr Gly Pro Thr Thr Cys
        500                 505                 510
Ala Ser Gly Thr Thr Cys Thr Val Val Asn Pro Tyr Tyr Ser Gln Cys
    515                 520                 525
Leu
```

<210> SEQ ID NO 73
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73

| | | | | | |
|---|---|---|---|---|---|
| atgtctgcct | tgaactcttt | caatatgtac | aagagcgccc | tcatcttggg ctccttgctg | 60 |
| gcaacagctg | gtgctcagca | aattggtact | tataccgctg | aagctcatcc ctctttgagc | 120 |
| tggtctactt | gcaaatcggg | tggtagctgc | accacaaact | ccggtgccat tacgttggat | 180 |
| gccaactggc | gttgggtcca | tggtgtcaat | accagcacca | actgctacac tggcaacact | 240 |
| tggaataccg | ccatctgcga | cactgatgca | tcctgtgccc | aggactgtgc tcttgatggt | 300 |
| gctgactact | ctggcacgta | cggtatcact | acctccggca | actcattgcg cctgaacttc | 360 |

```
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca aacacggtgg cctggcaaag   1140
atgggcgctg gtatggaagc tggtatggtc ttggtcatga gtttgtggga cgactactcc   1200
gccaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctgggtcag   1500
tgtggtggcc agggttggac tggtcctacc acctgcgcta gtggaaccac atgcaccgtc   1560
gtgaacccctt actactctca atgtttgtaa                                   1590
```

<210> SEQ ID NO 74
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Ala His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

```
Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
                195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
    275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
                355                 360                 365

Thr Ala Ser Phe Ser Lys His Gly Gly Leu Ala Lys Met Gly Ala Gly
                370                 375                 380

Met Glu Ala Gly Met Val Leu Val Met Ser Leu Trp Asp Asp Tyr Ser
385                 390                 395                 400

Ala Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
                420                 425                 430

Lys Thr Val Glu Ser Gln Ser Gly Ser Ser Tyr Val Thr Phe Ser Asp
                435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
                500                 505                 510

Ala Ser Gly Thr Thr Cys Thr Val Val Asn Pro Tyr Tyr Ser Gln Cys
                515                 520                 525

Leu

<210> SEQ ID NO 75
```

<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

| | | | | | |
|---|---|---|---|---|---|
| atgtctgcct | tgaactcttt | caatatgtac | aagagcgccc | tcatcttggg | ctccttgctg | 60 |
| gcaacagctg | gtgctcagca | aattggtact | tataccgctg | aaacccatcc | ctctttgagc | 120 |
| tggtctactt | gcaaatcggg | tggtagctgc | accacaaact | ccggtgccat | tacgttggat | 180 |
| gccaactggc | gttgggtcca | tggtgtcaat | accagcacca | actgctacac | tggcaacact | 240 |
| tggaataccg | ccatctgcga | cactgatgca | tcctgtgccc | aggactgtgc | tcttgatggt | 300 |
| gctgactact | ctggcacgta | cggtatcact | acctccggca | actcattgcg | cctgaacttc | 360 |
| gttaccggtt | ccaacgtcgg | atctcgtacc | tacctgatgg | ccgataacac | ccactaccaa | 420 |
| atcttcgact | tgttgaacca | ggagttcact | ttcaccgtcg | atgtctccca | cctcccttgc | 480 |
| ggtttgaacg | gtgccctcta | cttcgtgacc | atggacgccg | acggtggcgt | ctccaagtac | 540 |
| cccaacaaca | aggccggcgc | tcagtacggt | gttggatact | gtgactctca | atgccctcgt | 600 |
| gacttgaaat | tcatcgctgg | tcaggccaac | gttgagggct | ggacgccctc | ctccaacaac | 660 |
| gccaacactg | gacttggcaa | ccacggagct | tgctgcgcag | agcttgatat | ctgggaggca | 720 |
| aacagcatct | cagaggcttt | gactcctcac | ccttgcgata | caccccggtct | atctgtttgc | 780 |
| actactgatg | cctgcggtgg | tacctacagc | tccgatcgtt | acgccggtac | ctgcgaccct | 840 |
| gatggatgtg | acttcaaccc | ttaccgtctt | ggtgtcactg | acttctacgg | ctccggcaag | 900 |
| accgttgaca | ccaccaaacc | catcaccgtt | gtgactcaat | cgtcactga | cgacggcaca | 960 |
| tccaccggca | ccctctccga | gatcagacgt | tactacgttc | agaacggtgt | tgtcatcccc | 1020 |
| cagccttcct | ccaagatctc | cggagtcagc | ggaaatgtca | tcaactccga | cttctgcgat | 1080 |
| gctgagatct | ccacctttgg | cgagactgcc | tccttcagca | aacacggtgg | cctggcaaag | 1140 |
| atgggcgctg | gtatggaagc | tggtatggtc | ttgactatga | gtttgtggga | cgactactcc | 1200 |
| gtcaacatgc | tctggctcga | cagcacctac | cctacaaacg | cgactggtac | ccccggtgcc | 1260 |
| gctcgtggtt | cctgccctac | cacttctggg | gaccctaaga | ccgttgaatc | acaatccggc | 1320 |
| agctcctatg | tcaccttttc | tgacatccgg | gttggtcctt | tcaactctac | gttcagcggt | 1380 |
| ggttctagca | ccggtggcag | ctccactact | accgccagcg | gcaccaccac | caccaaggcc | 1440 |
| tcttccacct | ctacttccag | cacctctacc | ggcactggag | tcgctgctca | ctgggtcag | 1500 |
| tgtggtggcc | agggttggac | tggtcctacc | acctgcgcta | gtggaaccac | atgcaccgtc | 1560 |
| gtgaacccctt | actactctca | atgtttgtaa | | | | 1590 |

<210> SEQ ID NO 76
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

Met Ser Ala Leu Asn Ser Phe Asn Met Tyr Lys Ser Ala Leu Ile Leu
1               5                   10                  15

-continued

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Thr Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp

```
            435                 440                 445
Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu
```

<210> SEQ ID NO 77
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg acttggcaa ccacggagct tgctgcgcag agcttgatat ctgggaggca     720
aacagcatct cagaggcttt gactcctcac ccttgcgata caccggtct atctgtttgc     780
actactgatg cctgcggtgg tacctacagc tccgatcgtt acgccggtac ctgcgacccc     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga tcagacgt tactacgttc agaacggtgt tgtcatcccc    1020
cagccttcct ccaagatctc cggagtcagc ggaaatgtca tcaactccga cttctgcgat    1080
gctgagatct ccaccttgg cgagactgcc tccttcagca aacacggtgg cctggcaaag    1140
atgggcgctg gtatggaagc tggtatggtc ttggtcatga gtttgtggga cgacgattcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accgccagcg gcaccaccac caccaaggcc    1440
```

-continued

```
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaacccTT actactctca atgtttgtaa                                     1590
```

<210> SEQ ID NO 78
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly

```
                    325                 330                 335
Val Val Ile Pro Gln Pro Ser Ser Lys Ile Ser Gly Val Ser Gly Asn
                340                 345                 350
Val Ile Asn Ser Asp Phe Cys Asp Ala Glu Ile Ser Thr Phe Gly Glu
                355                 360                 365
Thr Ala Ser Phe Ser Lys His Gly Gly Leu Ala Lys Met Gly Ala Gly
            370                 375                 380
Met Glu Ala Gly Met Val Leu Val Met Ser Leu Trp Asp Asp Asp Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
            420                 425                 430
Lys Thr Val Glu Ser Gln Ser Gly Ser Ser Tyr Val Thr Phe Ser Asp
                435                 440                 445
Ile Arg Val Gly Pro Phe Asn Ser Thr Phe Ser Gly Gly Ser Ser Thr
            450                 455                 460
Gly Gly Ser Ser Thr Thr Thr Ala Ser Gly Thr Thr Thr Lys Ala
465                 470                 475                 480
Ser Ser Thr Ser Thr Ser Ser Thr Ser Thr Gly Thr Gly Val Ala Ala
                485                 490                 495
His Trp Gly Gln Cys Gly Gly Gln Gly Trp Thr Gly Pro Thr Thr Cys
            500                 505                 510
Ala Ser Gly Thr Thr Cys Thr Val Val Asn Pro Tyr Tyr Ser Gln Cys
            515                 520                 525
Leu

<210> SEQ ID NO 79
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt caacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgttgc      780 actactgatg cctgcggtgg tacctacagc tccgatcgtt acgccggtac ctgcgaccct     840
```

```
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acacggtgg cctggcaaag   1140
atgggcgctg gtatggaagc tggtatggtc ttggtcatga gtttgtggga cgactactcc   1200
gataacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt caactctac gttcagcggt    1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 80
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
```

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
            245                 250                 255

Leu Ser Val Cys Thr Thr Asp Ala Cys Gly Thr Tyr Ser Ser Asp
        260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
        370                 375                 380

Met Glu Ala Gly Met Val Leu Val Met Ser Leu Trp Asp Asp Tyr Ser
385                 390                 395                 400

Asp Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 81
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81
atgtctgcct tgaactcttt caatatgtac aagagcgccc tcatcttggg ctccttgctg     60
gcaacagctg gtgctcagca aattggtact tataccgctg aaacccatcc ctctttgagc    120
tggtctactt gcaaatcggg tggtagctgc accacaaact ccggtgccat tacgttggat    180

```
gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg tgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg acttggcaa ccacggagct tgctgcgcag agcttgatat ctgggaggca    720
aacagcatct cagaggcttt gactcctcac ccttgcgata caccgggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgacccaat cgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccaccttttgg cgagactgcc tccttcagca acacggtgg cctggcaaag   1140
atgggcgctg gtatggaagc tggtatggtc ttggccatga gtttgtggga cgactactcc   1200
gctaacatgc tctggctcga cagcacctac cctacaaacg cgactggtgc ccccggtgcc   1260
gctcgtggtt cctgccctac cacttctggg gaccctaaga ccgttgaatc acaatccggc   1320
agctcctatg tcaccttttc tgacatccgg gttggtcctt caactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 82
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 82

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser

```
                100                 105                 110
Gly Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
            195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
            290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
370                 375                 380

Met Glu Ala Gly Met Val Leu Ala Met Ser Leu Trp Asp Asp Tyr Ser
385                 390                 395                 400

Ala Asn Met Leu Trp Leu Asp Ser Thr Tyr Pro Thr Asn Ala Thr Gly
                405                 410                 415

Ala Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525
```

Leu

<210> SEQ ID NO 83
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggtg gacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gtcaacatga cttggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt tcaactctac gttcagcggt    1380
ggttctagca ccgtggcag ctccactact accgccagcg gcaccaccac caccaaggcc    1440
tcttccacct ctacttccag cacctctacc ggcactggag tcgctgctca ctgggtcag    1500
tgtggtggcc agggttggac tggtcctacc acctgcgcta gtggaaccac atgcaccgtc    1560
gtgaacccct actactctca atgtttgtaa                                      1590
```

<210> SEQ ID NO 84
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Thr Trp Leu Asp Ser Thr Tyr Pro Thr Asn Ala Thr Gly
                405                 410                 415
```

```
Thr Pro Gly Ala Ala Arg Gly Ser Cys Pro Thr Thr Ser Gly Asp Pro
            420                 425                 430
Lys Thr Val Glu Ser Gln Ser Gly Ser Ser Tyr Val Thr Phe Ser Asp
            435                 440                 445
Ile Arg Val Gly Pro Phe Asn Ser Thr Phe Ser Gly Gly Ser Ser Thr
            450                 455                 460
Gly Gly Ser Ser Thr Thr Thr Ala Ser Gly Thr Thr Thr Lys Ala
465                 470                 475                 480
Ser Ser Thr Ser Thr Ser Ser Thr Ser Thr Gly Thr Gly Val Ala Ala
                485                 490                 495
His Trp Gly Gln Cys Gly Gly Gln Gly Trp Thr Gly Pro Thr Thr Cys
            500                 505                 510
Ala Ser Gly Thr Thr Cys Thr Val Val Asn Pro Tyr Tyr Ser Gln Cys
            515                 520                 525
Leu
```

<210> SEQ ID NO 85
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 85

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540
cccaacaaca aggccggcgc tcagtacggt gttggatact gtgactctca atgccctcgt     600
gacttgaaat tcatcgctgg tcaggccaac gttgagggcg gacgccctc ctccaacaac     660
gccaacactg acttggcaa ccacggagct tgctgcgcag agcttgatat ctgggaggca     720
aacagcatct cagaggcttt gactcctcac ccttgcgata cccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccaccttgg cgagactgcc tccttcagca acacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg accctaaga ccgttgaatc acaatccggc    1320
```

```
agctcctatg tcaccttttc tgacatccgg gttggtcctt tcaactctac gttcagcggt    1380
ggttcttata ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 86
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 86

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300
```

```
Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
            325                 330                 335

Val Val Ile Pro Gln Pro Ser Ser Lys Ile Ser Gly Val Ser Gly Asn
        340                 345                 350

Val Ile Asn Ser Asp Phe Cys Asp Ala Glu Ile Ser Thr Phe Gly Glu
    355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
        420                 425                 430

Lys Thr Val Glu Ser Gln Ser Gly Ser Ser Tyr Val Thr Phe Ser Asp
    435                 440                 445

Ile Arg Val Gly Pro Phe Asn Ser Thr Phe Ser Gly Gly Ser Tyr Thr
450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
        500                 505                 510

Ala Ser Gly Thr Thr Cys Thr Val Val Asn Pro Tyr Tyr Ser Gln Cys
        515                 520                 525

Leu
```

<210> SEQ ID NO 87
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660
```

```
gtcaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcacg    960 tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acacggtgg cctggcaaag   1140 atgggcgctg gtatggaagc tggtatggtc ttggtcatga gtttgtggga cgactactcc   1200
gccaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccggtggcag ctccactact accgccagct ggaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                   1590
```

<210> SEQ ID NO 88  
<211> LENGTH: 529  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 88

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190
```

```
Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Val Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
            290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
            370                 375                 380

Met Glu Ala Gly Met Val Leu Val Met Ser Leu Trp Asp Asp Tyr Ser
385                 390                 395                 400

Ala Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
                420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
            450                 455                 460

Gly Gly Ser Ser Thr Thr Thr Ala Ser Trp Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu

<210> SEQ ID NO 89
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
atgtctgcct tgaactcttt caatatgtac aagagcgccc tcatcttggg ctccttgctg    60
```

```
gcaacagctg gtgctcagca aattggtact tataccgctg aaacccatcc ctctttgagc    120
tggtctactt gcaaatcggg tggtagctgc accacaaact ccggtgccat acgttggat     180 gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg tgccctcta cttcgtgacc atggacgccg acggtggcgt ctccaagtac     540
cccaacaaca aggccggcgc tcagtacggt gttggatact gtgactctca atgccctcgt    600
gacttgaaat tcatcgctgg tcaggccaac gttgagggtg gacgccctc ctccaacaac     660 gccaacactg acttggcaa ccacggagct tgctgcgcag agcttgatat ctgggaggca     720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca     960 tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca acacggtgg cctggcaaag    1140 atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accatgagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                    1590
```

<210> SEQ ID NO 90
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80
```

```
Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
        130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
                195                 200                 205

Ala Asn Val Glu Gly Trp Thr Pro Ser Ser Asn Asn Ala Asn Thr Gly
            210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
                420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Met Ser Gly Thr Thr Thr Lys Ala
465                 470                 475                 480

Ser Ser Thr Ser Thr Ser Ser Thr Gly Thr Gly Val Ala Ala
                485                 490                 495
```

His Trp Gly Gln Cys Gly Gly Gln Gly Trp Thr Gly Pro Thr Thr Cys
               500                 505                 510

Ala Ser Gly Thr Thr Cys Thr Val Val Asn Pro Tyr Tyr Ser Gln Cys
        515                 520                 525

Leu

<210> SEQ ID NO 91
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg tgccctcta cttcgtgacc atggacgccg acggtggcgt ctccaagtac     540
cccaacaaca aggccggcgc tcagtacggt gttggatact gtgactctca atgccctcgt     600
gacttgaaat catcgctgg tcaggccaac gttgagggc ggacgccctc ctccaacaac      660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca      960
tccaccggca ccctctccga gattagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gccaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt caactctac gttcagcggt    1380
ggttctagca ccggtggcag ctccactact accgccagcg gcaccaccac caccaaggcc    1440
tcttccacct ctacttccag cacctctacc ggcactggac ttgctgctca ctggggtcag    1500
tgtggtggcc agggttggac tggtcctacc acctgcgcta gtggaaccac atgcaccgtc    1560
gtgaacccttt actactctca atgtttgtaa                                    1590
```

<210> SEQ ID NO 92
<211> LENGTH: 529
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 92

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
370                 375                 380
```

```
Met Glu Ala Gly Met Val Leu Val Met Ser Leu Trp Asp Asp Tyr Ser
385                 390                 395                 400

Ala Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Leu Ala Ala
                485                 490                 495

His Trp Gly Gln Cys Gly Gly Gln Gly Trp Thr Gly Pro Thr Thr Cys
                500                 505                 510

Ala Ser Gly Thr Thr Cys Thr Val Val Asn Pro Tyr Tyr Ser Gln Cys
            515                 520                 525

Leu
```

<210> SEQ ID NO 93
<211> LENGTH: 1590
<212> TYPE: DNA
<213> ORGANISM: Unknown
<220> FEATURE:
<221> NAME/KEY: source
<223> OTHER INFORMATION: /note="Description of Unknown: Wildtype cellobiohydrolase polynucleotide"

<400> SEQUENCE: 93

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggc ggacgccctc ctccaacaac     660
gccaacactg gacttggcaa ccacggagct tgctgcgcag agcttgatat ctgggaggca     720
aacagcatct cagaggcttt gactcctcac ccttgcgata cccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
```

```
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg accctaaga ccgttgaatc acaatccggc    1320
agctcctatg tcaccttttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 94
<211> LENGTH: 529
<212> TYPE: PRT
<213> ORGANISM: Unknown
<220> FEATURE:
<221> NAME/KEY: source
<223> OTHER INFORMATION: /note="Description of Unknown: Wildtype cellobiohydrolase polypeptide"

<400> SEQUENCE: 94

```
Met Ser Ala Leu Asn Ser Phe Asn Met Tyr Lys Ser Ala Leu Ile Leu
1               5                  10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270
```

```
Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
        290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 95
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
atgtctgcct tgaactcttt caatatgtac aagagcgccc tcatcttggg ctccttgctg      60
gcaacagctg gtgctcagca aattggtact ctgcaggctg aaacccatcc ctctttgagc     120
tggtctactt gcaaatcggg tggtagctgc accacaaact ccggtgccat tacgttggat     180
gccaactggc gttgggtcca tggtgtcaat accgcccaga actgctacga tgcaacact      240 tggaataccg ccatctgcga cactgatgca tcctgtgccc aggactgtgc tcttgatggt     300
gctgactact ctggcacgta cggtatcact acctccggca actcattgcg cctgaacttc     360
gtccagcagg cccctactc caagaacgtc ggctcccgta cctacctgat ggccgataac     420
acccactacc aaatcttcga cttgttgaac caggagttca ctttcaccgt cgatgtctcc     480
cacctccctt gcggtttgaa cggtgccctc tacttcgtga ccatggacgc cgacggtggc     540
```

```
gtctccaagt accccaacaa caaggccggc gctcagtacg gtgttggata ctgtgactct      600
caatgccctc gtgacttgaa attcatcgct ggtcaggcca acgttgaggg ctggacgccc      660
tcctccaaca acgccaacac tggacttggc aaccacggag cttgctgcgc agagcttgat      720
atctgggagg caaacagcat ctcagaggct ttgactcctc accttgcga tacacccggt      780 ctatctgttt gcactactga tgcctgcggt ggtacctaca gctccgatcg ttacgccggt      840
acctgcgacc ctgatggatg tgacttcaac ccttaccgtc ttggtgtcac tgacttctac      900
ggctccggca agaccgttga caccaccaaa cccatcaccg ttgtgactca attcgtcact      960
gacgacggca catccaccgg caccctctcc gagatcagac gttactacgt tcagaacggt     1020
gttgtcatcc cccagccttc ctccaagatc tccggagtca gcggaaatgt catcaactcc     1080
gacttctgcg atgctgagat ctccaccttt ggcgagactg cctccttcag caaacacggt     1140
ggcctggcaa agatgggcgc tggtatggaa gctggtatgg tcttggtcat gagtttgtgg     1200
gacgactact ccgtcaacat gctctggctc gacagcacct accctacaaa cgcgactggt     1260 accccggtg ccgctcgtgg ttcctgccct accacttctg gggaccctaa gaccgttgaa     1320
tcacaatccg gcagctccta tgtcaccttt tctgacatcc gggttggtcc tttcaactct     1380
acgttcagcg gtggttctag caccggtggc agctccacta ctaccgccag cggcaccacc     1440
accaccaagg cctcttccac ctctacttcc agcacctcta ccggcactgg agtcgctgct     1500
cactggggtc agtgtggtgg ccagggttgg actggtccta ccacctgcgc tagtggaacc     1560
acatgcaccg tcgtgaaccc ttactactct caatgtttgt aa                        1602
```

<210> SEQ ID NO 96
<211> LENGTH: 533
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 96

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Leu Gln
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
    50                  55                  60

Trp Val His Gly Val Asn Thr Ala Gln Asn Cys Tyr Asp Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Gln Gln Gly Pro Tyr Ser Lys
        115                 120                 125

Asn Val Gly Ser Arg Thr Tyr Leu Met Ala Asp Asn Thr His Tyr Gln
    130                 135                 140

Ile Phe Asp Leu Leu Asn Gln Glu Phe Thr Phe Thr Val Asp Val Ser
145                 150                 155                 160
```

His Leu Pro Cys Gly Leu Asn Gly Ala Leu Tyr Phe Val Thr Met Asp
              165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
            195                 200                 205

Ile Ala Gly Gln Ala Asn Val Glu Gly Trp Thr Pro Ser Ser Asn Asn
210                 215                 220

Ala Asn Thr Gly Leu Gly Asn His Gly Ala Cys Cys Ala Glu Leu Asp
225                 230                 235                 240

Ile Trp Glu Ala Asn Ser Ile Ser Glu Ala Leu Thr Pro His Pro Cys
                245                 250                 255

Asp Thr Pro Gly Leu Ser Val Cys Thr Thr Asp Ala Cys Gly Gly Thr
            260                 265                 270

Tyr Ser Ser Asp Arg Tyr Ala Gly Thr Cys Asp Pro Asp Gly Cys Asp
            275                 280                 285

Phe Asn Pro Tyr Arg Leu Gly Val Thr Asp Phe Tyr Gly Ser Gly Lys
290                 295                 300

Thr Val Asp Thr Thr Lys Pro Ile Thr Val Thr Gln Phe Val Thr
305                 310                 315                 320

Asp Asp Gly Thr Ser Thr Gly Thr Leu Ser Glu Ile Arg Arg Tyr Tyr
            325                 330                 335

Val Gln Asn Gly Val Val Ile Pro Gln Pro Ser Ser Lys Ile Ser Gly
            340                 345                 350

Val Ser Gly Asn Val Ile Asn Ser Asp Phe Cys Asp Ala Glu Ile Ser
            355                 360                 365

Thr Phe Gly Glu Thr Ala Ser Phe Ser Lys His Gly Gly Leu Ala Lys
370                 375                 380

Met Gly Ala Gly Met Glu Ala Gly Met Val Leu Val Met Ser Leu Trp
385                 390                 395                 400

Asp Asp Tyr Ser Val Asn Met Leu Trp Leu Asp Ser Thr Tyr Pro Thr
            405                 410                 415

Asn Ala Thr Gly Thr Pro Gly Ala Ala Arg Gly Ser Cys Pro Thr Thr
            420                 425                 430

Ser Gly Asp Pro Lys Thr Val Glu Ser Gln Ser Gly Ser Ser Tyr Val
            435                 440                 445

Thr Phe Ser Asp Ile Arg Val Gly Pro Phe Asn Ser Thr Phe Ser Gly
            450                 455                 460

Gly Ser Ser Thr Gly Gly Ser Ser Thr Thr Ala Ser Gly Thr Thr
465                 470                 475                 480

Thr Thr Lys Ala Ser Ser Thr Ser Thr Ser Ser Thr Ser Thr Gly Thr
            485                 490                 495

Gly Val Ala Ala His Trp Gly Gln Cys Gly Gly Gln Gly Trp Thr Gly
            500                 505                 510

Pro Thr Thr Cys Ala Ser Gly Thr Thr Cys Thr Val Val Asn Pro Tyr
            515                 520                 525

Tyr Ser Gln Cys Leu
530

<210> SEQ ID NO 97
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 97

| | |
|---|---|
| atgtctgcct tgaactcttt caatatgtac aagagcgccc tcatcttggg ctccttgctg | 60 |
| gcaacagctg gtgctcagca aattggtact ctgaccgctg aaacccatcc ctctttgagc | 120 |
| tggtctactt gcaaatcggg tggtagctgc accacaaact ccggtgccat acgttggat | 180 |
| gccaactggc gttgggtcca tggtgtcaat acctggacca ctgctacga tgcaacact | 240 |
| tggaataccg ccatctgcga cactgatgca tcctgtgccc aggactgtgc tcttgatggt | 300 |
| gctgactact ctggcacgta cggtatcact acctccggca actcattgcg cctgaacttc | 360 |
| gtccagcagg gccctactc aagaacgtc ggctcccgta cctacctgat ggccgataac | 420 |
| acccactacc aaatcttcga cttgttgaac caggagttca ctttcaccgt cgatgtctcc | 480 |
| cacctccctt gcggtttgaa cggtgccctc tacttcgtga ccatggacgc cgacggtggc | 540 |
| gtctccaagt accccaacaa caaggccggc gctcagtacg tgttggata ctgtgactct | 600 |
| caatgccctc gtgacttgaa attcatcgct ggtcaggcca cgttgaggg ctggacgccc | 660 |
| tcctccaaca cgccaacac tggacttggc aaccacggag cttgctgcgc agagcttgat | 720 |
| atctgggagg caaacagcat ctcagaggct ttgactcctc acccttgcga tacacccggt | 780 |
| ctatctgttt gcactactga tgcctgcggt ggtacctaca gctccgatcg ttacgccggt | 840 |
| acctgcgacc ctgatggatg tgacttcaac ccttaccgtc ttggtgtcac tgacttctac | 900 |
| ggctccggca agaccgttga caccaccaaa cccatcaccg ttgtgactca attcgtcact | 960 |
| gacgacggca catccaccgg caccctctcc gagatcagac gttactacgt tcagaacggt | 1020 |
| gttgtcatcc cccagccttc ctccaagatc tccggagtca gcggaaatgt catcaactcc | 1080 |
| gacttctgcg atgctgagat ctccaccttt ggcgagactg cctccttcag caaacacggt | 1140 |
| ggcctggcaa agatgggcgc tggtatggaa gctggtatgg tcttggtcat gagtttgtgg | 1200 |
| gacgactact ccgtcaacat gctctggctc gacagcacct accctacaaa cgcgactggt | 1260 |
| accccggtg ccgctcgtgg ttcctgcct accacttctg ggaccctaa gaccgttgaa | 1320 |
| tcacaatccg gcagctccta tgtcaccttt tctgacatcc gggttggtcc tttcaactct | 1380 |
| acgttcagcg gtggttctag caccggtggc agctccacta ctaccgccag cggcaccacc | 1440 |
| accaccaagg cctcttccac ctctacttcc agcacctcta ccggcactgg agtcgctgct | 1500 |
| cactggggtc agtgtggtgg ccagggttgg actggtccta ccacctgcgc tagtggaacc | 1560 |
| acatgcaccg tcgtgaaccc ttactactct caatgtttgt aa | 1602 |

<210> SEQ ID NO 98
<211> LENGTH: 533
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 98

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Leu Thr
            20                  25                  30

Ala Glu Thr His Pro Ser Leu Ser Trp Ser Thr Cys Lys Ser Gly Gly
        35                  40                  45

-continued

```
Ser Cys Thr Thr Asn Ser Gly Ala Ile Thr Leu Asp Ala Asn Trp Arg
    50              55                  60

Trp Val His Gly Val Asn Thr Trp Thr Asn Cys Tyr Asp Gly Asn Thr
65              70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Gln Gln Gly Pro Tyr Ser Lys
        115                 120                 125

Asn Val Gly Ser Arg Thr Tyr Leu Met Ala Asp Asn Thr His Tyr Gln
    130                 135                 140

Ile Phe Asp Leu Leu Asn Gln Glu Phe Thr Phe Thr Val Asp Val Ser
145                 150                 155                 160

His Leu Pro Cys Gly Leu Asn Gly Ala Leu Tyr Phe Val Thr Met Asp
                165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
        195                 200                 205

Ile Ala Gly Gln Ala Asn Val Glu Gly Trp Thr Pro Ser Ser Asn Asn
    210                 215                 220

Ala Asn Thr Gly Leu Gly Asn His Gly Ala Cys Cys Ala Glu Leu Asp
225                 230                 235                 240

Ile Trp Glu Ala Asn Ser Ile Ser Glu Ala Leu Thr Pro His Pro Cys
                245                 250                 255

Asp Thr Pro Gly Leu Ser Val Cys Thr Thr Asp Ala Cys Gly Gly Thr
            260                 265                 270

Tyr Ser Ser Asp Arg Tyr Ala Gly Thr Cys Asp Pro Asp Gly Cys Asp
        275                 280                 285

Phe Asn Pro Tyr Arg Leu Gly Val Thr Asp Phe Tyr Gly Ser Gly Lys
    290                 295                 300

Thr Val Asp Thr Thr Lys Pro Ile Thr Val Val Thr Gln Phe Val Thr
305                 310                 315                 320

Asp Asp Gly Thr Ser Thr Gly Thr Leu Ser Glu Ile Arg Arg Tyr Tyr
                325                 330                 335

Val Gln Asn Gly Val Val Ile Pro Gln Pro Ser Ser Lys Ile Ser Gly
            340                 345                 350

Val Ser Gly Asn Val Ile Asn Ser Asp Phe Cys Asp Ala Glu Ile Ser
        355                 360                 365

Thr Phe Gly Glu Thr Ala Ser Phe Ser Lys His Gly Gly Leu Ala Lys
    370                 375                 380

Met Gly Ala Gly Met Glu Ala Gly Met Val Leu Val Met Ser Leu Trp
385                 390                 395                 400

Asp Asp Tyr Ser Val Asn Met Leu Trp Leu Asp Ser Thr Tyr Pro Thr
                405                 410                 415

Asn Ala Thr Gly Thr Pro Gly Ala Ala Arg Gly Ser Cys Pro Thr Thr
            420                 425                 430

Ser Gly Asp Pro Lys Thr Val Glu Ser Gln Ser Gly Ser Ser Tyr Val
        435                 440                 445

Thr Phe Ser Asp Ile Arg Val Gly Pro Phe Asn Ser Thr Phe Ser Gly
    450                 455                 460
```

Gly Ser Ser Thr Gly Gly Ser Ser Thr Thr Ala Ser Gly Thr Thr
465                 470                 475                 480

Thr Thr Lys Ala Ser Ser Thr Ser Thr Ser Thr Ser Thr Gly Thr
            485                 490                 495

Gly Val Ala Ala His Trp Gly Gln Cys Gly Gly Gln Gly Trp Thr Gly
                500                 505                 510

Pro Thr Thr Cys Ala Ser Gly Thr Ser Cys Thr Val Val Asn Pro Tyr
            515                 520                 525

Tyr Ser Gln Cys Leu
        530

<210> SEQ ID NO 99
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
atgtctgcct tgaactcttt caatatgtac aagagcgccc tcatcttggg ctccttgctg    60
gcaacagctg gtgctcagca aattggtact tataccgctg aaacccatcc ctctttgagc   120
tggtctactt gcaaatcggg tggtagctgc accacaaact ccggtgccat acgttggat    180
gccaactggc gttgggtcca tggtgtcaat acctaccaga actgctacac cggcaacact   240
tggaataccg ccatctgcga cactgatgca tcctgtgccc aggactgtgc tcttgatggt   300
gctgactact ctggcacgta cggtatcact acctccggca actcattgcg cctgaacttc   360
gtccagcagg gcccctactc caagaacgtc ggctcccgta cctacctgat ggccgataac   420
acccactacc aaatcttcga cttgttgaac caggagttca ctttcaccgt cgatgtctcc   480
cacctcccct tgcggtttga acggtgccctc tacttcgtga ccatggacgc cgacggtggc   540
gtctccaagt accccaacaa caaggccggc gctcagtacg tgttggata ctgtgactct    600
caatgccctc gtgacttgaa attcatcgct ggtcaggcca acgttgaggg ctggacgccc   660
tcctccaaca cgccaacac tggacttggc aaccacggag cttgctgcgc agagcttgat    720
atctgggagg caaacagcat ctcagaggct ttgactcctc accccttgcga tacacccggt   780
ctatctgttt gcactactga tgcctgcggt ggtacctaca gctccgatcg ttacgccggt   840
acctgcgacc ctgatggatg tgacttcaac ccttaccgtc ttggtgtcac tgacttctac   900
ggctccggca gaccgttga caccaccaaa cccatcaccg ttgtgactca attcgtcact   960
gacgacggca catccaccgg caccctctcc gagatcagac gttactacgt tcagaacggt  1020
gttgtcatcc cccagccttc ctccaagatc tccggagtca gcggaaatgt catcaactcc  1080
gacttctgcg atgctgagat ctccacccttt ggcgagactg cctccttcag caaacacggt  1140
ggcctggcaa agatgggcgc tggtatggaa gctggtatgg tcttggtcat gagtttgtgg  1200
gacgactact ccgtcaacat gctctggctc gacagcacct accctacaaa cgcgactggt  1260
acccccggtg ccgctcgtgg ttcctgcccct accactctg ggaccctaa gaccgttgaa   1320
tcacaatccg gcagctccta tgtcaccttt tctgacatcc gggttggtcc tttcaactct  1380
acgttcagcg gtggttctag caccggtggc agctccacta ctaccgccag cggcaccacc  1440
accaccaagg cctcttccac ctctacttcc agcacctcta ccggcactgg agtcgctgct  1500
cactggggtc agtgtggtgg ccagggttgg actggtccta ccacctgcgc tagtggaacc  1560
```
acatgcaccg tcgtgaaccc ttactactct caatgtttgt aa                          1602

<210> SEQ ID NO 100
<211> LENGTH: 533
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Tyr Gln Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Gln Gln Gly Pro Tyr Ser Lys
        115                 120                 125

Asn Val Gly Ser Arg Thr Tyr Leu Met Ala Asp Asn Thr His Tyr Gln
    130                 135                 140

Ile Phe Asp Leu Leu Asn Gln Glu Phe Thr Phe Thr Val Asp Val Ser
145                 150                 155                 160

His Leu Pro Cys Gly Leu Asn Gly Ala Leu Tyr Phe Val Thr Met Asp
                165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
        195                 200                 205

Ile Ala Gly Gln Ala Asn Val Glu Gly Trp Thr Pro Ser Ser Asn Asn
    210                 215                 220

Ala Asn Thr Gly Leu Gly Asn His Gly Ala Cys Cys Ala Glu Leu Asp
225                 230                 235                 240

Ile Trp Glu Ala Asn Ser Ile Ser Glu Ala Leu Thr Pro His Pro Cys
                245                 250                 255

Asp Thr Pro Gly Leu Ser Val Cys Thr Thr Asp Ala Cys Gly Gly Thr
            260                 265                 270

Tyr Ser Ser Asp Arg Tyr Ala Gly Thr Cys Asp Pro Asp Gly Cys Asp
        275                 280                 285

Phe Asn Pro Tyr Arg Leu Gly Val Thr Asp Phe Tyr Gly Ser Gly Lys
    290                 295                 300

Thr Val Asp Thr Thr Lys Pro Ile Thr Val Thr Gln Phe Val Thr
305                 310                 315                 320

Asp Asp Gly Thr Ser Thr Gly Thr Leu Ser Glu Ile Arg Arg Tyr Tyr
                325                 330                 335

Val Gln Asn Gly Val Val Ile Pro Gln Pro Ser Ser Lys Ile Ser Gly
            340                 345                 350

Val Ser Gly Asn Val Ile Asn Ser Asp Phe Cys Asp Ala Glu Ile Ser
         355                 360                 365

Thr Phe Gly Glu Thr Ala Ser Phe Ser Lys His Gly Gly Leu Ala Lys
370                 375                 380

Met Gly Ala Gly Met Glu Ala Gly Met Val Leu Val Met Ser Leu Trp
385                 390                 395                 400

Asp Asp Tyr Ser Val Asn Met Leu Trp Leu Asp Ser Thr Tyr Pro Thr
             405                 410                 415

Asn Ala Thr Gly Thr Pro Gly Ala Ala Arg Gly Ser Cys Pro Thr Thr
             420                 425                 430

Ser Gly Asp Pro Lys Thr Val Glu Ser Gln Ser Gly Ser Ser Tyr Val
         435                 440                 445

Thr Phe Ser Asp Ile Arg Val Gly Pro Phe Asn Ser Thr Phe Ser Gly
     450                 455                 460

Gly Ser Ser Thr Gly Gly Ser Ser Thr Thr Thr Ala Ser Gly Thr Thr
465                 470                 475                 480

Thr Thr Lys Ala Ser Ser Thr Ser Ser Ser Thr Ser Thr Ser Gly Thr
             485                 490                 495

Gly Val Ala Ala His Trp Gly Gln Cys Gly Gly Gln Gly Trp Thr Gly
         500                 505                 510

Pro Thr Thr Cys Ala Ser Gly Thr Thr Cys Thr Val Val Asn Pro Tyr
     515                 520                 525

Tyr Ser Gln Cys Leu
    530

<210> SEQ ID NO 101
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101
atgtctgcct tgaactcttt caatatgtac aagagcgccc tcatcttggg ctccttgctg      60
gcaacagctg gtgctcagca aattggtact ctgtgggctg aaacccatcc ctctttgagc     120
tggtctactt gcaaatcggg tggtagctgc accacaaact ccggtgccat acgttggat     180 gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gtccagcagg gccctactc caagaacgtc ggctcccgta cctacctgat ggccgataac     420
acccactacc aaatcttcga cttgttgaac caggagttca ctttcaccgt cgatgtctcc     480
cacctccctt gcggtttgaa cggtgccctc tacttcgtga ccatggacgc cgacggtggc     540
gtctccaagt accccaacaa caaggccggc gctcagtacg tgttggata ctgtgactct     600 caatgccctc gtgacttgaa attcatcgct ggtcaggcca acgttgaggg ctggacgccc     660
tcctccaaca cgccaacac tggacttggc aaccacggag cttgctgcgc agagcttgat     720
atctgggagg caaacagcat ctcagaggct tgactcctc acccttgcga tacacccggt     780
ctatctgttt gcactactga tgcctgcggt ggtacctaca gctccgatcg ttacgccggt     840
acctgcgacc ctgatggatg tgacttcaac ccttaccgtc ttggtgtcac tgacttctac     900

```
ggctccggca agaccgttga caccaccaaa cccatcaccg ttgtgactca attcgtcact      960
gacgacggca catccaccgg caccctctcc gagatcagac gttactacgt tcagaacggt     1020
gttgtcatcc cccagccttc ctccaagatc tccggagtca gcggaaatgt catcaactcc     1080
gacttctgcg atgctgagat ctccacccttt ggcgagactg cctccttcag caaacacggt    1140
ggcctggcaa agatgggcgc tggtatggaa gctggtatgg tcttggtcat gagtttgtgg     1200
gacgactact ccgtcaacat gctctggctc gacagcacct accctacaaa cgcgactggt     1260
acccccggtg ccgctcgtgg ttcctgccct accacttctg ggaccctaa gaccgttgaa      1320 tcacaatccg gcagctccta tgtcaccttt tctgacatcc gggttggtcc tttcaactct     1380
acgttcagcg gtggttctag caccggtggc agctccacta ctaccgccag cggcaccacc     1440
accaccaagg cctcttccac ctctacttcc agcacctcta ccggcactgg agtcgctgct     1500
cactggggtc agtgtggtgg ccagggttgg actggtccta ccacctgcgc tagtggaacc     1560
acatgcaccg tcgtgaaccc ttactactct caatgtttgt aa                        1602
```

<210> SEQ ID NO 102
<211> LENGTH: 533
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Leu Trp
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Gln Gln Gly Pro Tyr Ser Lys
        115                 120                 125

Asn Val Gly Ser Arg Thr Tyr Leu Met Ala Asp Asn Thr His Tyr Gln
    130                 135                 140

Ile Phe Asp Leu Leu Asn Gln Glu Phe Thr Phe Thr Val Asp Val Ser
145                 150                 155                 160

His Leu Pro Cys Gly Leu Asn Gly Ala Leu Tyr Phe Val Thr Met Asp
                165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
        195                 200                 205

Ile Ala Gly Gln Ala Asn Val Glu Gly Trp Thr Pro Ser Ser Asn Asn
    210                 215                 220

Ala Asn Thr Gly Leu Gly Asn His Gly Ala Cys Cys Ala Glu Leu Asp
```

```
                225                 230                 235                 240
Ile Trp Glu Ala Asn Ser Ile Ser Glu Ala Leu Thr Pro His Pro Cys
                245                 250                 255
Asp Thr Pro Gly Leu Ser Val Cys Thr Thr Asp Ala Cys Gly Gly Thr
            260                 265                 270
Tyr Ser Ser Asp Arg Tyr Ala Gly Thr Cys Asp Pro Asp Gly Cys Asp
            275                 280                 285
Phe Asn Pro Tyr Arg Leu Gly Val Thr Asp Phe Tyr Gly Ser Gly Lys
        290                 295                 300
Thr Val Asp Thr Thr Lys Pro Ile Thr Val Thr Gln Phe Val Thr
305                 310                 315                 320
Asp Asp Gly Thr Ser Thr Gly Thr Leu Ser Glu Ile Arg Arg Tyr Tyr
                325                 330                 335
Val Gln Asn Gly Val Val Ile Pro Gln Pro Ser Ser Lys Ile Ser Gly
            340                 345                 350
Val Ser Gly Asn Val Ile Asn Ser Asp Phe Cys Asp Ala Glu Ile Ser
            355                 360                 365
Thr Phe Gly Glu Thr Ala Ser Phe Ser Lys His Gly Gly Leu Ala Lys
        370                 375                 380
Met Gly Ala Gly Met Glu Ala Gly Met Val Leu Val Met Ser Leu Trp
385                 390                 395                 400
Asp Asp Tyr Ser Val Asn Met Leu Trp Leu Asp Ser Thr Tyr Pro Thr
                405                 410                 415
Asn Ala Thr Gly Thr Pro Gly Ala Ala Arg Gly Ser Cys Pro Thr Thr
            420                 425                 430
Ser Gly Asp Pro Lys Thr Val Glu Ser Gln Ser Gly Ser Ser Tyr Val
        435                 440                 445
Thr Phe Ser Asp Ile Arg Val Gly Pro Phe Asn Ser Thr Phe Ser Gly
        450                 455                 460
Gly Ser Ser Thr Gly Gly Ser Ser Thr Thr Ala Ser Gly Thr Thr
465                 470                 475                 480
Thr Thr Lys Ala Ser Ser Thr Ser Thr Ser Ser Thr Ser Thr Gly Thr
            485                 490                 495
Gly Val Ala Ala His Trp Gly Gln Cys Gly Gly Gln Gly Trp Thr Gly
            500                 505                 510
Pro Thr Thr Cys Ala Ser Gly Thr Thr Cys Thr Val Val Asn Pro Tyr
        515                 520                 525
Tyr Ser Gln Cys Leu
    530

<210> SEQ ID NO 103
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
atgtctgcct tgaactcttt caatatgtac aagagcgccc tcatcttggg ctccttgctg      60
gcaacagctg gtgctcagca aattggtact taccaggctg aaacccatcc ctctttgagc     120
tggtctactt gcaaatcggg tggtagctgc accacaaaact ccggtgccat tacgttggat    180
gccaactggc gttgggtcca tgtgtcaat accagcacca actgctacac tggcaacact    240
```

```
tggaataccg ccatctgcga cactgatgca tcctgtgccc aggactgtgc tcttgatggt        300
gctgactact ctggcacgta cggtatcact acctccggca actcattgcg cctgaacttc        360
gtcaccaagg gctccttctc ctccaacatc ggctcccgta cctacctgat ggccgataac        420
acccactacc aaatcttcga cttgttgaac caggagttca ctttcaccgt cgatgtctcc        480
cacctccctt gcggtttgaa cggtgccctc tacttcgtga ccatggacgc cgacggtggc        540
gtctccaagt accccaacaa caaggccggc gctcagtacg tgttggata ctgtgactct        600 caatgccctc gtgacttgaa attcatcgct ggtcaggcca acgttgaggg ctggacgccc        660
tcctccaaca cgccaacac tggacttggc aaccacggag cttgctgcgc agagcttgat        720
atctgggagg caaacagcat ctcagaggct ttgactcctc acccttgcga tacacccggt        780
ctatctgttt gcactactga tgcctgcggt ggtacctaca gctccgatcg ttacgccggt        840
acctgcgacc ctgatggatg tgacttcaac ccttaccgtc ttggtgtcac tgacttctac        900
ggctccggca agaccgttga caccaccaaa cccatcaccg ttgtgactca attcgtcact        960
gacgacggca catccaccgg caccctctcc gagatcagac gttactacgt tcagaacggt       1020
gttgtcatcc cccagccttc ctccaagatc tccggagtca gcggaaatgt catcaactcc       1080
gacttctgcg atgctgagat ctccacccttt ggcgagactg cctccttcag caaacacggt       1140
ggcctggcaa agatgggcgc tggtatggaa gctggtatgg tcttggtcat gagtttgtgg       1200
gacgactact ccgtcaacat gctctggctc gacagcacct accctacaaa cgcgactggt       1260 accccggtg ccgctcgtgg ttcctgccct accacttctg gggaccctaa gaccgttgaa       1320
tcacaatccg gcagctccta tgtcaccttt tctgacatcc gggttggtcc tttcaactct       1380
acgttcagcg gtggttctag caccggtggc agctccacta ctaccgccag cggcaccacc       1440
accaccaagg cctcttccac ctctacttcc agcacctcta ccggcactgg agtcgctgct       1500
cactggggtc agtgtggtgg ccagggttgg actggtccta ccacctgcgc tagtggaacc       1560
acatgcaccg tcgtgaaccc ttactactct caatgtttgt aa                          1602
```

<210> SEQ ID NO 104
<211> LENGTH: 533
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 104

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Gln
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

```
Gly Asn Ser Leu Arg Leu Asn Phe Val Thr Lys Gly Ser Phe Ser Ser
            115                 120                 125

Asn Ile Gly Ser Arg Thr Tyr Leu Met Ala Asp Asn Thr His Tyr Gln
        130                 135                 140

Ile Phe Asp Leu Leu Asn Gln Glu Phe Thr Phe Thr Val Asp Val Ser
145                 150                 155                 160

His Leu Pro Cys Gly Leu Asn Gly Ala Leu Tyr Phe Val Thr Met Asp
                165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
        195                 200                 205

Ile Ala Gly Gln Ala Asn Val Glu Gly Trp Thr Pro Ser Ser Asn Asn
210                 215                 220

Ala Asn Thr Gly Leu Gly Asn His Gly Ala Cys Cys Ala Glu Leu Asp
225                 230                 235                 240

Ile Trp Glu Ala Asn Ser Ile Ser Glu Ala Leu Thr Pro His Pro Cys
                245                 250                 255

Asp Thr Pro Gly Leu Ser Val Cys Thr Thr Asp Ala Cys Gly Gly Thr
            260                 265                 270

Tyr Ser Ser Asp Arg Tyr Ala Gly Thr Cys Asp Pro Asp Gly Cys Asp
        275                 280                 285

Phe Asn Pro Tyr Arg Leu Gly Val Thr Asp Phe Tyr Gly Ser Gly Lys
290                 295                 300

Thr Val Asp Thr Thr Lys Pro Ile Thr Val Thr Gln Phe Val Thr
305                 310                 315                 320

Asp Asp Gly Thr Ser Thr Gly Thr Leu Ser Glu Ile Arg Arg Tyr Tyr
                325                 330                 335

Val Gln Asn Gly Val Val Ile Pro Gln Pro Ser Ser Lys Ile Ser Gly
            340                 345                 350

Val Ser Gly Asn Val Ile Asn Ser Asp Phe Cys Asp Ala Glu Ile Ser
        355                 360                 365

Thr Phe Gly Glu Thr Ala Ser Phe Ser Lys His Gly Gly Leu Ala Lys
370                 375                 380

Met Gly Ala Gly Met Glu Ala Gly Met Val Leu Val Met Ser Leu Trp
385                 390                 395                 400

Asp Asp Tyr Ser Val Asn Met Leu Trp Leu Asp Ser Thr Tyr Pro Thr
                405                 410                 415

Asn Ala Thr Gly Thr Pro Gly Ala Ala Arg Gly Ser Cys Pro Thr Thr
            420                 425                 430

Ser Gly Asp Pro Lys Thr Val Glu Ser Gln Ser Gly Ser Ser Tyr Val
        435                 440                 445

Thr Phe Ser Asp Ile Arg Val Gly Pro Phe Asn Ser Thr Phe Ser Gly
450                 455                 460

Gly Ser Ser Thr Gly Gly Ser Thr Thr Thr Ala Ser Gly Thr Thr
465                 470                 475                 480

Thr Thr Lys Ala Ser Ser Thr Ser Thr Ser Thr Ser Thr Gly Thr
                485                 490                 495

Gly Val Ala Ala His Trp Gly Gln Cys Gly Gly Gln Gly Trp Thr Gly
            500                 505                 510

Pro Thr Thr Cys Ala Ser Gly Thr Thr Cys Thr Val Val Asn Pro Tyr
        515                 520                 525

Tyr Ser Gln Cys Leu
```

<210> SEQ ID NO 105
<211> LENGTH: 1599
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105

```
atgtctgcct tgaactcttt caatatgtac aagagcgccc tcatcttggg ctccttgctg    60
gcaacagctg gtgctcagca aattggtact cagcaggctg aaacccatcc ctctttgagc   120
tggtctactt gcaaatcggg tggtagctgc accacaaact ccggtgccat tacgttggat   180
gccaactggc gttgggtcca tggtgtcaat acctacacca actgctacga tggcaacact   240
tggaataccg ccatctgcga cactgatgca tcctgtgccc aggactgtgc tcttgatggt   300
gctgactact ctggcacgta cggtatcact acctccggca actcattgcg cctgaacttc   360
gtcacccagt ccgcccagaa gaacgtcggc gcccgtacct acctgatggc cgataacacc   420
cactaccaaa tcttcgactt gttgaaccag gagttcactt tcaccgtcga tgtctcccac   480
ctcccttgcg gtttgaacgg tgccctctac ttcgtgacca tggacgccga cggtggcgtc   540
tccaagtacc ccaacaacaa ggccggcgct cagtacggtg ttggatactg tgactctcaa   600
tgccctcgtg acttgaaatt catcgctggt caggccaacg ttgagggctg gacgccctcc   660
tccaacaacg ccaacactgg acttggcaac acggagctt gctgcgcaga gcttgatatc   720
tgggaggcaa acagcatctc agaggctttg actcctcacc cttgcgatac acccggtcta   780
tctgttttgca ctactgatgc ctgcggtggt acctacagct ccgatcgtta cgccggtacc   840
tgcgaccctg atggatgtga cttcaaccct taccgtcttg gtgtcactga cttctacggc   900
tccggcaaga ccgttgacac caccaaaccc atcaccgttg tgactcaatt cgtcactgac   960
gacggcacat ccaccggcac cctctccgag atcagacgtt actacgttca gaacggtgtt  1020
gtcatccccc agccttcctc caagatctcc ggagtcagcg gaaatgtcat caactccgac  1080
ttctgcgatg ctgagatctc caccttggc gagactgcct ccttcagcaa acacggtggc  1140
ctggcaaaga tgggcgctgg tatggaagct ggtatggtct tggtcatgag tttgtgggac  1200
gactactccg tcaacatgct ctggctcgac agcacctacc ctacaaacgc gactggtacc  1260
cccggtgccg ctcgtggttc ctgccctacc acttctgggg accctaagac cgttgaatca  1320
caatccggca gctcctatgt cacctttct gacatccggg ttggtccttt caactctacg  1380
ttcagcggtg gttctagcac cggtggcagc tccactacta ccgccagcgg caccaccacc  1440
accaaggcct cttccacctc tacttccagc acctctaccg gcactggagt cgctgctcac  1500
tggggtcagt gtggtggcca gggttggact ggtcctacca cctgcgctag tggaaccaca  1560
tgcaccgtcg tgaacccta ctactctcaa tgtttgtaa                          1599
```

<210> SEQ ID NO 106
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 106

-continued

```
Met Ser Ala Leu Asn Ser Phe Asn Met Tyr Lys Ser Ala Leu Ile Leu
1               5                   10                  15
Gly Ser Leu Leu Ala Thr Ala Gly Ala Gln Gln Ile Gly Thr Gln Gln
                20                  25                  30
Ala Glu Thr His Pro Ser Leu Ser Trp Ser Cys Lys Ser Gly Gly
                35                  40                      45
Ser Cys Thr Thr Asn Ser Gly Ala Ile Thr Leu Asp Ala Asn Trp Arg
    50                  55                  60
Trp Val His Gly Val Asn Thr Tyr Thr Asn Cys Tyr Asp Gly Asn Thr
65                      70                  75                  80
Trp Asn Thr Ala Ile Cys Asp Thr Asp Ala Ser Cys Ala Gln Asp Cys
                85                  90                  95
Ala Leu Asp Gly Ala Asp Tyr Ser Gly Thr Tyr Gly Ile Thr Thr Ser
                100                 105                 110
Gly Asn Ser Leu Arg Leu Asn Phe Val Thr Gln Ser Ala Gln Lys Asn
                115                 120                 125
Val Gly Ala Arg Thr Tyr Leu Met Ala Asp Asn Thr His Tyr Gln Ile
                130                 135                 140
Phe Asp Leu Leu Asn Gln Glu Phe Thr Phe Thr Val Asp Val Ser His
145                 150                 155                 160
Leu Pro Cys Gly Leu Asn Gly Ala Leu Tyr Phe Val Thr Met Asp Ala
                165                 170                 175
Asp Gly Gly Val Ser Lys Tyr Pro Asn Asn Lys Ala Gly Ala Gln Tyr
                180                 185                 190
Gly Val Gly Tyr Cys Asp Ser Gln Cys Pro Arg Asp Leu Lys Phe Ile
                195                 200                 205
Ala Gly Gln Ala Asn Val Glu Gly Trp Thr Pro Ser Ser Asn Asn Ala
                210                 215                 220
Asn Thr Gly Leu Gly Asn His Gly Ala Cys Cys Ala Glu Leu Asp Ile
225                 230                 235                 240
Trp Glu Ala Asn Ser Ile Ser Glu Ala Leu Thr Pro His Pro Cys Asp
                245                 250                 255
Thr Pro Gly Leu Ser Val Cys Thr Thr Asp Ala Cys Gly Gly Thr Tyr
                260                 265                 270
Ser Ser Asp Arg Tyr Ala Gly Thr Cys Asp Pro Asp Gly Cys Asp Phe
                275                 280                 285
Asn Pro Tyr Arg Leu Gly Val Thr Asp Phe Tyr Gly Ser Gly Lys Thr
                290                 295                 300
Val Asp Thr Thr Lys Pro Ile Thr Val Val Thr Gln Phe Val Thr Asp
305                 310                 315                 320
Asp Gly Thr Ser Thr Gly Thr Leu Ser Glu Ile Arg Arg Tyr Tyr Val
                325                 330                 335
Gln Asn Gly Val Val Ile Pro Gln Pro Ser Ser Lys Ile Ser Gly Val
                340                 345                 350
Ser Gly Asn Val Ile Asn Ser Asp Phe Cys Asp Ala Glu Ile Ser Thr
                355                 360                 365
Phe Gly Glu Thr Ala Ser Phe Ser Lys His Gly Gly Leu Ala Lys Met
                370                 375                 380
Gly Ala Gly Met Glu Ala Gly Met Val Leu Val Met Ser Leu Trp Asp
385                 390                 395                 400
Asp Tyr Ser Val Asn Met Leu Trp Leu Asp Ser Thr Tyr Pro Thr Asn
                405                 410                 415
```

| | | | | | | | | | | | |
|---|---|---|---|---|---|---|---|---|---|---|---|
|Ala|Thr|Gly|Thr|Pro|Gly|Ala|Ala|Arg|Gly|Ser|Cys|Pro|Thr|Thr|Ser|
| | | |420| | | |425| | | |430| | | | |
|Gly|Asp|Pro|Lys|Thr|Val|Glu|Ser|Gln|Ser|Gly|Ser|Ser|Tyr|Val|Thr|
| | |435| | | | |440| | | | |445| | | |
|Phe|Ser|Asp|Ile|Arg|Val|Gly|Pro|Phe|Asn|Ser|Thr|Phe|Ser|Gly|Gly|
| |450| | | | |455| | | | |460| | | | |
|Ser|Ser|Thr|Gly|Gly|Ser|Ser|Thr|Thr|Thr|Ala|Ser|Gly|Thr|Thr|Thr|
|465| | | | |470| | | | |475| | | | |480|
|Thr|Lys|Ala|Ser|Ser|Thr|Ser|Thr|Ser|Ser|Thr|Ser|Thr|Gly|Thr|Gly|
| | | | |485| | | | |490| | | | |495| |
|Val|Ala|Ala|His|Trp|Gly|Gln|Cys|Gly|Gly|Gln|Gly|Trp|Thr|Gly|Pro|
| | | |500| | | |505| | | | |510| | | |
|Thr|Thr|Cys|Ala|Ser|Gly|Thr|Thr|Cys|Thr|Val|Val|Asn|Pro|Tyr|Tyr|
| | |515| | | | |520| | | | |525| | | |
|Ser|Gln|Cys|Leu|
| |530| | |

```
<210> SEQ ID NO 107
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
atgtctgcct tgaactcttt caatatgtac aagagcgccc tcatcttggg ctccttgctg      60
gcaacagctg gtgctcagca aattggtact gcctacgctg aaacccatcc ctctttgagc     120
tggtctactt gcaaatcggg tggtagctgc accacaaact ccggtgccat tacgttggat     180
gccaactggc gttgggtcca tggtgtcaat acctactaca actgctacga tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gtcaccggct ccaacgtcgg ctcccgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggc ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cggcaca      960 tccaccggca ccctctccga tcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca acacggtgg cctggcaaag    1140 atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
```

```
agctcctatg tcaccttttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaacccct actactctca atgtttgtaa                                     1590
```

<210> SEQ ID NO 108
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Ala Tyr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
        50                  55                  60

Trp Val His Gly Val Asn Thr Tyr Tyr Asn Cys Tyr Asp Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300
```

| | | | | | | | | | | | | | | |
|---|---|---|---|---|---|---|---|---|---|---|---|---|---|---|
|Thr|Lys|Pro|Ile|Thr|Val|Val|Thr|Gln|Phe|Val|Thr|Asp|Asp|Gly|Thr|
|305| | | |310| | | |315| | | |320| | |

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 109
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
atgtctgcct tgaactcttt caatatgtac aagagcgccc tcatcttggg ctccttgctg      60
gcaacagctg gtgctcagca aattggtact cagcaggctg aaacccatcc ctctttgagc     120
tggtctactt gcaaatcggg tggtagctgc accacaaact ccggtgccat tacgttggat     180
gccaactggc gttgggtcca tgtgtcaat acctactaca actgctacga tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gtcaccggct ccaacgtcgg ctcccgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggct ggacgccctc ctccaacaac     660

```
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttt tgacatccgg gttggtcctt tcaactctac gttcagcggt   1380
ggttctagca ccggtggcag ctccactact accgccagcg caccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaaccctt actactctca atgtttgtaa                                    1590
```

<210> SEQ ID NO 110
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Gln Gln
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Tyr Tyr Asn Cys Tyr Asp Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190
```

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
            245                 250                 255

Leu Ser Val Cys Thr Thr Asp Ala Cys Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 111
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111
atgtctgcct tgaactcttt caatatgtac aagagcgccc tcatcttggg ctccttgctg     60

```
gcaacagctg gtgctcagca aattggtact tactgggctg aaacccatcc ctctttgagc    120
tggtctactt gcaaatcggg tggtagctgc accacaaact ccggtgccat acgttggat     180 gccaactggc gttgggtcca tggtgtcaat acctcctgga actgctacga tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gtcaccggct ccaacgtcgg ctcccgtacc tacctgatgg ccgataacac ccactaccaa    420
atcttcgact tgttgaacca ggagttcact ttcaccgtcg atgtctccca cctcccttgc    480
ggtttgaacg tgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggc ggacgccctc ctccaacaac    660
gccaacactg acttggcaa ccacggagct tgctgcgcag agcttgatat ctgggaggca    720
aacagcatct cagaggcttt gactcctcac ccttgcgata cccggtct atctgtttgc    780 actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960 tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccaccttgg cgagactgcc tccttcagca acacggtgg cctggcaaag    1140 atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                     1590
```

<210> SEQ ID NO 112  
<211> LENGTH: 529  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 112

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Trp
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Trp Asn Cys Tyr Asp Gly Asn Thr
65                  70                  75                  80
```

-continued

```
Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Gly Thr Gly Val Ala Ala
                485                 490                 495
```

-continued

His Trp Gly Gln Cys Gly Gly Gln Gly Trp Thr Gly Pro Thr Thr Cys
              500                 505                 510

Ala Ser Gly Thr Thr Cys Thr Val Val Asn Pro Tyr Tyr Ser Gln Cys
        515                 520                 525

Leu

<210> SEQ ID NO 113
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113

```
atgtctgcct tgaactcttt caatatgtac aagagcgccc tcatcttggg ctccttgctg      60
gcaacagctg gtgctcagca aattggtact gcccaggctg aaacccatcc ctctttgagc     120
tggtctactt gcaaatcggg tggtagctgc accacaaact ccggtgccat acgttggat     180
gccaactggc gttgggtcca tggtgtcaat acctcctaca actgctacga tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gtcaccggct ccaacgtcgg ctcccgtacc tacctgatgg ccgataacac ccactaccaa     420
atcttcgact tgttgaacca ggagttcact ttcaccgtcg atgtctccca cctcccttgc     480
ggtttgaacg tgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggcg gacgccctc ctccaacaac     660
gccaacactg acttggcaa ccacggagct tgctgcgcag agcttgatat ctgggaggca     720
aacagcatct cagaggcttt gactcctcac ccttgcgata caccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960
tccaccggca ccctctccga gatcagacgt tactacgttc agaacggtgt tgtcatcccc    1020
cagccttcct ccaagatctc cggagtcagc ggaaatgtca tcaactccga cttctgcgat    1080
gctgagatct ccacctttgg cgagactgcc tccttcagca aacacggtgg cctggcaaag    1140
atgggcgctg gtatggaagc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg gttggtcctt caactctac gttcagcgt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                    1590
```

<210> SEQ ID NO 114
<211> LENGTH: 529
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 114

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Ala Gln
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
50                  55                  60

Trp Val His Gly Val Asn Thr Ser Tyr Asn Cys Tyr Asp Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
                115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
    195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
    275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
                340                 345                 350

Val Ile Asn Ser Asp Phe Cys Asp Ala Glu Ile Ser Thr Phe Gly Glu
                355                 360                 365

Thr Ala Ser Phe Ser Lys His Gly Gly Leu Ala Lys Met Gly Ala Gly
                370                 375                 380
```

```
Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 115
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180 gccaactggc gttgggtcca tggtgtcaat acctggcaga actgctacac cggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gtccagcagg gccctactc caagaacgtc ggctcccgta cctacctgat ggccgataac     420
acccactacc aaatcttcga cttgttgaac caggagttca ctttcaccgt cgatgtctcc     480
cacctccctt gcggtttgaa cggtgccctc tacttcgtga ccatggacgc cgacggtggc     540
gtctccaagt accccaacaa caaggccggc gctcagtacg tgttggata ctgtgactct     600 caatgccctc gtgacttgaa attcatcgct ggtcaggcca acgttgaggg ctggacgccc     660
tcctccaaca cgccaacac tggacttggc aaccacggag cttgctgcgc agagcttgat     720
atctgggagg caaacagcat ctcagaggct ttgactcctc acccttgcga tacacccggt     780
ctatctgttt gcactactga tgcctgcggt ggtacctaca gctccgatcg ttacgccggt     840
acctgcgacc ctgatggatg tgacttcaac ccttaccgtc ttggtgtcac tgacttctac     900
ggctccggca gaccgttga caccaccaaa cccatcaccg ttgtgactca attcgtcact     960
gacgacggca catccaccgg caccctctcc gagatcagac gttactacgt tcagaacggt    1020
gttgtcatcc cccagccttc ctccaagatc tccggagtca gcggaaatgt catcaactcc    1080
gacttctgcg atgctgagat ctccaccttt ggcgagactg cctccttcag caaacacggt    1140
```

```
ggcctggcaa agatgggcgc tggtatggaa gctggtatgg tcttggtcat gagtttgtgg    1200
gacgactact ccgtcaacat gctctggctc gacagcacct accctacaaa cgcgactggt    1260 accccggtg ccgctcgtgg ttcctgccct accacttctg ggaccctaa gaccgttgaa     1320 tcacaatccg gcagctccta tgtcaccttt tctgacatcc gggttggtcc tttcaactct    1380
acgttcagcg gtggttctag caccggtggc agctccacta ctaccgccag cggcaccacc    1440
accaccaagg cctcttccac ctctacttcc agcacctcta ccggcactgg agtcgctgct    1500
cactggggtc agtgtggtgg ccagggttgg actggtccta ccacctgcgc tagtggaacc    1560
acatgcaccg tcgtgaaccc ttactactct caatgtttgt aa                      1602
```

<210> SEQ ID NO 116
<211> LENGTH: 533
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Trp Gln Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Gln Gln Gly Pro Tyr Ser Lys
        115                 120                 125

Asn Val Gly Ser Arg Thr Tyr Leu Met Ala Asp Asn Thr His Tyr Gln
    130                 135                 140

Ile Phe Asp Leu Leu Asn Gln Glu Phe Thr Phe Thr Val Asp Val Ser
145                 150                 155                 160

His Leu Pro Cys Gly Leu Asn Gly Ala Leu Tyr Phe Val Thr Met Asp
                165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
        195                 200                 205

Ile Ala Gly Gln Ala Asn Val Glu Gly Trp Thr Pro Ser Ser Asn Asn
    210                 215                 220

Ala Asn Thr Gly Leu Gly Asn His Gly Ala Cys Cys Ala Glu Leu Asp
225                 230                 235                 240

Ile Trp Glu Ala Asn Ser Ile Ser Glu Ala Leu Thr Pro His Pro Cys
                245                 250                 255

Asp Thr Pro Gly Leu Ser Val Cys Thr Thr Asp Ala Cys Gly Gly Thr
            260                 265                 270
```

Tyr Ser Ser Asp Arg Tyr Ala Gly Thr Cys Asp Pro Asp Gly Cys Asp
            275                 280                 285

Phe Asn Pro Tyr Arg Leu Gly Val Thr Asp Phe Tyr Gly Ser Gly Lys
        290                 295                 300

Thr Val Asp Thr Thr Lys Pro Ile Thr Val Val Thr Gln Phe Val Thr
305                 310                 315                 320

Asp Asp Gly Thr Ser Thr Gly Thr Leu Ser Glu Ile Arg Arg Tyr Tyr
                325                 330                 335

Val Gln Asn Gly Val Val Ile Pro Gln Pro Ser Ser Lys Ile Ser Gly
            340                 345                 350

Val Ser Gly Asn Val Ile Asn Ser Asp Phe Cys Asp Ala Glu Ile Ser
        355                 360                 365

Thr Phe Gly Glu Thr Ala Ser Phe Ser Lys His Gly Gly Leu Ala Lys
    370                 375                 380

Met Gly Ala Gly Met Glu Ala Gly Met Val Leu Val Met Ser Leu Trp
385                 390                 395                 400

Asp Asp Tyr Ser Val Asn Met Leu Trp Leu Asp Ser Thr Tyr Pro Thr
                405                 410                 415

Asn Ala Thr Gly Thr Pro Gly Ala Ala Arg Gly Ser Cys Pro Thr Thr
            420                 425                 430

Ser Gly Asp Pro Lys Thr Val Glu Ser Gln Ser Gly Ser Ser Tyr Val
        435                 440                 445

Thr Phe Ser Asp Ile Arg Val Gly Pro Phe Asn Ser Thr Phe Ser Gly
    450                 455                 460

Gly Ser Ser Thr Gly Gly Ser Ser Thr Thr Ala Ser Gly Thr Thr Thr
465                 470                 475                 480

Thr Thr Lys Ala Ser Ser Thr Ser Thr Ser Ser Thr Ser Thr Gly Thr
                485                 490                 495

Gly Val Ala Ala His Trp Gly Gln Cys Gly Gly Gln Gly Trp Thr Gly
            500                 505                 510

Pro Thr Thr Cys Ala Ser Gly Thr Thr Cys Thr Val Val Asn Pro Tyr
        515                 520                 525

Tyr Ser Gln Cys Leu
    530

<210> SEQ ID NO 117
<211> LENGTH: 1602
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
atgtctgcct tgaactcttt caatatgtac aagagcgccc tcatcttggg ctccttgctg      60
gcaacagctg gtgctcagca aattggtact ctgtacgctg aaacccatcc ctctttgagc     120
tggtctactt gcaaatcggg tggtagctgc accacaaact ccggtgccat tacgttggat     180
gccaactggc gttgggtcca tggtgtcaat acctccacca actgctacga tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gtccagcagg cccctactc caagaacgtc ggctcccgta cctacctgat ggccgataac     420
acccactacc aaatcttcga cttgttgaac caggagttca ctttcaccgt cgatgtctcc     480

```
cacctcccctt gcggtttgaa cggtgccctc tacttcgtga ccatggacgc cgacggtggc    540
gtctccaagt accccaacaa caaggccggc gctcagtacg gtgttggata ctgtgactct    600
caatgccctc gtgacttgaa attcatcgct ggtcaggcca acgttgaggg ctggacgccc    660
tcctccaaca acgccaacac tggacttggc aaccacggag cttgctgcgc agagcttgat    720
atctgggagg caaacagcat ctcagaggct ttgactcctc accttgcga tacaccccggt    780 ctatctgttt gcactactga tgcctgcggt ggtacctaca gctccgatcg ttacgccggt    840
acctgcgacc ctgatggatg tgacttcaac ccttaccgtc ttggtgtcac tgacttctac    900
ggctccggca agaccgttga caccaccaaa cccatcaccg ttgtgactca attcgtcact    960
gacgacggca catccaccgg caccctctcc gagatcagac gttactacgt tcagaacggt   1020
gttgtcatcc cccagccttc ctccaagatc tccggagtca gcggaaatgt catcaactcc   1080
gacttctgcg atgctgagat ctccacccttt ggcgagactg cctccttcag caaacacggt   1140
ggcctggcaa agatgggcgc tggtatggaa gctggtatgg tcttggtcat gagtttgtgg   1200
gacgactact ccgtcaacat gctctggctc gacagcacct accctacaaa cgcgactggt   1260
acccccggtg ccgctcgtgg ttcctgccct accacttctg gggaccctaa gaccgttgaa   1320
tcacaatccg gcagctccta tgtcaccttt tctgacatcc gggttggtcc tttcaactct   1380
acgttcagcg gtggttctag caccggtggc agctccacta ctaccgccag cggcaccacc   1440
accaccaagg cctcttccac ctctacttcc agcacctcta ccggcactgg agtcgctgct   1500
cactggggtc agtgtggtgg ccagggttgg actggtccta ccacctgcgc tagtggaacc   1560
acatgcaccg tcgtgaaccc ttactactct caatgtttgt aa                      1602
```

<210> SEQ ID NO 118  
<211> LENGTH: 533  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 118

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Leu Tyr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Asp Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Gln Gly Pro Tyr Ser Lys
        115                 120                 125

Asn Val Gly Ser Arg Thr Tyr Leu Met Ala Asn Thr His Tyr Gln
    130                 135                 140

Ile Phe Asp Leu Leu Asn Gln Glu Phe Thr Phe Thr Val Asp Val Ser
145                 150                 155                 160
```

His Leu Pro Cys Gly Leu Asn Gly Ala Leu Tyr Phe Val Thr Met Asp
            165                 170                 175

Ala Asp Gly Gly Val Ser Lys Tyr Pro Asn Asn Lys Ala Gly Ala Gln
            180                 185                 190

Tyr Gly Val Gly Tyr Cys Asp Ser Gln Cys Pro Arg Asp Leu Lys Phe
            195                 200                 205

Ile Ala Gly Gln Ala Asn Val Glu Gly Trp Thr Pro Ser Ser Asn Asn
210                 215                 220

Ala Asn Thr Gly Leu Gly Asn His Gly Ala Cys Cys Ala Glu Leu Asp
225                 230                 235                 240

Ile Trp Glu Ala Asn Ser Ile Ser Glu Ala Leu Thr Pro His Pro Cys
            245                 250                 255

Asp Thr Pro Gly Leu Ser Val Cys Thr Thr Asp Ala Cys Gly Gly Thr
            260                 265                 270

Tyr Ser Ser Asp Arg Tyr Ala Gly Thr Cys Asp Pro Asp Gly Cys Asp
            275                 280                 285

Phe Asn Pro Tyr Arg Leu Gly Val Thr Asp Phe Tyr Gly Ser Gly Lys
        290                 295                 300

Thr Val Asp Thr Thr Lys Pro Ile Thr Val Thr Gln Phe Val Thr
305                 310                 315                 320

Asp Asp Gly Thr Ser Thr Gly Thr Leu Ser Glu Ile Arg Arg Tyr Tyr
            325                 330                 335

Val Gln Asn Gly Val Val Ile Pro Gln Pro Ser Ser Lys Ile Ser Gly
            340                 345                 350

Val Ser Gly Asn Val Ile Asn Ser Asp Phe Cys Asp Ala Glu Ile Ser
            355                 360                 365

Thr Phe Gly Glu Thr Ala Ser Phe Ser Lys His Gly Gly Leu Ala Lys
        370                 375                 380

Met Gly Ala Gly Met Glu Ala Gly Met Val Leu Val Met Ser Leu Trp
385                 390                 395                 400

Asp Asp Tyr Ser Val Asn Met Leu Trp Leu Asp Ser Thr Tyr Pro Thr
            405                 410                 415

Asn Ala Thr Gly Thr Pro Gly Ala Ala Arg Gly Ser Cys Pro Thr Thr
            420                 425                 430

Ser Gly Asp Pro Lys Thr Val Glu Ser Gln Ser Gly Ser Ser Tyr Val
            435                 440                 445

Thr Phe Ser Asp Ile Arg Val Gly Pro Phe Asn Ser Thr Phe Ser Gly
        450                 455                 460

Gly Ser Ser Thr Gly Gly Ser Ser Thr Thr Ala Ser Gly Thr Thr
465                 470                 475                 480

Thr Thr Lys Ala Ser Ser Thr Ser Thr Ser Thr Ser Thr Gly Thr
            485                 490                 495

Gly Val Ala Ala His Trp Gly Gln Cys Gly Gly Gln Gly Trp Thr Gly
            500                 505                 510

Pro Thr Thr Cys Ala Ser Gly Thr Thr Cys Thr Val Val Asn Pro Tyr
            515                 520                 525

Tyr Ser Gln Cys Leu
        530

<210> SEQ ID NO 119
<211> LENGTH: 1590
<212> TYPE: DNA
<213> ORGANISM: Artificial Sequence
<220> FEATURE:

<220> FEATURE:
<221> NAME/KEY: source
<223> OTHER INFORMATION: /note="Description of Artificial Sequence: Synthetic polynucleotide"

<400> SEQUENCE: 119

| | | | | | |
|---|---|---|---|---|---|
| atgtctgcct | tgaactcttt | caatatgtac | aagagcgccc | tcatcttggg | ctccttgctg | 60 |
| gcaacagctg | gtgctcagca | aattggtact | tataccgctg | aaacccatcc | ctctttgagc | 120 |
| tggtctactt | gcaaatcggg | tggtagctgc | accacaaact | ccggtgccat | acgttggat | 180 |
| gccaactggc | gttgggtcca | tggtgtcaat | accagcacca | actgctacac | tggcaacact | 240 |
| tggaataccg | ccatctgcga | cactgatgca | tcctgtgccc | aggactgtgc | tcttgatggt | 300 |
| gctgactact | ctggcacgta | cggtatcact | acctccggca | actcattgcg | cctgaacttc | 360 |
| gttaccggtt | ccaacgtcgg | atctcgtacc | tacctgatgg | ccgataacac | ccactaccaa | 420 |
| atcttcgact | tgttgaacca | ggagttcact | ttcaccgtcg | atgtctccca | cctcccttgc | 480 |
| ggtttgaacg | gtgccctcta | cttcgtgacc | atggacgccg | acggtggcgt | ctccaagtac | 540 |
| cccaacaaca | aggccggcgc | tcagtacggt | gttggatact | gtgactctca | atgccctcgt | 600 |
| gacttgaaat | tcatcgctgg | tcaggccaac | gttgagggct | ggacgccctc | ctccaacaac | 660 |
| gccaacactg | gacttggcaa | ccacggagct | gctgcgcag | agcttgatat | ctgggaggca | 720 |
| aacagcatct | cagaggcttt | gactcctcac | ccttgcgata | caccgggtct | atctgtttgc | 780 |
| actactgatg | cctgcggtgg | tacctacagc | tccgatcgtt | acgccggtac | ctgcgaccct | 840 |
| gatggatgtg | acttcaaccc | ttaccgtctt | ggtgtcactg | acttctacgg | ctccggcaag | 900 |
| accgttgaca | ccaccaaacc | catcaccgtt | gtgactcaat | cgtcactga | cgacggcaca | 960 |
| tccaccggca | ccctctccga | gatcagacgt | tactacgttc | agaacggtgt | tgtcatcccc | 1020 |
| cagccttcct | ccaagatctc | cggagtcagc | ggaaatgtca | tcaactccga | cttctgcgat | 1080 |
| gctgagatct | ccacctttgg | cgagactgcc | tccttcagca | aacacggtgg | cctggcaaag | 1140 |
| atgggcgctg | gtatggaagc | tggtatggtc | ttggtcatga | gtttgtggga | tgattactcc | 1200 |
| gtcaacatgc | tctggctcga | cagcacctac | cctacaaacg | cgactggtac | ccccggtgcc | 1260 |
| gctcgtggtt | cctgccctac | cacttctggg | gaccctaaga | ccgttgaatc | acaatccggc | 1320 |
| agctcctatg | tcaccttttc | tgacatccgg | gttggtcctt | tcaactctac | gttcagcggt | 1380 |
| ggttctagca | ccggtggcag | ctccactact | accgccagcg | gcaccaccac | caccaaggcc | 1440 |
| tcttccacct | ctacttccag | cacctctacc | ggcactggag | tcgctgctca | ctgggtcag | 1500 |
| tgtggtggcc | agggttggac | tggtcctacc | acctgcgcta | gtggaaccac | atgcaccgtc | 1560 |
| gtgaacccttc | actactctca | atgtttgtaa | | | | 1590 |

<210> SEQ ID NO 120
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 120

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly

```
              35                  40                  45
Ser Cys Thr Thr Asn Ser Gly Ala Ile Thr Leu Asp Ala Asn Trp Arg
 50                  55                  60
Trp Val His Gly Val Asn Thr Ser Thr Asn Cys Tyr Thr Gly Asn Thr
 65                  70                  75                  80
Trp Asn Thr Ala Ile Cys Asp Thr Asp Ala Ser Cys Ala Gln Asp Cys
                     85                  90                  95
Ala Leu Asp Gly Ala Asp Tyr Ser Gly Thr Tyr Gly Ile Thr Thr Ser
                100                 105                 110
Gly Asn Ser Leu Arg Leu Asn Phe Val Thr Gly Ser Asn Val Gly Ser
            115                 120                 125
Arg Thr Tyr Leu Met Ala Asp Asn Thr His Tyr Gln Ile Phe Asp Leu
        130                 135                 140
Leu Asn Gln Glu Phe Thr Phe Thr Val Asp Val Ser His Leu Pro Cys
145                 150                 155                 160
Gly Leu Asn Gly Ala Leu Tyr Phe Val Thr Met Asp Ala Asp Gly Gly
                165                 170                 175
Val Ser Lys Tyr Pro Asn Asn Lys Ala Gly Ala Gln Tyr Gly Val Gly
                180                 185                 190
Tyr Cys Asp Ser Gln Cys Pro Arg Asp Leu Lys Phe Ile Ala Gly Gln
            195                 200                 205
Ala Asn Val Glu Gly Trp Thr Pro Ser Ser Asn Asn Ala Asn Thr Gly
        210                 215                 220
Leu Gly Asn His Gly Ala Cys Cys Ala Glu Leu Asp Ile Trp Glu Ala
225                 230                 235                 240
Asn Ser Ile Ser Glu Ala Leu Thr Pro His Pro Cys Asp Thr Pro Gly
                245                 250                 255
Leu Ser Val Cys Thr Thr Asp Ala Cys Gly Gly Thr Tyr Ser Ser Asp
                260                 265                 270
Arg Tyr Ala Gly Thr Cys Asp Pro Asp Gly Cys Asp Phe Asn Pro Tyr
            275                 280                 285
Arg Leu Gly Val Thr Asp Phe Tyr Gly Ser Gly Lys Thr Val Asp Thr
        290                 295                 300
Thr Lys Pro Ile Thr Val Val Thr Gln Phe Val Thr Asp Asp Gly Thr
305                 310                 315                 320
Ser Thr Gly Thr Leu Ser Glu Ile Arg Arg Tyr Tyr Val Gln Asn Gly
                325                 330                 335
Val Val Ile Pro Gln Pro Ser Ser Lys Ile Ser Gly Val Ser Gly Asn
                340                 345                 350
Val Ile Asn Ser Asp Phe Cys Asp Ala Glu Ile Ser Thr Phe Gly Glu
            355                 360                 365
Thr Ala Ser Phe Ser Lys His Gly Gly Leu Ala Lys Met Gly Ala Gly
        370                 375                 380
Met Glu Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
                420                 425                 430
Lys Thr Val Glu Ser Gln Ser Gly Ser Ser Tyr Val Thr Phe Ser Asp
            435                 440                 445
Ile Arg Val Gly Pro Phe Asn Ser Thr Phe Ser Gly Gly Ser Ser Thr
        450                 455                 460
```

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
        500                 505                 510

Ala Ser Gly Thr Thr Cys Thr Val Val Asn Pro Tyr Tyr Ser Gln Cys
        515                 520                 525

Leu

<210> SEQ ID NO 121
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 121
atgtctgcct tgaactcttt caatatgtac aagagcgccc tcatcttggg ctccttgctg     60
gcaacagctg gtgctcagca aattggtact tataccgctg aaacccatcc ctctttgagc    120
tggtctactt gcaaatcggg tggtagctgc accacaaact ccggtgccat acgttggat    180 gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcgggtgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgcccaa gtccaacaac    660
gcccatactg gatatggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgacct    840 gatggatgtg acttcaaccc ttaccgtctt ggtgtcactg acttctacgg ctccggcaag    900
accgttgaca ccaccaaacc catcaccgtt gtgactcaat cgtcactga cgacggcaca    960 tccaccggca ccctctccga gatcagacgt tactacgttc agaacggtgt tgtcatcccc   1020
cagccttcct ccgatatctc cggagtcagc ggagttgtca tcaactccga cttctgcgat   1080
gctgagatct ccaccttgg cgagactgcc tccttcagca acacggtgg cctggcaaag   1140 atgggcgctg gtatgaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg tgggtccttt caactctac gttcagcggt   1380 ggttctagca ccggtggcag ctccactact accgccagcg gcaccaccac caccaaggcc   1440
tcttccacct ctacttccag cacctctacc ggcactggag tcgctgctca ctgggtcag   1500 tgtggtggcc agggttggac tggtcctacc acctgcgcta gtggaaccac atgcaccgtc   1560

-continued

```
gtgaaccctt actactctca atgtttgtaa                                      1590
```

<210> SEQ ID NO 122
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Gly Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Lys Ser Asn Asn Ala His Thr Gly
    210                 215                 220

Tyr Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Asp Ile Ser Gly Val Ser Gly Val
            340                 345                 350

```
Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
            435                 440                 445

Ile Arg Trp Gly Pro Phe Asn Ser Thr Phe Ser Gly Gly Ser Ser Thr
            450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
            515                 520                 525

Leu

<210> SEQ ID NO 123
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat     180 gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggct ggacgccctc ctccaacaac     660
gcccatactg gatatggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat tcgtcactga cgacggcaca     960
```

-continued

```
tccaccggca ccctctccga gatcagacgt tactacgttc agaacggtgt tgtcatcccc    1020
cagccttcct ccgatatctc cggagtcagc ggagttgtca tcaactccga cttctgcgat    1080
gctgagatct ccacctttgg cgagactgcc tccttcagca acacggtgg cctggcaaag     1140 atgggcgctg gtatgagtgc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcaccttttc tgacatccgg tggggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560 gtgaacccctt actactctca atgtttgtaa                                    1590
```

<210> SEQ ID NO 124
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala His Thr Gly
    210                 215                 220

Tyr Gly Asn His Gly Ala Cys Cys Ala Glu Leu Asp Ile Trp Glu Ala
225                 230                 235                 240
```

Asn Ser Ile Ser Glu Ala Leu Thr Pro His Pro Cys Asp Thr Pro Gly
            245                 250                 255

Leu Ser Val Cys Thr Thr Asp Ala Cys Gly Gly Thr Tyr Ser Ser Asp
        260                 265                 270

Arg Tyr Ala Gly Thr Cys Asp Pro Asp Gly Cys Asp Phe Asn Pro Tyr
    275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Asp Ile Ser Gly Val Ser Gly Val
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Ser Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Trp Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 125
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 125
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tgtgtcaat accagcacca actgctacac tggcaacact     240
tggaataccg ccatctgcga cactgatgca tcctgtgccc aggactgtgc tcttgatggt     300

-continued

```
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg gtgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggct ggacgccctc ctccaacaac    660
gccaacactg gacttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat cgtcactga cgacggcaca    960
tccaccggca ccctccttga gatcagacgt tactacgttc agaacggtgt tgtcatcccc   1020
cagccttcct ccgatatctc cggagtcagc ggagttgtca tcaactccga cttctgcgat   1080
gctgagatct ccacctttgg cgagactgcc tccttcagca acacggtgg cctggcaaag   1140
atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcacctttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaacccctt actactctca atgtttgtaa                                   1590
```

<210> SEQ ID NO 126
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Met Ser Ala Leu Asn Ser Phe Asn Met Tyr Lys Ser Ala Leu Ile Leu
1               5                   10                  15
Gly Ser Leu Leu Ala Thr Ala Gly Ala Gln Gln Ile Gly Thr Tyr Thr
                20                  25                  30
Ala Glu Thr His Pro Ser Leu Ser Trp Ser Thr Cys Lys Ser Gly Gly
            35                  40                  45
Ser Cys Thr Thr Asn Ser Gly Ala Ile Thr Leu Asp Ala Asn Trp Arg
        50                  55                  60
Trp Val His Gly Val Asn Thr Ser Thr Asn Cys Tyr Thr Gly Asn Thr
65                  70                  75                  80
Trp Asn Thr Ala Ile Cys Asp Thr Asp Ala Ser Cys Ala Gln Asp Cys
                85                  90                  95
Ala Leu Asp Gly Ala Asp Tyr Ser Gly Thr Tyr Gly Ile Thr Thr Ser
            100                 105                 110
Gly Asn Ser Leu Arg Leu Asn Phe Val Thr Gly Ser Asn Val Gly Ser
        115                 120                 125
```

Arg Thr Tyr Leu Met Ala Asp Asn Thr His Tyr Gln Ile Phe Asp Leu
    130             135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
            165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
            245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Leu Glu Ile Arg Arg Tyr Tyr Val Gln Asn Gly
            325                 330                 335

Val Val Ile Pro Gln Pro Ser Ser Asp Ile Ser Gly Val Ser Gly Val
            340                 345                 350

Val Ile Asn Ser Asp Phe Cys Asp Ala Glu Ile Ser Thr Phe Gly Glu
            355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
    435                 440                 445

Ile Arg Val Gly Pro Phe Asn Ser Thr Phe Ser Gly Gly Ser Ser Thr
450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
        500                 505                 510

Ala Ser Gly Thr Thr Cys Thr Val Val Asn Pro Tyr Tyr Ser Gln Cys
        515                 520                 525

Leu

<210> SEQ ID NO 127
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg tgccctcta cttcgtgacc atggacgccg acggtggcgt ctccaagtac     540
cccaacaaca aggccggcgc tcagtacggt gttggatact gtgactctca atgccctcgt     600
gacttgaaat tcatcgctgg tcaggccaac gttgagggc ggacgccctc ctccaacaac     660
gccaacactg gatatggcaa ccacggagct tgctgcgcag agcttgatat ctgggaggca     720
aacagcatct cagaggcttt gactcctcac ccttgcgata cacccggtct atctgtttgc     780
actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga ccagggcaca     960
tccaccggcc gtctccttga gatcagacgt tactacgttc agaacggtgt tgtcatcccc    1020
cagccttcct ccgatatctc cggagtcagc ggaaatgtca tcaactccga cttctgcgat    1080
gctgagatct ccacctttgg cgagactgcc tccttcagca acacggtgg cctggcaaag    1140
atgggcgctg gtatgagtgc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accgccagcg gcaccaccac caccaaggcc    1440
tcttccacct ctacttccag cacctctacc ggcactggag tcgctgctca ctggggtcag    1500
tgtggtggcc agggttggac tggtcctacc acctgcgcta gtggaaccac atgcaccgtc    1560
gtgaaccctt actactctca atgtttgtaa                                    1590
```

<210> SEQ ID NO 128
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 128

```
Met Ser Ala Leu Asn Ser Phe Asn Met Tyr Lys Ser Ala Leu Ile Leu
1               5                   10                  15
```

```
Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
                35                  40                  45

Ser Cys Thr Thr Asn Ser Gly Ala Ile Thr Leu Asp Ala Asn Trp Arg
 50                  55                  60

Trp Val His Gly Val Asn Thr Ser Thr Asn Cys Tyr Thr Gly Asn Thr
 65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
            210                 215                 220

Tyr Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Gln Gly Thr
305                 310                 315                 320

Ser Thr Gly Arg Leu Leu Glu Ile Arg Arg Tyr Tyr Val Gln Asn Gly
                325                 330                 335

Val Val Ile Pro Gln Pro Ser Ser Asp Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Ser Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430
```

Lys Thr Val Glu Ser Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
        450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 129
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

```
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat acgttggat      180 gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcgggtgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggct ggacgcccaa gtccaacaac     660
gcccatactg gatatggcaa ccacggagct tgctgcgcag agcttgatat ctgggaggca     720
aacagcatct cagaggcttt gactcctcac ccttgcgata cccggtct atctgtttgc      780 actactgatg cctgcggtgg tacctacagc tccgatcgtt acgccggtac ctgcgaccct     840
gatggatgtg acttcaaccc ttaccgtctt ggtgtcactg acttctacgg ctccggcaag     900
accgttgaca ccaccaaacc catcaccgtt gtgactcaat cgtcactga cgacggcaca     960 tccaccggca cctctccga gatcagacgt tactacgtta gtaacggtgt tgtcatcccc    1020
cagccttcct ccgatatctc cggagtcagc ggaaatgtca tcaactccga cttctgcgat    1080
gctgagatct ccaccttggg cgagactgcc tccttcagca acacggtgg cctggcaaag    1140 atgggcgctg gtatgagtgc tggtatggtc ttggtcatga gtttgtggga cgactactcc    1200
gtcaacatgc tctggctcga cagcacctac cctacaaacg cgactggtac ccccggtgcc    1260
gctcgtggtt cctgccctac cacttctggg gaccctaaga ccgttgaatc acaatccggc    1320
agctcctatg tcacctttc tgacatccgg gttggtcctt tcaactctac gttcagcggt    1380
ggttctagca ccggtggcag ctccactact accgccagcg gcaccaccac caccaaggcc    1440
```

```
tcttccacct ctacttccag cacctctacc ggcactggag tcgctgctca ctggggtcag   1500
tgtggtggcc agggttggac tggtcctacc acctgcgcta gtggaaccac atgcaccgtc   1560
gtgaacccct actactctca atgtttgtaa                                    1590
```

<210> SEQ ID NO 130
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 130

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Gly Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Lys Ser Asn Asn Ala His Thr Gly
    210                 215                 220

Tyr Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320
```

Ser Thr Gly Thr Leu Ser Glu Ile Arg Arg Tyr Tyr Val Ser Asn Gly
            325                 330                 335

Val Val Ile Pro Gln Pro Ser Ser Asp Ile Ser Gly Val Ser Gly Asn
        340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Ser Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 131
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
gccaactggc gttgggtcca tggtgtcaat accagcacca actgctacac tggcaacact     240
tggaataccg ccatctgcga cactgatgca tcctgtgccc aggactgtgc tcttgatggt     300
gctgactact ctggcacgta cggtatcact acctccggca actcattgcg cctgaacttc     360
gttaccggtt ccaacgtcgg atctcgtacc tacctgatgg ccgataacac ccactaccaa     420
atcttcgact tgttgaacca ggagttcact ttcaccgtcg atgtctccca cctcccttgc     480
ggtttgaacg gtgccctcta cttcgtgacc atggacgccg acgtggcgt ctccaagtac     540 cccaacaaca aggccggcgc tcagtacggt gttggatact gtgactctca atgccctcgt     600
gacttgaaat tcatcgctgg tcaggccaac gttgagggct ggacgccctc ctccaacaac     660
gccaacactg gacttggcaa ccacggagct tgctgcgcag agcttgatat ctgggaggca     720
aacagcatct cagaggcttt gactcctcac ccttgcgata cacccggtct atctgtttgc     780

```
actactgatg cctgcggtgg tacctacagc tccgatcgtt acgccggtac ctgcgaccct   840
gatggatgtg acttcaaccc ttaccgtctt ggtgtcactg acttctacgg ctccggcaag   900
accgttgaca ccaccaaacc catcaccgtt gtgactcaat cgtcactga cgacggcaca   960
tccaccggca ccctctccga gatcagacgt tactacgttc agaacggtgt tgtcatcccc  1020
cagccttcct ccaagatctc cggagtcagc ggaaatgtca tcaactccga cttctgcgat  1080
gctgagatct ccacctttgg cgagactgcc tccttcagca acacggtgg cctggcaaag  1140
atgggcgctg gtatgagtgc tggtatggtc ttggtcatga gtttgtggga cgactactcc  1200
gtcaacatgc tctggctcga cagcacctac cctacaaacg cgactggtac ccccggtgcc  1260
gctcgtggtt cctgccctac cacttctggg accctaaga ccgttgaatc acaatccggc  1320
agctcctatg tcaccttttc tgacatccgg tggggtcctt tcaactctac gttcagcggt  1380
ggttctagca ccggtggcag ctccactact accgccagcg gcaccaccac caccaaggcc  1440
tcttccacct ctactccag cacctctacc ggcactggag tcgctgctca ctggggtcag  1500
tgtggtggcc agggttggac tggtcctacc acctgcgcta gtggaaccac atgcaccgtc  1560
gtgaacccctt actactctca atgtttgtaa                                   1590
```

<210> SEQ ID NO 132
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 132

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

```
Ala Asn Val Glu Gly Trp Thr Pro Ser Ser Asn Ala Asn Thr Gly
    210                 215                 220
Leu Gly Asn His Gly Ala Cys Cys Ala Glu Leu Asp Ile Trp Glu Ala
225                 230                 235                 240
Asn Ser Ile Ser Glu Ala Leu Thr Pro His Pro Cys Asp Thr Pro Gly
                245                 250                 255
Leu Ser Val Cys Thr Thr Asp Ala Cys Gly Gly Thr Tyr Ser Ser Asp
            260                 265                 270
Arg Tyr Ala Gly Thr Cys Asp Pro Asp Gly Cys Asp Phe Asn Pro Tyr
        275                 280                 285
Arg Leu Gly Val Thr Asp Phe Tyr Gly Ser Gly Lys Thr Val Asp Thr
    290                 295                 300
Thr Lys Pro Ile Thr Val Val Thr Gln Phe Val Thr Asp Asp Gly Thr
305                 310                 315                 320
Ser Thr Gly Thr Leu Ser Glu Ile Arg Arg Tyr Tyr Val Gln Asn Gly
                325                 330                 335
Val Val Ile Pro Gln Pro Ser Ser Lys Ile Ser Gly Val Ser Gly Asn
            340                 345                 350
Val Ile Asn Ser Asp Phe Cys Asp Ala Glu Ile Ser Thr Phe Gly Glu
        355                 360                 365
Thr Ala Ser Phe Ser Lys His Gly Gly Leu Ala Lys Met Gly Ala Gly
    370                 375                 380
Met Ser Ala Gly Met Val Leu Val Met Ser Leu Trp Asp Asp Tyr Ser
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Ser Cys Pro Thr Thr Ser Gly Asp Pro
            420                 425                 430
Lys Thr Val Glu Ser Gln Ser Gly Ser Ser Tyr Val Thr Phe Ser Asp
        435                 440                 445
Ile Arg Trp Gly Pro Phe Asn Ser Thr Phe Ser Gly Gly Ser Ser Thr
    450                 455                 460
Gly Gly Ser Ser Thr Thr Thr Ala Ser Gly Thr Thr Thr Lys Ala
465                 470                 475                 480
Ser Ser Thr Ser Thr Ser Ser Thr Ser Thr Gly Thr Gly Val Ala Ala
                485                 490                 495
His Trp Gly Gln Cys Gly Gly Gln Gly Trp Thr Gly Pro Thr Thr Cys
            500                 505                 510
Ala Ser Gly Thr Thr Cys Thr Val Val Asn Pro Tyr Tyr Ser Gln Cys
        515                 520                 525
Leu

<210> SEQ ID NO 133
<211> LENGTH: 1590
<212> TYPE: DNA
<213> ORGANISM: Unknown
<220> FEATURE:
<221> NAME/KEY: source
<223> OTHER INFORMATION: /note="Description of Unknown: Wildtype
      cellobiohydrolase polynucleotide"

<400> SEQUENCE: 133
atgtctgcct tgaactcttt caatatgtac aagagcgccc tcatcttggg ctccttgctg      60
gcaacagctg gtgctcagca aattggtact tataccgctg aaacccatcc ctctttgagc     120
tggtctactt gcaaatcggg tggtagctgc accacaaact ccggtgccat tacgttggat     180
```

```
gccaactggc gttgggtcca tggtgtcaat accagcacca actgctacac tggcaacact    240
tggaataccg ccatctgcga cactgatgca tcctgtgccc aggactgtgc tcttgatggt    300
gctgactact ctggcacgta cggtatcact acctccggca actcattgcg cctgaacttc    360
gttaccggtt ccaacgtcgg atctcgtacc tacctgatgg ccgataacac ccactaccaa    420
atcttcgact tgttgaacca ggagttcact ttcaccgtcg atgtctccca cctcccttgc    480
ggtttgaacg tgccctcta cttcgtgacc atggacgccg acggtggcgt ctccaagtac    540
cccaacaaca aggccggcgc tcagtacggt gttggatact gtgactctca atgccctcgt    600
gacttgaaat tcatcgctgg tcaggccaac gttgagggtg gacgccctc ctccaacaac    660 gccaacactg acttggcaa ccacggagct tgctgcgcag agcttgatat ctgggaggca    720
aacagcatct cagaggcttt gactcctcac ccttgcgata cacccggtct atctgtttgc    780
actactgatg cctgcggtgg tacctacagc tccgatcgtt acgccggtac ctgcgaccct    840
gatggatgtg acttcaaccc ttaccgtctt ggtgtcactg acttctacgg ctccggcaag    900
accgttgaca ccaccaaacc catcaccgtt gtgactcaat tcgtcactga cgacggcaca    960
tccaccggca ccctctccga gatcagacgt tactacgttc agaacggtgt tgtcatcccc   1020
cagccttcct ccaagatctc cggagtcagc ggaaatgtca tcaactccga cttctgcgat   1080
gctgagatct ccacctttgg cgagactgcc tccttcagca acacggtgg cctggcaaag   1140 atgggcgctg gtatggaagc tggtatggtc ttggtcatga gtttgtggga cgactactcc   1200
gtcaacatgc tctggctcga cagcacctac cctacaaacg cgactggtac ccccggtgcc   1260
gctcgtggtt cctgccctac cacttctggg gaccctaaga ccgttgaatc acaatccggc   1320
agctcctatg tcaccttttc tgacatccgg gttggtcctt tcaactctac gttcagcggt   1380
ggttctagca ccggtggcag ctccactact accgccagcg gcaccaccac caccaaggcc   1440
tcttccacct ctacttccag cacctctacc ggcactggag tcgctgctca ctggggtcag   1500
tgtggtggcc agggttggac tggtcctacc acctgcgcta gtggaaccac atgcaccgtc   1560 gtgaacccctt actactctca atgtttgtaa                                    1590
```

<210> SEQ ID NO 134
<211> LENGTH: 529
<212> TYPE: PRT
<213> ORGANISM: Unknown
<220> FEATURE:
<221> NAME/KEY: source
<223> OTHER INFORMATION: /note="Description of Unknown: Wildtype cellobiohydrolase polypeptide"

<400> SEQUENCE: 134

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95
```

```
Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
    370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
```

515                 520                 525

Leu

<210> SEQ ID NO 135
<211> LENGTH: 1590
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135

| | | | | | |
|---|---|---|---|---|---|
| atgtctgcct | tgaactcttt | caatatgtac | aagagcgccc | tcatcttggg | ctccttgctg | 60 |
| gcaacagctg | gtgctcagca | aattggtact | tataccgctg | aaacccatcc | ctctttgagc | 120 |
| tggtctactt | gcaaatcggg | tggtagctgc | accacaaact | ccggtgccat | tacgttggat | 180 |
| gccaactggc | gttgggtcca | tggtgtcaat | accagcacca | actgctacac | tggcaacact | 240 |
| tggaataccg | ccatctgcga | cactgatgca | tcctgtgccc | aggactgtgc | tcttgatggt | 300 |
| gctgactact | ctggcacgta | cggtatcact | acctccggca | actcattgcg | cctgaacttc | 360 |
| gttaccggtt | ccaacgtcgg | atctcgtacc | tacctgatgg | ccgataacac | ccactaccaa | 420 |
| atcttcgact | tgttgaacca | ggagttcact | ttcaccgtcg | atgtctccca | cctcccttgc | 480 |
| ggtttgaacg | gtgccctcta | cttcgtgacc | atggacgccg | acggtggcgt | ctccaagtac | 540 |
| cccaacaaca | aggccggcgc | tcagtacggt | gttggatact | gtgactctca | atgccctcgt | 600 |
| gacttgaaat | tcatcgctgg | tcaggccaac | gttgagggc | ggacgccctc | ctccaacaac | 660 |
| gccaacactg | gacttggcaa | ccacggagct | tgctgcgcag | agcttgatat | ctgggaggca | 720 |
| aacagcatct | cagaggcttt | gactcctcac | ccttgcgata | cacccggtct | atctgtttgc | 780 |
| actactgatg | cctgcggtgg | tacctacagc | tccgataagt | acgccggtac | ctgcgaccct | 840 |
| gatggatgtg | acttcaaccc | ttaccgtctt | ggtgtcactg | acttctacgg | ctccggcaag | 900 |
| accgttgaca | ccaccaaacc | catcaccgtt | gtgactcaat | cgtcactga | cgacggcaca | 960 |
| tccaccggca | ccctctccga | gatcagacgt | tactacgttc | agaacggtgt | tgtcatcccc | 1020 |
| cagccttcct | ccaagatctc | cggagtcagc | ggaaatgtca | tcaactccga | cttctgcgat | 1080 |
| gctgagatct | ccaccttttgg | cgagactgcc | tccttcagca | aacacggtgg | cctggcaaag | 1140 |
| atgggcgctg | gtatggaagc | tggtatggtc | ttggtcatga | gtttgtggga | cgactactcc | 1200 |
| gtcaacatgc | tctggctcga | cagcacctac | cctacaaacg | cgactggtac | ccccggtgcc | 1260 |
| gctaagggtt | cctgccctac | cacttctggg | gaccctaaga | ccgttgaatc | acaatccggc | 1320 |
| agctcctatg | tcaccttttc | tgacatccgg | gttggtcctt | tcaactctac | gttcagcggt | 1380 |
| ggttctagca | ccggtggcag | ctccactact | accgccagcg | gcaccaccac | caccaaggcc | 1440 |
| tcttccacct | ctacttccag | cacctctacc | ggcactggag | tcgctgctca | ctggggtcag | 1500 |
| tgtggtggcc | agggttggac | tggtcctacc | acctgcgcta | gtggaaccac | atgcaccgtc | 1560 |
| gtgaacccctt | actactctca | atgtttgtag | | | | 1590 |

<210> SEQ ID NO 136
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
210                 215                 220

Leu Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Lys Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
290                 295                 300

Thr Lys Pro Ile Thr Val Val Thr Gln Phe Val Thr Asp Asp Gly Thr
305                 310                 315                 320

Ser Thr Gly Thr Leu Ser Glu Ile Arg Arg Tyr Tyr Val Gln Asn Gly
                325                 330                 335

Val Val Ile Pro Gln Pro Ser Ser Lys Ile Ser Gly Val Ser Gly Asn
            340                 345                 350

Val Ile Asn Ser Asp Phe Cys Asp Ala Glu Ile Ser Thr Phe Gly Glu
        355                 360                 365

Thr Ala Ser Phe Ser Lys His Gly Gly Leu Ala Lys Met Gly Ala Gly
370                 375                 380

Met Glu Ala Gly Met Val Leu Val Met Ser Leu Trp Asp Asp Tyr Ser
385                 390                 395                 400

Val Asn Met Leu Trp Leu Asp Ser Thr Tyr Pro Thr Asn Ala Thr Gly
```

```
                  405                 410                 415
Thr Pro Gly Ala Ala Lys Gly Ser Cys Pro Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Ser Thr Thr Thr Ala Ser Gly Thr Thr Thr Lys Ala
465                 470                 475                 480

Ser Ser Thr Ser Thr Ser Ser Thr Ser Thr Gly Thr Gly Val Ala Ala
            485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu
```

VARIANT CBH I POLYPEPTIDES

1. CROSS REFERENCE TO RELATED APPLICATIONS

The present application claims the benefit of national stage application filed in compliance with 35 U.S.C. §371 of International Application No. PCT/US2011/055180, filed Oct. 6, 2011, which claims benefit under 35 U.S.C. §119(3) of U.S. Provisional Application No. 61/390,392, filed Oct. 6, 2010, and are herein incorporated in their entireties for all purposes.

2. FIELD OF THE INVENTION

This invention relates to molecular and cellular biology and biochemistry. In alternative embodiments, the invention provides polypeptides having a lignocellulolytic (lignocellulosic) activity, e.g., a ligninolytic and cellulolytic activity, including, e.g., a cellulase or a cellobiohydrolase (cbhI) (e.g., an exo-cellobiohydrolase, e.g., having an "exo" activity that can processively release cellobiose units β-1,4 glucose-glucose disaccharide), polynucleotides encoding these polypeptides, and methods of making and using these polynucleotides and polypeptides. In one embodiment, the invention provides thermostable and thermotolerant forms of polypeptides of the invention. The polypeptides and nucleic acids of the invention are used in a variety of pharmaceutical, agricultural and industrial contexts; for example, as enzymes for the bioconversion of a biomass, e.g., lignocellulosic residues, into fermentable sugars, where in one aspect these sugars are used as a chemical feedstock for the production of ethanol and fuels, e.g., biofuels, e.g., synthetic liquid or gas fuels, including ethanol, methanol and the like.

3. BACKGROUND

There is a great interest in the bioconversion of biomass, such as material comprising lignocellulosic residues, into fermentable sugars. These sugars can be used in turn as chemical feedstock for the production of a biofuel, which is a clean-burning renewable energy source. Accordingly, there is a need in the industry for non-chemical means for processing biomass to make clean-burning renewable fuels.

4. SUMMARY OF THE INVENTION

The present disclosure provides variant CBH I polypeptides comprising at least one amino acid substitution as compared to BD29555. "Variant" means a polypeptide that differs in sequence from BD29555 by substitution of one or more amino acids at one or a number of different sites in the amino acid sequence.

CBH I belong to the glycosyl hydrolase family 7 ("GH7"). The cellobiohydrolases of this family, which includes endoglucanases and cellobiohydrolases, act processively from the reducing ends of cellulose chains to generate cellobiose. Cellulases of bacterial and fungal origin characteristically have a small cellulose-binding domain ("CBD") connected to either the N or the C terminus of the catalytic domain ("CD") via a linker peptide (see Suumakki et al., 2000, Cellulose 7: 189-209). The CD contains the active site whereas the CBD interacts with cellulose by binding the enzyme to it (van Tilbeurgh et al., 1986, FEBS Lett. 204(2): 223-227; Tomme et al., 1988, Eur. J. Biochem. 170:575-581). The three-dimensional structure of the catalytic domain of *T. reesei* CBH I has been solved (Divne et al., 1994, Science 265:524-528). The CD consists of two β-sheets that pack face-to-face to form a β-sandwich. Most of the remaining amino acids in the CD are loops connecting the β-sheets. Some loops are elongated and bend around the active site, forming cellulose-binding tunnel of (~50 Å). Typically, the catalytic residues are glumates corresponding to E234 and E239 of BD29555. The loop characteristic of the active site ("the active site loops") of CBH I polypeptides, which are absent from GH7 family endoglucanases, corresponds to positions 214-226 of BD29555 (SEQ ID NO:134).

Many CBH I polypeptides do not have a CBD, and most studies concerning the activity of cellulase domains on different substrates have been carried out with only the catalytic domains of CBH I polypeptides. Because CDs with cellobiohydrolase activity can be generated by limited proteolysis of mature CBH I by papain (see, e.g., Chen et al., 1993, Biochem. Mol. Biol. Int. 30(5):901-10), they are often referred to as "core" domains. Accordingly, a variant BD29555 can include only a CD "core", which corresponds to positions 26-455 of SEQ ID NO:134.

The catalytic residues in the CD of BD29555, E234 and E239, are highly conserved. Accordingly, the CBH I variants of the disclosure preferably contain two glutamic acid residues at the positions corresponding to E234 and E239 Amino acid positions in the BD29555 variants (e.g., those that include an insertion or deletion) that correspond to E234 and E239 can be identified through alignment of their sequences with BD29555 using a sequence comparison algorithm Optimal alignment of sequences for comparison can be conducted, e.g., by the local homology algorithm of Smith & Waterman, 1981, Adv. Appl. Math. 2:482-89; by the homology alignment algorithm of Needleman & Wunsch, 1970, J. Mol. Biol. 48:443-53; by the search for similarity method of Pearson & Lipman, 1988, Proc. Nat'l Acad. Sci. USA 85:2444-48, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

The CBDs are particularly involved in the hydrolysis of crystalline cellulose. It has been shown that the ability of cellobiohydrolases to degrade crystalline cellulose decreases when the CBD is absent (Linder and Teeri, 1997, Journal of Biotechnol. 57:15-28). The variant CBH I polypeptides of the disclosure can further include a CBD. The CBD of BD29555 corresponds to positions 494 to 529 of SEQ ID NO:134.

The CD and CBD of a CBH I polypeptide are often connected via a linker. The CBD can be N- or C-terminal to the CD, and the CBD and CD are optionally connected via a linker sequence. The linker connecting the CD and CBD of BD29555 corresponds to positions 456 to 493 of SEQ ID NO:134.

Because CBH I polypeptides are modular, a CD variant of BD29555 can be combined with a CBD and/or linkers of a different CBH I polypeptide. In one embodiment, however, a variant CBH I polypeptide comprises a CD, CBD and linker that are related in sequence to BD29555.

Most CBH I polypeptides are secreted and are therefore expressed with a signal sequence that is cleaved upon secretion of the polypeptide from the cell. The variant CBH I polypeptides of the disclosure can be mature polypeptides or they may further comprise a signal sequence. The mature BD29555 corresponds to amino acids 26 to 529 of SEQ ID NO:134, and the signal sequence of BD29555 corresponds to amino acids 1 to 25 of SEQ ID NO:134. The variant CBH I polypeptides of the disclosure can be expressed with the signal sequence of BD29555, or with a heterologous signal sequence.

The variant CBH I polypeptides have at least one improved property (e.g., activity, improved thermotolerance, improved product tolerance) as compared to wild type BD29555 (whose sequence is provided as SEQ ID NO:60, 94, 120 or 134). Table A provides a summary of substitutions that can be introduced into a BD29555 polypeptide:

TABLE A

| Sequence Identifier (SEQ ID NO:) | Substitution(s) | Location of Substitution(s) | Improvement |
|---|---|---|---|
| 2 | N222H | CD (active site loop) | Activity |
| 4 | N222E | CD (active site loop) | Activity |
| 6 | S217K | CD (active site loop) | Activity |
| 8 | L225Y | CD (active site loop) | Activity |
| 10 | L225V | CD (active site loop) | Activity |
| 12 | H497S | CBD | Activity |
| 14 | T510K | CBD | Activity |
| 16 | D87L | CD | Activity |
| 18 | G256I | CD | Activity |
| 20 | H157G | CD | Activity |
| 22 | P159G | CD | Activity |
| 24 | N183A | CD | Activity |
| 26 | S156G | CD | Activity |
| 28 | S218P, T316S | S218P: CD (active site loop) T316S: CD | Activity |
| 30 | D318Q, T322S, I363V | CD | Activity |
| 32 | T324R | CD | Activity |
| 34 | S326L | CD | Activity |
| 36 | Q334S | CD | Activity |
| 38 | K345D | CD | Activity |
| 40 | K45R, T293A, S350C | CD | Activity |
| 42 | G351D | CD | Activity |
| 44 | N352V | CD | Activity |
| 46 | F358L | CD | Activity |
| 48 | A370I | CD | Activity |
| 50 | G376R | CD | Activity |
| 52 | E386S | CD | Activity |
| 54 | V451W | CD | Activity |
| 56 | N455G | CD | Activity |
| 58 | S463K | Linker | Activity |
| 60 | S104N | CD | Thermotolerance |
| 64 | V121S | CD | Thermotolerance |
| 66 | V121T | CD | Thermotolerance |
| 68 | G113N | CD | Thermotolerance |
| 70 | L116T | CD | Thermotolerance |
| 72 | T268V | CD | Thermotolerance |

TABLE A-continued

| Sequence Identifier (SEQ ID NO:) | Substitution(s) | Location of Substitution(s) | Improvement |
|---|---|---|---|
| 74 | T35A, V401A | CD | Thermotolerance |
| 76 | V392T | CD | Thermotolerance |
| 78 | Y399D | CD | Thermotolerance |
| 80 | V401D | CD | Thermotolerance |
| 82 | V392A, V401A, T417A | CD | Thermotolerance |
| 84 | L404T | CD | Thermotolerance |
| 86 | S463Y | CD | Thermotolerance |
| 88 | A221V, V401A, G474W | A221V: CD (active site loop)<br>V401A, G474W: CD | Thermotolerance |
| 90 | A472M | Linker | Thermotolerance |
| 92 | V401A, V494L | V401A: CD<br>V494L: CBD | Thermotolerance |
| 96 | Y31L, T32Q, S72A, T73Q, T77D, F120-VTGSNVG-S128 → F120-VQQGPYSKNVG-S132 | CD | Activity |
| 98 | Y31L, S72W, T77D, F120-VTGSNVG-S128 → F120-VQQGPYSKNVG-S132 | CD | Activity |
| 100 | S72Y, T73Q, F120-VTGSNVG-S128 → F120-VQQGPYSKNVG-S132 | CD | Activity |
| 102 | Y31L, T32W, F120-VTGSNVG-S128 → F120-VQQGPYSKNVG-S132 | CD | Activity |
| 104 | T32Q, F120-VTGSNVG-S128 → F120-VTKGSFSSNIG-S132 | CD | Activity |
| 106 | Y31Q, T32Q, S72Y, T77D, F120-VTGSNVG-S128 → F120-VTQSAQKNVG-A131 | CD | Activity |
| 108 | Y31A, T32Y, S72Y, T73Y, T77D | CD | Activity |
| 110 | Y31Q, T32Q, S72Y, T73Y, T77D | CD | Activity |
| 112 | T32W, T73W, T77D | CD | Activity |
| 114 | Y31A, T32Q, T73Y, T77D | CD | Activity |
| 116 | S72W, T73Q, F120-VTGSNVG-S128 → F120-VQQGPYSKNVG-S132 | CD | Activity |
| 118 | Y31L, T32Y, T77D, F120-VTGSNVG-S128 → F120-VQQGPYSKNVG-S132 | CD | Activity |
| 122 | P159G, S217K, N222H, L225Y, K345D, N352V, V451W | P159G, K345D, N352V, V451W: CD<br>S217K, N222H, L225Y: CD (active site loop) | Activity |
| 124 | N222H, L225Y, K345D, N352V, E386S, V451W | K345D, N352V, E386S, V451W: CD<br>N222H, L225Y: CD (active site loop) | Activity |
| 126 | S326L, K345D, N352V | CD | Activity |
| 128 | L225Y, D318Q, T324R, S326L, K345D, E386S | D318Q, T324R, S326L, K345D, E386S: CD<br>L225Y: CD (active site loop) | Activity |
| 130 | P159G, S217K, N222H, L225Y, Q334S, K345D, E386S | P159G, Q334S, K345D, E386S: CD<br>S217K, N222H, L225Y: CD (active site loop) | Activity |

TABLE A-continued

| Sequence Identifier (SEQ ID NO:) | Substitution(s) | Location of Substitution(s) | Improvement |
|---|---|---|---|
| 132 | E386S, V451W | CD | Activity |
| 136 | R273K, R422K | CD | Product Tolerance |

Accordingly, the present disclosure provides CBH I variant polypeptides having improved activity relative to BD29555, which have one or more the following substitutions or combinations of substitutitions as compared to the BD29555 sequence (SEQ ID NO:134): (a) N222H; (b) N222E; (c) S217K; (d) L225Y; (e) L225V; (f) H497S; (g) T510K; (h) D87L; (i) G256I; (j) H157G; (k) P159G; (l) N183A; (m) S156G; (n) S218P+T316S; (o) D318Q+T322S+I363V; (p) T324R; (q) S326L; (r) Q334S; (t) K345D; (u) K45R+ T293A+S350C; (v) G351D; (w) N352V; (x) F358L; (y) A370I; (z) G376R; (aa) E386S; (bb) V451W; (cc) N455G; (dd) S463K; (ee) Y31L+T32Q+S72A+T73Q+T77D+F120-VTGSNVG-S128→F120-VQQGPYSKNVG-S132; (ff) Y31L+S72W+T77D+F120-VTGSNVG-S128→F120-VQQGPYSKNVG-S132; (gg) S72Y+T73Q+F120-VTG-SNVG-S128→F120-VQQGPYSKNVG-S132; (hh) Y31L+T32W+F120-VTGSNVG-S128→F120-VQQGPYSKNVG-S132; (ii) T32Q+F120-VTGSNVG-S128→F120-VTKGSFSSNIG-S132; (jj) Y31Q+T32Q+S72Y+T77D+F120-VTGSNVG-S128→F120-VTQSAQKNVG-A131; (kk) Y31A+T32Y+S72Y+T73Y+T77D; (11) Y31Q+T32Q+S72Y+T73Y+T77D; (mm) T32W+T73W+T77D; (nn) Y31A+T32Q+T73Y+T77D; (oo) S72W+T73Q+F120-VTGSNVG-S128→F120-VQQGPYSKNVG-S132; (pp) Y31L+T32Y+T77D+F120-VTGSNVG-S128→F120-VQQGPYSKNVG-S132; (qq) P159G+S217K+N222H+L225Y+K345D+N352V+V451W; (a) N222H+L225Y+K345D+N352V+E386S+V451W; (ss) S326L+K345D+N352V; (tt) L225Y+D318Q+T324R+S326L+K345D+E386S; (uu) P159G+S217K+N222H+L225Y+Q334S+K345D+E386S; (vv) E386S+V451W.

The present disclosure also provides CBH I variant polypeptides having improved thermal tolerance relative to BD29555, which have one or more the following substitutions or combinations of substitutitions as compared to the BD29555 sequence (SEQ ID NO:134(a) S104N; (b) V121S; (c) V121T; (d) G113N; (e) L116T; (f) T268V; (g) T35A+V401A; (h) V392T; (i) Y399D; (j) V401D; (k) V392A+V401A+T417A; (l) L404T; (m) S463Y; (n) A221V+V401A+G474W; (o) A472M; (p) V401A+V494L.

BD29555 has a surface loop at amino acid positions 120-128, which together with positions 31, 32, 72, 73, and 77, forms the substrate entry site. A "substrate entry site" library with 12,800 variants was constructed with the aim to increase the hydrophobicity of the entry site for improved substrate uptake (the library contained 5 variants at position 31, and 4 variants each at positions 32, 72, 73, and 77; in addition, nine loops of various lengths and amino acid compositions from other CBH I sequences substituted the surface loop at positions 120-128). Several variants with improved activity were identified in the substrate entry site screen (corresponding to SEQ ID NOs:96, 98, 100, 102, 104, 106, 108, 110, 112, 114, 116 and 118. Additionally, SEQ ID NO:64 and SEQ ID NO:66 represent BD29555 variants with beneficial substitutions in the substrate entry site that were identified in other screens that improved the enzyme's thermal tolerance. Accordingly, in certain aspects, the present disclosure provides substrate entry site variants of BD29555 that increase CBH I activity or thermal tolerance. In some embodiments, the substrate entry site variants include one or more substitutions or combinations of substitutions selected from: (a) V121S; (b) V121T; (c) Y31L+T32Q+S72A+T73Q+T77D+F120-VTGSNVG-S128→F120-VQQGPYSKNVG-S132; (d) Y31L+S72W+T77D+F120-VTGSNVG-S128→F120-VQQGPYSKNVG-S132; (e) S72Y+T73Q+F120-VTG-SNVG-S128→F120-VQQGPYSKNVG-S132; (f) Y31L+T32W+F120-VTGSNVG-S128→F120-VQQGPYSKNVG-S132; (g) T32Q+F120-VTGSNVG-S128→F120-VTKGSFSSNIG-S132; (g) Y31Q+T32Q+S72Y+T77D+F120-VTGSNVG-S128→F120-VTQSAQKNVG-A131; (h) Y31A+T32Y+S72Y+T73Y+T77D; (i) Y31Q+T32Q+S72Y+T73Y+T77D; (j) T32W+T73W+T77D; (k) Y31A+T32Q+T73Y+T77D; (l) S72W+T73Q+F120-VTGSNVG-S128→F120-VQQGPYSKNVG-S132; and (m) Y31L+T32Y+T77D+F120-VTGSNVG-S128→F120-VQQGPYSKNVG-S132. It is noted that, as used herein in the context of the surface loop present at positions of 120-128, the term substitutions refers to either substitution of one or more individual amino acids or substitution of the entire loop (9 amino acids) with a loop of different length (e.g., 6, 7, 8, 10, 11, 12, 13, 14 or 15 amino acids).

The CBH I polypeptides of the disclosure comprise an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% sequence identity to the CD of BD29555. The sequence of BD29555 is set forth as SEQ ID NO:60, 94, 120 and 134. The CD of BD29555 corresponds to positions 26-455 of SEQ ID NO:60, 94, 120 or 134.

The CBH I polypeptides of the disclosure can also comprise an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% sequence identity to the mature polypeptide resulting from cleavage of the signal sequence of BD29555. The sequence of BD29555 is set forth as SEQ ID NO:60, 94, 120 and 134. The mature polypeptide corresponds to positions 26-529 of SEQ ID NO:60, 94, 120 or 134.

The present disclosure further provides compositions (including cellulase compositions, e.g., whole cellulase compositions, and fermentation broths) comprising variant CBH I polypeptides. The variant CBH I polypeptides and compositions comprising them can be used, inter alia, in processes for saccharifying biomass.

The present disclosure further provides nucleic acids (e.g., vectors) comprising nucleotide sequences encoding variant CBH I polypeptides as described herein, and recombinant cells engineered to express the variant CBH I polypeptides.

The recombinant cell can be a prokaryotic (e.g., bacterial) or eukaryotic (e.g., yeast or filamentous fungal) cell. Further provided are methods of producing and optionally recovering the variant CBH I polypeptides.

In alternative embodiments, the invention provides polypeptides having lignocellulolytic (lignocellulosic) activity, e.g., a ligninolytic and cellulolytic activity, including, e.g., having cellulase, endoglucanase, cellobiohydrolase (cbhI) (e.g., an exo-cellobiohydrolase, e.g., having an "exo" activity that can processively release cellobiose units (β-1,4 glucose-glucose disaccharide), β-glucosidase (beta-glucosidase), xylanase, xylosidase (e.g., β-xylosidase), and/or an arabinofuranosidase activity, and nucleic acids encoding them, and methods for making and using them. The invention provides enzymes for the bioconversion of any biomass, e.g., a lignocellulosic residue, into fermentable sugars or polysaccharides; and these sugars or polysaccharides can be used as a chemical feedstock for the production of alcohols such as ethanol, propanol, butanol and/or methanol, and in the production of fuels, e.g., biofuels such as synthetic liquids or gases, such as syngas.

In alternative embodiments, the enzymes of the invention have an increased catalytic rate to improve the process of substrate (e.g., a lignocellulosic residue, cellulose, bagasse) hydrolysis. This increased efficiency in catalytic rate leads to an increased efficiency in producing sugars or polysaccharides, which can be useful in industrial, agricultural or medical applications, e.g., to make a biofuel or an alcohol such as ethanol, propanol, butanol and/or methanol. In one aspect, sugars produced by hydrolysis using enzymes of this invention can be used by microorganisms for alcohol (e.g., ethanol, propanol, butanol and/or methanol) production and/or fuel (e.g., biofuel) production.

In alternative embodiments, the invention provides highly active polypeptides having lignocellulosic activity, e.g., polypeptides having an increased catalytic rate that include glycosyl hydrolases, endoglucanases, cellobiohydrolases (cbhI) (e.g., exo-cellobiohydrolases, e.g., having an "exo" activity that can processively release cellobiose units β-1,4 glucose-glucose disaccharide), β-glucosidases (beta-glucosidases), xylanases, xylosidase (e.g., β-xylosidase) and/or arabinofuranosidases.

In alternative embodiments, the invention provides industrial, agricultural or medical applications: e.g., biomass to biofuel, e.g., ethanol, propanol, butanol and/or methanol, using enzymes of the invention having decreased enzyme costs, e.g., decreased costs in biomass to biofuel conversion processes. Thus, the invention provides efficient processes for producing bioalcohols, biofuels and/or biofuel- (e.g., bioethanol-, propanol-, butanol- and/or methanol-) comprising compositions, including synthetic, liquid or gas fuels comprising a bioalcohol, from any biomass.

In alternative embodiments, enzymes of the invention, including the enzyme "cocktails" of the invention ("cocktails" meaning mixtures of enzymes comprising at least one enzyme of this invention), are used to hydrolyze the major components of a lignocellulosic biomass, or any composition comprising cellulose and/or hemicellulose (lignocellulosic biomass also comprises lignin), e.g., seeds, grains, tubers, plant waste (such as a hay or straw, e.g., a rice straw or a wheat straw, or any the dry stalk of any cereal plant) or byproducts of food processing or industrial processing (e.g., stalks), corn (including cobs, stover, and the like), grasses (e.g., Indian grass, such as *Sorghastrum nutans*; or, switch grass, e.g., *Panicum* species, such as *Panicum virgatum*), wood (including wood chips, processing waste, such as wood waste), paper, pulp, recycled paper (e.g., newspaper); also including a monocot or a dicot, or a monocot corn, sugarcane or parts thereof (e.g., cane tops), rice, wheat, barley, switchgrass or *Miscanthus*; or a dicot oilseed crop, soy, canola, rapeseed, flax, cotton, palm oil, sugar beet, peanut, tree, poplar or lupine.

In alternative embodiments, enzymes of the invention are used to hydrolyze cellulose comprising a linear chain of β-1, 4-linked glucose moieties, and/or hemicellulose as a complex structure that varies from plant to plant. In one aspect, enzymes of the invention are used to hydrolyze hemicelluloses containing a backbone of β-1,4 linked xylose molecules with intermittent branches of arabinose, galactose, glucuronic acid and/or mannose. In one aspect, enzymes of the invention are used to hydrolyze hemicellulose containing non-carbohydrate constituents such as acetyl groups on xylose and ferulic acid esters on arabinose. In one aspect, enzymes of the invention are used to hydrolyze hemicelluloses covalently linked to lignin and/or coupled to other hemicellulose strands via diferulate crosslinks.

In alternative embodiments, the compositions and methods of the invention are used in the enzymatic digestion of biomass and can comprise use of many different enzymes, including the cellulases and hemicellulases. Lignocellulosic enzymes used to practice the invention can digest cellulose to monomeric sugars, including glucose. In one aspect, compositions used to practice the invention can include mixtures of enzymes, e.g., glycosyl hydrolases, glucose oxidases, xylanases, xylosidases (e.g., β-xylosidases), cellobiohydrolases (cbhI) (e.g., exo-cellobiohydrolases, e.g., having an "exo" activity that can processively release cellobiose units β-1,4 glucose-glucose disaccharide) and/or arabinofuranosidases or other enzymes that can digest hemicellulose to monomer sugars. Mixtures of the invention can comprise, or consist of, only enzymes of this invention, or can include at least one enzyme of this invention and another enzyme, which can also be a lignocellulosic enzyme and/or any other enzyme, e.g., a glucose oxidase.

In alternative embodiments, compositions used to practice the invention include a "cellulase" or composition that is a mixture of at least three different enzyme types (or an enzyme having more than one enzymatic property): (1) an endoglucanase, which cleaves internal β-1,4 linkages resulting in shorter glucooligosaccharides, (2) a cellobiohydrolase, which can act in an "exo" manner processively releasing cellobiose units (β-1,4 glucose-glucose disaccharide), and (3) a β-glucosidase, releasing glucose monomer from short cellooligosaccharides (e.g. cellobiose); or a composition comprising one, two or all three of these enzyme types or enzyme activities.

In alternative embodiments, the enzymes of the invention have a glucanase, e.g., an endoglucanase, activity, e.g., catalyzing hydrolysis of internal endo-β-1,4- and/or β-1,3-glucanase linkages. In one aspect, the endoglucanase activity (e.g., endo-1,4-beta-D-glucan 4-glucano hydrolase activity) comprises hydrolysis of 1,4- and/or β-1,3-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans or xyloglucans and other plant material containing cellulosic parts.

In alternative embodiments, enzymes of the invention have endoglucanase (e.g., endo-beta-1,4-glucanases, EC 3.2.1.4; endo-beta-1,3(1)-glucanases, EC 3.2.1.6; endo-beta-1,3-glucanases, EC 3.2.1.39) activity and can hydrolyze internal β-1,4- and/or β-1,3-glucosidic linkages in cellulose and glucan to produce smaller molecular weight glucose and glucose oligomers. The invention provides methods for producing smaller molecular weight glucose and glucose oligomers using these enzymes of the invention.

In alternative embodiments, enzymes of the invention are used to generate glucans, e.g., polysaccharides formed from 1,4-β- and/or 1,3-glycoside-linked D-glucopyranose. In one aspect, the endoglucanases of the invention are used in the food industry, e.g., for baking and fruit and vegetable processing, breakdown of agricultural waste, in the manufacture of animal feed, in pulp and paper production, textile manufacture and household and industrial cleaning agents. In one aspect, the enzymes, e.g., endoglucanases, of the invention are produced by a microorganism, e.g., by a fungi and/or a bacteria.

In alternative embodiments, enzymes, e.g., endoglucanases, of the invention are used to hydrolyze beta-glucans (β-glucans) which are major non-starch polysaccharides of cereals. The glucan content of a polysaccharide can vary significantly depending on variety and growth conditions. The physicochemical properties of this polysaccharide are such that it gives rise to viscous solutions or even gels under oxidative conditions. In addition glucans have high water-binding capacity. All of these characteristics present problems for several industries including brewing, baking, animal nutrition. In brewing applications, the presence of glucan results in wort filterability and haze formation issues. In baking applications (especially for cookies and crackers), glucans can create sticky doughs that are difficult to machine and reduce biscuit size. Thus, the enzymes, e.g., endoglucanases, of the invention are used to decrease the amount of β-glucan in a β-glucan-comprising composition, e.g., enzymes of the invention are used in processes to decrease the viscosity of solutions or gels; to decrease the water-binding capacity of a composition, e.g., a β-glucan-comprising composition; in brewing processes (e.g., to increase wort filterability and decrease haze formation), to decrease the stickiness of doughs, e.g., those for making cookies, breads, biscuits and the like.

In alternative embodiments, enzymes, e.g., endoglucanases, of the invention are used to retain crispiness, increase crispiness, or reduce the rate of loss of crispiness, and to increase the shelf-life of any carbohydrate-comprising food, feed or drink, e.g., a β-glucan-comprising food, feed or drink. In alternative embodiments, enzymes, e.g., endoglucanases, of the invention are used to decrease the amount of carbohydrates (e.g., β-glucan) implicated in rapid rehydration of baked products and other food or baked products resulting in loss of crispiness and reduced shelf-life.

In alternative embodiments, enzymes, e.g., endoglucanases, of the invention are used to decrease the viscosity of gut contents (e.g., in animals, such as ruminant animals, or humans), e.g., those with cereal diets. Thus, in alternative aspects, enzymes, e.g., endoglucanases, of the invention are used to positively affect the digestibility of a food or feed and animal (e.g., human or domestic animal) growth rate, and in one aspect, are used to higher generate feed conversion efficiencies. For monogastric animal feed applications with cereal diets, beta-glucan is a contributing factor to viscosity of gut contents and thereby adversely affects the digestibility of the feed and animal growth rate. For ruminant animals, these beta-glucans represent substantial components of fiber intake and more complete digestion of glucans would facilitate higher feed conversion efficiencies. Accordingly, the invention provides animal feeds and foods comprising endoglucanases of the invention, and in one aspect, these enzymes are active in an animal digestive tract, e.g., in a stomach and/or intestine.

In alternative embodiments, enzymes of the invention are used to digest cellulose or any beta-1,4-linked glucan-comprising synthetic or natural material, including those found in any plant material. Enzymes, e.g., endoglucanases, of the invention are used as commercial enzymes to digest cellulose from any source, including all biological sources, such as plant biomasses, e.g., corn, grains, grasses (e.g., Indian grass, such as *Sorghastrum nutans*; or, switch grass, e.g., *Panicum* species, such as *Panicum virgatum*); also including a monocot or a dicot, or a monocot corn, sugarcane or parts thereof (e.g., cane tops), rice, wheat, barley, switchgrass or *Miscanthus*; or a dicot oilseed crop, soy, canola, rapeseed, flax, cotton, palm oil, sugar beet, peanut, tree, poplar or lupine; or, woods or wood processing byproducts, such as wood waste, e.g., in the wood processing, pulp and/or paper industry, in textile manufacture and in household and industrial cleaning agents, and/or in biomass waste processing.

In alternative embodiments, the invention provides compositions (e.g., pharmaceutical compositions, foods, feeds, drugs, dietary supplements) comprising the enzymes, polypeptides or polynucleotides of the invention. These compositions can be formulated in a variety of forms, e.g., as pills, capsules, tablets, gels, geltabs, lotions, pills, injectables, implants, liquids, sprays, powders, food, additives, supplements, feed or feed pellets, or as any type of encapsulated form, or any type of formulation.

The invention provides isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity (homology) to an exemplary nucleic acid of the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, and/or SEQ ID NO:135; which in alternative embodiments include complementary (partially or completely complementary) (e.g., antisense) sequence, cDNA coding sequences and genomic (e.g., "gDNA") sequences, and optionally include sequences over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues; or over a region consisting of the protein coding region (e.g., the cDNA) or the genomic sequence; and all of these nucleic acid sequences, and the polypeptides and peptides they encode, encompass "sequences of the invention".

In alternative aspects, these nucleic acids of the invention encode at least one polypeptide having a lignocellulolytic activity, e.g., a cellulase or a cellobiohydrolase (e.g., a cbhl) (e.g., an exo-cellobiohydrolase, e.g., having an "exo" activity that can processively release cellobiose units β-1,4 glucose-glucose disaccharide) activity. In alternative embodiments, a nucleic acid of the invention can encode a polypeptide capable of generating an antibody (or any binding fragment thereof) that can specifically bind to an exemplary polypeptide of the invention (listed below), or, these nucleic acids can be used as probes for identifying or isolating lignocellulotic enzyme-encoding nucleic acids, or to inhibit the expression of lignocellulotic enzyme-expressing nucleic acids (all these aspects referred to as the "nucleic acids of the invention"). In one aspect, the sequence identities are determined by analysis with a sequence comparison algorithm or by a visual inspection.

Nucleic acids of the invention also include isolated, synthetic or recombinant nucleic acids encoding an exemplary polypeptide (or peptide) of the invention which include polypeptides (e.g., enzymes) of the invention having the sequence of (or the subsequences of, or enzymatically active fragments of) SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58; SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and/or SEQ ID NO:136.

Alternative embodiments of the invention comprise isolated, synthetic or recombinant nucleic acids including at least 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more consecutive bases of a nucleic acid sequence of the invention, sequences substantially identical thereto, and the sequences (partially or completely) complementary thereto.

In alternative embodiments, isolated, synthetic or recombinant nucleic acids of the invention encode a polypeptide having a lignocellulosic activity, e.g., cellulase or cellobiohydrolase activity, which is thermostable. The polypeptide can retain a lignocellulosic activity under conditions comprising a temperature range of between about 37° C. to about 95° C.; between about 55° C. to about 85° C., between about 70° C. to about 95° C., or, between about 90° C. to about 95° C. The polypeptide can retain a lignocellulosic activity in temperatures in the range between about 1° C. to about 5° C., between about 5° C. to about 15° C., between about 15° C. to about 25° C., between about 25° C. to about 37° C., between about 37° C. to about 95° C., 96° C., 97° C., 98° C. or 99° C., between about 55° C. to about 85° C., between about 70° C. to about 75° C., or between about 90° C. to about 99° C., or 95° C., 96° C., 97° C., 98° C. or 99° C., or more.

In alternative embodiments, isolated, synthetic or recombinant nucleic acids of the invention encode a polypeptide having a lignocellulosic activity, e.g., cellulase or cellobiohydrolase activity, that can hydrolyze (degrade) soluble cellooligsaccharides into monomers, which is thermotolerant. The polypeptide can retain a lignocellulosic activity or cellulase or cellobiohydrolase activity after exposure to a temperature in the range from greater than 37° C. to about 95° C. or anywhere in the range from greater than 55° C. to about 85° C. The polypeptide can retain a lignocellulosic activity after exposure to a temperature in the range between about 1° C. to about 5° C., between about 5° C. to about 15° C., between about 15° C. to about 25° C., between about 25° C. to about 37° C., between about 37° C. to about 95° C., 96° C., 97° C., 98° C. or 99° C., between about 55° C. to about 85° C., between about 70° C. to about 75° C., or between about 90° C. to about 95° C., or more. In one aspect, the polypeptide retains a lignocellulosic activity after exposure to a temperature in the range from greater than 90° C. to about 99° C., or 95° C., 96° C., 97° C., 98° C. or 99° C., at about pH 4.5, or more.

In alternative embodiments the invention provides a nucleic acid probe for identifying or isolating a nucleic acid encoding a polypeptide having a lignocellulosic activity, or can hydrolyze (degrade) soluble saccharides or oligomers into monomers, wherein the probe comprises a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues of a nucleic acid of the invention, e.g., a polynucleotide having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention. In one aspect, the sequence identities are determined by analysis with a sequence comparison algorithm or by visual inspection. In alternative aspects, the probe can comprise an oligonucleotide comprising at least about 10 to 50, about 20 to 60, about 30 to 70, about 40 to 80, or about 60 to 100 consecutive bases of a nucleic acid sequence of the invention, or a subsequence thereof.

In alternative embodiments the invention provides an amplification primer pair for amplifying (e.g., by PCR) a nucleic acid encoding a polypeptide having a lignocellulosic activity, e.g., a cellulase or cellobiohydrolase, or can hydrolyze (degrade) soluble oligsaccharides and oligomers into monomers, wherein the primer pair is capable of amplifying a nucleic acid comprising a sequence of the invention, or fragments or subsequences thereof. One or each member of the amplification primer sequence pair can comprise an oligonucleotide comprising at least about 10 to 50, or more, consecutive bases of the sequence, or about 10, 11, 12, 13, 14, 15, 16, 17, 18, 19, 20, 21, 22, 23, 24, 25, 26, 27, 28, 29, 30, 31, 32, 33, 34, 35, 36 or more consecutive bases of the sequence. The invention provides amplification primer pairs, wherein the primer pair comprises a first member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36 or more residues of a nucleic acid of the invention, and a second member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36 or more residues of the complementary strand of the first member.

In alternative embodiments the invention provides cellobiohydrolase-encoding and cellulase-encoding nucleic acids, e.g., generated by amplification, e.g., polymerase chain reaction (PCR), using an amplification primer pair of the invention. The invention provides cellulase-encoding, e.g., cellobiohydrolase, generated by amplification, e.g., polymerase chain reaction (PCR), using an amplification primer pair of the invention. The invention provides methods of making nucleic acid encoding an enzyme with lignocellulosic activity, e.g., a cellobiohydrolase, by amplification, e.g., polymerase chain reaction (PCR), using an amplification primer pair of the invention. In one aspect, the amplification primer pair amplifies a nucleic acid from a library, e.g., a gene library, such as an environmental library.

In alternative embodiments the invention provides methods of amplifying a nucleic acid encoding a polypeptide having a lignocellulosic activity, e.g., a cellobiohydrolase, or can hydrolyze (degrade) soluble saccharides and/or oligomers into monomers, comprising amplification of a template nucleic acid with an amplification primer sequence pair capable of amplifying a nucleic acid sequence of the invention, or fragments or subsequences thereof.

In alternative embodiments the invention provides expression cassettes comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, a nucleic acid of the invention encoding an endogenous or heterologous signal sequence (see discussion, below) is expressed using an inducible promoter, an environmentally regulated or a developmentally regulated promoter, a tissue-specific promoter and the like. In alternative aspects, the promoter comprises a seed preferred promoter, such as e.g., the maize gamma zein promoter or the maize ADP-gpp promoter. In one aspect, the signal sequence targets the encoded protein of the invention to a vacuole, the endoplasmic reticulum, the chloroplast or a starch granule.

In alternative embodiments the expression cassette can further comprise a plant or plant virus expression vector. The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

In alternative embodiments the invention provides transformed cells comprising a nucleic acid of the invention or an expression cassette (e.g., a vector, plasmid, etc.) of the invention, or a cloning vehicle (e.g., artificial chromosome) of the invention. In one aspect, the transformed cell can be a bacterial cell, a mammalian cell, a fungal cell, a yeast cell, an insect cell or a plant cell. In one aspect, the plant cell can be soybeans, rapeseed, oilseed, tomato, cane sugar, a cereal, a potato, wheat, rice, corn, tobacco or barley cell; the plant cell also can be a monocot or a dicot, or a monocot corn, sugarcane, rice, wheat, barley, Indian grass, switchgrass or *Miscanthus*; or a dicot oilseed crop, soy, canola, rapeseed, flax, cotton, palm oil, sugar beet, peanut, tree, poplar or lupine.

In alternative embodiments the invention provides transgenic non-human animals comprising a nucleic acid of the invention or an expression cassette (e.g., a vector) of the invention. In one aspect, the animal is a mouse, a cow, a rat, a pig, a goat or a sheep.

In alternative embodiments the invention provides transgenic plants comprising a nucleic acid of the invention or an expression cassette (e.g., a vector) of the invention. The transgenic plant can be any cereal plant, a corn plant, a potato plant, a tomato plant, a wheat plant, an oilseed plant, a rapeseed plant, a soybean plant, a rice plant, a barley plant or a tobacco plant. The transgenic plant can be a monocot or a dicot, or a monocot corn, sugarcane, rice, wheat, barley, switchgrass or *Miscanthus*; or a dicot oilseed crop, soy, canola, rapeseed, flax, cotton, palm oil, sugar beet, peanut, tree, poplar or lupine.

In alternative embodiments the invention provides transgenic seeds comprising a nucleic acid of the invention or an expression cassette (e.g., a vector) of the invention. The transgenic seed can be a cereal plant, a corn seed, a wheat kernel, an oilseed, a rapeseed, a soybean seed, a palm kernel, a sunflower seed, a sesame seed, a peanut or a tobacco plant seed. The transgenic seed can be derived from a monocot or a dicot, or a monocot corn, sugarcane, rice, wheat, barley, switchgrass or *Miscanthus*; or a dicot oilseed crop, soy, canola, rapeseed, flax, cotton, palm oil, sugar beet, peanut, tree, poplar or lupine.

In alternative embodiments the invention provides an antisense oligonucleotide comprising a nucleic acid sequence complementary to or capable of hybridizing under stringent conditions to a nucleic acid of the invention. The invention provides methods of inhibiting the translation of a lignocellulosic enzyme, e.g., a cellulase or cellobiohydrolase, message in a cell comprising administering to the cell or expressing in the cell an antisense oligonucleotide comprising a nucleic acid sequence complementary to or capable of hybridizing under stringent conditions to a nucleic acid of the invention. In one aspect, the antisense oligonucleotide is between about 10 to 50, about 20 to 60, about 30 to 70, about 40 to 80, or about 60 to 100 bases in length, e.g., 10, 15, 20, 25, 30, 35, 40, 45, 50, 55, 60, 65, 70, 75, 80, 85, 90, 95, 100 or more bases in length. The invention provides methods of inhibiting the translation of a lignocellulosic enzyme message in a cell comprising administering to the cell or expressing in the cell an antisense oligonucleotide comprising a nucleic acid sequence complementary to or capable of hybridizing under stringent conditions to a nucleic acid of the invention.

In alternative embodiments the invention provides double-stranded inhibitory RNA (RNAi, or RNA interference) molecules (including small interfering RNA, or siRNAs, for inhibiting transcription, and microRNAs, or miRNAs, for inhibiting translation) comprising a subsequence of a sequence of the invention. In one aspect, the siRNA is between about 21 to 24 residues, or, about at least 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100 or more duplex nucleotides in length. The invention provides methods of inhibiting the expression of a lignocellulosic enzyme, e.g., a cellulase or cellobiohydrolase, in a cell comprising administering to the cell or expressing in the cell a double-stranded inhibitory RNA (siRNA or miRNA), wherein the RNA comprises a subsequence of a sequence of the invention.

In alternative embodiments the e invention provides isolated, synthetic or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 10, 15, 20, 25, 30, 35, 40, 45, 50, 55, 60, 65, 70, 75, 80, 85, 90, 95, 100, 125, 150, 175, 200, 225, 250, 275, 300, 325, 350 or more residues, or over the full length of the polypeptide. In one aspect, the sequence identities are determined by analysis with a sequence comparison algorithm or by a visual inspection. Exemplary polypeptide or peptide sequences of the invention include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and SEQ ID NO:136.

In alternative embodiments the lignocellulosic enzyme activity can be thermotolerant. The polypeptide can retain a lignocellulosic enzyme activity after exposure to a temperature in the range from about $-100°$ C. to about $-80°$ C., about $-80°$ C. to about $-40°$ C., about $-40°$ C. to about $-20°$ C., about $-20°$ C. to about $0°$ C., about $0°$ C. to about $5°$ C., about $5°$ C. to about $15°$ C., about $15°$ C. to about $25°$ C., about $25°$ C. to about $37°$ C., about $37°$ C. to about $45°$ C., about $45°$ C. to about $55°$ C., about $55°$ C. to about $70°$ C., about $70°$ C. to about $75°$ C., about $75°$ C. to about $85°$ C., about $85°$ C. to about $90°$ C., about $90°$ C. to about $95°$ C., about $95°$ C. to about $100°$ C., about $100°$ C. to about $105°$ C., about $105°$ C. to about $110°$ C., about $110°$ C. to about $120°$ C., or $95°$ C., $96°$ C., $97°$ C., $98°$ C., $99°$ C., $100°$ C., $101°$ C., $102°$ C., $103°$ C., $104°$ C., $105°$ C., $106°$ C., $107°$ C., $108°$ C., $109°$ C., $110°$ C., $111°$ C., $112°$ C., $113°$ C., $114°$ C., $115°$ C. or more. In some embodiments, the thermotolerant polypeptides according to the invention retain a lignocellulosic enzyme activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In alternative embodiments the invention provides an isolated, synthetic or recombinant polypeptide or peptide comprising at least 10, 15, 20, 25, 30, 35, 40, 45, 50, 55, 60, 65, 70, 75, 80, 85, 90, 95, 100, 125, 150 or more consecutive bases of a polypeptide or peptide sequence of the invention, sequences substantially identical thereto, and the sequences complementary thereto. The peptide can be, e.g., an immunogenic fragment, a motif (e.g., a binding site), a signal sequence, a prepro sequence or an active site.

In alternative embodiments the invention provides isolated, synthetic or recombinant nucleic acids comprising a sequence encoding a polypeptide having a lignocellulosic activity, e.g., a cellulose and/or a cellobiohydrolase activity, and a signal sequence, wherein the nucleic acid comprises a sequence of the invention. The signal sequence can be derived from another the lignocellulosic enzyme, e.g., a heterologous enzyme. The invention provides isolated, synthetic or recombinant nucleic acids comprising a sequence encoding a polypeptide having a lignocellulosic activity, e.g., a cellulose and/or a cellobiohydrolase activity, wherein the sequence does not contain a signal sequence and the nucleic acid comprises a sequence of the invention. In one aspect, the invention provides an isolated, synthetic or recombinant polypeptide comprising a polypeptide of the invention lacking all or part of a signal sequence. In one aspect, the isolated, synthetic or recombinant polypeptide can comprise the polypeptide of the invention comprising a heterologous signal sequence, such as a heterologous the lignocellulosic enzyme signal sequence.

In alternative embodiments the invention provides chimeric (e.g., multidomain recombinant) proteins comprising a first domain comprising a signal sequence and/or a carbohydrate binding domain (CBM) and at least a second domain. The protein can be a fusion protein. The second domain can comprise an enzyme. The chimeric protein can comprise a signal sequence and/or a CBM and a structural protein.

In alternative embodiments the invention provides chimeric polypeptides comprising (i) at least a first domain comprising (or consisting of) a carbohydrate binding domain (CBM), a signal peptide (SP), a prepro sequence and/or a catalytic domain (CD) of the invention; and, (ii) at least a second domain comprising a heterologous polypeptide or peptide, wherein the heterologous polypeptide or peptide is not naturally associated with the CBM, signal peptide (SP), prepro sequence and/or catalytic domain (CD). In one aspect, the heterologous polypeptide or peptide is not a lignocellulosic enzyme. The heterologous polypeptide or peptide can be amino terminal to, carboxy terminal to or on both ends of the CBM, signal peptide (SP), prepro sequence and/or catalytic domain (CD).

In alternative embodiments the invention provides isolated, synthetic or recombinant nucleic acids encoding a chimeric polypeptide, wherein the chimeric polypeptide comprises at least a first domain comprising, or consisting of, a CBM, a signal peptide (SP), a prepro domain and/or a catalytic domain (CD) of the invention; and, at least a second domain comprising a heterologous polypeptide or peptide, wherein the heterologous polypeptide or peptide is not naturally associated with the CBM, signal peptide (SP), prepro domain and/or catalytic domain (CD).

In alternative embodiments the invention provides isolated, synthetic or recombinant signal sequences (e.g., signal peptides) consisting of or comprising the sequence of (a sequence as set forth in) residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43, 1 to 44, 1 to 45, 1 to 46 or 1 to 47, of a polypeptide of the invention, e.g., the exemplary polypeptides of the invention.

In alternative embodiments the lignocellulosic enzyme, e.g., cellulase or cellobiohydrolase, activity comprises a specific activity at about 37° C. in the range from about 1 to about 1200 units per milligram of protein, or, about 100 to about 1000 units per milligram of protein. In another aspect, the lignocellulosic enzyme activity comprises a specific activity from about 100 to about 1000 units per milligram of protein, or, from about 500 to about 750 units per milligram of protein. Alternatively, the lignocellulosic enzyme activity comprises a specific activity at 37° C. in the range from about 1 to about 750 units per milligram of protein, or, from about 500 to about 1200 units per milligram of protein. In one aspect, the lignocellulosic enzyme activity comprises a specific activity at 37° C. in the range from about 1 to about 500 units per milligram of protein, or, from about 750 to about 1000 units per milligram of protein. In another aspect, the lignocellulosic enzyme activity comprises a specific activity at 37° C. in the range from about 1 to about 250 units per milligram of protein. Alternatively, the lignocellulosic enzyme activity comprises a specific activity at 37° C. in the range from about 1 to about 100 units per milligram of protein.

In alternative embodiments the thermotolerance comprises retention of at least half of the specific activity of the lignocellulosic enzyme at 37° C. after being heated to the elevated temperature. Alternatively, the thermotolerance can comprise retention of specific activity at 37° C. in the range from about 1 to about 1200 units per milligram of protein, or, from about 500 to about 1000 units per milligram of protein, after being heated to the elevated temperature. In another aspect, the thermotolerance can comprise retention of specific activity at 37° C. in the range from about 1 to about 500 units per milligram of protein after being heated to the elevated temperature.

In alternative embodiments, isolated, synthetic or recombinant polypeptides of the invention comprise at least one glycosylation site. In one aspect, glycosylation can be an N-linked glycosylation. In one aspect, the polypeptide can be glycosylated after being expressed in an *Aspergillus*, e.g., an *Aspergillus niger*, a *Pichia*, e.g., a *Pichia pastoris*, a *Schizosaccharomyces*, e.g., a *Schizosaccharomyces pombe*, and/or a *Pseudomonas*, e.g., a *Pseudomonas fluorescens*. In alternative embodiments, nucleic acids of the invention are expressed in an *Aspergillus*, e.g., an *Aspergillus niger*, a *Pichia*, e.g., a *Pichia pastoris*, a *Schizosaccharomyces*, e.g., a *Schizosaccharomyces pombe*, and/or a *Pseudomonas*, e.g., a *Pseudomonas fluorescens*; e.g., to express polypeptides of the invention.

In alternative embodiments the polypeptide can retain the activity under conditions comprising about pH 6.5, pH 6, pH 5.5, pH 5, pH 4.5 or pH 4 or more acidic. In another aspect, the polypeptide can retain the lignocellulosic enzyme activity under conditions comprising about pH 7, pH 7.5 pH 8.0, pH 8.5, pH 9, pH 9.5, pH 10, pH 10.5 or pH 11 or more basic pH. In one aspect, the polypeptide can retain the lignocellulosic enzyme activity after exposure to conditions comprising about pH 6.5, pH 6, pH 5.5, pH 5, pH 4.5 or pH 4 or more acidic pH. In another aspect, the polypeptide can retain the lignocellulosic enzyme activity after exposure to conditions comprising about pH 7, pH 7.5 pH 8.0, pH 8.5, pH 9, pH 9.5, pH 10, pH 10.5 or pH 11 or more basic pH.

In alternative embodiments the lignocellulosic enzyme has activity at under alkaline conditions, e.g., the alkaline conditions of the gut, e.g., the small intestine. In one aspect, the polypeptide can retains activity after exposure to the acidic pH of the stomach.

In alternative embodiments the invention provides protein preparations comprising a polypeptide (including peptides) of the invention, wherein the protein preparation comprises a liquid, a solid or a gel. The invention provides heterodimers comprising a polypeptide of the invention and a second protein or domain. The second member of the heterodimer can be a different lignocellulosic enzyme or another protein. In one aspect, the second domain can be a polypeptide and the heterodimer can be a fusion protein. In one aspect, the second domain can be an epitope or a tag. In one aspect, the invention provides homodimers comprising a polypeptide of the invention.

In alternative embodiments the invention provides immobilized polypeptides (including peptides) comprising or consisting of polypeptides of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube. The invention also provides arrays comprising polypeptides of the invention, or an immobilized nucleic acid of the invention, including, e.g., probes of the invention. The invention also provides arrays comprising an antibody of the invention.

In alternative embodiments the invention provides isolated, synthetic or recombinant antibodies that specifically bind to a polypeptide of the invention or to a polypeptide encoded by a nucleic acid of the invention. These antibodies of the invention can be a monoclonal or a polyclonal antibody. The invention provides hybridomas comprising an antibody of the invention, e.g., an antibody that specifically binds to a polypeptide of the invention or to a polypeptide encoded by a nucleic acid of the invention. The invention provides nucleic acids encoding these antibodies.

The invention provides method of isolating or identifying a polypeptide having a lignocellulosic enzyme activity, e.g., cellulase or cellobiohydrolase activity, comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having the lignocellulosic enzyme activity.

In alternative embodiments the invention provides methods of making an anti-cellulase, e.g., anti-cellobiohydrolase, enzyme antibody comprising administering to a non-human animal a nucleic acid of the invention or a polypeptide of the invention or subsequences thereof in an amount sufficient to generate a humoral immune response, thereby making the anti-enzyme antibody. The invention provides methods of making an anti-enzyme immune response(s) (cellular or humoral) comprising administering to a non-human animal a nucleic acid of the invention or a polypeptide of the invention or subsequences thereof in an amount sufficient to generate an immune response (cellular or humoral).

In alternative embodiments the invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

In alternative embodiments the invention provides methods for identifying a polypeptide having a lignocellulosic enzyme activity, e.g., cellulase or cellobiohydrolase enzyme activity, comprising the following steps: (a) providing a polypeptide of the invention; or a polypeptide encoded by a nucleic acid of the invention; (b) providing the lignocellulosic enzyme substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having the lignocellulosic enzyme activity. In one aspect, the substrate is a cellulose-comprising or a polysaccharide-comprising (e.g., soluble cellooligsaccharide- and/or arabinoxylan oligomer-comprising) compound.

In alternative embodiments the invention provides methods for identifying a lignocellulosic enzyme, e.g., a cellulase or cellobiohydrolase, substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a lignocellulosic enzyme substrate.

In alternative embodiments the invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

In alternative embodiments the invention provides methods for identifying a modulator of a lignocellulosic enzyme comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the lignocellulosic enzyme, wherein a change in the lignocellulosic enzyme activity measured in the presence of the test compound compared to the activity in the absence of the test compound provides a determination that the test compound modulates the lignocellulosic enzyme activity. In one aspect, the lignocellulosic enzyme activity can be measured by providing a lignocellulosic enzyme substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of the lignocellulosic enzyme activity. In alternative embodiments an increase in the amount of the substrate or a decrease in the amount of the reaction product with the test compound as compared to the amount of substrate or reaction product without the test compound identifies the test compound as an inhibitor of the lignocellulosic enzyme activity.

In alternative embodiments the invention provides computer systems comprising a processor and a data storage device wherein said data storage device has stored thereon a polypeptide sequence or a nucleic acid sequence of the invention (e.g., a polypeptide or peptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

In alternative embodiments the invention provides methods for isolating or recovering a nucleic acid encoding a polypeptide having the lignocellulosic enzyme, e.g., cellulase or cellobiohydrolase, from a sample, e.g. an environmental sample, comprising the steps of: (a) providing an amplification primer sequence pair for amplifying a nucleic acid encoding a polypeptide having a lignocellulosic activity, wherein the primer pair is capable of amplifying a nucleic acid of the invention; (b) isolating a nucleic acid from the sample, e.g. environmental sample, or treating the sample, e.g. environmental sample, such that nucleic acid in the sample is accessible for hybridization to the amplification primer pair; and, (c) combining the nucleic acid of step (b) with the amplification primer pair of step (a) and amplifying nucleic acid from the sample, e.g. environmental sample, thereby isolating or recovering a nucleic acid encoding a polypeptide having a lignocellulosic activity from a sample, e.g. an environmental sample. One or each member of the amplification primer sequence pair can comprise an oligonucleotide comprising an amplification primer sequence pair of the invention, e.g., having at least about 10 to 50 consecutive bases of a sequence of the invention.

In alternative embodiments the invention provides methods for isolating or recovering a nucleic acid encoding a polypeptide having a lignocellulosic activity, e.g., cellulase or cellobiohydrolase activity, from a sample, e.g. an environmental sample, comprising the steps of: (a) providing a polynucleotide probe comprising a nucleic acid of the invention or a subsequence thereof; (b) isolating a nucleic acid from the sample, e.g. environmental sample, or treating the sample, e.g. environmental sample, such that nucleic acid in the sample is accessible for hybridization to a polynucleotide probe of step (a); (c) combining the isolated nucleic acid or the treated sample, e.g. environmental sample, of step (b) with the polynucleotide probe of step (a); and (d) isolating a nucleic acid that specifically hybridizes with the polynucleotide probe of step (a), thereby isolating or recovering a nucleic acid encoding a polypeptide having a lignocellulosic activity from a sample, e.g. an environmental sample. The sample, e.g. environmental sample, can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

In alternative embodiments the invention provides methods of generating a variant of a nucleic acid encoding a polypeptide having a lignocellulosic activity, e.g., cellulase or cellobiohydrolase activity, comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant the lignocellulosic enzyme polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, GeneReassembly, Gene Site Saturation Mutagensis (or GSSM), Tailored Multi-Site Combinatorial Assembly, Chromosomal Saturation Mutagenesis (CSM) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In alternative embodiments the method can be iteratively repeated until a lignocellulosic enzyme, e.g., a cellobiohydrolase enzyme having an altered or different activity or an altered or different stability from that of a polypeptide encoded by the template nucleic acid is produced. In one aspect, the variant the lignocellulosic enzyme polypeptide is thermotolerant, and retains some activity after being exposed to an elevated temperature. In another aspect, the variant the lignocellulosic enzyme polypeptide has increased glycosylation as compared to the lignocellulosic enzyme encoded by a template nucleic acid. Alternatively, the variant the polypeptide has a lignocellulosic enzyme activity under a high temperature, wherein the lignocellulosic enzyme encoded by the template nucleic acid is not active under the high temperature. In one aspect, the method can be iteratively repeated until a lignocellulosic enzyme coding sequence having an altered codon usage from that of the template nucleic acid is produced. In another aspect, the method can be iteratively repeated until a lignocellulosic enzyme gene having higher or lower level of message expression or stability from that of the template nucleic acid is produced.

In alternative embodiments the invention provides methods for modifying codons in a nucleic acid encoding a polypeptide having a lignocellulosic activity to increase its expression in a host cell, the method comprising the following steps: (a) providing a nucleic acid of the invention encoding a polypeptide having a lignocellulosic enzyme activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

In alternative embodiments the invention provides methods for modifying codons in a nucleic acid encoding a polypeptide having a lignocellulosic activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding a lignocellulosic enzyme.

In alternative embodiments the invention provides methods for modifying codons in a nucleic acid encoding a polypeptide having a lignocellulosic activity to increase its expression in a host cell, the method comprising the following steps: (a) providing a nucleic acid of the invention encoding a lignocellulosic enzyme polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell. In alternative embodiments the invention provides methods for modifying a codon in a nucleic acid encoding a polypeptide having a lignocellulosic activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell. In alternative embodiments, host cells are bacterial cells including any species within the genera *Aspergillus, Escherichia, Bacillus, Streptomyces, Salmonella, Pseudomonas, Lactococcus*, and *Staphylococcus*, including, e.g., *Escherichia coli, Lactococcus lactis, Bacillus subtilis, Bacillus cereus, Salmonella typhimurium, Pseudomonas fluorescens*. In alternative embodiments, host cells are fungal cells including any species of *Aspergillus*, including *Aspergillus niger*. In alternative embodiments, host cells are yeast cells including any species of an *Aspergillus, Pichia, Saccharomyces, Schizosaccharomyces*, or *Schwanniomyces*, including *Aspergillus niger, Pichia pastoris, Saccharomyces cerevisiae*, or *Schizosaccharomyces pombe*.

In alternative embodiments the invention provides methods for producing a library of nucleic acids encoding a plurality of modified lignocellulosic enzyme, e.g., cellulase or cellobiohydrolase, active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes a lignocellulosic enzyme active site or a lignocellulosic enzyme substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified the lignocellulosic enzyme active sites or substrate binding sites. In one aspect, the method comprises mutagenizing the first nucleic acid of step (a) by a method comprising an optimized directed evolution system, Gene Site Saturation Mutagenesis$^{SM}$ (or GSSM$^{SM}$) technology, GeneReassembly$^{SM}$ technology, Tailored Multi-Site Combinatorial Assembly$^{SM}$ technology, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In alternative embodiments the invention provides methods for making a small molecule comprising the following steps: (a) providing a plurality of biosynthetic enzymes capable of synthesizing or modifying a small molecule, wherein one of the enzymes comprises a lignocellulosic enzyme, e.g., a cellulase or cellobiohydrolase, encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing a lignocellulosic enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the lignocellulosic enzyme, thereby modifying a small molecule by a lignocellulosic enzymatic reaction. In one aspect, the method can comprise a plurality of small molecule substrates for the enzyme of step (a), thereby generating a library of modified small molecules produced by at least one enzymatic reaction catalyzed by the lignocellulosic enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

In alternative embodiments the invention provides methods for determining a functional fragment of an enzyme of the invention comprising the steps of: (a) providing a polypeptide of the invention, or a polypeptide encoded by a nucleic acid of the invention, or a subsequence thereof; and (b) deleting a plurality of amino acid residues from the sequence of step (a) and testing the remaining subsequence for lignocellulosic enzyme activity, thereby determining a functional fragment of the enzyme. In one aspect, lignocellulosic enzyme activity, is measured by providing a substrate and detecting a decrease in the amount of the substrate or an increase in the amount of a reaction product.

In alternative embodiments the invention provides methods of increasing thermotolerance or thermostability of a lignocellulosic enzyme, the method comprising glycosylating a lignocellulosic enzyme polypeptide, wherein the polypeptide comprises at least thirty contiguous amino acids of a polypeptide of the invention; or a polypeptide encoded by a nucleic acid sequence of the invention, thereby increasing the thermotolerance or thermostability of the lignocellulosic enzyme polypeptide. In one aspect, the lignocellulosic enzyme specific activity can be thermostable or thermotolerant at a temperature in the range from greater than about 37° C. to about 95° C.

In alternative embodiments the invention provides methods for overexpressing a recombinant glucose oxidase and/or the lignocellulosic enzyme polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

In alternative embodiments the invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a cane sugar, beet, soybean, tomato, potato, corn, rice, wheat, tobacco or barley cell. The cell can be derived from a monocot or a dicot, or a monocot corn, sugarcane, rice, wheat, barley, switchgrass or *Miscanthus*; or a dicot oilseed crop, soy, canola, rapeseed, flax, cotton, palm oil, sugar beet, peanut, tree, poplar or lupine.

In alternative embodiments the invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell. The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell. In one aspect, the promoter is or comprises: a viral, bacterial, mammalian or plant promoter; or, a plant promoter; or, a potato, rice, corn, wheat, tobacco or barley promoter; or, a constitutive promoter or a CaMV35S promoter; or, an inducible promoter; or, a tissue-specific promoter or an environmentally regulated or a developmentally regulated promoter; or, a seed-specific, a leaf-specific, a root-specific, a stem-specific or an abscission-induced promoter; or, a seed preferred promoter, a maize gamma zein promoter or a maize ADP-gpp promoter. In one aspect, the plant cell is derived from is a monocot or dicot, or the plant is a monocot corn, sugarcane, rice, wheat, barley, switchgrass or *Miscanthus*; or the plant is a dicot oilseed crop, soy, canola, rapeseed, flax, cotton, palm oil, sugar beet, peanut, tree, poplar or lupine.

In alternative embodiments the invention provides methods for hydrolyzing, breaking up or disrupting a cellooligsaccharide, an arabinoxylan oligomer, or a glucan- or cellulose-comprising composition comprising the following steps: (a) providing a polypeptide of the invention; (b) providing a composition comprising a cellulose or a glucan; and (c) contacting the polypeptide of step (a) with the composition of step (b) under conditions wherein the cellulase hydrolyzes, breaks up or disrupts the cellooligsaccharide, arabinoxylan oligomer, or glucan- or cellulose-comprising composition; wherein optionally the composition comprises a plant cell, a bacterial cell, a yeast cell, an insect cell, or an animal cell. In one aspect, the polypeptide of the invention has a lignocellulosic activity, e.g., an activity comprising a cellulase or cellobiohydrolase activity.

In alternative embodiments the invention provides feeds or foods comprising a polypeptide of the invention, or a polypeptide encoded by a nucleic acid of the invention. In one aspect, the invention provides a food, feed, a liquid, e.g., a beverage (such as a fruit juice or a beer), a bread or a dough or a bread product, or a beverage precursor (e.g., a wort), comprising a polypeptide of the invention. The invention provides food or nutritional supplements for an animal comprising a polypeptide of the invention, e.g., a polypeptide encoded by the nucleic acid of the invention. In one aspect, the polypeptide of the invention has a lignocellulosic activity, e.g., an activity comprising a cellulase or cellobiohydrolase activity.

In alternative embodiments the polypeptide in the food or nutritional supplement can be glycosylated. The invention provides edible enzyme delivery matrices comprising a polypeptide of the invention, e.g., a polypeptide encoded by the nucleic acid of the invention. In one aspect, the delivery matrix comprises a pellet. In one aspect, the polypeptide can be glycosylated. In one aspect, the lignocellulosic enzyme, e.g., cellulase or cellobiohydrolase activity is thermotolerant. In another aspect, the lignocellulosic enzyme activity is thermostable.

In alternative embodiments the invention provides a food, a feed or a nutritional supplement comprising a polypeptide of the invention. The invention provides methods for utilizing a lignocellulosic enzyme of the invention, e.g., cellulase or cellobiohydrolase, as a nutritional supplement in an animal or human diet, the method comprising: preparing a nutritional supplement containing a lignocellulosic enzyme of the invention comprising at least thirty contiguous amino acids of a polypeptide of the invention; and administering the nutritional supplement to an animal. The animal can be a human, a ruminant or a monogastric animal. The lignocellulosic enzyme can be prepared by expression of a polynucleotide encoding the lignocellulosic enzyme in a host organism, e.g., a bacterium, a yeast, a plant, an insect, a fungus and/or an animal. The organism also can be an *S. pombe, S. cerevisiae, Pichia pastoris, E. coli, Streptomyces* sp., *Bacillus* sp. and/or *Lactobacillus* sp. In one aspect, the plant is a monocot or dicot, or the plant is a monocot corn, sugarcane, rice, wheat, barley, switchgrass or *Miscanthus*; or the plant is a dicot oilseed crop, soy, canola, rapeseed, flax, cotton, palm oil, sugar beet, peanut, tree, poplar or lupine.

In alternative embodiments the invention provides edible enzyme delivery matrix comprising a thermostable recombinant of a lignocellulosic enzyme of the invention, e.g., cellulase or cellobiohydrolase of the invention. The invention provides methods for delivering a lignocellulosic enzyme supplement to an animal or human, the method comprising: preparing an edible enzyme delivery matrix in the form of pellets comprising a granulate edible carrier and a thermostable recombinant the lignocellulosic enzyme, wherein the pellets readily disperse the lignocellulosic enzyme contained therein into aqueous media, and administering the edible enzyme delivery matrix to the animal. The recombinant lignocellulosic enzyme of the invention can comprise all or a subsequence of at least one polypeptide of the invention. The lignocellulosic enzyme can be glycosylated to provide thermostability at pelletizing conditions. The delivery matrix can be formed by pelletizing a mixture comprising a grain germ and a lignocellulosic enzyme. The pelletizing conditions can include application of steam. The pelletizing conditions can comprise application of a temperature in excess of about 80° C. for about 5 minutes and the enzyme retains a specific activity of at least 350 to about 900 units per milligram of enzyme.

In alternative embodiments the invention provides a pharmaceutical composition comprising a lignocellulosic enzyme of the invention, or a polypeptide encoded by a nucleic acid of the invention. In one aspect, the pharmaceutical composition acts as a digestive aid.

In alternative embodiments a cellulose-containing compound is contacted to (reacted with) a polypeptide of the invention having a lignocellulosic enzyme of the invention at a pH in the range of between about pH 3.0 to 9.0, 10.0, 11.0 or more. In other aspects, a cellulose-containing compound is contacted with the lignocellulosic enzyme at a temperature of about 55° C., 60° C., 65° C., 70° C., 75° C., 80° C., 85° C., 90° C., or more.

In alternative embodiments the invention provides methods for delivering an enzyme supplement, e.g., comprising an enzyme of the invention, to an animal or human, the method comprising: preparing an edible enzyme delivery matrix or pellets comprising a granulate edible carrier and a thermostable recombinant enzyme of the invention, wherein the pellets readily disperse the cellulase enzyme contained therein into aqueous media, and the recombinant enzyme of the invention, or a polypeptide encoded by a nucleic acid of the invention; and, administering the edible enzyme delivery matrix or pellet to the animal; and optionally the granulate edible carrier comprises a carrier selected from the group consisting of a grain germ, a grain germ that is spent of oil, a hay, an alfalfa, a timothy, a soy hull, a sunflower seed meal and a wheat midd, and optionally the edible carrier comprises grain germ that is spent of oil, and optionally the enzyme of the invention is glycosylated to provide thermostability at pelletizing conditions, and optionally the delivery matrix is formed by pelletizing a mixture comprising a grain germ and a cellulase, and optionally the pelletizing conditions include application of steam, and optionally the pelletizing conditions comprise application of a temperature in excess of about 80° C. for about 5 minutes and the enzyme retains a specific activity of at least 350 to about 900 units per milligram of enzyme.

In alternative embodiments the invention provides cellulose- or cellulose derivative-compositions comprising a polypeptide of the invention, or a polypeptide encoded by a nucleic acid of the invention, wherein in alternative embodiments the polypeptide has a cellulase or cellobiohydrolase activity.

In alternative embodiments the invention provides wood, wood pulp or wood products, or wood waste, comprising an enzyme of the invention, or an enzyme encoded by a nucleic acid of the invention, wherein optionally the activity of the enzyme of the invention comprises cellulase or cellobiohydrolase activity.

In alternative embodiments the invention provides paper, paper pulp or paper products, or paper waste byproducts or recycled material, comprising a polypeptide of the invention, or a polypeptide encoded by a nucleic acid of the invention, wherein optionally the polypeptide has cellulase or cellobiohydrolase activity.

In alternative embodiments the invention provides methods for reducing the amount of cellulose in a paper, a wood or wood product comprising contacting the paper, wood or wood product, or wood waste, with an enzyme of the invention, or an enzyme encoded by a nucleic acid of the invention, wherein optionally the enzyme activity comprises a cellulase or cellobiohydrolase activity.

In alternative embodiments the invention provides detergent compositions comprising an enzyme of the invention, or an enzyme encoded by a nucleic acid of the invention, wherein optionally the polypeptide is formulated in a non-aqueous liquid composition, a cast solid, a granular form, a particulate form, a compressed tablet, a gel form, a paste or a slurry form. In one aspect, the activity comprises a cellulase or cellobiohydrolase activity.

In alternative embodiments the invention provides pharmaceutical compositions or dietary supplements comprising an enzyme of the invention, or a cellulase encoded by a nucleic acid of the invention, wherein optionally the enzyme is formulated as a tablet, gel, pill, implant, liquid, spray, powder, food, feed pellet or as an encapsulated formulation. In one aspect, the activity comprises a cellulase or cellobiohydrolase activity.

In alternative embodiments the invention provides fuels comprising a polypeptide of the invention, or a polypeptide encoded by a nucleic acid of the invention, wherein optionally the fuel is derived from a plant material, which optionally comprises potatoes, soybean (rapeseed), barley, rye, corn, oats, wheat, beets or sugar cane. The plant material can be derived from a monocot or a dicot, or a monocot corn, sugarcane, rice, wheat, barley, switchgrass or *Miscanthus*; or a dicot oilseed crop, soy, canola, rapeseed, flax, cotton, palm oil, sugar beet, peanut, tree, poplar or lupine. The fuel can comprise a bioalcohol, e.g., a bioethanol or a gasoline-ethanol mix, a biomethanol or a gasoline-methanol mix, a biobutanol or a gasoline-butanol mix, or a biopropanol or a gasoline-propanol mix. In one aspect, the activity comprises a cellulase or cellobiohydrolase activity.

In alternative embodiments the invention provides methods for making a fuel or alcohol comprising contacting an enzyme of the invention, or a composition comprising an enzyme of the invention, or a polypeptide encoded by a nucleic acid of the invention, or any one of the mixtures or "cocktails" or products of manufacture of the invention, with a biomass, e.g., a composition comprising a cellulose, a fermentable sugar or polysaccharide, such as a lignocellulosic material. In alternative embodiments, the composition comprising cellulose or a fermentable sugar comprises a plant, plant product, plant waste or plant derivative, and the plant, plant waste or plant product can comprise cane sugar plants or plant products, beets or sugarbeets, wheat, corn, soybeans, potato, rice or barley. In alternative embodiments, the fuel comprises a bioethanol or a gasoline-ethanol mix, a biomethanol or a gasoline-methanol mix, a biobutanol or a gasoline-butanol mix, or a biopropanol or a gasoline-propanol mix. The enzyme of the invention of the invention can be part of a plant or seed, e.g., a transgenic plant or seed—and in one aspect, the enzyme of the invention is expressed as a heterologous recombinant enzyme in the very biomass (e.g., plant, seed, plant waste) which is targeted for hydrolysis and conversion into a fuel or alcohol by this method of the invention. In one aspect, the activity comprises cellulase or cellobiohydrolase activity.

In alternative embodiments the invention provides methods for making biofuel, e.g., comprising or consisting of a bioalcohol such as bioethanol, biomethanol, biobutanol or biopropanol, or a mixture thereof, comprising contacting a composition comprising an enzyme of the invention, or a fermentable sugar or lignocellulosic material comprising a polypeptide of the invention, or a polypeptide encoded by a nucleic acid of the invention, or any one of the mixtures or "cocktails" or products of manufacture of the invention, with a biomass, e.g., a composition comprising a cellulose, a fermentable sugar or polysaccharide, such as a lignocellulosic material. In alternative embodiments, the composition comprising the enzyme of the invention, and/or the material to be hydrolyzed, comprises a plant, plant waste, plant product or plant derivative. In alternative embodiments, the plant, plant waste or plant product comprises cane sugar plants or plant products (e.g., cane tops), beets or sugarbeets, wheat, corn, soybeans, potato, rice or barley. In one aspect, the plant is a monocot or dicot, or the plant is a monocot corn, sugarcane (including a cane part, e.g., cane tops), rice, wheat, barley, switchgrass or *Miscanthus*; or the plant is a dicot oilseed crop, soy, canola, rapeseed, flax, cotton, palm oil, sugar beet, peanut, tree, poplar or lupine. In one aspect, enzyme of the invention has an activity comprising a cellulase or cellobiohydrolase activity. In alternative embodiments the invention provides enzyme ensembles, or "cocktail", for depolymerization of cellulosic and hemicellulosic polymers to metabolizeable carbon moieties comprising a polypeptide of the invention, or a polypeptide encoded by a nucleic acid of the invention. In one aspect, enzyme of the invention has an activity comprising cellulase or cellobiohydrolase activity. The enzyme ensembles, or "cocktails", of the invention can be in the form of a composition (e.g., a formulation, liquid or solid), e.g., as a product of manufacture.

In alternative embodiments the invention provides compositions (including products of manufacture, enzyme ensembles, or "cocktails") comprising (a) a mixture (or "cocktail", "an enzyme ensemble", a product of manufacture)

of lignocellulosic enzymes, e.g., hemicellulose- and cellulose-hydrolyzing enzymes, including at least one enzyme of this invention.

In alternative embodiments the invention provides methods for processing a biomass material comprising lignocellulose comprising contacting a composition comprising a cellulose, a lignin, or a fermentable sugar with at least one polypeptide of the invention, or a polypeptide encoded by a nucleic acid of the invention, or an enzyme ensemble, product of manufacture or "cocktail" of the invention. In one aspect, the biomass material comprising lignocellulose is derived from an agricultural crop, is a byproduct of a food or a feed production, is a lignocellulosic waste product, or is a plant residue or a waste paper or waste paper product. In alternative embodiments the enzyme of the invention has an activity comprising a cellobiohydrolase activity. In alternative embodiments the plant residue(s) comprise grain, seeds, stems, leaves, hulls, husks, corn or corn cobs, corn stover, hay, straw (e.g., a rice straw or a wheat straw, or any the dry stalk of any cereal plant) and/or grasses (e.g., Indian grass or switch grass). In alternative embodiments the grasses are Indian grass or switch grass, wood, wood chips, wood pulp and sawdust, or wood waste, and optionally the paper waste comprises discarded or used photocopy paper, computer printer paper, notebook paper, notepad paper, typewriter paper, newspapers, magazines, cardboard and paper-based packaging materials. In one aspect, the processing of the biomass material generates a biofuel, e.g., a bioalcohol such as bioethanol, biomethanol, biobutanol or biopropanol.

In alternative embodiments the invention provides dairy products comprising a polypeptide of the invention, or a polypeptide encoded by a nucleic acid of the invention, or an enzyme ensemble, product of manufacture or "cocktail" of the invention. In one aspect, the dairy product comprises a milk, an ice cream, a cheese or a yogurt. In one aspect, the polypeptide of the invention has a lignocellulosic activity, e.g., an activity comprising a cellulose or cellobiohydrolase activity.

In alternative embodiments the invention provides method for improving texture and flavor of a dairy product comprising the following steps: (a) providing a polypeptide of the invention, or a polypeptide encoded by a nucleic acid of the invention, or an enzyme ensemble, product of manufacture or "cocktail" of the invention; (b) providing a dairy product; and (c) contacting the polypeptide of step (a) and the dairy product of step (b) under conditions wherein the polypeptide of the invention can improve the texture or flavor of the dairy product.

In alternative embodiments the invention provides textiles or fabrics comprising a polypeptide of the invention, or a polypeptide encoded by a nucleic acid of the invention, or an enzyme ensemble, product of manufacture or "cocktail" of the invention, wherein optionally the textile or fabric comprises a cellulose-containing fiber. In one aspect, the polypeptide of the invention has a lignocellulosic activity, e.g., an activity comprising a cellulase or cellobiohydrolase activity.

In alternative embodiments the invention provides methods for treating solid or liquid animal waste products comprising the following steps: (a) providing a polypeptide of the invention, or a polypeptide encoded by a nucleic acid of the invention, or an enzyme ensemble, product of manufacture or "cocktail" of the invention; (b) providing a solid or a liquid animal waste; and (c) contacting the polypeptide of step (a) and the solid or liquid waste of step (b) under conditions wherein the protease can treat the waste. In one aspect, the polypeptide of the invention has a lignocellulosic activity, e.g., an activity comprising a cellulase or cellobiohydrolase activity.

In alternative embodiments the invention provides processed waste products comprising a polypeptide of the invention, or a polypeptide encoded by a nucleic acid of the invention, or an enzyme ensemble, product of manufacture or "cocktail" of the invention. In one aspect, the polypeptide of the invention has a lignocellulosic activity, e.g., an activity comprising a cellulase or cellobiohydrolase activity.

In alternative embodiments the invention provides disinfectants comprising a polypeptide having glucose oxidase and/or cellulase activity, wherein the polypeptide comprises a sequence of the invention, or a polypeptide encoded by a nucleic acid of the invention, or an enzyme ensemble, product of manufacture or "cocktail" of the invention. In one aspect, the polypeptide of the invention has a lignocellulosic activity, e.g., an activity comprising a cellulase or cellobiohydrolase activity.

In alternative embodiments the invention provides biodefense or bio-detoxifying agents comprising a polypeptide having a lignocellulosic activity, e.g., a cellulase activity, wherein the polypeptide comprises a sequence of the invention, or a polypeptide encoded by a nucleic acid of the invention, or an enzyme ensemble, product of manufacture or "cocktail" of the invention. In one aspect, the polypeptide of the invention has a lignocellulosic activity, e.g., an activity comprising a cellulase or cellobiohydrolase activity.

In alternative embodiments the invention provides compositions (including enzyme ensembles and products of manufacture of the invention) comprising a mixture of enzymes of the invention, e.g., hemicellulose- and cellulose-hydrolyzing enzymes of the invention, and a biomass material, wherein optionally the biomass material comprises a lignocellulosic material derived from an agricultural crop, or the biomass material is a byproduct of a food or a feed production, or the biomass material is a lignocellulosic waste product, or the biomass material is a plant residue or a waste paper or waste paper product, or the biomass material comprises a plant residue, and optionally the plant residue comprises grains, seeds, stems, leaves, hulls, husks, corn or corn cobs, corn stover, grasses, wherein optionally grasses are Indian grass or switch grass, hay or straw (e.g., a rice straw or a wheat straw, or any the dry stalk of any cereal plant), wood, wood chips, wood pulp, wood waste, and/or sawdust, and optionally the paper waste comprises discarded or used photocopy paper, computer printer paper, notebook paper, notepad paper, typewriter paper, newspapers, magazines, cardboard and paper-based packaging materials. In alternative embodiments the polypeptide of the invention has a cellulase or cellobiohydrolase activity.

In alternative embodiments the invention provides methods for processing a biomass material comprising providing enzyme ensembles ("cocktails") or products of manufacture of the invention, or a mixture of hemicellulose- and cellulose-hydrolyzing enzymes of the invention, wherein the cellulose-hydrolyzing enzymes comprise at least one endoglucanase, cellobiohydrolase I, cellobiohydrolase II and β-glucosidase; and the hemicellulose-hydrolyzing enzymes comprise at least one xylanase, β-xylosidase and arabinofuranosidase, and contacting the mixture of enzymes with the biomass material, wherein optionally the biomass material comprising lignocellulose is derived from an agricultural crop, is a byproduct of a food or a feed production, is a lignocellulosic waste product, or is a plant residue or a waste paper or waste paper product, and optionally the plant residue comprise grains, seeds, stems, leaves, hulls, husks, corn or corn cobs, corn stover, grasses, wherein optionally grasses are Indian grass or switch grass, hay or straw (e.g., a rice straw or a wheat straw, or any the dry stalk of any cereal plant), wood, wood waste, wood chips, wood pulp and/or sawdust, and optionally the paper waste comprises discarded or used photocopy paper, computer printer paper, notebook paper, notepad paper, typewriter paper, newspapers, magazines, cardboard and paper-based packaging materials, and optionally method further comprises processing the biomass material to generate a biofuel, e.g., a bioalcohol such as bioethanol, biomethanol, biobutanol or biopropanol, an alcohol and/or a sugar (a saccharide). In one aspect, the polypeptide of the invention has a lignocellulosic activity, e.g., an activity comprising cellulase or cellobiohydrolase activity.

In alternative embodiments the invention provides methods for processing a biomass material comprising providing a mixture of enzymes of the invention (including enzyme ensembles ("cocktails") or products of manufacture of the invention), and contacting the enzyme mixture with the biomass material, wherein optionally the biomass material comprising lignocellulose is derived from an agricultural crop, is a byproduct of a food or a feed production, is a lignocellulosic waste product, or is a plant residue or a waste paper or waste paper product, and optionally the plant residue comprise seeds, stems, leaves, hulls, husks, corn or corn cobs, corn stover, corn fiber, grasses (e.g. Indian grass or switch grass), hay, grains, straw (e.g. rice straw or wheat straw or any the dry stalk of any cereal plant), sugarcane bagasse, sugar beet pulp, citrus pulp, and citrus peels, wood, wood thinnings, wood chips, wood pulp, pulp waste, wood waste, wood shavings and sawdust, construction and/or demolition wastes and debris (e.g. wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g. the paper fraction of municipal solid waste, municipal wood waste, and municipal green waste, along with other materials containing sugar, starch, and/or cellulose can be used. Optionally the processing of the biomass material generates a biofuel, e.g., a bioalcohol such as bioethanol, biomethanol, biobutanol or biopropanol. In one aspect, the polypeptide of the invention has a lignocellulosic activity, e.g., an activity comprising a cellulase or cellobiohydrolase activity.

The details of one or more aspects of the invention are set forth in the accompanying drawings and the description below. Other features, objects, and advantages of the invention will be apparent from the description and drawings, the numbered paragraphs preceding the claims, and from the claims themselves.

All publications, patents, patent applications, GenBank sequences and ATCC deposits, cited herein are hereby expressly incorporated by reference for all purposes.

5. BRIEF DESCRIPTION OF THE DRAWINGS

The following drawings are illustrative of aspects of the invention and are not meant to limit the scope of the invention as encompassed by the paragraphs.

Figure 1B:
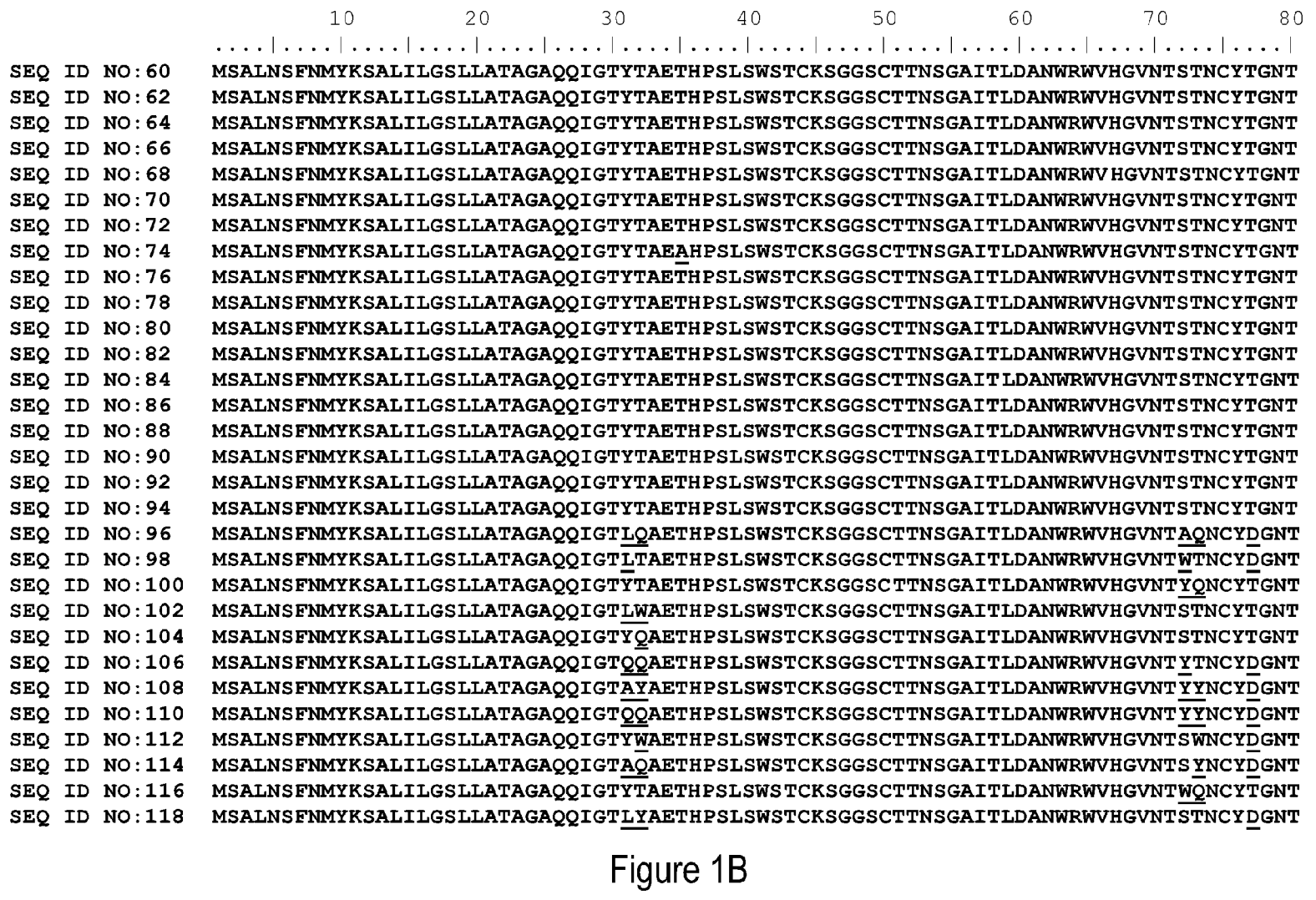
Figure 1G:
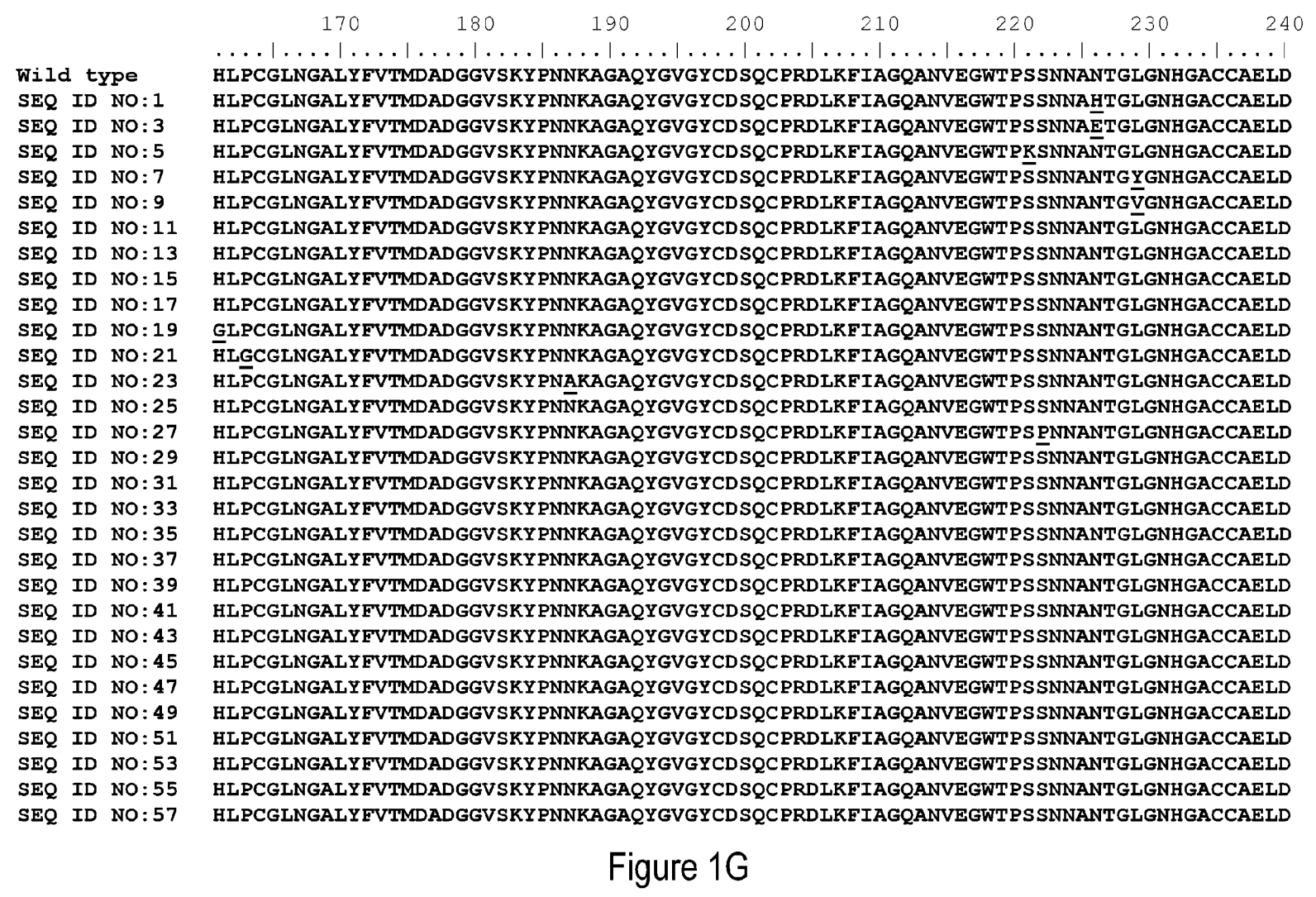

FIG. 1A-1F shows an alignment of variant CBH I polypeptide sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58; SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and/or SEQ ID NO:136. SEQ ID NO:60, 94, 120 and 134 are "wild type" BD29555 sequences; the amino acid substitutions (include the substitution of the 9-amino acid substrate entry loop at positions 120-128 of BD29555 with a longer (13-amino acid loop) are underlined. FIG. 1G-1U shows an alignment of variant CBH I polypeptide sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37,SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57: SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQID NO:133, and/or SEQ ID NO:135.

6. DETAILED DESCRIPTION OF THE INVENTION

In one aspect, the invention provides polypeptides having any lignocellulolytic (lignocellulosic) activity, including ligninolytic and cellulolytic activity, including, e.g., a cellulase and/or a cellobiohydrolase (cbhl) (e.g., an exo-cellobiohydrolase, e.g., having an "exo" activity that can processively release cellobiose units β-1,4 glucose-glucose disaccharide) activity, polynucleotides encoding these polypeptides, and methods of making and using these polynucleotides and polypeptides. In one aspect, the invention provides polypeptides having a lignocellulosic activity, e.g., cellulase and/or a cellobiohydrolase activity, including enzymes that convert soluble oligomers to fermentable monomeric sugars in the saccharification of biomass. In one aspect, an activity of a polypeptide of the invention comprises enzymatic hydrolysis of (to degrade) soluble celloligsaccharides and/or oligomers into monomers (e.g. xylose, arabinose or glucose). In one aspect, the invention provides thermostable and thermotolerant forms of polypeptides of the invention. The polypeptides of the invention can be used in a variety of pharmaceutical, agricultural and industrial contexts.

In one aspect, the invention provides a lignocellulosic enzyme, e.g., a cellulase or a cellobiohydrolase (cbhl) (e.g., an exo-cellobiohydrolase, e.g., having an "exo" activity that can processively release cellobiose units β-1,4 glucose-glucose disaccharide), with an increased catalytic rate, thus improving the process of substrate hydrolysis. In one aspect, the invention provides a lignocellulosic enzyme active under relatively extreme conditions, e.g., high or low temperatures or salt conditions, and/or acid or basic conditions, including pHs and temperatures higher or lower than physiologic. This increased efficiency in catalytic rate leads to an increased efficiency in producing sugars that, in one embodiment, are used by microorganisms for ethanol production. In one aspect, microorganisms generating enzyme of the invention are used with sugar hydrolyzing, e.g., ethanol-producing, microorganisms. Thus, the invention provides methods for biofuel, e.g., a bioalcohol such as bioethanol, biomethanol, biobutanol or biopropanol, production and making "clean fuels" based on alcohols, e.g., for transportation using biofuels.

In one aspect the invention provides compositions (e.g., enzyme preparations, feeds, drugs, dietary supplements) comprising the enzymes, polypeptides or polynucleotides of the invention. These compositions can be formulated in a variety of forms, e.g., as liquids, gels, pills, tablets, sprays, powders, food, feed pellets or encapsulated forms, including nanoencapsulated forms.

Assays for measuring cellulase activity, e.g., endoglucanase, a cellobiohydrolase (cbhI) (e.g., an exo-cellobiohydrolase, e.g., having an "exo" activity that can processively release cellobiose units β-1,4 glucose-glucose disaccharide) activity, e.g., for determining if a polypeptide has cellulase activity, e.g., cellobiohydrolase activity, are well known in the art and are within the scope of the invention; see, e.g., Baker W L, Panow A, Estimation of cellulase activity using a glucose-oxidase-Cu(II) reducing assay for glucose, J Biochem Biophys Methods. 1991 December, 23(4):265-73; Sharrock K R, Cellulase assay methods: a review, J Biochem Biophys Methods. 1988 October, 17(2):81-105; Carder J H, Detection and quantitation of cellulase by Congo red staining of substrates in a cup-plate diffusion assay, Anal Biochem. 1986 Feb. 15, 153(1):75-9; Canevascini G., A cellulase assay coupled to cellobiose dehydrogenase, Anal Biochem. 1985 June, 147(2):419-27; Huang J S, Tang J, Sensitive assay for cellulase and dextranase. Anal Biochem. 1976 June, 73(2): 369-77.

The pH of reaction conditions utilized by the invention is another variable parameter for which the invention provides. In certain aspects, the pH of the reaction is conducted in the range of about 3.0 or less to about 9.0 or more, and in one embodiment an enzyme of the invention is active under such acidic or basic conditions. In other aspects, a process of the invention is practiced at a pH of about 4.0, 4.5, 5.0, 5.5, 6.0, 6.5, 7.5, 8.0, 8.5, 9.0 or 9.5, or more, and in one embodiment an enzyme of the invention is active under such acidic or basic conditions. Reaction conditions conducted under alkaline conditions also can be advantageous, e.g., in some industrial or pharmaceutical applications of enzymes of the invention.

The invention provides compositions, including pharmaceuticals, additives and supplements, comprising a lignocellulosic enzyme of the invention, including polypeptides having a cellulase or a cellobiohydrolase (cbhI) (e.g., an exo-cellobiohydrolase, e.g., having an "exo" activity that can processively release cellobiose units β-1,4 glucose-glucose disaccharide) activity, in a variety of forms and formulations. In the methods of the invention, the lignocellulosic enzymes of the invention also are used in a variety of forms and formulations. For example, purified the lignocellulosic enzyme can be used in enzyme preparations deployed in a biofuel, e.g., a bioalcohol such as bioethanol, biomethanol, biobutanol or biopropanol, production or in pharmaceutical, food, feed or dietary aid applications. Alternatively, the enzymes of the invention can be used directly or indirectly in processes to produce a biofuel, e.g., a bioalcohol such as bioethanol, biomethanol, biobutanol or biopropanol, make clean fuels, process biowastes, process foods, chemicals, pharmaceuticals, supplements, liquids, foods or feeds, and the like.

Alternatively, the lignocellulosic enzyme, e.g., a cellulase or a cellobiohydrolase (cbhI) (e.g., an exo-cellobiohydrolase, e.g., having an "exo" activity that can processively release cellobiose units β-1,4 glucose-glucose disaccharide) polypeptide of the invention can be expressed in a microorganism (including bacterial, yeast, viruses, fungi and the like) using procedures known in the art. The microorganism expressing an enzyme of the invention can live on or in a plant, plant part (e.g., a seed) or an organism. In other aspects, the lignocellulosic enzyme of the invention can be immobilized on a solid support prior to use in the methods of the invention. Methods for immobilizing enzymes on solid supports are commonly known in the art, for example J. Mol. Cat. B: Enzymatic 6 (1999) 29-39; Chivata et al. Biocatalysis: Immobilized cells and enzymes, J. Mol. Cat. 37 (1986) 1-24: Sharma et al., Immobilized Biomaterials Techniques and Applications, Angew. Chem. Int. Ed. Engl. 21 (1982) 837-54: Laskin (Ed.), Enzymes and Immobilized Cells in Biotechnology.

6.1. Nucleic Acids, Probes and Inhibitory Molecules

In alternative embodiments, the invention provides nucleic acids encoding the polypeptides of the invention, e.g., a cellobiohydrolase (cbhI) (e.g., an exo-cellobiohydrolase, e.g., having an "exo" activity that can processively release cellobiose units β-1,4 glucose-glucose disaccharide). The invention also provides expression cassettes, vectors such as expression or cloning vectors, cloning vehicles such as a viral vector, a plasmid, a phage, a phagemid, a cosmid, a fosmid, a bacteriophage or an artificial chromosome, which can comprise, or have contained therein, a nucleic acid of the invention.

The invention also includes methods for discovering new enzyme sequences using the nucleic acids of the invention. Also provided are methods for modifying the nucleic acids of the invention by, e.g., Gene Site Saturation Mutagenesis[SM] technology, GeneReassembly[SM] technology, and/or Tailored Multi-Site Combinatorial Asembly[SM] technology.

In alternative embodiments, the invention provides a genus of nucleic acids based on the exemplary nucleic acids of the invention comprising:

The exemplary SEQ ID NO:1 encoding a polypeptide (e.g., the exemplary SEQ ID NO:2 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT
```

```
TTCACCGTCGATGTCTCCCACCTCCCTTGCGGTTTGAACGGTGCCCTCA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCCATACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:2 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNAHTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:3 encoding a polypeptide (e.g., the exemplary SEQ ID NO:4 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCGAGACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:4 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNAETGLGNHGACCAELDIWEANSISEALTPH
PCDTPGLSVCTTDACGGTYSSDRYAGTCDPDGCDFNPYRLGVTDFYGSGK
```

-continued

TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:5 encoding a polypeptide (e.g., the exemplary SEQ ID NO:6 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCAA
GTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA

A nucleic acid encoding a polypeptide having a cellobiohydrolase activity comprising or consisting of the exemplary SEQ ID NO:6 (or enzymatically active fragments thereof):

MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPKSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:7 encoding a polypeptide (e.g., the exemplary SEQ ID NO:8 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGATATGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC

```
GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:8 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGYGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:9 encoding a polypeptide (e.g., the exemplary SEQ ID NO:10 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGAGTGGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG
```

```
TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:10 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGVGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:11 encoding a polypeptide (e.g., the exemplary SEQ ID NO:12 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG
```

```
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTTCGTGGGTCAG
TGTGGTGGCCAGGGTTGGACTGGTCCTACCACCTGCGCTAGTGGAACCAC
ATGCACCGTCGTGAACCCTTACTACTCTCAATGTTTG TAA
```

A nucleic acid encoding a polypeptide having a cellobiohydrolase activity comprising or consisting of the exemplary SEQ ID NO:12 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAASWGQ
CGGQGWTGPTTCASGTTCTVVNPYYSQCL
```

The exemplary SEQ ID NO:13 encoding a polypeptide (e.g., the exemplary SEQ ID NO:14 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTAAGACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:14 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
```

-continued

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPKTCASGTTCTVVNPYYSQCL

The exemplary SEQ ID NO:15 encoding a polypeptide (e.g., the exemplary SEQ ID NO:16 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCCTTACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA

A nucleic acid encoding a polypeptide having a cellobiohydrolase activity comprising or consisting of the exemplary SEQ ID NO:16 (or enzymatically active fragments thereof):

MSALNSFNMYKSALILGSLLATAGAQQIGTYTAETHPSLSWSTCKSGGSC

TTNSGAITLDANWRWVHGVNTSTNCYTGNTWNTAICLTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL

The exemplary SEQ ID NO:17 encoding a polypeptide (e.g., the exemplary SEQ ID NO:18 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCATTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC

```
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:18 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPILSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:19 encoding a polypeptide (e.g., the exemplary SEQ ID NO:20 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCGGGCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:20 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSGLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:21 encoding a polypeptide (e.g., the exemplary SEQ ID NO:22 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
```

-continued
```
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCGGGTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:22 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLGCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:23 encoding a polypeptide (e.g., the exemplary SEQ ID NO:24 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACGCTA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:24 (or enzymatically active fragments thereof):

```
MSALNSFNMYKSALILGSLLATAGAQQIGTYTAETHPSLSWSTCKSGGS
CTTNSGAITLDANWRWVHGVNTSTNCYTGNTWNTAICDTDASCAQDCAL
DGADYSGTYGITTSGNSLRLNFVTGSNVGSRTYLMADNTHYQIFDLLNQ
EFTFTVDVSHLPCGLNGALYFVTMDADGGVSKYPNAKAGAQYGVGYCDS
QCPRDLKFIAGQANVEGWTPSSNNANTGLGNHGACCAELDIWEANSISE
ALTPHPCDTPGLSVCTTDACGGTYSSDRYAGTCDPDGCDFNPYRLGVTD
```

FYGSGKTVDTTKPITVVTQFVTDDGTSTGTLSEIRRYYVQNGVVIPQPS

SKISGVSGNVINSDFCDAEISTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQCL

The exemplary SEQ ID NO:25 encoding a polypeptide (e.g., the exemplary SEQ ID NO:26 and enzymatically active fragments thereof) having a cellobiohydrolase activity:

ATGTCTGCCTTGAACTCTTTCAATATGTACAAGAGCGCCCTCATCTTGG

GCTCCTTGCTGGCAACAGCTGGTGCTCAGCAAATTGGTACTTATACCGC

TGAAACCCATCCCTCTTTGAGCTGGTCTACTTGCAAATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCGGTCACCTCCCTTGCGGTTTGAACG

GTGCCCTCTACTTCGTGACCATGGACGCCGACGGTGGCGTCTCCAAGTA

CCCCAACAACAAGGCCGGCGCTCAGTACGGTGTTGGATACTGTGACTCT

CAATGCCCTCGTGACTTGAAATTCATCGCTGGTCAGGCCAACGTTGAGG

GCTGGACGCCCTCCTCCAACAACGCCAACACTGGACTTGGCAACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACGACGGCACATCCACCGGCACCCTCTCCGA

GATCAGACGTTACTACGTTCAGAACGGTGTTGTCATCCCCCAGCCTTCC

TCCAAGATCTCCGGAGTCAGCGGAAATGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA

A nucleic acid encoding a polypeptide having a cellobiohydrolase activity comprising or consisting of the exemplary SEQ ID NO:26 (or enzymatically active fragments thereof):

MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVGHLPCGLNGALYFVTMDADGGVSKYPNNKAGAQYGVGYCDS

QCPRDLKFIAGQANVEGWTPSSNNANTGLGNHGACCAELDIWEANSISE

ALTPHPCDTPGLSVCTTDACGGTYSSDRYAGTCDPDGCDFNPYRLGVTD

FYGSGKTVDTTKPITVVTQFVTDDGTSTGTLSEIRRYYVQNGVVIPQPS

SKISGVSGNVINSDFCDAEISTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQC

The exemplary SEQ ID NO:27 encoding a polypeptide (e.g., the exemplary SEQ ID NO:28 and enzymatically active fragments thereof) having a cellobiohydrolase activity:

ATGTCTGCCTTGAACTCTTTCAATATGTACAAGAGCGCCCTCATCTTGG

GCTCCTTGCTGGCAACAGCTGGTGCTCAGCAAATTGGTACTTATACCGC

TGAAACCCATCCCTCTTTGAGCTGGTCTACTTGCAAATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCTCCCACCTCCCTTGCGGTTTGAACG

GTGCCCTCTACTTCGTGACCATGGACGCCGACGGTGGCGTCTCCAAGTA

CCCCAACAACAAGGCCGGCGCTCAGTACGGTGTTGGATACTGTGACTCT

CAATGCCCTCGTGACTTGAAATTCATCGCTGGTCAGGCCAACGTTGAGG

GCTGGACGCCCTCCCCCAACAACGCCAACACTGGACTTGGCAACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCTCTGACGACGGCACATCCACCGGCACCCTCTCCGA

GATCAGACGTTACTACGTTCAGAACGGTGTTGTCATCCCCCAGCCTTCC

```
TCCAAGATCTCCGGAGTCAGCGGAAATGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTTGT AA
```

A nucleic acid encoding a polypeptide having a cellobiohydrolase activity comprising or consisting of the exemplary SEQ ID NO:28 (or enzymatically active fragments thereof):

```
MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSPNNANTGLGNHGACCAELDIWEANSISE

ALTPHPCDTPGLSVCTTDACGGTYSSDRYAGTCDPDGCDFNPYRLGVTD

FYGSGKTVDTTKPITVVTQFVSDDGTSTGTLSEIRRYYVQNGVVIPQPS

SKISGVSGNVINSDFCDAEISTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQCL
```

The exemplary SEQ ID NO:29 encoding a polypeptide (e.g., the exemplary SEQ ID NO:30 and enzymatically active fragments thereof) having a cellobiohydrolase activity:

```
ATGTCTGCCTTGAACTCTTTCAATATGTACAAGAGCGCCCTCATCTTGG

GCTCCTTGCTGGCAACAGCTGGTGCTCAGCAAATTGGTACTTATACCGC

TGAAACCCATCCCTCTTTGAGCTGGTCTACTTGCAAATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCTCCCACCTCCCTTGCGGTTTGAACG

GTGCCCTCTACTTCGTGACCATGGACGCCGACGGTGGCGTCTCCAAGTA
```

```
CCCCAACAACAAGGCCGGCGCTCAGTACGGTGTTGGATACTGTGACTCT

CAATGCCCTCGTGACTTGAAATTCATCGCTGGTCAGGCCAACGTTGAGG

GCTGGACGCCCTCCTCCAACAACGCCAACACTGGACTTGGCAACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACCAGGGCACATCCTCCGGCACCCTCTCCGA

GATCAGACGTTACTACGTTCAGAACGGTGTTGTCATCCCCCAGCCTTCC

TCCAAGATCTCCGGAGTCAGCGGAAATGTCATCAACTCCGACTTCTGCG

ATGCTGAGGTCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA
```

A nucleic acid encoding a polypeptide having a cellobiohydrolase activity comprising or consisting of the exemplary SEQ ID NO:30 (or enzymatically active fragments thereof):

```
MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSSNNANTGLGNHGACCAELDIWEANSISE

ALTPHPCDTPGLSVCTTDACGGTYSSDRYAGTCDPDGCDFNPYRLGVTD

FYGSGKTVDTTKPITVVTQFVTDQGTSSGTLSEIRRYYVQNGVVIPQPS

SKISGVSGNVINSDFCDAEVSTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQCL
```

The exemplary SEQ ID NO:31 encoding a polypeptide (e.g., the exemplary SEQ ID NO:32 and enzymatically active fragments thereof) having a cellobiohydrolase activity:

```
ATGTCTGCCTTGAACTCTTTCAATATGTACAAGAGCGCCCTCATCTTGG

GCTCCTTGCTGGCAACAGCTGGTGCTCAGCAAATTGGTACTTATACCGC
```

```
TGAAACCCATCCCTCTTTGAGCTGGTCTACTTGCAAATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCTCCCACCTCCCTTGCGGTTTGAACG

GTGCCCTCTACTTCGTGACCATGGACGCCGACGGTGGCGTCTCCAAGTA

CCCCAACAACAAGGCCGGCGCTCAGTACGGTGTTGGATACTGTGACTCT

CAATGCCCTCGTGACTTGAAATTCATCGCTGGTCAGGCCAACGTTGAGG

GCTGGACGCCCTCCTCCAACAACGCCAACACTGGACTTGGCAACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACGACGGCACATCCACCGGCCGTCTCTCCGA

GATCAGACGTTACTACGTTCAGAACGGTGTTGTCATCCCCCAGCCTTCC

TCCAAGATCTCCGGAGTCAGCGGAAATGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA
```

A nucleic acid encoding a polypeptide having a cellobiohydrolase activity comprising or consisting of the exemplary SEQ ID NO:32 (or enzymatically active fragments thereof):

```
MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSSNNANTGLGNHGACCAELDIWEANSISE

ALTPHPCDTPGLSVCTTDACGGTYSSDRYAGTCDPDGCDFNPYRLGVTD

FYGSGKTVDTTKPITVVTQFVTDDGTSTGRLSEIRRYYVQNGVVIPQPS

SKISGVSGNVINSDFCDAEISTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQCL
```

The exemplary SEQ ID NO:33 encoding a polypeptide (e.g., the exemplary SEQ ID NO:34 and enzymatically active fragments thereof) having a cellobiohydrolase activity:

```
ATGTCTGCCTTGAACTCTTTCAATATGTACAAGAGCGCCCTCATCTTGG

GCTCCTTGCTGGCAACAGCTGGTGCTCAGCAAATTGGTACTTATACCGC

TGAAACCCATCCCTCTTTGAGCTGGTCTACTTGCAAATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCTCCCACCTCCCTTGCGGTTTGAACG

GTGCCCTCTACTTCGTGACCATGGACGCCGACGGTGGCGTCTCCAAGTA

CCCCAACAACAAGGCCGGCGCTCAGTACGGTGTTGGATACTGTGACTCT

CAATGCCCTCGTGACTTGAAATTCATCGCTGGTCAGGCCAACGTTGAGG

AGCTGGACGCCCTCCTCCAACAACGCCAACACTGGACTTGGCACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACGACGGCACATCCACCGGCACCCTCCTTGA

GATCAGACGTTACTACGTTCAGAACGGTGTTGTCATCCCCCAGCCTTCC

TCCAAGATCTCCGGAGTCAGCGGAAATGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA
```

A nucleic acid encoding a polypeptide having a cellobiohydrolase activity comprising or consisting of the exemplary SEQ ID NO:34 (or enzymatically active fragments thereof):

MSALNSFNMYKSALILGSLLATAGAQQIGTYTAETHPSLSWSTCKSGGS
CTTNSGAITLDANWRWVHGVNTSTNCYTGNTWNTAICDTDASCAQDCAL
DGADYSGTYGITTSGNSLRLNFVTGSNVGSRTYLMADNTHYQIFDLLNQ
EFTFTVDVSHLPCGLNGALYFVTMDADGGVSKYPNNKAGAQYGVGYCDS
QCPRDLKFIAGQANVEGWTPSSNNANTGLGNHGACCAELDIWEANSISE
ALTPHPCDTPGLSVCTTDACGGTYSSDRYAGTCDPDGCDFNPYRLGVTD
FYGSGKTVDTTKPITVVTQFVTDDGTSTGTLLEIRRYYVQNGVVIPQPS
SKISGVSGNVINSDFCDAEISTFGETASFSKHGGLAKMGAGMEAGMVLV
MSLWDDYSVNMLWLDSTYPTNATGTPGAARGSCPTTSGDPKTVESQSGS
SYVTFSDIRVGPFNSTFSGGSSTGGSSTTTASGTTTTKASSTSTSSTST
GTGVAAHWGQCGGQGWTGPTTCASGTTCTVVNPYYSQCL

The exemplary SEQ ID NO:35 encoding a polypeptide (e.g., the exemplary SEQ ID NO:36 and enzymatically active fragments thereof) having a cellobiohydrolase activity:

ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
GTGCCCTCTACTTCGTGACCATGGACGCCGACGGTGGCGTCTCCAAGTA
CCCCAACAACAAGGCCGGCGCTCAGTACGGTGTTGGATACTGTGACTCT
CAATGCCCTCGTGACTTGAAATTCATCGCTGGTCAGGCCAACGTTGAGG
GCTGGACGCCCTCCTCCAACAACGCCAACACTGGACTTGGCAACCACGG
AGCTTGCTGCGCAGAGCTTGATATCTGGGAGGCAAACAGCATCTCAGAG
GCTTTGACTCCTCACCCTTGCGATACACCCGGTCTATCTGTTTGCACTA
CTGATGCCTGCGGTGGTACCTACAGCTCCGATCGTTACGCCGGTACCTG
CGACCCTGATGGATGTGACTTCAACCCTTACCGTCTTGGTGTCACTGAC
TTCTACGGCTCCGGCAAGACCGTTGACACCACCAAACCCATCACCGTTG
TGACTCAATTCGTCACTGACGACGGCACATCCACCGGCACCCTCTCCGA
GATCAGACGTTACTACGTTAGTAACGGTGTTGTCATCCCCCAGCCTTCC
TCCAAGATCTCCGGAGTCAGCGGAAATGTCATCAACTCCGACTTCTGCG
ATGCTGAGATCTCCACCTTTGGCGAGACTGCCTCCTTCAGCAAACACGG
TGGCCTGGCAAAGATGGGCGCTGGTATGGAAGCTGGTATGGTCTTGGTC

-continued
ATGAGTTTGTGGGACGACTACTCCGTCAACATGCTCTGGCTCGACAGCA
CCTACCCTACAAACGCGACTGGTACCCCCGGTGCCGCTCGTGGTTCCTG
CCCTACCACTTCTGGGGACCCTAAGACCGTTGAATCACAATCCGGCAGC
TCCTATGTCACCTTTTCTGACATCCGGGTTGGTCCTTTCAACTCTACGT
TCAGCGGTGGTTCTAGCACCGGTGGCAGCTCCACTACTACCGCCAGCGG
CACCACCACCACCAAGGCCTCTTCCACCTCTACTTCCAGCACCTCTACC
GGCACTGGAGTCGCTGCTCACTGGGGTCAGTGTGGTGGCCAGGGTTGGA
CTGGTCCTACCACCTGCGCTAGTGGAACCACATGCACCGTCGTGAACCC
TTACTACTCTCAATGTTT GTAA A nucleic acid encoding a polypeptide having a cellobiohydrolase activity comprising or consisting of the exemplary SEQ ID NO:36 (or enzymatically active fragments thereof):

MSALNSFNMYKSALILGSLLATAGAQQIGTYTAETHPSLSWSTCKSGGS
CTTNSGAITLDANWRWVHGVNTSTNCYTGNTWNTAICDTDASCAQDCAL
DGADYSGTYGITTSGNSLRLNFVTGSNVGSRTYLMADNTHYQIFDLLNQ
EFTFTVDVSHLPCGLNGALYFVTMDADGGVSKYPNNKAGAQYGVGYCDS
QCPRDLKFIAGQANVEGWTPSSNNANTGLGNHGACCAELDIWEANSISE
ALTPHPCDTPGLSVCTTDACGGTYSSDRYAGTCDPDGCDFNPYRLGVTD
FYGSGKTVDTTKPITVVTQFVTDDGTSTGTLSEIRRYYVSNGVVIPQPS
SKISGVSGNVINSDFCDAEISTFGETASFSKHGGLAKMGAGMEAGMVLV
MSLWDDYSVNMLWLDSTYPTNATGTPGAARGSCPTTSGDPKTVESQSGS
SYVTFSDIRVGPFNSTFSGGSSTGGSSTTTASGTTTTKASSTSTSSTST
GTGVAAHWGQCGGQGWTGPTTCASGTTCTVVNPYYSQCL

The exemplary SEQ ID NO:37 encoding a polypeptide (e.g., the exemplary SEQ ID NO:38 and enzymatically active fragments thereof) having a cellobiohydrolase activity:

ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
GTGCCCTCTACTTCGTGACCATGGACGCCGACGGTGGCGTCTCCAAGTA
CCCCAACAACAAGGCCGGCGCTCAGTACGGTGTTGGATACTGTGACTCT
CAATGCCCTCGTGACTTGAAATTCATCGCTGGTCAGGCCAACGTTGAGG
GCTGGACGCCCTCCTCCAACAACGCCAACACTGGACTTGGCAACCACGG
AGCTTGCTGCGCAGAGCTTGATATCTGGGAGGCAAACAGCATCTCAGAG

```
GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACGACGGCACATCCACCGGCACCCTCTCCGA

GATCAGACGTTACTACGTTCAGAACGGTGTTGTCATCCCCCAGCCTTCC

TCCGATATCTCCGGAGTCAGCGGAAATGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA
```

A nucleic acid encoding a polypeptide having a cellobiohydrolase activity comprising or consisting of the exemplary SEQ ID NO:38 (or enzymatically active fragments thereof):

```
MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSSNNANTGLGNHGACCAELDIWEANSISE

ALTPHPCDTPGLSVCTTDACGGTYSSDRYAGTCDPDGCDFNPYRLGVTD

FYGSGKTVDTTKPITVVTQFVTDDGTSTGTLSEIRRYYVQNGVVIPQPS

SDISGVSGNVINSDFCDAEISTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQCL
```

The exemplary SEQ ID NO:39 encoding a polypeptide (e.g., the exemplary SEQ ID NO:40 and enzymatically active fragments thereof) having a cellobiohydrolase activity:

```
ATGTCTGCCTTGAACTCTTTCAATATGTACAAGAGCGCCCTCATCTTGG

GCTCCTTGCTGGCAACAGCTGGTGCTCAGCAAATTGGTACTTATACCGC

TGAAACCCATCCCTCTTTGAGCTGGTCTACTTGCAGATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCTCCCACCTCCCTTGCGGTTTGAACG

GTGCCCTCTACTTCGTGACAGGCCAACGTTGAGGGCTGGACGCCCTCCT

CCAACAACGCCAACACTGGACTTGGCAACCACGGAGCTTGCTGCGCAGA

GCTTGATATCTGGGAGGCAAACAGCATCTCAGAGGCTTTGACTCCTCAC

CCTTGCGATACACCCGGTCTATCTGTTTGCACTACTGATGCCTGCGGTG

GTACCTACAGCTCCGATCGTTACGCCGGTACCTGCGACCCTGATGGATG

TGACTTCAACCCTTACCGTCTTGGTGTCGCTGACTTCTACGGCTCCGGC

AAGACCGTTGACACCACCAAACCCATCACCGTTGTGACTCAATTCGTCA

CTGACGACGGCACATCCACCGGCACCCTCTCCGAGATCAGACGTTACTA

CGTTCAGAACGGTGTTGTCATCCCCCAGCCTTCCTCCAAGATCTCCGGA

GTCTGTGGAAATGTCATCAACTCCGACTTCTGCGATGCTGAGATCTCCA

CCTTTGGCGAGACTGCCTCCTTCAGCAAACACGGTGGCCTGGCAAAGAT

GGGCGCTGGTATGGAAGCTGGTATGGTCTTGGTCATGAGTTTGTGGGAC

GACTACTCCGTCAACATGCTCTGGCTCGACAGCACCTACCCTACAAACG

CGACTGGTACCCCGGTGCCGCTCGTGGTTCCTGCCCTACCACTTCTGG

GGACCCTAAGACCGTTGAATCACAATCCGGCAGCTCCTATGTCACCTTT

TCTGACATCCGGGTTGGTCCTTTCAACTCTACGTTCAGCGGTGGTTCTA

GCACCGGTGGCAGCTCCACTACTACCGCCAGCGGCACCACCACCACCAA

GGCCTCTTCCACCTCTACTTCCAGCACCTCTACCGGCACTGGAGTCGCT

GCTCACTGGGGTCAGTGTGGTGGCCAGGGTTGGACTGGTCCTACCACCT

GCGCTAGTGGAACCACATGCACCGTCGTGAACCCTTACTACTCTCAATG

TTT GTAA
```

A nucleic acid encoding a polypeptide having a cellobiohydrolase activity comprising or consisting of the exemplary SEQ ID NO:40 (or enzymatically active fragments thereof):

```
MSALNSFNMYKSALILGSLLATAGAQQIGTYTAETHPSLSWSTCRSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSSNNANTGLGNHGACCAELDIWEANSISE

ALTPHPCDTPGLSVCTTDACGGTYSSDRYAGTCDPDGCDFNPYRLGVAD

FYGSGKTVDTTKPITVVTQFVTDDGTSTGTLSEIRRYYVQNGVVIPQPS

SKISGVCGNVINSDFCDAEISTFGETASFSKHGGLAKMGAGMEAGMVLV

MSLWDDYSVNMLWLDSTYPTNATGTPGAARGSCPTTSGDPKTVESQSGS

SYVTFSDIRVGPFNSTFSGGSSTGGSSTTTASGTTTTKASSTSTSSTST

GTGVAAHWGQCGGQGWTGPTTCASGTTCTVVNPYYSQCL
```

The exemplary SEQ ID NO:41 encoding a polypeptide (e.g., the exemplary SEQ ID NO:42 and enzymatically active fragments thereof) having a cellobiohydrolase activity:

```
ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
GTGCCCTCTACTTCGTGACCATGGACGCCGACGGTGGCGTCTCCAAGTA
CCCCAACAACAAGGCCGGCGCTCAGTACGGTGTTGGATACTGTGACTCT
CAATGCCCTCGTGACTTGAAATTCATCGCTGGTCAGGCCAACGTTGAGG
GCTGGACGCCCTCCTCCAACAACGCCAACACTGGACTTGGCAACCACGG
AGCTTGCTGCGCAGAGCTTGATATCTGGGAGGCAAACAGCATCTCAGAG
GCTTTGACTCCTCACCCTTGCGATACACCCGGTCTATCTGTTTGCACTA
CTGATGCCTGCGGTGGTACCTACAGCTCCGATCGTTACGCCGGTACCTG
CGACCCTGATGGATGTGACTTCAACCCTTACCGTCTTGGTGTCACTGAC
TTCTACGGCTCCGGCAAGACCGTTGACACCACCAAACCCATCACCGTTG
TGACTCAATTCGTCACTGACGACGGCACATCCACCGGCACCCTCTCCGA
GATCAGACGTTACTACGTTCAGAACGGTGTTGTCATCCCCCAGCCTTCC
TCCAAGATCTCCGGAGTCAGCGATAATGTCATCAACTCCGACTTCTGCG
ATGCTGAGATCTCCACCTTTGGCGAGACTGCCTCCTTCAGCAAACACGG
TGGCCTGGCAAAGATGGGCGCTGGTATGGAAGCTGGTATGGTCTTGGTC
ATGAGTTTGTGGGACGACTACTCCGTCAACATGCTCTGGCTCGACAGCA
CCTACCCTACAAACGCGACTGGTACCCCCGGTGCCGCTCGTGGTTCCTG
CCCTACCACTTCTGGGGACCCTAAGACCGTTGAATCACAATCCGGCAGC
TCCTATGTCACCTTTTCTGACATCCGGGTTGGTCCTTTCAACTCTACGT
TCAGCGGTGGTTCTAGCACCGGTGGCAGCTCCACTACTACCGCCAGCGG
CACCACCACCACCAAGGCCTCTTCCACCTCTACTTCCAGCACCTCTACC
GGCACTGGAGTCGCTGCTCACTGGGGTCAGTGTGGTGGCCAGGGTTGGA
CTGGTCCTACCACCTGCGCTAGTGGAACCACATGCACCGTCGTGAACCC
TTACTACTCTCAATGTTT GTAA
```

A nucleic acid encoding a polypeptide having a cellobiohydrolase activity comprising or consisting of the exemplary SEQ ID NO:42 (or enzymatically active fragments thereof):

```
MSALNSFNMYKSALILGSLLATAGAQQIGTYTAETHPSLSWSTCKSGGS
CTTNSGAITLDANWRWVHGVNTSTNCYTGNTWNTAICDTDASCAQDCAL
DGADYSGTYGITTSGNSLRLNFVTGSNVGSRTYLMADNTHYQIFDLLNQ
EFTFTVDVSHLPCGLNGALYFVTMDADGGVSKYPNNKAGAQYGVGYCDS
QCPRDLKFIAGQANVEGWTPSSNNANTGLGNHGACCAELDIWEANSISE
ALTPHPCDTPGLSVCTTDACGGTYSSDRYAGTCDPDGCDFNPYRLGVTD
FYGSGKTVDTTKPITVVTQFVTDDGTSTGTLSEIRRYYVQNGVVIPQPS
SKISGVSDNVINSDFCDAEISTFGETASFSKHGGLAKMGAGMEAGMVLV
MSLWDDYSVNMLWLDSTYPTNATGTPGAARGSCPTTSGDPKTVESQSGS
SYVTFSDIRVGPFNSTFSGGSSTGGSSTTTASGTTTTKASSTSTSSTST
GTGVAAHWGQCGGQGWTGPTTCASGTTCTVVNPYYSQCL
```

The exemplary SEQ ID NO:43 encoding a polypeptide (e.g., the exemplary SEQ ID NO:44 and enzymatically active fragments thereof) having a cellobiohydrolase activity:

```
ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
GTGCCCTCTACTTCGTGACCATGGACGCCGACGGTGGCGTCTCCAAGTA
CCCCAACAACAAGGCCGGCGCTCAGTACGGTGTTGGATACTGTGACTCT
CAATGCCCTCGTGACTTGAAATTCATCGCTGGTCAGGCCAACGTTGAGG
GCTGGACGCCCTCCTCCAACAACGCCAACACTGGACTTGGCAACCACGG
AGCTTGCTGCGCAGAGCTTGATATCTGGGAGGCAAACAGCATCTCAGAG
GCTTTGACTCCTCACCCTTGCGATACACCCGGTCTATCTGTTTGCACTA
CTGATGCCTGCGGTGGTACCTACAGCTCCGATCGTTACGCCGGTACCTG
CGACCCTGATGGATGTGACTTCAACCCTTACCGTCTTGGTGTCACTGAC
TTCTACGGCTCCGGCAAGACCGTTGACACCACCAAACCCATCACCGTTG
TGACTCAATTCGTCACTGACGACGGCACATCCACCGGCACCCTCTCCGA
GATCAGACGTTACTACGTTCAGAACGGTGTTGTCATCCCCCAGCCTTCC
TCCAAGATCTCCGGAGTTGTCATCAACTCCGACTTCTGCG
ATGCTGAGATCTCCACCTTTGGCGAGACTGCCTCCTTCAGCAAACACGG
TGGCCTGGCAAAGATGGGCGCTGGTATGGAAGCTGGTATGGTCTTGGTC
ATGAGTTTGTGGGACGACTACTCCGTCAACATGCTCTGGCTCGACAGCA
CCTACCCTACAAACGCGACTGGTACCCCCGGTGCCGCTCGTGGTTCCTG
CCCTACCACTTCTGGGGACCCTAAGACCGTTGAATCACAATCCGGCAGC
TCCTATGTCACCTTTTCTGACATCCGGGTTGGTCCTTTCAACTCTACGT
TCAGCGGTGGTTCTAGCACCGGTGGCAGCTCCACTACTACCGCCAGCGG
```

```
CACCACCACCACCAAGGCCTCTTCCACCTCTACTTCCAGCACCTCTACC
GGCACTGGAGTCGCTGCTCACTGGGGTCAGTGTGGTGGCCAGGGTTGGA
CTGGTCCTACCACCTGCGCTAGTGGAACCACATGCACCGTCGTGAACCC
TTACTACTCTCAATGTTT GTAA
```

A nucleic acid encoding a polypeptide having a cellobiohydrolase activity comprising or consisting of the exemplary SEQ ID NO:44 (or enzymatically active fragments thereof):

```
MSALNSFNMYKSALILGSLLATAGAQQIGTYTAETHPSLSWSTCKSGGS
CTTNSGAITLDANWRWVHGVNTSTNCYTGNTWNTAICDTDASCAQDCAL
DGADYSGTYGITTSGNSLRLNFVTGSNVGSRTYLMADNTHYQIFDLLNQ
EFTFTVDVSHLPCGLNGALYFVTMDADGGVSKYPNNKAGAQYGVGYCDS
QCPRDLKFIAGQANVEGWTPSSNNANTGLGNHGACCAELDIWEANSISE
ALTPHPCDTPGLSVCTTDACGGTYSSDRYAGTCDPDGCDFNPYRLGVTD
FYGSGKTVDTTKPITVVTQFVTDDGTSTGTLSEIRRYYVQNGVVIPQPS
SKISGVSGVVINSDFCDAEISTFGETASFSKHGGLAKMGAGMEAGMVLV
MSLWDDYSVNMLWLDSTYPTNATGTPGAARGSCPTTSGDPKTVESQSGS
SYVTFSDIRVGPFNSTFSGGSSTGGSSTTTASGTTTTKASSTSTSSTST
GTGVAAHWGQCGGQGWTGPTTCASGTTCTVVNPYYSQCL
```

The exemplary SEQ ID NO:45 encoding a polypeptide (e.g., the exemplary SEQ ID NO:46 and enzymatically active fragments thereof) having a cellobiohydrolase activity:

```
ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
GTGCCCTCTACTTCGTGACCATGGACGCCGACGGTGGCGTCTCCAAGTA
CCCCAACAACAAGGCCGGCGCTCAGTACGGTGTTGGATACTGTGACTCT
CAATGCCCTCGTGACTTGAAATTCATCGCTGGTCAGGCCAACGTTGAGG
GCTGGACGCCTCCTCCAACAACGCCAACACTGGACTTGGCAACCACGG
AGCTTGCTGCGCAGAGCTTGATATCTGGGAGGCAAACAGCATCTCAGAG
GCTTTGACTCCTCACCCTTGCGATACACCCGGTCTATCTGTTTGCACTA
CTGATGCCTGCGGTGGTACCTACAGCTCCGATCGTTACGCCGGTACCTG
CGACCCTGATGGATGTGACTTCAACCCTTACCGTCTTGGTGTCACTGAC
TTCTACGGCTCCGGCAAGACCGTTGACACCACCAAACCCATCACCGTTG
TGACTCAATTCGTCACTGACGACGGCACATCCACCGGCACCCTCTCCGA
GATCAGACGTTACTACGTTCAGAACGGTGTTGTCATCCCCCAGCCTTCC
TCCAAGATCTCCGGAGTCAGCGGAAATGTCATCAACTCCGACTTGTGCG
ATGCTGAGATCTCCACCTTTGGCGAGACTGCCTCCTTCAGCAAACACGG
TGGCCTGGCAAAGATGGGCGCTGGTATGGAAGCTGGTATGGTCTTGGTC
ATGAGTTTGTGGGACGACTACTCCGTCAACATGCTCTGGCTCGACAGCA
CCTACCCTACAAACGCGACTGGTACCCCCGGTGCCGCTCGTGGTTCCTG
CCCTACCACTTCTGGGGACCCTAAGACCGTTGAATCACAATCCGGCAGC
TCCTATGTCACCTTTTCTGACATCCGGGTTGGTCCTTTCAACTCTACGT
TCAGCGGTGGTTCTAGCACCGGTGGCAGCTCCACTACTACCGCCAGCGG
CACCACCACCACCAAGGCCTCTTCCACCTCTACTTCCAGCACCTCTACC
GGCACTGGAGTCGCTGCTCACTGGGGTCAGTGTGGTGGCCAGGGTTGGA
CTGGTCCTACCACCTGCGCTAGTGGAACCACATGCACCGTCGTGAACCC
TTACTACTCTCAATGTTT GTAA
```

A nucleic acid encoding a polypeptide having a cellobiohydrolase activity comprising or consisting of the exemplary SEQ ID NO:46 (or enzymatically active fragments thereof):

```
MSALNSFNMYKSALILGSLLATAGAQQIGTYTAETHPSLSWSTCKSGGS
CTTNSGAITLDANWRWVHGVNTSTNCYTGNTWNTAICDTDASCAQDCAL
DGADYSGTYGITTSGNSLRLNFVTGSNVGSRTYLMADNTHYQIFDLLNQ
EFTFTVDVSHLPCGLNGALYFVTMDADGGVSKYPNNKAGAQYGVGYCDS
QCPRDLKFIAGQANVEGWTPSSNNANTGLGNHGACCAELDIWEANSISE
ALTPHPCDTPGLSVCTTDACGGTYSSDRYAGTCDPDGCDFNPYRLGVTD
FYGSGKTVDTTKPITVVTQFVTDDGTSTGTLSEIRRYYVQNGVVIPQPS
SKISGVSGNVINSDLCDAEISTFGETASFSKHGGLAKMGAGMEAGMVLV
MSLWDDYSVNMLWLDSTYPTNATGTPGAARGSCPTTSGDPKTVESQSGS
SYVTFSDIRVGPFNSTFSGGSSTGGSSTTTASGTTTTKASSTSTSSTST
GTGVAAHWGQCGGQGWTGPTTCASGTTCTVVNPYYSQCL
```

The exemplary SEQ ID NO:47 encoding a polypeptide (e.g., the exemplary SEQ ID NO:48 and enzymatically active fragments thereof) having a cellobiohydrolase activity:

```
ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
```

```
GTGCCCTCTACTTCGTGACCATGGACGCCGACGGTGGCGTCTCCAAGTA
CCCCAACAACAAGGCCGGCGCTCAGTACGGTGTTGGATACTGTGACTCT
CAATGCCCTCGTGACTTGAAATTCATCGCTGGTCAGGCCAACGTTGAGG
GCTGGACGCCCTCCTCCAACAACGCCAACACTGGACTTGGCAACCACGG
AGCTTGCTGCGCAGAGCTTGATATCTGGGAGGCAAACAGCATCTCAGAG
GCTTTGACTCCTCACCCTTGCGATACACCCGGTCTATCTGTTTGCACTA
CTGATGCCTGCGGTGGTACCTACAGCTCCGATCGTTACGCCGGTACCTG
CGACCCTGATGGATGTGACTTCAACCCTTACCGTCTTGGTGTCACTGAC
TTCTACGGCTCCGGCAAGACCGTTGACACCACCAAACCCATCACCGTTG
TGACTCAATTCGTCACTGACGACGGCACATCCACCGGCACCCTCTCCGA
GATCAGACGTTACTACGTTCAGAACGGTGTTGTCATCCCCCAGCCTTCC
TCCAAGATCTCCGGAGTCAGCGGAAATGTCATCAACTCCGACTTCTGCG
ATGCTGAGATCTCCACCTTTGGCGAGACTATTTCCTTCAGCAAACACGG
TGGCCTGGCAAAGATGGGCGCTGGTATGGAAGCTGGTATGGTCTTGGTC
ATGAGTTTGTGGGACGACTACTCCGTCAACATGCTCTGGCTCGACAGCA
CCTACCCTACAAACGCGACTGGTACCCCGGTGCCGCTCGTGGTTCCTG
CCCTACCACTTCTGGGGACCCTAAGACCGTTGAATCACAATCCGGCAGC
TCCTATGTCACCTTTTCTGACATCCGGGTTGGTCCTTTCAACTCTACGT
TCAGCGGTGGTTCTAGCACCGGTGGCAGCTCCACTACTACCGCCAGCGG
CACCACCACCACCAAGGCCTCTTCCACCTCTACTTCCAGCACCTCTACC
GGCACTGGAGTCGCTGCTCACTGGGGTCAGTGTGGTGGCCAGGGTTGGA
CTGGTCCTACCACCTGCGCTAGTGGAACCACATGCACCGTCGTGAACCC
TTACTACTCTCAATGTTT GTAA
```

A nucleic acid encoding a polypeptide having a cellobiohydrolase activity comprising or consisting of the exemplary SEQ ID NO:48 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETISFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:49 encoding a polypeptide (e.g., the exemplary SEQ ID NO:50 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACCGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:50 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
```

```
TVDTTKPITVVTQFVTDDGTSTGTLSEIRRYYVQNGVVIPQPSSKISGVS
GNVINSDFCDAEISTFGETASFSKHRGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQC
```

The exemplary SEQ ID NO:51 encoding a polypeptide (e.g., the exemplary SEQ ID NO:52 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGAGTGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:52 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMSAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:53 encoding a polypeptide (e.g., the exemplary SEQ ID NO:54 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
```

```
GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

TGGGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:54 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

WGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:55 encoding a polypeptide (e.g., the exemplary SEQ ID NO:56 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG
```

```
TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCGGTTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:56 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFGSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:57 encoding a polypeptide (e.g., the exemplary SEQ ID NO:58 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG
```

```
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAAGACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:58 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSKTGGSSTTTASGTTTTKASSTSTSSTSTGTGVAAHWGQ
CGGQGWTGPTTCASGTTCTVVNPYYSQCL
```

The exemplary SEQ ID NO:59 encoding a polypeptide (e.g., the exemplary SEQ ID NO:60 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:60 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
```

-continued

```
TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:61 encoding a polypeptide (e.g., the exemplary SEQ ID NO:62 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACAATGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:62 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYNGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:63 encoding a polypeptide (e.g., the exemplary SEQ ID NO:62 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCAGTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC
```

```
GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:64 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFSTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:65 encoding a polypeptide (e.g., the exemplary SEQ ID NO:66 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCACTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:66 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFTTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:67 encoding a polypeptide (e.g., the exemplary SEQ ID NO:68 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCAATAACTCATTGCG
```

-continued
```
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:68 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSNNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:69 encoding a polypeptide (e.g., the exemplary SEQ ID NO:70 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCAACGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:70 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSTRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
```

-continued

TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:71 encoding a polypeptide (e.g., the exemplary SEQ ID NO:72 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TGTTTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA

A nucleic acid encoding a polypeptide having a cellobiohydrolase activity comprising or consisting of the exemplary SEQ ID NO:72 (or enzymatically active fragments thereof):

MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGVYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:73 encoding a polypeptide (e.g., the exemplary SEQ ID NO:74 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAGCTCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC

-continued
GCCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA A nucleic acid encoding a polypeptide having a cellobiohydrolase activity comprising or consisting of the exemplary SEQ ID NO:74 (or enzymatically active fragments thereof):

MSALNSFNMYKSALILGSLLATAGAQQIGTYTAEAHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
ANMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:75 encoding a polypeptide (e.g., the exemplary SEQ ID NO:76 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG

-continued
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGACTATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA A nucleic acid encoding a polypeptide having a cellobiohydrolase activity comprising or consisting of the exemplary SEQ ID NO:76 (or enzymatically active fragments thereof):

MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLTMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:77 encoding a polypeptide (e.g., the exemplary SEQ ID NO:78 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG

```
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACGATTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:78 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDDS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:79 encoding a polypeptide (e.g., the exemplary SEQ ID NO:80 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GATAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:80 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
```

TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
DNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:81 encoding a polypeptide (e.g., the exemplary SEQ ID NO:82 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACCCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGCCATGAGTTTGTGGGACGACTACTCC
GCTAACATGCTCTGGCTCGACAGCACCTACCCTACAAACGCGACTGGTGC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA

A nucleic acid encoding a polypeptide having a cellobiohydrolase activity comprising or consisting of the exemplary SEQ ID NO:82 (or enzymatically active fragments thereof):

MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLAMSLWDDYS
ANMLWLDSTYPTNATGAPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:83 encoding a polypeptide (e.g., the exemplary SEQ ID NO:84 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC

```
GTCAACATGACTTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:84 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMTWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:85 encoding a polypeptide (e.g., the exemplary SEQ ID NO:86 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG
```

```
TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTTATACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:86 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSYTGGSSTTTASGTTTTKASSTSTSSTSTGTGVAAHWGQ

CGGQGWTGPTTCASGTTCTVVNPYYSQCL
```

The exemplary SEQ ID NO:87 encoding a polypeptide (e.g., the exemplary SEQ ID NO:88 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG
```

```
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGTCAACACTGGACTTGGCAACCACGGAGCTTGCTGCGCAG
AGCTTGATATCTGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACGTCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GCCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCTGGACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:88 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNVNTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
ANMLWLDSTYPTNATGTPGAARGSCPTTSGDPKTVESQSGSSYVTFSDIR
VGPFNSTFSGGSSTGGSSTTTASWTTTTKASSTSTSSTSTGTGVAAHWGQ
CGGQGWTGPTTCASGTTCTVVNPYYSQCL
```

The exemplary SEQ ID NO:89 encoding a polypeptide (e.g., the exemplary SEQ ID NO:90 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCATGAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:90 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
```

-continued

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTMSGTTTTKASSTSTSSTSTGTGVAAHWGQ

CGGQGWTGPTTCASGTTCTVVNPYYSQCL

The exemplary SEQ ID NO:91 encoding a polypeptide (e.g., the exemplary SEQ ID NO:92 and enzymatically active fragments thereof) having a cellobiohydrolase activity:

ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATTAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GCCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGACTTGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTTGTAA

A nucleic acid encoding a polypeptide having a cellobiohydrolase activity comprising or consisting of the exemplary SEQ ID NO:92 (or enzymatically active fragments thereof):

MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

ANMLWLDSTYPTNATGTPGAARGSCPTTSGDPKTVESQSGSSYVTFSDIR

VGPFNSTFSGGSSTGGSSTTTASGTTTTKASSTSTSSTSTGTGLAAHWGQ

CGGQGWTGPTTCASGTTCTVVNPYYSQCL

The exemplary SEQ ID NO:93 encoding a polypeptide (e.g., the exemplary SEQ ID NO:94 and enzymatically active fragments thereof) having a cellobiohydrolase activity:

ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

```
GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:94 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:95 encoding a polypeptide (e.g., the exemplary SEQ ID NO:96 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTCTGCAGGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCGCCCAGAACTGCTACGATGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTCCAGCAGGGCCCCTACTCCAAGAACGTCGGCTCCCGTA

CCTACCTGATGGCCGATAACACCCACTACCAAATCTTCGACTTGTTGAAC

CAGGAGTTCACTTTCACCGTCGATGTCTCCCACCTCCCTTGCGGTTTGAA

CGGTGCCCTCTACTTCGTGACCATGGACGCCGACGGTGGCGTCTCCAAGT

ACCCCAACAACAAGGCCGGCGCTCAGTACGGTGTTGGATACTGTGACTCT

CAATGCCCTCGTGACTTGAAATTCATCGCTGGTCAGGCCAACGTTGAGGG

CTGGACGCCCTCCTCCAACAACGCCAACACTGGACTTGGCAACCACGGAG

CTTGCTGCGCAGAGCTTGATATCTGGGAGGCAAACAGCATCTCAGAGGCT

TTGACTCCTCACCCTTGCGATACACCCGGTCTATCTGTTTGCACTACTGA

TGCCTGCGGTGGTACCTACAGCTCCGATCGTTACGCCGGTACCTGCGACC

CTGATGGATGTGACTTCAACCCTTACCGTCTTGGTGTCACTGACTTCTAC

GGCTCCGGCAAGACCGTTGACACCACCAAACCCATCACCGTTGTGACTCA

ATTCGTCACTGACGACGGCACATCCACCGGCACCCTCTCCGAGATCAGAC

GTTACTACGTTCAGAACGGTGTTGTCATCCCCCAGCCTTCCTCCAAGATC

TCCGGAGTCAGCGGAAATGTCATCAACTCCGACTTCTGCGATGCTGAGAT

CTCCACCTTTGGCGAGACTGCCTCCTTCAGCAAACACGGTGGCCTGGCAA

AGATGGGCGCTGGTATGGAAGCTGGTATGGTCTTGGTCATGAGTTTGTGG

GACGACTACTCCGTCAACATGCTCTGGCTCGACAGCACCTACCCTACAAA

CGCGACTGGTACCCCCGGTGCCGCTCGTGGTTCCTGCCCTACCACTTCTG

GGGACCCTAAGACCGTTGAATCACAATCCGGCAGCTCCTATGTCACCTTT

TCTGACATCCGGGTTGGTCCTTTCAACTCTACGTTCAGCGGTGGTTCTAG

CACCGGTGGCAGCTCCACTACTACCGCCAGCGGCACCACCACCACCAAGG

CCTCTTCCACCTCTACTTCCAGCACCTCTACCGGCACTGGAGTCGCTGCT

CACTGGGGTCAGTGTGGTGGCCAGGGTTGGACTGGTCCTACCACCTGCGC

TAGTGGAACCACATGCACCGTCGTGAACCCTTACTACTCTCAATGTTTGT

AA
```

A nucleic acid encoding a polypeptide having a cellobiohydrolase activity comprising or consisting of the exemplary SEQ ID NO: 96 (or enzymatically active fragments thereof):

```
MSALNSFNMYKSALILGSLLATAGAQQIGTLQAETHPSLSWSTCKSGGSC

TTNSGAITLDANWRWVHGVNTAQNCYDGNTWNTAICDTDASCAQDCALDG

ADYSGTYGITTSGNSLRLNFVQQGPYSKNVGSRTYLMADNTHYQIFDLLN

QEFTFTVDVSHLPCGLNGALYFVTMDADGGVSKYPNNKAGAQYGVGYCDS

QCPRDLKFIAGQANVEGWTPSSNNANTGLGNHGACCAELDIWEANSISEA

LTPHPCDTPGLSVCTTDACGGTYSSDRYAGTCDPDGCDFNPYRLGVTDFY

GSGKTVDTTKPITVVTQFVTDDGTSTGTLSEIRRYYVQNGVVIPQPSSKI

SGVSGNVINSDFCDAEISTFGETASFSKHGGLAKMGAGMEAGMVLVMSLW

DDYSVNMLWLDSTYPTNATGTPGAARGSCPTTSGDPKTVESQSGSSYVTF

SDIRVGPFNSTFSGGSSTGGSSTTTASGTTTTKASSTSTSSTSTGTGVAA

HWGQCGGQGWTGPTTCASGTTCTVVNPYYSQCL
```

The exemplary SEQ ID NO:97 encoding a polypeptide (e.g., the exemplary SEQ ID NO:98 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTCTGACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCGGACCAACTGCTACGATGGCAACACTTGGAATACCG

CCATCTGCGACACTGATGCATCCTGTGCCCAGGACTGTGCTCTTGATGGT
```

```
GCTGACTACTCTGGCACGTACGGTATCACTACCTCCGGCAACTCATTGCG

CCTGAACTTCGTCCAGCAGGGCCCCTACTCCAAGAACGTCGGCTCCCGTA

CCTACCTGATGGCCGATAACACCCACTACCAAATCTTCGACTTGTTGAAC

CAGGAGTTCACTTTCACCGTCGATGTCTCCCACCTCCCTTGCGGTTTGAA

CGGTGCCCTCTACTTCGTGACCATGGACGCCGACGGTGGCGTCTCCAAGT

ACCCCAACAACAAGGCCGGCGCTCAGTACGGTGTTGGATACTGTGACTCT

CAATGCCCTCGTGACTTGAAATTCATCGCTGGTCAGGCCAACGTTGAGGG

CTGGACGCCCTCCTCCAACAACGCCAACACTGGACTTGGCAACCACGGAG

CTTGCTGCGCAGAGCTTGATATCTGGGAGGCAAACAGCATCTCAGAGGCT

TTGACTCCTCACCCTTGCGATACACCCGGTCTATCTGTTTGCACTACTGA

TGCCTGCGGTGGTACCTACAGCTCCGATCGTTACGCCGGTACCTGCGACC

CTGATGGATGTGACTTCAACCCTTACCGTCTTGGTGTCACTGACTTCTAC

GGCTCCGGCAAGACCGTTGACACCACCAAACCCATCACCGTTGTGACTCA

ATTCGTCACTGACGACGGCACATCCACCGGCACCCTCTCCGAGATCAGAC

GTTACTACGTTCAGAACGGTGTTGTCATCCCCCAGCCTTCCTCCAAGATC

TCCGGAGTCAGCGGAAATGTCATCAACTCCGACTTCTGCGATGCTGAGAT

CTCCACCTTTGGCGAGACTGCCTCCTTCAGCAAACACGGTGGCCTGGCAA

AGATGGGCGCTGGTATGGAAGCTGGTATGGTCTTGGTCATGAGTTTGTGG

GACGACTACTCCGTCAACATGCTCTGGCTCGACAGCACCTACCCTACAAA

CGCGACTGGTACCCCGGTGCCGCTCGTGGTTCCTGCCCTACCACTTCTG

GGGACCCTAAGACCGTTGAATCACAATCCGGCAGCTCCTATGTCACCTTT

TCTGACATCCGGGTTGGTCCTTTCAACTCTACGTTCAGCGGTGGTTCTAG

CACCGGTGGCAGCTCCACTACTACCGCCAGCGGCACCACCACCACCAAGG

CCTCTTCCACCTCTACTTCCAGCACCTCTACCGGCACTGGAGTCGCTGCT

CACTGGGGTCAGTGTGGTGGCCAGGGTTGGACTGGTCCTACCACCTGCGC

TAGTGGAACCACATGCACCGTCGTGAACCCTTACTACTCTCAATGTTTGT

AA
```

A nucleic acid encoding a polypeptide having a cellobiohydrolase activity comprising or consisting of the exemplary SEQ ID NO: 98 (or enzymatically active fragments thereof):

```
MSALNSFNMYKSALILGSLLATAGAQQIGTLTAETHPSLSWSTCKSGGSC

TTNSGAITLDANWRWVHGVNTWTNCYDGNTWNTAICDTDASCAQDCALDG

ADYSGTYGITTSGNSLRLNFVQQGPYSKNVGSRTYLMADNTHYQIFDLLN

QEFTFTVDVSHLPCGLNGALYFVTMDADGGVSKYPNNKAGAQYGVGYCDS

QCPRDLKFIAGQANVEGWTPSSNNANTGLGNHGACCAELDIWEANSISEA

LTPHPCDTPGLSVCTTDACGGTYSSDRYAGTCDPDGCDFNPYRLGVTDFY

GSGKTVDTTKPITVVTQFVTDDGTSTGTLSEIRRYYVQNGVVIPQPSSKI

SGVSGNVINSDFCDAEISTFGETASFSKHGGLAKMGAGMEAGMVLVMSLW

DDYSVNMLWLDSTYPTNATGTPGAARGSCPTTSGDPKTVESQSGSSYVTF

SDIRVGPFNSTFSGGSSTGGSSTTTASGTTTTKASSTSTSSTSTGTGVAA

HWGQCGGQGWTGPTTCASGTTCTVVNPYYSQCL
```

The exemplary SEQ ID NO:99 encoding a polypeptide (e.g., the exemplary SEQ ID NO:100 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCTACCAGAACTGCTACACCGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTCCAGCAGGGCCCCTACTCCAAGAACGTCGGCTCCCGTA

CCTACCTGATGGCCGATAACACCCACTACCAAATCTTCGACTTGTTGAAC

CAGGAGTTCACTTTCACCGTCGATGTCTCCCACCTCCCTTGCGGTTTGAA

CGGTGCCCTCTACTTCGTGACCATGGACGCCGACGGTGGCGTCTCCAAGT

ACCCCAACAACAAGGCCGGCGCTCAGTACGGTGTTGGATACTGTGACTCT

CAATGCCCTCGTGACTTGAAATTCATCGCTGGTCAGGCCAACGTTGAGGG

CTGGACGCCCTCCTCCAACAACGCCAACACTGGACTTGGCAACCACGGAG

CTTGCTGCGCAGAGCTTGATATCTGGGAGGCAAACAGCATCTCAGAGGCT

TTGACTCCTCACCCTTGCGATACACCCGGTCTATCTGTTTGCACTACTGA

TGCCTGCGGTGGTACCTACAGCTCCGATCGTTACGCCGGTACCTGCGACC

CTGATGGATGTGACTTCAACCCTTACCGTCTTGGTGTCACTGACTTCTAC

GGCTCCGGCAAGACCGTTGACACCACCAAACCCATCACCGTTGTGACTCA

ATTCGTCACTGACGACGGCACATCCACCGGCACCCTCTCCGAGATCAGAC

GTTACTACGTTCAGAACGGTGTTGTCATCCCCCAGCCTTCCTCCAAGATC

TCCGGAGTCAGCGGAAATGTCATCAACTCCGACTTCTGCGATGCTGAGAT

CTCCACCTTTGGCGAGACTGCCTCCTTCAGCAAACACGGTGGCCTGGCAA

AGATGGGCGCTGGTATGGAAGCTGGTATGGTCTTGGTCATGAGTTTGTGG

GACGACTACTCCGTCAACATGCTCTGGCTCGACAGCACCTACCCTACAAA

CGCGACTGGTACCCCGGTGCCGCTCGTGGTTCCTGCCCTACCACTTCTG

GGGACCCTAAGACCGTTGAATCACAATCCGGCAGCTCCTATGTCACCTTT

TCTGACATCCGGGTTGGTCCTTTCAACTCTACGTTCAGCGGTGGTTCTAG

CACCGGTGGCAGCTCCACTACTACCGCCAGCGGCACCACCACCACCAAGG

CCTCTTCCACCTCTACTTCCAGCACCTCTACCGGCACTGGAGTCGCTGCT

CACTGGGGTCAGTGTGGTGGCCAGGGTTGGACTGGTCCTACCACCTGCGC

TAGTGGAACCACATGCACCGTCGTGAACCCTTACTACTCTCAATGTTTGT

AA
```

A nucleic acid encoding a polypeptide having a cellobiohydrolase activity comprising or consisting of the exemplary SEQ ID NO: 100 (or enzymatically active fragments thereof):

```
MSALNSFNMYKSALILGSLLATAGAQQIGTYTAETHPSLSWSTCKSGGSC

TTNSGAITLDANWRWVHGVNTYQNCYTGNTWNTAICDTDASCAQDCALDG
```

ADYSGTYGITTSGNSLRLNFVQQGPYSKNVGSRTYLMADNTHYQIFDLLN

QEFTFTVDVSHLPCGLNGALYFVTMDADGGVSKYPNNKAGAQYGVGYCDS

QCPRDLKFIAGQANVEGWTPSSNNANTGLGNHGACCAELDIWEANSISEA

LTPHPCDTPGLSVCTTDACGGTYSSDRYAGTCDPDGCDFNPYRLGVTDFY

GSGKTVDTTKPITVVTQFVTDDGTSTGTLSEIRRYYVQNGVVIPQPSSKI

SGVSGNVINSDFCDAEISTFGETASFSKHGGLAKMGAGMEAGMVLVMSLW

DDYSVNMLWLDSTYPTNATGTPGAARGSCPTTSGDPKTVESQSGSSYVTF

SDIRVGPFNSTFSGGSSTGGSSTTTASGTTTTKASSTSTSSTSTGTVAA

HWGQCGGQGWTGPTTCASGTTCTVVNPYYSQCL

The exemplary SEQ ID NO:101 encoding a polypeptide (e.g., the exemplary SEQ ID NO:102 and enzymatically active fragments thereof) having a cellobiohydrolase activity:

ATGTCTGCCTTGAACTCTTTCAATATGTACAAGAGCGCCCTCATCTTGGG

CTCCTTGCTGGCAACAGCTGGTGCTCAGCAAATTGGTACTCTGTGGGCTG

AAACCCATCCCTCTTTGAGCTGGTCTACTTGCAAATCGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTCCAGCAGGGCCCCTACTCCAAGAACGTCGGCTCCCGTA

CCTACCTGATGGCCGATAACACCCACTACCAAATCTTCGACTTGTTGAAC

CAGGAGTTCACTTTCACCGTCGATGTCTCCCACCTCCCTTGCGGTTTGAA

CGGTGCCCTCTACTTCGTGACCATGGACGCCGACGGTGGCGTCTCCAAGT

ACCCCAACAACAAGGCCGGCGCTCAGTACGGTGTTGGATACTGTGACTCT

CAATGCCCTCGTGACTTGAAATTCATCGCTGGTCAGGCCAACGTTGAGGG

CTGGACGCCCTCCTCCAACAACGCCAACACTGGACTTGGCAACCACGGAG

CTTGCTGCGCAGAGCTTGATATCTGGGAGGCAAACAGCATCTCAGAGGCT

TTGACTCCTCACCCTTGCGATACACCCGGTCTATCTGTTTGCACTACTGA

TGCCTGCGGTGGTACCTACAGCTCCGATCGTTACGCCGGTACCTGCGACC

CTGATGGATGTGACTTCAACCCTTACCGTCTTGGTGTCACTGACTTCTAC

GGCTCCGGCAAGACCGTTGACACCACCAAACCCATCACCGTTGTGACTCA

ATTCGTCACTGACGACGGCACATCCACCGGCACCCTCTCCGAGATCAGAC

GTTACTACGTTCAGAACGGTGTTGTCATCCCCCAGCCTTCCTCCAAGATC

TCCGGAGTCAGCGGAAATGTCATCAACTCCGACTTCTGCGATGCTGAGAT

CTCCACCTTTGGCGAGACTGCCTCCTTCAGCAAACACGGTGGCCTGGCAA

AGATGGGCGCTGGTATGGAAGCTGGTATGGTCTTGGTCATGAGTTTGTGG

GACGACTACTCCGTCAACATGCTCTGGCTCGACAGCACCTACCCTACAAA

CGCGACTGGTACCCCCGGTGCCGCTCGTGGTTCCTGCCCTACCACTTCTG

GGGACCCTAAGACCGTTGAATCACAATCCGGCAGCTCCTATGTCACCTTT

TCTGACATCCGGGTTGGTCCTTTCAACTCTACGTTCAGCGGTGGTTCTAG

CACCGGTGGCAGCTCCACTACTACCGCCAGCGGCACCACCACCACCAAGG

CCTCTTCCACCTCTACTTCCAGCACCTCTACCGGCACTGGAGTCGCTGCT

CACTGGGGTCAGTGTGGTGGCCAGGGTTGGACTGGTCCTACCACCTGCGC

TAGTGGAACCACATGCACCGTCGTGAACCCTTACTACTCTCAATGTTGT

AA

A nucleic acid encoding a polypeptide having a cellobiohydrolase activity comprising or consisting of the exemplary SEQ ID NO:102 (or enzymatically active fragments thereof):

MSALNSFNMYKSALILGSLLATAGAQQIGTLWAETHPSLSWSTCKSGGSC

TTNSGAITLDANWRWVHGVNTSTNCYTGNTWNTAICDTDASCAQDCALDG

ADYSGTYGITTSGNSLRLNFVQQGPYSKNVGSRTYLMADNTHYQIFDLLN

QEFTFTVDVSHLPCGLNGALYFVTMDADGGVSKYPNNKAGAQYGVGYCDS

QCPRDLKFIAGQANVEGWTPSSNNANTGLGNHGACCAELDIWEANSISEA

LTPHPCDTPGLSVCTTDACGGTYSSDRYAGTCDPDGCDFNPYRLGVTDFY

GSGKTVDTTKPITVVTQFVTDDGTSTGTLSEIRRYYVQNGVVIPQPSSKI

SGVSGNVINSDFCDAEISTFGETASFSKHGGLAKMGAGMEAGMVLVMSLW

DDYSVNMLWLDSTYPTNATGTPGAARGSCPTTSGDPKTVESQSGSSYVTF

SDIRVGPFNSTFSGGSSTGGSSTTTASGTTTTKASSTSTSSTSTGTVAA

HWGQCGGQGWTGPTTCASGTTCTVVNPYYSQCL

The exemplary SEQ ID NO:103 encoding a polypeptide (e.g., the exemplary SEQ ID NO:104 and enzymatically active fragments thereof) having a cellobiohydrolase activity:

ATGTCTGCCTTGAACTCTTTCAATATGTACAAGAGCGCCCTCATCTTGGG

CTCCTTGCTGGCAACAGCTGGTGCTCAGCAAATTGGTACTTACCAGGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTCACCAAGGGCTCCTTCTCCTCCAACATCGGCTCCCGTA

CCTACCTGATGGCCGATAACACCCACTACCAAATCTTCGACTTGTTGAAC

CAGGAGTTCACTTTCACCGTCGATGTCTCCCACCTCCCTTGCGGTTTGAA

CGGTGCCCTCTACTTCGTGACCATGGACGCCGACGGTGGCGTCTCCAAGT

ACCCCAACAACAAGGCCGGCGCTCAGTACGGTGTTGGATACTGTGACTCT

CAATGCCCTCGTGACTTGAAATTCATCGCTGGTCAGGCCAACGTTGAGGG

CTGGACGCCCTCCTCCAACAACGCCAACACTGGACTTGGCAACCACGGAG

CTTGCTGCGCAGAGCTTGATATCTGGGAGGCAAACAGCATCTCAGAGGCT

TTGACTCCTCACCCTTGCGATACACCCGGTCTATCTGTTTGCACTACTGA

TGCCTGCGGTGGTACCTACAGCTCCGATCGTTACGCCGGTACCTGCGACC

CTGATGGATGTGACTTCAACCCTTACCGTCTTGGTGTCACTGACTTCTAC

GGCTCCGGCAAGACCGTTGACACCACCAAACCCATCACCGTTGTGACTCA

```
ATTCGTCACTGACGACGGCACATCCACCGGCACCCTCTCCGAGATCAGAC
GTTACTACGTTCAGAACGGTGTTGTCATCCCCCAGCCTTCCTCCAAGATC
TCCGGAGTCAGCGGAAATGTCATCAACTCCGACTTCTGCGATGCTGAGAT
CTCCACCTTTGGCGAGACTGCCTCCTTCAGCAAACACGGTGGCCTGGCAA
AGATGGGCGCTGGTATGGAAGCTGGTATGGTCTTGGTCATGAGTTTGTGG
GACGACTACTCCGTCAACATGCTCTGGCTCGACAGCACCTACCCTACAAA
CGCGACTGGTACCCCGGTGCCGCTCGTGGTTCCTGCCCTACCACTTCTG
GGGACCCTAAGACCGTTGAATCACAATCCGGCAGCTCCTATGTCACCTTT
TCTGACATCCGGGTTGGTCCTTTCAACTCTACGTTCAGCGGTGGTTCTAG
CACCGGTGGCAGCTCCACTACTACCGCCAGCGGCACCACCACCACCAAGG
CCTCTTCCACCTCTACTTCCAGCACCTCTACCGGCACTGGAGTCGCTGCT
CACTGGGGTCAGTGTGGTGGCCAGGGTTGGACTGGTCCTACCACCTGCGC
TAGTGGAACCACATGCACCGTCGTGAACCCTTACTACTCTCAATGTTTGT
AA
```

A nucleic acid encoding a polypeptide having a cellobiohydrolase activity comprising or consisting of the exemplary SEQ ID NO:104 (or enzymatically active fragments thereof):

```
MSALNSFNMYKSALILGSLLATAGAQQIGTYQAETHPSLSWSTCKSGGSC
TTNSGAITLDANWRWVHGVNTSTNCYTGNTWNTAICDTDASCAQDCALDG
ADYSGTYGITTSGNSLRLNFVTKGSFSSNIGSRTYLMADNTHYQIFDLLN
QEFTFTVDVSHLPCGLNGALYFVTMDADGGVSKYPNNKAGAQYGVGYCDS
QCPRDLKFIAGQANVEGWTPSSNNANTGLGNHGACCAELDIWEANSISEA
LTPHPCDTPGLSVCTTDACGGTYSSDRYAGTCDPDGCDFNPYRLGVTDFY
GSGKTVDTTKPITVVTQFVTDDGTSTGTLSEIRRYYVQNGVVIPQPSSKI
SGVSGNVINSDFCDAEISTFGETASFSKHGGLAKMGAGMEAGMVLVMSLW
DDYSVNMLWLDSTYPTNATGTPGAARGSCPTTSGDPKTVESQSGSSYVTF
SDIRVGPFNSTFSGGSSTGGSSTTTASGTTTTKASSTSTSSTSTGTGVAA
HWGQCGGQGWTGPTTCASGTTCTVVNPYYSQCL
```

The exemplary SEQ ID NO:105 encoding a polypeptide (e.g., the exemplary SEQ ID NO:106 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTCAGCAGGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCTACACCAACTGCTACGATGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCACCCAGTCCGCCCAGAAGAACGTCGGCGCCCGTACCT
ACCTGATGGCCGATAACACCCACTACCAAATCTTCGACTTGTTGAACCAG
GAGTTCACTTTCACCGTCGATGTCTCCCACCTCCCTTGCGGTTTGAACGG
TGCCCTCTACTTCGTGACCATGGACGCCGACGGTGGCGTCTCCAAGTACC
CCAACAACAAGGCCGGCGCTCAGTACGGTGTTGGATACTGTGACTCTCAA
TGCCCTCGTGACTTGAAATTCATCGCTGGTCAGGCCAACGTTGAGGGCTG
GACGCCCTCCTCCAACAACGCCAACACTGGACTTGGCAACCACGGAGCTT
GCTGCGCAGAGCTTGATATCTGGGAGGCAAACAGCATCTCAGAGGCTTTG
ACTCCTCACCCTTGCGATACACCCGGTCTATCTGTTTGCACTACTGATGC
CTGCGGTGGTACCTACAGCTCCGATCGTTACGCCGGTACCTGCGACCCTG
ATGGATGTGACTTCAACCCTTACCGTCTTGGTGTCACTGACTTCTACGGC
TCCGGCAAGACCGTTGACACCACCAAACCCATCACCGTTGTGACTCAATT
CGTCACTGACGACGGCACATCCACCGGCACCCTCTCCGAGATCAGACGTT
ACTACGTTCAGAACGGTGTTGTCATCCCCCAGCCTTCCTCCAAGATCTCC
GGAGTCAGCGGAAATGTCATCAACTCCGACTTCTGCGATGCTGAGATCTC
CACCTTTGGCGAGACTGCCTCCTTCAGCAAACACGGTGGCCTGGCAAAGA
TGGGCGCTGGTATGGAAGCTGGTATGGTCTTGGTCATGAGTTTGTGGGAC
GACTACTCCGTCAACATGCTCTGGCTCGACAGCACCTACCCTACAAACGC
GACTGGTACCCCGGTGCCGCTCGTGGTTCCTGCCCTACCACTTCTGGGG
ACCCTAAGACCGTTGAATCACAATCCGGCAGCTCCTATGTCACCTTTTCT
GACATCCGGGTTGGTCCTTTCAACTCTACGTTCAGCGGTGGTTCTAGCAC
CGGTGGCAGCTCCACTACTACCGCCAGCGGCACCACCACCACCAAGGCCT
CTTCCACCTCTACTTCCAGCACCTCTACCGGCACTGGAGTCGCTGCTCAC
TGGGGTCAGTGTGGTGGCCAGGGTTGGACTGGTCCTACCACCTGCGCTAG
TGGAACCACATGCACCGTCGTGAACCCTTACTACTCTCAATGTTTGTAA
```

A nucleic acid encoding a polypeptide having a cellobiohydrolase activity comprising or consisting of the exemplary SEQ ID NO:106 (or enzymatically active fragments thereof):

```
MSALNSFNMYKSALILGSLLATAGAQQIGTQQAETHPSLSWSTCKSGGSC
TTNSGAITLDANWRWVHGVNTYTNCYDGNTWNTAICDTDASCAQDCALDG
ADYSGTYGITTSGNSLRLNFVTQSAQKNVGARTYLMADNTHYQIFDLLNQ
EFTFTVDVSHLPCGLNGALYFVTMDADGGVSKYPNNKAGAQYGVGYCDSQ
CPRDLKFIAGQANVEGWTPSSNNANTGLGNHGACCAELDIWEANSISEAL
TPHPCDTPGLSVCTTDACGGTYSSDRYAGTCDPDGCDFNPYRLGVTDFYG
SGKTVDTTKPITVVTQFVTDDGTSTGTLSEIRRYYVQNGVVIPQPSSKIS
GVSGNVINSDFCDAEISTFGETASFSKHGGLAKMGAGMEAGMVLVMSLWD
DYSVNMLWLDSTYPTNATGTPGAARGSCPTTSGDPKTVESQSGSSYVTFS
DIRVGPFNSTFSGGSSTGGSSTTTASGTTTTKASSTSTSSTSTGTGVAAH
WGQCGGQGWTGPTTCASGTTCTVVNPYYSQCL
```

The exemplary SEQ ID NO:107 encoding a polypeptide (e.g., the exemplary SEQ ID NO:108 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTGCCTACGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCTACTACAACTGCTACGATGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCACCGGCTCCAACGTCGGCTCCCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:108 (or enzymatically active fragments thereof):

```
MSALNSFNMYKSALILGSLLATAGAQQIGTAYAETHPSLSWSTCKSGGSC
TTNSGAITLDANWRWVHGVNTYYNCYDGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
GVGPFNSTFSGSSTGGSSTTTASGTTTTKASSTSTSSTSTGTGVAAHWGQ
CGGQGWTGPTTCASGTTCTVVNPYYSQCL
```

The exemplary SEQ ID NO:109 encoding a polypeptide (e.g., the exemplary SEQ ID NO:110 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTCAGCAGGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCTACTACAACTGCTACGATGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCACCGGCTCCAACGTCGGCTCCCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:110 (or enzymatically active fragments thereof):

MSALNSFNMYKSALILGSLLATAGAQQIGTQQAETHPSLSWSTCKSGGSC
TTNSGAITLDANWRWVHGVNTYYNCYDGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:111 encoding a polypeptide (e.g., the exemplary SEQ ID NO:112 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTACTGGGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCTCCTGGAACTGCTACGATGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCACCGGCTCCAACGTCGGCTCCCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC

GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA

A nucleic acid encoding a polypeptide having a cellobiohydrolase activity comprising or consisting of the exemplary SEQ ID NO:112 (or enzymatically active fragments thereof):

MSALNSFNMYKSALILGSLLATAGAQQIGTYWAETHPSLSWSTCKSGGSC
TTNSGAITLDANWRWVHGVNTSWNCYDGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:113 encoding a polypeptide (e.g., the exemplary SEQ ID NO:114 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTGCCCAGGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCTCCTACAACTGCTACGATGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCACCGGCTCCAACGTCGGCTCCCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG

-continued
```
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:114 (or enzymatically active fragments thereof):

```
MSALNSFNMYKSALILGSLLATAGAQQIGTAQAETHPSLSWSTCKSGGSC
TTNSGAITLDANWRWVHGVNTSYNCYDGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:115 encoding a polypeptide (e.g., the exemplary SEQ ID NO:116 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCTGGCAGAACTGCTACACCGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCCAGCAGGGCCCCTACTCCAAGAACGTCGGCTCCCGTA
CCTACCTGATGGCCGATAACACCCACTACCAAATCTTCGACTTGTTGAAC
CAGGAGTTCACTTTCACCGTCGATGTCTCCCACCTCCCTTGCGGTTTGAA
CGGTGCCCTCTACTTCGTGACCATGGACGCCGACGGTGGCGTCTCCAAGT
ACCCCAACAACAAGGCCGGCGCTCAGTACGGTGTTGGATACTGTGACTCT
CAATGCCCTCGTGACTTGAAATTCATCGCTGGTCAGGCCAACGTTGAGGG
CTGGACGCCCTCCTCCAACAACGCCAACACTGGACTTGGCAACCACGGAG
CTTGCTGCGCAGAGCTTGATATCTGGGAGGCAAACAGCATCTCAGAGGCT
TTGACTCCTCACCCTTGCGATACACCCGGTCTATCTGTTTGCACTACTGA
TGCCTGCGGTGGTACCTACAGCTCCGATCGTTACGCCGGTACCTGCGACC
CTGATGGATGTGACTTCAACCCTTACCGTCTTGGTGTCACTGACTTCTAC
GGCTCCGGCAAGACCGTTGACACCACCAAACCCATCACCGTTGTGACTCA
ATTCGTCACTGACGACGGCACATCCACCGGCACCCTCTCCGAGATCAGAC
GTTACTACGTTCAGAACGGTGTTGTCATCCCCCAGCCTTCCTCCAAGATC
TCCGGAGTCAGCGGAAATGTCATCAACTCCGACTTCTGCGATGCTGAGAT
CTCCACCTTTGGCGAGACTGCCTCCTTCAGCAAACACGGTGGCCTGGCAA
AGATGGGCGCTGGTATGGAAGCTGGTATGGTCTTGGTCATGAGTTTGTGG
GACGACTACTCCGTCAACATGCTCTGGCTCGACAGCACCTACCCTACAAA
CGCGACTGGTACCCCCGGTGCCGCTCGTGGTTCCTGCCCTACCACTTCTG
GGGACCCTAAGACCGTTGAATCACAATCCGGCAGCTCCTATGTCACCTTT
TCTGACATCCGGGTTGGTCCTTTCAACTCTACGTTCAGCGGTGGTTCTAG
CACCGGTGGCAGCTCCACTACTACCGCCAGCGGCACCACCACCACCAAGG
CCTCTTCCACCTCTACTTCCAGCACCTCTACCGGCACTGGAGTCGCTGCT
CACTGGGGTCAGTGTGGTGGCCAGGGTTGGACTGGTCCTACCACCTGCGC
TAGTGGAACCACATGCACCGTCGTGAACCCTTACTACTCTCAATGTTTGT
AA
```

A nucleic acid encoding a polypeptide having a cellobiohydrolase activity comprising or consisting of the exemplary SEQ ID NO:116 (or enzymatically active fragments thereof):

```
MSALNSFNMYKSALILGSLLATAGAQQIGTYTAETHPSLSWSTCKSGGSC
TTNSGAITLDANWRWVHGVNTWQNCYTGNTWNTAICDTDASCAQDCALDG
ADYSGTYGITTSGNSLRLNFVQQGPYSKNVGSRTYLMADNTHYQIFDLLN
QEFTFTVDVSHLPCGLNGALYFVTMDADGGVSKYPNNKAGAQYGVGYCDS
QCPRDLKFIAGQANVEGWTPSSNNANTGLGNHGACCAELDIWEANSISEA
LTPHPCDTPGLSVCTTDACGGTYSSDRYAGTCDPDGCDFNPYRLGVTDFY
GSGKTVDTTKPITVVTQFVTDDGTSTGTLSEIRRYYVQNGVVIPQPSSKI
SGVSGNVINSDFCDAEISTFGETASFSKHGGLAKMGAGMEAGMVLVMSLW
DDYSVNMLWLDSTYPTNATGTPGAARGSCPTTSGDPKTVESQSGSSYVTF
SDIRVGPFNSTFSGGSSTGGSSTTTASGTTTTKASSTSTSSTSTGTGVAA
HWGQCGGQGWTGPTTCASGTTCTVVNPYYSQCL
```

The exemplary SEQ ID NO:117 encoding a polypeptide (e.g., the exemplary SEQ ID NO:118 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTCTGTACGCTG
CAAACCCATCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCTCCACCAACTGCTACGATGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTCCAGCAGGGCCCCTACTCCAAGAACGTCGGCTCCCGTA
CCTACCTGATGGCCGATAACACCCACTACCAAATCTTCGACTTGTTGAAC
CAGGAGTTCACTTTCACCGTCGATGTCTCCCACCTCCCTTGCGGTTTGAA
CGGTGCCCTCTACTTCGTGACCATGGACGCCGACGGTGGCGTCTCCAAGT
ACCCCAACAACAAGGCCGGCGCTCAGTACGGTGTTGGATACTGTGACTCT
CAATGCCCTCGTGACTTGAAATTCATCGCTGGTCAGGCCAACGTTGAGGG
CTGGACGCCCTCCTCCAACAACGCCAACACTGGACTTGGCAACCACGGAG
CTTGCTGCGCAGAGCTTGATATCTGGGAGGCAAACAGCATCTCAGAGGCT
TTGACTCCTCACCCTTGCGATACACCCGGTCTATCTGTTTGCACTACTGA
TGCCTGCGGTGGTACCTACAGCTCCGATCGTTACGCCGGTACCTGCGACC
CTGATGGATGTGACTTCAACCCTTACCGTCTTGGTGTCACTGACTTCTAC
GGCTCCGGCAAGACCGTTGACACCACCAAACCCATCACCGTTGTGACTCA
ATTCGTCACTGACGACGGCACATCCACCGGCACCCTCTCCGAGATCAGAC
GTTACTACGTTCAGAACGGTGTTGTCATCCCCCAGCCTTCCTCCAAGATC
TCCGGAGTCAGCGGAAATGTCATCAACTCCGACTTCTGCGATGCTGAGAT
CTCCACCTTTGGCGAGACTGCCTCCTTCAGCAAACACGGTGGCCTGGCAA
AGATGGGCGCTGGTATGGAAGCTGGTATGGTCTTGGTCATGAGTTTGTGG
GACGACTACTCCGTCAACATGCTCTGGCTCGACAGCACCTACCCTACAAA
CGCGACTGGTACCCCCGGTGCCGCTCGTGGTTCCTGCCCTACCACTTCTG
GGGACCCTAAGACCGTTGAATCACAATCCGGCAGCTCCTATGTCACCTTT
TCTGACATCCGGGTTGGTCCTTTCAACTCTACGTTCAGCGGTGGTTCTAG
CACCGGTGGCAGCTCCACTACTACCGCCAGCGGCACCACCACCACCAAGG
CCTCTTCCACCTCTACTTCCAGCACCTCTACCGGCACTGGAGTCGCTGCT
CACTGGGGTCAGTGTGGTGGCCAGGGTTGGACTGGTCCTACCACCTGCGC
TAGTGGAACCACATGCACCGTCGTGAACCCTTACTACTCTCAATGTTTGT
AA
```

A nucleic acid encoding a polypeptide having a cellobiohydrolase activity comprising or consisting of the exemplary SEQ ID NO:118 (or enzymatically active fragments thereof):

```
MSALNSFNMYKSALILGSLLATAGAQQIGTLYAETHPSLSWSTCKSGGSC
TTNSGAITLDANWRWVHGVNTSTNCYDGNTWNTAICDTDASCAQDCALDG
ADYSGTYGITTSGNSLRLNFVQQGPYSKNVGSRTYLMADNTHYQIFDLLN
QEFTFTVDVSHLPCGLNGALYFVTMDADGGVSKYPNNKAGAQYGVGYCDS
QCPRDLKFIAGQANVEGWTPSSNNANTGLGNHGACCAELDIWEANSISEA
LTPHPCDTPGLSVCTTDACGGTYSSDRYAGTCDPDGCDFNPYRLGVTDFY
GSGKTVDTTKPITVVTQFVTDDGTSTGTLSEIRRYYVQNGVVIPQPSSKI
SGVSGNVINSDFCDAEISTFGETASFSKHGGLAKMGAGMEAGMVLVMSLW
DDYSVNMLWLDSTYPTNATGTPGAARGSCPTTSGDPKTVESQSGSSYVTF
SDIRVGPFNSTFSGGSSTGGSSTTTASGTTTTKASSTSTSSTSTGTGVAA
HWGQCGGQGWTGPTTCASGTTCTVVNPYYSQCL
```

The exemplary SEQ ID NO:119 encoding a polypeptide (e.g., the exemplary SEQ ID NO:120 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGACTTGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC
AGAACGGTGTTGTCATCCCCCAGCCTTCCTCCAAGATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGATGATTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
```

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTTGTAA

A nucleic acid encoding a polypeptide having a cellobiohydrolase activity comprising or consisting of the exemplary SEQ ID NO:120 (or enzymatically active fragments thereof):

MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGLGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:121 encoding a polypeptide (e.g., the exemplary SEQ ID NO:122 and enzymatically active fragments thereof) having a cellobiohydrolase activity:

ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCGGGTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCAA
GTCCAACAACGCCCATACTGGATATGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTC

AGAACGGTGTTGTCATCCCCCAGCCTTCCTCCGATATCTCCGGAGTCAGC
GGAGTTGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGGAAGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
TGGGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA

A nucleic acid encoding a polypeptide having a cellobiohydrolase activity comprising or consisting of the exemplary SEQ ID NO:122 (or enzymatically active fragments thereof):

MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLGCGLNGALYFVTMDADGGVSKYPNNKAGAQYGVGYCDSQCPR
DLKFIAGQANVEGWTPKSNNAHTGYGNHGACCAELDIWEANSISEALTPH
PCDTPGLSVCTTDACGGTYSSDRYAGTCDPDGCDFNPYRLGVTDFYGSGK
TVDTTKPITVVTQFVTDDGTSTGTLSEIRRYYVQNGVVIPQPSSDISGVS
GVVINSDFCDAEISTFGETASFSKHGGLAKMGAGMEAGMVLVMSLWDDYS
VNMLWLDSTYPTNATGTPGAARGSCPTTSGDPKTVESQSGSSYVTFSDIR
WGPFNSTFSGGSSTGGSSTTTASGTTTTKASSTSTSSTSTGTGVAAHWGQ
CGGQGWTGPTTCASGTTCTVVNPYYSQCL

The exemplary SEQ ID NO:123 encoding a polypeptide (e.g., the exemplary SEQ ID NO:124 and enzymatically active fragments thereof) having a cellobiohydrolase activity:

ATGTCTGCCTTGAACTCTTTCAATATGTACAAGAGCGCCCTCATCTTGG
GCTCCTTGCTGGCAACAGCTGGTGCTCAGCAAATTGGTACTTATACCGC
TGAAACCCATCCCTCTTTGAGCTGGTCTACTTGCAAATCGGGTGGTAGC
TGCACCACAAACTCCGGTGCCATTACGTTGGATGCCAACTGGCGTTGGG
TCCATGGTGTCAATACCAGCACCAACTGCTACACTGGCAACACTTGGAA
TACCGCCATCTGCGACACTGATGCATCCTGTGCCCAGGACTGTGCTCTT
GATGGTGCTGACTACTCTGGCACGTACGGTATCACTACCTCCGGCAACT
CATTGCGCCTGAACTTCGTTACCGGTTCCAACGTCGGATCTCGTACCTA
CCTGATGGCCGATAACACCCACTACCAAATCTTCGACTTGTTGAACCAG
GAGTTCACTTTCACCGTCGATGTCTCCCACCTCCCTTGCGGTTTGAACG
GTGCCCTCTACTTCGTGACCATGGACGCCGACGGTGGCGTCTCCAAGTA
CCCCAACAACAAGGCCGGCGCTCAGTACGGTGTTGGATACTGTGACTCT

CAATGCCCTCGTGACTTGAAATTCATCGCTGGTCAGGCCAACGTTGAGG

GCTGGACGCCCTCCTCCAACAACGCCCATACTGGATATGGCAACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACGACGGCACATCCACCGGCACCCTCTCCGA

GATCAGACGTTACTACGTTCAGAACGGTGTTGTCATCCCCCAGCCTTCC

TCCGATATCTCCGGAGTCAGCGGAGTTGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGAGTGCTGGTATGGTCTTGGTC

ATGAGTTTGTGGGACGACTACTCCGTCAACATGCTCTGGCTCGACAGCA

CCTACCCTACAAACGCGACTGGTACCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGTGGGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA

A nucleic acid encoding a polypeptide having a cellobiohydrolase activity comprising or consisting of the exemplary SEQ ID NO:124 (or enzymatically active fragments thereof):

MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSSNNAHTGYGNHGACCAELDIWEANSISE

ALTPHPCDTPGLSVCTTDACGGTYSSDRYAGTCDPDGCDFNPYRLGVTD

FYGSGKTVDTTKPITVVTQFVTDDGTSTGTLSEIRRYYVQNGVVIPQPS

SDISGVSGVVINSDFCDAEISTFGETASFSKHGGLAKMGAGMSAGMVLV

MSLWDDYSVNMLWLDSTYPTNATGTPGAARGSCPTTSGDPKTVESQSGS

SYVTFSDIRWGPFNSTFSGGSSTGGSSTTTASGTTTTKASSTSTSSTST

GTGVAAHWGQCGGQGWTGPTTCASGTTCTVVNPYYSQCL

The exemplary SEQ ID NO:125 encoding a polypeptide (e.g., the exemplary SEQ ID NO:126 and enzymatically active fragments thereof) having a cellobiohydrolase activity:

ATGTCTGCCTTGAACTCTTTCAATATGTACAAGAGCGCCCTCATCTTGG

GCTCCTTGCTGGCAACAGCTGGTGCTCAGCAAATTGGTACTTATACCGC

TGAAACCCATCCCTCTTTGAGCTGGTCTACTTGCAAATCGGGTGGTAGC

TGCACCACAAACTCCGGTGCCATTACGTTGGATGCCAACTGGCGTTGGG

TCCATGGTGTCAATACCAGCACCAACTGCTACACTGGCAACACTTGGAA

TACCGCCATCTGCGACACTGATGCATCCTGTGCCCAGGACTGTGCTCTT

GATGGTGCTGACTACTCTGGCACGTACGGTATCACTACCTCCGGCAACT

CATTGCGCCTGAACTTCGTTACCGGTTCCAACGTCGGATCTCGTACCTA

CCTGATGGCCGATAACACCCACTACCAAATCTTCGACTTGTTGAACCAG

GAGTTCACTTTCACCGTCGATGTCTCCCACCTCCCCTTGCGGTTTGAACG

GTGCCCTCTACTTCGTGACCATGGACGCCGACGGTGGCGTCTCCAAGTA

CCCCAACAACAAGGCCGGCGCTCAGTACGGTGTTGGATACTGTGACTCT

CAATGCCCTCGTGACTTGAAATTCATCGCTGGTCAGGCCAACGTTGAGG

GCTGGACGCCCTCCTCCAACAACGCCAACACTGGACTTGGCAACCACGG

AGCTTGCTGCGCAGAGCTTGATATCTGGGAGGCAAACAGCATCTCAGAG

GCTTTGACTCCTCACCCTTGCGATACACCCGGTCTATCTGTTTGCACTA

CTGATGCCTGCGGTGGTACCTACAGCTCCGATCGTTACGCCGGTACCTG

CGACCCTGATGGATGTGACTTCAACCCTTACCGTCTTGGTGTCACTGAC

TTCTACGGCTCCGGCAAGACCGTTGACACCACCAAACCCATCACCGTTG

TGACTCAATTCGTCACTGACGACGGCACATCCACCGGCACCCTCCTTGA

GATCAGACGTTACTACGTTCAGAACGGTGTTGTCATCCCCCAGCCTTCC

TCCGATATCTCCGGAGTCAGCGGAGTTGTCATCAACTCCGACTTCTGCG

ATGCTGAGATCTCCACCTTTGGCGAGACTGCCTCCTTCAGCAAACACGG

TGGCCTGGCAAAGATGGGCGCTGGTATGGAAGCTGGTATGGTCTTGGTC

ATGAGTTTGTGGGACGACTACTCCGTCAACATGCTCTGGCTCGACAGCA

CCTACCCTACAAACGCGACTGGTACCCCGGTGCCGCTCGTGGTTCCTG

CCCTACCACTTCTGGGGACCCTAAGACCGTTGAATCACAATCCGGCAGC

TCCTATGTCACCTTTTCTGACATCCGGGTTGGTCCTTTCAACTCTACGT

TCAGCGGTGGTTCTAGCACCGGTGGCAGCTCCACTACTACCGCCAGCGG

CACCACCACCACCAAGGCCTCTTCCACCTCTACTTCCAGCACCTCTACC

GGCACTGGAGTCGCTGCTCACTGGGGTCAGTGTGGTGGCCAGGGTTGGA

CTGGTCCTACCACCTGCGCTAGTGGAACCACATGCACCGTCGTGAACCC

TTACTACTCTCAATGTTT GTAA

A nucleic acid encoding a polypeptide having a cellobiohydrolase activity comprising or consisting of the exemplary SEQ ID NO:126 (or enzymatically active fragments thereof):

MSALNSFNMYKSALILGSLLATAGAQQIGTYTAETHPSLSWSTCKSGGS

CTTNSGAITLDANWRWVHGVNTSTNCYTGNTWNTAICDTDASCAQDCAL

DGADYSGTYGITTSGNSLRLNFVTGSNVGSRTYLMADNTHYQIFDLLNQ

EFTFTVDVSHLPCGLNGALYFVTMDADGGVSKYPNNKAGAQYGVGYCDS

QCPRDLKFIAGQANVEGWTPSSNNANTGLGNHGACCAELDIWEANSISE

ALTPHPCDTPGLSVCTTDACGGTYSSDRYAGTCDPDGCDFNPYRLGVTD

FYGSGKTVDTTKPITVVTQFVTDDGTSTGTLLEIRRYYVQNGVVIPQPS

SDISGVSGVVINSDFCDAEISTFGETASFSKHGGLAKMGAGMEAGMVLV
MSLWDDYSVNMLWLDSTYPTNATGTPGAARGSCPTTSGDPKTVESQSGS
SYVTFSDIRVGPFNSTFSGGSSTGGSSTTTASGTTTTKASSTSTSSTST
GTGVAAHWGQCGGQGWTGPTTCASGTTCTVVNPYYSQCL

The exemplary SEQ ID NO:127 encoding a polypeptide (e.g., the exemplary SEQ ID NO:128 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCCCTTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCTC
CTCCAACAACGCCAACACTGGATATGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CCAGGGCACATCCACCGGCCGTCTCCTTGAGATCAGACGTTACTACGTTC
AGAACGGTGTTGTCATCCCCCAGCCTTCCTCCGATATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGAGTGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
GTTGGTCCTTTCAACTCTACGTTCAGCGGTGGTTCTAGCACCGGTGGCAG
CTCCACTACTACCGCCAGCGGCACCACCACCACCAAGGCCTCTTCCACCT
CTACTTCCAGCACCTCTACCGGCACTGGAGTCGCTGCTCACTGGGGTCAG
TGTGGTGGCCAGGGTTGGACTGGTCCTACCACCTGCGCTAGTGGAACCAC
ATGCACCGTCGTGAACCCTTACTACTCTCAATGTTT GTAA
```

A nucleic acid encoding a polypeptide having a cellobiohydrolase activity comprising or consisting of the exemplary SEQ ID NO:128 (or enzymatically active fragments thereof):

```
MSALNSFNMYKSALILGSLLATAGAQQIGTYTAETHPSLSWSTCKSGGSC
TTNSGAITLDANWRWVHGVNTSTNCYTGNTWNTAICDTDASCAQDCALDG
ADYSGTYGITTSGNSLRLNFVTGSNVGSRTYLMADNTHYQIFDLLNQEFT
FTVDVSHLPCGLNGALYFVTMDADGGVSKYPNNKAGAQYGVGYCDSQCPR
DLKFIAGQANVEGWTPSSNNANTGYGNHGACCAELDIWEANSISEALTPH
PCDTPGLSVCTTDACGGTYSSDRYAGTCDPDGCDFNPYRLGVTDFYGSGK
TVDTTKPITVVTQFVTDQGTSTGRLLEIRRYYVQNGVVIPQPSSDISGVS
GNVINSDFCDAEISTFGETASFSKHGGLAKMGAGMSAGMVLVMSLWDDYS
VNMLWLDSTYPTNATGTPGAARGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The exemplary SEQ ID NO:129 encoding a polypeptide (e.g., the exemplary SEQ ID NO:130 and enzymatically active fragments thereof) having a cellobiohydrolase activity:

```
ATGTCTGCCTTGAACTCTTTCAATATGTACAAGAGCGCCCTCATCTTGGG
CTCCTTGCTGGCAACAGCTGGTGCTCAGCAAATTGGTACTTATACCGCTG
AAACCCATCCCTCTTTGAGCTGGTCTACTTGCAAATCGGTGGTAGCTGC
ACCACAAACTCCGGTGCCATTACGTTGGATGCCAACTGGCGTTGGGTCCA
TGGTGTCAATACCAGCACCAACTGCTACACTGGCAACACTTGGAATACCG
CCATCTGCGACACTGATGCATCCTGTGCCCAGGACTGTGCTCTTGATGGT
GCTGACTACTCTGGCACGTACGGTATCACTACCTCCGGCAACTCATTGCG
CCTGAACTTCGTTACCGGTTCCAACGTCGGATCTCGTACCTACCTGATGG
CCGATAACACCCACTACCAAATCTTCGACTTGTTGAACCAGGAGTTCACT
TTCACCGTCGATGTCTCCCACCTCGGGTGCGGTTTGAACGGTGCCCTCTA
CTTCGTGACCATGGACGCCGACGGTGGCGTCTCCAAGTACCCCAACAACA
AGGCCGGCGCTCAGTACGGTGTTGGATACTGTGACTCTCAATGCCCTCGT
GACTTGAAATTCATCGCTGGTCAGGCCAACGTTGAGGGCTGGACGCCCAA
GTCCAACAACGCCCATACTGGATATGGCAACCACGGAGCTTGCTGCGCAG
AGCTTGATATCTGGGAGGCAAACAGCATCTCAGAGGCTTTGACTCCTCAC
CCTTGCGATACACCCGGTCTATCTGTTTGCACTACTGATGCCTGCGGTGG
TACCTACAGCTCCGATCGTTACGCCGGTACCTGCGACCCTGATGGATGTG
ACTTCAACCCTTACCGTCTTGGTGTCACTGACTTCTACGGCTCCGGCAAG
ACCGTTGACACCACCAAACCCATCACCGTTGTGACTCAATTCGTCACTGA
CGACGGCACATCCACCGGCACCCTCTCCGAGATCAGACGTTACTACGTTA
GTAACGGTGTTGTCATCCCCCAGCCTTCCTCCGATATCTCCGGAGTCAGC
GGAAATGTCATCAACTCCGACTTCTGCGATGCTGAGATCTCCACCTTTGG
CGAGACTGCCTCCTTCAGCAAACACGGTGGCCTGGCAAAGATGGGCGCTG
GTATGAGTGCTGGTATGGTCTTGGTCATGAGTTTGTGGGACGACTACTCC
GTCAACATGCTCTGGCTCGACAGCACCTACCCTACAAACGCGACTGGTAC
CCCCGGTGCCGCTCGTGGTTCCTGCCCTACCACTTCTGGGGACCCTAAGA
CCGTTGAATCACAATCCGGCAGCTCCTATGTCACCTTTTCTGACATCCGG
```

```
GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:130 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLGCGLNGALYFVTMDADGGVSKYPNNKAGAQYGVGYCDSQCPR

DLKFIAGQANVEGWTPKSNNAHTGYGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVSNGVVIPQPSSDISGVS

GNVINSDFCDAEISTFGETASFSKHGGLAKMGAGMSAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:131 encoding a polypeptide (e.g., the exemplary SEQ ID NO:132 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG
```

```
ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGAGTGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

TGGGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:132 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMSAGMVLVMSLWDDYS

VNMLWLDSTYPTNATGTPGAARGSCPTTSGDPKTVESQSGSSYVTFSDIR

WGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:133 encoding a polypeptide (e.g., the exemplary SEQ ID NO:134 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA
```

```
CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATCGTTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTCGTGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAA
```

A nucleic acid encoding a polypeptide having a cellobiohydrolase activity comprising or consisting of the exemplary SEQ ID NO:134 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDRYAGTCDPDGCDFNPYRLGVTDFYGSGK

TVDTTKPITVVTQFVTDDGTSTGTLSEIRRYYVQNGVVIPQPSSKISGVS

GNVINSDFCDAEISTFGETASFSKHGGLAKMGAGMEAGMVLVMSLWDDYS

VNMLWLDSTYPTNATGTPGAARGSCPTTSGDPKTVESQSGSSYVTFSDIR

VGPFNSTFSGGSSTGGSSTTTASGTTTTKASSTSTSSTSTGTGVAAHWGQ

CGGQGWTGPTTCASGTTCTVVNPYYSQCL
```

The exemplary SEQ ID NO:135 encoding a polypeptide (e.g., the exemplary SEQ ID NO:136 and enzymatically active fragments thereof) having a cellobiohydrolase activity:

```
ATGTCTGCCTTGAACTCTTTCAATATGTACAAGAGCGCCCTCATCTTGGG

CTCCTTGCTGGCAACAGCTGGTGCTCAGCAAATTGGTACTTATACCGCTG

AAACCCATCCCTCTTTGAGCTGGTCTACTTGCAAATCGGGTGGTAGCTGC

ACCACAAACTCCGGTGCCATTACGTTGGATGCCAACTGGCGTTGGGTCCA

TGGTGTCAATACCAGCACCAACTGCTACACTGGCAACACTTGGAATACCG

CCATCTGCGACACTGATGCATCCTGTGCCCAGGACTGTGCTCTTGATGGT

GCTGACTACTCTGGCACGTACGGTATCACTACCTCCGGCAACTCATTGCG

CCTGAACTTCGTTACCGGTTCCAACGTCGGATCTCGTACCTACCTGATGG

CCGATAACACCCACTACCAAATCTTCGACTTGTTGAACCAGGAGTTCACT

TTCACCGTCGATGTCTCCCACCTCCCTTGCGGTTTGAACGGTGCCCTCTA

CTTCGTGACCATGGACGCCGACGGTGGCGTCTCCAAGTACCCCAACAACA

AGGCCGGCGCTCAGTACGGTGTTGGATACTGTGACTCTCAATGCCCTCGT

GACTTGAAATTCATCGCTGGTCAGGCCAACGTTGAGGGCTGGACGCCCTC

CTCCAACAACGCCAACACTGGACTTGGCAACCACGGAGCTTGCTGCGCAG

AGCTTGATATCTGGGAGGCAAACAGCATCTCAGAGGCTTTGACTCCTCAC

CCTTGCGATACACCCGGTCTATCTGTTTGCACTACTGATGCCTGCGGTGG

TACCTACAGCTCCGATAAGTACGCCGGTACCTGCGACCCTGATGGATGTG

ACTTCAACCCTTACCGTCTTGGTGTCACTGACTTCTACGGCTCCGGCAAG

ACCGTTGACACCACCAAACCCATCACCGTTGTGACTCAATTCGTCACTGA

CGACGGCACATCCACCGGCACCCTCTCCGAGATCAGACGTTACTACGTTC

AGAACGGTGTTGTCATCCCCCAGCCTTCCTCCAAGATCTCCGGAGTCAGC

GGAAATGTCATCAACTCCGACTTCTGCGATGCTGAGATCTCCACCTTTGG

CGAGACTGCCTCCTTCAGCAAACACGGTGGCCTGGCAAAGATGGGCGCTG

GTATGGAAGCTGGTATGGTCTTGGTCATGAGTTTGTGGGACGACTACTCC

GTCAACATGCTCTGGCTCGACAGCACCTACCCTACAAACGCGACTGGTAC

CCCCGGTGCCGCTAAGGGTTCCTGCCCTACCACTTCTGGGGACCCTAAGA

CCGTTGAATCACAATCCGGCAGCTCCTATGTCACCTTTTCTGACATCCGG

GTTGGTCCTTTCAACTCTACGTTCAGCGGTGGTTCTAGCACCGGTGGCAG

CTCCACTACTACCGCCAGCGGCACCACCACCACCAAGGCCTCTTCCACCT

CTACTTCCAGCACCTCTACCGGCACTGGAGTCGCTGCTCACTGGGGTCAG

TGTGGTGGCCAGGGTTGGACTGGTCCTACCACCTGCGCTAGTGGAACCAC

ATGCACCGTCGTGAACCCTTACTACTCTCAATGTTT GTAG
```

A nucleic acid encoding a polypeptide having a cellobiohydrolase activity comprising or consisting of the exemplary SEQ ID NO:136 (or enzymatically active fragments thereof):

```
MSALNSFNMYKSALILGSLLATAGAQQIGTYTAETHPSLSWSTCKSGGSC

TTNSGAITLDANWRWVHGVNTSTNCYTGNTWNTAICDTDASCAQDCALDG

ADYSGTYGITTSGNSLRLNFVTGSNVGSRTYLMADNTHYQIFDLLNQEFT

FTVDVSHLPCGLNGALYFVTMDADGGVSKYPNNKAGAQYGVGYCDSQCPR

DLKFIAGQANVEGWTPSSNNANTGLGNHGACCAELDIWEANSISEALTPH

PCDTPGLSVCTTDACGGTYSSDKYAGTCDPDGCDFNPYRLGVTDFYGSGK
```

```
TVDTTKPITVVTQFVTDDGTSTGTLSEIRRYYVQNGVVIPQPSSKISGVS
GNVINSDFCDAEISTFGETASFSKHGGLAKMGAGMEAGMVLVMSLWDDYS
VNMLWLDSTYPTNATGTPGAAKGSCPTTSGDPKTVESQSGSSYVTFSDIR
VGPFNSTFSGGSSTGGSSTTTASGTTTTKASSTSTSSTSTGTGVAAHWGQ
CGGQGWTGPTTCASGTTCTVVNPYYSQCL
```

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

6.2. General Techniques

The nucleic acids used to practice this invention, whether RNA, iRNA, miRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In alternative aspects, the phrases "nucleic acid" or "nucleic acid sequence" refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

In one aspect, a nucleic acid encoding a polypeptide of the invention further comprises a sequence encoding a leader sequence assembled in appropriate phase with the polypeptide to direct secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purificationTranscriptional and translational control sequences The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector.

Any promoter known to control expression of genes in prokaryotic or eukaryotic cells or their viruses can be used.

6.3. Expression Vectors and Cloning Vehicles

The invention provides expression systems, e.g., expression cassettes, vectors, cloning vehicles and the like, comprising nucleic acids of the invention, e.g., sequences encoding polypeptides of the invention, for expression, and overexpression, of the polypeptides of the invention (and nucleic acids, e.g., antisense). Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest, such as *bacillus, Aspergillus* and yeast. In alternative embodiments, nucleic acids of the invention are expressed in a *Pichia*, e.g., a *Pichia pastoris*, a *Schizosaccharomyces*, e.g., a *Schizosaccharomyces pombe*, and/or a *Pseudomonas*, e.g., a *Pseudomonas fluorescens*; e.g., to express a polypeptide of the invention.

Vectors of the invention can include chromosomal, non-chromosomal and synthetic DNA sequences. Large numbers of suitable vectors are known to those of skill in the art, and are commercially available. Any plasmid or other vector can be used, e.g., those replicable and viable in a desired host. Low copy number or high copy number vectors may be employed in practicing the present invention.

In one aspect, expression cassettes of the invention comprise a sequence of the invention and a nucleotide sequence which is capable of affecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. Expression cassettes used to practice the invention include plasmids, expression vectors, recombinant viruses, any form of recombinant "naked DNA" vector, and the like. In one aspect, a "vector" comprises a nucleic acid that can infect, transfect, transiently or permanently transduce a cell. A vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). In one aspect, vectors include, but are not limited to, replicons (e.g., RNA replicons, bacteriophages) to which fragments of DNA may be attached and become replicated. In one aspect, vectors include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

In one aspect, the expression vectors contain one or more selectable marker genes to permit selection of host cells containing the vector.

6.4. Host Cells and Transformed Cells

The invention also provides a transformed cell comprising a nucleic acid sequence of the invention, e.g., a sequence encoding a polypeptide of the invention, or comprising an expression cassette, vector, cloning vehicle, expression vector, or cloning vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia, Bacillus, Streptomyces, Salmonella, Pseudomonas, Lactococcus*, and *Staphylococcus*, including, e.g., *Escherichia coli, Lactococcus lactis, Bacillus subtilis, Bacillus cereus, Salmonella typhimurium, Pseudomonas fluorescens*. Exemplary fungal cells include any species of *Aspergillus*, including *Aspergillus niger*. Exemplary yeast cells include any species of *Pichia, Saccharomyces, Schizosaccharomyces*, or *Schwanniomyces*, including *Pichia pastoris, Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary insect cells include *Drosophila* S2 and *Spodoptera* Sf9. Exemplary yeast cells include *Pichia pastoris, Saccharomyces cerevisiae* or *Schizosaccharomyces pombe*. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The nucleic acids of the invention can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295-8)), media, culture systems and the like. In one aspect, gene amplification using selection markers, e.g., glutamine synthetase (see, e.g., Sanders (1987) Dev. Biol. Stand. 66:55-63), in cell systems are used to overexpress the polypeptides of the invention.

6.5. Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides with e.g., a cellulase or a cellobiohydrolase activity, or subsequences thereof, where the primer pairs are capable of amplifying nucleic acid sequences including an exemplary sequence of the invention, and at least one of the specific sequence modifications set forth above. One of skill in the art can design amplification primer sequence pairs for any part of or the full length of these sequences; for example:

6.6. Determining the Degree of Sequence Identity

The invention provides an isolated, synthetic or recombinant nucleic acid comprising a nucleic acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to an exemplary sequence of the invention, and including at least one of the specifically enumerated modifications to an exemplary sequence of the invention discussed above. In one aspect, the extent of sequence identity (homology) may be determined using any computer program and associated parameters, including those described herein, such as BLAST 2.2.2. or FASTA version 3.0t78, with the default parameters.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993.

In alternative embodiments, BLAST, BLAST 2.0 and BLAST 2.2.2 algorithms are used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, less than about 0.01, or less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which can be obtained from a protein or nucleic acid sequence database. High-scoring segment pairs can be identified (i.e., aligned) by means of a scoring matrix, many of which are known in the art. An exemplary scoring matrix used is the BLOSUM62 matrix (Gonnet et al., Science 256:1443-1445, 1992; Henikoff and Henikoff, Proteins 17:49-61, 1993). Alternatively, the PAM or PAM250 matrices may be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "—F F" setting is used, which disables filtering. Use of default filtering often results in Karlin-Altschul violations due to short length of sequence.

The default values used in this exemplary aspect of the invention include:
"Filter for low complexity: ON
>Word Size: 3
>Matrix: Blosum62
>Gap Costs: Existence:11
    >Extension:1"
"Filter for low complexity: ON Other default settings are: filter for low complexity OFF, word size of 3 for protein, BLOSUM62 matrix, gap existence penalty of −11 and a gap extension penalty of −1.

6.7. Inhibiting Expression of a Polypeptide

The invention further provides for nucleic acids complementary (partially or completely complementary) to (e.g., antisense sequences to) the nucleic acid sequences of the invention, including nucleic acids comprising e.g., antisense, iRNA, miRNA, ribozymes. Antisense sequences are capable of inhibiting the transport, splicing or transcription of polypeptide-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind polypeptide-encoding genes or messages, in either case preventing or inhibiting the production or function of the polypeptide. The association can be though sequence specific hybridization. Another useful class of inhibitors includes oligonucleotides which cause inactivation or cleavage of the polypeptide message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

6.8. Antisense Oligonucleotides

The invention provides antisense oligonucleotides capable of binding messages and/or genes of nucleic acids of the invention; which in alternative embodiments can inhibit polypeptide activity by targeting gene or mRNA. Strategies for designing antisense oligonucleotides are well described in the scientific and patent literature, and the skilled artisan can design such oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Euro. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agarwal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense ENZYME sequences of the invention (see, e.g., Gold (1995) J. of Biol. Chem. 270:13581-13584).

6.9. Inhibitory Ribozymes

The invention provides ribozymes comprising nucleic acid sequences of the invention, where in alternative embodiments the ribozymes of the invention are capable of binding messages or genes which can inhibit enzyme activity or expression by targeting mRNA or genes. Strategies for designing ribozymes and selecting the polypeptide-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site. The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

6.10. RNA Interference (RNAi)

In one aspect, the invention provides an RNA inhibitory molecule, a so-called "RNAi" molecule, comprising an enzyme sequence of the invention. The RNAi molecule comprises a double-stranded RNA (dsRNA) molecule. The RNAi molecule, e.g., siRNA and/or miRNA, can inhibit expression of a nucleic acid of the invention, e.g., a message or a gene. In one aspect, the RNAi molecule, e.g., siRNA and/or miRNA, is about 15, 16, 17, 18, 19, 20, 21, 22, 23, 24, 25 or more duplex nucleotides in length.

While the invention is not limited by any particular mechanism of action, the RNAi, e.g., siRNA and/or miRNA, can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's molecules, e.g., siRNA and/or miRNA, of the invention. In one aspect, the micro-inhibitory RNA (miRNA) inhibits translation, and the siRNA inhibits transcription. The process may be practiced in vitro, ex vivo or in vivo. In one aspect, the RNAi molecules of the invention can be used to generate a loss-of-function mutation in a cell, an organ or an animal Methods for making and using RNAi molecules, e.g., siRNA and/or miRNA, for selectively degrade RNA are well known in the art, see, e.g., U.S. Pat. Nos. 6,506,559; 6,511, 824; 6,515,109; 6,489,127.

6.11. Modification of Nucleic Acids

The invention provides methods of generating variants of the nucleic acids of the invention, e.g., those encoding a cellulase or a cellobiohydrolase (cbhl) enzyme. These methods can be repeated or used in various combinations to generate cellulase or cellobiohydrolase (cbhl) enzymes having an altered or different activity or an altered or different stability from that of a polypeptide encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

The invention also provides methods for changing the characteristics of a polypeptide of the invention by mutagenesis and other method, including directed evolution, e.g., Direct-Evolution® technology; (see, e.g., U.S. Pat. No. 5,830,696; Gene Site Saturation Mutagenesis$^{SM}$ (GSSM$^{SM}$) technology (see, e.g., U.S. Pat. Nos. 6,171,820 and 6,579,258), Exonuclease-Mediated Gene Assembly in Directed Evolution (see, e.g., U.S. Pat. Nos. 6,361,974 and 6,352,842), End Selection in Directed Evolution (see, e.g., U.S. Pat. Nos. 6,358,709 and 6,238,884), Recombination-Based Synthesis Shuffling (see, e.g., U.S. Pat. Nos. 5,965,408 and 6,440,668, and Australian Patent No. AU724521), and Directed Evolution of Thermophilic Enzymes (see, e.g., U.S. Pat. Nos. 5,830,696 and 6,335, 179).

A nucleic acid of the invention can be altered by any means. For example, random or stochastic methods, or, non-stochastic, or "directed evolution," methods. Methods for random mutation of genes are well known in the art, see, e.g., U.S. Pat. No. 5,830,696.

Alternatively, nucleic acids, e.g., genes, can be reassembled after random, or "stochastic," fragmentation, see, e.g., U.S. Pat. Nos. 6,291,242; 6,287,862; 6,287,861; 5,955, 358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, GeneReassembly, Gene Site Saturation Mutagenesis (GSSM), Tailored Multi-Site Combinatorial Assembly, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

In alternative embodiments, a non-stochastic gene modification system such as "GeneReassembly" technology or a "directed evolution process," is used to generate polypeptides, e.g., enzymes or antibodies of the invention, with new or altered properties. GeneRessembly technology is a method of ligating oligonucleotide segments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773, 900; 6,740,506; 6,713,282; 6,635,449; 6,605,449; 6,537,776.

In alternative embodiments, Tailored Multi-Site Combinatorial Assembly (TMCA) technology, TMCA technology (see PCT Publication No. WO 09/018,449), is used to produce a plurality of progeny polynucleotides having different combinations of various mutations at multiple sites.

6.12. Transgenic Plants and Seeds

The invention provides transgenic plants and seeds comprising a nucleic acid, a polypeptide, an expression cassette, cloning mechanism or vector of the invention, or a transfected or transformed cell of the invention. The invention also provides plant products, e.g., oils, seeds, leaves, extracts and the like, comprising a nucleic acid and/or a polypeptide of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

The recombinant expression, or over-expression, of the sequences of the invention may be achieved in combination with one or more additional molecules such as, for example, other enzymes. This approach is useful for producing combination products, such as a plant or plant part that contains sequences of the invention as well as one or more additional molecules. The molecules of this invention and the additional molecules can be used in a combination treatment. The resulting recombinantly expressed molecules may be used in homogenized and/or purified form or alternatively in relatively unpurified form (e.g. as consumable plant parts that are useful when admixed with other foodstuffs for catalyzing the degradation of phytate).

In a particular aspect, the present invention provides for the expression of sequences of the invention in transgenic plants or plant organs and methods for the production thereof. DNA expression constructs are provided for the transformation of plants with a gene encoding sequences of the invention under the control of regulatory sequences which are capable of directing the expression of sequences of the invention. These regulatory sequences include sequences capable of directing transcription in plants, either constitutively, or in stage and/or tissue specific manners.

The manner of expression depends, in part, on the use of the plant or parts thereof. The transgenic plants and plant organs provided by the present invention may be applied to a variety of industrial processes either directly, e.g. in animal feeds or alternatively, the expressed polypeptide of the invention may be extracted and if desired, purified before application. Alternatively, the recombinant host plant or plant part may be used directly. In a particular aspect, the present invention provides methods of catalyzing phytate-hydrolyzing reactions using seeds containing enhanced amounts of polypeptide. The method involves contacting transgenic, non-wild type seeds, e.g., in a ground or chewed form, with phytate-containing substrate and allowing the enzymes in the seeds to increase the rate of reaction. By directly adding the seeds to a phytate-containing substrate, the invention provides a solution to the expensive and problematic process of extracting and purifying the enzyme. In one exemplification the present invention provides methods of treatment whereby an organism lacking a sufficient supply of an enzyme is administered the enzyme in the form of seeds containing enhanced amounts of the enzyme. In one aspect, the timing of the administration of the enzyme to an organism is coordinated with the consumption of a phytate-containing foodstuff.

The expression of polypeptides and nucleic acids of the invention in plants can be achieved by a variety of means. Specifically, for example, technologies are available for transforming a large number of plant species, including dicotyledonous species (e.g. tobacco, potato, tomato, Petunia, *Brassica*) and monocot species. Additionally, for example, strategies for the expression of foreign genes in plants are available. Additionally still, regulatory sequences from plant genes have been identified that are serviceable for the construction of chimeric genes that can be functionally expressed in plants and in plant cells (e.g. Klee (1987) Ann. Rev. of Plant Phys. 38:467-486; Clark et al. (1990) Virology December; 179(2):640-7; Smith et al. (1990) Mol. Gen. Genet. December; 224(3):477-81.

The introduction of gene constructs into plants can be achieved using several technologies including transformation with *Agrobacterium tumefaciens* or *Agrobacterium rhizogenes*. Non-limiting examples of plant tissues that can be transformed thusly include protoplasts, microspores or pollen, and explants such as leaves, stems, roots, hypocotyls, and cotyls. Furthermore, DNA can be introduced directly into protoplasts and plant cells or tissues by microinjection, electroporation, particle bombardment, and direct DNA uptake.

Proteins may be produced in plants by a variety of expression systems. For instance, the use of a constitutive promoter such as the 35S promoter of Cauliflower Mosaic Virus (Guilley et al., 1982) is serviceable for the accumulation of the expressed protein in virtually all organs of the transgenic plant. Alternatively, the use of promoters that are highly tissue-specific and/or stage-specific are serviceable for this invention (Higgins, 1984; Shotwell, 1989) in order to bias expression towards desired tissues and/or towards a desired stage of development. The invention also uses protocols for expression in plants of ENZYME molecules of the instant invention as disclosed in, for example, U.S. Pat. No. 5,770,413 (Van Ooijen et al.) and U.S. Pat. No. 5,593,963 (Van Ooijen et al.), that teaches use of fungal enzymes.

6.13. Modification of Coding Sequences and Adjacent Sequences

In alternative embodiments, the invention provides transgenic expression in plants and plant cells of nucleic acids (e.g., genes) of the invention, and modification of those nucleic acids and genes of the invention to achieve and optimize their expression in host expression plants and plant cells. In alternative embodiments, bacterial ORFs which encode separate enzymes but which are encoded by the same transcript in the native microbe are used for expression in plants on separate transcripts. In alternative embodiments, to achieve this, each microbial ORF is isolated individually and cloned within a cassette which provides a plant promoter sequence at the 5' end of the ORF and a plant transcriptional terminator at the 3' end of the ORF. The isolated ORF sequence can includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. "Plant promoters" and "plant transcriptional terminators" that can be used to practice this invention include any promoters and/or transcriptional terminators which operate within plant cells. This includes promoters and transcription terminators which may be derived from non-plant sources such as viruses (e.g., a Cauliflower Mosaic Virus).

In alternative embodiments, modification to the ORF coding sequences and adjacent sequence is not required. It is sufficient to isolate a fragment containing the ORF of interest and to insert it downstream of a plant promoter. For example, Gaffney et. al. (*Science* 261: 754-756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In alternative embodiments, expression of genes derived from microbial sources may provide problems in expression. These problems have been well characterized in the art and are particularly common with genes initially derived from certain microbial sources. These problems may apply to the nucleotide sequence of this invention and the modification of these genes can be undertaken using techniques now well known in the art. The following problems may be encountered:

6.14. Codon Usage

In alternative embodiments, the invention provides nucleic acids having codons modified for usage in plants; in some cases preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

6.15. GC/AT Content

In alternative embodiments, the invention provides nucleic acids having their GC content modified, e.g., for usage in plants; plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

Sequences Adjacent to the Initiating Methionine

In alternative embodiments, the invention provides nucleic acids having nucleotides adjacent to the ATG modified and/or added; plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the E. coli uidA gene in plants. Further, Joshi (N.A.R. 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. In some aspects, preferred sequences adjacent to the initiating methionine may differ between different plant species. A survey of 14 maize genes located in the GenBank database provided the following results:

Position Before the Initiating ATG in 14 Maize Genes

|   | -10 | -9 | -8 | -7 | -6 | -5 | -4 | -3 | -2 | -1 |
|---|-----|----|----|----|----|----|----|----|----|----|
| C | 3   | 8  | 4  | 6  | 2  | 5  | 6  | 0  | 10 | 7  |
| T | 3   | 0  | 3  | 4  | 3  | 2  | 1  | 1  | 1  | 0  |
| A | 2   | 3  | 1  | 4  | 3  | 2  | 3  | 7  | 2  | 3  |
| G | 6   | 3  | 6  | 0  | 6  | 5  | 4  | 6  | 1  | 5  |

This analysis can be done for the desired plant species into which the nucleotide sequence is being incorporated, and the sequence adjacent to the ATG modified to incorporate the preferred nucleotides.

6.16. Removal of Illegitimate Splice Sites

In alternative embodiments, the invention provides nucleic acids having illegitimate splice sites modified or removed or functionally "knocked out"; genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

6.17. Plant Promoters and Transcriptional Control Motifs

In alternative embodiments, nucleic acids of the invention comprise transcriptional control motifs, e.g., promoters, e.g., for transformation and expression in a plant of interest. The nucleic acid sequences may be present in DNA constructs or expression cassettes. Nucleic acids of the invention can be, or comprise, "expression cassettes", including any nucleic acid molecule capable of directing expression of a particular nucleotide sequence in an appropriate host cell comprising a promoter operatively linked to the nucleotide sequence of interest which is operatively linked to termination signals.

The compositions (e.g., nucleic acid sequences) of the invention also can comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

In alternative embodiments the invention provides for the transformation of plants with expression cassettes capable of expressing polynucleotides of the invention. The expression cassette will include in the 5'-3' direction of transcription, a transcriptional and translational initiation region (i.e., a promoter) and a polynucleotide of interest. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et. al. (2003) Plant J. 34:383-92 and Chen et. al. (2003) Plant J. 36:731-40 for examples of sequences allowing for inducible expression.

In alternative embodiments regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. In alternative embodiments, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. In alternative embodiments, a "homologous"

nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et. al., Plant Cell, 1:855-866 (1989); Bustos, et. al., Plant Cell, 1:839-854 (1989); Green, et. al., EMBO J. 7, 4035-4044 (1988); Meier, et. al., Plant Cell, 3, 309-316 (1991); and Zhang, et. al., Plant Physiology 110: 1069-1079 (1996).

In alternative embodiments tissue-preferred regulated genes and/or promoters for plants or specific tissues, organs and/or cells are used. Some reported tissue preferred genes include the genes encoding the seed storage proteins (such as napin, cruciferin, beta-conglycinin, and phaseolin, prolamines, glutelins, globulins, and zeins) zeins or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et. al., (1991) Seed Science Research, 1:209).

Examples of tissue-specific promoters which can be used to practice this invention include the lectin (Vodkin, Prog. Clin. Biol. Res., 138; 87 (1983); Lindstrom et. al., (1990) Der. Genet., 11:160), corn alcohol dehydrogenase 1 (Dennis et. al., Nucleic Acids Res., 12:3983 (1984)), corn light harvesting complex (see, e.g., Simpson, (1986) Science, 233:34; Bansal (1992) Proc. Natl. Acad. Sci. USA 89:3654), corn heat shock protein (see, e.g., Odell et. al., (1985) Nature, 313:810; pea small subunit RuBP carboxylase (see, e.g., Poulsen et. al., (1986) Mol. Gen. Genet., 205:193-200; Cashmore et. al., (1983) Gen. Eng. of Plants, Plenum Press, New York, 29-38); Ti plasmid mannopine synthase (see, e.g., Langridge et. al., (1989) Proc. Natl. Acad. Sci. USA, 86:3219-3223), Ti plasmid nopaline synthase (Langridge et. al., (1989) Proc. Natl. Acad. Sci. USA, 86:3219-3223), petunia chalcone isomerase (see, e.g., vanTunen (1988) EMBO J. 7:1257); bean glycine rich protein 1 (see, e.g., Keller (1989) Genes Dev. 3:1639); truncated CaMV 35S (see, e.g., Odell (1985) Nature 313: 810); potato patatin (see, e.g., Wenzler (1989) Plant Mol. Biol. 13:347; root cell (see, e.g., Yamamoto (1990) Nucleic Acids Res. 18:7449); maize zein (see, e.g., Reina (1990) Nucleic Acids Res. 18:6425; Lopes et. al. (1995) Mol. Gen. Genet. 247: 603-613; Kriz (1987) Mol. Gen. Genet. 207:90; Wandelt (1989) Nucleic Acids Res., 17:2354; Langridge (1983) Cell, 34:1015; Reina (1990) Nucleic Acids Res., 18:7449), ADP-gpp promoter (see, e.g., U.S. Pat. No. 7,102, 057); globulin-1 (see, e.g., Belanger (1991) Genetics 129: 863); α-globulin (Sunilkumar, et. al. (2002), Transgenic Res. 11:347-359); □-tubulin; cab (see, e.g., Sullivan (1989) Mol. Gen. Genet., 215:431); PEPCase (see e.g., Hudspeth & Grula, (1989) Plant Molec. Biol., 12:579-589); R gene complex-associated promoters (Chandler et. al., (1989) Plant Cell, 1:1175); pea vicilin promoter (Czako et. al., (1992) Mol. Gen. Genet., 235:33; U.S. Pat. No. 5,625,136); GTL1 promoter (Takaiwa et. al. (1991) Plant Mol. Biol. 16 (1), 49-58); chalcone synthase promoters (Franken et. al., (1991) EMBO J., 10:2605); GY1 promoter (Sims & Goldburg (1989) Nuc. Acid Res. 17(11) 4368) and the like; all of which are herein incorporated by reference.

In alternative embodiments the invention uses fruit-preferred promoters, including any class of fruit-preferred promoters, e.g., as expressed at or during antithesis through fruit development, at least until the beginning of ripening, e.g., as discussed in U.S. Pat. No. 4,943,674, the disclosure of which is hereby incorporated by reference. The promoter for polygalacturonase gene is active in fruit ripening. The invention can use the polygalacturonase gene as described, e.g., in U.S. Pat. No. 4,535,060, U.S. Pat. No. 4,769,061, U.S. Pat. No. 4,801,590, and U.S. Pat. No. 5,107,065, which disclosures are incorporated herein by reference.

In alternative embodiments the invention uses any tissue-preferred promoter or transcriptional control element, including e.g., those that direct expression in leaf cells following damage to the leaf (for example, from chewing insects), in tubers (for example, patatin gene promoter), and in fiber cells (an example of a developmentally-regulated fiber cell protein is E6 (John & Crow (1992) PNAS 89:5769-5773). The E6 gene is most active in fiber, although low levels of transcripts are found in leaf, ovule and flower.

In alternative embodiments the invention uses promoters active in photosynthetic tissue, e.g., in order to drive transcription in green tissues such as leaves and stems, are suitable when they drive expression only or predominantly in such tissues. Alternatively, the invention can use promoters to confer expression constitutively throughout the plant, or differentially with respect to the green tissues, or differentially with respect to the developmental stage of the green tissue in which expression occurs, or in response to external stimuli.

Exemplary promoters used to practice this invention include the ribulose-1,5-bisphosphate carboxylase (RbcS) promoters such as the RbcS promoter from eastern larch (*Larix laricina*), the pine cab6 promoter (Yamamoto et. al. (1994) Plant Cell Physiol. 35:773-778), the Cab-1 gene promoter from wheat (Fejes et. al. (1990) Plant Mol. Biol. 15:921-932), the CAB-1 promoter from spinach (Lubberstedt et. al. (1994) Plant Physiol. 104:997-1006), the cab1R promoter from rice (Luan et. al. (1992) Plant Cell 4:971-981), the pyruvate orthophosphate dikinase (PPDK) promoter from corn (Matsuoka et. al. (1993) Proc Natl Acad Sci USA 90:9586-9590), the tobacco Lhcbl*2 promoter (Cerdan et. al. (1997) Plant Mol. Biol. 33:245-255), the *Arabidopsis thaliana* SUC2 sucrose-H+symporter promoter (Truernit et. al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346.

In some embodiments, the tissue specificity of some "tissue preferred" promoters may not be absolute and may be tested reporter genes such as Gus or green fluorescent protein, cyan fluorescent protein, yellow fluorescent protein or red fluorescent protein. One can also achieve tissue preferred expression with "leaky" expression by a combination of different tissue-preferred promoters. Other tissue preferred promoters can be isolated by one skilled in the art (see U.S. Pat. No. 5,589,379).

In alternative embodiments, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant. Microbe Interact. 10:933-937); and, the promoter responsive to the stress hormone abscisic acid (Sheen (1996) Science 274:1900-1902).

In alternative embodiments the nucleic acids of the invention can also be operably linked to plant promoters which are inducible upon exposure to chemicals reagents which can be applied to the plant, such as herbicides or antibiotic. For example, gene expression systems that are activated in the presence of a chemical ligand, including ethanol, such as can be found in WO 96/27673; WO 93/01294; WO 94/03619; WO 02/061102, all of which are hereby incorporated by reference. The maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); estrogen, such as, the ecdysone receptor (WO 01/52620) or, a salicylic acid-responsive element (Stange (1997) Plant J. 11:1315-1324). In alternative embodiments, chemically- (e.g., hormone- or pesticide-) induced promoters, i.e., promoter responsive to a chemical are used, e.g., they can be applied to a transgenic plant in the field, expression of a polypeptide of the invention can be induced at a particular stage of development of the plant.

6.18. Targeting of the Gene Product Within the Cell

Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference). Optionally, the signal sequence may be an N-terminal signal sequence from waxy, an N-terminal signal sequence from y-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368).

In alternative embodiments, the signal sequence selected should include the known cleavage site, and the fusion constructed should take into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

In alternative embodiments, the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

A variety of means can be used to practice this invention, including any means to achieve the recombinant expression of a polypeptide or nucleic acid of the invention in a transgenic plant, seed, organ or any plant part. Such a transgenic plants and plant parts are serviceable as sources of recombinantly expressed polypeptide or nucleic acid of the invention, which can be added directly to phytate-containing sources. Alternatively, the recombinant plant-expressed polypeptide or nucleic acid of the invention can be extracted away from the plant source and, if desired, purified prior to contacting the polypeptide substrate.

Within the context of the present invention, plants that can be selected (used to practice this invention) include, but are not limited to crops producing edible flowers such as cauliflower (*Brassica oleracea*), artichoke (*Cynara scolymus*), fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, Juglans, e.g. regia; peanut, *Arachis* hypogeae), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata*), tomato (*Lycopersicon*, e.g. *esculentum*), leafs, such as alfalfa (*Medicago*, e.g. *sativa*), cabbages (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*), roots, such as arrowroot (*Maranta*, e.g. *arundinacea*), beet (*Beta*, e.g. *vulgaris*), carrot (*Daucus*, e.g. *carota*), cassaya (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*) and seeds, such as bean (*Phaseolus*, e.g. *vulgaris*), pea (*Pisum*, e.g. *sativum*), soybean (*Glycin*, e.g. *max*), wheat (*Triticum*, e.g. *aestivum*), barley (*Hordeum*, e.g. *vulgare*), corn (*Zea*, e.g. *mays*), rice (*Oryza*, e.g. *sativa*), rapeseed (*Brassica napus*), millet (*Panicum* L.), sunflower (*Helianthus annus*), oats (*Avena sativa*), tubers, such as kohlrabi (*Brassica*, e.g. *oleraceae*), potato (*Solanum*, e.g. *tuberosum*) and the like.

In alternative embodiments, the nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as festuca, lolium, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium*,

*Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants which contain fiber cells, including, e.g., cotton, silk cotton tree (Kapok, *Ceiba pentandra*), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum;. G. herbaceum, G. barbadense*, and *G. hirsutum*.

Additional plants as well as non-plant expression systems can be used to practice this invention. The choice of the plant species is primarily determined by the intended use of the plant or parts thereof and the amenability of the plant species to transformation.

In alternative embodiments, any technique available for the introduction of an expression construct containing a polypeptide-encoding DNA sequence into a targeted cell, organ, tissue or plant can be used. Techniques for transforming a wide variety of higher plant species are well known and described in the technical and scientific literature. See, e.g., Weising (1988) Ann. Rev. Genet. 22:421-477; U.S. Pat. No. 5,750, 870. Such techniques also can include but are not limited to transformation of protoplasts using the calcium/polyethylene glycol method, electroporation and microinjection or (coated) particle bombardment (Potrykus, 1990). In addition to these so-called direct DNA transformation methods, transformation systems involving vectors are widely available, such as viral vectors (e.g. from the Cauliflower Mosaic Cirus (CaMV) and bacterial vectors (e.g. from the genus *Agrobacterium*) (Potrykus, 1990). After selection and/or screening, the protoplasts, cells or plant parts that have been transformed can be regenerated into whole plants, using methods known in the art (Horsch et al., 1985). The choice of the transformation and/or regeneration techniques is not critical for this invention.

In alternative embodiments, the invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci. USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In alternative embodiments, the invention provides for regeneration and selection of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

In alternative embodiments, nucleic acids of the invention are defined and identified by nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

In alternative embodiments, hybridizations are carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately 2×10^7 cpm (specific activity 4–9×10^8 cpm/ug) of 32P end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na2EDTA) containing 0.5% SDS, followed by a 30 minute wash in fresh 1×SET at Tm-10° C. for the oligonucleotide probe. The membrane is then exposed to auto-radiographic film for detection of hybridization signals.

In alternative embodiments, following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

6.19. Transgenic Non-Human Animals

In alternative embodiments, the invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study ENZYME activity, or, as models to screen for modulators of ENZYME activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art. "Knockout animals" can also be used to practice the methods of the invention. For example, in one aspect, the transgenic or modified animals of the invention comprise a "knockout animal," e.g., a "knockout mouse," engineered not to express or to be unable to express a nucleic acid or polypeptide.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for activity, to screen compounds as potential modulators of activity (e.g., potentiation or inhibition of enzyme activity), for antibodies that bind to a polypeptide of the invention, for nucleic acids that hybridize to a nucleic acid of the invention, and the like.

6.20. Immobilized Enzyme Solid Supports

In alternative embodiments, polypeptides of the invention, fragments thereof and nucleic acids that encode the enzymes and fragments can be affixed to a solid support. This is often economical and efficient in their use in industrial processes. For example, a consortium or cocktail of enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

6.21. Methods of Immobilization

In alternative embodiments, any method known to one of skill in the art for immobilizing enzymes or fragments thereof, or nucleic acids, onto a solid support is used to practice the invention. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

6.22. Arrays, or "BioChips"

In alternative embodiments, nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified.

Alternatively, arrays comprising genomic nucleic acid can also be used to determine the genotype of a newly engineered strain made by the methods of the invention. "Polypeptide arrays" can also be used to simultaneously quantify a plurality of proteins.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Polypeptides and Peptides

The invention provides isolated, synthetic or recombinant polypeptides having an amino acid sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptides (e.g., enzymes) of the invention (or the subsequences of, or enzymatically active fragments thereof), which include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58; SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92 and SEQ ID NO:94 and enzymatically active fragments thereof.

The invention further provides isolated, synthetic or recombinant nucleic acids encoding polypeptides of the invention.

In alternative invention, polypeptides and peptides of the invention are synthetic or are recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3 13) and automated synthesis may be achieved, e.g., using the ABI 431A Peptide Synthesizer (Perkin Elmer) in accordance with the instructions provided by the manufacturer.

In alternative embodiments, "recombinant" polypeptides or proteins of the invention include (refer to) polypeptides or proteins produced by recombinant DNA techniques; e.g., produced from cells transformed by an exogenous DNA construct encoding the desired polypeptide or protein. In alternative embodiments, "Synthetic" nucleic acids (including oligonucleotides), polypeptides or proteins of the invention include those prepared by chemical synthesis, as described in detail herein. In alternative embodiments, polypeptides or proteins of the invention comprise amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation.

In alternative embodiments, "synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem. Soc.,* 85:2149-2154, 1963) (See also Stewart, J. M. and Young, J. D., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals).

In alternative aspects, peptides and polypeptides of the invention are glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked, or, a combination thereof.

In alternative aspects, peptides and polypeptides of the invention, as defined above, comprise "mimetic" and "peptidomimetic" forms, either in part or completely. In one aspect, the terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a ENZYME activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropyl-carbodiimide (DIC) Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

In alternative embodiments, a polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

In alternative embodiments, mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, which for these reagents it may be preferable to use alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

In alternative embodiments, a residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

In alternative embodiments, the invention provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

In alternative embodiments, provides polypeptides having no or modified signal sequences (also called signal peptides (SPs), or leader peptides), or heterologous signal sequences. The polypeptides of the invention also can have no or modified or heterologous prepro domains and/or catalytic domains (CDs). The modified or heterologous SPs, prepro domains and/or CDs incorporated in a polypeptide the invention can be part of a fusion protein, e.g., as a heterologous domain in a chimeric protein, or added by a chemical linking agent. For example, an enzyme of the invention can comprise a heterologous SP and/or prepro in a vector, e.g., a pPIC series vector (Invitrogen, Carlsbad, Calif.).

In alternative embodiments, polypeptides of the invention comprise epitopes or purification tags, signal sequences or other fusion sequences, etc. In one aspect, polypeptides of the invention can be fused to a random peptide to form a fusion polypeptide. By "fused" or "operably linked" herein is meant that the random peptide and the polypeptide are linked together, in such a manner as to minimize the disruption to the stability of polypeptide activity. The fusion polypeptide (or fusion polynucleotide encoding the fusion polypeptide) can comprise further components as well, including multiple peptides at multiple loops.

In one aspect, polypeptides of the invention are chimeric polypeptides, e.g., comprising heterologous SPs, carbohydrate binding modules, enzyme catalytic domains, linkers and/or non-cellulase catalytic domains. The invention provides a means for generating chimeric polypeptides which may encode biologically active hybrid polypeptides (e.g., hybridenzymes). In one aspect, the original polynucleotides encode biologically active polypeptides.

In one aspect, the instant invention provides a method (and products thereof) of producing stabilized aqueous liquid formulations having polypeptide activity that exhibit increased resistance to heat inactivation of the enzyme activity and which retain their activity during prolonged periods of storage. The liquid formulations are stabilized by means of the addition of urea and/or a polyol such as sorbitol and glycerol as stabilizing agent. Also provided are feed preparations for monogastric animals and methods for the production thereof that result from the use of such stabilized aqueous liquid formulations. Additional details regarding this approach are in the public literature and/or are known to the skilled artisan. In a particular non-limiting exemplification, such publicly available literature includes EP 0626010 (WO 9316175 A1)

(Barendse et al.), although references in the publicly available literature do not teach the inventive molecules of the instant application.

6.23. Antibodies and Antibody-Based Screening Methods

The invention provides isolated, synthetic or recombinant antibodies that specifically bind to a polypeptide of the invention. These antibodies can be used to isolate, identify or quantify polypeptides of the invention or related polypeptides. These antibodies can be used to inhibit the activity of an enzyme of the invention. These antibodies can be used to isolated polypeptides related to those of the invention, e.g., related enzymes.

Antibodies of the invention can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

6.24. Kits

The invention provides kits comprising the compositions, e.g., nucleic acids, expression cassettes, vectors, cells, polypeptides (e.g., celluloses or a cellobiohydrolases) and/or antibodies of the invention. The kits also can contain instructional material teaching the methodologies and industrial uses of the invention, as described herein.

The polypeptides of the invention may also be used to generate antibodies which bind specifically to the enzyme polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of a polypeptide of the invention, sequences substantially identical thereto, or fragments of the foregoing sequences.

6.25. Enzyme Delivery Matrices

In alternative embodiments, the invention provides an edible pelletized enzyme delivery matrix and method of use for delivery of a polypeptide of the invention to an animal, for example as a nutritional supplement. The enzyme delivery matrix readily releases a polypeptide of the invention, such as an enzyme of the invention, in aqueous media, such as, for example, the digestive fluid of an animal. The invention enzyme delivery matrix is prepared from a granulate edible carrier selected from such components as grain germ that is spent of oil, hay, alfalfa, timothy, soy hull, sunflower seed meal, wheat meal, and the like, that readily disperse the recombinant enzyme contained therein into aqueous media. In use, the edible pelletized enzyme delivery matrix is administered to an animal to delivery of polypeptide of the invention to the animal. Suitable grain-based substrates may comprise or be derived from any suitable edible grain, such as wheat, corn, soy, sorghum, alfalfa, barley, and the like. An exemplary grain-based substrate is a corn-based substrate. The substrate may be derived from any suitable part of the grain, e.g., a grain germ, approved for animal feed use, such as corn germ that is obtained in a wet or dry milling process. The grain germ can comprise spent germ, which is grain germ from which oil has been expelled, such as by pressing or hexane or other solvent extraction. Alternatively, the grain germ is expeller extracted, that is, the oil has been removed by pressing.

6.26. Industrial/Upscale Expression of Enzymes of the Invention

In alternative embodiments, the invention provides for upscale production of polypeptides of the invention. Any known industrial process, bioreactor and/or cell-based expression system can be used to practice the invention. In one aspect, commercial (e.g., "upscaled") enzyme production systems are used, and this invention can use any polypeptide production system known the art, including any cell-based expression system, which include numerous strains, including any eukaryotic or prokaryotic system, including any insect, microbial, yeast, bacterial and/or fungal expression system; these alternative expression systems are well known and discussed in the literature and all are contemplated for commercial use for producing and using the enzymes of the invention. In alternative embodiments, nucleic acids of the invention are expressed in an *Aspergillus*, e.g., an *Aspergillus*

*niger*, a *Pichia*, e.g., a *Pichia pastoris*, a *Schizosaccharomyces*, e.g., a *Schizosaccharomyces pombe*, and/or a *Pseudomonas*, e.g., a *Pseudomonas fluorescens*; e.g., to express polypeptides of the invention in an industrial, or upscale, production system. For example, *Bacillus* species can be used for industrial production (see, e.g., Canadian Journal of Microbiology, 2004 January, 50(1):1-17). Alternatively, *Streptomyces* species, such as *S. lividans, S. coelicolor,* S. limosus, S. rimosus, S. roseosporus, and *S. lividans* can be used for industrial and sustainable production hosts (see, e.g., Appl Environ Microbiol. 2006 August; 72(8): 5283-5288). *Aspergillus* strains such as *Aspergillus phoenicis, A. niger* and *A. carbonarius* can be used to practice this invention, e.g., to produce an enzyme, such as a beta-glucosidase, of this invention (see, e.g., World Journal of Microbiology and Biotechnology, 2001, 17(5):455-461). Any *Fusarium* sp. can be used in an expression system to practice this invention, including e.g., *Fusarium graminearum*; see e.g., Royer et al. Bio/Technology 13:1479-1483 (1995). Any *Aspergillus* sp. can be used in an expression system to practice this invention, including e.g., *A. nidulans; A. fumigatus; A. niger* or *A. oryzae*. For example, the genome for *A. niger* CBS513.88, a parent of commercially used enzyme production strains, was recently sequenced (see, e.g., Nat. Biotechnol. 2007 February, 25(2): 221-31) and can be used as an expression system to practice the invention. Similarly, the genomic sequencing of *Aspergillus oryzae* was recently completed (Nature. 2005 Dec. 22, 438(7071):1157-61). For alternative fungal expression systems that can be used to practice this invention, e.g., to express enzymes for use in industrial applications, such as biofuel production, see e.g., Advances in Fungal Biotechnology for Industry, Agriculture, and Medicine. Edited by Jan S. Tkacz & Lene Lange. 2004. Kluwer Academic & Plenum Publishers, New York; and e.g., Handbook of Industrial Mycology. Edited by Zhiqiang An. 24 Sep. 2004. Mycology Series No. 22. Marcel Dekker, New York; and e.g., Talbot (2007) "Fungal genomics goes industrial", Nature Biotechnology 25(5):542; and in USPNs 4,885,249; 5,866,406; and international patent publication WO/2003/012071.

Cells for expressing enzymes of this invention can be manipulated e.g., to increase efficiencies and/or yields, etc., as described e.g., in U.S. Pat. No. 7,517,668; U.S. Pat. App. Pub. Nos. 20030119013; 20100120029; 20060235200. Specific expression vehicles and/or transcriptional regulatory or other motifs (e.g., to facilitate secretion) can be used to e.g., maximize efficiencies and/or yields, etc., as described e.g., in U.S. Pat. Nos. 5,198,345; 5,364,770; 5,578,463; 5,536,661; 6,255,115; 6,080,564, describing a method for inactivating undesired acid labile proteases which are expressed into culture medium simultaneously with desired enzymes by *Aspergillus*; U.S. Pat. No. 5,324,660, describing strains of *Pichia* which are deficient in proteolytic activity; U.S. Pat. App. Pub. Nos. 20060105425; 20080227148; 20030013154, 7,741,075 and 7,271,255, describing *Pichia* secretory leaders for protein expression. See also e.g., U.S. Pat. App. Pub. No. 20080044858 describing methods of producing a biological substances in *Aspergillus*; 6,316,245, describing a fermentation process to have a high productivity with a novel mutant of *Pichia* sp.; 20100175147, describing a *Pichia* expression system; U.S. Pat. No. 6,451,063, describing production of cellulases for industrial uses.

For example, in one embodiment, enzymes are produced as described in U.S. Pat. No. 7,695,949, which describes a process that uses a fermentation medium containing a recombinantly-produced microorganism that over-produces a fermentation product and contains a mutation which causes auxotrophic growth of the microorganism, and the auxotrophy within the microorganism does not compromise the ability of the microorganism to produce the fermentation product. The medium is then supplied in excess with all substrates required for production of the fermentation product and in growth limiting amounts with a substrate complementing the auxotrophy. In one embodiment, enzymes are produced as described in U.S. Pat. App. Pub. No. 20090280212, describing a method of adjusting productivity of enzymes in a filamentous fungus culture product; or U.S. Pat. No. 6,893,849 describing a *Pichia* expression system. Any culture medium known in the art can be used, e.g., as described in U.S. Pat. App. Pub. No. 20100062513.

In one embodiment, any bioreactor, culture vessel or cell growth product of manufacture can be used to practice the invention, e.g., as described in U.S. Pat. Nos. 6,001,643; 6,642,019; 7,112,441; 7,163,821; 7,604,987, which describes e.g. a chamber for containing cells or tissue cultures within a culture medium; 7,749,750; and U.S. Pat. App. Pub. Nos. 20040152186; 20030040104, describing an automated cell management system which can be programmed to perform and control various operations of the essential phases of cell culturing, of cell culture manipulation, and of cell culture evaluation; 20100062483; 20090068739; 20080233631.

6.27. Enzymatic Processes for Sugarcane Bagasse

In alternative embodiments, polypeptides of the invention are used to enzymatically process (hydrolyze) sugarcane (Saccharum), sugarcane parts (e.g., cane tops) and/or sugarcane bagasse, i.e., for sugarcane degradation, or for biomass processing, and polynucleotides encoding these enzymes, and making and using these polynucleotides and polypeptides. The invention provides polypeptides and methods for processing lignocellulosic residues, including sugarcane bagasse, or any waste product of the sugar milling or related industries, into a lignocellulosic hydrolysis product, which itself can be a biofuel or which can be further processed to become a biofuel, including liquid or gas fuels. Because the invention provides enzymes and methods for sugar cane processing, it also provides methods for making (methods for the production of) edible sugar, garapa, rapadura (papelón), falernum, molasses, rum, cachaça, in addition to alcohols (for any purpose) and/or biofuels, e.g., bioethanol. Thus, the invention also provides edible sugar, garapa, rapadura (papelón), falernum, molasses, rum, cachaça, alcohols, biofuels, e.g., bioethanol and the like, and their intermediate, comprising a polypeptide of the invention.

In some aspects, are several advantages to using sugarcane, e.g., bagasse, as a substrate for bioconversion:
1. It has high carbohydrate content (cellulose, 40-50%, and hemicellulose, 20-30%);
2. It is collected at the site of processing;
3. It is a cheap substrate, and there is a constant, although seasonal supply generated within the sugarcane industry.

The invention provides polypeptides and methods for hydrolyzing cellulose and hemicellulose polysaccharides in sugarcane, e.g., bagasse, which are associated with lignin, which can act as a barrier shielding the polysaccharides from attack by microorganisms and their associated enzyme systems. Because of the structural characteristics of lignocellulose, such as its lignin barrier and cellulose crystallinity, in one aspect a pretreatment process is used to enhance the access of enzyme(s) of this invention to the polysaccharide components in a biomass (a bagasse) to increase the conversion yields into the building block monosaccharides, such as hexose and pentose sugars. In one exemplary system of this invention using enzyme(s) of this invention, sugars produced are efficiently fermented to ethanol, and burning unhydrolyzed carbohydrate plus lignin provides enough steam to fuel the sugar mills.

In alternative aspects, the processes of the invention use various pretreatments, which can be grouped into three categories: physical, chemical, and multiple (physical+chemical). Any chemicals can be used as a pretreatment agent, e.g., acids, alkalis, gases, cellulose solvents, alcohols, oxidizing agents and reducing agents. Among these chemicals, alkali is the most popular pretreatment agent because it is relatively inexpensive and results in less cellulose degradation. The common alkalis sodium hydroxide and lime also can be used as pretreatment agents. Although sodium hydroxide increases biomass digestibility significantly, it is difficult to recycle, is relatively expensive, and is dangerous to handle. In contrast, lime has many advantages: it is safe and very inexpensive, and can be recovered by carbonating wash water with carbon dioxide.

In one aspect, the invention provides a multi-enzyme system (including at least one enzyme of this invention) that can hydrolyze polysaccharides in a sugarcane, e.g., bagasse, component of sugarcane processed in sugar mills. In one aspect, the sugarcane, e.g., bagasse, is processed by an enzyme of the invention made by an organism (e.g., transgenic animal, plants, transformed microorganism) and/or byproduct (e.g., harvested plant, fruit, seed) expressing an enzyme of the invention. In one aspect, the enzyme is a recombinant enzyme made by the plant or biomass which is to be processed to a fuel, e.g., the invention provides a transgenic sugarcane bagasse comprising an enzyme of the invention. In one aspect, these compositions and products used in methods of the invention comprising chemical cycles for natural biomass conversion, e.g., for the hydrolysis of a biomass to make a biofuel, e.g., bioethanol, biopropanol, bio-butanol, biomethanol, a synthetic fuel in the form of a liquid or a gas, such as a "syngas".

In one aspect, the invention provides a biofuel, e.g., a biogas, produced by the process of anaerobic digestion of organic material by anaerobes, wherein the process comprises use of an enzyme of the invention or a method of the invention. This biofuel, e.g., a biogas, can be produced either from biodegradable waste materials or by the use of energy crops fed into anaerobic digesters to supplement gas yields. The solid output, digestate, can also be used as a biofuel.

In one aspect, the invention provides a biofuel, e.g., a biogas, comprising a methane, wherein the process comprises use of an enzyme of the invention or a method of the invention. This biofuel, e.g., a biogas, can be recovered in industrial anaerobic digesters and mechanical biological treatment systems. Landfill gas can be further processed using an enzyme of this invention or a process of this invention; before processing landfill gas can be a less clean form of biogas produced in landfills through naturally occurring anaerobic digestion. Paradoxically if landfill gas is allowed to escape into the atmosphere it is a potent greenhouse gas.

The invention provides methods for making biologically produced oils and gases from various wastes, wherein the process comprises use of an enzyme of the invention or a method of the invention. In one aspect, these methods comprise thermal depolymerization of waste to extract methane and other oils similar to petroleum; or, e.g., a bioreactor system that utilizes nontoxic photosynthetic algae to take in smokestacks flue gases and produce biofuels such as biodiesel, biogas and a dry fuel comparable to coal, e.g., as designed by GreenFuel Technologies Corporation, of Cambridge, Mass.

The invention provides methods for making biologically produced oils, including crude oils, and gases that can be used in diesel engines, wherein the process comprises use of an enzyme of the invention or a method of the invention. In one aspect, these methods can refine petroleum, e.g., crude oils, into kerosene, petroleum, diesel and other fractions.

The invention provides methods (using an enzyme of the invention or a method of the invention) for making biologically produced oils from:
Straight vegetable oil (SVO).
Waste vegetable oil (WVO)—waste cooking oils and greases produced in quantity mostly by commercial kitchens.
Biodiesel obtained from transesterification of animal fats and vegetable oil, directly usable in petroleum diesel engines.
Biologically derived crude oil, together with biogas and carbon solids via the thermal depolymerization of complex organic materials including non oil based materials; for example, waste products such as old tires, offal, wood and plastic.
Pyrolysis oil; which may be produced out of biomass, wood waste etc. using heat only in the flash pyrolysis process (the oil may have to be treated before using in conventional fuel systems or internal combustion engines).
Wood, charcoal, and dried dung.

6.28. Animal Feeds and Food or Feed Additives

In alternative embodiments, addition to providing dietary aids or supplements, or food supplements and additives for human use, the invention also provides compositions and methods for treating animal feeds and foods and food or feed additives using a polypeptide of the invention, e.g., a protein having a lignocellulosic activity, e.g., a cellobiohydrolase enzyme of the invention, and/or the antibodies of the invention. The invention provides animal feeds, foods, and additives comprising the lignocellulosic enzymes of the invention and/or antibodies of the invention. The animal can be any farm animal or any animal.

In alternative embodiments, the animal feed additive of the invention may be a granulated enzyme product that may readily be mixed with feed components. Alternatively, feed additives of the invention can form a component of a pre-mix. The granulated enzyme product of the invention may be coated or uncoated. The particle size of the enzyme granulates can be compatible with that of feed and pre-mix components. This provides a safe and convenient mean of incorporating enzymes into feeds. Alternatively, the animal feed additive of the invention may be a stabilized liquid composition. This may be an aqueous or oil-based slurry. See, e.g., U.S. Pat. No. 6,245,546.

In alternative embodiments, the lignocellulosic enzyme of the present invention, in the modification of animal feed or a food, can process the food or feed either in vitro (by modifying components of the feed or food) or in vivo. Polypeptides of the invention can be added to animal feed or food compositions.

In alternative embodiments, an enzyme of the invention is added in combination with another enzyme, e.g., beta-galactosidases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases, and/or glucose oxidases. These enzyme digestion products are more digestible by the animal. Thus, the lignocellulosic enzyme, e.g., glycosyl hydrolase, cellulase, endoglucanase, cellobiohydrolase, beta-glucosidase, xylanase, mannanse, β-xylosidase and/or arabinofuranosidase enzymes of the invention can contribute to the available energy of the feed or food, or to the digestibility of the food or feed by breaking down cellulose.

In alternative embodiments, a lignocellulosic enzyme, e.g., cellulose or, cellobiohydrolase, enzyme of the invention can be supplied by expressing the enzymes directly in transgenic feed crops (as, e.g., transgenic plants, seeds and the like), such as grains, cereals, corn, soy bean, rape seed, lupin and the like. As discussed above, the invention provides transgenic plants, plant parts and plant cells comprising a nucleic acid sequence encoding a polypeptide of the invention. In one aspect, the nucleic acid is expressed such that the lignocellulosic enzyme of the invention is produced in recoverable quantities. The lignocellulosic enzyme can be recovered from any plant or plant part. Alternatively, the plant or plant part containing the recombinant polypeptide can be used as such for improving the quality of a food or feed, e.g., improving nutritional value, palatability, etc.

In one aspect, the enzyme delivery matrix of the invention is in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in animal feed. Since the matrix is itself approved for use in animal feed, it can be used as a diluent for delivery of enzymes in animal feed.

In alternative embodiments, the lignocellulosic enzyme is contained in the invention enzyme delivery matrix and methods is a thermostable the lignocellulosic enzyme, as described herein, so as to resist inactivation of the lignocellulosic enzyme during manufacture where elevated temperatures and/or steam may be employed to prepare the palletized enzyme delivery matrix. During digestion of feed containing the invention enzyme delivery matrix, aqueous digestive fluids will cause release of the active enzyme. Other types of thermostable enzymes and nutritional supplements that are thermostable can also be incorporated in the delivery matrix for release under any type of aqueous conditions.

In alternative embodiments, a coating is applied to the enzyme matrix particles for many different purposes, such as to add a flavor or nutrition supplement to animal feed, to delay release of animal feed supplements and enzymes in gastric conditions, and the like. In one aspect, the coating is applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

In alternative embodiments, the invention provides processes for preparing an enzyme-releasing matrix. In alternative embodiments, the process comprises providing discrete plural particles of a grain-based substrate in a particle size suitable for use as an enzyme-releasing matrix, wherein the particles comprise a lignocellulosic enzyme, e.g., a glycosyl hydrolase, cellulase, endoglucanase, cellobiohydrolase, beta-glucosidase, xylanase, mannanse, β-xylosidase and/or arabinofuranosidase enzyme encoded by an amino acid sequence of the invention. In one aspect, the process includes compacting or compressing the particles of enzyme-releasing matrix into granules, which most in one aspect is accomplished by pelletizing. The mold inhibitor and cohesiveness agent, when used, can be added at any suitable time, and in one aspect are mixed with the grain-based substrate in the desired proportions prior to pelletizing of the grain-based substrate. Moisture content in the pellet mill feed in one aspect is in the ranges set forth above with respect to the moisture content in the finished product, and in one aspect is about 14-15%. In one aspect, moisture is added to the feedstock in the form of an aqueous preparation of the enzyme to bring the feedstock to this moisture content. The temperature in the pellet mill in one aspect is brought to about 82° C. with steam. The pellet mill may be operated under any conditions that impart sufficient work to the feedstock to provide pellets. The pelleting process itself is a cost-effective process for removing water from the enzyme-containing composition.

In alternative embodiments, the compositions and methods of the invention can be practiced in conjunction with administration of prebiotics, which are high molecular weight sugars, e.g., fructo-oligosaccharides (FOS); galacto-oligosaccharides (GOS), GRAS (Generally Recognized As Safe) material. These prebiotics can be metabolized by some probiotic lactic acid bacteria (LAB). They are non-digestible by the majority of intestinal microbes.

6.29. Treating Foods and Food Processing

In alternative embodiments, the invention provides foods and feeds comprising enzymes of the invention, and methods for using enzymes of the invention in processing foods and feeds. Cellulases, e.g., cellobiohydrolase enzymes, of the invention have numerous applications in food processing industry. The invention provides methods for hydrolyzing cellulose-comprising compositions, including, e.g., a plant cell, a bacterial cell, a yeast cell, an insect cell, or an animal cell, or any plant or plant part, or any food or feed, a waste product and the like.

For example, the invention provides feeds or foods comprising a lignocellulosic enzyme of the invention, e.g., in a feed, a liquid, e.g., a beverage (such as a fruit juice or a beer), a bread or a dough or a bread product, or a drink (e.g., a beer) or a beverage precursor (e.g., a wort). The food treatment processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases, and/or glucose oxidases.

In one aspect, the invention provides enzymes and processes for hydrolyzing liquid (liquefied) and granular starch. Such starch can be derived from any source, e.g., beet, cane sugar, potato, corn, wheat, milo, sorghum, rye or bulgher. The invention applies to any plant starch source, e.g., a grain starch source, which is useful in liquefaction (for example, to make biofuels comprising, e.g., a bioalcohol such as bioethanol, biomethanol, biobutanol or biopropanol), including any other grain or vegetable source known to produce starch suitable for liquefaction. The methods of the invention comprise liquefying starch (e.g., making biofuels comprising, e.g., a bioalcohol such as bioethanol, biomethanol, biobutanol or biopropanol) from any natural material, such as rice, germinated rice, corn, barley, milo, wheat, legumes, potato, beet, cane sugar and sweet potato. The liquefying process can substantially hydrolyze the starch to produce a syrup. The temperature range of the liquefaction can be any liquefaction temperature which is known to be effective in liquefying starch. For example, the temperature of the starch can be between about 80° C. to about 115° C., between about 100° C. to about 110° C., and from about 105° C. to about 108° C. The bioalcohols made using the enzymes and processes of the invention can be used as fuels or in fuels (e.g., auto fuels), e.g., as discussed below, in addition to their use in (or for making) foods and feeds, including alcoholic beverages.

6.30. Waste Treatment

In alternative embodiments, the invention provides enzymes for use in waste treatment. Enzymes of the invention can be used in a variety of waste treatment or related industrial applications, e.g., in waste treatment related to biomass conversion to generate fuels. For example, in one aspect, the invention provides a solid and/or liquid waste digestion process using the lignocellulosic enzyme of the invention. The methods can comprise reducing the mass and volume of substantially untreated solid waste. Solid waste can be treated with an enzymatic digestive process in the presence of an enzymatic solution (including the lignocellulosic enzymes of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796. In one aspect, the compositions and methods of the invention are used for odor removal, odor prevention or odor reduction, e.g., in animal waste lagoons, e.g., on swine farms, in other agricultural, food or feed processing, in clothing and/or textile processing, cleaning or recycling, or other industrial processes.

In alternative embodiments, enzymes and methods for the conversion of biomass (e.g., lignocellulosic materials) to fuels (e.g., biofuels comprising, e.g., a bioalcohol such as bioethanol, biomethanol, biobutanol or biopropanol) can incorporate the treatment/recycling of municipal solid waste material, including waste obtained directly from a municipality or municipal solid waste that was previously land-filled and subsequently recovered, or sewage sludge, e.g., in the form of sewage sludge cake which contains substantial amounts of cellulosic material. Since sewage sludge cakes will normally not contain substantial amounts of recyclable materials (aluminum, glass, plastics, etc.), they can be directly treated with concentrated sulfuric acid (to reduce the heavy metal content of the cellulosic component of the waste) and processed in the ethanol production system. See, e.g., U.S. Pat. Nos. 6,267,309; 5,975,439.

Another exemplary method using enzymes of the invention for recovering organic and inorganic matter from waste material comprises sterilizing a solid organic matter and softening it by subjecting it to heat and pressure. This exemplary process may be carried out by first agitating waste material and then subjecting it to heat and pressure, which sterilizes it and softens the organic matter contained therein. In one aspect, after heating under pressure, the pressure may be suddenly released from a perforated chamber to forces the softened organic matter outwardly through perforations of the container, thus separating the organic matter from the solid inorganic matter. The softened sterilized, organic matter is then fermented in fermentation chamber, e.g., using enzymes of the invention, e.g., to form a mash. The mash may be subjected to further processing by centrifuge, distillation column and/or anaerobic digester to recover fuels such as ethanol and methane, and animal feed supplements. See, e.g., U.S. Pat. No. 6,251,643.

Enzymes of the invention can also be used in processes, e.g., pretreatments, to reduce the odor of an industrial waste, or a waste generated from an animal production facility, and the like. For example, enzymes of the invention can be used to treat an animal waste in a waste holding facility to enhance efficient degradation of large amounts of organic matter with reduced odor. The process can also include inoculation with sulfide-utilizing bacteria and organic digesting bacteria and lytic enzymes (in addition to an enzyme of the invention). See, e.g., U.S. Pat. No. 5,958,758.

Enzymes of the invention can also be used in mobile systems, e.g., batch type reactors, for bioremediation of aqueous, hazardous wastes, e.g., as described in U.S. Pat. No. 5,833,857. Batch type reactors can be large vessels having circulatory capability wherein bacteria (e.g., expressing an enzyme of the invention) are maintained in an efficient state by nutrients being feed into the reactor. Such systems can be used where effluent can be delivered to the reactor or the reactor is built into a waste water treatment system. Enzymes of the invention can also be used in treatment systems for use at small or temporary remote locations, e.g., portable, high volume, highly efficient, versatile waste water treatment systems. The waste treatment processes of the invention can include the use of any combination of other enzymes such as other the lignocellulosic enzyme, e.g., glycosyl hydrolase, cellulase, endoglucanase, cellobiohydrolase, beta-glucosidase, xylanase, mannanse, β-xylosidase and/or arabinofuranosidase enzymes, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, phytases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases, and/or glucose oxidases.

6.31. Detergent Compositions

In alternative embodiments, the invention provides detergent compositions comprising one or more polypeptides of the invention (e.g., enzymes having cellulase or cellobiohydrolase activity) and methods of making and using these compositions. The invention incorporates all methods of making and using detergent compositions, see, e.g., U.S. Pat. No. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Enzymes of the invention can facilitate the removal of starchy stains by means of catalytic hydrolysis of the starch polysaccharide. Enzymes of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of glucosidase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Enzymes of the present invention can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, and/or glucose oxidases, as well as builders and stabilizers. The addition of enzymes of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A polypeptide of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a polypeptide of the invention. Alternatively, a polypeptide of the invention can be formulated as a detergent composition for use in general household hard surface cleaning operations.

In alternative aspects, detergent additives and detergent compositions of the invention may comprise one or more other enzymes such as a protease, a lipase, a cutinase, another glucosidase, a carbohydrase, another cellulase, a pectinase, a mannanase, an arabinase, a galactanase, a xylanase, an oxidase, e.g., a lactase, and/or a peroxidase, and/or glucose oxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

In alternative embodiments, the detergents and related processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases, and/or glucose oxidases.

6.32. Treating Fabrics and Textiles

In alternative embodiments, the invention provides methods of treating fabrics and textiles using one or more polypeptides of the invention. The polypeptides of the invention can be used in any fabric-treating method, which are well known in the art, see, e.g., U.S. Pat. No. 6,077,316. For example, in one aspect, the feel and appearance of a fabric is improved by a method comprising contacting the fabric with an enzyme of the invention in a solution. In one aspect, the fabric is treated with the solution under pressure.

In one aspect, the enzymes of the invention are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes of the invention can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. The invention provides a method of desizing comprising enzymatic hydrolysis of the size by the action of an enzyme of the invention.

The enzymes of the invention can be used to desize fabrics, including cotton-containing fabrics, as detergent additives, e.g., in aqueous compositions. The invention provides methods for producing a stonewashed look on indigo-dyed denim fabric and garments. For the manufacture of clothes, the fabric can be cut and sewn into clothes or garments, which is afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of finishing denim garments (e.g., a "bio-stoning process"), enzymatic desizing and providing softness to fabrics using the Enzymes of the invention. The invention provides methods for quickly softening denim garments in a desizing and/or finishing process. The invention also provides disinfectants comprising enzymes of the invention.

The fabric or textile treatment processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases, and/or glucose oxidases.

6.33. Paper or Pulp Treatment

In alternative embodiments, enzymes of the invention can be in paper or pulp treatment or paper deinking. For example, in one aspect, the invention provides a paper treatment process using enzymes of the invention. In one aspect, the enzymes of the invention can be used to modify starch in the paper thereby converting it into a liquefied form. In another aspect, paper components of recycled photocopied paper during chemical and enzymatic deinking processes. In alternative embodiments, enzymes of the invention can be used in combination with other enzymes, including other cellulases (including other endoglucanases, cellobiohydrolases and/or beta-glucosidases). The wood, wood waste, paper, paper product or pulp can be treated by the following three processes: 1) disintegration in the presence of an enzyme of the invention, 2) disintegration with a deinking chemical and an enzyme of the invention, and/or 3) disintegration after soaking with an enzyme of the invention. The recycled paper treated with an enzyme of the invention can have a higher brightness due to removal of toner particles as compared to the paper treated with just cellulase. While the invention is not limited by any particular mechanism, the effect of an enzyme of the invention may be due to its behavior as surface-active agents in pulp suspension.

In alternative embodiments, the invention provides methods of treating paper and paper pulp using one or more polypeptides of the invention. The polypeptides of the invention can be used in any paper- or pulp-treating method, which are well known in the art, see, e.g., U.S. Pat. Nos. 6,241,849; 6,066,233; 5,582,681. For example, in one aspect, the invention provides a method for deinking and decolorizing a printed paper containing a dye, comprising pulping a printed paper to obtain a pulp slurry, and dislodging an ink from the pulp slurry in the presence of an enzyme of the invention (other enzymes can also be added). In another aspect, the invention provides a method for enhancing the freeness of pulp, e.g., pulp made from secondary fiber, by adding an enzymatic mixture comprising an enzyme of the invention (can also include other enzymes, e.g., pectinase enzymes) to the pulp and treating under conditions to cause a reaction to produce an enzymatically treated pulp. The freeness of the enzymatically treated pulp is increased from the initial freeness of the secondary fiber pulp without a loss in brightness.

In alternative embodiments, the paper, wood, wood waste, or pulp treatment or recycling processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases, and/or glucose oxidase.

6.34. Repulping: Treatment of Lignocellulosic Materials

In alternative embodiments, the invention also provides a method for the treatment of lignocellulosic fibers, wherein the fibers are treated with a polypeptide of the invention, in an amount which is efficient for improving the fiber properties. The enzymes of the invention may also be used in the production or recycling of lignocellulosic materials such as pulp, paper and cardboard, from starch reinforced waste paper and cardboard, especially where repulping or recycling occurs at pH above 7 and where the enzymes of the invention can facilitate the disintegration of the waste material through degradation of the reinforcing starch. The enzymes of the invention can be useful in a process for producing a papermaking pulp from starch-coated printed paper. The process may be performed as described in, e.g., WO 95/14807. An exemplary process comprises disintegrating the paper to produce a pulp, treating with a starch-degrading enzyme before, during or after the disintegrating, and separating ink particles from the pulp after disintegrating and enzyme treatment. See also U.S. Pat. No. 6,309,871 and other US patents cited herein. Thus, the invention includes a method for enzymatic deinking of recycled paper pulp, wherein the polypeptide is applied in an amount which is efficient for effective de-inking of the fiber surface.

6.35. Brewing and Fermenting

The invention provides methods of brewing (e.g., fermenting) beer comprising an enzyme of the invention. In one exemplary process, starch-containing raw materials are disintegrated and processed to form a malt. An enzyme of the invention is used at any point in the fermentation process. For example, enzymes of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15-25° C. for 3 to 6 days when enzyme synthesis is stimulated under the control of gibberellins. During this time enzyme levels rise significantly. In one aspect, enzymes of the invention are added at this (or any other) stage of the process. The action of the enzyme results in an increase in fermentable reducing sugars. This can be expressed as the diastatic power, DP, which can rise from around 80 to 190 in 5 days at 12° C.

Enzymes of the invention can be used in any beer producing process, as described, e.g., in U.S. Pat. Nos. 5,762,991; 5,536,650; 5,405,624; 5,021,246; 4,788,066.

6.36. Increasing the Flow of Production Fluids from a Subterranean Formation

In alternative embodiments, the invention provides methods for using an enzyme of the invention to increase the flow of production fluids from a subterranean formation by removing viscous, starch-containing, damaging fluids formed during production operations; these fluids can be found within the subterranean formation which surrounds a completed well bore. In alternative embodiments, this results in production fluids being able to flow from the well bore. This method of the invention also addresses the problem of damaging fluids reducing the flow of production fluids from a formation below expected flow rates.

In alternative embodiments, the invention provides for formulating an enzyme treatment (using an enzyme of the invention) by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

In alternative embodiments, the subterranean formation enzyme treatment processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases, and/or glucose oxidase.

6.37. Pharmaceutical Compositions and Dietary Supplements

In alternative embodiments, the invention also provides pharmaceutical compositions and dietary supplements (e.g., dietary aids) comprising a polypeptide, e.g., a cellulase, of the invention. In alternative embodiments, the cellulase activity comprises endoglucanase, cellobiohydrolase, beta-glucosidase, xylanase, mannanse, β-xylosidase and/or arabinofuranosidase activity. In one aspect, the pharmaceutical compositions and dietary supplements (e.g., dietary aids) are formulated for oral ingestion, e.g., to improve the digestibility of foods and feeds having a high cellulose or lignocellulosic component.

In alternative embodiments, periodontal treatment compounds can comprise an enzyme of the invention, e.g., as described in U.S. Pat. No. 6,776,979. Compositions and methods for the treatment or prophylaxis of acidic gut syndrome can comprise an enzyme of the invention, e.g., as described in U.S. Pat. No. 6,468,964.

In alternative embodiments, wound dressings, implants and the like comprise antimicrobial (e.g., antibiotic-acting) enzymes, including an enzyme of the invention (including, e.g., exemplary sequences of the invention). Enzymes of the invention can also be used in alginate dressings, antimicrobial barrier dressings, burn dressings, compression bandages, diagnostic tools, gel dressings, hydro-selective dressings, hydrocellular (foam) dressings, hydrocolloid dressings, I.V dressings, incise drapes, low adherent dressings, odor absorbing dressings, paste bandages, post operative dressings, scar management, skin care, transparent film dressings and/or wound closure. Enzymes of the invention can be used in wound cleansing, wound bed preparation, to treat pressure ulcers, leg ulcers, burns, diabetic foot ulcers, scars, IV fixation, surgical wounds and minor wounds. Enzymes of the invention can be used to in sterile enzymatic debriding compositions, e.g., ointments. In various aspects, the cellulase is formulated as a tablet, gel, pill, implant, liquid, spray, powder, food, feed pellet or as an encapsulated formulation.

6.38. Biodefense Applications

In other aspects, polypeptides, enzymes and antibodies of this invention, including enzymes having lignocellulosic activity, including polypeptides having cellulase or cellobiohydrolase activity, can be used in biodefense; e.g., for the destruction of spores or microorganisms, e.g., bacteria, fungi, yeast, etc., comprising a lignocellulosic material or any biologic polymer susceptible to hydrolysis by a polypeptide of this invention. Use of enzymes and antibodies of this invention, including enzymes having lignocellulosic activity, in biodefense applications offers a significant benefit, in that they can be very rapidly manufactured and/or developed against any currently unknown or biological warfare agents of the future. In addition, enzymes having lignocellulosic activity, including polypeptides having cellulase, etc. activity, can be used for decontamination of affected environments or materials, including clothing, or individuals. Thus, in aspect, the invention provides a biodefense or bio-detoxifying agent (s), or disinfecting agent, comprising a polypeptide having lignocellulosic activity, including polypeptides having cellulase, etc. activity, wherein the polypeptide comprises a sequence of the invention (including, e.g., exemplary sequences of the invention), or a polypeptide encoded by a nucleic acid of the invention (including, e.g., exemplary sequences of the invention), and methods of making and using them.

7. EXAMPLES

Example 1

This example describes an exemplary protocol for the genetic engineering of an enzyme of the invention. The engineered, or "optimized", enzyme of the invention can be used in the conversion of biomass (e.g., bagasse) to monosaccharides, fuels and/or chemicals or other useful products; e.g., for making effective and sustainable alternatives to petroleum-based products. The engineered, or "optimized", enzyme of the invention can be expressed in organisms (e.g., microorganisms, such as bacteria or fungi) for its participation in chemical cycles involving natural biomass conversion. In one aspect, this engineered, or "optimized", enzyme of the invention is used in "enzyme ensembles" for the efficient depolymerization of cellulosic and hemicellulosic polymers to metabolizable carbon moieties. As discussed above, the invention provides methods for discovering and implementing the most effective of enzymes to enable these important new "biomass conversion" and alternative energy industrial processes. Evolution technologies, for example, Gene Site Saturation Mutagenesis (or GSSM) technology (as discussed above, see also U.S. Pat. Nos. 6,171,820 and 6,579,258), GeneReassembly technology (as discussed above, see also, e.g., U.S. Pat. No. 6,537,776), or Tailored Multi-Site Combinatorial Assembly$^{SM}$ (TMCA$^{SM}$) technology (as discussed above, see also, e.g. PCT Publication Number WO 2009/018449), can be used for the discovery and optimization of an enzyme component for lignocellulosic biomass material (e.g., cellulose) reduction (e.g., hydrolysis) to monosaccharides (e.g., glucose), cellobiohydrolase and other carbohydrates.

In one embodiment, an enzyme discovery screen can be implemented using Verenium Corporation's GIGAMATRIX® high throughput expression screening platform (discussed above) to identify enzymes, for example, to identify cellobiohydrolases using methylumbelliferyl cellobioside, methylumbelliferyl lactoside (MUL), phosphoric acid swollen cellulose (PASC), or bagasse (e.g., pretreated bagasse) as a substrate.

In one aspect, an enzyme can be chosen as a candidate for optimization using Gene Site Saturation Mutagenesis (or GSSM) technology. In one embodiment, before performing GSSM evolution, the signal sequence, if present, can be removed and a starting methionine added. As discussed above, GSSM technology can rapidly mutate all amino acids in the protein to the 19 other amino acids in a sequential fashion. Mutants can be screened using a fiber-based assay and potential upmutants representing single amino acid changes can be identified. These upmutants can be combined into a new library representing combinations of the upmutants. This library can be screened resulting in identification of several candidate enzymes for commercialization.

Using GeneReassembly technology or Tailored Multi-Site Combinatorial Assembly technology, GSSM upmutants (enzyme-encoding sequence variants) can be "blended" (mixed together to achieve an optimal result) in order to construct an enzyme with a desired activity or trait. The resulting enzymes can then be screened to identify candidate(s) with the best desired activity or trait (e.g., thermotolerance).

Example 2

Variant CBHI enzymes of the invention were made using GSSM technology (described above), see e.g. variants in Tables 1 and 3, were made using SEQ ID NO:134 (encoded by SEQ ID NO:133) as the wild-type (parent). The parent gene was inserted into the pDC-A2 vector and the variants were made using GSSM technology. The library was transformed into *E. coli* Stbl2, sequenced, and then passed on for fungal transformations into *Aspergillus niger*.

Entry Site variants, as well as Point Mutant Recombination variants, of the invention (see e.g. variants in Table 5), were made by combining individual mutations using Tailored Multi-Site Combinatorial Assemble (described above). The parent gene was inserted into the pDC-A2 vector and the variants were made using GSSM technology. The library was transformed into *E. coli* Stbl2, sequenced, and then passed on for fungal transformations into *Aspergillus niger*.

CBHI variants of the invention in the Loop GeneReassembly library (see Table 5) were made using GeneReassembly technology (described above), with the variants generated through "liquid ligation" of PCR products and/or oligos followed by ligation into the pDC-A2 vector. This library was transformed into *E. coli* XL1-Blue, sequenced and then passed on for fungal transformations into *Aspergillus niger*.

The pDC-A2 vector used in making the CBH variants of the invention was a reconstruction of the vector pGBFin-5 (described, e.g., in U.S. Pat. No. 7,220,542), which was remade to reduce the total size of the vector. The 2.1 kb 3' Gla region of pGBFin-5 was reduced to 0.54 kb, the gpd promoter remained the same, but the 2.24 kb amdS sequence was replaced by the 1.02 kb hygB gene encoding hygromycin phosphotransferase. The 2.3 kb 3' Gla region of pGBFin-5 was reduced to a 1.1 kb fragment representing the 5' end of the original sequence. The *E. coli* replicon for pDC-A2 was taken from pUC 18.

After transformation of the vector into *E. coli* Stbl2 or *E. coli* XL1-Blue, individual *E. coli* transformants were picked into 96-well plates and grown in liquid culture in 200 μl LB plus ampicillin (100 μg/ml) per well overnight at 30° C. The cells were then used to generate template for sequencing reactions by colony PCR. The sequence data from the library of clones was analyzed to identify unique variants of CBHI. The *E. coli* transformants containing the selected variants were then rearrayed in 96-well format and used to prepare linear DNA of the entire expression cassette (the contents of pDC-A2 with the exception of the *E. coli* replicon) by PCR, using primers hybridizing to the ends of the 3' and 3" Gla regions. Approximately 1 μg of PCR product from each clone was then used to transform *A. niger* protoplasts in a PEG-mediated transformation in one well of a 96-well plate (i.e. one clone per well). Transformants were selected on regeneration agar (200 μl per well of PDA plus sucrose at 340 g/l and hygromycin at 200 μg/ml) in the same 96-well format. After 7 days incubation at 30° C., transformants were replicated to 96-well plates containing PDA plus hygromycin (200 μg/ml) using a pintool. Following incubation at 30° C. for a further 7 days, spores from each well were used to inoculate 200 μl liquid media per well of a 96-well plate. The plates were incubated at 30° C. for 7 days, and the supernatant from each well, containing the secreted CBH variant, was recovered.

The media used to grow the *Aspergillus* transformed with expression constructs containing the variants had the following composition: $NaNO_3$, 3.0 g/l; KCl, 0.26 g/l; $KH_2PO_4$, 0.76 g/l; 4M KOH, 0.56 ml/l; D-Glucose, 5.0 g/l; Casamino Acids, 0.5 g/l; Trace Element Solution 0.5 ml/l; Vitamin Solution 5 ml/l; Penicillin-Streptomycin Solution (10,000 U/ml and 10,000 μg/ml respectively) 5.0 ml/l; Maltose, 66.0 g/l; Soytone, 26.4 g/l; $(NH_4)_2SO_4$, 6.6 g/l; $NaH_2PO_4.H_2O$, 0.44 g/l; $MgSO_4.7H_2O$, 0.44 g/l; Arginine, 0.44 g/l; Tween-80, 0.035 ml/l; Pleuronic Acid Antifoam, 0.0088 ml/l; MES, 18.0 g/l. The Trace Element Solution had the following composition in 100 ml: $ZnSO_4.7H_2O$, 2.2 g; $H_3BO_3$, 1.1 g; $FeSO_4.7H_2O$, 0.5 g; $CoCl_2.6H_2O$, 0.17 g; $CuSO_4.5H_2O$, 0.16; $MnCl_2.4H_2O$, 0.5 g/l; $NaMoO_4.2H_2O$, 0.15 g/l; EDTA, 5 g/l. The Vitamin Solution had the following composition in 500 ml: Riboflavin, 100 mg; Thiamine HCl, 100 mg; Nicotinamide, 100 mg; Pyridoxine.HCl, 50 mg; Panthotenic Acid, 10 mg; Biotin 0.2 mg.

Example 3

CBHI variants shown in Tables 1 and 5 were assayed under the following conditions:
5% w/v pretreated bagasse (62.07% cellulose)
35° C., 300 rpm shaking with 2 BBs per rxn
pH5.2
1 mM Sodium Azide
5 ml total volume
Enzyme Dosing Overview:

| Enzyme | Ratio |
| --- | --- |
| CBHI | 4 mg/g cellulose |
| CBHII | 2 mg/g cellulose |
| EG | 4 mg/g cellulose |

Time point: T=0, 48 hours
Time point (for Point Mutant Recombinants): T=0, 72 hours
% improvement over wt=(% conversion of variant−% conversion of wt)/
% conversion of wt
Results of these assays are shown in Tables 2 and 6.
CBHI variants shown in Table 3 were assayed under the following conditions:
Samples heat challenged at 22 C, 60 C, 65 C, 70 C, 75 C, and 80 C for 20 minutes. After heat challenge, samples cooled on ice. Residual activity determined on MUL at 22 C.

Calculations for % residual activity:

% Residual Activity = Activity heat challenged sample/
Activity non-challenged sample (22 C).

All residual activities calculated indepentyl from parent residual activity Melting Temperatures were determined by Differential Scanning calorimetry, using 500-700 μg/mL of degassed sample.
Results of these assays are shown in Table 4.

Example 4

The parent (wild-type) CBHI (SEQ ID NO:134, encoded by SEQ ID NO:133) and variant CBHI (SEQ ID NO:136, encoded by SEQ ID NO:135) were assayed to determine their cellobiose (product) inhibition.

In one assy, cellobiose inhibition was measured using methylumbelliferyl lactoside (MUL) as the substrate. $IC_{50}$, the half maximal inhibitory concentration of cellobiose, was determined. The wild-type CBHI (SEQ ID NO:134) had an $IC_{50}$ of 0.06 g/L, while the CBHI mutant (SEQ ID NO:136) showed no inhibition up to 0.25 g/L cellobiose.

In another assay, cellobiose inhibition was measured using 0.1% phosphoric acid swollen cellulose (PASC) as the substrate. CBHI was incubated with PASC and Calcofluor (which intercalates between cellulose strands and fluoresces upon binding to cellulose) for 2 hours at 35° C. $IC_{50}$ was measured. The wild-type CBHI (SEQ ID NO:134) had an $IC_{50}$ of 2.2 g/L, while the CBHI mutant (SEQ ID NO:136) showed no inhibition up to 25 g/L cellobiose.

In another assay, cellobiose inhibition was measured in saccharification assays using bagasse (12% solids in 200 mM MES buffer, pH 6) as the substrate. 5% w/v pretreated bagasse was incubated with 4 mg/g of CBHI at 35° C. at 20 RPM in hybridization ovens. Although the activity of the wild-type CBHI (SEQ ID NO:134) was higher than that of the CBHI mutant (SEQ ID NO:136), the activity of the mutant was less affected by the presence of cellobiose (under either when no beta-glucosidase was added or when gluconolactone was added). At 48 hours, wild-type CBHI activity decreased by 60% when no beta-glucosidase was added, whereas the activity of the CBHI mutant only decreased by 22% when beta-glucosidase was added. At 72 hours, wild-type CBHI activity decreased by 50% when beta-glucosidase was added, whereas the activity of the CBHI mutant only decreased by 14% when beta-glucosidase was added.

A number of embodiments as provided herein have been described. Nevertheless, it will be understood that various modifications may be made without departing from the spirit and scope as provided herein. Accordingly, other embodiments are within the scope of the claims.

TABLE 1

| Plate Name | Well | Mutation Type | Mutant Property | Nucleotide Sequence | AA Sequence |
|---|---|---|---|---|---|
| 119484 | B7 | GSSM | Activity-SEQ ID NO: 1, 2 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCCATACTGGACTTGGC CAACCACGGAGCTTGCTGCGCAGAGCTTGATATCTGGGAGGCAAACAGCAT CTCAGAGGCTTTGACTCCTCACCCTTGCGATACACCCGGTCTATCTGTTTGCA CTACTGATGCCTGCGGTGGTACCTACAGCTCCGATCGTTACGCCGGTACCTG CGACCCTGATGGATGTGACTTCAACCCTTACCGTCTTGGTGTCACTGACTTCT ACGGCTCCGGCAAGACCGTTGACACCACCAAACCCATCACCGTTGTGACTCA ATTCGTCACTGACGACGGCACATCCACCGGCACCCTCTCCGAGATCAGACGT TACTACGTTCAGAACGGTGTTGTCATCCCCCAGCCTTCCTCCAAGATCTCCG GAGTCAGCGGAAATGTCATCAACTCCGACTTCTGCGATGCTGAGATCTCCAC CTTTGGCGAGACTGCCTCCTTCAGCAAACACGGTGGCCTGGCAAGATGGGC GCTGGTATGGAAGCTGGTATGGTCTTGGTCATGAGTTTGTGGGACGACTACT CCGTCAACATGCTCTGGCTCGACAGCACCTACCCCTACAAACGCGACTGGTAC CCCCGGTGCCGCTCGTGGTTCCTGCCCTACCACTTCTGGGGACCCTAAGACC GTTGAATCACAATCCGGCAGCTCCTATGTCACCTTTTCTGACATCCGGGTTG GTCCTTTCAACTCTACGTTCAGCGGTGGTTCTAGCACCGGTGGCAGCTCCAC TACTACCGCCAGCGGCACCACCACCACCAAGGCCTCTTCCACCTCTACTTCC AGCACCTCTACCGGCACTGAGTCGCTGCTCACTGGGGTCAGTGGTGGCC AGGGTTGGACTGGTCCTACCACCTGCGCTAGTGGAACCACATGCACCGTCGT GAACCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPKSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 119484 | H8 | GSSM | Activity-SEQ ID NO: 3, 4 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD |

TABLE 1-continued

| Plate Name | Well | Mutation Type | Mutant Property | Nucleotide Sequence | AA Sequence |
|---|---|---|---|---|---|
| | | | | GATACTGTGACTCTCAATGCCCTCGTGACTTGAAATTCATCGCTGGTCAGGC<br>CAACGTTGAGGGCTGGACGCCCTCCTCCAACAACGCCGAGACTGGACTTGGC<br>AACCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGGTGGTGGCAGG<br>GTTGGACTGGTCCTACCACCTGCGCTAGTGGAACCACATGCACCGTCGTGAA<br>CCCTTACTACTCTCAATGTTTGTAA | SQCPRDLKFIAGQANVEG<br>WTPSSNNAETGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST<br>SSTSTGTGVAAHWGQCG<br>GQGWTGPTTCASGTTCT<br>VVNPYYSQCL |
| 119483 | H2 | GSSM | Activity-<br>SEQ ID<br>NO: 5, 6 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCAAGTCCAACAACGCCAACACTGGACTTGG<br>CAACCACGGAGCTTGCTGCGCAGAGCTTGATATCTGGGAGGCAAACAGCAT<br>CTCAGAGGCTTTGACTCCTCACCCTTGCGATACACCCGGTCTATCTGTTTGCA<br>CTACTGATGCCTGCGGTGGTACCTACAGCTCCGATCGTTACGCCGGTACCTG<br>CGACCCTGATGGATGTGACTTCAACCCTTACCGTCTTGGTGTCACTGACTTCT<br>ACGGCTCCGGCAAGACCGTTGACACCACCAAACCCATCACCGTTGTGACTCA<br>ATTCGTCACTGACGACGGCACATCCACCGGCACCCTCTCCGAGATCAGACGT<br>TACTACGTTCAGAACGGTGTTGTCATCCCCCAGCCTTCCTCCAAGATCTCCG<br>GAGTCAGCGGAAATGTCATCAACTCCGACTTCTGCGATGCTGAGATCTCCAC<br>CTTTGGCGAGACTGCCTCCTTCAGCAAACACGGTGGCCTGGCAAAGATGGGC<br>GCTGGTATGGAAGCTGGTATGGTCTTGGTCATGAGTTTGTGGGACGACTACT<br>CCGTCAACATGCTCTGGCTCGACAGCACCTACCCTACAAACGCGACTGGTAC<br>CCCGGTGCCGCTCGTGGTTCCTGCCCTACCACTTCTGGGGACCCTAAGACC<br>GTTGAATCACAATCCGGCAGCTCCTATGTCACCTTTTCTGACATCCGGGTTG<br>GTCCTTTCAACTCTACGTTCAGCGGTGGTTCTAGCACCGGTGGCAGCTCCAC<br>TACTACCGCCAGCGGCACCACCACCACCAAGGCCTCTTCCACCTCTACTTCC<br>AGCACCTCTACCGGCACTGGAGTCGCTGCTCACTGGGGTCAGTGGTGGTGGCC<br>GGGCAGGGTTGGACTGGTCCTACCACCTGCGCTAGTGGAACCACATGCACCGTCGT<br>GAACCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSKSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST<br>SSTSTGTGVAAHWGQCG<br>GQGWTGPTTCASGTTCT<br>VVNPYYSQCL |
| 119498 | A1 | GSSM | Activity-<br>SEQ ID<br>NO: 7, 8 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGATATGGC<br>AACCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGYGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP |

TABLE 1-continued

| Plate Name | Well | Mutation Type | Mutant Property | Nucleotide Sequence | AA Sequence |
|---|---|---|---|---|---|
| | | | | GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 119498 | C1 | GSSM | Activity- SEQ ID NO: 9, 10 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGAGTGGGC TGGACTCCCTCCTCCAACAATGCCAACGCAATCTGGACCTTGGCCAAGGCCAACGCAATCTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGVGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 120175 | D8 | GSSM | Activity- SEQ ID NO: 11, 12 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTTCGTGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAASWGQCG GQGWTGPTTCASGTTCT VVNPYYSQCL |
| 120177 | B4 | GSSM | Activity- SEQ ID NO: 13, 14 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA | MSALNSFNMYKSALILGS LLATAGAQQIGTYTAETH PSLSWSTCKSGGSCTTNS |

TABLE 1-continued

| Plate Name | Well | Mutation Type | Mutant Property | Nucleotide Sequence | AA Sequence |
|---|---|---|---|---|---|
| | | | | ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGTGGTGGCCAGG<br>GTTGGACTGGTCCTAAGACCTGCGCTAGTGGAACCACATGCACCGTCGTGAA<br>CCCCTTACTACTCTCAATGTTTGTAA | GAITLDANWRWVHGVNT<br>STNCYTGNTWNTAICDTD<br>ASCAQDCALDGADYSGT<br>YGIITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST<br>SSTSTGTGVAAHWGQCG<br>GQGWTGPKTCASGTTCT<br>VVNPYYSQCL |
| 131921 | A2 | GSSM | Activity-<br>SEQ ID<br>NO: 15, 16 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCCTT<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGTGGTGGCCAGG<br>GTTGGACTGGTCCTACCACCTGCGCTAGTGGAACCACATGCACCGTCGTGAA<br>CCCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICLTD<br>ASCAQDCALDGADYSGT<br>YGIITSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST<br>SSTSTGTGVAAHWGQCG<br>GQGWTGPTTCASGTTCT<br>VVNPYYSQCL |
| 132325 | G11 | GSSM | Activity-<br>SEQ ID<br>NO: 17, 18 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCCACGGAGCTTGCTGCGCAGAGCTTGATATCTGGGAGGCAAACAGCATCT<br>CAGAGGCTTTGACTCCTCACCCTTGCGATACACCCATTCTATCTGTTTGCACT | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGIITSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPILSVCTTDACGGT |

TABLE 1-continued

| Plate Name | Well | Mutation Type | Mutant Property | Nucleotide Sequence | AA Sequence |
|---|---|---|---|---|---|
| | | | | ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGGTGGCAGG<br>GTTGGACTGGTCCTACCACCTGCGCTAGTGGAACCACATGCACCGTCGTGAA<br>CCCTTACTACTCTCAATGTTTGTAA | YSSDRYAGTCDPDGCDFN<br>PYRLGVTDFYGSGKTVDT<br>TKPITVVTQFVTDDGTST<br>GTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST<br>SSTSTGTGVAAHWGQCG<br>GQGWTGPTTCASGTTCT<br>VVNPYYSQCL |
| 131900 | C9 | GSSM | Activity-<br>SEQ ID<br>NO: 19, 20 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCG<br>GGCTCCCTTGCGGTTTGAACGGTGCCCTCTACTTCGTGACCATGGACGCCGA<br>CGGTGGCGTCTCCAAGTACCCCAACAACAAGGCCGGCGCTCAGTACGGTGTT<br>GGATACTGTGACTCTCAATGCCCTCGTGACTTGAAATTCATCGCTGGTCAGG<br>CCAACGTTGAGGGCTGGACGCCCCTCCAACAACGCCAACACTGGACTTGG<br>CAACCACGGAGCTTGCTGCGCAGAGCTTGATATCTGGGAGGCAAACAGCAT<br>CTCAGAGGCTTTGACTCCTCACCCTTGCGATACACCCGGTCTATCTGTTTGCA<br>CTACTGATGCCTGCGGTGGTACCTACAGCTCCGATCGTTACGCCGGTACCTG<br>CGACCCTGATGGATGTGACTTCAACCCTTACCGTCTTGGTGTCACTGACTTCT<br>ACGGCTCCGGCAAGACCGTTGACACCACCAAACCCATCACCGTTGTGACTCA<br>ATTCGTCACTGACGACGGCACATCCACCGGCACCCTCTCCGAGATCAGACGT<br>TACTACGTTCAGAACGGTGTTGTCATCCCCCAGCCTTCCTCCAAGATCTCCG<br>GAGTCAGCGGAAATGTCATCAACTCCGACTTCTGCGATGCTGAGATCTCCAC<br>CTTTGGCGAGACTGCCTCCTTCAGCAAACACGGTGGCCTGGCAAAGATGGGC<br>GCTGGTATGGAAGCTGGTATGGTCTTGGTCATGAGTTTGTGGGACGACTACT<br>CCGTCAACATGCTCTGGCTCGACAGCACCTACCCTACAAACGCGACTGGTAC<br>CCCGGTGCCGCTCGTGGTTCCTGCCCTACCACTTCTGGGGACCCTAAGACC<br>GTTGAATCACAATCCGGCAGCTCCTATGTCACCTTTTCTGACATCCGGGTTG<br>GTCCTTTCAACTCTACGTTCAGCGGTGGTTCTAGCACCGGTGGCAGCTCCAC<br>TACTACCGCCAGCGGCACCACCACCACCAAGGCCTCTTCCACCTCTACTTCC<br>AGCACCTCTACCGGCACTGGAGTCGCTGCTCACTGGGGTCAGTGGTGGTGGCC<br>AGGGTTGGACTGGTCCTACCACCTGCGCTAGTGGAACCACATGCACCGTCGT<br>GAACCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSGLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST<br>SSTSTGTGVAAHWGQCG<br>GQGWTGPTTCASGTTCT<br>VVNPYYSQCL |
| 131901 | G9 | GSSM | Activity-<br>SEQ ID<br>NO: 21, 22 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCGGGTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCCTCCAACAACGCCAACACTGGACTTGGC<br>AACCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLGCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTTASGTTTTKASSTST |

TABLE 1-continued

| Plate Name | Well | Mutation Type | Mutant Property | Nucleotide Sequence | AA Sequence |
|---|---|---|---|---|---|
| | | | | | SSTSTGTVAAHWGQCG |
| | | | | TACCGCCAGCGGCACCACCACCACCAAGGCCTCTTCCACCTCTACTTCCAGC | GQGWTGPTTCASGTTCT |
| | | | | ACCTCTACCGGCACTGGAGTCGCTGCTCACTGGGGTCAGTGTGGTGGCCAGG | VVNPYYSQCL |
| | | | | GTTGGACTGGTCCTACCACCTGCGCTAGTGGAACCACATGCACCGTCGTGAA | |
| | | | | CCCTTACTACTCTCAATGTTTGTAA | |
| 131909 | G8 | GSSM | Activity-SEQ ID NO: 23, 24 | ATGTCTGCCTTGAACTCTTTCAATATGTACAAGAGCGCCCTCATCTTGGGCTC | MSALNSFNMYKSALILGS |
| | | | | CTTGCTGGCAACAGCTGGTGCTCAGCAAATTGGTACTTATACCGCTGAAACC | LLATAGAQQIGTYTAETH |
| | | | | CATCCCTCTTTGAGCTGGTCTACTTGCAAATCGGGTGGTAGCTGCACCACAA | PSLSWSTCKSGGSCTTNS |
| | | | | ACTCCGGTGCCATTACGTTGGATGCCAACTGGCGTTGGGTCCATGGTGTCAA | GAITLDANWRWVHGVNT |
| | | | | TACCAGCACCAACTGCTACACTGGCAACACTTGGAATACCGCCATCTGCGAC | STNCYTGNTWNTAICDTD |
| | | | | ACTGATGCATCCTGTGCCCAGGACTGTGCTCTTGATGGTGCTGACTACTCTG | ASCAQDCALDGADYSGT |
| | | | | GCACGTACGGTATCACTACCTCCGGCAACTCATTGCGCCTGAACTTCGTTAC | YGITTSGNSLRLNFVTGSN |
| | | | | CGGTTCCAACGTCGGATCTCGTACCTACCTGATGGCCGATAACACCCACTAC | VGSRTYLMADNTHYQIFD |
| | | | | CAAATCTTCGACTTGTTGAACCAGGAGTTCACTTTCACCGTCGATGTCTCCA | LLNQEFTFTVDVSHLPCG |
| | | | | CCTCCCTTGCGGTTTGAACGGTGCCCTCTACTTCGTGACCATGGACGCCGAC | LNGALYFVTMDADGGVS |
| | | | | GGTGGCGTCTCCAAGTACCCCAACGCTAAGGCCGGCGCTCAGTACGGTGTTG | KYPNAKAGAQYGVGYCD |
| | | | | GATACTGTGACTCTCAATGCCCTCGTGACTTGAAATTCATCGCTGGTCAGGC | SQCPRDLKFIAGQANVEG |
| | | | | CAACGTTGAGGGCTGGACGCCCTCCTCCAACAACGCCAACACTGGACTTGGC | WTPSSNNANTGLGNHGA |
| | | | | AACCACGGAGCTTGCTGCGCAGAGCTTGATATCTGGGAGGCAAACAGCATCT | CCAELDIWEANSISEALTP |
| | | | | CAGAGGCTTTGACTCCTCACCCTTGCGATACACCCGGTCTATCTGTTTGCACT | HPCDTPGLSVCTTDACGG |
| | | | | ACTGATGCCTGCGGTGGTACCTACAGCTCCGATCGTTACGCCGGTACCTGCG | TYSSDRYAGTCDPDGCDF |
| | | | | ACCCTGATGGATGTGACTTCAACCCTTACCGTCTTGGTGTCACTGACTTCTAC | NPYRLGVTDFYGSGKTVD |
| | | | | GGCTCCGGCAAGACCGTTGACACCACCAAACCCATCACCGTTGTGACTCAAT | TTKPITVVTQFVTDDGTS |
| | | | | TCGTCACTGACGACGGCACATCCACCGGCACCCTCTCCGAGATCAGACGTTA | TGTLSEIRRYYVQNGVVIP |
| | | | | CTACGTTCAGAACGGTGTTGTCATCCCCCAGCCTTCCTCCAAGATCTCCGGA | QPSSKISGVSGNVINSDFC |
| | | | | GTCAGCGGAAATGTCATCAACTCCGACTTCTGCGATGCTGAGATCTCCACCT | DAEISTFGETASFSKHGGL |
| | | | | TTGGCGAGACTGCCTCCTTCAGCAAACACGGTGGCCTGGCAAAGATGGGCGC | AKMGAGMEAGMVLVMS |
| | | | | TGGTATGGAAGCTGGTATGGTCTTGGTCATGAGTTTGTGGGACGACTACTCC | LWDDYSVNMLWLDSTYP |
| | | | | GTCAACATGCTCTGGCTCGACAGCACCTACCCTACAAACGCGACTGGTACC | TNATGTPGAARGSCPTTS |
| | | | | CCGGTGCCGCTCGTGGTTCCTGCCCTACCACTTCTGGGGACCCTAAGACCGT | GDPKTVESQSGSSYVTFS |
| | | | | TGAATCACAATCCGGCAGCTCCTATGTCACCTTTTCTGACATCCGGGTTGGTC | DIRVGPFNSTFSGGSSTGG |
| | | | | CTTTCAACTCTACGTTCAGCGGTGGTTCTAGCACCGGTGGCAGCTCCACTAC | SSTTASGTTTTKASSTST |
| | | | | TACCGCCAGCGGCACCACCACCACCAAGGCCTCTTCCACCTCTACTTCCAGC | SSTSTGTVAAHWGQCG |
| | | | | ACCTCTACCGGCACTGGAGTCGCTGCTCACTGGGGTCAGTGTGGTGGCCAGG | GQGWTGPTTCASGTTCT |
| | | | | GTTGGACTGGTCCTACCACCTGCGCTAGTGGAACCACATGCACCGTCGTGAA | VVNPYYSQCL |
| | | | | CCCTTACTACTCTCAATGTTTGTAA | |
| 131900 | A2 | GSSM | Activity-SEQ ID NO: 25, 26 | ATGTCTGCCTTGAACTCTTTCAATATGTACAAGAGCGCCCTCATCTTGGGCTC | MSALNSFNMYKSALILGS |
| | | | | CTTGCTGGCAACAGCTGGTGCTCAGCAAATTGGTACTTATACCGCTGAAACC | LLATAGAQQIGTYTAETH |
| | | | | CATCCCTCTTTGAGCTGGTCTACTTGCAAATCGGGTGGTAGCTGCACCACAA | PSLSWSTCKSGGSCTTNS |
| | | | | ACTCCGGTGCCATTACGTTGGATGCCAACTGGCGTTGGGTCCATGGTGTCAA | GAITLDANWRWVHGVNT |
| | | | | TACCAGCACCAACTGCTACACTGGCAACACTTGGAATACCGCCATCTGCGAC | STNCYTGNTWNTAICDTD |
| | | | | ACTGATGCATCCTGTGCCCAGGACTGTGCTCTTGATGGTGCTGACTACTCTG | ASCAQDCALDGADYSGT |
| | | | | GCACGTACGGTATCACTACCTCCGGCAACTCATTGCGCCTGAACTTCGTTAC | YGITTSGNSLRLNFVTGSN |
| | | | | CGGTTCCAACGTCGGATCTCGTACCTACCTGATGGCCGATAACACCCACTAC | VGSRTYLMADNTHYQIFD |
| | | | | CAAATCTTCGACTTGTTGAACCAGGAGTTCACTTTCACCGTCGATGTCGGTC | LLNQEFTFTVDVGHLPCG |
| | | | | ACCTCCCTTGCGGTTTGAACGGTGCCCTCTACTTCGTGACCATGGACGCCGA | LNGALYFVTMDADGGVS |
| | | | | CGGTGGCGTCTCCAAGTACCCCAACAACAAGGCCGGCGCTCAGTACGGTGTT | KYPNNKAGAQYGVGYCD |
| | | | | GGATACTGTGACTCTCAATGCCCTCGTGACTTGAAATTCATCGCTGGTCAGG | SQCPRDLKFIAGQANVEG |
| | | | | CCAACGTTGAGGGCTGGACGCCCTCCTCCAACAACGCCAACACTGGACTTGG | WTPSSNNANTGLGNHGA |
| | | | | CAACCACGGAGCTTGCTGCGCAGAGCTTGATATCTGGGAGGCAAACAGCAT | CCAELDIWEANSISEALTP |
| | | | | CTCAGAGGCTTTGACTCCTCACCCTTGCGATACACCCGGTCTATCTGTTTGCA | HPCDTPGLSVCTTDACGG |
| | | | | CTACTGATGCCTGCGGTGGTACCTACAGCTCCGATCGTTACGCCGGTACCTG | TYSSDRYAGTCDPDGCDF |
| | | | | CGACCCTGATGGATGTGACTTCAACCCTTACCGTCTTGGTGTCACTGACTTCT | NPYRLGVTDFYGSGKTVD |
| | | | | ACGGCTCCGGCAAGACCGTTGACACCACCAAACCCATCACCGTTGTGACTCA | TTKPITVVTQFVTDDGTS |
| | | | | ATTCGTCACTGACGACGGCACATCCACCGGCACCCTCTCCGAGATCAGACGT | TGTLSEIRRYYVQNGVVIP |
| | | | | TACTACGTTCAGAACGGTGTTGTCATCCCCCAGCCTTCCTCCAAGATCTCCG | QPSSKISGVSGNVINSDFC |
| | | | | GAGTCAGCGGAAATGTCATCAACTCCGACTTCTGCGATGCTGAGATCTCCAC | DAEISTFGETASFSKHGGL |
| | | | | CTTTGGCGAGACTGCCTCCTTCAGCAAACACGGTGGCCTGGCAAAGATGGGC | AKMGAGMEAGMVLVMS |
| | | | | GCTGGTATGGAAGCTGGTATGGTCTTGGTCATGAGTTTGTGGGACGACTACT | LWDDYSVNMLWLDSTYP |
| | | | | CCGTCAACATGCTCTGGCTCGACAGCACCTACCCTACAAACGCGACTGGTAC | TNATGTPGAARGSCPTTS |
| | | | | CCCGGTGCCGCTCGTGGTTCCTGCCCTACCACTTCTGGGGACCCTAAGACC | GDPKTVESQSGSSYVTFS |
| | | | | GTTGAATCACAATCCGGCAGCTCCTATGTCACCTTTTCTGACATCCGGGTTG | DIRVGPFNSTFSGGSSTGG |
| | | | | GTCCTTTCAACTCTACGTTCAGCGGTGGTTCTAGCACCGGTGGCAGCTCCAC | SSTTASGTTTTKASSTST |
| | | | | TACTACCGCCAGCGGCACCACCACCACCAAGGCCTCTTCCACCTCTACTTCC | SSTSTGTVAAHWGQCG |
| | | | | AGCACCTCTACCGGCACTGGAGTCGCTGCTCACTGGGGTCAGTGTGGTGGCC | GQGWTGPTTCASGTTCT |
| | | | | AGGGTTGGACTGGTCCTACCACCTGCGCTAGTGGAACCACATGCACCGTCGT | VVNPYYSQCL |
| | | | | GAACCCTTACTACTCTCAATGTTTGTAA | |
| 132821 | H1 | GSSM | Activity-SEQ ID NO: 27, 28 | ATGTCTGCCTTGAACTCTTTCAATATGTACAAGAGCGCCCTCATCTTGGGCTC | MSALNSFNMYKSALILGS |
| | | | | CTTGCTGGCAACAGCTGGTGCTCAGCAAATTGGTACTTATACCGCTGAAACC | LLATAGAQQIGTYTAETH |
| | | | | CATCCCTCTTTGAGCTGGTCTACTTGCAAATCGGGTGGTAGCTGCACCACAA | PSLSWSTCKSGGSCTTNS |
| | | | | ACTCCGGTGCCATTACGTTGGATGCCAACTGGCGTTGGGTCCATGGTGTCAA | GAITLDANWRWVHGVNT |
| | | | | TACCAGCACCAACTGCTACACTGGCAACACTTGGAATACCGCCATCTGCGAC | STNCYTGNTWNTAICDTD |
| | | | | ACTGATGCATCCTGTGCCCAGGACTGTGCTCTTGATGGTGCTGACTACTCTG | ASCAQDCALDGADYSGT |
| | | | | GCACGTACGGTATCACTACCTCCGGCAACTCATTGCGCCTGAACTTCGTTAC | YGITTSGNSLRLNFVTGSN |

TABLE 1-continued

| Plate Name | Well | Mutation Type | Mutant Property | Nucleotide Sequence | AA Sequence |
|---|---|---|---|---|---|
| | | | | CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCCCCAACAACGCCAACACTGGACTTGGC AACCCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCTCTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | VGSRTYLMADNTHYQIFD LLNQEFTFTVDVSHLPCG LNGALYFVTMDADGGVS KYPNNKAGAQYGVGYCD SQCPRDLKFIAGQANVEG WTPSPNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVSDDGTST GTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 132821 | F9 | GSSM | Activity-SEQ ID NO: 29, 30 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACCAGGGCACATCCTCCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGGTCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDQGTSS GTLSEIRRYYVQNGVVIP QPSSKISGVSGNVINSDFC DAEVSTFGETASFSKHGG LAKMGAGMEAGMVLVM SLWDDYSVNMLWLDSTY PTNATGTPGAARGSCPTT SGDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 132824 | G7 | GSSM | Activity-SEQ ID NO: 31, 32 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCCGTCTCTCCGAGATCAGACGTTA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGRLSEIRRYYVQNGVVIP |

TABLE 1-continued

| Plate Name | Well | Mutation Type | Mutant Property | Nucleotide Sequence | AA Sequence |
|---|---|---|---|---|---|
| | | | | CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 132825 | B2 | GSSM | Activity- SEQ ID NO: 33, 34 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCCTTGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLLEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 132828 | G11 | GSSM | Activity- SEQ ID NO: 35, 36 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTAGTAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVSNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |

TABLE 1-continued

| Plate Name | Well | Mutation Type | Mutant Property | Nucleotide Sequence | AA Sequence |
|---|---|---|---|---|---|
| 132832 | G9 | GSSM | Activity- SEQ ID NO: 37, 38 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCGATATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC AGCACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSDISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTASGTTTTKASSTST SSTSTGTGVAAHWGQCG GQGWTGPTTCASGTTCT VVNPYYSQCL |
| 132834 | G4 | GSSM | Activity- SEQ ID NO: 39, 40 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAGATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCTGTGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC AGCACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCRSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVADFYGSGKTV DTTKPITVVTQFVTDDGT STGTLSEIRRYYVQNGVVI PQPSSKISGVCGNVINSDF CDAEISTFGETASFSKHGG LAKMGAGMEAGMVLVM SLWDDYSVNMLWLDSTY PTNATGTPGAARGSCPTT SGDPKTVESQSGSSYVTFS DIRVGPFNSTFSGGSSTGG SSTTASGTTTTKASSTST SSTSTGTGVAAHWGQCG GQGWTGPTTCASGTTCT VVNPYYSQCL |
| 132834 | H7 | GSSM | Activity- SEQ ID NO: 41, 42 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD |

TABLE 1-continued

| Plate Name | Well | Mutation Type | Mutant Property | Nucleotide Sequence | AA Sequence |
|---|---|---|---|---|---|
| | | | | GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGATAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGGTGGCCAGG<br>GTTGGACTGGTCCTACCACCTGCGCTAGTGGAACCACATGCACCGTCGTGAA<br>CCCTTACTACTCTCAATGTTTGTAA | SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSDNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTASGTTTTKASSTST<br>SSTSTGTGVAAHWGQCG<br>GQGWTGPTTCASGTTCT<br>VVNPYYSQCL |
| 132835 | G5 | GSSM | Activity-<br>SEQ ID<br>NO: 43, 44 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGTGTCATCAACTCCGACTTGTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGGTGGCCAGG<br>GTTGGACTGGTCCTACCACCTGCGCTAGTGGAACCACATGCACCGTCGTGAA<br>CCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSSTGG<br>SSTTASGTTTTKASSTST<br>SSTSTGTGVAAHWGQCG<br>GQGWTGPTTCASGTTCT<br>VVNPYYSQCL |
| 132836 | H7 | GSSM | Activity-<br>SEQ ID<br>NO: 45, 46 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTGTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDLC<br>DAEISTFGETASFSKHGGL<br>AKMGAGMEAGMVLVMS<br>LWDDYSVNMLWLDSTYP |

TABLE 1-continued

| Plate Name | Well | Mutation Type | Mutant Property | Nucleotide Sequence | AA Sequence |
|---|---|---|---|---|---|
| | | | | GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | TNATGTPGAARGSCPTTS GDPKTVESQSGSSYVTFS DIRVGPFNSTFSGGSSTGG SSTTTASGTTTTKASSTST SSTSTGTVAAHWGQCG GQGWTGPTTCASGTTCT VVNPYYSQCL |
| 133543 | H4 | GSSM | Activity- SEQ ID NO: 47, 48 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAAGTGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTATTTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETISFSKHGGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTVAAHWGQCG GQGWTGPTTCASGTTCT VVNPYYSQCL |
| 133544 | H2 | GSSM | Activity- SEQ ID NO: 49, 50 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACCGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETASFSKHRGL AKMGAGMEAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTVAAHWGQCG GQGWTGPTTCASGTTCT VVNPYYSQCL |

TABLE 1-continued

| Plate Name | Well | Mutation Type | Mutant Property | Nucleotide Sequence | AA Sequence |
|---|---|---|---|---|---|
| 133547 | G11 | GSSM | Activity- SEQ ID NO: 51, 52 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGAGTGCTGGTATGGTCTTGGTCATGAGTTTGTGGGACGACTACTCC GTCAACATGCTCTGGCTCGACAGCACCTACCCTACAAACGCGACTGGTACCC CCGGTGCCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETASFSKHGGL AKMGAGMSAGMVLVMS LWDDYSVNMLWLDSTYP TNATGTPGAARGSCPTTS GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |
| 133562 | H4 | GSSM | Activity- SEQ ID NO: 53, 54 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC CAACGTTGAGGGCTGGACGCCCTCCTCCAACAACGCCAACACTGGACTTGGC AACCACGGAGCTTGCTGCGCAGAGCTTGATATCTGGGAGGCAAACAGCATCT CAGAGGCTTTGACTCCTCACCCTTGCGATACACCCGGTCTATCTGTTTGCACT ACTGATGCCTGCGGTGGTACCTACAGCTCCGATCGTTACGCCGGTACCTGCG ACCCTGATGGATGTGACTTCAACCCTTACCGTCTTGGTGTCACTGACTTCTAC GGCTCCGGCAAGACCGTTGACACCACCAAACCCATCACCGTTGTGACTCAAT TCGTCACTGACGACGGCACATCCACCGGCACCCTCTCCGAGATCAGACGTTA CTACGTTCAGAACGGTGTTGTCATCCCCCAGCCTTCCTCCAAGATCTCCGGA GTCAGCGGAAATGTCATCAACTCCGACTTCTGCGATGCTGAGATCTCCACCT TTGGCGAGACTGCCTCCTTCAGCAAACACGGTGGCCTGGCAAAGATGGGCGC TGGTATGGAAGCTGGTATGGTCTTGGTCATGAGTTTGTGGGACGACTACTCC GTCAACATGCTCTGGCTCGACAGCACCTACCCTACAAACGCGACTGGTACCC CCGGTGCCGCTCGTGGTTCCTGCCCTACCACTTCTGGGGACCCTAAGACCGT TGAATCACAATCCGGCAGCTCCTATGTCACCTTTTCTGACATCCGGTGGGGT CCTTTCAACTCTACGTTCAGCGGTGGTTCTAGCACCGGTGGCAGCTCCACTA CTACCGCCAGCGGCACCACCACCACCAAGGCCTCTTCCACCTCTACTTCCAG CACCTCTACCGGCACTGGAGTCGCTGCTCACTGGGGTCAGTGTGGTGGCCAG GGTTGGACTGGTCCTACCACCTGCGCTAGTGGAACCACATGCACCGTCGTGA ACCCTTACTACTCTCAATGTTTGTAA | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG WTPSSNNANTGLGNHGA CCAELDIWEANSISEALTP HPCDTPGLSVCTTDACGG TYSSDRYAGTCDPDGCDF NPYRLGVTDFYGSGKTVD TTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFS DIRWGPFNSTFSGGSSTGG SSTTTASGTTTTKASSTST SSTSTGTGVAAHWGQCG GQGWTGPTTCASGTTCT VVNPYYSQCL |
| 133694 | B3 | GSSM | Activity- SEQ ID NO: 55, 56 | ATGTCTGCCTTGAACTCTTTCAATATGTACAAGAGCGCCCTCATCTTGGGCTC CTTGCTGGCAACAGCTGGTGCTCAGCAAATTGGTACTTATACCGCTGAAACC CATCCCTCTTTGAGCTGGTCTACTTGCAAATCGGTGGTAGCTGCACCACAA ACTCCGGTGCCATTACGTTGGATGCCAACTGGCGTTGGGTCCATGGTGTCAA TACCAGCACCAACTGCTACACTGGCAACACTTGGAATACCGCCATCTGCGAC ACTGATGCATCCTGTGCCCAGGACTGTGCTCTTGATGGTGCTGACTACTCTG GCACGTACGGTATCACTACCTCCGGCAACTCATTGCGCCTGAACTTCGTTAC CGGTTCCAACGTCGGATCTCGTACCTACCTGATGGCCGATAACACCCACTAC CAAATCTTCGACTTGTTGAACCAGGAGTTCACTTTCACCGTCGATGTCTCCCA CCTCCCTTGCGGTTTGAACGGTGCCCTCTACTTCGTGACCATGGACGCCGAC GGTGGCGTCTCCAAGTACCCCAACAACAAGGCCGGCGCTCAGTACGGTGTTG GATACTGTGACTCTCAATGCCCTCGTGACTTGAAATTCATCGCTGGTCAGGC | MSALNSFNMYKSALILGS LLATAGAQQIGTYTAETH PSLSWSTCKSGGSCTTNS GAITLDANWRWVHGVNT STNCYTGNTWNTAICDTD ASCAQDCALDGADYSGT YGITTSGNSLRLNFVTGSN VGSRTYLMADNTHYQIFD LLNQEFTFTVDVSHLPCG LNGALYFVTMDADGGVS KYPNNKAGAQYGVGYCD SQCPRDLKFIAGQANVEG |

TABLE 1-continued

| Plate Name | Well | Mutation Type | Mutant Property | Nucleotide Sequence | AA Sequence |
|---|---|---|---|---|---|
| | | | | CAACGTTGAGGGCTGGACGCCCTCCTCCAACAACGCCAACACTGGACTTGGC<br>AACCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTTCTGGGGACCCTAAGACCGT<br>TGAATCACAATCCGGCAGCTCCTATGTCACCTTTTCTGACATCCGGGTTGGTC<br>CTTTCGGTTCTACGTTCAGCGGTGGTTCTAGCACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGTGGTGGCCAGG<br>GTTGGACTGGTCCTACCACCTGCGCTAGTGGAACCACATGCACCGTCGTGAA<br>CCCTTACTACTCTCAATGTTTGTAA | WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFGSTFSGGSSTGG<br>SSTTTASGTTTTKASSTST<br>SSTSTGTGVAAHWGQCG<br>GQGWTGPTTCASGTTCT<br>VVNPYYSQCL |
| 133696 | D5 | GSSM | Activity-<br>SEQ ID<br>NO: 57, 58 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC<br>CCGGTGCCGCTCGTGGTTCCTGCCCTACCACTTTCTGGGGACCCTAAGACCGT<br>TGAATCACAATCCGGCAGCTCCTATGTCACCTTTTCTGACATCCGGGTTGGTC<br>CTTTCAACTCTACGTTCAGCGGTGGTTCTAAGACCGGTGGCAGCTCCACTAC<br>TACCGCCAGCGGCACCACCACCACCAAGGCCTCTTCCACCTCTACTTCCAGC<br>ACCTCTACCGGCACTGGAGTCGCTGCTCACTGGGGTCAGTGTGGTGGCCAGG<br>GTTGGACTGGTCCTACCACCTGCGCTAGTGGAACCACATGCACCGTCGTGAA<br>CCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFS<br>DIRVGPFNSTFSGGSKTGG<br>SSTTTASGTTTTKASSTST<br>SSTSTGTGVAAHWGQCG<br>GQGWTGPTTCASGTTCT<br>VVNPYYSQCL |
| | | | Parent Activity-<br>SEQ ID<br>NO: 59, 60 | ATGTCTGCCTTGAACTCTTTCAATATGTACAAGAGCGCCCTCATCTTGGGCTC<br>CTTGCTGGCAACAGCTGGTGCTCAGCAAATTGGTACTTATACCGCTGAAACC<br>CATCCCTCTTTGAGCTGGTCTACTTGCAAATCGGTGGTAGCTGCACCACAA<br>ACTCCGGTGCCATTACGTTGGATGCCAACTGGCGTTGGGTCCATGGTGTCAA<br>TACCAGCACCAACTGCTACACTGGCAACACTTGGAATACCGCCATCTGCGAC<br>ACTGATGCATCCTGTGCCCAGGACTGTGCTCTTGATGGTGCTGACTACTCTG<br>GCACGTACGGTATCACTACCTCCGGCAACTCATTGCGCCTGAACTTCGTTAC<br>CGGTTCCAACGTCGGATCTCGTACCTACCTGATGGCCGATAACACCCACTAC<br>CAAATCTTCGACTTGTTGAACCAGGAGTTCACTTTCACCGTCGATGTCTCCCA<br>CCTCCCTTGCGGTTTGAACGGTGCCCTCTACTTCGTGACCATGGACGCCGAC<br>GGTGGCGTCTCAAGTACCCCAACAACAAGGCCGGCGCTCAGTACGGTGTTG<br>GATACTGTGACTCTCAATGCCCTCGTGACTTGAAATTCATCGCTGGTCAGGC<br>CAACGTTGAGGGCTGGACGCCCTCCTCCAACAACGCCAACACTGGACTTGGC<br>AACCACGGAGCTTGCTGCGCAGAGCTTGATATCTGGGAGGCAAACAGCATCT<br>CAGAGGCTTTGACTCCTCACCCTTGCGATACACCCGGTCTATCTGTTTGCACT<br>ACTGATGCCTGCGGTGGTACCTACAGCTCCGATCGTTACGCCGGTACCTGCG<br>ACCCTGATGGATGTGACTTCAACCCTTACCGTCTTGGTGTCACTGACTTCTAC<br>GGCTCCGGCAAGACCGTTGACACCACCAAACCCATCACCGTTGTGACTCAAT<br>TCGTCACTGACGACGGCACATCCACCGGCACCCTCTCCGAGATCAGACGTTA<br>CTACGTTCAGAACGGTGTTGTCATCCCCCAGCCTTCCTCCAAGATCTCCGGA<br>GTCAGCGGAAATGTCATCAACTCCGACTTCTGCGATGCTGAGATCTCCACCT<br>TTGGCGAGACTGCCTCCTTCAGCAAACACGGTGGCCTGGCAAAGATGGGCGC<br>TGGTATGGAAGCTGGTATGGTCTTGGTCATGAGTTTGTGGGACGACTACTCC<br>GTCAACATGCTCTGGCTCGACAGCACCTACCCTACAAACGCGACTGGTACCC | MSALNSFNMYKSALILGS<br>LLATAGAQQIGTYTAETH<br>PSLSWSTCKSGGSCTTNS<br>GAITLDANWRWVHGVNT<br>STNCYTGNTWNTAICDTD<br>ASCAQDCALDGADYSGT<br>YGITTSGNSLRLNFVTGSN<br>VGSRTYLMADNTHYQIFD<br>LLNQEFTFTVDVSHLPCG<br>LNGALYFVTMDADGGVS<br>KYPNNKAGAQYGVGYCD<br>SQCPRDLKFIAGQANVEG<br>WTPSSNNANTGLGNHGA<br>CCAELDIWEANSISEALTP<br>HPCDTPGLSVCTTDACGG<br>TYSSDRYAGTCDPDGCDF<br>NPYRLGVTDFYGSGKTVD<br>TTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS |

TABLE 1-continued

| Plate Name | Well | Mutation Type | Mutant Property | Nucleotide Sequence | AA Sequence |
|---|---|---|---|---|---|
| | | | | CCGGTGCCGCTCGTGGTTCCTGCCCTACCACTTCTGGGGACCCTAAGACCGT TGAATCACAATCCGGCAGCTCCTATGTCACCTTTTCTGACATCCGGGTTGGTC CTTTCAACTCTACGTTCAGCGGTGGTTCTAGCACCGGTGGCAGCTCCACTAC TACCGCCAGCGGCACCACCACCACCAAGGCCTCTTCCACCTCTACTTCCAGC ACCTCTACCGGCACTGGAGTCGCTGCTCACTGGGGTCAGTGTGGTGGCCAGG GTTGGACTGGTCCTACCACCTGCGCTAGTGGAACCACATGCACCGTCGTGAA CCCTTACTACTCTCAATGTTTGTAA | GDPKTVESQSGSSYVTFS DIRVGPFNSTFSGGSSTGG SSTTTASGTTTTKASSTST SSTSTGTGVAAHWGQCG GQGWTGPTTCASGTTCT VVNPYYSQCL |

TABLE 2

| Plate Name | Well | Mutation Type | Mutant Property | % improvement over WT @ 48 hr | Dose Reduction |
|---|---|---|---|---|---|
| 119484 | B7 | GSSM | Activity-SEQ ID NO: 1, 2 | 12.3% | |
| 119484 | H8 | GSSM | Activity-SEQ ID NO: 3, 4 | 7.2% | |
| 119483 | H2 | GSSM | Activity-SEQ ID NO: 5, 6 | 13.0% | |
| 119498 | A1 | GSSM | Activity-SEQ ID NO: 7, 8 | 11.4% | 0.75X |
| 119498 | C1 | GSSM | Activity-SEQ ID NO: 9, 10 | 13.3% | 0.75X |
| 120175 | D8 | GSSM | Activity-SEQ ID NO: 11, 12 | 0.0% | 0.94X |
| 120177 | B4 | GSSM | Activity-SEQ ID NO: 13, 14 | 0.0% | 0.87X |
| 131921 | A2 | GSSM | Activity-SEQ ID NO: 15, 16 | 1.0% | |
| 132325 | G11 | GSSM | Activity-SEQ ID NO: 17, 18 | 2.3% | 0.75X |
| 131900 | C9 | GSSM | Activity-SEQ ID NO: 19, 20 | 8.8% | 0.75X |
| 131901 | G9 | GSSM | Activity-SEQ ID NO: 21, 22 | 11.0% | 0.75X |
| 131909 | G8 | GSSM | Activity-SEQ ID NO: 23, 24 | 0.9% | 0.75X |
| 131900 | A2 | GSSM | Activity-SEQ ID NO 25, 26 | 5.8% | 0.75X |
| 132821 | H1 | GSSM | Activity-SEQ ID NO: 27, 28 | 2.9% | 0.75X |
| 132821 | F9 | GSSM | Activity-SEQ ID NO: 29, 30 | 13.9% | 0.75X |
| 132824 | G7 | GSSM | Activity-SEQ ID NO: 31, 32 | 11.1% | 0.75X |
| 132825 | B2 | GSSM | Activity-SEQ ID NO: 33, 34 | 13.4% | 0.75X |
| 132828 | G11 | GSSM | Activity-SEQ ID NO: 35, 36 | 7.5% | 0.75X |
| 132832 | G9 | GSSM | Activity-SEQ ID NO: 37, 38 | 6.9% | 0.75X |
| 132834 | G4 | GSSM | Activity-SEQ ID NO: 39, 40 | 4.0% | 1X |
| 132834 | H7 | GSSM | Activity-SEQ ID NO: 41, 42 | 3.8% | 1X |
| 132835 | G5 | GSSM | Activity-SEQ ID NO: 43, 44 | 8.7% | 0.75X |
| 132836 | H7 | GSSM | Activity-SEQ ID NO: 45, 46 | 3.9% | 0.75X |
| 133543 | H4 | GSSM | Activity-SEQ ID NO: 47, 48 | 4.8% | 1X |
| 133544 | H2 | GSSM | Activity-SEQ ID NO: 49, 50 | 1.7% | 1X |
| 133547 | G11 | GSSM | Activity-SEQ ID NO: 51, 52 | 7.7% | 0.75X |
| 133562 | H4 | GSSM | Activity-SEQ ID NO: 53, 54 | 8.7% | 0.75X |
| 133694 | B3 | GSSM | Activity-SEQ ID NO: 55, 56 | 0.8% | 1X |
| 133696 | D5 | GSSM | Activity-SEQ ID NO: 57, 58 | 1.1% | |
| | | Parent | Activity-SEQ ID NO: 59, 60 | 0.0% | |

TABLE 3

| Plate Name | Well | Mutation Type | Mutant Property | Nucleotide Sequence | AA Sequence |
|---|---|---|---|---|---|
| 131175 | B1 | GSSM | Thermo-tolerance SEQ ID 61, 62 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACAATGGCACGTA CGGTATCACTACCTCCGGCAACTCATTGCGCCTGAACTTCGTTACCGGTTCCAA CGTCGGATCTCGTACCTACCTGATGGCCGATAACACCCACTACCAAATCTTCG ACTTGTTGAACCAGGAGTTCACTTTCACCGTCGATGTCTCCCACCTCCCTTGCG GTTTGAACGGTGCCCTCTACTTCGTGACCATGGACGCCGACGGTGGCGTCTCC AAGTACCCCAACAACAAGGCCGGCGCTCAGTACGGTGTTGGATACTGTGACTC TCAATGCCCTCGTGACTTGAAATTCATCGCTGGTCAGGCAACGTTGAGGGCT GGACGCCTCCTCCAACAACGCCAACACTGGCAACCACCGGAGCTTGC TGCGCAGAGCTTGATATCTGGGAGGCAAACAGCATCTCAGAGGCTTTGACTCC TCACCCTTGCGATACACCCGGTCTATCTGTTTGCACTACTGATGCCTGCGGTGG TACCTACAGCTCCGATCGTTACGCCGGTACCTGCGACCCTGATGGATGTGACTT CAACCCTTACCGTCTCTTGGTGTCACTGACTTCTACGGCTCCGGCAAGACCGTTGA CACCACCAAACCCATCACCGTTGTGACTCAATTCGTCACTGACGACGGACACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYN GYTGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG |

TABLE 3-continued

| Plate Name | Well | Mutation Type | Mutant Property | Nucleotide Sequence | AA Sequence |
|---|---|---|---|---|---|
| | | | | CATGAGTTTGTGGGACGACTACTCCGTCAACATGCTCTGGCTCGACAGCACCT ACCCTACAAACGCGACTGGTACCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSSTSTG TGVAAHWGQCGGQGWT GPTTCASGTTCTVVNPY YSQCL |
| 132309 | B7 | GSSM | Thermo-tolerance SEQ ID 63, 64 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCAGTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTTT CAACCCTTACCGTCTTGGTGTCACTGACTTCTACGGCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGATGGAAGCTGGTATGGTCTTGGT CATGAGTTTGTGGGACGACTACTCCGTCAACATGCTCTGGCTCGACAGCACCT ACCCTACAAACGCGACTGGTACCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GYIGITTSGNSLRLNFST GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSSTSTG TGVAAHWGQCGGQGWT GPTTCASGTTCTVVNPY YSQCL |
| 132309 | H7 | GSSM | Thermo-tolerance SEQ ID 65, 66 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCACTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTTT CAACCCTTACCGTCTTGGTGTCACTGACTTCTACGGCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGATGGAAGCTGGTATGGTCTTGGT CATGAGTTTGTGGGACGACTACTCCGTCAACATGCTCTGGCTCGACAGCACCT ACCCTACAAACGCGACTGGTACCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GYIGITTSGNSLRLNFTT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSSTSTG TGVAAHWGQCGGQGWT GPTTCASGTTCTVVNPY YSQCL |

TABLE 3-continued

| Plate Name | Well | Mutation Type | Mutant Property | Nucleotide Sequence | AA Sequence |
|---|---|---|---|---|---|
| 131179 | G5 | GSSM | Thermo-tolerance SEQ ID 67, 68 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCAATAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGTCAACATGCTCTGGCTCGACAGCACCT ACCCTACAAACGCGACTGGTACCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSNNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQGWT GPTTCASGTTCTVVNPY YSQCL |
| 131180 | D10 | GSSM | Thermo-tolerance SEQ ID 69, 70 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCAACGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGTCAACATGCTCTGGCTCGACAGCACCT ACCCTACAAACGCGACTGGTACCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSTRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQGWT GPTTCASGTTCTVVNPY YSQCL |
| 132330 | D8 | GSSM | Thermo-tolerance SEQ ID 71, 72 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL |

TABLE 3-continued

| Plate Name | Well | Mutation Type | Mutant Property | Nucleotide Sequence | AA Sequence |
|---|---|---|---|---|---|
| | | | | GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT GTTTACAGCTCCGATCGTTACGCCGGTACCTGCGACCCTGATGGATGTGACTTC AACCCTTACCGTCTTGGTGTCACTGACTTCTACGGCTCCGGCAAGACCGTTGAC ACCACCAAACCCATCACCGTTGACTCACTGACGACGGCACATC CACCGGCACCCTCTCCGAGATCAGACGTTACTACGTTCAGAACGGTGTTGTCA TCCCCCAGCCTTCCTCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGTCAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCCAATGTTTGTAA | GNHGACCAELDIWEANSI SEALTPHPCDTPGLSVCT TDACGGVYSSDRYAGTC DPDGCDFNPYRLGVTDF YGSGKTVDTTKPITVVTQ FVTDDGSTGTLSEIRRY YVQNGVVIPQPSSKISGV SGNVINSDFCDAEISTFGE TASFSKHGGLAKMGAG MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQWT GPTTCASGTTCTVVNPY YSQCL |
| 131194 | E5 | GSSM | Thermo-tolerance SEQ ID 73, 74 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAGCTCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCCTTACCGTCTTGGTGTCACTGACTTCTACGGCTCCGGCAAGACCGTTGA CACCACCAAACCCATCACCGTTGTGACTCAATTCGTCACTGACGACGGACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGCAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCCAATGTTTGTAA | MSALNSFNMYKSALILGS LLATAGAQQIGTYTAEA HPSLSWSTCKSGGSCTTN SGAITLDANWRWVHGV NTSTNCYTGNTWNTAIC DTDASCAQDCALDGADY SGTYGITTSGNSLRLNFV TGSNVGSRTYLMADNTH YQIFDLLNQEFTFTVDVS HLPCGLNGALYFVTMDA DGGVSKYPNNKAGAQY GVGYCDSQCPRDLKFIAG QANVEGWTPSSNNANTG LGNHGACCAELDIWEAN SISEALTPHPCDTPGLSVC TTDACGGTYSSDRYAGT CDPDGCDFNPYRLGVTD FYGSGKTVDTTKPITVVT QFVTDDGSTGTLSEIRR YVQNGVVIPQPSSKISG VSGNVINSDFCDAEISTFG ETASFSKHGGLAKMGAG MEAGMVLVMSLWDDYS ANMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQWT GPTTCASGTTCTVVNPY YSQCL |
| 132839 | A3 | GSSM | Thermo-tolerance SEQ ID 75, 76 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACTCAATTCGTCACTGACGACGGACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGAC TATGAGTTTGTGGGACGACTACTCCGTCAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGSTGTLSEIRRY YVQNGVVIPQPSSKISGV SGNVINSDFCDAEISTFGE TASFSKHGGLAKMGAG MEAGMVLTMSLWDDYS VNMLWLDSTYPTNATGT PGAARGSCPTTSGDPKTV ESQSGSSYVTFSDIRVGPF |

TABLE 3-continued

| Plate Name | Well | Mutation Type | Mutant Property | Nucleotide Sequence | AA Sequence |
|---|---|---|---|---|---|
| | | | | CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | NSTFSGGSSTGGSSTTTA SGTTTTKASSTSTSSTSTG TGVAAHWGQCGGQGWT GPTTCASGTTCTVVNPY YSQCL |
| 134379 | H7 | GSSM | Thermo- tolerance SEQ ID 77, 78 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTTT CAACCCTTACCGTCTTGGTGTCACTGACTTCTACGACCCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACGATTCCGTCAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDDS VNMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQGWT GPTTCASGTTCTVVNPY YSQCL |
| 133964 | C2 | GSSM | Thermo- tolerance SEQ ID 79, 80 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTTT CAACCCTTACCGTCTTGGTGTCACTGACTTCTACGACCCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGATAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS DNMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQGWT GPTTCASGTTCTVVNPY YSQCL |
| 133964 | H3 | GSSM | Thermo- tolerance SEQ ID 81, 82 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT |

TABLE 3-continued

| Plate Name | Mutation Well | Mutant Type | Property | Nucleotide Sequence | AA Sequence |
|---|---|---|---|---|---|
| | | | | GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACCCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGC CATGAGTTTGTGGGACGACTACTCCGCTAACATGCTCTGGCTCGACAGCACCT ACCCTACAAACGCGACTGGTGCCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLAMSLWDDYS ANMLWLDSTYPTNATGA PGAARGSCPTTSGDPKTV ESQSGSSYVTFSDIRVGPF NSTFSGGSSTGGSSTTTA SGTTTTKASSTSTSSSTSTG TGVAAHWGQCGGQGWT GPTTCASGTTCTVVNPY YSQCL |
| 133550 C4 | GSSM | | Thermo-tolerance SEQ ID 83, 84 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGTCAACATGACTTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GYITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS VNMTWLDSTYPTNATGT PGAARGSCPTTSGDPKTV ESQSGSSYVTFSDIRVGPF NSTFSGGSSTGGSSTTTA SGTTTTKASSTSTSSSTSTG TGVAAHWGQCGGQGWT GPTTCASGTTCTVVNPY YSQCL |
| 133696 G4 | GSSM | | Thermo-tolerance SEQ ID 85, 86 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACCCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GYITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV |

TABLE 3-continued

| Plate Name | Well | Mutation Type | Mutant Property | Nucleotide Sequence | AA Sequence |
|---|---|---|---|---|---|
| | | | | GACTTCTGCGATGCTGAGATCTCCACCTTTGGCGAGACTGCCTCCTTCAGCAAA<br>CACGGTGGCCTGGCAAAGATGGGCGCTGGTATGGAAGCTGGTATGGTCTTGGT<br>CATGAGTTTGTGGGACGACTACTCCGTCAACATGCTCTGGCTCGACAGCACCT<br>ACCCTACAAACGCGACTGGTACCCCCGGTGCCGCTCGTGGTTCCTGCCCTACC<br>ACTTCTGGGGACCCTAAGACCGTTGAATCACAATCCGGCAGCTCCTATGTCAC<br>CTTTTCTGACATCCGGGTTGGTCCTTTCAACTCTACGTTCAGCGGTGGTTCTTA<br>TACCGGTGGCAGCTCCACTACTACCGCCAGCGGCACCACCACCACCAAGGCCT<br>CTTCCACCTCTACTTCCAGCACCTCTACCGGCACTGGAGTCGCTGCTCACTGGG<br>GTCAGTGTGGTGGCCAGGGTTGGACTGGTCCTACCACCTGCGCTAGTGGAACC<br>ACATGCACCGTCGTGAACCCTTACTACTCTCAATGTTTGTAA | SGNVINSDFCDAEISTFGE<br>TASFSKHGGLAKMGAG<br>MEAGMVLVMSLWDDYS<br>VNMLWLDSTYPTNATGT<br>PGAARGSCPTTSGDPKTV<br>ESQSGSSYVTFSDIRVGPF<br>NSTFSGGSYTGGSSTTTA<br>SGTTTTKASSTSTSSTSTG<br>TGVAAHWGQCGGQGWT<br>GPTTCASGTTCTVVNPY<br>YSQCL |
| 133700 | E5 | GSSM | Thermo-<br>tolerance<br>SEQ ID<br>87, 88 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCA<br>TCCCTCTTTGAGCTGGTCTACTTGCAAATCGGGTGGTAGCTGCACCACAAACTC<br>CGGTGCCATTACGTTGGATGCCAACTGGCGTTGGGTCCATGGTGTCAATACCA<br>GCACCAACTGCTACACTGGCAACACTTGGAATACCGCCATCTGCGACACTGAT<br>GCATCCTGTGCCCAGGACTGTGCTCTTGATGGTGCTGACTACTCTGGCACGTAC<br>GGTATCACTACCTCCGGCAACTCATTGCGCCTGAACTTCGTTACCGGTTCCAAC<br>GTCGGATCTCGTACCTACCTGATGGCCGATAACACCCACTACCAAATCTTCGA<br>CTTGTTGAACCAGGAGTTCACTTTCACCGTCGATGTCTCCCACCTCCCTTGCGG<br>TTTGAACGGTGCCCTCTACTTCGTGACCATGGACGCCGACGGTGGCGTCTCCA<br>AGTACCCCAACAACAAGGCCGGCGCTCAGTACGGTGTTGGATACTGTGACTCT<br>CAATGCCCTCGTGACTTGAAATTCATCGCTGGTCAGGCCAACGTTGAGGGCTG<br>GACGCCCTCCTCCAACAACGTCAACACTGGACTTGGCAACCACGGAGCTTGCT<br>GCGCAGAGCTTGATATCTGGGAGGCAAACAGCATCTCAGAGGCTTTGACTCCT<br>CACCCTTGCGATACACCCGGTCTATCTGTTTGCACTACTGATGCCTGCGGTGGT<br>ACCTACAGCTCCGATCGTTACGCCGGTACCTGCGACCCTGATGGATGTGACTT<br>CAACCCTTACCGTCTTGGTGTCACTGACTTCTACGGCTCCGGCAAGACCGTTGA<br>CACCACCAAACCCATCACCGTTGTGACTCAATTCGTCACTGACGACGGCACGT<br>CCACCGGCACCCTCTCCGAGATCAGACGTTACTACGTTCAGAACGGTGTTGTC<br>ATCCCCCAGCCTTCCTCCAAGATCTCCGGAGTCAGCGGAAATGTCATCAACTCC<br>GACTTCTGCGATGCTGAGATCTCCACCTTTGGCGAGACTGCCTCCTTCAGCAAA<br>CACGGTGGCCTGGCAAAGATGGGCGCTGGTATGGAAGCTGGTATGGTCTTGGT<br>CATGAGTTTGTGGGACGACTACTCCGTCAACATGCTCTGGCTCGACAGCACCT<br>ACCCTACAAACGCGACTGGTACCCCCGGTGCCGCTCGTGGTTCCTGCCCTACC<br>ACTTCTGGGGACCCTAAGACCGTTGAATCACAATCCGGCAGCTCCTATGTCAC<br>CTTTTCTGACATCCGGGTTGGTCCTTTCAACTCTACGTTCAGCGGTGGTTCTAG<br>CACCGGTGGCAGCTCCACTACTACCGCCAGCGGCACCACCACCACCAAGGCCT<br>CTTCCACCTCTACTTCCAGCACCTCTACCGGCACTGGAGTCGCTGCTCACTGGG<br>GTCAGTGTGGTGGCCAGGGTTGGACTGGTCCTACCACCTGCGCTAGTGGAACC<br>ACATGCACCGTCGTGAACCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVN<br>TSTNCYTGNTWNTAICD<br>TDASCAQDCALDGADYS<br>GTYGITTSGNSLRLNFVT<br>GSNVGSRTYLMADNTHY<br>QIFDLLNQEFTFTVDVSH<br>LPCGLNGALYFVTMDAD<br>GGVSKYPNNKAGAQYG<br>VGYCDSQCPRDLKFIAGQ<br>ANVEGWTPSSNNVNTGL<br>GNHGACCAELDIWEANSI<br>SEALTPHPCDTPGLSVCT<br>TDACGGTYSSDRYAGTC<br>DPDGCDFNPYRLGVTDF<br>YGSGKTVDTTKPITVVTQ<br>FVTDDGTSTGTLSEIRRY<br>YVQNGVVIPQPSSKISGV<br>SGNVINSDFCDAEISTFGE<br>TASFSKHGGLAKMGAG<br>MEAGMVLVMSLWDDYS<br>ANMLWLDSTYPTNATGT<br>PGAARGSCPTTSGDPKTV<br>ESQSGSSYVTFSDIRVGPF<br>NSTFSGGSSTGGSSTTTA<br>SWTTTTKASSTSTSSTST<br>GTGVAAHWGQCGGQGW<br>TGPTTCASGTTCTVVNPY<br>YSQCL |
| 134441 | A2 | GSSM | Thermo-<br>tolerance<br>SEQ ID<br>89, 90 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCA<br>TCCCTCTTTGAGCTGGTCTACTTGCAAATCGGGTGGTAGCTGCACCACAAACTC<br>CGGTGCCATTACGTTGGATGCCAACTGGCGTTGGGTCCATGGTGTCAATACCA<br>GCACCAACTGCTACACTGGCAACACTTGGAATACCGCCATCTGCGACACTGAT<br>GCATCCTGTGCCCAGGACTGTGCTCTTGATGGTGCTGACTACTCTGGCACGTAC<br>GGTATCACTACCTCCGGCAACTCATTGCGCCTGAACTTCGTTACCGGTTCCAAC<br>GTCGGATCTCGTACCTACCTGATGGCCGATAACACCCACTACCAAATCTTCGA<br>CTTGTTGAACCAGGAGTTCACTTTCACCGTCGATGTCTCCCACCTCCCTTGCGG<br>TTTGAACGGTGCCCTCTACTTCGTGACCATGGACGCCGACGGTGGCGTCTCCA<br>AGTACCCCAACAACAAGGCCGGCGCTCAGTACGGTGTTGGATACTGTGACTCT<br>CAATGCCCTCGTGACTTGAAATTCATCGCTGGTCAGGCCAACGTTGAGGGCTG<br>GACGCCCTCCTCCAACAACGCCAACACTGGACTTGGCAACCACGGAGCTTGCT<br>GCGCAGAGCTTGATATCTGGGAGGCAAACAGCATCTCAGAGGCTTTGACTCCT<br>CACCCTTGCGATACACCCGGTCTATCTGTTTGCACTACTGATGCCTGCGGTGGT<br>ACCTACAGCTCCGATCGTTACGCCGGTACCTGCGACCCTGATGGATGTGACTT<br>CAACCCTTACCGTCTTGGTGTCACTGACTTCTACGGCTCCGGCAAGACCGTTGA<br>CACCACCAAACCCATCACCGTTGTGACTCAATTCGTCACTGACGACGGCACAT<br>CCACCGGCACCCTCTCCGAGATCAGACGTTACTACGTTCAGAACGGTGTTGTC<br>ATCCCCCAGCCTTCCTCCAAGATCTCCGGAGTCAGCGGAAATGTCATCAACTCC<br>GACTTCTGCGATGCTGAGATCTCCACCTTTGGCGAGACTGCCTCCTTCAGCAAA<br>CACGGTGGCCTGGCAAAGATGGGCGCTGGTATGGAAGCTGGTATGGTCTTGGT<br>CATGAGTTTGTGGGACGACTACTCCGTCAACATGCTCTGGCTCGACAGCACCT<br>ACCCTACAAACGCGACTGGTACCCCCGGTGCCGCTCGTGGTTCCTGCCCTACC<br>ACTTCTGGGGACCCTAAGACCGTTGAATCACAATCCGGCAGCTCCTATGTCAC<br>CTTTTCTGACATCCGGGTTGGTCCTTTCAACTCTACGTTCAGCGGTGGTTCTAG<br>CACCGGTGGCAGCTCCACTACTACCATGAGCGGCACCACCACCACCAAGGCCT<br>CTTCCACCTCTACTTCCAGCACCTCTACCGGCACTGGAGTCGCTGCTCACTGGG<br>GTCAGTGTGGTGGCCAGGGTTGGACTGGTCCTACCACCTGCGCTAGTGGAACC<br>ACATGCACCGTCGTGAACCCTTACTACTCTCAATGTTTGTAA | MSALNSFNMYKSALILGS<br>LLATAGAQQIGTYTAETH<br>PSLSWSTCKSGGSCTTNS<br>GAITLDANWRWVHGVN<br>TSTNCYTGNTWNTAICD<br>TDASCAQDCALDGADYS<br>GTYGITTSGNSLRLNFVT<br>GSNVGSRTYLMADNTHY<br>QIFDLLNQEFTFTVDVSH<br>LPCGLNGALYFVTMDAD<br>GGVSKYPNNKAGAQYG<br>VGYCDSQCPRDLKFIAGQ<br>ANVEGWTPSSNNANTGL<br>GNHGACCAELDIWEANSI<br>SEALTPHPCDTPGLSVCT<br>TDACGGTYSSDRYAGTC<br>DPDGCDFNPYRLGVTDF<br>YGSGKTVDTTKPITVVTQ<br>FVTDDGTSTGTLSEIRRY<br>YVQNGVVIPQPSSKISGV<br>SGNVINSDFCDAEISTFGE<br>TASFSKHGGLAKMGAG<br>MEAGMVLVMSLWDDYS<br>VNMLWLDSTYPTNATGT<br>PGAARGSCPTTSGDPKTV<br>ESQSGSSYVTFSDIRVGPF<br>NSTFSGGSSTGGSSTTTM<br>SGTTTTKASSTSTSSTSTG<br>TGVAAHWGQCGGQGWT<br>GPTTCASGTTCTVVNPY<br>YSQCL |

TABLE 3-continued

| Plate Name | Well | Mutation Type | Mutant Property | Nucleotide Sequence | AA Sequence |
|---|---|---|---|---|---|
| 135067 | A2 | GSSM | Thermo-tolerance SEQ ID 91, 92 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGCCAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGACTTGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS ANMLWLDSTYPTNATGT PGAARGSCPTTSGDPKTV ESQSGSSYVTFSDIRVGPF NSTFSGGSSTGGSSTTTA SGTTTTKASSTSTSSTSTG TGLAAHWGQCGGQGWT GPTTCASGTTCTVVNPY YSQCL |
| | | Parent | Thermo-tolerance SEQ ID 93, 94 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCA TCCCTCTTTGAGCTGGTCTACTTGCAAATCGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTTACCGGTTCCAAC GTCGGATCTCGTACCTACCTGATGGCCGATAACACCCACTACCAAATCTTCGA CTTGTTGAACCAGGAGTTCACTTTCACCGTCGATGTCTCCCACCTCCCTTGCGG TTTGAACGGTGCCCTCTACTTCGTGACCATGGACGCCGACGGTGGCGTCTCCA AGTACCCCAACAACAAGGCCGGCGCTCAGTACGGTGTTGGATACTGTGACTCT CAATGCCCTCGTGACTTGAAATTCATCGCTGGTCAGGCCAACGTTGAGGGCTG GACGCCCTCCTCCAACAACGCCAACACTGGACTTGGCAACCACGGAGCTTGCT GCGCAGAGCTTGATATCTGGGAGGCAAACAGCATCTCAGAGGCTTTGACTCCT CACCCTTGCGATACACCCGGTCTATCTGTTTGCACTACTGATGCCTGCGGTGGT ACCTACAGCTCCGATCGTTACGCCGGTACCTGCGACCCTGATGGATGTGACTT CAACCCTTACCGTCTTGGTGTCACTGACTTCTACGGCTCCGGCAAGACCGTTGA CACCACCAAACCCATCACCGTTGTGACTCAATTCGTCACTGACGACGGCACAT CCACCGGCACCCTCTCCGAGATCAGACGTTACTACGTTCAGAACGGTGTTGTC ATCCCCCAGCCTTCCTCCAAGATCTCCGGAGTCAGCGGAAATGTCATCAACTCC GACTTCTGCGATGCTGAGATCTCCACCTTTGGCGAGACTGCCTCCTTCAGCAAA CACGGTGGCCTGGCAAAGATGGGCGCTGGTATGGAAGCTGGTATGGTCTTGGT CATGAGTTTGTGGGACGACTACTCCGTCAACATGCTCTGGCTCGACAGCACCT ACCCTACAAACGCGACTGGTACCCCCGGTGCCGCTCGTGGTTCCTGCCCTACC ACTTCTGGGGACCCTAAGACCGTTGAATCACAATCCGGCAGCTCCTATGTCAC CTTTTCTGACATCCGGGTTGGTCCTTTCAACTCTACGTTCAGCGGTGGTTCTAG CACCGGTGGCAGCTCCACTACTACCGCCAGCGGCACCACCACCACCAAGGCCT CTTCCACCTCTACTTCCAGCACCTCTACCGGCACTGGAGTCGCTGCTCACTGGG GTCAGTGTGGTGGCCAGGGTTGGACTGGTCCTACCACCTGCGCTAGTGGAACC ACATGCACCGTCGTGAACCCTTACTACTCTCAATGTTTGTAA | MSALNSFNMYKSALILGS LLATAGAQQIGTYTAETH PSLSWSTCKSGGSCTTNS GAITLDANWRWVHGVN TSTNCYTGNTWNTAICD TDASCAQDCALDGADYS GTYGITTSGNSLRLNFVT GSNVGSRTYLMADNTHY QIFDLLNQEFTFTVDVSH LPCGLNGALYFVTMDAD GGVSKYPNNKAGAQYG VGYCDSQCPRDLKFIAGQ ANVEGWTPSSNNANTGL GNHGACCAELDIWEANSI SEALTPHPCDTPGLSVCT TDACGGTYSSDRYAGTC DPDGCDFNPYRLGVTDF YGSGKTVDTTKPITVVTQ FVTDDGTSTGTLSEIRRY YVQNGVVIPQPSSKISGV SGNVINSDFCDAEISTFGE TASFSKHGGLAKMGAG MEAGMVLVMSLWDDYS VNMLWLDSTYPTNATGT PGAARGSCPTTSGDPKTV ESQSGSSYVTFSDIRVGPF NSTFSGGSSTGGSSTTTA SGTTTTKASSTSTSSTSTG TGVAAHWGQCGGQGWT GPTTCASGTTCTVVNPY YSQCL |

TABLE 4

| PlateName | Well | Mutation Type | Mutant Property | % Residual Activity @ 60° C. | % Residual Activity @ 65° C. | % Residual Activity @ 70° C. | % Residual Activity @ 75° C. | % Residual Activity @ 80° C. | Melting Temperature ° C. |
|---|---|---|---|---|---|---|---|---|---|
| 131175 | B1 | GSSM | Thermotolerance-SEQ ID 61, 62 | 97% | 87% | 46% | 54% | 56% | 71.1 |
| 132309 | B7 | GSSM | Thermotolerance-SEQ ID 63, 64 | 80% | 39% | 51% | 53% | 54% | 68.7 |
| 132309 | H7 | GSSM | Thermotolerance-SEQ ID 65, 66 | 83% | 64% | 60% | 63% | 59% | 69.6 |
| 131179 | G5 | GSSM | Thermotolerance-SEQ ID 67, 68 | 100% | 87% | 62% | 71% | 69% | 71.6 |
| 131180 | D10 | GSSM | Thermotolerance-SEQ ID 69, 70 | 107% | 89% | 72% | 71% | 74% | 71.2 |
| 132330 | D8 | GSSM | Thermotolerance-SEQ ID 71, 72 | 92% | 65% | 33% | 44% | 42% | 71.1 |
| 131194 | E5 | GSSM | Thermotolerance-SEQ ID 73, 74 | 100% | 95% | 55% | 57% | 68% | 73.8 |
| 132839 | A3 | GSSM | Thermotolerance-SEQ ID 75, 76 | 94% | 70% | 56% | 54% | 59% | 70.7 |
| 134379 | H7 | GSSM | Thermotolerance-SEQ ID 77, 78 | 91% | 43% | 52% | 56% | 58% | 68.7 |
| 133964 | C2 | GSSM | Thermotolerance-SEQ ID 79, 80 | 93% | 88% | 60% | 62% | 67% | 73.1 |
| 133964 | H3 | GSSM | Thermotolerance-SEQ ID 81, 82 | 96% | 88% | 71% | 67% | 71% | 74.9 |
| 133550 | C4 | GSSM | Thermotolerance-SEQ ID 83, 84 | 93% | 77% | 69% | 69% | 72% | 70.3 |
| 133696 | G4 | GSSM | Thermotolerance-SEQ ID 85, 86 | 99% | 96% | 41% | 42% | 48% | 74.2 |
| 133700 | E5 | GSSM | Thermotolerance-SEQ ID 87, 88 | 99% | 96% | 35% | 43% | 51% | 73.3 |
| 134441 | A2 | GSSM | Thermotolerance-SEQ ID 89, 90 | 96% | 47% | 28% | 54% | 52% | 70.7 |
| 135067 | A2 | GSSM | Thermotolerance-SEQ ID 91, 92 | 96% | 92% | 52% | 61% | 58% | 73.6 |
| | | Parent | Thermotolerance-SEQ ID 93, 94 | 83% | 26% | 18% | 31% | 43% | 69.5 |

TABLE 5

| Plate Name | Well | Mutation Type | Mutant Property | Nucleotide Sequence | AA Sequence |
|---|---|---|---|---|---|
| 143588 | B10 | Entry-Site | Activity-SEQ ID 95, 96 | ATGTCTGCCTTGAACTCTTTCAATATGTACAAGAGCGCCCTCATCTTGGGCTCC TTGCTGGCAACAGCTGGTGCTCAGCAAATTGGTACTCTGCAGGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCG CCCAGAACTGCTACGATGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTCCAGCAGGGCCCC TACTCCAAGAACGTCGGCTCCCGTACCTACCTGATGGCCGATAACACCCACTAC CAAATCTTCGACTTGTTGAACCAGGAGTTCACTTTCACCGTCGATGTCTCCCAC CTCCCTTGCGGTTTGAACGGTGCCCTCTACTTCGTGACCATGGACGCCGACGGT GGCGTCTCCAAGTACCCCAACAACAAGGCCGGCGCTCAGTACGGTGTTGGATA CTGTGACTCTCAATGCCCTCGTGACTTGAAATTCATCGCTGGTCAGGCAACGT TGAGGGCTGGACGCCCTCCTCCAACAACGCCAACACTGGACTTGGCAACCACG GAGCTTGCTGCGCAGAGCTTGATATCTGGGAGGCAAACAGCATCTCAGAGGCT TTGACTCCTCACCCTTGCGATACACCCGGTCTATCTGTTTGCACTACTGATGCC TGCGGTGGTACCTACAGCTCCGATCGTTACGCCGGTACCTGCGACCCTGATGG ATGTGACTTCAACCCTTACCGTCTTGGTGTCACTGACTTCTACGGCTCCGGCAA GACCGTTGACACCACCAAACCCATCACCGTTGTGACTCAATTCGTCACTGACGA CGGCACATCCACCGGCACCCTCTCCGAGATCAGACGTTACTACGTTCAGAACG GTGTTGTCATCCCCCAGCCTTCCTCCAAGATCTCCGGAGTCAGCGGAAATGTCA TCAACTCCGACTTCTGCGATGCTGAGATCTCCACCTTTGGCGAGACTGCCTCCT TCAGCAAACACGGTGGCCTGCAAAGATGGGCGCTGGTATGGAAGCTGGTATG GTCTTGGTCATGAGTTTGTGGGACGACTACTCCGTCAACATGCTCTGGCTCGAC AGCACCTACCCTACAAACGCGACTGGTACCCCCGGTGCCGCTCGTGGTTCCTGC CCTACCACTTCTGGGGACCCTAAGACCGTTAATACAATCCGGCAGCTCCTAT GTCACCTTTTCTGACATCCGGGTTGGTCCTTTCAACTCTGACGGTTCAGCGGTGGT TCTAGCACCGGTGGCAGCTCCACTACTACCGCCAGCGGCACCACCACCACCAA TSSTSTGTGVAAHWGQCG GGCCTCTTCCACCTCTACTTCCAGCACCTCTACCGGCACTGGAGTCGCTGCTCA CTGGGGTCAGTGTGGTGGCAGGGTTGGACTGGTCCTACCACCTGCGCTAGTG GAACCCATGCACCGTCGTGAACCCTTACTACTCTCAATGTTTGTAA | MSALNSFNMYKSALILGS LLATAGAQQIGTLQAETH PSLSWSTCKSGGSCTTNSG AITLDANWRWVHGVNTA QNCYDGNTWNTAICDTD ASCAQDCALDGADYSGTY GITTSGNSLRLNFVQQGPY SKNVGSRTYLMADNTHY QIFDLLNQEFTFTVDVSHL PCGLNGALYFVTMDADG GVSKYPNNKAGAQYGVG YCDSQCPRDLKFIAGQAN VEGWTPSSNNANTGLGNH GACCAELDIWEANSISEAL TPHPCDTPGLSVCTTDAC GGTYSSDRYAGTCDPDGC DFNPYRLGVTDFYGSGKT VDTTKPITVVTQFVTDDG TSTGTLSEIRRYYVQNGV VIPQPSSKISGVSGNVINSD FCDAEISTFGETASFSKHG GLAKMGAGMEAGMVLV MSLWDDYSVNMLWLDST YPTNATGTPAARGSCPT TSGDPKTVESQSGSSYVTF SDIRVGPFNSTFSGGSSTG GSSTTTASGTTTTKASSTS TSSTSTGTGVAAHWGQCG GQGWTGPTTCASGTTCTV VNPYYSQCL |

TABLE 5-continued

| Plate Name | Well | Mutation Type | Mutant Property | Nucleotide Sequence | AA Sequence |
|---|---|---|---|---|---|
| 143593 | H9 | Entry-Site | Activity-SEQ ID 97, 98 | ATGTCTGCCTTGAACTCTTTCAATATGTACAAGAGCGCCCTCATCTTGGGCTCC TTGCTGGCAACAGCTGGTGCTCAGCAAATTGGTACTCTGACCGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCTG GACCAACTGCTACGATGGCAACACTTGGAATACCGCCATCTGCGACACTGATG CATCCTGTGCCCAGGACTGTGCTCTTGATGGTGCTGACTACTCTGGCACGTACG GTATCACTACCTCCGGCAACTCATTGCGCCTGAACTTCGTCCAGCAGGGCCCCT ACTCCAAGAACGTCGGCTCCCGTACCTACCTGATGGCCGATAACACCCACTACC AAATCTTCGACTTGTTGAACCAGGAGTTCACTTTCACCGTCGATGTCTCCCACC TCCCTTGCGGTTTTGAACGGTGCCCTCTACTTCGTGACCATGGACGCCGACGGTG GCGTCTCCAAGTACCCCAACAACAAGGCCGGCGCTCAGTACGGTGTTGGATAC TGTGACTCTCAATGCCCTCGTGACTTGAAATTCATCGCTGGTCAGGCCAACGTT GAGGGCTGGACGCCCTCCTCCAACAACGCCAACACTGGACTTGGCAACCACGG AGCTTGCTGCGCAGAGCTTGATATCTGGGAGGCAAACAGCATCTCAGAGGCTT TGACTCCTCACCCTTGCGATACACCCGGTCTATCTGTTTGCACTACTGATGCCT GCGGTGGTACCTACAGCTCCGATCGTTACGCCGGTACCTGCGACCCTGATGGA TGTGACTTCAACCCTTACCGTCTTGGTGTCACTGACTTCTACGGCTCCGGCAAG ACCGTTGACACCACCAAACCCATCACCGTTGTGACTCAATTCGTCACTGACGAC GGCACATCCACCGGCACCCTCTCCGAGATCAGACGTTACTACGTTCAGAACGG TGTTGTCATCCCCCAGCCTTCCTCCAAGATCTCCGGAGTCAGCGGAAATGTCAT CAACTCCGACTTCTGCGATGCTGAGATCTCCACCTTTGGCGAGACTGCCTCCTT CAGCAAGCACGGTGGCCTGGCAAAGATGGGCGCTGGTATGGAAGCTGGTATGG TCTTGGTCATGAGTTTGTGGGACGACTACTCCGTCAACATGCTCTGGCTCGACA GCACCTACCCTACAAACGCGACTGGTACCCCGGTGCCGCTCGTGGTTCCTGCC CTACCACTTCTGGGGACCCTAAGACCGTTGAATCACAATCCGGCAGCTCCTATG TCACCTTTTCTGACATCCGGGTTGGTCCTTTCAACTCTACGTTCAGCGGTGGTT CTAGCACCGGTGGCAGCTCCACTACTACCGCCAGCGGCACCACCACCACCAAG CCTCTTCCACCTCTACTTCCAGCACCTCTACCGGCACTGGAGTCGCTGCTCAC TGGGGTCAGTGTGGTGGCCAGGGTTGGACTGGTCCTACCACCTGCGCTAGTGG AACCACATGCACCGTCGTGAACCCTTACTACTCAATGTTTGTAA | MSALNSFNMYKSALILGS LLATAGAQQIGTLTAETHP SLSWSTCKSGGSCTTNSG AITLDANWRWVHGVNTW TNCYDGNTWNTAICDTDA SCAQDCALDGADYSGTYG ITTSGNSLRLNFVQQGPYS KNVGSRTYLMADNTHYQI FDLLNQEFTFTVDVSHLPC GLNGALYFVTMDADGGV SKYPNNKAGAQYGVGYC DSQCPRDLKFIAGQANVE GWTPSSNNANTGLGNHG ACCAELDIWEANSISEALT PHPCDTPGLSVCTTDACG GTYSSDRYAGTCDPDGCD FNPYRLGVTDFYGSGKTV DTTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFSD IRVGPFNSTFSGGSSTGGSS TTTASGTTTTKASSTSTSS TSTGTVAAHWGQCGGQ GWTGPTTCASGTTCTVVN PYYSQCL |
| 143603 | H11 | Entry-Site | Activity-SEQ ID 99, 100 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCAT CCCTCTTTGAGCTGGTCTACTTGCAAATCGGGTGGTAGCTGCACCACAAACTCC GGTGCCATTACGTTGGATGCCAACTGGCGTTGGGTCCATGGTGTCAATACCTAC CAGAACTGCTACACCGGCAACACTTGGAATACCGCCATCTGCGACACTGATGC ATCCTGTGCCCAGGACTGTGCTCTTGATGGTGCTGACTACTCTGGCACGTACGG TATCACTACCTCCGGCAACTCATTGCGCCTGAACTTCGTCCAGCAGGGCCCCTA CTCCAAGAACGTCGGCTCCCGTACCTACCTGATGGCCGATAACACCCACTACCA AATCTTCGACTTGTTGAACCAGGAGTTCACTTTCACCGTCGATGTCTCCCACCT CCCTTGCGGTTTGAACGGTGCCCTCTACTTCGTGACCATGGACGCCGACGGTGG CGTCTCCAAGTACCCCAACAACAAGGCCGGCGCTCAGTACGGTGTTGGATACT GTGACTCTCAATGCCCTCGTGACTTGAAATTCATCGCTGGTCAGGCCAACGTTG AGGGCTGGACGCCCTCCTCCAACAACGCCAACACTGGACTTGGCAACCACGGA GCTTGCTGCGCAGAGCTTGATATCTGGGAGGCAAACAGCATCTCAGAGGCTTT GACTCCTCACCCTTGCGATACACCCGGTCTATCTGTTTGCACTACTGATGCCTG CGGTGGTACCTACAGCTCCGATCGTTACGCCGGTACCTGCGACCCTGATGGAT GTGACTTCAACCCTTACCGTCTTGGTGTCACTGACTTCTACGGCTCCGGCAAGA CCGTTGACACCACCAAACCCATCACCGTTGTGACTCAATTCGTCACTGACGACG GCACATCCACCGGCACCCTCTCCGAGATCAGACGTTACTACGTTCAGAACGGT GTTGTCATCCCCCAGCCTTCCTCCAAGATCTCCGGAGTCAGCGGAAATGTCATC AACTCCGACTTCTGCGATGCTGAGATCTCCACCTTTGGCGAGACTGCCTCCTTC AGCAAACACGGTGGCCTGGCAAAGATGGGCGCTGGTATGGAAGCTGGTATGGT CTTGGTCATGAGTTTGTGGGACGACTACTCCGTCAACATGCTCTGGCTCGACAG CACCTACCCTACAAACGCGACTGGTACCCCGGTGCCGCTCGTGGTTCCTGCCC TACCACTTCTGGGGACCCTAAGACCGTTGAATCACAATCCGGCAGCTCCTATGT CACCTTTTCTGACATCCGGGTTGGTCCTTTCAACTCTACGTTCAGCGGTGGTTC TAGCACCGGTGGCAGCTCCACTACTACCGCCAGCGGCACCACCACCACCAAGG CCTCTTCCACCTCTACTTCCAGCACCTCTACCGGCACTGGAGTCGCTGCTCACT GGGGTCAGTGTGGTGGCCAGGGTTGGACTGGTCCTACCACCTGCGCTAGTGGA ACCACATGCACCGTCGTGAACCCTTACTACTCAATGTTTGTAA | MSALNSFNMYKSALILGS LLATAGAQQIGTYTAETH PSLSWSTCKSGGSCTTNSG AITLDANWRWVHGVNTY QNCYTGNTWNTAICDTDA SCAQDCALDGADYSGTYG ITTSGNSLRLNFVQQGPYS KNVGSRTYLMADNTHYQI FDLLNQEFTFTVDVSHLPC GLNGALYFVTMDADGGV SKYPNNKAGAQYGVGYC DSQCPRDLKFIAGQANVE GWTPSSNNANTGLGNHG ACCAELDIWEANSISEALT PHPCDTPGLSVCTTDACG GTYSSDRYAGTCDPDGCD FNPYRLGVTDFYGSGKTV DTTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS GDPKTVESQSGSSYVTFSD IRVGPFNSTFSGGSSTGGSS TTTASGTTTTKASSTSTSS TSTGTVAAHWGQCGGQ GWTGPTTCASGTTCTVVN PYYSQCL |
| 143606 | E8 | Entry-Site | Activity-SEQ ID 101, 102 | ATGTCTGCCTTGAACTCTTTCAATATGTACAAGAGCGCCCTCATCTTGGGCTCC TTGCTGGCAACAGCTGGTGCTCAGCAAATTGGTCTGTGGGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCA GCACCAACTGCTACACTGGCAACACTTGGAATACCGCCATCTGCGACACTGAT GCATCCTGTGCCCAGGACTGTGCTCTTGATGGTGCTGACTACTCTGGCACGTAC GGTATCACTACCTCCGGCAACTCATTGCGCCTGAACTTCGTCCAGCAGGGCCCC TACTCCAAGAACGTCGGCTCCCGTACCTACCTGATGGCCGATAACACCCACTAC CAAATCTTCGACTTGTTGAACCAGGAGTTCACTTTCACCGTCGATGTCTCCCAC CTCCCTTGCGGTTTGAACGGTGCCCTCTACTTCGTGACCATGGACGCCGACGGT GGCGTCTCCAAGTACCCCAACAACAAGGCCGGCGCTCAGTACGGTGTTGGATA CTGTGACTCTCAATGCCCTCGTGACTTGAAATTCATCGCTGGTCAGGCCAACGT TGAGGGCTGGACGCCCTCCTCCAACAACGCCAACACTGGACTTGGCAACCACG GAGCTTGCTGCGCAGAGCTTGATATCTGGGAGGCAAACAGCATCTCAGAGGCT TTGACTCCTCACCCTTGCGATACACCCGGTCTATCTGTTTGCACTACTGATGCC | MSALNSFNMYKSALILGS LLATAGAQQIGTLWAETH PSLSWSTCKSGGSCTTNSG AITLDANWRWVHGVNTS TNCYTGNTWNTAICDTDA SCAQDCALDGADYSGTYG ITTSGNSLRLNFVQQGPYS KNVGSRTYLMADNTHYQI FDLLNQEFTFTVDVSHLPC GLNGALYFVTMDADGGV SKYPNNKAGAQYGVGYC DSQCPRDLKFIAGQANVE GWTPSSNNANTGLGNHG ACCAELDIWEANSISEALT PHPCDTPGLSVCTTDACG |

TABLE 5-continued

| Plate Name | Well | Mutation Type | Mutant Property | Nucleotide Sequence | AA Sequence |
|---|---|---|---|---|---|
| | | | | TGCGGTGGTACCTACAGCTCCGATCGTTACGCCGGTACCTGCGACCCTGATGG<br>ATGTGACTTCAACCCTTACCGTCTTGGTGTCACTGACTTCTACGGCTCCGGCAA<br>GACCGTTGACACCACCAAACCCATCACCGTTGTGACTCAATTCGTCACTGACGA<br>CGGCACATCCACCGGCACCCTCTCCGAGATCAGACGTTACTACGTTCAGAACG<br>GTGTTGTCATCCCCCAGCCTTCCTCCAAGATCTCCGGAGTCAGCGGAAATGTCA<br>TCAACTCCGACTTCTGCGATGCTGAGATCTCCACCTTTGGCGAGACTGCCTCCT<br>TCAGCAAACACGGTGGCCTGGCAAAGATGGGCGCTGGTATGGAAGCTGGTATG<br>GTCTTGGTCATGAGTTTGTGGGACGACTACTCCGTCAACATGCTCTGGCTCGAC<br>AGCACCTACCCTACAAACGCGACTGGTACCCCCGGTGCCGCTCGTGGTTCCTGC<br>CCTACCACTTCTGGGGACCCTAAGACCGTTAATCACAATCCGGCAGCTCCTAT<br>GTCACCTTTTCTGACATCCGGTTGGTCCTTTCAACTCTACGTTCAGCGGTGGT<br>TCTAGCACCGGTGGCAGCTCCACTACTACCGCCAGCGGCACCACCACCACCAA<br>GGCCTCTTCCACCTCTACTTCCAGCACCTCTACCGGCACTGGAGTCGCTGCTCA<br>CTGGGGTCAGTGTGGTGGCCAGGGTTGGACTGGTCCTACCACCTGCGCTAGTG<br>GAACCACATGCACCGTCGTGAACCCTTACTACTCTCAATGTTTGTAA | GTYSSDRYAGTCDPDGCD<br>FNPYRLGVTDFYGSGKTV<br>DTTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYYTFSD<br>IRVGPFNSTFSGGSSTGGSS<br>TTTASGTTTTKASSTSTSS<br>TSTGTGVAAHWGQCGGQ<br>GWTGPTTCASGTTCTVVN<br>PYYSQCL |
| 143678 | H8 | Entry-Site | Activity-SEQ ID 103, 104 | ATGTCTGCCTTGAACTCTTTCAATATGTACAAGAGCGCCCTCATCTTGGGCTCC<br>TTGCTGGCAACAGCTGGTGCTCAGCAAATTGGTACTTACCAGGCTGAAACCCA<br>TCCCTCTTTGAGCTGGTCTACTTGCAAATCGGGTGGTAGCTGCACCACAAACTC<br>CGGTGCCATTACGTTGGATGCCAACTGGCGTTGGGTCCATGGTGTCAATACCA<br>GCACCAACTGCTACACTGGCAACACTTGGAATACCGCCATCTGCGACACTGAT<br>GCATCCTGTGCCCAGGACTGTGCTCTTGATGGTGCTGACTACTCTGGCACGTAC<br>GGTATCACTACCTCCGGCAACTCATTGCGCCTGAACTTCGTCACCAAGGGCTCC<br>TTCTCCTCCAACATCGGCTCCCGTACCTACCTGATGGCCGATAACACCCACTAC<br>CAAATCTTCGACTTGTTGAACCAGGAGTTCACTTTCACCGTCGATGTCTCCCAC<br>CTCCCTTGCGGTTTGAACGGTGCCCTCTACTTCGTGACCATGGACGCCGACGGT<br>GGCGTCTCCAAGTACCCCAACAACAAGGCCGGCGCTCAGTACGGTGTTGGATA<br>CTGTGACTCTCAATGCCCTCGTGACTTGAAATTCATCGCTGGTCAGGCCAACGT<br>TGAGGGCTGGACGCCCTCCTCCAACAACGCCAACACTGGACTTGGCAACCACG<br>GAGCTTGCTGCGCAGAGCTTGATATCTGGGAGGCAAACAGCATCTCAGAGGCT<br>TTGACTCCTCACCCTTGCGATACACCCGGTCTATCTGTTTGCACTACTGATGCC<br>TGCGGTGGTACCTACAGCTCCGATCGTTACGCCGGTACCTGCGACCCTGATGG<br>ATGTGACTTCAACCCTTACCGTCTTGGTGTCACTGACTTCTACGGCTCCGGCAA<br>GACCGTTGACACCACCAAACCCATCACCGTTGTGACTCAATTCGTCACTGACGA<br>CGGCACATCCACCGGCACCCTCTCCGAGATCAGACGTTACTACGTTCAGAACG<br>GTGTTGTCATCCCCCAGCCTTCCTCCAAGATCTCCGGAGTCAGCGGAAATGTCA<br>TCAACTCCGACTTCTGCGATGCTGAGATCTCCACCTTTGGCGAGACTGCCTCCT<br>TCAGCAAACACGGTGGCCTGGCAAAGATGGGCGCTGGTATGGAAGCTGGTATG<br>GTCTTGGTCATGAGTTTGTGGGACGACTACTCCGTCAACATGCTCTGGCTCGAC<br>AGCACCTACCCTACAAACGCGACTGGTACCCCCGGTGCCGCTCGTGGTTCCTGC<br>CCTACCACTTCTGGGGACCCTAAGACCGTTAATCACAATCCGGCAGCTCCTAT<br>GTCACCTTTTCTGACATCCGGTTGGTCCTTTCAACTCTACGTTCAGCGGTGGT<br>TCTAGCACCGGTGGCAGCTCCACTACTACCGCCAGCGGCACCACCACCACCAA<br>GGCCTCTTCCACCTCTACTTCCAGCACCTCTACCGGCACTGGAGTCGCTGCTCA<br>CTGGGGTCAGTGTGGTGGCCAGGGTTGGACTGGTCCTACCACCTGCGCTAGTG<br>GAACCACATGCACCGTCGTGAACCCTTACTACTCTCAATGTTTGTAA | MSALNSFNMYKSALILGS<br>LLATAGAQQIGTYQAETH<br>PSLSWSTCKSGGSCTTNSG<br>AITLDANWRWVHGVNTS<br>TNCYTGNTWNTAICDTDA<br>SCAQDCALDGADYSGTYG<br>ITTSGNSLRLNFVTKGSFSS<br>NIGSRTYLMADNTHYQIF<br>DLLNQEFTFTVDVSHLPC<br>GLNGALYFVTMDADGGV<br>SKYPNNKAGAQYGVGYC<br>DSQCPRDLKFIAGQANVE<br>GWTPSSNNANTGLGNHG<br>ACCAELDIWEANSISEALT<br>PHPCDTPGLSVCTTDACG<br>GTYSSDRYAGTCDPDGCD<br>FNPYRLGVTDFYGSGKTV<br>DTTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYYTFSD<br>IRVGPFNSTFSGGSSTGGSS<br>TTTASGTTTTKASSTSTSS<br>TSTGTGVAAHWGQCGGQ<br>GWTGPTTCASGTTCTVVN<br>PYYSQCL |
| 143581 | H2 | Entry-Site | Activity-SEQ ID 105, 106 | ATGTCTGCCTTGAACTCTTTCAATATGTACAAGAGCGCCCTCATCTTGGGCTCC<br>TTGCTGGCAACAGCTGGTGCTCAGCAAATTGGTACTCAGCAGGCTGAAACCCA<br>TCCCTCTTTGAGCTGGTCTACTTGCAAATCGGGTGGTAGCTGCACCACAAACTC<br>CGGTGCCATTACGTTGGATGCCAACTGGCGTTGGGTCCATGGTGTCAATACGTA<br>CACCAACTGCTACGATGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTCACCCAGTCCGCCC<br>AGAAGAACGTCGGCGCCCGTACCTACCTGATGGCCGATAACACCCACTACCAA<br>ATCTTCGACTTGTTGAACCAGGAGTTCACTTTCACCGTCGATGTCTCCCACCTC<br>CCTTGCGGTTTGAACGGTGCCCTCTACTTCGTGACCATGGACGCCGACGGTGGC<br>GTCTCCAAGTACCCCAACAACAAGGCCGGCGCTCAGTACGGTGTTGGATACTG<br>TGACTCTCAATGCCCTCGTGACTTGAAATTCATCGCTGGTCAGGCCAACGTTGA<br>GGGCTGGACGCCCTCCTCCAACAACGCCAACACTGGACTTGGCAACCACGGAG<br>CTTGCTGCGCAGAGCTTGATATCTGGGAGGCAAACAGCATCTCAGAGGCTTTG<br>ACTCCTCACCCTTGCGATACACCCGGTCTATCTGTTTGCACTACTGATGCCTGC<br>GGTGGTACCTACAGCTCCGATCGTTACGCCGGTACCTGCGACCCTGATGGATGT<br>GACTTCAACCCTTACCGTCTTGGTGTCACTGACTTCTACGGCTCCGGCAAGACC<br>GTTGACACCACCAAACCCATCACCGTTGTGACTCAATTCGTCACTGACGACGGC<br>ACATCCACCGGCACCCTCTCCGAGATCAGACGTTACTACGTTCAGAACGGTGTT<br>GTCATCCCCAGCCTTCCTCCAAGATCTCCGGAGTCAGCGGAAATGTCATCAAC<br>TCCGACTTCTGCGATGCTGAGATCTCCACCTTTGGCGAGACTGCCTCCTTCAGC<br>AAACACGGTGGCCTGGCAAAGATGGGCGCTGGTATGGAAGCTGGTATGGTCTT<br>GGTCATGAGTTTGTGGGACGACTACTCCGTCAACATGCTCTGGCTCGACAGCA<br>CCTACCCTACAAACGCGACTGGTACCCCCGGTGCCGCTCGTGGTTCCTGCCCTA<br>CCACTTCTGGGGACCCTAAGACCGTTAATCACAATCCGGCAGCTCCTATGTCA<br>CCTTTTCTGACATCCGGTTGGTCCTTTCAACTCTACGTTCAGCGGTGGTTCTA<br>GCACCGGTGGCAGCTCCACTACTACCGCCAGCGGCACCACCACCACCAAGGCC<br>TCTTCCACCTCTACTTCCAGCACCTCTACCGGCACTGGAGTCGCTGCTCACTGG<br>GGTCAGTGTGGTGGCCAGGGTTGGACTGGTCCTACCACCTGCGCTAGTGGAAC<br>CACATGCACCGTCGTGAACCCTTACTACTCTCAATGTTTGTAA | MSALNSFNMYKSALILGS<br>LLATAGAQQIGTQQAETH<br>PSLSWSTCKSGGSCTTNSG<br>AITLDANWRWVHGVNTY<br>TNCYDGNTWNTAICDTDA<br>SCAQDCALDGADYSGTYG<br>ITTSGNSLRLNFVTQSAQK<br>NVGARTYLMADNTHYQIF<br>DLLNQEFTFTVDVSHLPC<br>GLNGALYFVTMDADGGV<br>SKYPNNKAGAQYGVGYC<br>DSQCPRDLKFIAGQANVE<br>GWTPSSNNANTGLGNHG<br>ACCAELDIWEANSISEALT<br>PHPCDTPGLSVCTTDACG<br>GTYSSDRYAGTCDPDGCD<br>FNPYRLGVTDFYGSGKTV<br>DTTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYYTFSD<br>IRVGPFNSTFSGGSSTGGSS<br>TTTASGTTTTKASSTSTSS<br>TSTGTGVAAHWGQCGGQ<br>GWTGPTTCASGTTCTVVN<br>PYYSQCL |

TABLE 5-continued

| Plate Name | Well | Mutation Type | Mutant Property | Nucleotide Sequence | AA Sequence |
|---|---|---|---|---|---|
| 143458 | H9 | Entry-Site | Activity- SEQ ID 107, 108 | ATGTCTGCCTTGAACTCTTTCAATATGTACAAGAGCGCCCTCATCTTGGGCTCC TTGCTGGCAACAGCTGGTGCTCAGCAAATTGGTACTGCCTACGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCTA CTACAACTGCTACGATGGCAACACTTGGAATACCGCCATCTGCGACACTGATG CATCCTGTGCCCAGGACTGTGCTCTTGATGGTGCTGACTACTCTGGCACGTACG GTATCACTACCTCCGGCAACTCATTGCGCCTGAACTTCGTCACCGGCTCCAACG TCGGCTCCCGTACCTACCTGATGGCCGATAACACCCACTACCAAATCTTCGACT TGTTGAACCAGGAGTTCACTTTCACCGTCGATGTCTCCCACCTCCCTTGCGGTT TGAACGGTGCCCTCTACTTCGTGACCATGGACGCCGACGGTGGCGTCTCCAAG TACCCCAACAACAAGGCCGGCGCTCAGTACGGTGTTGGATACTGTGACTCTCA ATGCCCTCGTGACTTGAAATTCATCGCTGGTCAGGCCAACGTTGAGGGCTGGA CGCCCTCCTCCAACAACGCCAACACTGGACTTGGCAACCACGGAGCTTGCTGC GCAGAGCTTGATATCTGGGAGGCAAACAGCATCTCAGAGGCTTTGACTCCTCA CCCTTGCGATACACCCGGTCTATCTGTTTGCACTACTGATGCCTGCGGTGGTAC CTACAGCTCCGATCGTTACGCCGGTACCTGCGACCCTGATGGATGTGACTTCAA CCCTTACCGTCTTGGTGTCACTGACTTCTACGGCTCCGGCAAGACCGTTGACAC CACCAAACCCATCACCGTTGTGACTCAATTCGTCACTGACGACGGCACATCCAC CGGCACCCTCTCCGAGATCAGACGTTACTACGTTCAGAACGGTGTTGTCATCCC CCAGCCTTCCTCCAAGATCTCCGGAGTCAGCGGAAATGTCATCAACTCCGACTT CTGCGATGCTGAGATCTCCACCTTTGGCGAGACTGCCTCCTTCAGCAAACACGG TGGCCTGGCAAAGATGGGCGCTGGTATGGAAGCTGGTATGGTCTTGGTCATGA GTTTGTGGGACGACTACTCCGTCAACATGCTCTGGCTCGACAGCACCTACCCTA CAAACGCGACTGGTACCCCCGGTGCCGCTCGTGGTTCCTGCCCTACCACTTCTG GGGACCCTAAGACCGTTGAATCACAATCCGGCAGCTCCTATGTCACCTTTTCTG ACATCCGGGTTGGTCCTTTCAACTCTACGTTCAGCGGTGGTTCTAGCACCGGTG GCAGCTCCACTACTACCGCCAGCGGCACCACCACCACCAAGGCCTCTTCCACCT CTACTTCCAGCACCTCTACCGGCACTGGAGTCGCTGCTCACTGGGGTCAGTGTG GTGGCCAGGGTTGGACTGGTCCTACCACCTGCGCTAGTGGAACCACATGCACC GTCGTGAACCCTTACTACTCTCAATGTTGTAA | MSALNSFNMYKSALILGS LLATAGAQQIGTAYAETH PSLSWSTCKSGGSCTTNSG AITLDANWRWVHGVNTY YNCYDGNTWNTAICDTD ASCAQDCALDGADYSGTY GITTSGNSLRLNFVTGSNV GSRTYLMADNTHYQIFDL LNQEFTFTVDVSHLPCGL NGALYFVTMDADGGVSK YPNNKAGAQYGVGYCDS QCPRDLKFIAGQANVEGW TPSSNNANTGLGNHGACC AELDIWEANSISEALTPHP CDTPGLSVCTTDACGGTY SSDRYAGTCDPDGCDFNP YRLGVTDFYGSGKTVDTT KPITVVTQFVTDDGTSTGT LSEIRRYYVQNGVVIPQPS SKISGVSGNVINSDFCDAEI STFGETASFSKHGGLAKM GAGMEAGMVLVMSLWD DYSVNMLWLDSTYPTNA TGTPGAARGSCPTTSGDP KTVESQSGSSYVTFSDIRV GPFNSTFSGGSSTGGSSTT TASGTTTTKASSTSTSSTS TGTGVAAHWGQCGGQG WTGPTTCASGTTCTVVNP YYSQCL |
| 143496 | H1 | Entry-Site | Activity- SEQ ID 109, 110 | ATGTCTGCCTTGAACTCTTTCAATATGTACAAGAGCGCCCTCATCTTGGGCTCC TTGCTGGCAACAGCTGGTGCTCAGCAAATTGGTACTCAGCAGGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCTA CTACAACTGCTACGATGGCAACACTTGGAATACCGCCATCTGCGACACTGATG CATCCTGTGCCCAGGACTGTGCTCTTGATGGTGCTGACTACTCTGGCACGTACG GTATCACTACCTCCGGCAACTCATTGCGCCTGAACTTCGTCACCGGCTCCAACG TCGGCTCCCGTACCTACCTGATGGCCGATAACACCCACTACCAAATCTTCGACT TGTTGAACCAGGAGTTCACTTTCACCGTCGATGTCTCCCACCTCCCTTGCGGTT TGAACGGTGCCCTCTACTTCGTGACCATGGACGCCGACGGTGGCGTCTCCAAG TACCCCAACAACAAGGCCGGCGCTCAGTACGGTGTTGGATACTGTGACTCTCA ATGCCCTCGTGACTTGAAATTCATCGCTGGTCAGGCCAACGTTGAGGGCTGGA CGCCCTCCTCCAACAACGCCAACACTGGACTTGGCAACCACGGAGCTTGCTGC GCAGAGCTTGATATCTGGGAGGCAAACAGCATCTCAGAGGCTTTGACTCCTCA CCCTTGCGATACACCCGGTCTATCTGTTTGCACTACTGATGCCTGCGGTGGTAC CTACAGCTCCGATCGTTACGCCGGTACCTGCGACCCTGATGGATGTGACTTCAA CCCTTACCGTCTTGGTGTCACTGACTTCTACGGCTCCGGCAAGACCGTTGACAC CACCAAACCCATCACCGTTGTGACTCAATTCGTCACTGACGACGGCACATCCAC CGGCACCCTCTCCGAGATCAGACGTTACTACGTTCAGAACGGTGTTGTCATCCC CCAGCCTTCCTCCAAGATCTCCGGAGTCAGCGGAAATGTCATCAACTCCGACTT CTGCGATGCTGAGATCTCCACCTTTGGCGAGACTGCCTCCTTCAGCAAACACGG TGGCCTGGCAAAGATGGGCGCTGGTATGGAAGCTGGTATGGTCTTGGTCATGA GTTTGTGGGACGACTACTCCGTCAACATGCTCTGGCTCGACAGCACCTACCCTA CAAACGCGACTGGTACCCCCGGTGCCGCTCGTGGTTCCTGCCCTACCACTTCTG GGGACCCTAAGACCGTTGAATCACAATCCGGCAGCTCCTATGTCACCTTTTCTG ACATCCGGGTTGGTCCTTTCAACTCTACGTTCAGCGGTGGTTCTAGCACCGGTG GCAGCTCCACTACTACCGCCAGCGGCACCACCACCACCAAGGCCTCTTCCACCT CTACTTCCAGCACCTCTACCGGCACTGGAGTCGCTGCTCACTGGGGTCAGTGTG GTGGCCAGGGTTGGACTGGTCCTACCACCTGCGCTAGTGGAACCACATGCACC GTCGTGAACCCTTACTACTCTCAATGTTGTAA | MSALNSFNMYKSALILGS LLATAGAQQIGTQQAETH PSLSWSTCKSGGSCTTNSG AITLDANWRWVHGVNTY YNCYDGNTWNTAICDTD ASCAQDCALDGADYSGTY GITTSGNSLRLNFVTGSNV GSRTYLMADNTHYQIFDL LNQEFTFTVDVSHLPCGL NGALYFVTMDADGGVSK YPNNKAGAQYGVGYCDS QCPRDLKFIAGQANVEGW TPSSNNANTGLGNHGACC AELDIWEANSISEALTPHP CDTPGLSVCTTDACGGTY SSDRYAGTCDPDGCDFNP YRLGVTDFYGSGKTVDTT KPITVVTQFVTDDGTSTGT LSEIRRYYVQNGVVIPQPS SKISGVSGNVINSDFCDAEI STFGETASFSKHGGLAKM GAGMEAGMVLVMSLWD DYSVNMLWLDSTYPTNA TGTPGAARGSCPTTSGDP KTVESQSGSSYVTFSDIRV GPFNSTFSGGSSTGGSSTT TASGTTTTKASSTSTSSTS TGTGVAAHWGQCGGQG WTGPTTCASGTTCTVVNP YYSQCL |
| 143497 | A9 | Entry-Site | Activity- SEQ ID 111, 112 | ATGTCTGCCTTGAACTCTTTCAATATGTACAAGAGCGCCCTCATCTTGGGCTCC TTGCTGGCAACAGCTGGTGCTCAGCAAATTGGTACTTACTGGGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCTC CTGGAACTGCTACGATGGCAACACTTGGAATACCGCCATCTGCGACACTGATG CATCCTGTGCCCAGGACTGTGCTCTTGATGGTGCTGACTACTCTGGCACGTACG GTATCACTACCTCCGGCAACTCATTGCGCCTGAACTTCGTCACCGGCTCCAACG TCGGCTCCCGTACCTACCTGATGGCCGATAACACCCACTACCAAATCTTCGACT TGTTGAACCAGGAGTTCACTTTCACCGTCGATGTCTCCCACCTCCCTTGCGGTT TGAACGGTGCCCTCTACTTCGTGACCATGGACGCCGACGGTGGCGTCTCCAAG TACCCCAACAACAAGGCCGGCGCTCAGTACGGTGTTGGATACTGTGACTCTCA ATGCCCTCGTGACTTGAAATTCATCGCTGGTCAGGCCAACGTTGAGGGCTGGA CGCCCTCCTCCAACAACGCCAACACTGGACTTGGCAACCACGGAGCTTGCTGC GCAGAGCTTGATATCTGGGAGGCAAACAGCATCTCAGAGGCTTTGACTCCTCA | MSALNSFNMYKSALILGS LLATAGAQQIGTYWAETH PSLSWSTCKSGGSCTTNSG AITLDANWRWVHGVNTS WNCYDGNTWNTAICDTD ASCAQDCALDGADYSGTY GITTSGNSLRLNFVTGSNV GSRTYLMADNTHYQIFDL LNQEFTFTVDVSHLPCGL NGALYFVTMDADGGVSK YPNNKAGAQYGVGYCDS QCPRDLKFIAGQANVEGW TPSSNNANTGLGNHGACC AELDIWEANSISEALTPHP |

TABLE 5-continued

| Plate Name | Mutation Well | Mutant Type | Property | Nucleotide Sequence | AA Sequence |
|---|---|---|---|---|---|
| | | | | CCCTTGCGATACACCCGGTCTATCTGTTTGCACTACTGATGCCTGCGGTGGTAC | CDTPGLSVCTTDACGGTY |
| | | | | CTACAGCTCCGATCGTTACGCCGGTACCTGCGACCCTGATGGATGTGACTTCAA | SSDRYAGTCDPDGCDFNP |
| | | | | CCCTTACCGTCTTGGTGTCACTGACTTCTACGGCTCCGGCAAGACCGTTGACAC | YRLGVTDFYGSGKTVDTT |
| | | | | CACCAAACCCATCACCGTTGTGACTCAATTCGTCACTGACGACGGCACATCCAC | KPITVVTQFVTDDGTSTGT |
| | | | | CGGCACCCTCTCCGAGATCAGACGTTACTACGTTCAGAACGGTGTTGTCATCCC | LSEIRRYYVQNGVVIPQPS |
| | | | | CCAGCCTTCCTCCAAGATCTCCGGAGTCAGCGGAAATGTCATCAACTCCGACTT | SKISGVSGNVINSDFCDAEI |
| | | | | CTGCGATGCTGAGATCTCCACCTTTGGCGAGACTGCCTCCTTCAGCAAACACGG | STFGETASFSKHGGLAKM |
| | | | | TGGCCTGGCAAAGATGGGCGCTGGTATGGAAGCTGGTATGGTCTTGGTCATGA | GAGMEAGMVLVMSLWD |
| | | | | GTTTGTGGGACGACTACTCCGTCAACATGCTCTGGCTCGACAGCACCTACCCTA | DYSVNMLWLDSTYPTNA |
| | | | | CAAACGCGACTGGTACCCCGGTGCCGCTCGTGGTTCCTGCCCTACCACTTCTG | TGTPGAARGSCPTTSGDP |
| | | | | GGGACCCTAAGACCGTTAATACAATCCGGCAGCTCCTATGTCACCTTTTCTG | KTVESQSGSSYVTFSDIRV |
| | | | | ACATCCGGGTTGGTCCTTTCAACTCTACGTTCAGCGGTGGTTCTAGCACCGTG | GPFNSTFSGGSSTGGSSTT |
| | | | | GCAGCTCCACTACTACCGCCAGCGGCACCACCACCAAGGCCTCTTCCCACCT | TASGTTTTKASSTSTSSTS |
| | | | | CTACTTCCAGCACCTCTACCGGCACTGGAGTCGCTGCTCACTGGGGTCAGTGTG | TGTGVAAHWGQCGQG |
| | | | | GTGGCCAGGGTTGGACTGGTCCTACCACCTGCGCTAGTGGAACCACATGCACC | WTGPTTCASGTTCTVVNP |
| | | | | GTCGTGAACCCTTACTACTCTCAATGTTGTAA | YYSQCL |
| 143461 H2 | | Entry-Site | Activity-SEQ ID 113, 114 | ATGTCTGCCTTGAACTCTTTCAATATGTACAAGAGCGCCCTCATCTTGGGCTCC TTGCTGGCAACAGCTGGTGCTCAGCAAATTGGTACTGCCCAGGCTGAAACCCA TCCCTCTTTGAGCTGGTCTACTTGCAAATCGGGTGGTAGCTGCACCACAAACTC CGGTGCCATTACGTTGGATGCCAACTGGCGTTGGGTCCATGGTGTCAATACCTC CTACAACTGCTACGATGGCAACACTTGGAATACCGCCATCTGCGACACTGATG CATCCTGTGCCCAGGACTGTGCTCTTGATGGTGCTGACTACTCTGGCACGTACG GTATCACTACCTCCGGCAACTCATTGCGCCTGAACTTCGTCACCGGCTCCAACG TCGGCTCCCGTACCTACCTGATGGCCGATAACACCCACTACCAAATCTTCGACT TGTTGAACCAGGAGTTCACTTTCACCGTCGATGTCTCCCACCTCCCTTGCGGTT TGAACGGTGCCCTCTACTTCGTGACCATGGACGCCGACGGTGGCGTCTCCAAG TACCCCAACAACAAGGCCGGCGCTCAGTACGGTGTTGGATACTGTGACTCTCA ATGCCCTCGTGACTTGAAATTCATCGCTGGTCAGGCCAACGTTGAGGGCTGGA CGCCCTCCTCCAACAACGCCAACACTGGACTTGGCAACCACGGAGCTTGCTGC GCAGAGCTTGATATCTGGGAGGCAAACAGCATCTCAGAGGCTTTGACTCCTCA CCCTTGCGATACACCCGGTCTATCTGTTTGCACTACTGATGCCTGCGGTGGTAC CTACAGCTCCGATCGTTACGCCGGTACCTGCGACCCTGATGGATGTGACTTCAA CCCTTACCGTCTTGGTGTCACTGACTTCTACGGCTCCGGCAAGACCGTTGACAC CACCAAACCCATCACCGTTGTGACTCAATTCGTCACTGACGACGGCACATCCAC CGGCACCCTCTCCGAGATCAGACGTTACTACGTTCAGAACGGTGTTGTCATCCC CCAGCCTTCCTCCAAGATCTCCGGAGTCAGCGGAAATGTCATCAACTCCGACTT CTGCGATGCTGAGATCTCCACCTTTGGCGAGACTGCCTCCTTCAGCAAACACGG TGGCCTGGCAAAGATGGGCGCTGGTATGGAAGCTGGTATGGTCTTGGTCATGA GTTTGTGGGACGACTACTCCGTCAACATGCTCTGGCTCGACAGCACCTACCCTA CAAACGCGACTGGTACCCCGGTGCCGCTCGTGGTTCCTGCCCTACCACTTCTG GGGACCCTAAGACCGTTAATACAATCCGGCAGCTCCTATGTCACCTTTTCTG ACATCCGGGTTGGTCCTTTCAACTCTACGTTCAGCGGTGGTTCTAGCACCGTG GCAGCTCCACTACTACCGCCAGCGGCACCACCACCAAGGCCTCTTCCCACCT CTACTTCCAGCACCTCTACCGGCACTGGAGTCGCTGCTCACTGGGGTCAGTGTG GTGGCCAGGGTTGGACTGGTCCTACCACCTGCGCTAGTGGAACCACATGCACC GTCGTGAACCCTTACTACTCTCAATGTTGTAA | MSALNSFNMYKSALILGS LLATAGAQQIGTAQAETH PSLSWSTCKSGGSCTTNSG AITLDANWRWVHGVNTS YNCYDGNTWNTAICDTD ASCAQDCALDGADYSGTY GITTSGNSLRLNFVTGSNV GSRTYLMADNTHYQIFDL LNQEFTFTVDVSHLPCGL NGALYFVTMDADGGVSK YPNNKAGAQYGVGYCDS QCPRDLKFIAGQANVEGW TPSSNNANTGLGNHGACC AELDIWEANSISEALTPHP CDTPGLSVCTTDACGGTY SSDRYAGTCDPDGCDFNP YRLGVTDFYGSGKTVDTT KPITVVTQFVTDDGTSTGT LSEIRRYYVQNGVVIPQPS SKISGVSGNVINSDFCDAEI STFGETASFSKHGGLAKM GAGMEAGMVLVMSLWD DYSVNMLWLDSTYPTNA TGTPGAARGSCPTTSGDP KTVESQSGSSYVTFSDIRV GPFNSTFSGGSSTGGSSTT TASGTTTTKASSTSTSSTS TGTGVAAHWGQCGQG WTGPTTCASGTTCTVVNP YYSQCL |
| 143602 H11 | | Entry-Site | Activity-SEQ ID 115, 116 | ATGTCTGCCTTGAACTCTTTCAATATGTACAAGAGCGCCCTCATCTTGGGCTCC TTGCTGGCAACAGCTGGTGCTCAGCAAATTGGTACTTATACCGCTGAAACCCAT CCCTCTTTGAGCTGGTCTACTTGCAAATCGGGTGGTAGCTGCACCACAAACTCC GGTGCCATTACGTTGGATGCCAACTGGCGTTGGGTCCATGGTGTCAATACCTG GCAGAACTGCTACACCGGCAACACTTGGAATACCGCCATCTGCGACACTGATG CATCCTGTGCCCAGGACTGTGCTCTTGATGGTGCTGACTACTCTGGCACGTACG GTATCACTACCTCCGGCAACTCATTGCGCCTGAACTTCGTCCAGCAGGGCCCCT ACTCCAAGAACGTCGGCTCCCGTACCTACCTGATGGCCGATAACACCCACTACC AAATCTTCGACTTGTTGAACCAGGAGTTCACTTTCACCGTCGATGTCTCCCACC TCCCTTGCGGTTTGAACGGTGCCCTCTACTTCGTGACCATGGACGCCGACGGTG GCGTCTCCAAGTACCCCAACAACAAGGCCGGCGCTCAGTACGGTGTTGGATAC TGTGACTCTCAATGCCCTCGTGACTTGAAATTCATCGCTGGTCAGGCCAACGTT GAGGGCTGGACGCCCTCCTCCAACAACGCCAACACTGGACTTGGCAACCACGG AGCTTGCTGCGCAGAGCTTGATATCTGGGAGGCAAACAGCATCTCAGAGGCTT TGACTCCTCACCCTTGCGATACACCCGGTCTATCTGTTTGCACTACTGATGCCT GCGGTGGTACCTACAGCTCCGATCGTTACGCCGGTACCTGCGACCCTGATGGA TGTGACTTCAACCCTTACCGTCTTGGTCACTGACTTCTACGGCTCCGGCAAG ACCGTTGACACCACCAAACCCATCACCGTTGTGACTCAATTCGTCACTGACGAC GGCACATCCACCGGCACCCTCTCCGAGATCAGACGTTACTACGTTCAGAACGG TGTTGTCATCCCCCAGCCTTCCTCCAAGATCTCCGGAGTCAGCGGAAATGTCAT CAACTCCGACTTCTGCGATGCTGAGATCTCCACCTTTGGCGAGACTGCCTCCTT CAGCAAACACGGTGGCCTGGCAAAGATGGGCGCTGGTATGGAAGCTGGTATGG TCTTGGTCATGAGTTTGTGGGACGACTACTCCGTCAACATGCTCTGGCTCGACA GCACCTACCCTACAAACGCGACTGGTACCCCGGTGCCGCTCGTGGTTCCTGCC | MSALNSFNMYKSALILGS LLATAGAQQIGTYTAETH PSLSWSTCKSGGSCTTNSG AITLDANWRWVHGVNTW QNCYTGNTWNTAICDTDA SCAQDCALDGADYSGTYG ITTSGNSLRLNFVQQGPYS KNVGSRTYLMADNTHYQI FDLLNQEFTFTVDVSHLPC GLNGALYFVTMDADGGV SKYPNNKAGAQYGVGYC DSQCPRDLKFIAGQANVE GWTPSSNNANTGLGNHG ACCAELDIWEANSISEALT PHPCDTPGLSVCTTDACG GTYSSDRYAGTCDPDGCD FNPYRLGVTDFYGSGKTV DTTKPITVVTQFVTDDGTS TGTLSEIRRYYVQNGVVIP QPSSKISGVSGNVINSDFC DAEISTFGETASFSKHGGL AKMGAGMEAGMVLVMS LWDDYSVNMLWLDSTYP TNATGTPGAARGSCPTTS |

TABLE 5-continued

| Plate Name | Well | Mutation Type | Mutant Property | Nucleotide Sequence | AA Sequence |
|---|---|---|---|---|---|
| | | | | CTACCACTTCTGGGGACCCTAAGACCGTTGAATCACAATCCGGCAGCTCCTATG<br>TCACCTTTTCTGACATCCGGGTTGGTCCTTTCAACTCTACGTTCAGCGGTGGTT<br>CTAGCACCGGTGGCAGCTCCACTACTACCGCCAGCGGCACCACCACCACCAAG<br>GCCTCTTCCACCTCTACTTCCAGCACCTCTACCGGCACTGGAGTCGCTGCTCAC<br>TGGGGTCAGTGTGGTGGCCAGGGTTGGACTGGTCCTACCACCTGCGCTAGTGG<br>AACCACATGCACCGTCGTGAACCCTTACTACTCTCAATGTTTGTAA | GDPKTVESQSGSSYVTFSD<br>IRVGPFNSTFSGGSSTGGSS<br>TTTASGTTTTKASSTSTSS<br>TSTGTGVAAHWGQCGGQ<br>GWTGPTTCASGTTCTVVN<br>PYYSQCL |
| 143606 | A11 | Entry-Site | Activity-<br>SEQ ID<br>117, 118 | ATGTCTGCCTTGAACTCTTTCAATATGTACAAGAGCGCCCTCATCTTGGGCTCC<br>TTGCTGGCAACAGCTGGTGCTCAGCAAATTGGTACTCTGTACGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCTCC<br>ACCAACTGCTACGATGGCAACACTTGGAATACCGCCATCTGCGACACTGATGC<br>ATCCTGTGCCCAGGACTGTGCTCTTGATGGTGCTGACTACTCTGGCACGTACG<br>TATCACTACCTCCGGCAACTCATTGCGCCTGAACTTCGTCCAGCAGGGCCCTA<br>CTCCAAGAACGTCGGCTCCCGTACCTACCTGATGGCCGATAACACCCACTACCA<br>AATCTTCGACTTGTTGAACCAGGAGTTCACTTTCACCGTCGATGTCTCCCACCT<br>CCCCTTGCGGTTTGAACGGTGCCCTCTACTTCGTGACCATGGACGCCGACGGTGG<br>CGTCTCCAAGTACCCCAACAACAAGGCCGGCGCTCAGTACGGTGTTGGATACT<br>GTGACTCTCAATGCCCTCGTGACTTGAAATTCATCGCTGGTCAGGCCAACGTTG<br>AGGGCTGGACGCCCTCCTCCAACAACGCCAACACTGGACTTGGCAACCACGGA<br>GCTTGCTGCGCAGAGCTTGATATCTGGGAGGCAAACAGCATCTCAGAGGCTTT<br>GACTCCTCACCCTTGCGATACACCCGGTCTATCTGTTTGCACTACTGATGCCTG<br>CGGTGGTACCTACAGCTCCGATCGTTACGCCGGTACCTGCGACCCTGATGGAT<br>GTGACTTCAACCCTTACCGTCTTGGTGTCACTGACTTCTACGGCTCCGGCAAGA<br>CCGTTGACACCACCAAACCCATCACCGTTGTGACTCAATTCGTCACTGACGACG<br>GCACATCCACCGGCACCCTCTCCGAGATCAGACGTTACTACGTTCAGAACGGT<br>GTTGTCATCCCCCAGCCTTCCTCCAAGATCTCCGGAGTCAGCGGAAATGTCATC<br>AACTCCGACTTCTGCGATGCTGAGATCTCCACCTTTGGCGAGACTGCCTCCTTC<br>AGCAAACACGGTGGCCTGGCAAAGATGGGCGCTGGTATGGAAGCTGGTATGGT<br>CTTGGTCATGAGTTTGTGGGACGATTACTCCGTCAACATGCTCTGGCTCGACAG<br>CACCTACCCTACAAACGCGACTGGTACCCCCGGTGCCGCTCGTGGTTCCTGCCC<br>TACCACTTCTGGGGACCCTAAGACCGTTGAATCACAATCCGGCAGCTCCTATG<br>CACCTTTTCTGACATCCGGGTTGGTCCTTTCAACTCTACGTTCAGCGGTGGTTC<br>TAGCACCGGTGGCAGCTCCACTACTACCGCCAGCGGCACCACCACCACCAAGG<br>CCTCTTCCACCTCTACTTCCAGCACCTCTACCGGCACTGGAGTCGCTGCTCACT<br>GGGGTCAGTGTGGTGGCCAGGGTTGGACTGGTCCTACCACCTGCGCTAGTGGA<br>ACCACATGCACCGTCGTGAACCCTTACTACTCTCAATGTTTGTAA | MSALNSFNMYKSALILGS<br>LLATAGAQQIGTLYAETH<br>PSLSWSTCKSGGSCTTNSG<br>AITLDANWRWVHGVNTS<br>TNCYDGNTWNTAICDTDA<br>SCAQDCALDGADYSGTYG<br>ITTSGNSLRLNFVQGPYS<br>KNVGSRTYLMADNTHYQI<br>FDLLNQEFTFTVDVSHLPC<br>GLNGALYFVTMDADGGV<br>SKYPNNKAGAQYGVGYC<br>DSQCPRDLKFIAGQANVE<br>GWTPSSNNANTGLGNHG<br>ACCAELDIWEANSISEALT<br>PHPCDTPGLSVCTTDACG<br>GTYSSDRYAGTCDPDGCD<br>FNPYRLGVTDFYGSGKTV<br>DTTKPITVVTQFVTDDGTS<br>TGTLSEIRRYYVQNGVVIP<br>QPSSKISGVSGNVINSDFC<br>DAEISTFGETASFSKHGGL<br>AKMGAGMEAGMVLVMS<br>LWDDYSVNMLWLDSTYP<br>TNATGTPGAARGSCPTTS<br>GDPKTVESQSGSSYVTFSD<br>IRVGPFNSTFSGGSSTGGSS<br>TTTASGTTTTKASSTSTSS<br>TSTGTGVAAHWGQCGGQ<br>GWTGPTTCASGTTCTVVN<br>PYYSQCL |
| 156605 | H4 | Parent | Activity-<br>SEQ ID<br>119, 120 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG<br>TCGGATCTCGTACCTACCTGATGGCCGATAACACCCACTACCAAATCTTCGACT<br>TGTTGAACCAGGAGTTCACTTTCACCGTCGATGTCTCCCACCTTCCCTTGCGGTT<br>TGAACGGTGCCCTCTACTTCGTGACCATGGACGCCGACGGTGGCGTCTCCAAG<br>TACCCCAACAACAAGGCCGGCGCTCAGTACGGTGTTGGATACTGTGACTCTCA<br>ATGCCCTCGTGACTTGAAATTCATCGCTGGTCAGGCCAACGTTGAGGGCTGGA<br>CGCCCTCCTCCAACAACGCCAACACTGGACTTGGCAACCACGGAGCTTGCTGC<br>GCAGAGCTTGATATCTGGGAGGCAAACAGCATCTCAGAGGCTTTGACTCCTCA<br>CCCTTGCGATACACCCGGTCTATCTGTTTGCACTACTGATGCCTGCGGTGGTAC<br>CTACAGCTCCGATCGTTACGCCGGTACCTGCGACCCTGATGGATGTGACTTCAA<br>CCCTTACCGTCTTGGTGTCACTGACTTCTACGGCTCCGGCAAGACCGTTGACAC<br>CACCAAACCCATCACCGTTGTGACTCAATTCGTCACTGACGACGGCACATCCAC<br>CGGCACCCTCTCCGAGATCAGACGTTACTACGTTCAGAACGGTGTTGTCATCCC<br>CCAGCCTTCCTCCAAGATCTCCGGAGTCAGCGGAAATGTCATCAACTCCGACTT<br>CTGCGATGCTGAGATCTCCACCTTTGGCGAGACTGCCTCCTTCAGCAAACACG<br>TGGCCTGGCAAAGATGGGCGCTGGTATGGAAGCTGGTATGGTCTTGGTCATGA<br>GTTTGTGGGATGATTACTCCGTCAACATGCTCTGGCTCGACAGCACCTACCCTA<br>CAAACGCGACTGGTACCCCCGGTGCCGCTCGTGGTTCCTGCCCTACCACTTCTG<br>GGGACCCTAAGACCGTTGAATCACAATCCGGCAGCTCCTATGTCACCTTTTCTG<br>ACATCCGGGTTGGTCCTTTCAACTCTACGTTCAGCGGTGGTTCTAGCACCGGTG<br>GCAGCTCCACTACTACCGCCAGCGGCACCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | MSALNSFNMYKSALILGS<br>LLATAGAQQIGTYTAETH<br>PSLSWSTCKSGGSCTTNSG<br>AITLDANWRWVHGVNTS<br>TNCYGNTWNTAICDTDA<br>SCAQDCALDGADYSGTYG<br>ITTSGNSLRLNFVTGSNVG<br>SRTYLMADNTHYQIFDLL<br>NQEFTFTVDVSHLPCGLN<br>GALYFVTMDADGGVSKY<br>PNNKAGAQYGVGYCDSQ<br>CPRDLKFIAGQANVEGWT<br>PSSNNANTGLGNHGACCA<br>ELDIWEANSISEALTPHPC<br>DTPGLSVCTTDACGGTYS<br>SDRYAGTCDPDGCDFNPY<br>RLGVTDFYGSGKTVDTTK<br>PITVVTQFVTDDGTSTGTL<br>SEIRRYYVQNGVVIPQPSS<br>KISGVSGNVINSDFCDAEIS<br>TFGETASFSKHGGLAKMG<br>AGMEAGMVLVMSLWDD<br>YSVNMLWLDSTYPTNAT<br>GTPGAARGSCPTTSGDPK<br>TVESQSGSSYVTFSDIRVG<br>PFNSTFSGGSSTGGSSTTT<br>ASGTTTTKASSTSTSSTST<br>GTGVAAHWGQCGGQGW<br>TGPTTCASGTTCTVVNPY<br>YSQCL |
| 159293 | E7 | Point Mutant Recombi-nation | Activity-<br>SEQ ID<br>121, 122 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG<br>TCGGATCTCGTACCTACCTGATGGCCGATAACACCCACTACCAAATCTTCGACT | MSALNSFNMYKSALILGS<br>LLATAGAQQIGTYTAETH<br>PSLSWSTCKSGGSCTTNSG<br>AITLDANWRWVHGVNTS<br>TNCYGNTWNTAICDTDA<br>SCAQDCALDGADYSGTYG<br>ITTSGNSLRLNFVTGSNVG<br>SRTYLMADNTHYQIFDLL |

TABLE 5-continued

| Plate Name | Well | Mutation Type | Mutant Property | Nucleotide Sequence | AA Sequence |
|---|---|---|---|---|---|
| | | | | TGTTGAACCAGGAGTTCACTTTCACCGTCGATGTCTCCCACCTCGGGTGCGGTT<br>TGAACGGTGCCCTCTACTTCGTGACCATGGACGCCGACGGTGGCGTCTCCAAG<br>TACCCCAACAACAAGGCCGGCGCTCAGTACGGTGTTGGATACTGTGACTCTCA<br>ATGCCCTCGTGACTTGAAATTCATCGCTGGTCAGGCCAACGTTGAGGGCTGGA<br>CGCCCAAGTCCAACAACGCCATACTGGATATGGCAACCACGGAGCTTGCTGC<br>GCAGAGCTTGATATCTGGGAGGCAAACAGCATCTCAGAGGCTTTGACTCCTCA<br>CCCTTGCGATACACCCGGTCTATCTGTTTGCACTACTGATGCCTGCGGTGGTAC<br>CTACAGCTCCGATCGTTACGCCGGTACCTGCGACCCTGATGGATGTGACTTCAA<br>CCCTTACCGTCTTGGTGTCACTGACTTCTACGGCTCCGGCAAGACCGTTGACAC<br>CACCAAACCCATCACCGTTGTGACTCAATTCGTCACTGACGACGGCACATCCAC<br>CGGCACCCTCTCCGAGATCAGACGTTACTACGTTCAGAACGGTGTTGTCATCCC<br>CCAGCCTTCCTCCGATATCTCCGGAGTCAGCGGAGTTGTCATCAACTCCGACTT<br>CTGCGATGCTGAGATCTCCACCTTTGGCGAGACTGCCTCCTTCAGCAAACACGG<br>TGGCCTGGCAAAGATGGGCGCTGGTATGGAAGCTGGTATGGTCTTGGTCATGA<br>GTTTGTGGGACGACTACTCCGTCAACATGCTCTGGCTCGACAGCACCTACCCTA<br>CAAACGCGACTGGTACCCCCGGTGCCGCTCGTGGTTCCTGCCCTACCACTTCTG<br>GGGACCCTAAGACCGTTAATACAATCCGGCAGCTCCTATGTCACCTTTTCTG<br>ACATCCGGTGGGTCCTTTCAACTCTACGTTCAGCGGTGTTCTAGCACCGGTG<br>GCAGCTCCACTACTACCGCCAGCGGCACCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | NQEFTFTVDVSHLGCGLN<br>GALYFVTMDADGGVSKY<br>PNNKAGAQYGVGYCDSQ<br>CPRDLKFIAGQANVEGWT<br>PKSNNAHTGYGNHGACC<br>AELDIWEANSISEALTPHP<br>CDTPGLSVCTTDACGGTY<br>SSDRYAGTCDPDGCDFNP<br>YRLGVTDFYGSGKTVDTT<br>KPITVVTQFVTDDGTSTGT<br>LSEIRRYYVQNGVVIPQPS<br>SDISGVSGVVINSDFCDAEI<br>STFGETASFSKHGGLAKM<br>GAGMEAGMVLVMSLWD<br>DYSVNMLWLDSTYPTNA<br>TGTPGAARGSCPTTSGDP<br>KTVESQSGSSYVTFSDIRW<br>GPFNSTFSGGSSTGGSSTT<br>TASGTTTTKASSTSTSSTS<br>TGTGVAAHWGQCGGQG<br>WTGPTTCASGTTCTVVNP<br>YYSQCL |
| 159294 | E3 | Point Mutant Recombi-nation | Activ-ity-SEQ ID 123, 124 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACACTGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG<br>TCGGATCTCGTACCTACCTGATGGCCGATAACACCCACTACCAAATCTTCGACT<br>TGTTGAACCAGGAGTTCACTTTCACCGTCGATGTCTCCCACCTCCCTTGCGTT<br>TGAACGGTGCCCTCTACTTCGTGACCATGGACGCCGACGGTGGCGTCTCCAAG<br>TACCCCAACAACAAGGCCGGCGCTCAGTACGGTGTTGGATACTGTGACTCTCA<br>ATGCCCTCGTGACTTGAAATTCATCGCTGGTCAGGCCAACGTTGAGGGCTGGA<br>CGCCCTCCTCCAACAACGCCCATACTGGATATGGCAACCACGGAGCTTGCTGC<br>GCAGAGCTTGATATCTGGGAGGCAAACAGCATCTCAGAGGCTTTGACTCCTCA<br>CCCTTGCGATACACCCGGTCTATCTGTTTGCACTACTGATGCCTGCGGTGGTAC<br>CTACAGCTCCGATCGTTACGCCGGTACCTGCGACCCTGATGGATGTGACTTCAA<br>CCCTTACCGTCTTGGTGTCACTGACTTCTACGGCTCCGGCAAGACCGTTGACAC<br>CACCAAACCCATCACCGTTGTGACTCAATTCGTCACTGACGACGGCACATCCAC<br>CGGCACCCTCTCCGAGATCAGACGTTACTACGTTCAGAACGGTGTTGTCATCCC<br>CCAGCCTTCCTCCGATATCTCCGGAGTCAGCGGAGTTGTCATCAACTCCGACTT<br>CTGCGATGCTGAGATCTCCACCTTTGGCGAGACTGCCTCCTTCAGCAAACACGG<br>TGGCCTGGCAAAGATGGGCGCTGGTATGAGTGCTGGTATGGTCTTGGTCATGA<br>GTTTGTGGGACGACTACTCCGTCAACATGCTCTGGCTCGACAGCACCTACCCTA<br>CAAACGCGACTGGTACCCCCGGTGCCGCTCGTGGTTCCTGCCCTACCACTTCTG<br>GGGACCCTAAGACCGTTAATACAATCCGGCAGCTCCTATGTCACCTTTTCTG<br>ACATCCGGTGGGTCCTTTCAACTCTACGTTCAGCGGTGTTCTAGCACCGGTG<br>GCAGCTCCACTACTACCGCCAGCGGCACCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | MSALNSFNMYKSALILGS<br>LLATAGAQQIGTYTAETH<br>PSLSWSTCKSGGSCTTNSG<br>AITLDANWRWVHGVNTS<br>TNCYTGNTWNTAICDTDA<br>SCAQDCALDGADYSGTYG<br>ITTSGNSLRLNFVTGSNVG<br>SRTYLMADNTHYQIFDLL<br>NQEFTFTVDVSHLPCGLN<br>GALYFVTMDADGGVSKY<br>PNNKAGAQYGVGYCDSQ<br>CPRDLKFIAGQANVEGWT<br>PSSNNAHTGYGNHGACCA<br>ELDIWEANSISEALTPHPC<br>DTPGLSVCTTDACGGTYS<br>SDRYAGTCDPDGCDFNPY<br>RLGVTDFYGSGKTVDTTK<br>PITVVTQFVTDDGTSTGTL<br>SEIRRYYVQNGVVIPQPSS<br>DISGVSGVVINSDFCDAEIS<br>TFGETASFSKHGGLAKMG<br>AGMSAGMVLVMSLWDD<br>YSVNMLWLDSTYPTNAT<br>GTPGAARGSCPTTSGDPK<br>TVESQSGSSYVTFSDIRWG<br>PFNSTFSGGSSTGGSSTTT<br>ASGTTTTKASSTSTSSTST<br>GTGVAAHWGQCGGQGW<br>TGPTTCASGTTCTVVNPY<br>YSQCL |
| 159294 | G10 | Point Mutant Recombi-nation | Activ-ity-SEQ ID 125, 126 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACACTGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG<br>TCGGATCTCGTACCTACCTGATGGCCGATAACACCCACTACCAAATCTTCGACT<br>TGTTGAACCAGGAGTTCACTTTCACCGTCGATGTCTCCCACCTCCCTTGCGTT<br>TGAACGGTGCCCTCTACTTCGTGACCATGGACGCCGACGGTGGCGTCTCCAAG<br>TACCCCAACAACAAGGCCGGCGCTCAGTACGGTGTTGGATACTGTGACTCTCA<br>ATGCCCTCGTGACTTGAAATTCATCGCTGGTCAGGCCAACGTTGAGGGCTGGA<br>CGCCCTCCTCCAACAACGCCAACACTGGACTTGGCAACCACGGAGCTTGCTGC<br>GCAGAGCTTGATATCTGGGAGGCAAACAGCATCTCAGAGGCTTTGACTCCTCA<br>CCCTTGCGATACACCCGGTCTATCTGTTTGCACTACTGATGCCTGCGGTGGTAC<br>CTACAGCTCCGATCGTTACGCCGGTACCTGCGACCCTGATGGATGTGACTTCAA<br>CCCTTACCGTCTTGGTGTCACTGACTTCTACGGCTCCGGCAAGACCGTTGACAC<br>CACCAAACCCATCACCGTTGTGACTCAATTCGTCACTGACGACGGCACATCCAC<br>CGGCACCCTCCTTGAGATCAGACGTTACTACGTTCAGAACGGTGTTGTCATCCC<br>CCAGCCTTCCTCCGATATCTCCGGAGTCAGCGGAGTTGTCATCAACTCCGACTT<br>CTGCGATGCTGAGATCTCCACCTTTGGCGAGACTGCCTCCTTCAGCAAACACGG<br>TGGCCTGGCAAAGATGGGCGCTGGTATGGAAGCTGGTATGGTCTTGGTCATGA<br>GTTTGTGGGACGACTACTCCGTCAACATGCTCTGGCTCGACAGCACCTACCCTA | MSALNSFNMYKSALILGS<br>LLATAGAQQIGTYTAETH<br>PSLSWSTCKSGGSCTTNSG<br>AITLDANWRWVHGVNTS<br>TNCYTGNTWNTAICDTDA<br>SCAQDCALDGADYSGTYG<br>ITTSGNSLRLNFVTGSNVG<br>SRTYLMADNTHYQIFDLL<br>NQEFTFTVDVSHLPCGLN<br>GALYFVTMDADGGVSKY<br>PNNKAGAQYGVGYCDSQ<br>CPRDLKFIAGQANVEGWT<br>PSSNNANTGLGNHGACCA<br>ELDIWEANSISEALTPHPC<br>DTPGLSVCTTDACGGTYS<br>SDRYAGTCDPDGCDFNPY<br>RLGVTDFYGSGKTVDTTK<br>PITVVTQFVTDDGTSTGTL<br>LEIRRYYVQNGVVIPQPSS<br>DISGVSGVVINSDFCDAEIS<br>TFGETASFSKHGGLAKMG<br>AGMEAGMVLVMSLWDD<br>YSVNMLWLDSTYPTNAT |

TABLE 5-continued

| Plate Name | Well | Mutation Type | Mutant Property | Nucleotide Sequence | AA Sequence |
|---|---|---|---|---|---|
| | | | | CAAACGCGACTGGTACCCCGGTGCCGCTCGTGGTTCCTGCCCTACCACTTCTG<br>GGGACCCTAAGACCGTTAATCACAATCCGGCAGCTCCTATGTCACCTTTTCTG<br>ACATCCGGGTTGGTCCTTTCAACTCTACGTTCAGCGGTGGTTCTAGCACCGGT<br>GCAGCTCCACTACTACCGCCAGCGGCACCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | GTPGAARGSCPTTSGDPK<br>TVESQSGSSYVTFSDIRVG<br>PFNSTFSGGSSTGGSSTTT<br>ASGTTTTKASSTSTSSTST<br>GTGVAAHWGQCGGQGW<br>TGPTTCASGTTCTVVNPY<br>YSQCL |
| 159297 | B8 | Point Mutant Recombination | Activity-<br>SEQ ID<br>127, 128 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACACTGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG<br>TCGGATCTCGTACCTACCTGATGGCCGATAACACCCACTACCAAATCTTCGACT<br>TGTTGAACCAGGAGTTCACTTTCACCGTCGATGTCTCCCACCTCCCTTGCGGTT<br>TGAACGGTGCCCTCTACTTCGTGACCATGGACGCCGACGGTGGCGTCTCCAAG<br>TACCCCAACAACAAGGCCGGCGCTCAGTACGGTGTTGGATACTGTGACTCTCA<br>ATGCCCTCGTGACTTGAAATTCATCGCTGGTCAGGCCAACGTTGAGGGCTGGA<br>CGCCCTCCTCCAACAACGCCAACACTGGATATGGCAACCACGGAGCTTGCTGC<br>GCAGAGCTTGATATCTGGGAGGCAAACAGCATCTCAGAGGCTTTGACTCCTCA<br>CCCCTTGCGATACACCCGGTCTATCTGTTTGCACTACTGATGCCTGCGGTGGTAC<br>CTACAGCTCCGATCGTTACGCCGGTACCTGCGACCCTGATGGATGTGACTTCAA<br>CCCCTTACCGTCTTGGTGTCACTGACTTCTACGGCTCCGGCAAGACCGTTGACAC<br>CACCAAACCCATCACCGTTGTGACTCAATTCGTCACTGACCAGGGCACATCCAC<br>CGGCCGTCTCCTTGAGATCAGACGTTACTACGTTCAGAACGGTGTTGTCATCCC<br>CCAGCCTTCCTCCGATATCTCCGGAGTCAGCGGAAATGTCATCAACTCCGACTT<br>CTGCGATGCTGAGATCTCCACCTTTGGCGAGACTGCCTCCTTCAGCAAACACGG<br>TGGCCTGGCAAAGATGGGCGCTGGTATGAGTGCTGGTATGGTCTTGGTCATGA<br>GTTTGTGGGACGACTACTCCGTCAACATGCTCTGGCTCGACAGCACCTACCCTA<br>CAAACGCGACTGGTACCCCGGTGCCGCTCGTGGTTCCTGCCCTACCACTTCTG<br>GGGACCCTAAGACCGTTAATCACAATCCGGCAGCTCCTATGTCACCTTTTCTG<br>ACATCCGGGTTGGTCCTTTCAACTCTACGTTCAGCGGTGGTTCTAGCACCGGTG<br>GCAGCTCCACTACTACCGCCAGCGGCACCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | MSALNSFNMYKSALILGS<br>LLATAGAQQIGTYTAETH<br>PSLSWSTCKSGGSCTTNSG<br>AITLDANWRWVHGVNTS<br>TNCYTGNTWNTAICDTDA<br>SCAQDCALDGADYSGTYG<br>ITTSGNSLRLNFVTGSNVG<br>SRTYLMADNTHYQIFDLL<br>NQEFTFTVDVSHLPCGLN<br>GALYFVTMDADGGVSKY<br>PNNKAGAQYGVGYCDSQ<br>CPRDLKFIAGQANVEGWT<br>PSSNNANTGYGNHGACCA<br>ELDIWEANSISEALTPHPC<br>DTPGLSVCTTDACGGTYS<br>SDRYAGTCDPDGCDFNPY<br>RLGVTDFYGSGKTVDTTK<br>PITVVTQFVTDQGTSTGRL<br>LEIRRYYVQNGVVIPQPSS<br>DISGVSGNVINSDFCDAEIS<br>TFGETASFSKHGGLAKMG<br>AGMSAGMVLVMSLWDD<br>YSVNMLWLDSTYPTNAT<br>GTPGAARGSCPTTSGDPK<br>TVESQSGSSYVTFSDIRVG<br>PFNSTFSGGSSTGGSSTTT<br>ASGTTTTKASSTSTSSTST<br>GTGVAAHWGQCGGQGW<br>TGPTTCASGTTCTVVNPY<br>YSQCL |
| 159305 | E7 | Point Mutant Recombination | Activity-<br>SEQ ID<br>129, 130 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACACTGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG<br>TCGGATCTCGTACCTACCTGATGGCCGATAACACCCACTACCAAATCTTCGACT<br>TGTTGAACCAGGAGTTCACTTTCACCGTCGATGTCTCCCACCTCGGTGCGGTT<br>TGAACGGTGCCCTCTACTTCGTGACCATGGACGCCGACGGTGGCGTCTCCAAG<br>TACCCCAACAACAAGGCCGGCGCTCAGTACGGTGTTGGATACTGTGACTCTCA<br>ATGCCCTCGTGACTTGAAATTCATCGCTGGTCAGGCCAACGTTGAGGGCTGGA<br>CGCCCAAGTCCAACAACGCCCATACTGGATATGGCAACCACGGAGCTTGCTGC<br>GCAGAGCTTGATATCTGGGAGGCAAACAGCATCTCAGAGGCTTTGACTCCTCA<br>CCCCTTGCGATACACCCGGTCTATCTGTTTGCACTACTGATGCCTGCGGTGGTAC<br>CTACAGCTCCGATCGTTACGCCGGTACCTGCGACCCTGATGGATGTGACTTCAA<br>CCCCTTACCGTCTTGGTGTCACTGACTTCTACGGCTCCGGCAAGACCGTTGACAC<br>CACCAAACCCATCACCGTTGTGACTCAATTCGTCACTGACGACGGCACATCCAC<br>CGGCACCCTCTCCGAGATCAGACGTTACTACGTTAGTAACGGTGTTGTCATCCC<br>CCAGCCTTCCTCCGATATCTCCGGAGTCAGCGGAAATGTCATCAACTCCGACTT<br>CTGCGATGCTGAGATCTCCACCTTTGGCGAGACTGCCTCCTTCAGCAAACACGG<br>TGGCCTGGCAAAGATGGGCGCTGGTATGAGTGCTGGTATGGTCTTGGTCATGA<br>GTTTGTGGGACGACTACTCCGTCAACATGCTCTGGCTCGACAGCACCTACCCTA<br>CAAACGCGACTGGTACCCCGGTGCCGCTCGTGGTTCCTGCCCTACCACTTCTG<br>GGGACCCTAAGACCGTTAATCACAATCCGGCAGCTCCTATGTCACCTTTTCTG<br>ACATCCGGGTTGGTCCTTTCAACTCTACGTTCAGCGGTGGTTCTAGCACCGGTG<br>GCAGCTCCACTACTACCGCCAGCGGCACCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | MSALNSFNMYKSALILGS<br>LLATAGAQQIGTYTAETH<br>PSLSWSTCKSGGSCTTNSG<br>AITLDANWRWVHGVNTS<br>TNCYTGNTWNTAICDTDA<br>SCAQDCALDGADYSGTYG<br>ITTSGNSLRLNFVTGSNVG<br>SRTYLMADNTHYQIFDLL<br>NQEFTFTVDVSHLGCGLN<br>GALYFVTMDADGGVSKY<br>PNNKAGAQYGVGYCDSQ<br>CPRDLKFIAGQANVEGWT<br>PKSNNAHTGYGNHGACC<br>AELDIWEANSISEALTPHP<br>CDTPGLSVCTTDACGGTY<br>SSDRYAGTCDPDGCDFNP<br>YRLGVTDFYGSGKTVDTT<br>KPITVVTQFVTDDGTSTGT<br>LSEIRRYYVSNGVVIPQPS<br>SDISGVSGNVINSDFCDAEI<br>STFGETASFSKHGGLAKM<br>GAGMSAGMVLVMSLWD<br>DYSVNMLWLDSTYPTNA<br>TGTPGAARGSCPTTSGDP<br>KTVESQSGSSYVTFSDIRV<br>GPFNSTFSGGSSTGGSSTT<br>TASGTTTTKASSTSTSSTS<br>TGTGVAAHWGQCGGQG<br>WTGPTTCASGTTCTVVNP<br>YYSQCL |
| 159734 | B5 | Point Mutant Recombination | Activity-<br>SEQ ID<br>131, 132 | ATGTCTGCCTTGAACTCTTTCAATATGTACAAGAGCGCCCTCATCTTGGGCTCC<br>TTGCTGGCAACAGCTGGTGCTCAGCAAATTGGTACTTATACCGCTGAAACCCAT<br>CCCTCTTTGAGCTGGTCTACTTGCAAATCGGGTGGTAGCTGCACCACAAACTCC<br>GGTGCCATTACGTTGGATGCCAACTGGCGTTGGGTCCATGGTGTCAATACCAG<br>CACCAACTGCTACACTGGCAACACTTGGAATACCGCCATCTGCGACACTGATG<br>CATCCTGTGCCCAGGACTGTGCTCTTGATGGTGCTGACTACTCTGGCACGTACG<br>GTATCACTACCTCCGGCAACTCATTGCGCCTGAACTTCGTTACCGGTTCCAACG | MSALNSFNMYKSALILGS<br>LLATAGAQQIGTYTAETH<br>PSLSWSTCKSGGSCTTNSG<br>AITLDANWRWVHGVNTS<br>TNCYTGNTWNTAICDTDA<br>SCAQDCALDGADYSGTYG<br>ITTSGNSLRLNFVTGSNVG |

TABLE 5-continued

| Plate Name | Mutation Well | Mutant Type | Property | Nucleotide Sequence | AA Sequence |
|---|---|---|---|---|---|
| | | | | TCGGATCTCGTACCTACCTGATGGCCGATAACACCCACTACCAAATCTTCGACT | SRTYLMADNTHYQIFDLL |
| | | | | TGTTGAACCAGGAGTTCACTTTCACCGTCGATGTCTCCCACCTCCCTTGCCGTT | NQEFTFTVDVSHLPCGLN |
| | | | | TGAACGGTGCCCTCTACTTCGTGACCATGGACGCCGACGGTGGCGTCTCCAAG | GALYFVTMDADGGVSKY |
| | | | | TACCCCAACAACAAGGCCGGCGCTCAGTACGGTGTTGGATACTGTGACTCTCA | PNNKAGAQYGVGYCDSQ |
| | | | | ATGCCCTCGTGACTTGAAATTCATCGCTGGTCAGGCCAACGTTGAGGGCTGGA | CPRDLKFIAGQANVEGWT |
| | | | | CGCCCTCCTCCAACAACGCCAACACTGGACTTGGCAACCACGGAGCTTGCTGC | PSSNNANTGLGNHGACCA |
| | | | | GCAGAGCTTGATATCTGGGAGGCAAACAGCATCTCAGAGGCTTTGACTCCTCA | ELDIWEANSISEALTPHPC |
| | | | | CCCTTGCGATACACCCGGTCTATCTGTTTGCACTACTGATGCCTGCGGTGGTAC | DTPGLSVCTTDACGGTYS |
| | | | | CTACAGCTCCGATCGTTACGCCGGTACCTGCGACCCTGATGGATGTGACTTCAA | SDRYAGTCDPDGCDFNPY |
| | | | | CCCTTACCGTCTTGGTGTCACTGACTTCTACGGCTCCGGCAAGACCGTTGACAC | RLGVTDFYGSGKTVDTTK |
| | | | | CACCAAACCCATCACCGTTGTGACTCAATTCGTCACTGACGACGGCACATCCAC | PITVVTQFVTDDGTSTGTL |
| | | | | CGGCACCCTCTCCGAGATCAGACGTTACTACGTTCAGAACGGTGTTGTCATCCC | SEIRRYYVQNGVVIPQPSS |
| | | | | CCAGCCTTCCTCCAAGATCTCCGGAGTCAGCGGAAATGTCATCAACTCCGACTT | KISGVSGNVINSDFCDAEIS |
| | | | | CTGCGATGCTGAGATCTCCACCTTTGGCGAGACTGCCTCCTTCAGCAAACACGG | TFGETASFSKHGGLAKMG |
| | | | | TGGCCTGGCAAAGATGGGCGCTGGTATGAGTGCTGGTATGGTCTTGGTCATGA | AGMSAGMVLVMSLWDD |
| | | | | GTTTGTGGGACGACTACTCCGTCAACATGCTCTGGCTCGACAGCACCTACCCTA | YSVNMLWLDSTYPTNAT |
| | | | | CAAACGCGACTGGTACCCCCGGTGCCGCTCGTGGTTCCTGCCCTACCACTTCTG | GTPGAARGSCPTTSGDPK |
| | | | | GGGACCCTAAGACCGTTGAATCACAATCCGGCAGCTCCTATGTCACCTTTTCTG | TVESQSGSSYVTFSDIRWG |
| | | | | ACATCCGGTGGGGTCCTTTCAACTCTACGTTCAGCGGTGGTTCTAGCACCGGTG | PFNSTFSGGSSTGGSSTTT |
| | | | | GCAGCTCCACTACTACCGCCAGCGGCACCACCACCACCAAGGCCTCTTCCACCT | ASGTTTTKASSTSTSSSTST |
| | | | | CTACTTCCAGCACCTCTACCGGCACTGGAGTCGCTGCTCACTGGGGTCAGTGTG | GTGVAAHWGQCGGQGW |
| | | | | GTGGCCAGGGTTGGACTGGTCCTACCACCTGCGCTAGTGGAACCACATGCACC | TGPTTCASGTTCTVVNPY |
| | | | | GTCGTGAACCCTTACTACTCTCAATGTTTGTAA | YSQCL |
| | Product Release Site | Activity-SEQ ID 135, 136 | | ATGTCTGCCTTGAACTCTTTCAATATGTACAAGAGCGCCCTCATCTTGGGCTCC | MSALNSFNMYKSALILGS |
| | | | | TTGCTGGCAACAGCTGGTGCTCAGCAAATTGGTACTTATACCGCTGAAACCCAT | LLATAGAQQIGTYTAETH |
| | | | | CCCTCTTTGAGCTGGTCTACTTGCAAATCGGGTGGTAGCTGCACCACAAACTCC | PSLSWSTCKSGGSCTTNSG |
| | | | | GGTGCCATTACGTTGGATGCCAACTGGCGTTGGGTCCATGGTGTCAATACCAG | AITLDANWRWVHGVNTS |
| | | | | CACCAACTGCTACACTGGCAACACTTGGAATACCGCCATCTGCGACACTGATG | TNCYTGNTWNTAICDTDA |
| | | | | CATCCTGTGCCCAGGACTGTGCTCTTGATGGTGCTGACTACTCTGGCACGTACG | SCAQDCALDGADYSGTYG |
| | | | | GTATCACTACCTCCGGCAACTCATTGCGCCTGAACTTCGTTACCGGTTCCAACG | ITTSGNSLRLNFVTGSNVG |
| | | | | TCGGATCTCGTACCTACCTGATGGCCGATAACACCCACTACCAAATCTTCGACT | SRTYLMADNTHYQIFDLL |
| | | | | TGTTGAACCAGGAGTTCACTTTCACCGTCGATGTCTCCCACCTCCCTTGCCGTT | NQEFTFTVDVSHLPCGLN |
| | | | | TGAACGGTGCCCTCTACTTCGTGACCATGGACGCCGACGGTGGCGTCTCCAAG | GALYFVTMDADGGVSKY |
| | | | | TACCCCAACAACAAGGCCGGCGCTCAGTACGGTGTTGGATACTGTGACTCTCA | PNNKAGAQYGVGYCDSQ |
| | | | | ATGCCCTCGTGACTTGAAATTCATCGCTGGTCAGGCCAACGTTGAGGGCTGGA | CPRDLKFIAGQANVEGWT |
| | | | | CGCCCTCCTCCAACAACGCCAACACTGGACTTGGCAACCACGGAGCTTGCTGC | PSSNNANTGLGNHGACCA |
| | | | | GCAGAGCTTGATATCTGGGAGGCAAACAGCATCTCAGAGGCTTTGACTCCTCA | ELDIWEANSISEALTPHPC |
| | | | | CCCTTGCGATACACCCGGTCTATCTGTTTGCACTACTGATGCCTGCGGTGGTAC | DTPGLSVCTTDACGGTYS |
| | | | | CTACAGCTCCGATAAGTACGCCGGTACCTGCGACCCTGATGGATGTGACTTCA | SDKYAGTCDPDGCDFNPY |
| | | | | ACCCTTACCGTCTTGGTGTCACTGACTTCTACGGCTCCGGCAAGACCGTTGACA | RLGVTDFYGSGKTVDTTK |
| | | | | CCACCAAACCCATCACCGTTGTGACTCAATTCGTCACTGACGACGGCACATCCA | PITVVTQFVTDDGTSTGTL |
| | | | | CCGGCACCCTCTCCGAGATCAGACGTTACTACGTTCAGAACGGTGTTGTCATCC | SEIRRYYVQNGVVIPQPSS |
| | | | | CCCAGCCTTCCTCCAAGATCTCCGGAGTCAGCGGAAATGTCATCAACTCCGACT | KISGVSGNVINSDFCDAEIS |
| | | | | TCTGCGATGCTGAGATCTCCACCTTTGGCGAGACTGCCTCCTTCAGCAAACACG | TFGETASFSKHGGLAKMG |
| | | | | GTGGCCTGGCAAAGATGGGCGCTGGTATGGAAGCTGGTATGGTCTTGGTCATG | AGMEAGMVLVMSLWDD |
| | | | | AGTTTGTGGGACGACTACTCCGTCAACATGCTCTGGCTCGACAGCACCTACCCT | YSVNMLWLDSTYPTNAT |
| | | | | ACAAACGCGACTGGTACCCCCGGTGCCGCTAAGGGTTCCTGCCCTACCACTTCT | GTPGAAKGSCPTTSGDPK |
| | | | | GGGGACCCTAAGACCGTTGAATCACAATCCGGCAGCTCCTATGTCACCTTTTCT | TVESQSGSSYVTFSDIRVG |
| | | | | GACATCCGGGTTGGTCCTTTCAACTCTACGTTCAGCGGTGGTTCTAGCACCGGT | PFNSTFSGGSSTGGSSTTT |
| | | | | GGCAGCTCCACTACTACCGCCAGCGGCACCACCACCACCAAGGCCTCTTCCACC | ASGTTTTKASSTSTSSSTST |
| | | | | TCTACTTCCAGCACCTCTACCGGCACTGGAGTCGCTGCTCACTGGGGTCAGTGT | GTGVAAHWGQCGGQGW |
| | | | | GGTGGCCAGGGTTGGACTGGTCCTACCACCTGCGCTAGTGGAACCACATGCAC | TGPTTCASGTTCTVVNPY |
| | | | | CGTCGTGAACCCTTACTACTCTCAATGTTTGTAG | YSQCL |
| | Parent | Activity-SEQ ID 133, 134 | | ATGTCTGCCTTGAACTCTTTCAATATGTACAAGAGCGCCCTCATCTTGGGCTCC | MSALNSFNMYKSALILGS |
| | | | | TTGCTGGCAACAGCTGGTGCTCAGCAAATTGGTACTTATACCGCTGAAACCCAT | LLATAGAQQIGTYTAETH |
| | | | | CCCTCTTTGAGCTGGTCTACTTGCAAATCGGGTGGTAGCTGCACCACAAACTCC | PSLSWSTCKSGGSCTTNSG |
| | | | | GGTGCCATTACGTTGGATGCCAACTGGCGTTGGGTCCATGGTGTCAATACCAG | AITLDANWRWVHGVNTS |
| | | | | CACCAACTGCTACACTGGCAACACTTGGAATACCGCCATCTGCGACACTGATG | TNCYTGNTWNTAICDTDA |
| | | | | CATCCTGTGCCCAGGACTGTGCTCTTGATGGTGCTGACTACTCTGGCACGTACG | SCAQDCALDGADYSGTYG |
| | | | | GTATCACTACCTCCGGCAACTCATTGCGCCTGAACTTCGTTACCGGTTCCAACG | ITTSGNSLRLNFVTGSNVG |
| | | | | TCGGATCTCGTACCTACCTGATGGCCGATAACACCCACTACCAAATCTTCGACT | SRTYLMADNTHYQIFDLL |
| | | | | TGTTGAACCAGGAGTTCACTTTCACCGTCGATGTCTCCCACCTCCCTTGCCGTT | NQEFTFTVDVSHLPCGLN |
| | | | | TGAACGGTGCCCTCTACTTCGTGACCATGGACGCCGACGGTGGCGTCTCCAAG | GALYFVTMDADGGVSKY |
| | | | | TACCCCAACAACAAGGCCGGCGCTCAGTACGGTGTTGGATACTGTGACTCTCA | PNNKAGAQYGVGYCDSQ |
| | | | | ATGCCCTCGTGACTTGAAATTCATCGCTGGTCAGGCCAACGTTGAGGGCTGGA | CPRDLKFIAGQANVEGWT |
| | | | | CGCCCTCCTCCAACAACGCCAACACTGGACTTGGCAACCACGGAGCTTGCTGC | PSSNNANTGLGNHGACCA |
| | | | | GCAGAGCTTGATATCTGGGAGGCAAACAGCATCTCAGAGGCTTTGACTCCTCA | ELDIWEANSISEALTPHPC |
| | | | | CCCTTGCGATACACCCGGTCTATCTGTTTGCACTACTGATGCCTGCGGTGGTAC | DTPGLSVCTTDACGGTYS |
| | | | | CTACAGCTCCGATCGTTACGCCGGTACCTGCGACCCTGATGGATGTGACTTCAA | SDRYAGTCDPDGCDFNPY |
| | | | | CCCTTACCGTCTTGGTGTCACTGACTTCTACGGCTCCGGCAAGACCGTTGACAC | RLGVTDFYGSGKTVDTTK |
| | | | | CACCAAACCCATCACCGTTGTGACTCAATTCGTCACTGACGACGGCACATCCAC | PITVVTQFVTDDGTSTGTL |
| | | | | CGGCACCCTCTCCGAGATCAGACGTTACTACGTTCAGAACGGTGTTGTCATCCC | SEIRRYYVQNGVVIPQPSS |
| | | | | CCAGCCTTCCTCCAAGATCTCCGGAGTCAGCGGAAATGTCATCAACTCCGACTT | KISGVSGNVINSDFCDAEIS |
| | | | | CTGCGATGCTGAGATCTCCACCTTTGGCGAGACTGCCTCCTTCAGCAAACACGG | TFGETASFSKHGGLAKMG |
| | | | | TGGCCTGGCAAAGATGGGCGCTGGTATGGAAGCTGGTATGGTCTTGGTCATGA | AGMEAGMVLVMSLWDD |

TABLE 5-continued

| Plate Name | Well | Mutation Type | Mutant Property | Nucleotide Sequence | AA Sequence |
|---|---|---|---|---|---|
| | | | | GTTTGTGGGACGACTACTCCGTCAACATGCTCTGGCTCGACAGCACCTACCCTA<br>CAAACGCGACTGGTACCCCCGGTGCCGCTCGTGGTTCCTGCCCTACCACTTCTG<br>GGGACCCTAAGACCGTTGAATCACAATCCGGCAGCTCCTATGTCACCTTTTCTG<br>ACATCCGGGTTGGTCCTTTCAACTCTACGTTCAGCGGTGGTTCTAGCACCGGTG<br>GCAGCTCCACTACTACCGCCAGCGGCACCACCACCAAGGCCTCTTCCACCT<br>CTACTTCCAGCACCTCTACCGGCACTGGAGTCGCTGCTCACTGGGGTCAGTGTG<br>GTGGCCAGGGTTGGACTGGTCCTACCACCTGCGCTAGTGGAACCACATGCACC<br>GTCGTGAACCCTTACTACTCTCAATGTTTGTAA | YSVNMLWLDSTYPTNAT<br>GTPGAARGSCPTTSGDPK<br>TVESQSGSSYVTFSDIRVG<br>PFNSTFSGGSSTGGSSTTT<br>ASGTTTTKASSTSTSSTST<br>GTGVAAHWGQCGGQGW<br>TGPTTCASGTTCTVVNPY<br>YSQCL |

TABLE 6

| Plate Name | Well | Mutation Type | Mutant Property | % improvement over WT @ 48 hr | % improvement over WT @ 72 hr | Dose Reduction |
|---|---|---|---|---|---|---|
| 143588 | B10 | EntrySite | Activity-SEQ ID 95, 96 | 10.3% | NA | |
| 143593 | H9 | EntrySite | Activity-SEQ ID 97, 98 | 8.5% | NA | |
| 143603 | H11 | EntrySite | Activity-SEQ ID 99, 100 | 6.7% | NA | 0.5X |
| 143606 | E8 | EntrySite | Activity-SEQ ID 101, 102 | 10.9% | NA | |
| 143678 | H8 | EntrySite | Activity-SEQ ID 103, 104 | 15.9% | NA | |
| 143581 | H2 | EntrySite | Activity-SEQ ID 105, 106 | 11.8% | NA | 0.5X |
| 143458 | H9 | EntrySite | Activity-SEQ ID 107, 108 | 23.2% | NA | 0.75X |
| 143496 | H1 | EntrySite | Activity-SEQ ID 109, 110 | 11.9% | NA | |
| 143497 | A9 | EntrySite | Activity-SEQ ID 111, 112 | 9.5% | NA | |
| 143461 | H2 | EntrySite | Activity-SEQ ID 113, 114 | 22.2% | NA | 0.8X |
| 143602 | H11 | EntrySite | Activity-SEQ ID 115, 116 | 18.3% | NA | 0.75X |
| 143606 | A11 | EntrySite | Activity-SEQ ID 117, 118 | 7.9% | NA | |
| 156605 | H4 | Loop GeneReassembly | Activity-SEQ ID 119, 120 | 18.1% | NA | |
| 159293 | E7 | PointMutantRecombination | Activity-SEQ ID 121, 122 | NA | 5.4% | |
| 159294 | E3 | PointMutantRecombination | Activity-SEQ ID 123, 124 | NA | 19.6% | 0.75X |
| 159294 | G10 | PointMutantRecombination | Activity-SEQ ID 125, 126 | NA | 18.6% | 0.6X |
| 159297 | B8 | PointMutantRecombination | Activity-SEQ ID 127, 128 | NA | 19.2% | 1X |
| 159305 | E7 | PointMutantRecombination | Activity-SEQ ID 129, 130 | NA | 17.2% | 0.65X |
| 159734 | B5 | PointMutantRecombination | Activity-SEQ ID 131, 132 | NA | 12.2% | 0.75X |
| | | PointMutantRecombination | Activity-SEQ ID 135, 136 | N/A | N/A | N/A |
| | | Parent | Activity-SEQ ID 133, 134 | NULL | NULL | NULL |

The invention is further described by the embodiments of following numbered paragraphs. Most embodiments relate to CBH I polypeptides, CBH I nucleic acids, and their uses. The CBH I polypeptides are preferably variant CBH I polypeptides with improved characteristics relative to BD29555, such as improved activity, thermal tolerance or product inhibition. The polypeptides preferably include one or more of the substitutions (or combinations of substitutions) described in Table A and in the Summary. The nucleic acids preferably encode such variant CBH I polypeptides, and the uses (e.g., methods of making fuel) also employ the variant CBH I polypeptides described herein.

1. An isolated, synthetic or recombinant nucleic acid comprising (a) a nucleic acid sequence (polynucleotide) having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete (100%) sequence identity to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, and/or SEQ ID NO:135, over a region of at least about 20, 30, 40, 50, 75, 100, 150, 200, 250, 300, 350, 400, 450, 500, 550, 600, 650, 700, 750, 800, 850, 900, 950, 1000, 1050, 1100, 1150 or more residues, or the full length of a cDNA, transcript (mRNA) or gene, wherein optionally the nucleic acid (polynucleotide) encodes a polypeptide having a lignocellulosic activity, or encodes a polypeptide or peptide capable of generating an antibody that specifically binds to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132 and/or SEQ ID NO:134, and/or enzymatically active subsequences (fragments) thereof, wherein optionally the lignocellulosic activity comprises a cellulase, a cellulolytic activity or a cellobiohydrolase activity, and optionally the sequence identities are determined by analysis with a sequence comparison algorithm or by a visual inspection, and optionally the sequence comparison algorithm comprises a BLAST version 2.2.2 algorithm where a filtering setting is set to blastall -p blastp -d "nr pataa"-F F, and all other options are set to default;

(b) a nucleic acid sequence (a polynucleotide) that hybridizes under stringent conditions to the nucleic acid of (a), wherein the nucleic acid encodes a polypeptide having a lignocellulosic activity, and optionally the lignocellulosic activity comprises a cellulase, a cellulolytic activity or a cellobiohydrolase activity, and the stringent conditions comprise a wash step comprising a wash in 0.2×SSC at a temperature of about 65° C. for about 15 minutes, and optionally the nucleic acid is at least about 20, 30, 40, 50, 60, 75, 100, 150, 200, 300, 400, 500, 600, 700, 800, 900, 1000 or more residues in length or the full length of the gene, cDNA or transcript (mRNA);

(c) a nucleic acid sequence encoding a polypeptide having the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and/or SEQ ID NO:136, or enzymatically active subsequences (fragments) thereof;

(d) the nucleic acid (polynucleotide) of (a), (b) or (c) and encoding a polypeptide having at least one conservative amino acid substitution and retaining its lignocellulosic activity, wherein optionally the conservative amino acid substitution comprise substituting an amino acid with another amino acid of like characteristics, and optionally a conservative substitution comprises: replacement of an aliphatic amino acid with another aliphatic amino acid; replacement of a Serine with a Threonine or vice versa; replacement of an acidic residue with another acidic residue; replacement of a residue bearing an amide group with another residue bearing an amide group; exchange of a basic residue with another basic residue; or replacement of an aromatic residue with another aromatic residue;

(e) the nucleic acid (polynucleotide) of (a), (b), (c) or (d) encoding a polypeptide having a lignocellulosic activity but lacking a signal sequence, a prepro domain, a dockerin domain, and/or a carbohydrate binding module (CBM), wherein optionally the carbohydrate binding module (CBM) comprises, or consists of, a cellulose binding module, a lignin binding module, a xylose binding module, a mannanse binding module, a xyloglucan-specific module and/or a arabinofuranosidase binding module;

(f) the nucleic acid (polynucleotide) of (a), (b), (c), (d) or (e) encoding a polypeptide having a lignocellulosic activity further comprising a heterologous sequence;

(g) the nucleic acid (polynucleotide) of (f), wherein the heterologous sequence comprises, or consists of a sequence encoding: (i) a heterologous signal sequence, a heterologous carbohydrate binding module, a heterologous dockerin domain, a heterologous catalytic domain (CD), or a combination thereof; (ii) the sequence of (ii), wherein the heterologous signal sequence, carbohydrate binding module or catalytic domain (CD) is derived from a heterologous lignocellulosic enzyme; or, (iii) a tag, an epitope, a targeting peptide, a cleavable sequence, a detectable moiety or an enzyme;

(h) the nucleic acid (polynucleotide) of (g), wherein the heterologous carbohydrate binding module (CBM) comprises, or consists of, a cellulose binding module, a lignin binding module, a xylose binding module, a mannanse binding module, a xyloglucan-specific module and/or a arabinofuranosidase binding module;

(i) the nucleic acid (polynucleotide) of (g), wherein the heterologous signal sequence targets the encoded protein to a vacuole, the endoplasmic reticulum, a chloroplast or a starch granule; or (j) a nucleic acid sequence (polynucleotide) fully (completely) complementary to (a), (b), (c), (d), (e), (f), (g), (h) or (i).

2. The isolated, synthetic or recombinant nucleic acid of paragraph [0317], wherein the lignocellulosic activity comprises (a) a cellulase, a cellulolytic activity or a cellobiohydrolase activity, or any combination thereof;

(b) an activity comprising hydrolyzing (degrading) soluble oligomers to fermentable, monomeric sugars;

(c) an activity comprising hydrolyzing (degrading) soluble cellooligsaccharides and arabinoxylan oligomers into monomers, and optionally the monomers comprise xylose, arabinose and glucose;

(d) catalyzing the hydrolysis of (degrading) plant biomass polysaccharides;

(e) catalyzing the hydrolysis of (degrading) a glucan or lignin to produce a smaller molecular weight polysaccharides or oligomers or monomers;

(f) catalyzing hydrolysis of 1,4-beta-D-glycosidic linkages;

(g) an endocellulase activity comprising an endo-1,4-beta-endocellulase activity;

(f) a 1,4-beta-D-glycosidic linkage hydrolysis activity comprising hydrolysis of a 1,4-beta-D-glycosidic linkage in a cellulose, a cellulose derivative, a lichenin or a cereal, wherein optionally the cellulose derivative comprises a carboxy methyl cellulose or a hydroxy ethyl cellulose, or the cereal comprises a beta-D-glucan or a xyloglucan;

(g) catalyzing hydrolysis of glucanase linkages;

(h) catalyzing hydrolysis of β-1,4- and/or β-1,3-glucanase linkages;

(i) catalyzing hydrolysis of endo-glucan linkages;

(j) catalyzing hydrolysis of endo-1,4-beta-D-glucan 4-glucano hydrolase activity;

(k) catalyzing hydrolysis of internal endo-β-1,4-glucanase linkages and/or β-1,3-glucanase linkages;

(l) catalyzing hydrolysis of internal β-1,3-glucosidic linkages;

(m) catalyzing hydrolysis of polysaccharides comprising glucopyranose;

(n) catalyzing hydrolysis of polysaccharides comprising 1,4-β-glycoside-linked D-glucopyranoses;

(o) catalyzing hydrolysis of cellulose, a cellulose derivative or a hemicellulose;

(p) the activity of (o), wherein the cellulase activity (hydrolysis of cellulose, a cellulose derivative or a hemicellulose) comprises hydrolyzing (degrading) a cellulose or a hemicellulose in sugar cane bagasse, corn fiber, corn seed fiber, wood, wood waste, wood pulp, paper pulp, a wood product or paper product, a plant biomass, a plant biomass comprising seeds, grains, tubers, plant wastes or byproducts of food or feed processing or industrial processing, stalks, corn, cobs, stover, grasses, an Indian grass or a switch grass;

(q) catalyzing hydrolysis of glucan in a feed, a food product or a beverage;

(r) the activity of (q), wherein the feed, food product or beverage comprises a cereal-based animal feed, a wort or a beer, a dough, a fruit or a vegetable;

(s) catalyzing hydrolysis of a glucan in a microbial cell, a fungal cell, a mammalian cell, a plant cell or any plant material comprising a cellulosic part;

(t) the activity of any of (a) to (s), wherein the activity is thermostable or thermotolerant;

(u) the activity of any of (t), wherein activity is stable or tolerant under conditions comprising a temperature range of between about 37° C. to about 95° C., or between about 55° C. to about 85° C., or between about 70° C. to about 75° C., or between about 70° C. to about 95° C., or between about 90° C. to about 95° C., or retains a lignocellulosic activity in a temperature in the range between about 1° C. to about 5° C., between about 5° C. to about 15° C., between about 15° C. to about 25° C., between about 25° C. to about 37° C., or between about 37° C. to about 95° C., 96° C., 97° C., 98° C. or 99° C.;

(v) the activity of any of (t), wherein activity is stable or tolerant after exposure to a temperature in the range from greater than 37° C. to about 95° C., from greater than 55° C. to about 85° C., or between about 70° C. to about 75° C., or from greater than 90° C. to about 95° C., or after exposure to a temperature in the range between about 1° C. to about 5° C., between about 5° C. to about 15° C., between about 15° C. to about 25° C., between about 25° C. to about 37° C., or between about 37° C. to about 95° C., 96° C., 97° C., 98° C. or 99° C.; or (w) the activity of any of (a) to (s), wherein the enzyme is active under conditions comprising about pH 6.5, pH 6, pH 5.5, pH 5, pH 4.5 or pH 4 or more acidic; or, under conditions comprising about pH 7, pH 7.5 pH 8.0, pH 8.5, pH 9, pH 9.5, pH 10, pH 10.5 or pH 11 or more basic pH.

3. A nucleic acid probe for identifying a nucleic acid encoding a polypeptide with a lignocellulosic activity, wherein the probe comprises (a) at least 20, 30, 40, 50, 60, 75, 100, 125, 150, or 200 or more consecutive bases of the nucleic acid sequence (polynucleotide) of paragraph [0317], wherein the probe identifies the nucleic acid by binding or hybridization;

(b) the probe of (a), wherein the probe comprises an oligonucleotide comprising at least about 10 to 50, about 20 to 60, about 30 to 70, about 40 to 80, about 60 to 100, or about 50 to 150 consecutive bases;

(c) the probe of (a) or (b), wherein the probe comprises consecutive bases of the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, and/or SEQ ID NO:135;

(d) the probe of (a), (b) or (c) further comprising a detectable agent; or (e) the probe of (d), wherein the detectable agent comprises a radioactive isotope, a fluorescent dye or an enzyme capable of catalyzing the formation of a detectable product.

4. An amplification primer pair for amplifying a nucleic acid encoding a polypeptide having a lignocellulosic activity, wherein the amplification primer pair (a) is capable of amplifying a nucleic acid comprising the nucleic acid sequence of paragraph [0317], or a subsequence thereof;

(b) comprises a first member having a sequence as set forth by about the first (the 5') 12, 13, 14, 15, 16, 17, 18, 19, 20, 21, 22, 23, 24, 25, 26, 27, 28, 29, 30 or more residues of SEQ ID NO:1, etc, and a second member having a sequence as set forth by about the first (the 5') 12, 13, 14, 15, 16, 17, 18, 19, 20, 21, 22, 23, 24, 25, 26, 27, 28, 29, 30 or more residues of the complementary strand of the first member; or (c) comprises the amplification primer pair or (a) or (b), wherein a member of the amplification primer pair comprises an oligonucleotide comprising at least about 10 to 50 consecutive bases of the sequence, or, about 12, 13, 14, 15, 16, 17, 18, 19, 20, 21, 22, 23, 24, 25, 26, 27, 28, 29, 30 or more consecutive bases of the sequence.

5. An isolated or recombinant lignocellulosic enzyme-encoding nucleic acid comprising:

(a) a nucleic acid generated by amplification of a polynucleotide using the amplification primer pair of paragraph 4;

(b) the nucleic acid of (a), wherein the amplification is by polymerase chain reaction (PCR);

(c) the nucleic acid of (a), wherein the nucleic acid is generated by amplification of a gene library;

(d) the nucleic acid of (c), wherein the gene library is an environmental library.

(e) the nucleic acid of (a), (b), (c) or (d) encoding a polypeptide having a lignocellulosic activity but lacking a signal sequence, a prepro domain, a dockerin domain, and/or a carbohydrate binding module (CBM),
wherein optionally the carbohydrate binding module (CBM) comprises, or consists of, a cellulose binding module, a lignin binding module, cellulase or a cellobiohydrolase module; or (f) the nucleic acid of (a), (b), (c), (d) or (e) encoding a polypeptide having a lignocellulosic activity further comprising a heterologous sequence.

6. An isolated, synthetic or recombinant lignocellulosic enzyme encoded by the nucleic acid of paragraph 5.

7. A method of amplifying a nucleic acid encoding a polypeptide having a lignocellulosic enzyme activity comprising amplification of a template nucleic acid with the amplification primer pair of paragraph 4.

8. An expression cassette comprising a nucleic acid comprising the nucleic acid sequence of paragraph 1 or paragraph 5.

9. A vector comprising a nucleic acid comprising the nucleic acid sequence of paragraph 1 or paragraph 5, or the expression cassette of paragraph 8, wherein optionally the vector comprises an expression vector or a cloning vector.

10. A cloning vehicle comprising a nucleic acid comprising the nucleic acid sequence of paragraph 1 or paragraph 5, the vector of paragraph 9, or the expression cassette of paragraph 8, wherein optionally the cloning vehicle comprises a viral vector, a plasmid, a phage, a phagemid, a cosmid, a fosmid, a bacteriophage or an artificial chromosome, and optionally the viral vector comprises an adenovirus vector, a retroviral vector or an adeno-associated viral vector, and optionally the cloning vehicle comprises a bacterial artificial chromosome (BAC), a plasmid, a bacteriophage P1-derived vector (PAC), a yeast artificial chromosome (YAC), or a mammalian artificial chromosome (MAC).

11. A transformed, infected, transformed or host cell comprising
(a) a nucleic acid comprising the nucleic acid sequence of paragraph 1 or paragraph 5, or the expression cassette of paragraph 8, the vector of paragraph 9, or a cloning vehicle of paragraph 10;
(b) the cell of (a), wherein the cell is a bacterial cell, a mammalian cell, a fungal cell, a yeast cell, an insect cell or a plant cell;
(c) the plant cell of (b), wherein the plant cell is derived from a plant of the genera *Anacardium, Arachis, Asparagus, Atropa, Avena, Brassica, Citrus, Citrullus, Capsicum, Carthamus, Cocos, Coffea, Cruciferae, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*; or
(d) the plant cell of (b), wherein the plant cell is derived from a corn plant, a sorghum plant, a potato plant, a tomato plant, a wheat plant, an oilseed plant, a rapeseed plant, a soybean plant, a rice plant, a barley plant, a grass, or a tobacco plant.

12. A transgenic non-human animal comprising the nucleic acid sequence of paragraph 1 or paragraph 5, or the expression cassette of paragraph 8, the vector of paragraph 9, or a cloning vehicle of paragraph 10, wherein optionally the transgenic non-human animal is a mouse, rat, pig, cow or goat.

13. A transgenic plant comprising
(a) the nucleic acid sequence of paragraph 1 or paragraph 5, or the expression cassette of paragraph 8, the vector of paragraph 9, or a cloning vehicle of paragraph 10;
(b) the transgenic plant of (a), wherein the plant is a corn plant, a sorghum plant, a potato plant, a tomato plant, a wheat plant, an oilseed plant, a rapeseed plant, a soybean plant, a rice plant, a barley plant, a grass, or a tobacco plant; or
(c) the transgenic plant of (a), wherein the plant is of the genera *Anacardium, Arachis, Asparagus, Atropa, Avena, Brassica, Citrus, Citrullus, Capsicum, Carthamus, Cocos, Coffea, Cruciferae, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

14. A transgenic seed comprising
(a) the nucleic acid sequence of paragraph 1 or paragraph 5, or the expression cassette of paragraph 8, the vector of paragraph 9, or a cloning vehicle of paragraph 10;
(b) the transgenic seed of (a), wherein the seed is a corn seed, a wheat kernel, an oilseed, a rapeseed, a soybean seed, a palm kernel, a sunflower seed, a sesame seed, a rice, a barley, a peanut or a tobacco plant seed; or
(c) the transgenic seed of (a), wherein the seed is derived from a plant of the genera *Anacardium, Arachis, Asparagus, Atropa, Avena, Brassica, Citrus, Citrullus, Capsicum, Carthamus, Cocos, Coffea, Cruciferae, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* or *Zea*.

15. An antisense oligonucleotide comprising a nucleic acid sequence complementary to or capable of hybridizing under stringent conditions to the nucleic acid sequence of paragraph 1 or paragraph 5, wherein optionally the antisense oligonucleotide has a length of between about 10 to 50, about 20 to 60, about 30 to 70, about 40 to 80, or about 60 to 100 bases, wherein optionally the antisense oligonucleotide comprises an RNAi, miRNA, iRNA, or a ribozyme.

16. A method of inhibiting the translation of an enzyme message in a cell comprising administering to the cell or expressing in the cell an antisense oligonucleotide comprising a nucleic acid sequence complementary to or capable of hybridizing under stringent conditions to the nucleic acid sequence of paragraph 1 or paragraph 5.

17. A double-stranded interference RNA (RNAi) molecule comprising a subsequence of the nucleic acid sequence of paragraph 1, wherein optionally the RNAi comprises an siRNA or an miRNA, and optionally the RNAi molecule is about 11, 12, 13, 14, 15, 16, 17, 18, 19, 20, 21, 22, 23, 24, 25, 26 or more duplex nucleotides in length.

18. A method of inhibiting the expression of a lignocellulosic enzyme or message (mRNA) in a cell comprising administering to the cell or expressing in the cell a double-stranded interference RNA (RNAi) molecule as set forth in paragraph 17.

19. An isolated, synthetic or recombinant polypeptide comprising
(a) an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and/or SEQ ID NO:136, or enzymatically active subsequences (fragments) thereof, over a region of at least about 20, 25, 30, 35, 40, 45, 50, 55, 60, 75, 100, 150, 200, 250, 300 or more residues, or over the full length of the polypeptide or enzyme, wherein the nucleic acid encodes a polypeptide having a lignocellulosic activity, and optionally the lignocellulosic activity comprises a cellulase, a cellulolytic activity, an endoglucanase or a cellobiohydrolase activity, wherein optionally the sequence identities are determined by analysis with a sequence comparison algorithm or by a visual inspection, and optionally the sequence comparison algorithm is a BLAST version 2.2.2 algorithm where a filtering setting is set to blastall -p blastp -d "nr pataa"-F F, and all other options are set to default;

(b) an amino acid sequence encoded by the nucleic acid of paragraph 1, wherein the polypeptide has (i) a lignocellulosic activity, and optionally the lignocellulosic activity comprises a cellulase, a cellulolytic activity, an endoglucanase or a cellobiohydrolase activity, or, (ii) has immunogenic activity in that it is capable of generating an antibody that specifically binds to a polypeptide having the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and/or SEQ ID NO:136, and/or enzymatically active subsequences (fragments) thereof;

(c) the amino acid sequence of (a) or (b), and comprising at least one amino acid residue conservative substitution, (d) the amino acid sequence of (c), wherein the conservative substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof, and optionally the aliphatic residue comprises Alanine, Valine, Leucine, Isoleucine or a synthetic equivalent thereof; the acidic residue comprises Aspartic acid, Glutamic acid or a synthetic equivalent thereof; the residue comprising an amide group comprises Aspartic acid, Glutamic acid or a synthetic equivalent thereof; the basic residue comprises Lysine, Arginine or a synthetic equivalent thereof; or, the aromatic residue comprises Phenylalanine, Tyrosine or a synthetic equivalent thereof;

(e) the polypeptide of (a), (b), (c) or (d) having a lignocellulosic activity but lacking a signal sequence, a prepro domain, a dockerin domain, and/or a carbohydrate binding module (CBM), wherein optionally the carbohydrate binding module (CBM) comprises, or consists of, a cellulose binding module, a lignin binding module, a xylose binding module, a mannanse binding module, a xyloglucan-specific module and/or a arabinofuranosidase binding module;

(f) the polypeptide of (a), (b), (c), (d) or (e) having a lignocellulosic activity further comprising a heterologous sequence;

(g) the polypeptide of (f), wherein the heterologous sequence comprises, or consists of: (i) a heterologous signal sequence, a heterologous carbohydrate binding module, a heterologous dockerin domain, a heterologous catalytic domain (CD), or a combination thereof; (ii) the sequence of (ii), wherein the heterologous signal sequence, carbohydrate binding module or catalytic domain (CD) is derived from a heterologous lignocellulosic enzyme; and/or, (iii) a tag, an epitope, a targeting peptide, a cleavable sequence, a detectable moiety or an enzyme;

(h) the polypeptide of (g), wherein the heterologous carbohydrate binding module (CBM) comprises, or consists of, a cellulose binding module, a lignin binding module, a xylose binding module, a mannanse binding module, a xyloglucan-specific module and/or a arabinofuranosidase binding module; or (i) polypeptide of (g), wherein the heterologous signal sequence targets the encoded protein to a vacuole, the endoplasmic reticulum, a chloroplast or a starch granule.

20. The isolated, synthetic or recombinant polypeptide of paragraph 19, or the lignocellulosic enzyme of paragraph 6, wherein the lignocellulosic activity comprises (a) a cellulase, a cellulolytic activity, an endoglucanase or a cellobiohydrolase activity, or any combination thereof;

(b) an activity comprising hydrolyzing (degrading) soluble oligomers to fermentable, monomeric sugars;

(c) an activity comprising hydrolyzing (degrading) soluble cellooligsaccharides and arabinoxylan oligomers into monomers, and optionally the monomers comprise xylose, arabinose and glucose;

(d) catalyzing the hydrolysis of (degrading) plant biomass polysaccharides;

(e) catalyzing the hydrolysis of (degrading) a glucan or lignin to produce a smaller molecular weight polysaccharides or oligomers or monomers;

(f) catalyzing hydrolysis of 1,4-beta-D-glycosidic linkages;

(g) an endocellulase activity comprising an endo-1,4-beta-endocellulase activity;

(f) a 1,4-beta-D-glycosidic linkage hydrolysis activity comprising hydrolysis of a 1,4-beta-D-glycosidic linkage in a cellulose, a cellulose derivative, a lichenin or a cereal, wherein optionally the cellulose derivative comprises a carboxy methyl cellulose or a hydroxy ethyl cellulose, or the cereal comprises a beta-D-glucan or a xyloglucan;

(g) catalyzing hydrolysis of glucanase linkages;

(h) catalyzing hydrolysis of β-1,4- and/or β-1,3-glucanase linkages;

(i) catalyzing hydrolysis of endo-glucan linkages;

(j) catalyzing hydrolysis of endo-1,4-beta-D-glucan 4-glucano hydrolase activity;

(k) catalyzing hydrolysis of internal endo-β-1,4-glucanase linkages and/or β-1,3-glucanase linkages;

(l) catalyzing hydrolysis of internal β-1,3-glucosidic linkages;

(m) catalyzing hydrolysis of polysaccharides comprising glucopyranose;

(n) catalyzing hydrolysis of polysaccharides comprising 1,4-β-glycoside-linked D-glucopyranoses;

(o) catalyzing hydrolysis of cellulose, a cellulose derivative or a hemicellulose;

(p) the activity of (o), wherein the enzymatic activity comprises hydrolyzing (degrading) a cellulose or a hemicellulose in sugar cane bagasse, corn fiber, corn seed fiber, wood, wood pulp, paper pulp, a wood product, wood waste or paper product, a plant biomass, a plant biomass comprising seeds, grains, tubers, plant wastes or byproducts of food or feed processing or industrial processing, stalks, corn, cobs, stover, grasses, an Indian grass or a switch grass;

(q) catalyzing hydrolysis of glucan in a feed, a food product or a beverage;

(r) the activity of (q), wherein the feed, food product or beverage comprises a cereal-based animal feed, a wort or a beer, a dough, a fruit or a vegetable;

(s) catalyzing hydrolysis of a glucan in a microbial cell, a fungal cell, a mammalian cell, a plant cell or any plant material comprising a cellulosic part;

(t) the activity of any of (a) to (s), wherein the activity is thermostable or thermotolerant;

(u) the activity of any of (t), wherein activity is stable or tolerant under conditions comprising a temperature range of between about 37° C. to about 95° C., or between about 55° C. to about 85° C., or between about 70° C. to about 75° C., or between about 70° C. to about 95° C., or between about 90° C. to about 95° C., or retains a lignocellulosic activity in a temperature in the range between about 1° C. to about 5° C., between about 5° C. to about 15° C., between about 15° C. to about 25° C., between about 25° C. to about 37° C., or between about 37° C. to about 95° C., 96° C., 97° C., 98° C. or 99° C.;

(v) the activity of any of (t), wherein activity is stable or tolerant after exposure to a temperature in the range from greater than 37° C. to about 95° C., from greater than 55° C. to about 85° C., or between about 70° C. to about 75° C., or from greater than 90° C. to about 95° C., or after exposure to a temperature in the range between about 1° C. to about 5° C., between about 5° C. to about 15° C., between about 15° C. to about 25° C., between about 25° C. to about 37° C., or between about 37° C. to about 95° C., 96° C., 97° C., 98° C. or 99° C.; or (w) the activity of any of (a) to (s), wherein the enzyme is active under conditions comprising about pH 6.5, pH 6, pH 5.5, pH 5, pH 4.5 or pH 4 or more acidic; or, under conditions comprising about pH 7, pH 7.5 pH 8.0, pH 8.5, pH 9, pH 9.5, pH 10, pH 10.5 or pH 11 or more basic pH.

21. The isolated, synthetic or recombinant polypeptide of paragraph 19, or the lignocellulosic enzyme of paragraph 6, wherein the polypeptide or enzyme comprises at least one glycosylation site, and optionally the glycosylation is an N-linked glycosylation, and optionally the polypeptide is glycosylated after being expressed in a *Pichia*, e.g., a *Pichia pastoris*, a *Schizosaccharomyces*, e.g., a *Schizosaccharomyces pombe*, and/or a *Pseudomonas*, e.g., a *Pseudomonas fluorescens*.

22. A protein preparation comprising the polypeptide of paragraph 19, or the lignocellulosic enzyme of paragraph 6, wherein the protein preparation comprises a liquid, a solid or a gel.

23. A heterodimer comprising the polypeptide of paragraph 19, or the lignocellulosic enzyme of paragraph 6, and a second domain, wherein optionally the second domain comprises a polypeptide and the heterodimer is a fusion protein, and optionally the second domain comprises an epitope, a heterologous enzyme, a detectable protein or peptide, an immunogenic protein or peptide or a tag.

24. A homodimer comprising the polypeptide of paragraph 19 or the lignocellulosic enzyme of paragraph 6.

25. An immobilized polypeptide or enzyme, or an immobilized nucleic acid, wherein the polypeptide comprises the sequence of paragraph 19, or the lignocellulosic enzyme of paragraph 6, or the nucleic acid comprises the nucleic acid sequence of paragraph 1 or paragraph 5, or the probe of paragraph 3, wherein optionally the polypeptide or nucleic acid is immobilized on a cell, a metal, a resin, a polymer, a ceramic, a glass, a microelectrode, a graphitic particle, a bead, a gel, a plate, an array or a capillary tube.

26. An array comprising the immobilized polypeptide or immobilized nucleic acid of paragraph 25.

27. An isolated, synthetic or recombinant antibody that specifically binds to the polypeptide of paragraph 19, wherein optionally the antibody is a monoclonal or a polyclonal antibody.

28. A hybridoma comprising an antibody that specifically binds to the polypeptide of paragraph 19.

29. A method of isolating or identifying a polypeptide with a lignocellulosic activity comprising the steps of:

(a) providing the antibody of paragraph 27;

(b) providing a sample comprising polypeptides; and (c) contacting the sample of step (b) with the antibody of step (a) under conditions wherein the antibody can specifically bind to the polypeptide, thereby isolating or identifying a polypeptide having a lignocellulosic activity.

30. A method of making an anti-cellulase or an anti-lignocellulosic enzyme antibody comprising (a) administering to a non-human animal the nucleic acid of paragraph 1 or paragraph 5 in an amount sufficient to generate a humoral immune response, thereby making an anti-lignocellulosic enzyme or an anti-cellulase antibody, or (b) administering to a non-human animal the polypeptide of paragraph 19 in an amount sufficient to generate a humoral immune response, thereby making an anti-lignocellulosic enzyme or an anti-cellulase antibody.

31. A method of producing a recombinant polypeptide comprising:

(A) (a) providing a nucleic acid operably linked to a promoter, wherein the nucleic acid comprises the nucleic acid sequence of paragraph 1 or paragraph 5; and (b) expressing the nucleic acid of step (a) under conditions that allow expression of the polypeptide, thereby producing a recombinant polypeptide; or (B) the method of (A), wherein the method further comprises transforming a host cell with the nucleic acid of step (a) followed by expressing the nucleic acid of step (a), thereby producing a recombinant polypeptide in a transformed cell; or (C) the method of (A) or (B), wherein the promoter is or comprises: a viral, bacterial, mammalian or plant promoter; or, a plant promoter; or, a potato, rice, corn, wheat, tobacco or barley promoter; or, a constitutive promoter or a CaMV35S promoter; or, an inducible promoter; or, a tissue-specific promoter or an environmentally regulated or a developmentally regulated promoter; or, a seed-specific, a leaf-specific, a root-specific, a stem-specific or an abscission-induced promoter; or, a seed preferred promoter, a maize gamma zein promoter or a maize ADP-gpp promoter.

32. A method for identifying a polypeptide having a lignocellulosic activity comprising the following steps:
 (a) providing the polypeptide of paragraph 19, or the lignocellulosic enzyme of paragraph 6;
 (b) providing a substrate for a lignocellulosic enzyme; and
 (c) contacting the polypeptide with the substrate of step (b) and detecting a decrease in the amount of substrate or an increase in the amount of a reaction product, wherein a decrease in the amount of the substrate or an increase in the amount of the reaction product detects a polypeptide having a lignocellulosic activity.

33. A method for identifying an lignocellulosic enzyme substrate comprising the following steps:
 (a) providing the polypeptide of paragraph 19;
 (b) providing a test substrate; and
 (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a lignocellulosic enzyme substrate.

34. A method of determining whether a test compound specifically binds to a polypeptide comprising the following steps:
 (a) expressing a nucleic acid or a vector comprising the nucleic acid under conditions permissive for translation of the nucleic acid to a polypeptide, wherein the nucleic acid has the nucleic acid sequence of paragraph 1 or paragraph 5;
 (b) providing a test compound;
 (c) contacting the polypeptide with the test compound; and
 (d) determining whether the test compound of step (b) specifically binds to the polypeptide.

35. A method of determining whether a test compound specifically binds to a polypeptide comprising the following steps:
 (a) providing the polypeptide of paragraph 19;
 (b) providing a test compound;
 (c) contacting the polypeptide with the test compound; and
 (d) determining whether the test compound of step (b) specifically binds to the polypeptide.

36. A method for identifying a modulator of a lignocellulosic activity comprising the following steps:
 (a) providing the polypeptide of paragraph 19;
 (b) providing a test compound;
 (c) contacting the polypeptide of step (a) with the test compound of step (b) and measuring an activity of the lignocellulosic enzyme, wherein a change in the lignocellulosic enzyme activity measured in the presence of the test compound compared to the activity in the absence of the test compound provides a determination that the test compound modulates the lignocellulosic enzyme activity.

37. The method of paragraph 97, wherein the lignocellulosic enzyme activity is measured by providing a lignocellulosic enzyme substrate and detecting a decrease in the amount of the substrate or an increase in the amount of a reaction product, or, an increase in the amount of the substrate or a decrease in the amount of a reaction product,
 wherein optionally a decrease in the amount of the substrate or an increase in the amount of the reaction product with the test compound as compared to the amount of substrate or reaction product without the test compound identifies the test compound as an activator of a lignocellulosic activity,
 and optionally an increase in the amount of the substrate or a decrease in the amount of the reaction product with the test compound as compared to the amount of substrate or reaction product without the test compound identifies the test compound as an inhibitor of a lignocellulosic activity.

38. A computer system comprising a processor and a data storage device wherein said data storage device has stored thereon a polypeptide sequence or a nucleic acid sequence, wherein the polypeptide sequence comprises sequence as set forth in paragraph 19, a polypeptide encoded by the nucleic acid of paragraph 1 or paragraph 5,
 wherein optionally the method further comprises a sequence comparison algorithm and a data storage device having at least one reference sequence stored thereon, or further comprises an identifier that identifies one or more features in said sequence
 and optionally the sequence comparison algorithm comprises a computer program that indicates polymorphisms.

39. A computer readable medium having stored thereon a polypeptide sequence or a nucleic acid sequence, wherein the polypeptide sequence comprises the polypeptide of paragraph 19, or a polypeptide encoded by the nucleic acid of paragraph 1 or paragraph 5.

40. A method for identifying a feature in a sequence comprising the steps of: (a) reading the sequence using a computer program which identifies one or more features in a sequence, wherein the sequence comprises a polypeptide sequence or a nucleic acid sequence, wherein the polypeptide sequence comprises the polypeptide of paragraph 19; a polypeptide encoded by the nucleic acid of paragraph 1 or paragraph 5; and (b) identifying one or more features in the sequence with the computer program.

41. A method for comparing a first sequence to a second sequence comprising the steps of: (a) reading the first sequence and the second sequence through use of a computer program which compares sequences, wherein the first sequence comprises a polypeptide sequence or a nucleic acid sequence, wherein the polypeptide sequence comprises the polypeptide of paragraph 19 or a polypeptide encoded by the nucleic acid of paragraph 1 or paragraph 5; and (b) determining differences between the first sequence and the second sequence with the computer program.
 wherein optionally the method further comprises a step of determining differences between the first sequence and the second sequence, or optionally the method further comprises the step of identifying polymorphisms, or optionally the method further comprises use of an identifier that identifies one or more features in a sequence,
 and optionally the method comprises reading the first sequence using a computer program and identifying one or more features in the sequence.

42. A method for isolating or recovering a nucleic acid encoding a polypeptide with a lignocellulosic activity from a sample comprising the steps of:

(a) providing the amplification primer pair of paragraph 4;
(b) isolating a nucleic acid from the sample or treating the sample such that nucleic acid in the sample is accessible for hybridization to the amplification primer pair; and,
(c) combining the nucleic acid of step (b) with the amplification primer pair of step (a) and amplifying nucleic acid from the sample, thereby isolating or recovering a nucleic acid encoding a polypeptide with a lignocellulosic activity from a sample;
wherein optionally the sample is an environmental sample, or optionally the sample comprises a water sample, a liquid sample, a soil sample, an air sample or a biological sample, and optionally the biological sample is derived from a bacterial cell, a protozoan cell, an insect cell, a yeast cell, a plant cell, a fungal cell or a mammalian cell.

43. A method for isolating or recovering a nucleic acid encoding a polypeptide with a lignocellulosic activity from a sample comprising the steps of:
(a) providing a polynucleotide probe comprising, or consisting of, the nucleic acid sequence of paragraph 1, or the probe of paragraph 3;
(b) isolating a nucleic acid from the sample or treating the sample such that nucleic acid
(c) combining the isolated nucleic acid or the treated sample of step (b) with the polynucleotide probe of step (a); and
(d) isolating a nucleic acid that specifically hybridizes with the polynucleotide probe of step (a), thereby isolating or recovering a nucleic acid encoding a polypeptide with a lignocellulosic activity from an sample;
wherein optionally the sample is an environmental sample, or optionally the sample comprises a water sample, a liquid sample, a soil sample, an air sample or a biological sample, and optionally the biological sample is derived from a bacterial cell, a protozoan cell, an insect cell, a yeast cell, a plant cell, a fungal cell or a mammalian cell.

44. A method of generating a variant of a nucleic acid encoding a polypeptide with a lignocellulosic activity comprising the steps of:
(a) providing a template nucleic acid comprising the nucleic acid sequence of paragraph 1 or paragraph 5; and
(b) modifying, deleting or adding one or more nucleotides in the template sequence, or a combination thereof, to generate a variant of the template nucleic acid
wherein optionally the method further comprises expressing the variant nucleic acid to generate a variant polypeptide with a lignocellulosic activity,
and optionally the modifications, additions or deletions are introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, GeneReassembly, Gene Site Saturation Mutagenesis (GSSM), Tailored Multi-Site Combinatorial Assembly, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof
and optionally the method is iteratively repeated until a lignocellulosic enzyme having an altered or different activity or an altered or different stability from that of a polypeptide encoded by the template nucleic acid is produced.

45. The method of paragraph 44, wherein
(A) the variant lignocellulosic enzyme: (a) is thermotolerant, and retains some activity after being exposed to an elevated temperature; (b) has increased glycosylation as compared to the lignocellulosic enzyme encoded by a template nucleic acid; or, (c) has a lignocellulosic activity under a high temperature, wherein the lignocellulosic enzyme encoded by the template nucleic acid is not active under the high temperature; or
(B) the method is iteratively repeated until (a) a lignocellulosic enzyme-coding sequence having an altered codon usage from that of the template nucleic acid is produced, or, (b) a lignocellulosic enzyme gene having higher or lower level of message expression or stability from that of the template nucleic acid is produced.

46. A method for modifying codons in a nucleic acid encoding a polypeptide with a lignocellulosic activity to increase its expression in a host cell, the method comprising the following steps:
(a) providing a nucleic acid encoding a polypeptide with a lignocellulosic activity comprising the nucleic acid sequence of paragraph 1 or paragraph 5; and,
(b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

47. A method for modifying codons in a nucleic acid encoding a lignocellulosic enzyme, the method comprising the following steps:
(a) providing a nucleic acid encoding a polypeptide with a lignocellulosic activity comprising the nucleic acid sequence of paragraph 1 or paragraph 5; and,
(b) identifying a codon in the nucleic acid of step (a) and replacing it with a different codon encoding the same amino acid as the replaced codon, thereby modifying codons in a nucleic acid encoding a lignocellulosic enzyme.

48. A method for modifying codons in a nucleic acid encoding a lignocellulosic enzyme to increase its expression in a host cell, the method comprising the following steps:
(a) providing a nucleic acid encoding a lignocellulosic enzyme comprising the nucleic
(b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

49. A method for modifying a codon in a nucleic acid encoding a polypeptide having a lignocellulosic activity to decrease its expression in a host cell, the method comprising the following steps:
(a) providing a nucleic acid encoding a lignocellulosic enzyme comprising the nucleic acid sequence of paragraph 1 or paragraph 5; and
(b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell, wherein optionally the host cell is a bacterial cell, a fungal cell, an insect cell, a yeast cell, a plant cell or a mammalian cell.

50. A method for producing a library of nucleic acids encoding a plurality of modified lignocellulosic enzyme active sites or substrate binding sites, wherein the modified active sites or substrate binding sites are derived from a first nucleic acid comprising a sequence encoding a first active site or a first substrate binding site the method comprising the following steps:

(a) providing a first nucleic acid encoding a first active site or first substrate binding site, wherein the first nucleic acid sequence comprises a sequence that hybridizes under stringent conditions to the nucleic acid sequence (polynucleotide) of paragraph 1, and the nucleic acid encodes a lignocellulosic enzyme active site or a lignocellulosic enzyme substrate binding site;

(b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified lignocellulosic enzyme active sites or substrate binding sites.

wherein optionally a mutagenic oligonucleotide or a variant nucleic acid is generated by a method comprising an optimized directed evolution system, Gene Site Saturation Mutagenesis (GSSM), GeneReassembly, Tailored Multi-Site Combinatorial Assembly, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

51. A method for making a small molecule comprising the following steps:

(a) providing a plurality of biosynthetic enzymes capable of synthesizing or modifying a small molecule, wherein one of the enzymes comprises a lignocellulosic enzyme encoded by a nucleic acid comprising the nucleic acid sequence of paragraph 1 or paragraph 5;

(b) providing a substrate for at least one of the enzymes of step (a); and (c) reacting the substrate of step (b) with the enzymes under conditions that facilitate a plurality of biocatalytic reactions to generate a small molecule by a series of biocatalytic reactions.

52. A method for modifying a small molecule comprising the following steps:

(a) providing a lignocellulosic enzyme, wherein the enzyme comprises the polypeptide of paragraph 19, or a polypeptide encoded by a nucleic acid sequence comprising the sequence of paragraph 1 or paragraph 5;

(b) providing a small molecule; and (c) reacting the enzyme of step (a) with the small molecule of step (b) under conditions that facilitate an enzymatic reaction catalyzed by the lignocellulosic enzyme, thereby modifying a small molecule by a lignocellulosic enzymatic reaction.

wherein optionally step (b) comprises providing a plurality of small molecule substrates for the enzyme of step (a), thereby generating a library of modified small molecules produced by at least one enzymatic reaction catalyzed by the lignocellulosic enzyme;

and optionally the method further comprises providing a plurality of additional enzymes under conditions that facilitate a plurality of biocatalytic reactions by the enzymes to form a library of modified small molecules produced by the plurality of enzymatic reactions;

and optionally the method further comprises the step of testing the library to determine if a particular modified small molecule which exhibits a desired activity is present within the library, wherein optionally the step of testing the library further comprises the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

53. A method for determining a functional fragment of a lignocellulosic enzyme comprising the steps of:

(a) providing a lignocellulosic enzyme, wherein the enzyme comprises the polypeptide of paragraph 19, or a polypeptide encoded by the nucleic acid of paragraph 1 or paragraph 5; and (b) deleting a plurality of amino acid residues from the sequence of step (a) and testing the remaining subsequence for a lignocellulosic activity, thereby determining a functional fragment of a lignocellulosic enzyme.

wherein optionally the lignocellulosic enzyme activity is measured by providing a lignocellulosic enzyme substrate and detecting a decrease in the amount of the substrate or an increase in the amount of a reaction product.

54. A method for whole cell engineering of new or modified phenotypes by using real-time metabolic flux analysis, the method comprising the following steps:

(a) making a modified cell by modifying the genetic composition of a cell, wherein the genetic composition is modified by addition to the cell of a nucleic acid comprising the nucleic acid sequence of paragraph 1 or paragraph 5;

(b) culturing the modified cell to generate a plurality of modified cells;

(c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis.

wherein optionally the genetic composition of the cell is modified by a method comprising deletion of a sequence or modification of a sequence in the cell, or, knocking out the expression of a gene, and optionally the method further comprises selecting a cell comprising a newly engineered phenotype, and optionally the method further comprises culturing the selected cell, thereby generating a new cell strain comprising a newly engineered phenotype.

55. An isolated, synthetic or recombinant signal (or leader) sequence (signal peptide (SP)) consisting of an amino acid sequence as set forth in the amino terminal residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43 or 1 to 44, of (a) an amino acid sequence as set forth in paragraph 19; or, (b) an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and/or SEQ ID NO:136, and/or enzymatically active subsequences (fragments) thereof.

56. A chimeric polypeptide comprising at least a first domain comprising a signal sequence (signal peptide (SP)) or leader sequence having the amino acid sequence of paragraph 55, and at least a second domain comprising a heterologous polypeptide or peptide, wherein the heterologous polypeptide or peptide is not naturally associated with the signal peptide (SP) or leader sequence,
and optionally the heterologous polypeptide or peptide is not a lignocellulosic enzyme, and optionally the heterologous polypeptide or peptide is amino terminal to, carboxy terminal to or on both ends of the signal peptide (SP) or leader sequence.

57. An isolated, synthetic or recombinant nucleic acid encoding a chimeric polypeptide, wherein the chimeric polypeptide comprises at least a first domain comprising signal peptide (SP) or leader sequence having the amino acid sequence of paragraph 55 and at least a second domain comprising a heterologous polypeptide or peptide, wherein the heterologous polypeptide or peptide is not naturally associated with the signal peptide (SP) or leader sequence.

58. An isolated, synthetic or recombinant nucleic acid comprising: (a) a sequence encoding a polypeptide having a lignocellulosic activity and a heterologous signal (or leader) sequence (signal peptide (SP)), wherein the nucleic acid comprises the nucleic acid sequence of paragraph 1 or paragraph 5; (b) the sequence of (a) wherein the signal (or leader) sequence (signal peptide (SP)) is derived from another lignocellulosic enzyme or a non-lignocellulosic enzyme; or, (c) the sequence of (a) wherein the heterologous signal sequence targets the encoded protein to a vacuole, the endoplasmic reticulum, a chloroplast or a starch granule.

59. An isolated, synthetic or recombinant nucleic acid comprising a sequence encoding a polypeptide having a lignocellulosic activity, wherein the sequence does not contain a signal sequence and the polypeptide-encoding nucleic acid comprises the nucleic acid sequence of paragraph 1 or paragraph 5.

60. A method of increasing thermotolerance or thermostability of a lignocellulosic polypeptide, the method comprising glycosylating a lignocellulosic enzyme, wherein the polypeptide comprises at least thirty contiguous amino acids of the polypeptide of paragraph 19, or a polypeptide encoded by the nucleic acid of paragraph 1 or paragraph 5, thereby increasing the thermotolerance or thermostability of the lignocellulosic enzyme.

61. A method for overexpressing a recombinant lignocellulosic enzyme in a cell comprising
(A) expressing a vector comprising the nucleic acid sequence of paragraph 1, wherein overexpression is effected by use of a high activity promoter, a dicistronic vector or by gene amplification of the vector; or
(B) the method of (A), wherein the high activity promoter is or comprises: a viral, bacterial, mammalian or plant promoter; or, a plant promoter; or, a potato, rice, corn, wheat, tobacco or barley promoter; or, a constitutive promoter or a CaMV35S promoter; or, an inducible promoter; or, a tissue-specific promoter or an environmentally regulated or a developmentally regulated promoter; or, a seed-specific, a leaf-specific, a root-specific, a stem-specific or an abscission-induced promoter; or, a seed preferred promoter, a maize gamma zein promoter or a maize ADP-gpp promoter.

62. A method of making a transgenic plant comprising the following steps:
(A) (a) introducing a heterologous nucleic acid sequence into the cell, wherein the heterologous nucleic sequence comprises the nucleic acid sequence of paragraph 1, thereby producing a transformed plant cell; and
(b) producing a transgenic plant from the transformed cell;
(B) the method of (A), wherein the step (A)(a) further comprises introducing the heterologous nucleic acid sequence by electroporation or microinjection of plant cell protoplasts;
(C) the method of (A) or (B), comprising introducing the heterologous nucleic acid sequence directly to plant tissue by DNA particle bombardment or by using an *Agrobacterium tumefaciens* host; or
(D) the method of (A), (B) or (C), wherein the plant is a monocot or dicot, or the plant is a monocot corn, sugarcane, rice, wheat, barley, switchgrass or *Miscanthus*; or the plant is a dicot oilseed crop, soy, canola, rapeseed, flax, cotton, palm oil, sugar beet, peanut, tree, poplar or lupine.

63. A method of expressing a heterologous nucleic acid sequence in a plant cell comprising the following steps:
(A) (a) transforming the plant cell with a heterologous nucleic acid sequence operably linked to a promoter, wherein the heterologous nucleic sequence comprises the nucleic acid sequence of paragraph 1 or paragraph 5; and
(b) growing the plant under conditions wherein the heterologous nucleic acids sequence is expressed in the plant cell;
(B) the method of (A), wherein the plant is a monocot or dicot, or the plant is a monocot corn, sugarcane, rice, wheat, barley, switchgrass or *Miscanthus*; or the plant is a dicot oilseed crop, soy, canola, rapeseed, flax, cotton, palm oil, sugar beet, peanut, tree, poplar or lupine; or
(C) the method of (A) or (B), wherein the promoter is or comprises: a viral, bacterial, mammalian or plant promoter; or, a plant promoter; or, a potato, rice, corn, wheat, tobacco or barley promoter; or, a constitutive promoter or a CaMV35S promoter; or, an inducible promoter; or, a tissue-specific promoter or an environmentally regulated or a developmentally regulated promoter; or, a seed-specific, a leaf-specific, a root-specific, a stem-specific or an abscission-induced promoter; or, a seed preferred promoter, a maize gamma zein promoter or a maize ADP-gpp promoter.

64. A method for hydrolyzing, breaking up or disrupting a cellooligsaccharide, an arabinoxylan oligomer, or a lignocellulose-, lignin-, xylan-, glucan- or cellulose-comprising composition comprising the following steps:

(A) (a) providing a polypeptide having a lignocellulosic activity as set forth in paragraph 19, or a polypeptide encoded by the nucleic acid of paragraph 1 or paragraph 5, or the composition or product of manufacture of paragraphs 91 to 93 or paragraph 96;

(b) providing a composition comprising a lignocellulose, lignin, xylan, cellulose and/or glucan; and (c) contacting the polypeptide of step (a) with the composition of step (b) under conditions wherein the lignocellulosic enzyme hydrolyzes, breaks up or disrupts the lignin-, xylan-, cellooligsaccharide, arabinoxylan oligomer, or glucan- or cellulose-comprising composition;

(B) the method of (A), wherein the composition comprises a plant cell, a bacterial cell, a yeast cell, an insect cell, or an animal cell, (C) the method of (A) or (B), wherein the polypeptide has glycosyl hydrolase, endoglucanase, cellobiohydrolase, beta-glucosidase, xylanase, mannanse, β-xylosidase and/or arabinofuranosidase activity;

(D) the method of (A), (B) or (C), wherein the polypeptide of (A)(a) is a recombinant polypeptide;

(E) the method of (D), wherein the recombinant polypeptide is produced as a heterologous recombinant polypeptide within the lignocellulose-, xylan-, lignin-, glucan- or cellulose-comprising composition to be hydrolyzed;

(F) the method of (D), wherein the recombinant polypeptide is produced by expression of a heterologous polynucleotide encoding the recombinant polypeptide in a bacterium, a yeast, a plant, an insect, a fungus and an animal, and optionally the organism is selected from the group consisting of an *S. pombe, S. cerevisiae, Pichia pastoris, E. coli, Streptomyces* sp., *Bacillus* sp. or a *Lactobacillus* sp.; or (G) the methods of (A) to (F), wherein the lignocellulose-, lignin-, xylan-, glucan- or cellulose-comprising composition comprises: a monocot or dicot plant or plant product; or, a monocot corn, sugarcane, rice, wheat, barley, switchgrass or *Miscanthus*; or a dicot oilseed crop, soy, canola, rapeseed, flax, cotton, palm oil, sugar beet, peanut, tree, poplar or lupine.

65. A dough or a bread product comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has a glycosyl hydrolase, cellulase, endoglucanase, cellobiohydrolase, beta-glucosidase, xylanase, mannanse, β-xylosidase and/or arabinofuranosidase activity.

66. A method of dough conditioning comprising contacting a dough or a bread product with at least one polypeptide as set forth in paragraph 19, or a polypeptide encoded by the nucleic acid of paragraph 1 or paragraph 5, or the composition or product of manufacture of paragraphs 91 to 93 or paragraph 96, under conditions sufficient for conditioning the dough.

67. A beverage comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has endoglucanase, cellobiohydrolase, beta-glucosidase, xylanase, mannanse, β-xylosidase and/or arabinofuranosidase activity.

68. A method of beverage production comprising administration of at least one polypeptide as set forth in paragraph 19, or a polypeptide encoded by the nucleic acid of paragraph 1 or paragraph 5, or the composition or product of manufacture of paragraphs 91 to 93 or paragraph 96, to a beverage or a beverage precursor under conditions sufficient for decreasing the viscosity of the beverage, wherein optionally the beverage or beverage precursor is a wort or a beer.

69. A food, a feed, food or feed supplement, or a nutritional supplement, comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has glycosyl hydrolase, cellulase, endoglucanase, cellobiohydrolase, beta-glucosidase, xylanase, mannanse, β-xylosidase and/or arabinofuranosidase activity.

70. A method for utilizing a lignocellulosic enzyme as a nutritional supplement in an animal diet, the method comprising:

(A) (a) preparing a nutritional supplement containing a lignocellulosic enzyme comprising at least one polypeptide of paragraph 19, or a polypeptide encoded by the nucleic acid of paragraph 1 or paragraph 5; or the composition or product of manufacture of paragraphs 91 to 93 or paragraph 96; or (b) administering the nutritional supplement to an animal to increase utilization of a xylan contained in a feed or a food ingested by the animal;

(B) the method of (A), wherein the animal is a human, or the animal is a ruminant or a monogastric animal;

(C) the method of (A) or (B), wherein the lignocellulosic enzyme is prepared by expression of a polynucleotide encoding the lignocellulosic enzyme in an organism selected from the group consisting of a bacterium, a yeast, a plant, an insect, a fungus, an animal, an *S. pombe, S. cerevisiae, Pichia pastoris, E. coli, Streptomyces* sp., *Bacillus* sp. and *Lactobacillus* sp., or a *Pichia*, e.g., a *Pichia pastoris*, a *Schizosaccharomyces*, e.g., a *Schizosaccharomyces pombe*, and/or a *Pseudomonas*, e.g., a *Pseudomonas fluorescens*.

71. An edible enzyme delivery matrix or pellet comprising a thermostable recombinant lignocellulosic enzyme comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has cellulase and/or cellobiohydrolase activity.

72. A method for delivering a lignocellulosic enzyme supplement to an animal or a human, the method comprising: preparing an edible enzyme delivery matrix or pellets comprising a granulate edible carrier and a thermostable recombinant a lignocellulosic enzyme, wherein the pellets readily disperse the lignocellulosic enzyme contained therein into aqueous media, and the recombinant lignocellulosic enzyme comprises the polypeptide of paragraph 19, or a polypeptide encoded by the nucleic acid of paragraph 1 or paragraph 5, or is the composition or product of manufacture of paragraphs 91 to 93 or paragraph 96; and, administering the edible enzyme delivery matrix or pellet to the animal or human, wherein optionally the granulate edible carrier comprises a carrier selected from the group consisting of a grain germ, a grain germ that is spent of oil, a hay, an alfalfa, a timothy, a soy hull, a sunflower seed meal and a wheat midd, and optionally the edible carrier comprises grain germ that is spent of oil, and optionally the lignocellulosic enzyme is glycosylated to provide thermostability at pelletizing conditions, and optionally the delivery matrix is formed by pelletizing a mixture comprising a grain germ and a lignocellulosic enzyme, and optionally the pelletizing conditions include application of steam, and optionally the pelletizing conditions comprise application of a temperature in excess of about 80° C. for about 5 minutes and the enzyme retains a specific activity of at least 350 to about 900 units per milligram of enzyme.

73. A lignocellulosic-comprising composition comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has cellulase and/or cellobiohydrolase activity.

74. A wood, wood pulp, wood waste or wood product comprising a lignocellulosic enzyme and/or a cellulase as set forth in paragraph 19, or a cellulase or a lignocellulosic enzyme encoded by the nucleic acid of paragraph 1 or paragraph 5, or the composition or product of manufacture of paragraphs 91 to 93 or paragraph 96, wherein optionally the cellulase activity comprises cellobiohydrolase activity.

75. A paper, paper pulp or paper product comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has cellulase and/or cellobiohydrolase activity.

76. A method for reducing the amount of cellulose in a paper, a wood, wood waste or wood product comprising contacting the paper, wood or wood product with a lignocellulosic enzyme and/or a cellulase as set forth in paragraph 19, or a lignocellulosic enzyme and/or a cellulase encoded by the nucleic acid of paragraph 1 or paragraph 5, or the composition or product of manufacture of paragraphs 91 to 93 or paragraph 96, wherein optionally the cellulase activity comprises cellobiohydrolase activity.

77. A detergent composition comprising a lignocellulosic enzyme and/or a cellulase as set forth in paragraph 19, or a lignocellulosic enzyme or a cellulase encoded by the nucleic acid of paragraph 1 or paragraph 5, or the composition or product of manufacture of paragraphs 91 to 93 or paragraph 96, wherein optionally the polypeptide is formulated in a non-aqueous liquid composition, a cast solid, a granular form, a particulate form, a compressed tablet, a gel form, a paste or a slurry form, and optionally the lignocellulosic enzyme and/or cellulase activity comprises a cellobiohydrolase activity.

78. A pharmaceutical composition or dietary supplement comprising a lignocellulosic enzyme and/or a cellulase as set forth in paragraph 19, or a lignocellulosic enzyme and/or a cellulase encoded by the nucleic acid of paragraph 1 or paragraph 5, or the composition or product of manufacture of paragraphs 91 to 93 or paragraph 96, wherein optionally the lignocellulosic enzyme and/or cellulase is formulated as a tablet, gel, pill, implant, liquid, spray, powder, food, feed pellet or as an encapsulated formulation and optionally the lignocellulosic enzyme and/or cellulase activity comprises a cellobiohydrolase activity, wherein optionally the composition further comprises a glucose oxidase, a glucose oxidase-1 (a β-glucosidase) or a glucose oxidase-2 (a β-xylosidase).

79. A fuel comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has activity comprising lignocellulosic enzyme and/or a cellulase or cellobiohydrolase activity, wherein optionally the composition further comprises a glucose oxidase, a glucose oxidase-1 (a β-glucosidase) or a glucose oxidase-2 (a β-xylosidase), wherein optionally the fuel is derived from a plant material, which optionally comprises potatoes, soybean (rapeseed), barley, rye, corn, oats, wheat, beets or sugar cane, and optionally the fuel comprises a liquid or a gas, and optionally the fuel is a biofuel or synthetic fuel, or the fuel comprises a bioethanol, biomethanol, biopropanol or bio-butanol, or the fuel comprises a gasoline-ethanol, methanol, propanol and/or butanol mix.

80. A method for making a fuel comprising (A) contacting a composition comprising a cellooligsaccharide, an arabinoxylan oligomer, a lignin, a lignocellulose, a xylan, a glucan, a cellulose or a fermentable sugar with the polypeptide of paragraph 19, or a polypeptide encoded by the nucleic acid of paragraph 1 or paragraph 5, or the composition or product of manufacture of paragraphs 91 to 93 or paragraph 96;

(B) the method of (A), wherein the composition comprising the cellooligsaccharide, arabinoxylan oligomer, lignin, lignocellulose, xylan, glucan, cellulose or fermentable sugar comprises a plant, plant product or plant derivative;

(C) the method of (A) or (B), wherein the plant or plant product comprises cane sugar plants or plant products, beets or sugarbeets, wheat, corn, soybeans, potato, rice or barley;

(D) the method of (C), wherein the plant is a monocot or dicot, or the plant is a monocot corn, sugarcane, rice, wheat, barley, switchgrass or *Miscanthus*; or the plant is a dicot oilseed crop, soy, canola, rapeseed, flax, cotton, palm oil, sugar beet, peanut, tree, poplar or lupine;

(E) the method of (A), (B), (C) or (D), wherein the polypeptide has activity comprising a cellulase or cellobiohydrolase, wherein optionally the composition further comprises a glucose oxidase, a glucose oxidase-1 (a β-glucosidase) or a glucose oxidase-2 (a β-xylosidase), (F) the method of (A), (B), (C), (D) or (E), wherein the fuel comprises a liquid and/or a gas, or the fuel comprises a biofuel and/or a synthetic fuel, or the fuel comprises bioethanol, biomethanol, biopropanol and/or, bio-butanol; and/or a gasoline-ethanol, -methanol, -butanol and/or -propanol mix.

81. A method for making bioethanol, biomethanol, biopropanol and/or, bio-butanol comprising (A) contacting a composition comprising a cellooligsaccharide, an arabinoxylan oligomer, a lignin, a lignocellulose, a xylan, a glucan, a cellulose or a fermentable sugar with the polypeptide of paragraph 19, or a polypeptide encoded by the nucleic acid of paragraph 1 or paragraph 5, or the composition or product of manufacture of paragraphs 91 to 93 or paragraph 96;

(B) the method of (A), wherein the composition of comprises a plant, plant product or plant derivative, and optionally the plant or plant product comprises cane sugar plants or plant products, beets or sugarbeets, wheat, corn, soybeans, potato, rice or barley, (C) the method of (A) or (B), wherein the polypeptide has activity comprising lignocellulosic enzyme and/or a cellulase or cellobiohydrolase, wherein optionally the composition further comprises a glucose oxidase, a glucose oxidase-1 (a β-glucosidase) or a glucose oxidase-2 (a β-xylosidase); or (D) the method of (A), (B) or (C), wherein the plant is a monocot or dicot, or the plant is a monocot corn, sugarcane, rice, wheat, barley, switchgrass or *Miscanthus*; or the plant is a dicot oilseed crop, soy, canola, rapeseed, flax, cotton, palm oil, sugar beet, peanut, tree, poplar or lupine.

(E) the method of (A), (B), (C) or (D), further comprising processing and/or formulating the bioethanol, biomethanol, bipropanol and/or, bio-butanol as a liquid fuel and/or a gas fuel, wherein optionally the fuel comprises a biofuel and/or a synthetic fuel, or the fuel comprises bioethanol, biomethanol, biopropanol and/or, bio-butanol; and/or a gasoline-ethanol, -methanol, -butanol and/or -propanol mix.

82. An enzyme ensemble, or "cocktail", for depolymerization of cellulosic and hemicellulosic polymers to metabolizeable carbon moieties comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has activity comprising lignocellulosic enzyme and/or a cellulase or cellobiohydrolase, wherein optionally the composition further comprises a glucose oxidase, a glucose oxidase-1 (a β-glucosidase) or a glucose oxidase-2 (a β-xylosidase).

83. A method for processing a biomass material comprising lignocellulose comprising contacting a composition comprising a cellulose or a fermentable sugar with the polypeptide of paragraph 19, or a polypeptide encoded by the nucleic acid of paragraph 1 or paragraph 5, or the composition or product of manufacture of paragraphs 91 to 93 or paragraph 96, wherein optionally the biomass material comprising lignocellulose is derived from an agricultural crop, is a byproduct of a food or a feed production, is a lignocellulosic waste product, or is a plant residue or a waste paper or waste paper product, and optionally the polypeptide has activity comprising lignocellulosic enzyme and/or cellulase or cellobiohydrolase activity, wherein optionally the composition further comprises a glucose oxidase, a glucose oxidase-1 (a β-glucosidase) or a glucose oxidase-2 (a β-xylosidase), and optionally the plant residue comprise stems, leaves, hulls, husks, corn or corn cobs, corn stover, hay, straw, wood, wood chips, wood pulp, wood waste and sawdust, and optionally the paper waste comprises discarded or used photocopy paper, computer printer paper, notebook paper, notepad paper, typewriter paper, newspapers, magazines, cardboard and paper-based packaging materials, and optionally the processing of the biomass material generates a bioalcohol, a bioethanol, biomethanol, biobutanol or biopropanol.

84. A dairy product comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the dairy product comprises a milk, an ice cream, a cheese or a yogurt, and optionally the polypeptide has activity comprising a cellobiohydrolase activity.

85. A method for improving texture and flavor of a dairy product comprising the following steps: (a) providing the polypeptide of paragraph 19, or a polypeptide encoded by the nucleic acid of paragraph 1 or paragraph 5, or the composition or product of manufacture of paragraphs 91 to 93 or paragraph 96; (b) providing a dairy product; and (c) contacting the polypeptide of step (a) and the dairy product of step (b) under conditions wherein the lignocellulosic enzyme and/or cellulase can improve the texture or flavor of the dairy product.

86. A textile or fabric comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the textile or fabric comprises a cellulose-containing fiber, and optionally the polypeptide has activity comprising a cellobiohydrolase activity.

87. A method for treating solid or liquid animal waste products comprising the following steps:

(a) providing the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has activity comprising a cellobiohydrolase activity;

(b) providing a solid or a liquid animal waste; and (c) contacting the polypeptide of step (a) and the solid or liquid waste of step (b) under conditions wherein the protease can treat the waste.

88. A processed waste product comprising the polypeptide of paragraph 19, or a polypeptide encoded by the nucleic acid of paragraph 1 or paragraph 5, or the composition or product of manufacture of paragraphs 91 to 93 or paragraph 96, wherein optionally the polypeptide has activity comprising a cellobiohydrolase activity.

89. A disinfectant comprising a polypeptide having a lignocellulosic activity, wherein the polypeptide comprises the nucleic acid sequence of paragraph 19, or a polypeptide encoded by the nucleic acid of paragraph 1 or paragraph 5, or the composition or product of manufacture of paragraphs 91 to 93 or paragraph 96, wherein optionally the polypeptide has activity comprising a cellobiohydrolase activity.

90. A bio-detoxifying agent or a biodefense agent comprising a polypeptide having a lignocellulosic enzyme, a cellulase and/or a cellulolytic activity, wherein the polypeptide comprises the sequence of paragraph 19, or a polypeptide encoded by the nucleic acid of paragraph 1 or paragraph 5, or the composition or product of manufacture of paragraphs 91 to 93 or paragraph 96, wherein optionally the polypeptide has activity comprising endoglucanase, cellobiohydrolase, beta-glucosidase, xylanase, mannanse, β-xylosidase and/or arabinofuranosidase activity.

91. A composition or product of manufacture comprising (a) a mixture (or "cocktail") of lignocellulosic enzymes comprising: (i) at least one of each of a endoglucanase, cellobiohydrolase I (CBH I), cellobiohydrolase II (CBH II) and β-glucosidase; (ii) at least one of each of an xylanase, β-xylosidase and arabinofuranosidase; or, (iii) a combination of at least one of (i) or (ii); wherein the mixture of (a) comprises at least one enzyme of paragraph 19;

(b) a mixture (or "cocktail") of hemicellulose- and cellulose-hydrolyzing enzymes comprising: (i) at least one of each of a endoglucanase, lignocellulosic enzyme, cellobiohydrolase I (CBH I), cellobiohydrolase II (CBH II), arabinofuranosidase and xylanase; (ii) the mixture of (i), wherein the glucose oxidase is a glucose oxidase-1 or β-glucosidase; or (iii) the mixture of (i) or (ii), wherein the glucose oxidase is a glucose oxidase-2 or β-xylosidase; wherein the mixture of (b) comprises at least one enzyme of paragraph 19;

(c) a mixture (or "cocktail") of hemicellulose- and cellulose-hydrolyzing enzymes comprising: at least one of each of a endoglucanase; a cellobiohydrolase I (CBH I); a cellobiohydrolase II (CBH II); an arabinofuranosidase; a xylanase; a glucose oxidase-1 (a β-glucosidase); and, a glucose oxidase-2 or β-xylosidase; wherein the mixture of (c) comprises at least one enzyme of paragraph 19; or (d) a mixture (or "cocktail") of enzymes comprising: (1) an endoglucanase which cleaves internal β-1,4 linkages resulting in shorter glucooligosaccharides, (2) a cellobiohydrolase which acts in an "exo" manner processively releasing cellobiose units (β-1,4 glucose-glucose disaccharide), and (3) a β-glucosidase for releasing glucose monomer from short cellooligosaccharides (e.g. cellobiose); wherein the mixture of (d) comprises at least one enzyme of paragraph 19.

92. The composition or product of manufacture of paragraph 91, wherein at least one enzyme comprises an additional carbohydrate binding domain (CBM).

93. A composition or product of manufacture comprising: (a) a mixture (or "cocktail") of enzymes as set forth in paragraph 91, or at least one lignocellulosic enzyme of paragraph 19, and a biomass material; (b) the mixture of (a) wherein the biomass material comprises a lignocellulosic material derived from an agricultural crop, or the biomass material is a byproduct of a food or a feed production, or the biomass material is a lignocellulosic waste product, or the biomass material is a plant residue or a waste paper or waste paper product, or the biomass material comprises a plant residue; (c) the mixture of (a) or (b), wherein the plant residue or the biomass material comprises sugar cane bagasse, a stems, leaves, hulls, husks, corn or corn cobs, corn stover, hay, straw, wood, wood chips, wood pulp, wood waste and/or sawdust, or, the paper waste comprises discarded or used photocopy paper, computer printer paper, notebook paper, notepad paper, typewriter paper, newspapers, magazines, cardboard and paper-based packaging materials.

94. A method for processing a biomass material comprising (a) providing: (i) (A) a mixture (or "cocktail") of enzymes, or (B) the composition or product of manufacture of paragraphs 91 to 93 or paragraph 96; and (ii) a biomass material;

wherein the mixture (or "cocktail") of enzymes comprises: (I) at least one lignocellulosic enzyme of paragraph 19; or, (II) the mixture of (I), comprising a mixture (or "cocktail") of enzymes comprising hemicellulose- and cellulose-hydrolyzing enzymes, wherein the cellulose-hydrolyzing enzymes comprise at least one glucose oxidase, endoglucanase, cellobiohydrolase I, cellobiohydrolase II and β-glucosidase; and the hemicellulose-hydrolyzing enzymes comprise at least one xylanase, β-xylosidase and arabinofuranosidase, and optionally the enzymes comprise activity comprising glucose oxidase, cellulase, endoglucanase, cellobiohydrolase, beta-glucosidase, xylanase, mannanse, β-xylosidase and/or arabinofuranosidase activity; and, (b) contacting the mixture of enzymes with the biomass material.

95. The method of paragraph 94, wherein the biomass material comprising lignocellulose is derived from an agricultural crop, is a byproduct of a food or a feed production, is a lignocellulosic waste product, or is a plant residue or plant material, or a waste paper or waste paper product, and optionally the plant residue or plant material comprise sugar cane bagasse, stems, leaves, hulls, husks, corn or corn cobs, corn stover, hay or straw, wood, wood chips, wood pulp, wood waste and sawdust, and optionally the paper waste comprises discarded or used photocopy paper, computer printer paper, notebook paper, notepad paper, typewriter paper, newspapers, magazines, cardboard and paper-based packaging materials, and optionally the processing of the biomass material generates a bioethanol.

96. A mixture or cocktail of enzymes comprising (a) at least one lignocellulosic enzyme of paragraph 19;

(b) a combination of enzymes as set forth in paragraph 19;

(c) at least one of each of a endoglucanase, cellobiohydrolase I (CBH I), cellobiohydrolase II (CBH II) and β-glucosidase; (ii) at least one of each of an xylanase, β-xylosidase and arabinofuranosidase; or, (iii) a combination of at least one of (i) or (ii); wherein the mixture comprises at least one enzyme of paragraph 19;

(d) at least one hemicellulose- and/or cellulose-hydrolyzing enzyme comprising: (i) at least one of each of a endoglucanase, glucose oxidase, cellobiohydrolase I (CBH I), cellobiohydrolase II (CBH II), arabinofuranosidase and xylanase; (ii) the mixture of (i), wherein the glucose oxidase is a glucose oxidase-1 or β-glucosidase; and/or (iii) the mixture of (i) or (ii), wherein the glucose oxidase is a glucose oxidase-2 or β-xylosidase; wherein the mixture comprises at least one enzyme of paragraph 19;

(e) at least one hemicellulose- and/or cellulose-hydrolyzing enzyme comprising: at least one of each of a endoglucanase; a cellobiohydrolase I (CBH I); a cellobiohydrolase II (CBH II); an arabinofuranosidase; a xylanase; a glucose oxidase-1 (a β-glucosidase); and/or, a glucose oxidase-2 or β-xylosidase; wherein the mixture of (c) comprises at least one enzyme of paragraph 19; or (f) at least one (1) endoglucanase which cleaves internal β-1,4 linkages resulting in shorter glucooligosaccharides, (2) cellobiohydrolase which acts in an "exo" manner processively releasing cellobiose units (β-1,4 glucose-glucose disaccharide), and/or (3) β-glucosidase for releasing glucose monomer from short cellooligosaccharides (e.g. cellobiose); wherein the mixture of (d) comprises at least one enzyme of paragraph 19.

97. A method for processing a biomass material comprising (a) (i) providing a mixture of enzymes as set forth in paragraph 96; and (ii) contacting the enzyme mixture with the biomass material;

(b) the process of (a), wherein the biomass material comprising lignocellulose is derived from an agricultural crop, is a byproduct of a food or a feed production, is a lignocellulosic waste product, or is a plant material, plant byproduct of a process, or a plant residue, or a waste paper or waste paper product;

(c) the process of (a) or (b), wherein the polypeptide has activity comprising glucose oxidase, cellulase, endoglucanase, cellobiohydrolase, beta-glucosidase, xylanase, mannanse, β-xylosidase and/or arabinofuranosidase activity;

(d) the process of (a), (b) or (c), wherein the wherein the biomass material comprises a plant residue comprising sugar cane bagasse, stems, leaves, hulls, husks, corn or corn cobs, corn stover, hay or straw, wood, wood chips, wood pulp, a paper waste, wood waste and/or sawdust;

(e) the process of (d), wherein the paper waste comprises discarded or used photocopy paper, computer printer paper, notebook paper, notepad paper, typewriter paper, newspapers, magazines, cardboard and paper-based packaging materials;

(f) the process of (a), (b), (c), (d) or (e), further comprising processing the biomass material to generate a carbohydrate, bioethanol and/or an alcohol.

98. A chimeric polypeptide comprising (a) a first domain and at least a second domain, wherein the first domain comprises an enzyme of paragraph 19, and the second domain comprises a heterologous or modified carbohydrate binding domain (CBM), a heterologous or modified dockerin domain, a heterologous or modified prepro domain, or a heterologous or modified active site;

(b) the chimeric polypeptide of (a), wherein the carbohydrate binding domain (CBM) is a cellulose-binding module or a lignin-binding domain;

(c) the chimeric polypeptide of (a) or (b), wherein the CBM is approximate to the enzyme's catalytic domain;

(d) the chimeric polypeptide of (a), (b) or (c), wherein the at least one CBM is positioned approximate to the polypeptide's catalytic domain;

(e) the chimeric polypeptide of (d), wherein the at least one CBM is positioned: approximate to the C-terminus of the polypeptide's catalytic domain, or, approximate to the N-terminus of the polypeptide's catalytic domain, or both;

(f) the chimeric polypeptide of any of (a), (b), (c) or (e), wherein the chimeric polypeptide is a recombinant chimeric protein.

99. A chimeric polypeptide comprising (a) a polypeptide of paragraph 19 having a lignocellulosic enzyme activity, and a domain comprising at least one heterologous or modified carbohydrate binding domain (CBM), or at least one internally rearranged CBM, or any combination thereof.

What is claimed is:

1. A polypeptide comprising the amino acid sequence of a variant cellobiohydrolase I ("CBH I") catalytic domain, said variant CBH I catalytic domain having at least 90% sequence identity to a reference catalytic domain corresponding to amino acid positions 26-455 of SEQ ID NO:134, and which comprises a N222H amino acid substitution that results in increased activity as compared to the reference catalytic domain.

2. The polypeptide of claim 1, further comprising one or more of the following substitutions or combinations of substitutions: (a) N222E; (b) S217K; (c) L225Y; (d) L225V; (e) D87L; (f) G256I; (g) H157G; (h) P159G; (i) N183A; (j) S156G; (k) S218P+T316S; (l) D318Q+T322S+I363V; (m) T324R; (n) S326L; (o) Q334S; (p) K345D; (q) K45R+T293A+S350C; (r) G351D; (s) N352V; (t) F358L; (u) A370I; (v) G376R; (w) E386S; (x) V451W; (y) N455G; (z) Y31L+T32Q+S72A+T73Q+T77D+F120-VTGSNVG-S128→F120-VQQGPYSKNVG-S132; (aa) Y31L+S72W+T77D+F120-VTGSNVG-S128→F120-VQQGPYSKNVG-S132; (bb) S72Y+T73Q+F120-VTGSNVG-S128→F120-VQQGPYSKNVG-S132; (cc) Y31L+T32W+F120-VTGSNVG-S128→F120-VQQGPYSKNVG-S132; (dd) T32Q+F120-VTGSNVG-S128→F120-VTKGSFSSNIG-S132; (ee) Y31Q+T32Q+S72Y+T77D+F120-VTGSNVG-S128→F120-VTQSAQKNVG-A131; (ff) Y31A+T32Y+S72Y+T73Y+T77D; (gg) Y31Q+T32Q+S72Y+T73Y+T77D; (hh) T32W+T73W+T77D; (ii) Y31A+T32Q+T73Y+T77D; (jj) S72W+T73Q+F120-VTGSNVG-S128→F120-VQQGPYSKNVG-S132; (kk) Y31L+T32Y+T77D+F120-VTGSNVG-S128→F120-VQQGPYSKNVG-S132; (ll) P159G+S217K+N222H+L225Y+K345D+N352V+V451W; (mm) L225Y+K345D+N352V+E386S+V451W; (nn) S326L+K345D+N352V; (oo) L225Y+D318Q+T324R+S326L+K345D+E386S; (pp) P159G+S217K+L225Y+Q334S+K345D+E386S; and (qq) E386S+V451W.

3. The polypeptide of claim 1, wherein the variant CBH I catalytic domain comprises an amino acid sequence having at least 95% sequence identity to amino acid positions 26-455 of SEQ ID NO:134.

4. The polypeptide of claim 1 in which the variant CBH I catalytic domain is operably linked to a heterologous cellulose binding domain.

5. The polypeptide of claim 4 in which catalytic domain is operably linked to a cellulose binding domain via a linker.

6. The polypeptide of claim 5 in which the cellulose binding domain is C-terminal to the catalytic domain.

7. The polypeptide of claim 5 in which the cellulose binding domain is N-terminal to the catalytic domain.

8. The polypeptide of claim 7 which is a mature polypeptide.

9. The polypeptide of claim 7 which further comprises a signal sequence.

10. A composition comprising a polypeptide according to claim 1.

11. The composition of claim 10 in which said polypeptide represents at least 5% of all polypeptides in said composition.

12. The composition of claim 11 in which said polypeptide represents at least 25% of all polypeptide in said composition.

13. The composition of claim 10 which is a whole cellulase.

14. The composition of claim 13, wherein the whole cellulase is produced by a host cell that recombinantly expresses said polypeptide.

15. The composition of claim 14 which is filamentous fungal whole cellulase.

16. A fermentation broth comprising a polypeptide according to claim 1.

17. The fermentation broth of claim 16, which is a filamentous fungal fermentation broth.

18. The fermentation broth of claim 17 which is a cell-free fermentation broth.

19. A polypeptide comprising a variant CBH I amino acid sequence, said variant CBH I amino acid sequence having at least 90% sequence identity to a reference CBH I corresponding to amino acid positions 26-529 of SEQ ID NO:134, and which comprises a N222H amino acid substitutions that result in increased activity as compared to the reference to the reference CBH I.

20. The polypeptide of claim 19, which has one or more of the following substitutions or combinations of substitutions: (a) N222E; (b) S217K; (c) L225Y; (d) L225V; (e) H497S; (f) T510K; (g) D87L; (h) G256I; (i) H157G; (j) P159G; (k) N183A; (l) S156G; (m) S218P+T316S; (n) D318Q+T322S+I363V; (o) T324R; (p) S326L; (q) ☐334S; (r) K345D; (s) K45R+T293A+S350C; (t) G351D; (u) N352V; (v) F358L;

(w) A370I; (x) G376R; (y) E386S; (z) V451W; (aa) N455G; (bb) S463K; (cc) Y31L+T32Q+S72A+T73Q+T77D+F120-VTGSNVG-S128→F120-VQQGPYSKNVG-S132; (dd) Y31L+S72W+T77D+F120-VTGSNVG-S128→F120-VQQGPYSKNVG-S132; (ee) S72Y+T73Q+F120-VTG-SNVG-S128→F120-VQQGPYSKNVG-S132; (ff) Y31L+T32W+F120-VTGSNVG-S128→F120-VQQGPYSKNVG-S132; (gg) T32Q+F120-VTGSNVG-S128→F120-VTKGSFSSNIG-S132; (hh) Y31Q+T32Q+S72Y+T77D+F120-VTGSNVG-S128→F120-VTQSAQKNVG-A131; (ii) Y31A+T32Y+S72Y+T73Y+T77D; (jj) Y31Q+T32Q+S72Y+T73Y+T77D; (kk) T32W+T73W+T77D; (ll) Y31A+T32Q+T73Y+T77D; (mm) S72W+T73Q+F120-VTG-SNVG-S128→F120-VQQGPYSKNVG-S132; (nn) Y31L+T32Y+T77D+F120-VTGSNVG-5128→F120-VQQGPYSKNVG-S132; (oo) P159G+S217K+N222H+L225Y+K345D+N352V+V451W; (pp) N222H+L225Y+K345D+N352V+E386S+V451W; (qq) S326L+K345D+N352V; (rr) L225Y+D318Q+T324R+S326L+K345D+E386S; (ss) P159G+S217K+N222H+L225Y+Q334S+K345D+E386S; and (tt) E386S+V451W.

21. The polypeptide of claim 19, wherein the variant CBH I catalytic domain comprises an amino acid sequence having at least 95% sequence identity to amino acid positions 26-529 of SEQ ID NO:134.

22. The polypeptide of claim 19 which is a mature polypeptide.

23. The polypeptide claim 19 which further comprises a signal sequence.

24. A nucleic acid comprising a nucleotide sequence encoding the polypeptide claim 1.

25. A vector comprising the nucleic acid of claim 24.

26. The vector of claim 25 which further comprises an origin of replication.

27. The vector of claim 25 which further comprises a promoter sequence operably linked to said nucleotide sequence.

28. The vector of claim 27, wherein the promoter sequence is operable in yeast.

29. The vector of claim 27, wherein the promoter sequence is operable in filamentous fungi.

30. A recombinant cell engineered to express the nucleic acid of claim 24.

31. The recombinant cell of claim 30 which is a eukaryotic cell.

32. The recombinant cell of claim 31 which is a filamentous fungal cell.

33. The recombinant cell of claim 32, wherein the filamentous fungal cell is of the genus *Aspergillus, Penicillium, Rhizopus, Chrysosporium, Myceliophthora, Trichoderma, Humicola, Acremonium* or *Fusarium*.

34. The recombinant cell of claim 32, wherein the filamentous fungal cell is of the species *Aspergillus niger, Aspergillus oryzae, Trichoderma reesei, Penicillium chrysogenum, Myceliophthora thermophila*, or *Rhizopus oryzae*.

35. The recombinant cell of claim 31 which is a yeast cell.

36. The recombinant cell of claim 35 which is a yeast cell of the genus *Saccharomyces, Kluyveromyces, Candida, Pichia, Schizosaccharomyces, Hansenula, Klockera, Schwanniomyces* or *Yarrowia*.

37. The recombinant cell of claim 36, wherein the yeast cell is of the species *S. cerevisiae, S. bulderi, S. barnetti, S. exiguus, S. uvarum, S. diastaticus, K. lactis, K. marxianus* or *K. fragilis*.

38. The recombinant cell of claim 37, which is a *S. cerevisiae* cell.

39. A host cell transformed with the vector of claim 25.

40. The host cell of claim 39 which is a prokaryotic cell.

41. The host cell of claim 40 which is a bacterial cell.

42. The host cell of claim 39 which is a eukaryotic cell.

43. A method of producing a polypeptide according to claim 1 comprising culturing the recombinant cell engineered to express said polypeptide under conditions in which the polypeptide is expressed.

44. The method of claim 43, wherein the polypeptide comprises a signal sequence and wherein the recombinant cell is cultured under conditions in which the polypeptide is secreted from the recombinant cell.

45. The method of claim 44, further comprising recovering the polypeptide from the cell culture.

46. The method of claim 45, wherein recovering the polypeptide comprises a step of centrifuging away cells and/or cellular debris.

47. The method of claim 45, wherein recovering the polypeptide comprises a step of filtering away cells and/or cellular debris.

48. A polypeptide comprising the amino acid sequence of a variant cellobiohydrolase I ("CBH I") catalytic domain, said variant CBH I catalytic domain having at least 90% sequence identity to a reference catalytic domain corresponding to amino acid positions 26-455 of SEQ ID NO: 134, and which comprises a V121T amino acid substitution that results in increased activity as compared to the reference catalytic domain.

49. The polypeptide of claim 48, further comprising one or more of the following substitutions or combinations of substitutions: (a) V121S; (b) Y31L+T32Q+S72A+T73Q+T77D+F120-VTGSNVG-S128→F120-VQQGPYSKNVG-S132; (c) Y31L+S72W+T77D+F120-VTGSNVG-S128→F120-VQQGPYSKNVG-S132; (d) S72Y+T73Q+F120-VTGSNVG-S128→F120-VQQGPYSKNVG-S132; (e) Y31L+T32W+F120-VTGSNVG-S128→F120-VQQG-PYSKNVG-S132; (g) T32Q+F120-VTGSNVG-S128→F120-VTKGSFSSNIG-S132; (f) Y31Q+T32Q+S72Y+T77D+F120-VTGSNVG-S128→F120-VTQSAQKNVG-A131; (f) Y31A+T32Y+S72Y+T73Y+T77D; (h) Y31Q+T32Q+S72Y+T73Y+T77D; (i) T32W+T73W+T77D; (j) Y31A+T32Q+T73Y+T77D; (k) S72W+T73Q+F120-VTGSNVG-S128→F120-VQQGPYSKNVG-S132; and (l) Y31L+T32Y+T77D+F120-VTGSNVG-S128→F120-VQQGPYSKNVG-S132.

50. A composition comprising the polypeptide of claim 48.

51. A nucleic acid comprising a nucleotide sequence encoding the polypeptide of claim 48.

52. A vector comprising the nucleic acid of claim 51.

53. The vector of claim 52 which further comprises an origin of replication.

54. The vector of claim 53 which further comprises a promoter sequence operably linked to said nucleotide sequence.

55. The vector of claim 54, wherein the promoter sequence is operable in yeast.

56. The vector of claim 54, wherein the promoter sequence is operable in filamentous fungi.

57. A recombinant cell engineered to express the nucleic acid of claim 51.

58. The recombinant cell of claim 57 which is a eukaryotic cell.

59. The recombinant cell of claim 58 which is a yeast cell.

60. The recombinant cell of claim 59 which is a yeast cell of the genus *Saccharomyces, Kluyveromyces, Candida, Pichia, Schizosaccharomyces, Hansenula, Klockera, Schwanniomyces* or *Yarrowia*.

61. The recombinant cell of claim 59, wherein the yeast cell is of the species *S. cerevisiae, S. bulderi, S. barnetti, S. exiauus, S. uvarum, S. diastaticus, K. lactis, K. marxilanus* or *K. fragilis*.

62. The recombinant cell of claim 61, which is a *S. cerevisiae* cell.

63. The recombinant cell of claim 58 which is a filamentous fungal cell.

64. The recombinant cell of claim 63, wherein the filamentous fungal cell is of the genus *Aspergillus, Penicillium, Rhizopus, Chrysosporium, Myceliophthora, Trichoderma, Humicola, Acremonium* or *Fusarium*.

65. The recombinant cell of claim 63, wherein the filamentous fungal cell is of the species *Aspergillus niger, Aspergillus oryzae, Trichoderma reesei, Penicillium chrysogenum, Myceliophthora thermophila*, or *Rhizopus oryzae*.

66. A host cell transformed with the vector of claim 52.

67. The host cell of claim 66 which is a prokaryotic cell.

68. The host cell of claim 67 which is a bacterial cell.

69. The host cell of claim 66 which is a eukaryotic cell.

70. A method of producing a polypeptide according to claim 48 comprising culturing the recombinant cell engineered to express said polypeptide under conditions in which the polypeptide is expressed.

71. The method of claim 70, wherein the polypeptide comprises a signal sequence and wherein the recombinant cell is cultured under conditions in which the polypeptide is secreted from the recombinant cell.

72. The method of claim 71, further comprising recovering the polypeptide from the cell culture.

73. The method of claim 72, wherein recovering the polypeptide comprises a step of centrifuging away cells and/or cellular debris.

74. The method of claim 72, wherein recovering the polypeptide comprises a step of filtering away cells and/or cellular debris.

75. A polypeptide comprising the amino acid sequence of a variant cellobiohydrolase I ("CBH I") catalytic domain, said variant CBH I catalytic domain having at least 90% sequence identity to a reference catalytic domain corresponding to amino acid positions 26-455 of SEQ ID NO: 134, and which comprises a V392A +V401A+T417A amino acid substitution that results in improved thermotolerance as compared to the reference catalytic domain.

76. The polypeptide of claim 75, further comprising one or more of the following substitutions or combinations of substitutions: (a) S104N; (b) V121S; (c) V121T; (d) G113N; (e) L116T; (f) T268V; (g) T35A+V401A; (h) V392T; (i) Y399D; (j) V401D; (k) L404T; (l) S463Y; (m) A221V+V401A+G474W; and (n) A472M.

77. A composition comprising the polypeptide of claim 75.

78. A nucleic acid comprising a nucleotide sequence encoding the polypeptide of claim 75.

79. A vector comprising the nucleic acid of claim 78.

80. The vector of claim 79 which further comprises an origin of replication.

81. The vector of claim 80 which further comprises a promoter sequence operably linked to said nucleotide sequence.

82. The vector of claim 81, wherein the promoter sequence is operable in yeast.

83. The vector of claim 81, wherein the promoter sequence is operable in filamentous fungi.

84. A recombinant cell engineered to express the nucleic acid of claim 78.

85. The recombinant cell of claim 84 which is a eukaryotic cell.

86. The recombinant cell of claim 85 which is a filamentous fungal cell.

87. The recombinant cell of claim 86, wherein the filamentous fungal cell is of the genus *Aspergilius, Penicillium, Rhizopus, Chrysosporium, Myceliophthora, Trichoderma, Humicola, Acremonium* or *Fusarium*.

88. The recombinant cell of claim 86, wherein the filamentous fungal cell is of the species *Aspergillus niger, Aspergillus oryzae, Trichoderma reesei, Penicillium chrysogenum, Myceliophthora thermophila*, or *Rhizopus oryzae*.

89. The recombinant cell of claim 85 which is a yeast cell.

90. The recombinant cell of claim 89 which is a yeast cell of the genus *Saccharomyces, Kluyveromyces, Candida, Pichia, Schizosaccharomyces, Hansenula, Klockera, Schwanniomyces* or *Yarrowia*.

91. The recombinant cell of claim 89, wherein the yeast cell is of the species *S. cerevisiae, S. bulderi, S. barnetti, S. exiguus, S. uvarum, S. diastaticus, K. lactis, K. marxianus* or *K. fragilis*.

92. The recombinant cell of claim 91, which is a *S. cerevisiae* cell.

93. A host cell transformed with the vector of claim 79.

94. The host cell of claim 93 which is a prokaryotic cell.

95. The host cell of claim 94 which is a bacterial cell.

96. The host cell of claim 93 which is a eukaryotic cell.

97. A method of producing a polypeptide according to claim 75 comprising culturing the recombinant cell engineered to express said polypeptide under conditions in which the polypeptide is expressed.

98. The method of claim 97, wherein the polypeptide comprises a signal sequence and wherein the recombinant cell is cultured under conditions in which the polypeptic is secreted from the recombinant cell.

99. The method of claim 98. further comprising recovering the polypeptide from the cell culture.

100. The method of claim 99, wherein recovering the polypeptide comprises a step of centrifuging away cells and/or cellular debris.

101. The method of claim 99, wherein recovering the polypeptide comprises a step of filtering away cells and/or cellular debris.

102. A polypeptide comprising the amino acid sequence of a variant cellobiohydrolase I ("CBH I") catalytic domain, said variant CBH I catalytic domain having at least 90% sequence identity to a reference catalytic domain corresponding to amino acid positions 26-455 of SEQ ID NO: 134, and which comprises a V121T amino acid substitution that results in increased thermotolerance as compared to the reference catalytic domain.

103. The polypeptide of claim 102, further comprising one or more of the following substitutions or combinations of substitutions: (a) V121S; (b) Y31L+T32Q+S72A+T73Q+T77D+F120-VTGSNVG-S128→F120-VQQGPYSKNVG-S132; (c) Y31L+S72W+T77D+F120-VTGSNVG-S128→F120-VQQGPYSKNVG-S132; (d) S72Y+T73Q+F120-VTGSNVG-S128→F120-VQQGPYSKNVG-S132; (e) Y31L+T32W+F120-VTGSNVG-S128→F120-VQQGPYSKNVG-S132; (g) T32Q+F120-VTGSNVG-S128→F120-VTKGSFSSNIG-S132; (f) Y31Q+T32Q+S72Y+T77D+F120-VTGSNVG-S128→F120-VTQSAQKNVG-A131; (f) Y31A+T32Y+S72Y+T73Y+T77D; (h) Y31Q+T32Q+S72Y+T73Y+T77D; (i) T32W+T73W+T77D; (j) Y31A+T32Q+T73Y+T77D; (k) S72W+T73Q+F120-VTGSNVG-S128→F120-VQQGPYSKNVG-S132; and (l) Y31L+T32Y+T77D+F120-VTGSNVG-S128→F120-VQQGPYSKNVG-S132.

104. A composition comprising the polypeptide of claim 102.

105. A nucleic acid comprising a nucleotide sequence encoding the polypeptide of claim 102.

106. A vector comprising the nucleic acid of claim 105.

107. The vector of claim 106 which further comprises an origin of replication.

108. The vector of claim 107 which further comprises a promoter sequence operably linked to said nucleotide sequence.

109. The vector of claim 108, wherein the promoter sequence is operable in yeast.

110. The vector of claim 108, wherein the promoter sequence is operable in filamentous fungi.

111. A recombinant cell engineered to express the nucleic acid of claim 105.

112. The recombinant cell of claim 111 which is a eukaryotic cell.

113. The recombinant cell of claim 112 which is a filamentous fungal cell.

114. The recombinant cell of claim 113, wherein the filamentous fungal cell is of the genus *Aspergillus, Penicillium, Rhizopus, Chrysosporium, Mycellophthora, Trichoderma, Humicola, Acremonium* or *Fusarium*.

115. The recombinant cell of claim 113, wherein the filamentous fungal cell is of the species *Aspergillus niger, Aspergillus oryzae, Trichoderma reesei, Penicillium chrysogenum, Myceliophthora thermophila*, or *Rhizopus oryzae*.

116. The recombinant cell of claim 112 which is a yeast cell.

117. The recombinant cell of claim 116 which is a yeast cell of the genus *Saccharomyces, Kluyveromyces, Candida, Pichia, Schizosaccharomyces, Hansenula, Klockera, Schwanniomyces* or *Yarrowia*.

118. The recombinant cell of claim 116, wherein the yeast cell is of the species *S. cerevisiae, S. bulderi, S. barnetti, S. exiguus, S. uvarum, S. diastaticus, K. lactis, K. marxianus* or *K. fragilis*.

119. The recombinant cell of claim 118, which is a *S. cerevisiae* cell.

120. A host cell transformed with the vector of claim 106.

121. The host cell of claim 120 which is a prokaryotic cell.

122. The host cell of claim 121 which is a bacterial cell.

123. The host cell of claim 120 which is a eukaryotic cell.

124. A method of producing a polypeptide according to claim 102 comprising culturing the recombinant cell engineered to express said polypeptide under conditions in which the polypeptide is expressed.

125. The method of claim 124, wherein the polypeptide comprises a signal sequence and wherein the recombinant cell is cultured under conditions in which the polypeptide is secreted from the recombinant cell.

126. The method of claim 125, further comprising recovering the polypeptide from the cell culture.

127. The method of claim 126, wherein recovering the polypeptide comprises a step of centrifuging away cells and/or cellular debris.

128. The method of claim 126, wherein recovering the polypeptide comprises a step of filtering away cells and/or cellular debris.

129. A polypeptide comprising a variant cellobiohydrolase I ("CBH I") catalytic domain amino acid sequence, said variant CBH I amino acid sequence having at least 90% sequence identity to a reference CBH I corresponding to amino acid positions 26-529 of SEQ ID NO:134, and which comprises a V121S amino acid substitution that result in-improved thermotolerance as compared to the reference to the reference CBH I.

130. The polypeptide of claim 129, further comprising one or more of the following substitutions or combinations of substitutions: (a) S104N; (b) V121T; (c) G113N; (d) L116T; (e) T268V; (f) T35A+V401A; (g) V392T; (h) Y399D; (i) V401D; (j) V392A+V401A+T417A; (k) L404T; (l) S463Y; (m) A221V+V401A+G474W; (n) A472M; and (o) V401A+V494L.

131. A composition comprising the polypeptide of claim 129.

132. A nucleic acid comprising a nucleotide sequence encoding the polypeptide of claim 129.

133. A vector comprising the nucleic acid of claim 132.

134. The vector of claim 133 which further comprises an origin of replication.

135. The vector of claim 134 which further comprises a promoter sequence operably linked to said nucleotide sequence.

136. The vector of claim 135, wherein the promoter sequence is operable in yeast.

137. The vector of claim 135, wherein the promoter sequence is operable in filamentous fungi.

138. A recombinant cell engineered to express the nucleic acid of claim 132.

139. The recombinant cell of claim 138 which is a eukaryotic cell.

140. The recombinant cell of claim 139 which is a filamentous fungal cell.

141. The recombinant cell of claim 140, wherein the filamentous fungal cell is of the genus *Aspergilius, Penicillium, Rhizopus, Chrysosporium, Myceliophthora, Trichoderma, Humicola, Acremonium* or *Fusarium*.

142. The recombinant cell of claim 140, wherein the filamentous fungal cell is of the species *Aspergillus niger, Aspergillus oryzae, Trichoderma reesei, Penicillium chrysogenum, Myceliophthora therrnophila*, or *Rhizopus oryzae*.

143. The recombinant cell of claim 139 which is a yeast cell.

144. The recombinant cell of claim 143 which is a yeast cell of the genus *Saccharomyces, Kluyveromyces, Candida, Pichia, Schizosaccharomyces, Hansenula, Klockera, Schwanniomyces* or *Yarrowia*.

145. The recombinant cell of claim 143, wherein the yeast cell is of the species *S. cerevisiae, S. bulderi, S. barnetti, S. exiguus, S. uvarum, S. diastaticus, K. lactis, K. marxianus* or *K. fragilis*.

146. The recombinant cell of claim 145, which is a *S. cerevisiae* cell.

147. A host cell transformed with the vector of claim 133.

148. The host cell of claim 147 which is a prokaryotic cell.

149. The host cell of claim 148 which is a bacterial cell.

150. The host cell of claim 147 which is a eukaryotic cell.

151. A method of producing a polypeptide according to claim 129 comprising culturing the recombinant cell engineered to express said polypeptide under conditions in which the polypeptide is expressed.

152. The method of claim 151, wherein the polypeptide comprises a signal sequence and wherein the recombinant cell is cultured under conditions in which the polypeptic is secreted from the recombinant cell.

153. The method of claim 152, further comprising recovering the polypeptide from the cell culture.

154. The method of claim 153, wherein recovering the polypeptide comprises a step of centrifuging away cells and/or cellular debris.

155. The method of claim 153, wherein recovering the polypeptide comprises a step of filtering away cells and/or debris.

156. A method for saccharifying biomass, comprising: treating biomass with a composition according to claim 10.

157. The method of claim 156, further comprising recovering monosaccharides.

158. A method for producing ethanol, comprising: (a) treating biomass with a composition according to claim 10, thereby producing monosaccharides; and (b) culturing a fermenting microorganism in the presence of the monosaccharides produced in step (a) under fermentation conditions, thereby producing ethanol.

159. The method of claim 158, further comprising, prior to step (a), pretreating the biomass.

160. The method of claim 158, wherein said fermenting microorganism is a bacterium or a yeast.

161. The method of claim 160, wherein said fermenting microorganism is a bacterium selected from *Zymomonas mobilis, Escherichia coli* and *Klebsiella oxytoca*.

162. The method of claim 160, wherein said fermenting microorganism is a yeast selected from *Saccharomyces cerevisiae, Saccharomyces uvarum, Kluyveromyces fragilis, Kluyveromyces lactis, Candida pseudotropicalis*, and *Pachysolen tannophilus*.

163. The method of claim 158, wherein said biomass is corn stover, bagasses, sorghum, giant reed, elephant grass, miscanthus, Japanese cedar, wheat straw, switchgrass, hardwood pulp, softwood pulp, crushed sugar cane, energy cane, or Napier grass.

164. A method for saccharifying biomass, comprising: treating biomass with a composition with a fermentation broth according to claim 17.

165. A method for producing ethanol, comprising: (a) treating biomass with a fermentation broth according to claim 17, thereby producing monosaccharides; and (b) culturing a fermenting microorganism in the presence of the monosaccharides produced in step (a) under fermentation conditions, thereby producing ethanol.

166. A method for saccharifying biomass, comprising: treating biomass with a composition according to claim 50.

167. The method of claim 166, further comprising recovering monosaccharides.

168. A method for producing ethanol, comprising: (a) treating biomass with a composition according to claim 50, thereby producing monosaccharides; and (b) culturing a fermenting microorganism in the presence of the monosaccharides produced in step (a) under fermentation conditions, thereby producing ethanol.

169. The method of claim 168, further comprising, prior to step (a), pretreating the biomass.

170. The method of claim 168, wherein said fermenting microorganism is a bacterium or a yeast.

171. The method of claim 170, wherein said fermenting microorganism is a bacterium selected from *Zymomonas mobilis, Escherichia coli* and *Klebsiella oxytoca*.

172. The method of claim 170, wherein said fermenting microorganism is a yeast selected from *Saccharomyces cerevisiae, Saccharomyces uvarum, Kluyveromyces fragilis, Kluyveromyces lactis, Candida pseudotropicalis*, and *Pachysolen tannophilus*.

173. The method of claim 168, wherein said biomass is corn stover, bagasses, sorghum, giant reed, elephant grass, miscanthus, Japanese cedar, wheat straw, switchgrass, hardwood pulp, softwood pulp, crushed sugar cane, energy cane, or Napier grass.

174. A method for saccharifying biomass, comprising: treating biomass with a composition according to claim 77.

175. The method of claim 174, further comprising recovering monosaccharides.

176. A method for producing ethanol, comprising; (a) treating biomass with a composition according to claim 77, thereby producing monosaccharides; and (b) culturing a fermenting microorganism in the presence of the monosaccharides produced in step (a) under fermentation conditions, thereby producing ethanol.

177. The method of claim 176, further comprising, prior to step (a), pretreating the biomass.

178. The method of claim 176, wherein said fermenting microorganism is a bacterium or a yeast.

179. The method of claim 178, wherein said fermenting microorganism is a bacterium selected from *Zymomonas mobilis, Escherichia coli* and *Klebsiella oxytoca*.

180. The method of claim 178, wherein said fermenting microorganism is a yeast selected from *Saccharomyces cerevisiae, Saccharomyces uvarum, Kluyveromyces fragilis, Kluyveromyces lactis, Candida pseudotropicalis*, and *Pachysolen tannophilus*.

181. The method of claim 176, wherein said biomass is corn stover, bagasses, sorghum, giant reed, elephant grass, miscanthus, Japanese cedar, wheat straw, switchgrass, hardwood pulp, softwood pulp, crushed sugar cane, energy cane, or Napier grass.

182. A method for saccharifying biomass, comprising: treating biomass with a composition according to claim 104.

183. The method of claim 182, further comprising recovering monosaccharides.

184. A method for producing ethanol, comprising: (a) treating biomass with a composition according to claim 104, thereby producing monosaccharides; and (b) culturing a fermenting microorganism in the presence of the monosaccharides produced in step (a) under fermentation conditions, thereby producing ethanol.

185. The method of claim 184, further comprising, prior to step (a), pretreating the biomass.

186. The method of claim 184, wherein said fermenting microorganism is a bacterium or a yeast.

187. The method of claim 186, wherein said fermenting microorganism is a bacterium selected from *Zymomonas mobilis, Escherichia coli* and *Klebsiella oxytoca*.

188. The method of claim 186, wherein said fermenting microorganism is a yeast selected from *Saccharornyces cerevisiae, Saccharomyces uvarum, Kluyveromyces fragilis, Kluyveromyces lactis, Candida pseudotropicalis*, and *Pachysolen tannophilus*.

189. The method of claim 184, wherein said biomass is corn stover, bagasses, sorghum, giant reed, elephant grass, miscanthus, Japanese cedar, wheat straw, switchgrass, hardwood pulp, softwood pulp, crushed sugar cane, energy cane, or Napier grass.

190. A method for saccharifying biomass, comprising: treating biomass with a composition according to claim 131.

191. The method of claim 190, further comprising recovering monosaccharides.

192. A method for producing ethanol, comprising: (a) treating biomass with a composition according to claim 131, thereby producing monosaccharides; and (b) culturing a fermenting microorganism in the presence of the monosaccharides produced in step (a) under fermentation conditions, thereby producing ethanol.

193. The method of claim 192, further comprising, prior to step (a), pretreating the biomass.

194. The method of claim 192, wherein said fermenting microorganism is a bacterium or a yeast.

195. The method of claim 194, wherein said fermenting microorganism is a bacterium selected from *Zymomonas mobilis, Escherichia coli* and *Klebsiella oxytoca*.

196. The method of claim 194, wherein said fermenting microorganism is a yeast selected from *Saccharomyces cerevisiae, Saccharomyces uvarum, Kluyverornyces fragilis, Kluyveromyces lactis, Candida pseudotropicalis*, and *Pachysoien tannophilus*.

197. The method of claim 192, wherein said biomass is corn stover, bagasses, sorghum, giant reed, elephant grass, miscanthus, Japanese cedar, wheat straw, switchorass, hardwood pulp, softwood pulp, crushed sugar cane, energy cane, or Napier grass.

\* \* \* \* \*